(12) United States Patent
Noronha et al.

(10) Patent No.: US 8,138,199 B2
(45) Date of Patent: Mar. 20, 2012

(54) USE OF BI-ARYL META-PYRIMIDINE INHIBITORS OF KINASES

(75) Inventors: Glenn Noronha, Fort Worth, TX (US); John D. Hood, San Diego, CA (US); Richard M. Soll, San Diego, CA (US)

(73) Assignee: TargeGen, Inc., San Diego, CA (US)

( * ) Notice: Subject to any disclaimer, the term of this patent is extended or adjusted under 35 U.S.C. 154(b) by 557 days.

(21) Appl. No.: 12/253,374

(22) Filed: Oct. 17, 2008

(65) Prior Publication Data

US 2009/0275582 A1 Nov. 5, 2009

Related U.S. Application Data

(63) Continuation of application No. 11/588,638, filed on Oct. 26, 2006, now Pat. No. 7,528,143.

(60) Provisional application No. 60/732,629, filed on Nov. 1, 2005, provisional application No. 60/838,003, filed on Aug. 15, 2006.

(51) Int. Cl.
*A01N 43/54* (2006.01)
*A61K 31/505* (2006.01)

(52) U.S. Cl. ...................................... 514/275

(58) Field of Classification Search ........................ None
See application file for complete search history.

(56) References Cited

U.S. PATENT DOCUMENTS

| | | | |
|---|---|---|---|
| 2,001,051 A | 5/1935 | Bruno | |
| 2,002,165 A | 5/1935 | Winslow | |
| 2,003,060 A | 5/1935 | Thomas | |
| 2,003,065 A | 5/1935 | Boyce | |
| 2,003,149 A | 5/1935 | Johnson | |
| 2,003,166 A | 5/1935 | Zancan | |
| 2,003,187 A | 5/1935 | Good | |
| 2,003,199 A | 5/1935 | Johnson et al. | |
| 2,004,092 A | 6/1935 | Chaney | |
| 2,004,102 A | 6/1935 | Dickey | |
| 2,004,138 A | 6/1935 | Story et al. | |
| 2,667,486 A | 1/1954 | Cain | |
| 4,160,833 A | 7/1979 | Diel | |
| 4,309,211 A | 1/1982 | Serban et al. | |
| 5,214,059 A | 5/1993 | Tegeler et al. | |
| 5,231,097 A | 7/1993 | Klausener et al. | |
| 5,332,745 A | 7/1994 | Carter et al. | |
| 5,527,763 A | 6/1996 | Miyazaki et al. | |
| 5,530,000 A | 6/1996 | Sanfilippo et al. | |
| 5,597,826 A | 1/1997 | Howard et al. | |
| 5,597,901 A | 1/1997 | Stern | |
| 5,665,724 A | 9/1997 | Sanfilippo et al. | |
| 5,776,502 A | 7/1998 | Foulkes et al. | |
| 5,830,880 A | 11/1998 | Sedlacek et al. | |
| 5,849,738 A | 12/1998 | Lee et al. | |
| 5,935,383 A | 8/1999 | Sun et al. | |
| 5,958,935 A | 9/1999 | Davis et al. | |
| 5,965,761 A | 10/1999 | Buchecker et al. | |
| 5,972,580 A | 10/1999 | Fukui et al. | |
| 6,048,675 A | 4/2000 | Hirano et al. | |
| 6,070,126 A | 5/2000 | Kokolus et al. | |
| 6,093,838 A | 7/2000 | Vasudevan et al. | |
| 6,121,434 A | 9/2000 | Peyman et al. | |
| 6,127,382 A | 10/2000 | Beard et al. | |
| 6,136,779 A | 10/2000 | Foulkes et al. | |
| 6,136,971 A | 10/2000 | Harrington et al. | |
| 6,153,752 A | 11/2000 | Bauer et al. | |
| 6,194,191 B1 | 2/2001 | Zhang et al. | |
| 6,197,779 B1 | 3/2001 | Andries et al. | |
| 6,204,260 B1 | 3/2001 | Bruns, Jr. et al. | |
| 6,235,746 B1 | 5/2001 | Davis et al. | |
| 6,277,502 B1 | 8/2001 | Buchecker et al. | |
| 6,288,082 B1 | 9/2001 | Wissner et al. | |
| 6,297,258 B1 | 10/2001 | Wissner et al. | |
| 6,326,487 B1 | 12/2001 | Peyman et al. | |
| 6,348,312 B1 | 2/2002 | Peyman et al. | |
| 6,378,526 B1 | 4/2002 | Bowman et al. | |
| 6,432,963 B1 | 8/2002 | Hisamichi et al. | |
| 6,471,968 B1 | 10/2002 | Baker, Jr. et al. | |
| 6,489,328 B2 | 12/2002 | Snow et al. | |
| 6,506,769 B2 | 1/2003 | Snow et al. | |
| 6,605,615 B2 | 8/2003 | Medina et al. | |
| 6,613,773 B2 | 9/2003 | Clough et al. | |
| 6,635,626 B1 | 10/2003 | Barrish et al. | |
| 6,649,608 B2 | 11/2003 | Pease et al. | |
| 6,685,938 B1 | 2/2004 | Cheresh et al. | |
| 6,689,778 B2 | 2/2004 | Bemis et al. | |
| 6,777,412 B2 | 8/2004 | Clough et al. | |
| 6,794,378 B2 | 9/2004 | Lino et al. | |
| 6,838,464 B2 | 1/2005 | Pease et al. | |

(Continued)

FOREIGN PATENT DOCUMENTS

AU A-38554/93 11/1993

(Continued)

OTHER PUBLICATIONS

Borisi, A. A. et al. (Jun. 24, 2003, e-pub Jun. 10, 2003). "Systematic Discovery of Multicomponent Therapeutics," *Proc. Natl. Acad. Sci. USA* 100(13):7977-7982.

(Continued)

*Primary Examiner* — Jeffrey Murray
(74) *Attorney, Agent, or Firm* — Morrison & Foerster LLP

(57) ABSTRACT

The invention provides biaryl meta-pyrimidine compounds having the general structure (A). The pyrimidine compounds of the invention are capable of inhibiting kinases, such as members of the Jak kinase family, and various other specific receptor and non-receptor kinases.

(A)

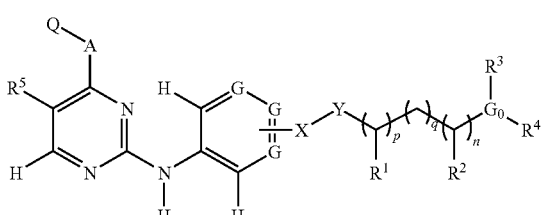

31 Claims, 2 Drawing Sheets

U.S. PATENT DOCUMENTS

| | | | |
|---|---|---|---|
| 7,067,522 B2 | 6/2006 | Pease et al. |
| 7,087,597 B1 | 8/2006 | Miwa et al. |
| 7,208,493 B2 | 4/2007 | Wrasidlo et al. |
| 7,282,504 B2 | 10/2007 | Armistead et al. |
| 7,452,911 B2 | 11/2008 | Stenkamp et al. |
| 7,528,143 B2 | 5/2009 | Noronha et al. |
| 7,652,051 B2 | 1/2010 | Wrasidlo et al. |
| 7,691,858 B2 | 4/2010 | Doukas et al. |
| 7,825,246 B2 | 11/2010 | Noronha et al. |
| 2001/0051620 A1 | 12/2001 | Berger et al. |
| 2002/0052386 A1 | 5/2002 | Armistead et al. |
| 2002/0165244 A1 | 11/2002 | Zhou et al. |
| 2003/0060626 A1 | 3/2003 | Clough et al. |
| 2003/0065180 A1 | 4/2003 | Tsou et al. |
| 2003/0096816 A1 | 5/2003 | Cao et al. |
| 2003/0134838 A1 | 7/2003 | Bornemann et al. |
| 2003/0149061 A1 | 8/2003 | Nishihara et al. |
| 2003/0149064 A1 | 8/2003 | Pease et al. |
| 2003/0166932 A1 | 9/2003 | Beard et al. |
| 2003/0199511 A1 | 10/2003 | Li et al. |
| 2004/0029902 A1 | 1/2004 | Singh et al. |
| 2004/0092746 A1 | 5/2004 | Clough et al. |
| 2004/0102630 A1 | 5/2004 | Brumby et al. |
| 2004/0106615 A1 | 6/2004 | Cochran et al. |
| 2004/0138257 A1 | 7/2004 | Bouchard et al. |
| 2005/0234049 A1 | 10/2005 | Singh et al. |
| 2005/0234083 A1 | 10/2005 | Chamberlain et al. |
| 2005/0239852 A1 | 10/2005 | Ciufolini et al. |
| 2005/0245524 A1 | 11/2005 | Noronha et al. |
| 2005/0282814 A1 | 12/2005 | Wrasidlo et al. |
| 2006/0079526 A1 | 4/2006 | Wrasidlo et al. |
| 2006/0100227 A1 | 5/2006 | Baenteli et al. |
| 2006/0131762 A1 | 6/2006 | Meudt et al. |
| 2006/0131835 A1 | 6/2006 | Simpson |
| 2006/0247250 A1 | 11/2006 | Cao et al. |
| 2006/0292203 A1 | 12/2006 | Dellamary et al. |
| 2006/0293311 A1 | 12/2006 | Li et al. |
| 2007/0027120 A1 | 2/2007 | Whitehouse et al. |
| 2007/0032493 A1 | 2/2007 | Foley et al. |
| 2007/0060603 A1 | 3/2007 | Singh et al. |
| 2007/0072682 A1 | 3/2007 | Crawford et al. |
| 2007/0149508 A1 | 6/2007 | Noronha et al. |
| 2007/0161645 A1 | 7/2007 | Noronha et al. |
| 2007/0191405 A1 | 8/2007 | Noronha et al. |
| 2007/0203162 A1 | 8/2007 | Li et al. |
| 2007/0208019 A1 | 9/2007 | Wrasidlo et al. |
| 2007/0259876 A1 | 11/2007 | Doukas et al. |
| 2007/0259904 A1 | 11/2007 | Noronha et al. |
| 2007/0299095 A1 | 12/2007 | Singh et al. |
| 2008/0021013 A1 | 1/2008 | Dobrzanski et al. |
| 2008/0027070 A1 | 1/2008 | Noronha et al. |
| 2008/0039622 A1 | 2/2008 | Singh et al. |
| 2009/0197869 A1 | 8/2009 | Arvanitis et al. |
| 2009/0286789 A1 | 11/2009 | Noronha et al. |
| 2010/0016218 A1 | 1/2010 | Lichter et al. |
| 2010/0022522 A1 | 1/2010 | Rodgers et al. |
| 2010/0278811 A1 | 11/2010 | Wrasidlo et al. |
| 2010/0278921 A1 | 11/2010 | Fischer et al. |
| 2010/0330030 A1 | 12/2010 | Noronha et al. |

FOREIGN PATENT DOCUMENTS

| | | |
|---|---|---|
| CA | 2375982 | 2/2001 |
| DE | 3205638 | 8/1983 |
| DE | 10024622 | 11/2001 |
| EP | 444769 | 9/1991 |
| EP | 1170353 | 1/2002 |
| EP | 1562938 | 8/2005 |
| EP | 1 054 004 B1 | 7/2008 |
| JP | 02064553 | 3/1990 |
| JP | 03127790 | 5/1991 |
| JP | 03240066 | 10/1991 |
| JP | 07041461 | 2/1995 |
| JP | 07082183 | 3/1995 |
| JP | 09274290 | 10/1997 |
| JP | 10153838 | 6/1998 |
| JP | 10207019 | 8/1998 |
| JP | 10213820 | 8/1998 |
| JP | 10260512 | 9/1998 |
| JP | 10310583 | 11/1998 |
| JP | 2001089412 | 4/2001 |
| JP | 2001247411 | 9/2001 |
| JP | 2002221770 | 8/2002 |
| WO | WO-91/18887 | 12/1991 |
| WO | WO-92/01675 | 2/1992 |
| WO | WO-94/15622 | 7/1994 |
| WO | WO-97/09315 | 3/1997 |
| WO | WO 97/24122 | 7/1997 |
| WO | WO-98/24974 | 6/1998 |
| WO | WO-98/28282 | 7/1998 |
| WO | WO-99/09016 | 2/1999 |
| WO | WO-99/24404 | 5/1999 |
| WO | WO-99/31073 | 6/1999 |
| WO | WO-99/32454 | 7/1999 |
| WO | WO-99/41253 | 8/1999 |
| WO | WO-99/50250 | 10/1999 |
| WO | WO-00/18740 | 4/2000 |
| WO | WO-00/18761 | 4/2000 |
| WO | WO-00/39101 | 7/2000 |
| WO | WO-00/39108 | 7/2000 |
| WO | WO-00/46203 | 8/2000 |
| WO | WO-00/62778 | 10/2000 |
| WO | WO-00/66583 | 11/2000 |
| WO | WO-00/71536 | 11/2000 |
| WO | WO-01/07027 | 2/2001 |
| WO | WO-01/07401 | 2/2001 |
| WO | WO-01/12227 | 2/2001 |
| WO | WO-01/17995 | 3/2001 |
| WO | WO-01/21597 | 3/2001 |
| WO | WO-01/27105 | 4/2001 |
| WO | WO-01/32628 | 5/2001 |
| WO | WO-01/44194 | 6/2001 |
| WO | WO-01/47892 | 7/2001 |
| WO | WO-01/55116 | 8/2001 |
| WO | WO-01/62233 | 8/2001 |
| WO | WO-01/64646 | 9/2001 |
| WO | WO-01/64655 | 9/2001 |
| WO | WO-01/64656 A1 | 9/2001 |
| WO | WO-01/64674 | 9/2001 |
| WO | WO-01/68186 | 9/2001 |
| WO | WO-01/70668 | 9/2001 |
| WO | WO-01/72758 | 10/2001 |
| WO | WO-01/76582 | 10/2001 |
| WO | WO-02/22608 | 3/2002 |
| WO | WO-02/30358 | 4/2002 |
| WO | WO-02/36570 | 5/2002 |
| WO | WO-02/42272 | 5/2002 |
| WO | WO-02/44166 | 6/2002 |
| WO | WO-02/053101 | 7/2002 |
| WO | WO-02/053160 | 7/2002 |
| WO | WO-02/064096 | 8/2002 |
| WO | WO-02/068409 | 9/2002 |
| WO | WO-02/076438 | 10/2002 |
| WO | WO-02/083667 A2 | 10/2002 |
| WO | WO-02/083667 A3 | 10/2002 |
| WO | WO-02/090347 | 11/2002 |
| WO | WO-02/092087 | 11/2002 |
| WO | WO-02/094766 | 11/2002 |
| WO | WO-02/096905 A1 | 12/2002 |
| WO | WO-02/097116 | 12/2002 |
| WO | WO-03/004018 | 1/2003 |
| WO | WO-03/016306 | 2/2003 |
| WO | WO-03/024448 | 3/2003 |
| WO | WO-03/030909 | 4/2003 |
| WO | WO-03/032994 | 4/2003 |
| WO | WO-03/033503 | 4/2003 |
| WO | WO-03/033504 | 4/2003 |
| WO | WO-03/033505 | 4/2003 |
| WO | WO-03/037869 | 5/2003 |
| WO | WO-03/037891 | 5/2003 |
| WO | WO-03/045921 | 6/2003 |
| WO | WO-03/050090 | 6/2003 |
| WO | WO-03/051366 | 6/2003 |
| WO | WO-03/057165 | 7/2003 |
| WO | WO-03/066575 | 8/2003 |
| WO | WO-03/066601 A1 | 8/2003 |
| WO | WO-03/078404 | 9/2003 |

| | | |
|---|---|---|
| WO | WO-03/099771 | 12/2003 |
| WO | WO-04/000833 | 12/2003 |
| WO | WO-2004/005283 | 1/2004 |
| WO | WO-2004/014382 A1 | 2/2004 |
| WO | WO-2004/018433 | 3/2004 |
| WO | WO-2004/024663 | 3/2004 |
| WO | WO-2004/032709 | 4/2004 |
| WO | WO-2004/037176 | 5/2004 |
| WO | WO-2004/037814 | 5/2004 |
| WO | WO-2004/039780 | 5/2004 |
| WO | WO2004/046118 | 6/2004 |
| WO | WO-2004/052373 | 6/2004 |
| WO | WO-2004/054186 | 6/2004 |
| WO | WO-2004/056786 | 7/2004 |
| WO | WO-2004/058254 | 7/2004 |
| WO | WO-2004/058782 | 7/2004 |
| WO | WO-2004/060305 | 7/2004 |
| WO | WO-2004/060376 | 7/2004 |
| WO | WO-2004/069812 | 8/2004 |
| WO | WO-2004/071426 | 8/2004 |
| WO | WO-2004/074261 | 9/2004 |
| WO | WO-2004/074262 | 9/2004 |
| WO | WO-2004/074266 | 9/2004 |
| WO | WO2004/080980 | 9/2004 |
| WO | WO-2004/080980 | 9/2004 |
| WO | WO-2004/097504 | 11/2004 |
| WO | WO-2005/016894 | 2/2005 |
| WO | WO-2005/026130 | 3/2005 |
| WO | WO-2005/026158 | 3/2005 |
| WO | WO-2006/074057 A2 | 7/2006 |
| WO | WO-2006/074057 A3 | 7/2006 |
| WO | WO-2006/101977 A2 | 9/2006 |
| WO | WO-2006-101977 A3 | 9/2006 |
| WO | WO-2006/128129 | 11/2006 |
| WO | WO-2006/131835 | 12/2006 |
| WO | WO-2006/133426 A2 | 12/2006 |
| WO | WO-2006/133426 A3 | 12/2006 |
| WO | WO-2006/137658 A1 | 12/2006 |
| WO | WO-2007/008541 | 1/2007 |
| WO | WO-2007/022380 | 2/2007 |
| WO | WO-2007/053452 A1 | 5/2007 |
| WO | WO-2007/053776 A1 | 5/2007 |
| WO | WO-2007/058627 A1 | 5/2007 |
| WO | WO-2007/058628 A1 | 5/2007 |
| WO | WO-2008/009458 | 1/2008 |
| WO | WO-2008/157208 A2 | 12/2008 |
| WO | WO-2008/157208 A3 | 12/2008 |
| WO | WO-2009/046416 A1 | 4/2009 |
| WO | WO-2010/017122 A2 | 2/2010 |
| WO | WO-2010/017122 A3 | 2/2010 |
| WO | WO-2010/068182 A1 | 6/2010 |

OTHER PUBLICATIONS

Cao, J. et al. (Mar. 2007). "MEDI 119—Design, Syntheses and SAR of Low nM Inhibitors Targeting JAK2," *233rd ACS National Meeting*, Chicago, IL, Mar. 25-29, 2007, located at <http://oasys2.confex.com/acs/233nm/techprogram/P1064195.htm>, last visited Oct. 27, 2010, 1 page.

Carbuccia, N. et al. (Nov. 2009, e-pub. Jul. 16, 2009). "Mutations of *ASXL1* Gene in Myeloproliferative Neoplasms," *Leukemia* 23(11):2183-2186.

Cervantes, F. (Oct. 2007). "Myelofibrosis: Biology and Treatment Options," *Eur. J. Haematol. Suppl.* 79(68):13-17.

Cervantes, F et al. (Mar. 26, 2009, e-pub. Nov. 6, 2008). "New Prognostic Scoring System for Primary Myelofibrosis Based on a Study of the International Working Group for Myelofibrosis Research and Treatment," *Blood* 113(13):2895-2901.

Committee Orphan Medicinal Products (Oct. 12, 2010). "Public Summary of Opinion on Orphan Designation (EU/3/10/794) N-tert-butyl-3-[(5-methyl-2-{[4-(2-pyrrolidin-1-yletthoxy)phenyl]amino}pyrimidin-4-yl)amino] benzenesulfonamide dihydrocholoride monohydrate for the Treatment of Primary Myelofibrosis," European Medicines Agency database, under Human Medicines, further under Rare Disease Designations, located at <URL: http://www.ema.europa.eu/docs/en_GB/document_library/Orphan_designation/2010/10/WC500097767.pdf>, last retrieved Feb. 2, 2011, EMA/COMP/477791/2010, 5 pages.

Cotto, M. et al. (Jun. 2010). "Epigenetic Therapy of Lymphoma Using Histone Deacetylase Inhibitors," *Clin. Transl. Oncol.* 12(6):401-409.

Clinicaltrials.gov, (2009). "A Long-Term Study of the Effects of Orally Administered TG101348 in Patients With Myelofibrosis," Study first received on Jul. 17, 2008, last updated Dec. 9, 2009, ClinicalTrials.gov Identifier: NCT00724334, Drug No. TG101348 for Myelofibrosis, with all results, 3 pages.

Clinicaltrials.Gov, (2009). "A Dose-Escalation Study of the Safety and Tolerability of Orally Administered TG101348 in Patients With Myelofibrosis," Study first received Jan. 29, 2008, last updated Oct. 22, 2009, ClinicalTrials.gov Identifier: NCT00631462, Drug No. TG101348 for Myelofibrosis, will all results, 3 pages.

Delhommeau, F. et al. (May 28, 2009). "Mutations in *TET2* in Myeloid Cancers," *N. Engl. J. Med.* 360(22):2289-2301.

Epstein, J. (Feb. 15, 2010). "Hematology—Myeloproliferative Neoplasms," in *Highlights of the 2009 Meeting of the American Society of Hematology Myeloproliferative Neoplasms, OncoFact*, located at <URL: http://oncofacts.com/archives/highlights-of-the-2009-meeting-of-the-american-society-of-hematology-myeloproliferative-neoplasms/>, last retrieved Jan. 10, 2011, Abstract 755, for a total of 7 pages.

Ernst, T et al. (Aug. 2010). "Inactivating Mutations of the Histone Methyltransferase Gene *EZH2* in Myeloid Disorders," *Nat. Genet.* 42(8):722-726.

Fda.Gov (2009). "N-Tert-Butyl-3-[5-Methyl-2-{[4-(2-Pryyolidin-1-Ylethoxy)Phenyl]Amino}Pyrimidin-4-Yl-Amino] Benzenesulfonamide Dihydrochloride Monohydrate," FDA U.S. Food and Drug Administration, FDA Application Results for Orphan Drug Product Designations Search for the Treatment of Secondary and Primary Myelofibrosis, Sponsored by TargeGen, Inc., application located at <http://www.accessdata.fda.gov/scripts/opdlisting/oopd/O0PD_Results_2.cfm?Index_Number =279409>, 1 page total.

Geron, I. et al. (Apr. 2008). "Selective Inhibition of JAK2-Driven Erythroid Differentiation of Polycythemia Vera Progenitors," *Cancer Cell* 13(4):321-330.

Ghobadi, A. (Feb. 5, 2010). "JAK2 Inhibitors," Oral Presentation presented at Washington University in St Louis, located at <hematology.wust.edu/conferences/presentations/Ghobadi20100205.ppt>, 34 pages total.

Grand, F. H. et al. (Jun. 11, 2009; e-pub. Apr. 22, 2009). "Frequent CBL Mutations Associated With 11q Acquired Uniparental Disomy in Myeloproliferative Neoplasms," *Blood* 113(24):6182-6192.

Green, A. et al. (Jan. 28, 2010). "Somatic Mutations of *IDH1* and *IDH2* in the Leukemic Transformation of Myeloproliferative Neoplasms," *N. Engl. J. Med.* 362(4):369-370.

Guy, E. et al. (Nov. 2007). "Accelerated Proliferation and Limited Differentiation, Mediated through Jak2, Exacerbate Ineffective Erythropoiesis in β-Thalassemia," *Blood* (ASH Annual Meeting Abstracts), 49th Annual Meeting of the American-Society-of_Hematology, Atlanta, GA, USA, Dec. 8-11, 2007, Database Biosis [online] Accession No. PREV200800215548, also located at <http://abstracts.hematologylibrary.org/cgi/content/abstract/ashmtg;110/11/275?maxtoshow=& hits=10&RESULTSFORMAT=1 &author1=Guy%2C+Ella&andorexacttitle=and &andorexacttitleabs=and&andorexactfulltext=and&searchid=1 &FIRSTINDEX=0&sortspec=relevance&volume=11 0&resourcetype=HWCIT>, last visited on Nov. 9, 2010, vol. 110, No. 11, Part 1, p. 88A, Abstract 275, 2 pages.

Hood, J. et al. (2007). "TG101348, A Potent, Highly Selective JAK2 Inhibitor, Inhibits Colony Formation in Stem Cells From Polycythemia Vera Patients and Prevents JAK2V617F-Mediated Splenomegaly and Death in a Mouse Model," *ASCO Annual Meeting*, Abstract No. 7031, 3 pages total located at <http://www.asco.org/ascov2/Meetings/Abstracts?&vmview=abst_detail_view&conf ID=47&abstractID=36203>, last visited on Mar. 14, 2011, and also published in *J. Clin. Oncol.* (2007), Vol. 25, No. 18S (Jun. 20 Suppl.) p. 7031.

Hussein, K. et al. (Jan. 21, 2010; e-pub. Nov. 9, 2009). "International Prognostic Scoring System-Independent Cytogenetic Risk Categorization in Primary Myelofibrosis," *Blood* 115(3):496-499.

Jäger, R. et al. (Jul. 2010; e-pub. May 27, 2010). "Deletions of the Transcription Factor *Ikaros* in Myeloproliferative Neoplasms," *Leukemia* 24(7):1290-1298.

James, C. et al. (Apr. 28, 2005). "A Unique Clonal *JAK2* Mutation Leading to Constitutive Signalling Causes Polycythaemia Vera," *Nature* 434(7037):1144-1148.

Kantarjian, H. M. et al. (Nov. 15, 2007; e-pub. Aug. 22, 2007). "Nilotinib (formerly AMN 107), A Highly Selective BCR-ABL Tyrosine Kinase Inhibitor, Is Effective in Patients With Philadelphia Chromosome-Positive Chronic Myelogenous Leukemia in Chronic Phase Following Imatinib Resistance and Intolerance," *Blood* 110(10):3540-3546.

Kittur, J. et al. (Jun. 1, 2007). "Clinical Correlates of *JAK2*V617F Allele Burden in Essential Thrombocythemia," *Cancer* 109(11):2279-2284.

Lasho, T. L. et al. (Sep. 2008, Epub: Mar. 20, 2008). "TG101348, a JAK2-Selective Antagonist, Inhibits Primary Hematopoietic Cells Derived From Myeloproliferative Disorder Patients with *JAK2V617F*, *MPLW515K*, or *JAK2* Exon 12 Mutations as Well as Mutation Negative Patients," *Leukemia* 22(9):1790-1792.

Lasho, T. et al. (Jul. 2010, Epub: May 20, 2010). "Inhibition of JAK-STAT Signaling by TG101348: A Novel Mechanism for Inhibition of KITD816V-Dependent Growth in Mast Cell Leukemia Cells," *Leukemia* 24(7):1378-1380.

Libani, I. V. et al. (Aug. 1, 2008, e-pub: May 14, 2008). "Decreased Differentiation of Erythroid Cells Exacerbates Ineffective Erythropoiesis in β-Thalassemia," *Blood* 112(3):875-885.

Ma, A. C. H. et al. (Dec. 2009, e-pub. Sep. 20, 2009). "A Novel Zebrafish jak2a$^{V581F}$ Model Shared Features of Human JAK2$^{V617F}$ Polycythemia Vera," *Exp. Hematol.* 37(12):1379-1386.

Mak, C.-C. et al. (Mar. 2007). "MEDI—118: A Novel Series of Low nM JAK2 Selective Inhibitors Exhibit Potent in Vitro Activities with Favorable Preclinical Properties," *233$^{rd}$ ACS National Meeting*, Chicago, IL, Mar. 25-29, 2007, located at <http://oasys2.confex.com/acs/233nm/techprogram/P1064196.htm>, last visited Oct. 27, 2010, 1 page.

McLorman, D. et al. (May 2006). "*JAK2* V617F: A Single Mutation in the Myeloproliferative Group of Disorders," *Ulster Med. J.* 75(2):112-119.

Mesa, R. A. et al. (Sep. 2009). "Emerging Drugs for the Therapy of Primary and Post Essential Thrombocythemia, Post Polycythemia Vera Myelofibrosis," *Expert Opin. Emerg. Drugs* 14(3):471-479.

Mullally, A. et al. (Jun. 15, 2010). "Physiological Jak2V617F Expression Causes a Lethal Myeloproliferative Neoplasm With Differential Effects on Hematopoietic Stem and Progenitor Cells," *Cancer Cell* 17(6):584-596.

McPherson, A. et al. (Mar. 2007). "MEDI 120—Development of Novel and Potent Inhibitors of JAK2: Structure Activity Relationship Studies for Optimization of JAK2 Potency while Minimizing JAK3 Activity," *233$^{rd}$ ACS National Meeting*, Chicago, IL, Mar. 25-29, 2007, located at <http://oasys2.confex.com/acs/233nm/techprogram/P1064173.htm>, last visited Oct. 27, 2010, 1 page.

Oh. S. T. et al. (Aug. 12, 2010). "Novel Mutations in the Inhibitory Adaptor Protein LNK Drive JAK-STAT Signaling in Patients With Myeloproliferative Neoplasms," *Blood* 116(6):988-992.

Pardanani, A. D. et al. (Nov. 15, 2006; e-pub. Jul. 25, 2006). "*MPL515* Mutations in Myeloproliferative and Other Myeloid Disorders: A Study of 1182 Patients," *Blood* 108(10):3472-3476.

Pardanani, A. et al. (Aug. 2007). "TG101209, a Small Molecule JAK-2 Selective Kinase Inhibitor Potently Inhibits Myeloproliferative Disorder-Associated JAK2V617F and MPLW515L/K Mutations," *Leukemia* 21(8):1658-1668.

Pardanani, A. D. et al. (Dec. 7, 2008). "A Phase I Study of TG101348, An Orally Bioavailable JAK2-Selective Inhibitor, in Patients With Myelofibrosis," *50$^{th}$ Annual American Society of Hematology (ASH) Annual Meeting and Exposition*, San Francisco, California, Dec. 6-9, 2008, *Posters, online Abstract No. 97*, located at <http://ash.confex.com/ash/2008/webprogram/Paper10141.html>, last visited on Nov. 29, 2010, 2 pages.

Pardanani, A. D. et al. (Dec. 7, 2009). "A Phase I Evaluation of TG101348, a Selective JAK2 Inhibitor, in Myelofibrosis: Clinical Response is Accompanied by Significant Reduction in JAK2V617F Allele Burden," *51$^{st}$ Annual American Society of Hematology (ASH) Annual Meeting and Exposition*, New Orleans, Dec. 5-8, 2009, *Posters, online Abstract No. 755*, located at <http://ash.confex.com/ash/2009/webprogram/Paper20584.html>, last visited on Nov. 29, 2010, 2 pages.

Pardanani, A. et al. (2009). "TG101348, a JAK2-Selective Inhibitor, is Well Tolerated in Patients With Myelofibrosis and Shows Substantial Therapeutic Activity Accompanied by a Reduction in JAK2V617F Allele Burden," *14$^{th}$ European Hematology Association (EHA) Congress*, Jun. 4-7, 2009, Berlin, online Abstract No. 1088, presented on Sunday, Jun. 7, 2009, *Hall 3, under "Myeloproliferative Disorders—Clinical*,"located at <http://www.eventure-online.com/eventure/publicAbstractView.do?id=102769&congressId=2432>, last visited on Nov. 30, 2010, one page.

Pardanani, A. et al. (2010; e.pub. Aug. 19, 2010). "LNK Mutation Studies in Blast-Phase Myeloproliferative Neoplasms, and in Chronic-Phase Disease With *TET2, IDH, JAK2* or *MPL* Mutations," *Leukemia* 24:1713-1718.

Pardanani, A. et al. (Dec. 6, 2010). "Longer-Term Follow up With TG101348 Therapy in Myelofibrosis Confirms Sustained Improvement in Splenomegaly, Disease-Related Symptoms, and *JAK2*V617F Allele Burden," *52$^{nd}$ Annual American Society of Hematology (ASH) Annual Meeting and Exposition*, Orlando, Florida, Dec. 4-7, 2010, *posters, online Abstract No. 459*, located at <http://ash.confex.com/ash/2010/webprogram/Paper28895.html>, last visited on Nov. 29, 2010, 2 pages.

Pardanani, A. et al. (Mar. 1, 2011, e-pub. Jan. 10, 2011). "Safety and Efficacy of TG101348, A Selective JAK2 Inhibitor, in Myelofibrosis," *J. Clin. Oncol.* 29(7):789-796.

Patnaik, M. M. et al. (Feb. 1, 2010). "Age and Platelet Count Are IPSS-Independent Prognostic Factors in Young Patients With Primary Myelofibrosis and Complement IPSS in Predicting Very Long or Very Short Survival," *Eur. J. Haematol.* 84(2):105-108.

Pikman, Y. et al. (Jul. 18, 2006). "*MPLW515L* is a Novel Somatic Activating Mutation in Myelofibrosis With Myeloid Metaplasia," *PLoS Med.* 3(7):1140-1151 (e270).

Quintás-Cardama, A. et al. (Apr. 15, 2010, e-pub. Feb. 3, 2010). "Preclinical Characterization of the Selective JAK1/2 Inhibitor INCB018424: Therapeutic Implications for the Treatment of Myeloproliferative Neoplasms," *Blood* 115(15):3109-3117.

Rivella, S. et al, (Apr. 15, 2003). "A Novel Murine Model of Cooley Anemia and its Rescue by Lentiviral Mediated Human β-Globin Gene Transfer," *Blood* 101(8): 2932-2939.

Ramakrishnan, V. et al. (Sep. 2010). "TG101209, A Novel JAK2 Inhibitor, Has Significant in Vitro Activity in Multiple Myeloma and Displays Preferential Cytotoxicity for CD45+ Myeloma Cells," *Am. J. Hematol.* 85(9):675-686.

Samanta, a. et al. (Mar. 2011, e-pub. Dec. 24, 2010). "Janus Kinase 2 Regulates Bcr-Abl Signaling in Chronic Myeloid Leukemia," *Leukemia* 25(3):463-472.

Scott, L. M. et al. (Feb. 1, 2007). "*JAK2* Exon 12 Mutations in Polycythemia Vera and Idiopathic Erythrocytosis," *N. Engl. J. Med.* 356(5):459-468.

Sun, Y. et al. (Feb. 15, 2011). "Inhibition of JAK2 Signaling by TG101209 Enhances Radiotherapy in Lung Cancer Models," *J. Thorac. Oncol.* 6:699-706.

Tam, C. S. et al. (Sep. 1, 2008, e-pub. Jun. 19, 2008). "The Natural History and Treatment Outcome of Blast Phase BCR-ABL-Myeloproliferative Neoplasms," *Blood* 112(5):1628-1637.

Tefferi, A. (Apr. 27, 2000). "Myelofibrosis With Myeloid Metaplasia," *N. Engl. J. Med.* 342(17):1255-1265.

Tefferi, A. et al. (Sep. 1, 2006). "International Working Group (IWG) Consensus Criteria for Treatment Response in Myelofibrosis With Myeloid Metaplasia, for the IWG for Myelofibrosis Research and Treatment (IWG-MRT)," *Blood* 108(5):1497-1503.

Tefferi, a. et al. (Jan. 2008). "Classification and Diagnosis of Myeloproliferative Neoplasms: The 2008 World Health Organization Criteria and Point-of-Care Diagnostic Algorithms," *Leukemia* 22(1):14-22.

Tefferi, A. et al. (Jul. 2010). "*IDH1* and *IDH2* Mutation Studies in 1473 Patients With Chronic-, Fibrotic- or Blast-Phase Essential Thrombocythemia, Polycythemia Vera or Myelofibrosis," *Leukemia* 24(7):1302-1309.

Verstovsek, S. et al. (2008). "Characterization of JAK2 V617F Allele Burden in Advanced Myelofibrosis (MF) Patients: No Change in V617F: WT JAK2 Ratio in Patients With High Allele Burdens Despite Profound Clinical Improvement Following Treatment With the JAK Inhibitor, INCB018424," *Blood* (*ASH Annual Meeting Abstracts*), located at <http://abstracts.hematologylibrary.org/cgi/content/abstract/112/11/2802?maxtoshow=&hits=10&RESULTSFORMAT=&fulltext=myelofibrosis&searchid=1&FIRSTINDEX=0&volume=112&issue=11&resourcetype=HWCIT>, 112: Abstract 2802, 2 pages.

Verstovsek, S. (2009). "Therapeutic Potential of JAK2 Inhibitors," *Hematology Am Soc. Hematol. Educ. Program* pp. 636-642.

Verstovsek, S. et al. (Sep. 16, 2010). "Safety and Efficacy of INCB018424, a JAK1 and JAK2 Inhibitor, in Myelofibrosis," *N. Eng. J. Med.* 363(12):1117-1127.

Wadleigh, M. et al. (Aug. 2010). "Preclinical and Clinical Activity of ATP Mimetic JAK2 Inhibitors," *Clinical Advances in Hematology & Oncology* 8(8):557-563.

Wernig, G. et al. (Apr. 2008). "Efficacy of TG101348, a Selective JAK2 Inhibitor, in Treatment of a Murine Model of JAK2V617F-Induced Polycythemia Vera," *Cancer Cell* 13(4):311-320.

Wikipedia (2010). "Leukemia," located at <http://en.wikipedia.org/wiki/Leukemia>, last accessed on Jan. 19, 2011, last edited on Jan. 18, 2011, created on Aug. 14, 2004, 11 pages total.

Zimmermann, J. et al. (Jul. 1996). "Phenylamino-Pyrimidine (PAP) Derivatives: A New Class of Potent and Selective Inhibitors of Protein Kinase C (PKC)," *Arch. Der Pharm., Pharmaceutical and Medicinal Chemistry* 329(7):371-376.

International Search Report mailed on Mar. 28, 2007, for PCT Patent Application No. PCT/US06/042044, filed on Oct. 26, 2006, 3 pages.

Written Opinion mailed on Mar. 28, 2007, for PCT Patent Application No. PCT/US06/042044, filed on Oct. 26, 2006, 5 pages.

European Search Report mailed on Nov. 4, 2010, for European Patent Application No. 06836583.2, filed on Oct. 26, 2006, 3 pages.

European Search Opinion mailed on Nov. 4, 2010, for European Patent Application No. 06836583.2, filed on Oct. 26, 2006, 3 pages.

European Search Report mailed on Dec. 14, 2010, replacing previous European Search Report mailed on Nov. 4, 2010, for European Patent Application No. 06836583.2, filed on Oct. 26, 2006, 3 pages.

International Search Report mailed on Feb. 3, 2009, for PCT Patent Application No. PCT/US2008/078932, filed on Apr. 9, 2009, 3 pages.

Written Opinion mailed on Feb. 3, 2009, for PCT Patent Application No. PCT/US2008/078932, filed on Apr. 9, 2009, 3 pages.

International Search Report mailed on Feb. 12, 2010, for PCT Patent Application No. PCT/US2009/052544, filed on Aug. 3, 2009, 4 pages.

Written Opinion mailed on Feb. 12, 2010, for PCT Patent Application No. PCT/US2009/052544, filed on Aug. 3, 2009, 5 pages.

European Search Report mailed on May 31, 2011 for European Patent Application No. 09741504.6, filed on Aug. 3, 2009, 2 pages.

International Search Report mailed on Jan. 21, 2011, for PCT Patent Application No. PCT/US2010/56280, filed on Nov. 10, 2010, 5 pages.

Written Opinion mailed on Jan. 21, 2011, for PCT Patent Application No. PCT/US2010/56280, filed on Nov. 10, 2010, 6 pages.

Non Final Office Action mailed on Feb. 12, 2008, for U.S. Appl. No. 11/588,638, filed Oct. 26, 2006, 18 pages total.

Final Office Action mailed on Jul. 1, 2008, for U.S. Appl. No. 11/588,638, filed Oct. 26, 2006, 10 pages total.

Non Final Office Action mailed on Mar. 23, 2009, for U.S. Appl. No. 11/796,717, filed Apr. 16, 2007, 17 pages total.

Final Office Action mailed on Nov. 6, 2009, for U.S. Appl. No. 11/796,717, filed Apr. 16, 2007, 7 pages total.

Non Final Office Action mailed on Jan. 13, 2011, for U.S. Appl. No. 12/251,061, filed Oct. 14, 2008, 17 pages.

U.S. Appl. No. 12/846,702, filed Jul. 29, 2010, for Noronha et al.

U.S. Appl. No. 12/862,517, filed Aug. 4, 2010, for Noronha et al.

Barosi, G. et al. (2007, E-pub. Nov. 16, 2006). "A Unified Definition of Clinical Resistance/Intolerance to Hydroxyurea in Essential Thrombocythemia: Results of a Consensus Process by an International Working Group," *Leukemia*, 21(2):277-280.

Barosi, G. et al. (Mar. 2010, E-pub. Nov. 23, 2009). "A Unified Definition of Clinical Resistance and Intolerance to Hydroxycarbamide in Polycythaemia Vera and Primary Myelofibrosis: Results of a European LeukemiaNet (ELN) Consensus Process," *British Journal of Haematology* 148(6):961-963.

Verstovsek, S. (Apr. 1, 2010, E-pub. Mar. 9, 2010). "Therapeutic Potential of Janus-Activated Kinase-2-Inhibitors for the Management of Myelofibrosis," *Clin. Cancer Res.* 16(7):1988-1996.

Wadleigh, M. et al. (Mar. 2010, E-pub. Feb. 27, 2010). "Classification and Diagnosis of Myeloproliferative Neoplasms According to the 2008 World Health Organization Criteria," *Int. J. Hematol.* 91(2):174-179.

Bolen et al., "Expression and interaction of the SRC family of tyrosine protein kinases in T lymphocytes", Adv. Cancer Res., vol. 57., 103-149, PMID 1950702, 1991.

Chawla et al., "Challenges in Polymorphism of Pharmaceuticals", CRIPS vol. 5, not, Jan.-Mar. 2004 ("4 PAGES").

Dorwald, F. Zaragoza, "Side Reactions in Organic Synthesis, A Guide to Successful Synthesis Design," 2005, p. IX.

Frohlich et al., "Inhibition of Neuronal Nitric Oxide Synthase by 4-Amino Pteridine Derivatives: Structures-Activity Relationship of Antagonists of (6R)-5,6,7,8-Tetrahydrobiopterin Cofactor", J. Med. Chem., vol. 42, 4108-4121, 1999.

Ghosh, et. al., Journal of Medicinal Chemistry, (1967), 10(5), 974-5.

Kobayashi et al., "Functional coupling of the src-family protein tyrosine kinases p59fyn and p53/61yn with the interleukin 2 receptor: implications for redundancy and pleiotropism in cytokine signal transduction", Proc. Natl. Acad. Sci., USA vol. 1:90, No. 9, 4201-4205, Abstract PMID 8483935, May 1993.

New Mexico Department of Health, Interleukin-2, http://www.aidsinfonet.org. *A Project of the New Mexico Aids Education and Training Center*, Fact Sheet No. 622, Apr. 30, 2002.

Newman et al., "Solid-state analysis of the active pharmaceutical ingredient in drug products", DDT vol. 8, No. 19, Oct. 2003, p. 898-905.

O'Shea et al., "Expression of v-src in a Murine T-cell Hybridoma Results in Constitutive T-cell Receptor Phosphorylation and Interleukin 2 Production", Proc. Natl. Acad. Sci., 88:1741-1745 (1991).

Taghavi-Moghadam et al., "A New, General and Regioselective Method for the Synthesis of 2,6-Disubstituted 4-Aminopteridines", Elsevier Science Ltd., Pergamon, 6835-6836, 1997.

Tanaka et al., "novel human tyrosine kinase gene inducible in T cells by interleukin 2", *FEBS* Lett., vol. 7:324, No. 1, 1-5, PMID 9504851, Jun. 1993.

Torigoe et al., "Regulation of SRC-family protein tyrosine kinases by interleukin, IL-2, and IL-3", Leukemia, vol. 6, Supplemental 3, 94S-97S, PMID 1602836, 1992.

Vippagunta et. al. Advanced Drug Delivery Reviews 48 (2001) 3-26.

Weber, Molecular Approaches to Study Cellular Roadblocks to Transfection and Transduction (Non-Viral Vectors and AAV-Based Vectors for Gene Therapy), <http://www.mssm.edu/genetherapy/weber.htm>, 1-8, Nov. 11, 2002.

Wills et al., The New England Journal of Medicine, 2005, 353, 9, 877-889.

Yamamoto et al., "Role of scr-like protooncogenes in lymphocotye proliferation", Princess Takamastu Symp., vol. 22, 293-305 Review, PMID 1668889, 1991.

Banker, G. S. (ed.) et al. (1996). *Modern Pharmaceutics*, 3$^{rd}$ edition, Revised and Expanded, Marcel Dekker, Inc. New York, p. 596.

Granelli-Piperno, A. (Apr. 1992). "SRC-Related Proto-Oncogenes and Transcription Factors in Primary Human T Cells: Modulation by Cyclosporine A and FK506," *J. Autoimmun.* 5(A):145-158.

Wikipedia, (Nov. 19, 2007). "Acute Respiratory Distress Syndrome," located at http://en.wikipedia.org/wiki/Acute_respiratory_distress_syndrome, last visited Dec. 10, 2007, 11 pages.

Emedicinehealth, (Nov. 19, 2007). "Acute Respiratory Distress Syndrome," located at http://www.emedicinehealth.com/acute_respiratory_distress_syndrome/page2_em.htm, last visited Dec. 10, 2007, 3 pages.

Mayoclinic, (Nov. 19, 2007). "Stroke," article located at http://www.mayoclinic.com/health/stroke/DS00150/dsection=7, last visited Dec. 10, 2007, 4 pages.

Medscape, (Sep. 5, 2006). "VEGF Manipulation Ameliorates Murine Asthma Symptoms," located at http://www.medscape.com/viewarticle/544205_print, last visited Dec. 10, 2007, one page.

Jacobson, J. R. et al. (Jun. 2005). "Simvastatin Attenuates Vascular Leak and Inflammation in Murine Inflammatory Lung Injury," *Am. J. Physiol. Lung. Cell. Mol. Physiol.* 288(6):L1026-L1032.

Wolff, M. E. ed. (1995). *Burger's Medicinal Chemistry and Drug Discovery*, 5$^{th}$ edition, vol. 1: Principles and Practice, John Wiley & Sons, Inc., New York, pp. 975-982.

Drug given orally bid beginning on day 3 after tumor injection

USE OF BI-ARYL META-PYRIMIDINE INHIBITORS OF KINASES

CROSS REFERENCE TO RELATED APPLICATIONS

This application is a continuation of U.S. patent application Ser. No. 11/588,637 (U.S. Pat. No. 7,528,143), filed Oct. 26, 2006, which claims the benefit of priority under 35 U.S.C. §119(e) of U.S. Provisional Application Nos. 60/732,629, filed Nov. 1, 2005, and 60/838,003, filed Aug. 15, 2006, the disclosures of which are incorporated herein by reference in their entirety.

BACKGROUND

1. Field of Invention

The present invention relates to the field of inhibitors of protein tyrosine kinases, their pharmaceutically acceptable compositions comprising the compounds of the invention and the methods of using the compositions in the treatment of various disorders. In particular, the present invention relates to inhibitors of the JAK family of protein tyrosine kinases.

2. Background of Invention

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation or de-regulation, as well as over- or under-production of growth factors or cytokines has been implicated in many diseases, including but not limited too cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases.

Protein kinases have emerged as an important class of enzymes as targets for therapeutic intervention. In particular, the JAK family of cellular protein tyrosine kinases (Jak1, Jak2, Jak3, and Tyk2) play a central role in cytokine signaling (Kisseleva et al, Gene, 2002, 285, 1; Yamaoka et al. Genome Biology 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family. These cytokines include, the IFN family (IFN-αs/β/ω/Limitin, IFN-γ, IL-10, IL-19, IL-20, IL-22), the gp130 family (IL-6, IL-11, OSM, LIF, CNTF, NNT-1/BSF-3, G-CSF, CT-1, Leptin, IL-12, IL-23), γC family (IL-2, IL-7, TSLP, IL-9, IL-15, IL-21, IL-4, IL-13), IL-3 family (IL-3, IL-5, GM-CSF), single chain family (EPO, GH, PRL, TPO), receptor tyrosine kinases (EGF, PDGF, CSF-1, HGF), and G-protein coupled receptors (AT1).

Until recently, the therapeutic potential of JAK inhibitors has focused on diseases affecting various pathologies of the immune system. These include, but are not limited to atopy (allergic asthma, atopic dermatitis, allergic rhinitis), cell mediated hypersensitivity (allergic contact dermatitis, hypersensitivity pneumonitis), rheumatic diseases (systemic lupus erythematosus (SLE), rheumatoid arthritis, juvenile arthritis, Sjogren's Syndrome, scleroderma, polymyositis, ankylosing spondylitis, psoriatic arthritis), transplantation (transplant rejection, graft vs host disease), viral diseases (Epstein Barr Virus, Hepatitis B, Hepatitis C, HIV, HTLV1, Vaicella-Zoster Virus, Human Papilloma Virus), cancer (leukemia, lymphoma), cardiovascular disease (cardiac hypertrophy, atherosclerosis and arteriosclerosis), neurodegenerative diseases (motor neuron disease), food allergy, inflammatory bowel disease, Crohn's disease, cutaneous inflammation, and immune suppression induced by solid tumors. Most efforts to date have targeted JAK3 inhibition for immunosuppression, for example organ transplantation and allograft acceptance (for a review, see Borie et al. Current Opinion in Investigational Drugs, 2003, 4(11), 1297).

Most recently, two significant findings of the role of the EPO-JAK2 signaling pathway in myeloproliferative disorders and proliferative diabetic retinopathy were found. First, a gain-of-function, somatic (acquired) mutation of the JAK2 kinase (V617F) was reported to be a causative factor in a number of "typical" myeloproliferative disorders, including polycethemia vera, essential thrombocythemia and myelofibrosis with myeloid metaplasia, and the mutation has been found in patients with either "atypical" myeloproliferative disorders and myelodysplastic syndrome (for reviews see Tefferi and Gilliland, Cell Cycle 2005, 4(8), e61; Pesu et. al. Molecular Interventions 2005, 5(4), 211). Additionally it was found that (a) the V617F JAK2 mutation was associated with constitutive phosphorylation of JAK2 and its downstream effectors as well as induction of erythropoietin hypersensitivity in cell based experiments, (b) V617F JAK2-induced cell proliferation signals were inhibited by small molecule inhibitors of JAK2, and (c) murine bone marrow transduced with a retrovirus containing V617F JAK2 included erythrocytosis in the transplanted mice.

Furthermore, recently it has been found that mutations in EPO-R also keep the JAK pathway constitutively activated leading to myeloproliferative disorders.

Second, EPO was found to be a potent angiogenic factor in proliferative diabetic retinopathy, a major cause of vision loss affecting diabetic, working-age persons (see for example Aiello, New England Journal of Medicine, 2005, 353 (8), 839; Watanabe et al. New England Journal of Medicine 2005 353 (8), 782).

Further, findings from the Watanabe research showed (a) intraocular EPO levels and VEGF (another well-known angiogenic factor in proliferative diabetic retinopathy) were significantly higher among those with proliferative diabetic retinopathy than those with quiescent disease or non-diabetic control, (b) EPO and VEGF levels were not closely correlated, (c) EPO levels were more strongly correlated with the presence of proliferative diabetic retinopathy than VEGF, (d) EPO stimulated growth and intracellular signaling in retinal endothelial cells, and (e) inhibitors of either EPO or VEGF reduced hypoxia-induced retinal neovascularization in rodent models.

Recently it has been shown that mutations in the EPO receptor may also affect the signaling related to the JAK pathway and this may have implications in terms of disease states where JAK signaling is important in the cell cycle.

There is another feature regarding inhibitors of the JAK pathway. It has been demonstrated that the JAK pathway may be recruited in cell survival and proliferation. For example, in the case of the cells that are Philadelphia chromosome positive that result in chronic myelogenous leukemia (CML), there is evidence that the Jak pathway is recruited in constitutive activation. Accordingly, using a JAK inhibitor may have use in CML in which the Philadelphia chromosome has been shown to produce the hybrid Bcr-Abl, thus keeping cells constitutively active.

More telling is that in cases of resistance mutations that arise on account of specific inhibitors to BCR-ABL, as in the case of the T315I gatekeeper mutation, or any other mutation, it may be possible to use a JAK inhibitor on account of the pathway used by the BCR-ABL mutant (as in the case of BCR-ABL(T315I) mutation) utilizing the Jak pathway. Thus Jak inhibitors may be used in the treatment of patients with resistance to known therapies where BCR-ABL is directly targeted and drug resistance has now been shown as the dominant (50-90%) of all resistance in patients where existing therapies fail.

The use of JAK inhibitors may also find utility in other myeloid disease states, both blood disorders and other disease states with myeloid implications, and other disease states in which the JAK pathway is implicated directly or indirectly.

Accordingly, there is a need to develop compounds useful as inhibitors of kinases, particularly, JAK kinase, given the inadequate treatments available for the aforementioned diseases where the JAK signaling pathway is dysregulated, or recruited directly or indirectly.

SUMMARY

According to one embodiment, a compound having the structure (A) is provided:

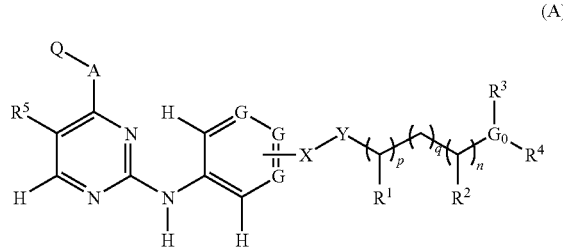

(A)

According to another embodiment, a method is provided for treating an angiogenic-associated disorder, the method including administering to a subject in need thereof a therapeutically effective amount of at least one compound having the structure (A), or pharmaceutically acceptable salts, hydrates, solvates, polymorphs, crystal forms, N-oxides, and individual enantiomers and diastereomers thereof, to a subject in need of such treatment.

According to other embodiments, pharmaceutical compositions and articles of manufacture are provided, including at least one compound having the structure (A), or pharmaceutically acceptable salts, hydrates, solvates, crystal forms and individual diastereomers thereof.

DETAILED DESCRIPTION

A. Terms and Definitions

Figure 1:
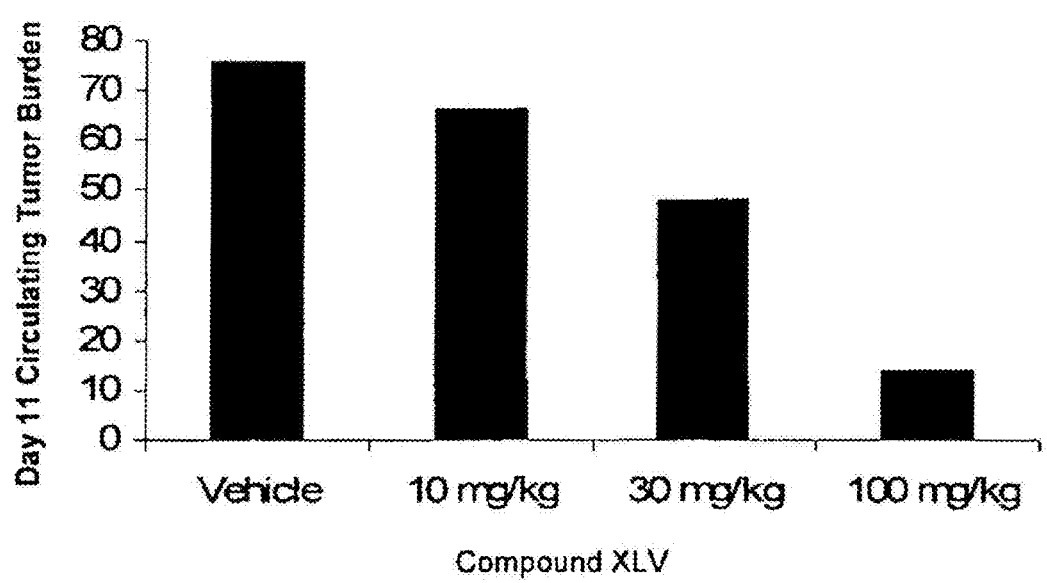
FIG. 1 shows the results of an FACS analysis on isolated JAK2$^{V617F}$ tumor cells as described in Example 244.

The following terminology and definitions apply as used in the present application, generally in conformity with the terminology recommended by the International Union of Pure and Applied Chemistry (IUPAC):

The term "heteroatom" refers to any atom other than carbon, for example, N, O, or S.

The term "aromatic" refers to a cyclically conjugated molecular entity with a stability, due to delocalization, significantly greater than that of a hypothetical localized structure, such as the Kekulé structure.

The term "heterocyclic," when used to describe an aromatic ring, refers to the aromatic rings containing at least one heteroatom, as defined above.

The term "heterocyclic," when not used to describe an aromatic ring, refers to cyclic (i.e., ring-containing) groups other than aromatic groups, the cyclic group being formed by between 3 and about 14 carbon atoms and at least one heteroatom described above.

The term "substituted heterocyclic" refers, for both aromatic and non-aromatic structures, to heterocyclic groups further bearing one or more substituents described below.

The term "alkyl" refers to a monovalent straight or branched chain hydrocarbon group having from one to about 12 carbon atoms, for example, methyl, ethyl, n-propyl, iso-propyl, n-butyl, iso-butyl, tert-butyl, n-pentyl (also known as n-amyl), n-hexyl, and the like. The term "lower alkyl" refers to alkyl groups having from 1 to about 6 carbon atoms.

The term "substituted alkyl" refers to alkyl groups further bearing one or more substituents such as hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, aldehyde, acyl, oxyacyl, carboxyl, sulfonyl, sulfonamide, sulfuryl, and the like.

The term "alkenyl" refers to straight-chained or branched hydrocarbyl groups having at least one carbon-carbon double bond, and having between about 2 and about 12 carbon atoms, and the term "substituted alkenyl" refers to alkenyl groups further bearing one or more substituents described above.

The term "alkynyl" refers to straight-chained or branched hydrocarbyl groups having at least one carbon-carbon triple bond, and having between about 2 and about 12 carbon atoms, and the term "substituted alkynyl" refers to alkynyl groups further bearing one or more substituents described above.

The term "aryl" refers to aromatic groups having between about 5 and about 14 carbon atoms and the term "substituted aryl" refers to aryl groups further bearing one or more substituents described above.

The term "heteroaryl" refers to aromatic rings, where the ring structure is formed by between 3 and about 14 carbon atoms and by at least one heteroatom described above, and the term "substituted heteroaryl" refers to heteroaryl groups further bearing one or more substituents described above.

The term "alkoxy" refers to the moiety —O-alkyl, wherein alkyl is as defined above, and the term "substituted alkoxy" refers to alkoxy groups further bearing one or more substituents described above.

The term "cycloalkyl" refers to alkyl groups having between 3 and about 8 carbon atoms arranged as a ring, and the term "substituted cycloalkyl" refers to cycloalkyl groups further bearing one or more substituents described above.

The term "alkylaryl" refers to alkyl-substituted aryl groups and the term "substituted alkylaryl" refers to alkylaryl groups further bearing one or more substituents described above.

The term "arylalkyl" refers to aryl-substituted alkyl groups and the term "substituted arylalkyl" refers to arylalkyl groups further bearing one or more substituents described above.

The term "arylalkenyl" refers to aryl-substituted alkenyl groups and the term "substituted arylalkenyl" refers to arylalkenyl groups further bearing one or more substituents described above.

The term "arylalkynyl" refers to aryl-substituted alkynyl groups and the term "substituted arylalkynyl" refers to arylalkynyl groups further bearing one or more substituents described above.

The term "arylene" refers to divalent aromatic groups having between 5 and about 14 carbon atoms and the term "substituted arylene" refers to arylene groups further bearing one or more substituents described above.

The term "chemically connected" is defined as forming a chemical entity in which two moieties form a direct chemical bond between them.

The term "kinase" refers to any enzyme that catalyzes the addition of phosphate groups to a protein residue; for example, serine and threonine kinases catalyze the addition of phosphate groups to serine and threonine residues.

The term "JAK kinase" refers to an enzyme found in cells in the immune system that participates in the cell signaling process resulting in the development of white blood cells.

The term "therapeutically effective amount" refers to the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

The term "pharmaceutically acceptable" refers to the fact that the carrier, diluent or excipient must be compatible with the other ingredients of the formulation and not deleterious to the recipient thereof.

The terms "administration of a compound" or "administering a compound" refer to the act of providing a compound of the invention or pharmaceutical composition to the subject in need of treatment.

The term "antibody" refers to intact molecules of polyclonal or monoclonal antibodies, as well as fragments thereof, such as Fab and $F(ab')_2$, Fv and SCA fragments which are capable of binding an epitopic determinant.

The term "vasculostasis" refers to the maintenance of the homeostatic vascular functioning leading to the normal physiologic functioning.

The term "vasculostatic agents" refers to agents that seek to address conditions in which vasculostasis is compromised by preventing the loss of or restoring or maintaining vasculostasis.

B. Embodiments of the Invention

According to an embodiment of the invention, compounds having the structure (A) are provided for treatment of various diseases, disorders, and pathologies:

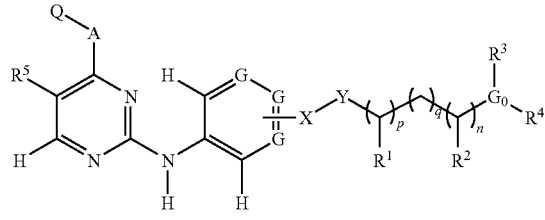

(A)

In the structure (A), X can be any of a bond, O, C=O, $SO_2$, or $CH_2$ and Y can be a bond or $NR^9$; or X and Y taken together can be a bond. Further, in the structure (A) each of $R^1$ and $R^2$ can be any of H, $C_1$-$C_6$ substituted or unsubstituted alkyl, substituted or unsubstituted cycloalkyl, substituted or unsubstituted heterocycle, substituted or unsubstituted aryl, or substituted or unsubstituted heteroaryl; or $R^1$ and $R^2$ taken together can be a bond; or $R^1$ and $R^2$ taken together can form a moiety such as one of $(CH_2)_m$, $(CH_2)_r$—S—$(CH_2)_m$, $(CH_2)_r$—SO—$(CH_2)_m$, $(CH_2)_r$—$SO_2$—$(CH_2)_m$, $(CH_2)_r$—$NR^9$—$(CH_2)_m$, or $(CH_2)_r$—O—$(CH_2)_m$, wherein each of p, q, r, n, m is independently an integer having the value between 0 and 6.

Further, in the structure (A) $R^9$ can be one of H, $C_1$-$C_6$ alkyl, $C_1$-$C_6$ cycloalkyl, $C_1$-$C_6$ branched alkyl, $C_1$-$C_6$ substituted alkyl, $C_1$-$C_6$ aminoalkyl, or $C_1$-$C_6$ hydroxyalkyl; $G_0$ can be one of N, O, H, of CH, with the proviso that if $G_0$ is N, then each of $R^3$ and $R^4$ can be one of H, $C_1$-$C_6$ alkyl, $C_1$-$C_6$ substituted or unsubstituted hydroxyalkyl or aminoalkyl, $C_1$-$C_6$ substituted or unsubstituted branched alkyl, substituted or unsubstituted aryl, or substituted or unsubstituted heteroaryl, or $R^3$ and $R^4$ taken together can form a moiety such as one of $(CH_2)_m$, $(CH_2)_r$—S—$(CH_2)_m$, $(CH_2)_r$—SO—$(CH_2)_m$, $(CH_2)_r$—$SO_2$—$(CH_2)_m$, $(CH_2)_r$—$NR^9$—$(CH_2)_m$, or $(CH_2)_r$—O—$(CH_2)_m$.

There are some additional provisos further directed to $G_0$ in the structure (A). More specifically, if $G_0$ is N, then $R^1$ and $R^9$ taken together can form a moiety such as one of $(CH_2)_m$, $(CH_2)_r$—S—$(CH_2)_m$, $(CH_2)_r$—SO—$(CH_2)_m$, $(CH_2)_r$—$SO_2$—$(CH_2)_m$, $(CH_2)_r$—$NR^9$—$(CH_2)_m$, or $(CH_2)_r$—O—$(CH_2)_m$; or $R^1$ and $R^4$ taken together can form a moiety such as one of $(CH_2)_m$, $(CH_2)_r$—S—$(CH_2)_m$, $(CH_2)_r$—SO—$(CH_2)_m$, $(CH_2)_r$—$SO_2$—$(CH_2)_m$, $(CH_2)_r$—$NR^9$—$(CH_2)_m$, or $(CH_2)_r$—O—$(CH_2)_m$; or $R^9$ and $R^4$ taken together can form a moiety such as one of $(CH_2)_m$, $(CH_2)_r$—S—$(CH_2)_m$, $(CH_2)_r$—SO—$(CH_2)_m$, $(CH_2)_r$—$SO_2$—$(CH_2)_m$, $(CH_2)_r$—$NR^9$—$(CH_2)_m$, or $(CH_2)_r$—O—$(CH_2)_m$; or $R^3$ and $R^4$ taken together can form a moiety such as one of $(CH_2)_m$, $(CH_2)_r$—S—$(CH_2)_m$, $(CH_2)_r$—SO—$(CH_2)_m$, $(CH_2)_r$—$SO_2$—$(CH_2)_m$, $(CH_2)_r$—$NR^6$—$(CH_2)_m$, or $(CH_2)_r$—O—$(CH_2)_m$.

If in the structure (A) $G_0$ is O, then $R^3$ can be one of H, $C_1$-$C_6$ alkyl and $C_1$-$C_6$ substituted or unsubstituted hydroxyalkyl or aminoalkyl, substituted or unsubstituted branched alkyl, substituted or unsubstituted cycloalkyl, substituted heterocyclic connected through carbon or nitrogen, substituted or unsubstituted aryl, or substituted or unsubstituted heteroaryl connected through carbon or nitrogen, with no group $R^4$; $R^1$ and $R^9$ taken together can form a moiety such as one of $(CH_2)_m$, $(CH_2)_r$—S—$(CH_2)_m$, $(CH_2)_r$—SO—$(CH_2)_m$, $(CH_2)_r$—$SO_2$—$(CH_2)_m$, $(CH_2)_r$—$NR^9$—$(CH_2)_m$, or $(CH_2)_r$—O—$(CH_2)_m$; or $R^1$ and $R^3$ taken together can form a moiety such as one of $(CH_2)_m$, $(CH_2)_r$—S—$(CH_2)_m$, $(CH_2)_r$—SO—$(CH_2)_m$, $(CH_2)_r$—$SO_2$—$(CH_2)_m$, $(CH_2)_r$—$NR^9$—$(CH_2)_m$, or $(CH_2)_r$—O—$(CH_2)_m$; or $R^9$ and $R^3$ taken together can form a moiety such as one of $(CH_2)_m$, $(CH_2)_r$—S—$(CH_2)_m$, $(CH_2)_r$—SO—$(CH_2)_m$, $(CH_2)_r$—$SO_2$—$(CH_2)_m$, $(CH_2)_r$—$NR^9$—$(CH_2)_m$, or $(CH_2)_r$—O—$(CH_2)_m$.

If in the structure (A) $G_0$=CH, then each of $R^3$ and $R^4$ can be one of H, $C_1$-$C_6$ alkyl, $C_1$-$C_6$ substituted or unsubstituted hydroxyalkyl or aminoalkyl, $C_1$-$C_6$ substituted or unsubstituted branched alkyl, substituted or unsubstituted aryl, $C_1$-$C_6$ substituted or unsubstituted heterocycle connected through carbon or nitrogen, or substituted or unsubstituted heteroaryl connected through carbon or nitrogen, or $R^3$ and $R^4$ taken together can form a moiety such as one of $(CHR^9)_r$—$(CHR^9)_m$—$(CHR^9)_p$, $(CHR^9)_r$—S—$(CHR^9)_m$, $(CHR^9)_r$—SO—$(CHR^9)_m$, $(CHR^9)_r$—$SO_2$—$(CHR^9)_m$, $(CHR^9)_r$—$NR^9$—$(CHR^9)_m$, or $(CHR^9)_r$—O—$(CHR^9)_m$.

Further, in the structure (A) G can be N or $CR^6$, and each G is independent of each other G, with the further proviso that not more than two groups G can be N, with the further proviso that for each $CR^6$, each $R^6$ is independent of each other group $R^6$.

Further, in the structure (A) $R^5$ is methyl and the moiety Q is as shown below

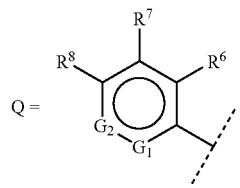

In the moiety Q, each of $R^6$, $R^7$, $R^8$ can be one of H, $C_1$-$C_6$ substituted or unsubstituted alkyl, $C_1$-$C_6$ substituted or unsubstituted alkenyl, $C_1$-$C_6$ substituted or unsubstituted alkynyl, $C_1$-$C_6$ substituted or unsubstituted hydroxyalkyl or aminoalkyl, $C_1$-$C_6$ substituted or unsubstituted branched alkyl, $C_1$-$C_6$ substituted or unsubstituted cycloalkyl, substituted or unsubstituted aryl connected through carbon or a heteroatom, substituted or unsubstituted heteroaryl connected through carbon or a heteroatom, $C_1$-$C_6$ alkoxy, a halogen, $CF_3$, —$OCF_3$, $CHR^3R^4$, $SR^3$, $SOR^3$, $SO_2R^3$, $SO_2NR^3R^4$, $SO_3R^3$, $POR^3$, $PO_2R^3$, $PO_2NR^3R^4$, $PO_2CR^3R^4$, $PO_3R^3$, $NR^3R^4$, $NO_2$, CN, OH, $CONR^3R^4$, $COR^3$, $COOR^3$, $NR^3COR^4$, $NR^3CONR^3R^4$, $OCONR^3R^4$, $CSNR^3R^4$, $CSR^3$, $NR^3CSNR^3R^4$, $SCONR^3R^4$, $SCSNR^3R^4$, or $SCSNR^3R^4$; or any of $R^6$ and $R^7$ taken together, or $R^7$ and $R^8$ taken together, or $R^6$ and $R^8$ taken together can form a moiety independently selected from any of —HN—CH=CH—, —HN—N=CH—, —HN—N=N—, —O($CH_2$)$_n$O—, —S($CH_2$)$_n$S—, —N=CH—S—, —CH=N—O—, —CH=N—S—, —N=CH—O—, —C=N—O—, —C=N—O—, —CH=CH—CH=CH—, —N=CH—CH=CH—, —CH=N—CH=CH—, —O—CH=CH, and —S—CH=CH—; or $R^3$ and $R^4$ taken together can form a moiety such as one of $(CHR^9)_r$—$(CHR^9)_m$—$(CHR^9)_p$, $(CHR^9)_r$—S—$(CHR^9)_m$, $(CHR^9)_r$—SO—$(CHR^9)_m$, $(CHR^9)_r$—$SO_2$—$(CHR^9)_m$, $(CHR^9)_r$—$NR^9$—$(CHR^9)_m$, or $(CHR^9)_r$—O—$(CHR^9)_m$.

Further, in the structure (A), A can be one of O, $NR^3$, $CR^3R^4$, S, SO, and $SO_2$; and in the moiety Q, $G_1$ can be any of CH, N, NH, S, and O, and $G_2$ can be any of $CR^7$, N, NH, S, and O, with each group $R^7$ being independent of every other group $R^7$; and if $G_1$ or $G_2$ is NH, S, or O, then Q is a five membered heteroaromatic ring, optionally fused to a six member aromatic or non-aromatic ring; and if $G_1$ or $G_2$ is N, then Q is a five or a six membered aromatic ring, optionally fused to a six member aromatic or non-aromatic ring, with the further proviso that X or $G_0$ includes at least one heteroatom included with X and selected from O, S and N, or $G_0$ comprises at least four non-hydrogen atoms, inclusive of the heteroatom, and $R^3$ and $R^4$, or $R^1$ and $R^9$, or $R^1$ and $R^4$, or $R^9$ and $R^4$ taken together can form an aromatic, heteroaromatic, cyclic or heterocyclic ring system, or if a noncyclic system is present, then more than one heteroatom is present, and if A is $NR_3$, then any of $R_6$, $R_7$ or $R_8$, or any combination thereof independently includes at least two non-hydrogen substituents, or if A is $NR_3$, then Q forms a fused ring from $R_6$ to $R_7$, or from $R_7$ to $R_8$.

Some exemplary compounds described by structure (A) that can be used include, but are not limited to, the following compounds I through CLXII shown below:

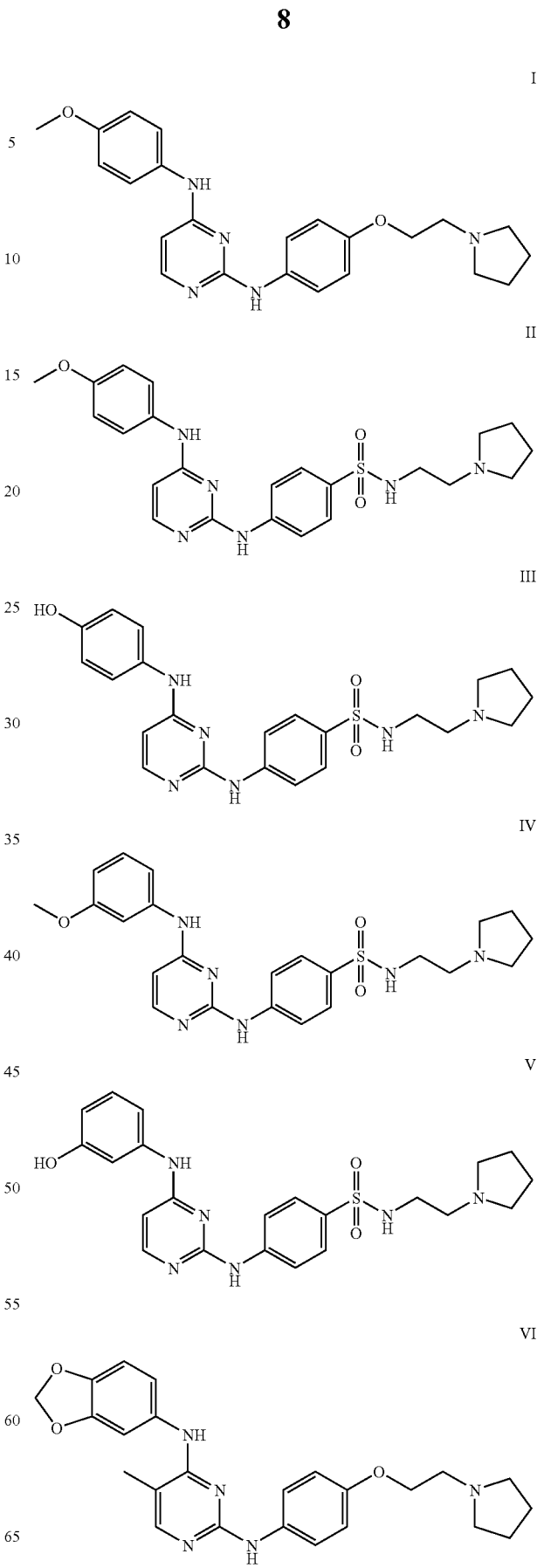

-continued
VII
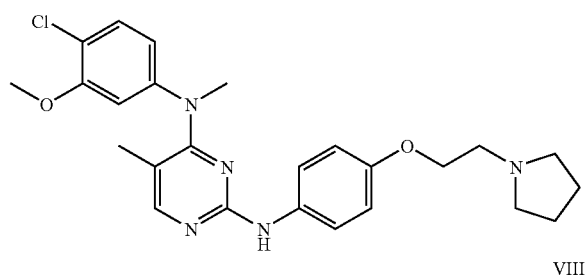
VIII
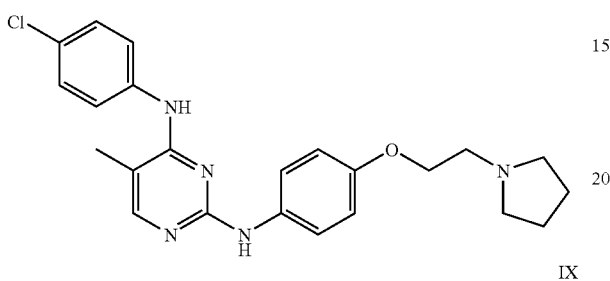
IX
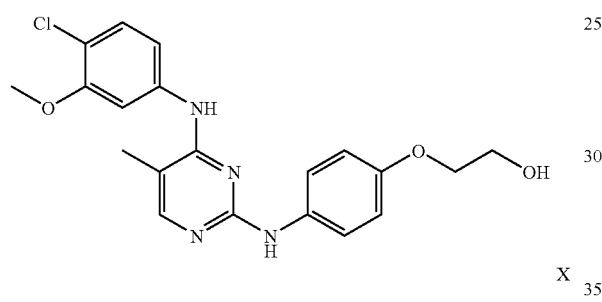
X
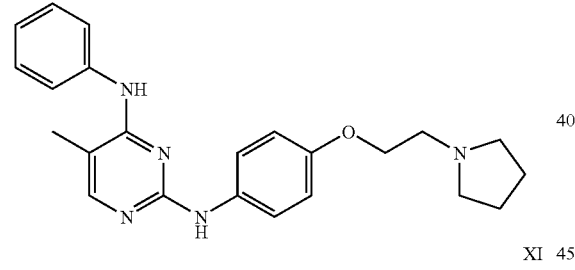
XI
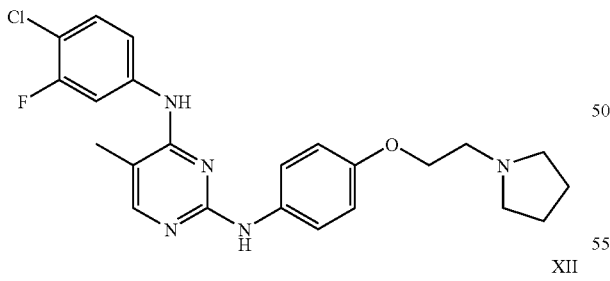
XII
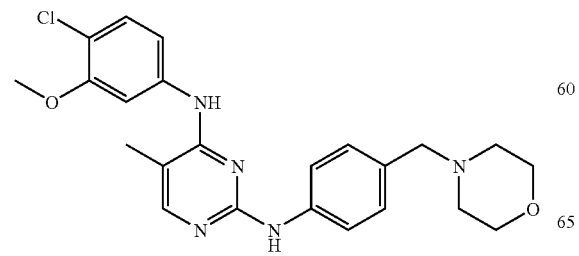
-continued
XIII
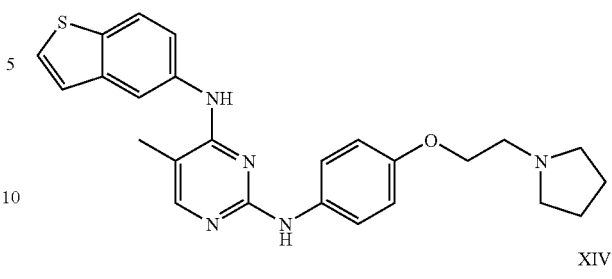
XIV
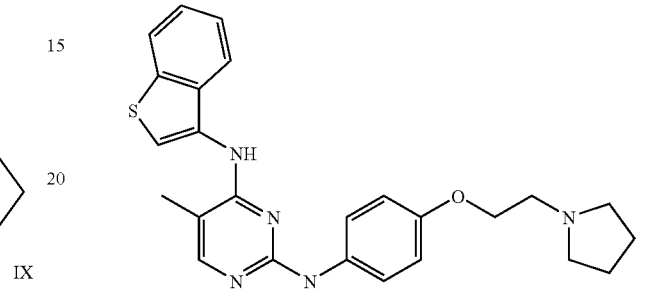
XV
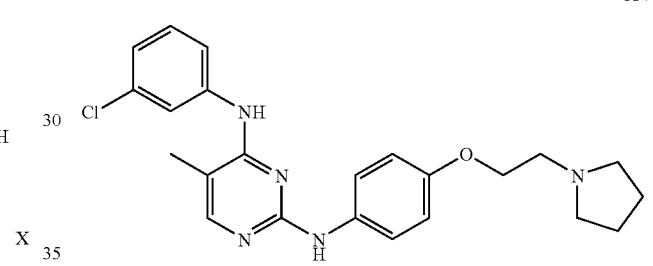
XVI
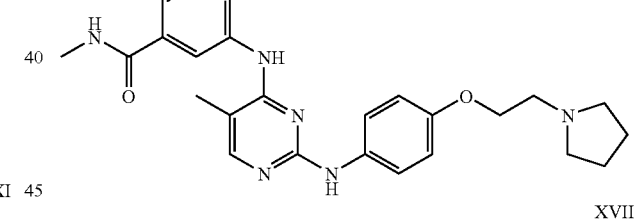
XVII
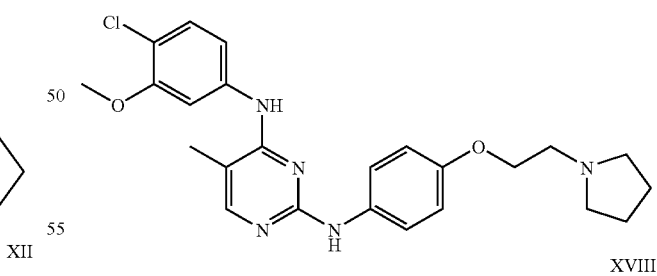
XVIII
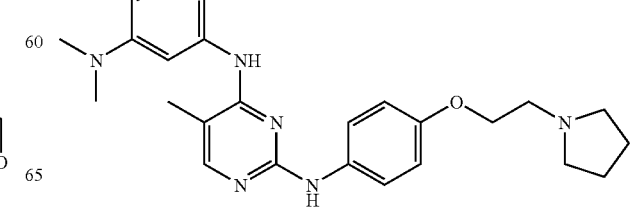

XIX
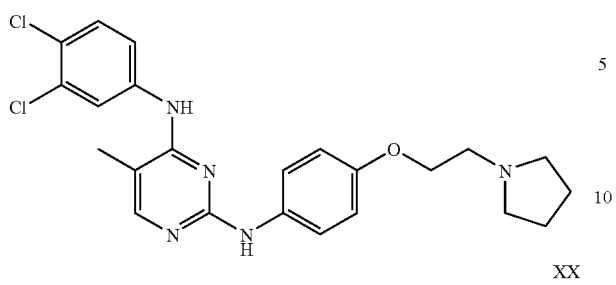
XX
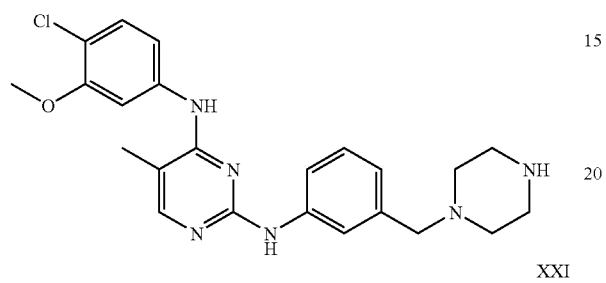
XXI
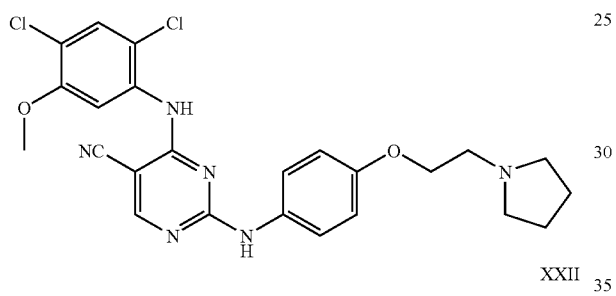
XXII
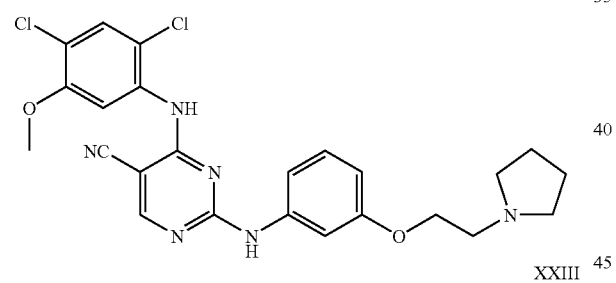
XXIII
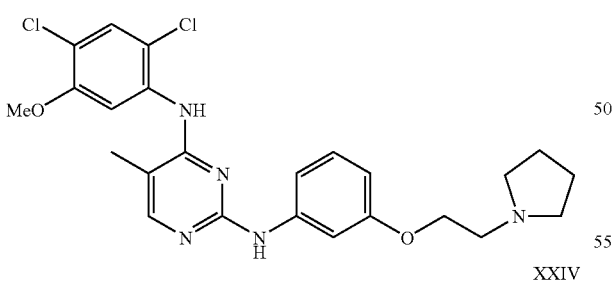
XXIV
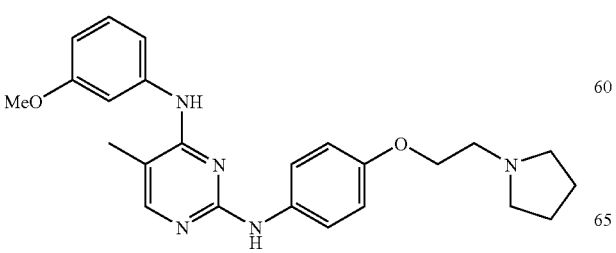
XXV
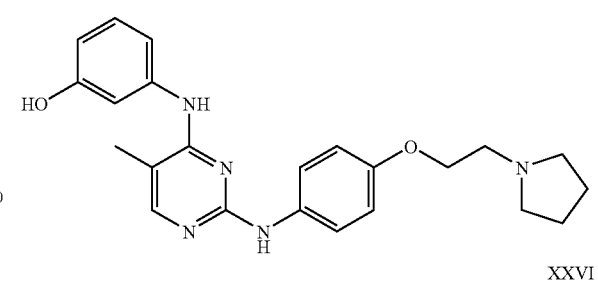
XXVI
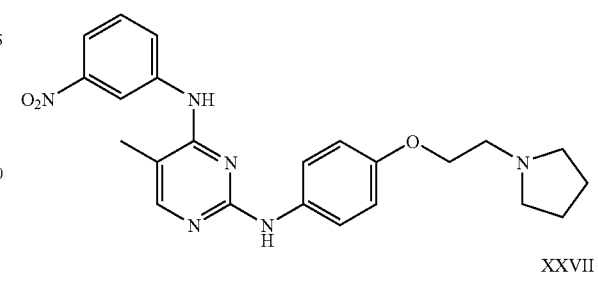
XXVII
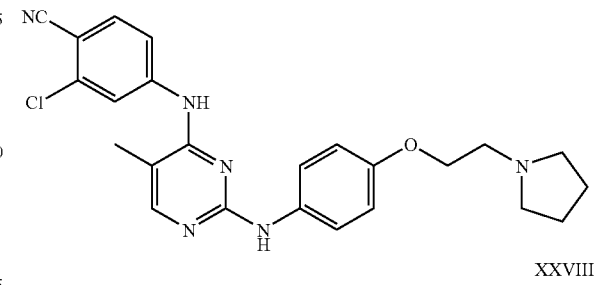
XXVIII
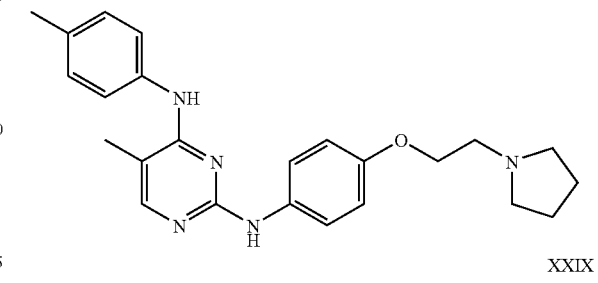
XXIX
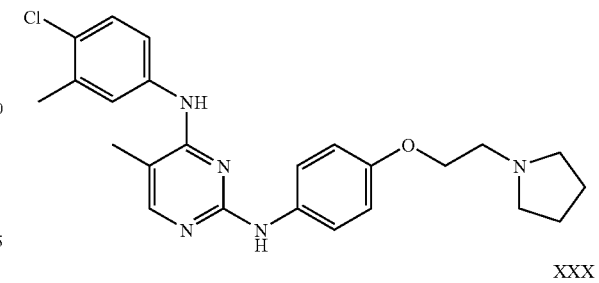
XXX
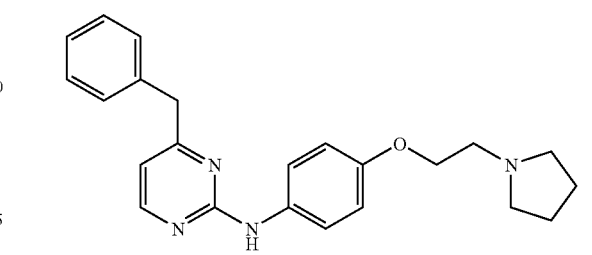

XXXI
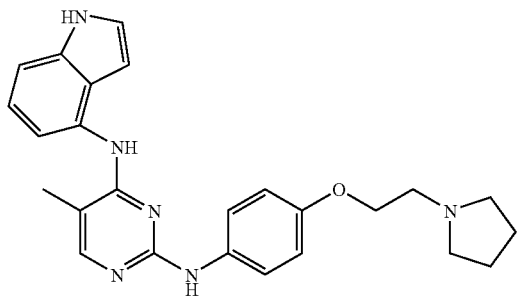
XXXII
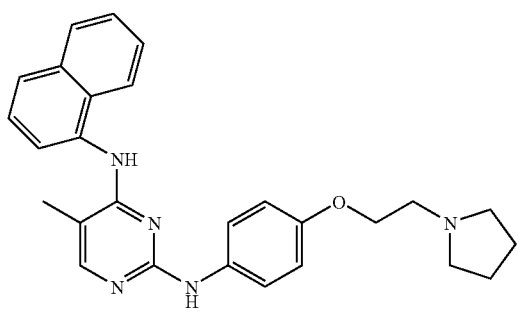
XXXIII
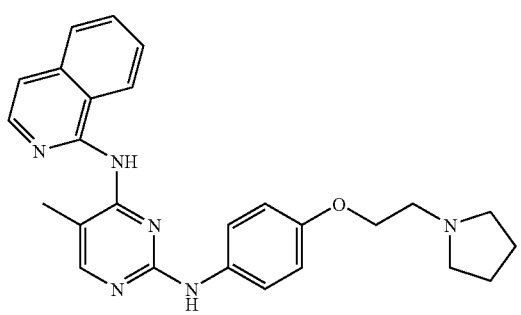
XXXIV
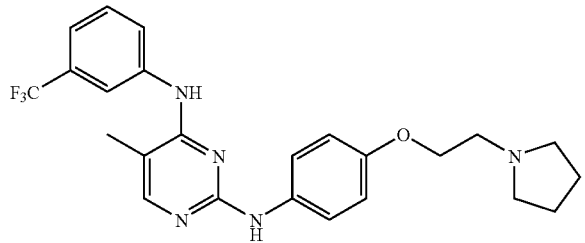
XXXV
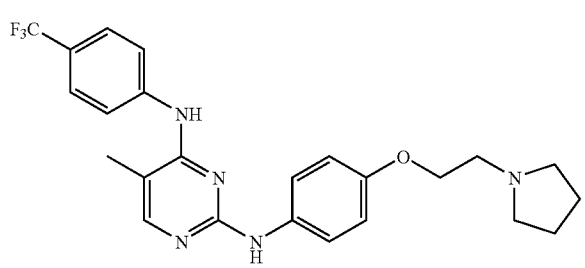
XXXVI
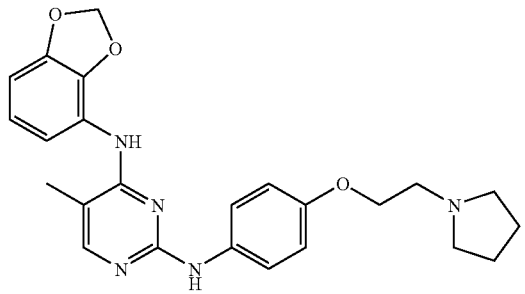
XXXVII
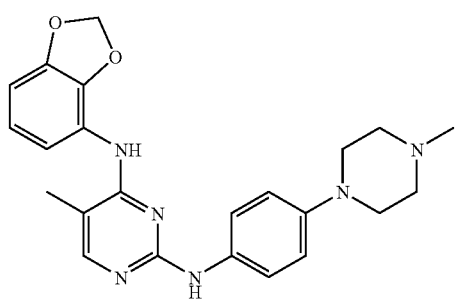
XXXVIII
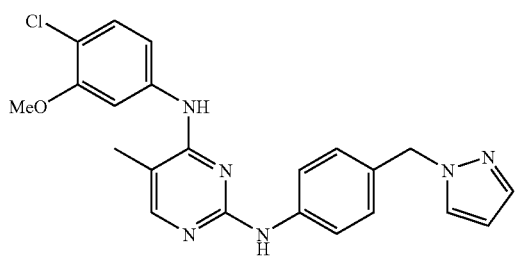
XXXIX
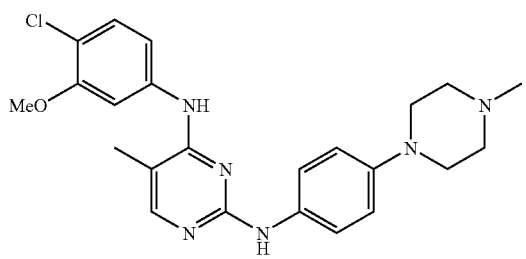
XL
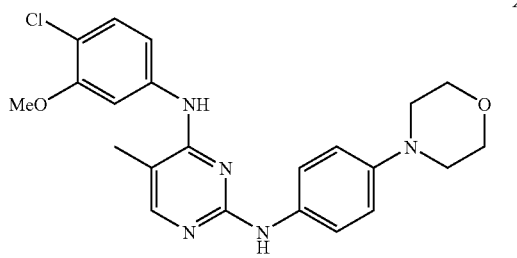

XLI
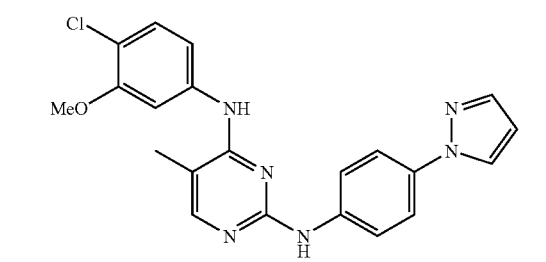
XLII
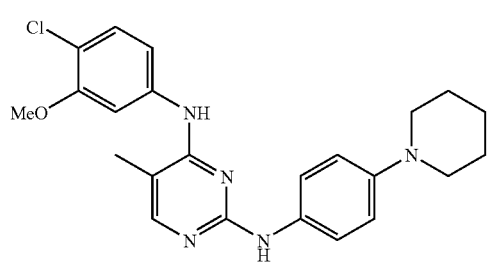
XLIII
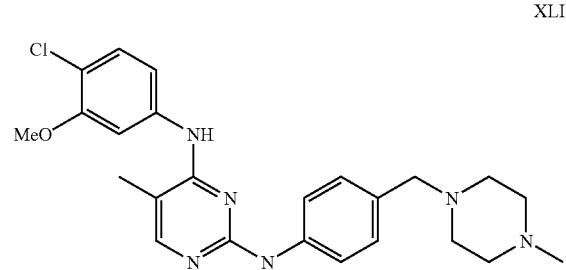
XLIV
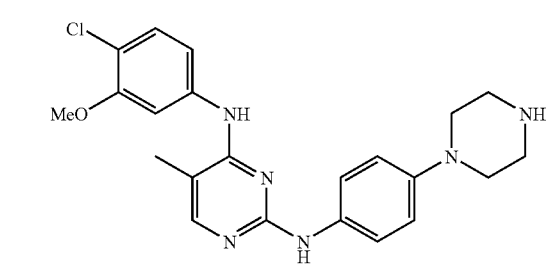
XLV
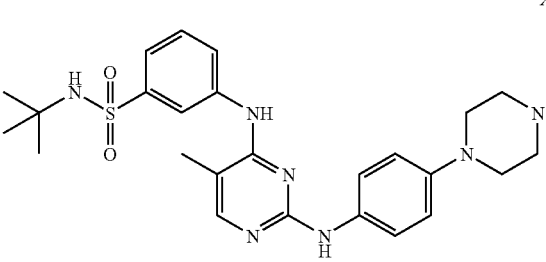
XLVI
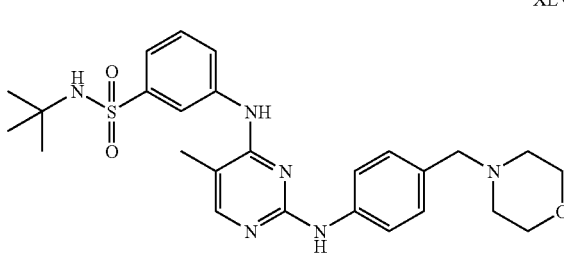
XLVII
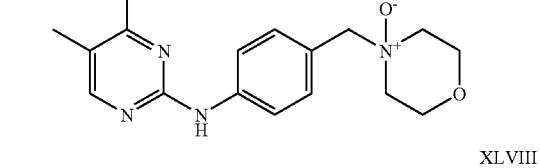
XLVIII
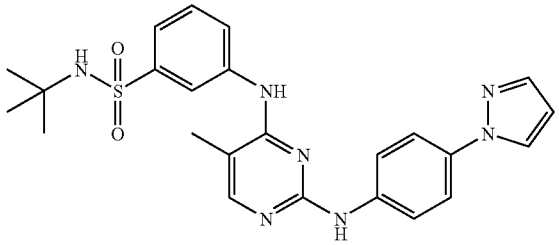
XLIX
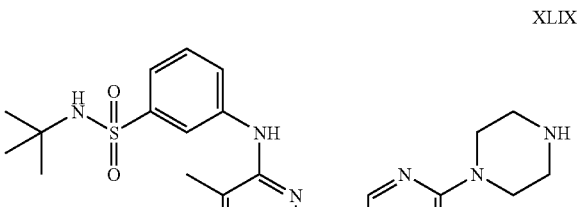
L
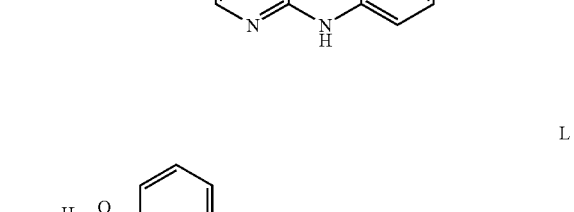
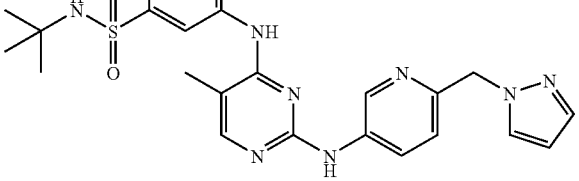
LI
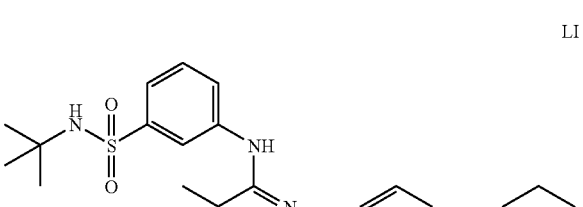
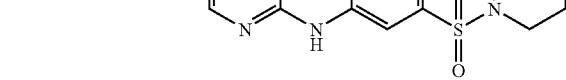

-continued
LII
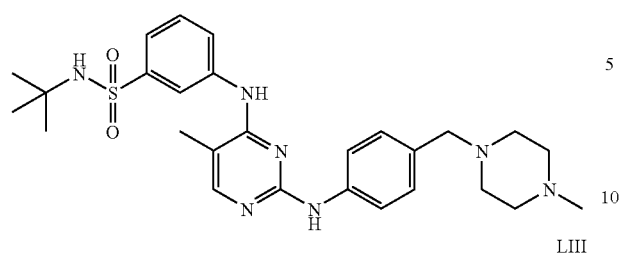
LIII
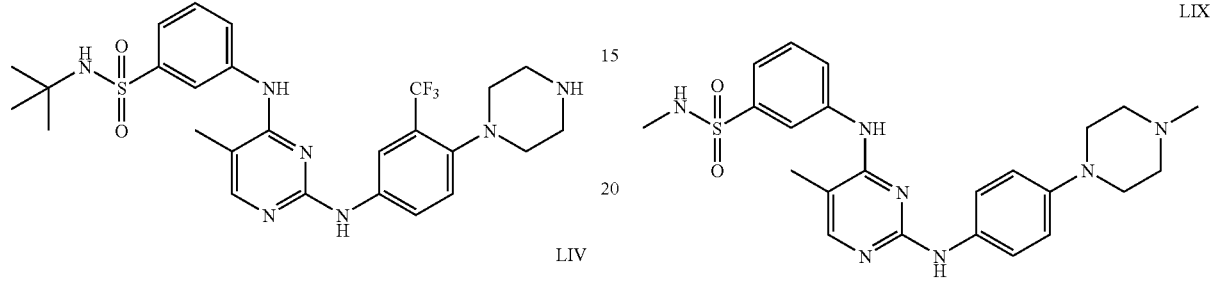
LIV
LV
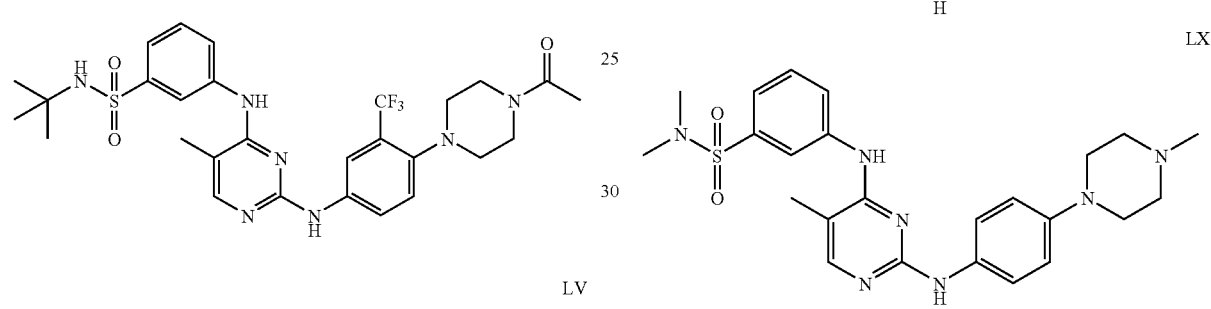
LVI
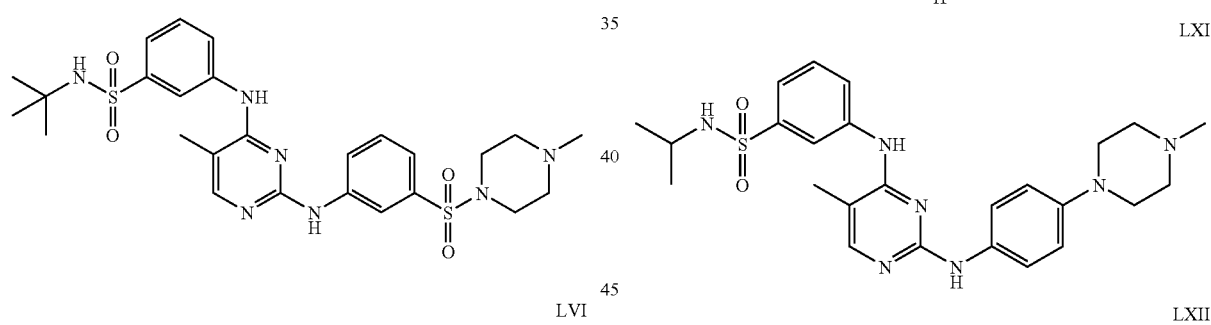
LVII
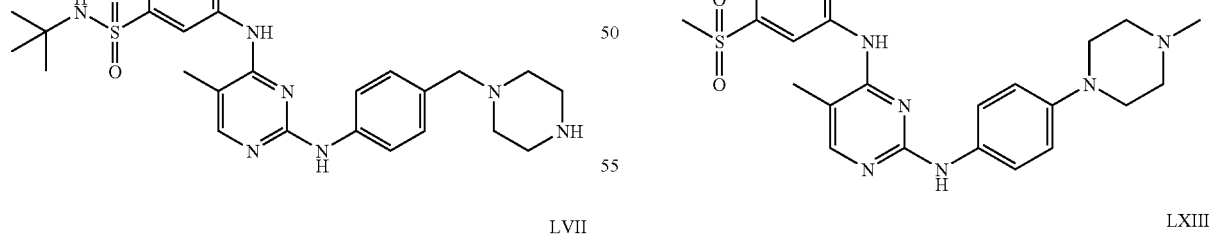
-continued
LVIII
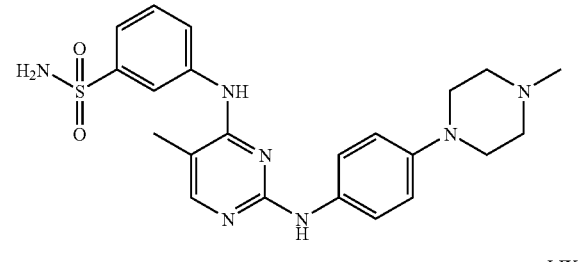
LIX
LX
LXI
LXII
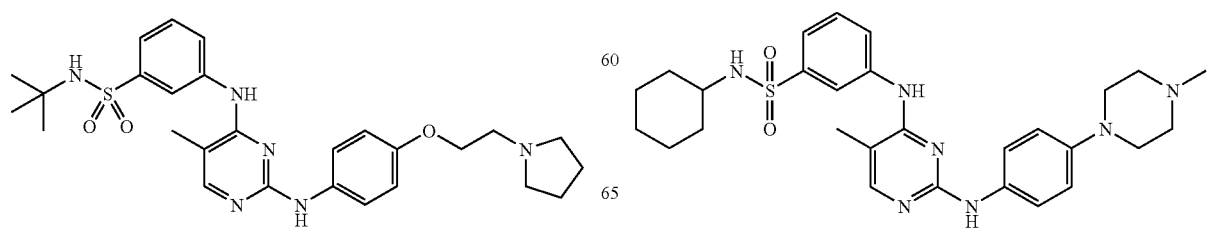
LXIII LXIV
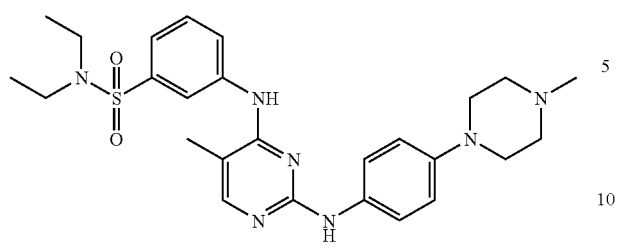
LXV
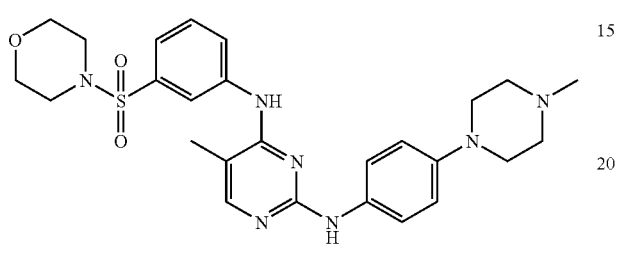
LXVI
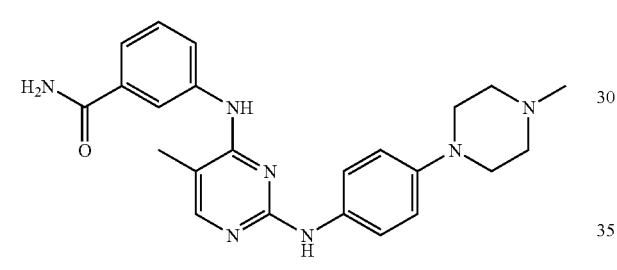
LXVII
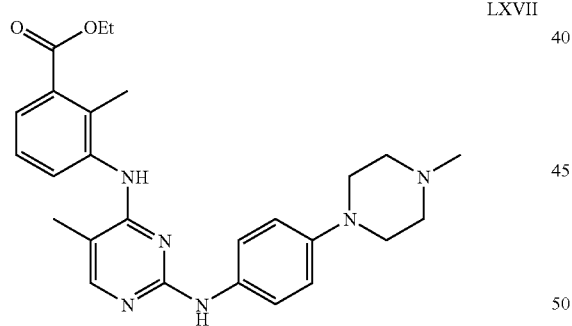
LXVIII
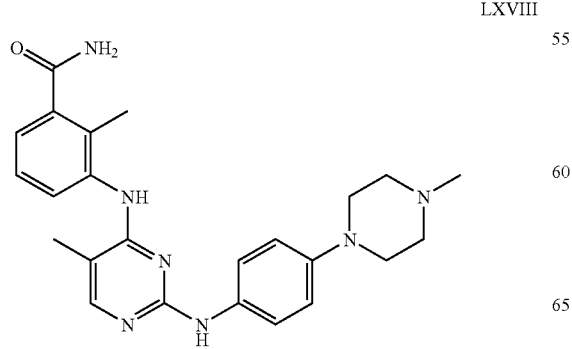
LXIX
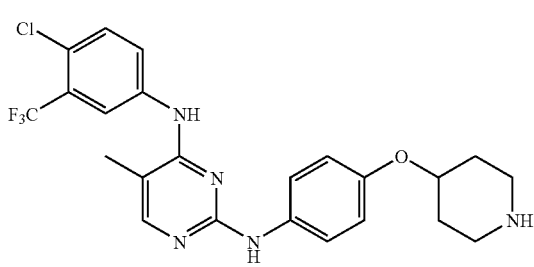
LXX
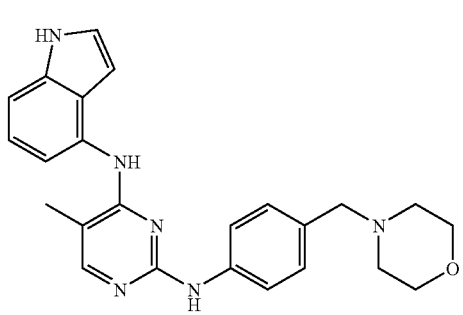
LXXI
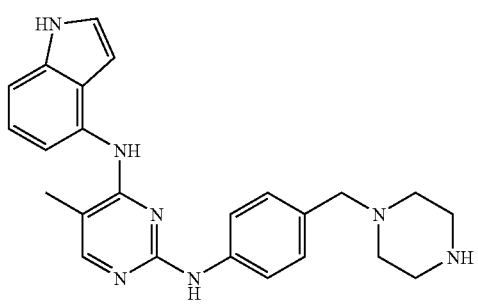
LXXII
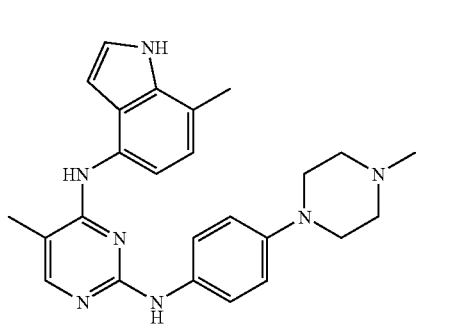
LXXIII LXXIV
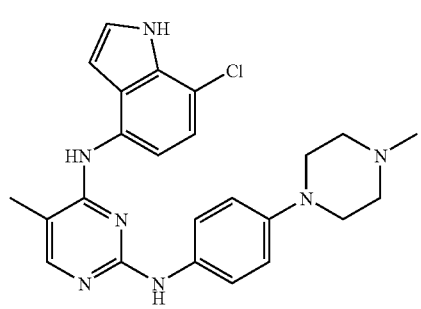
LXXV
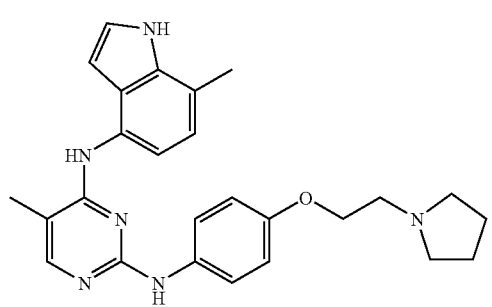
LXXVI
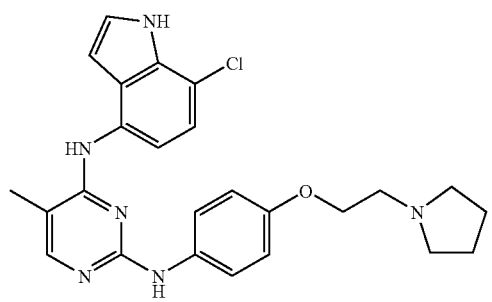
LXXVII
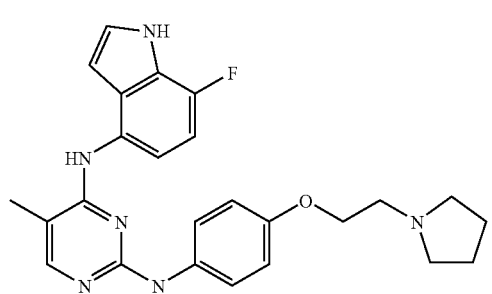
LXXVIII
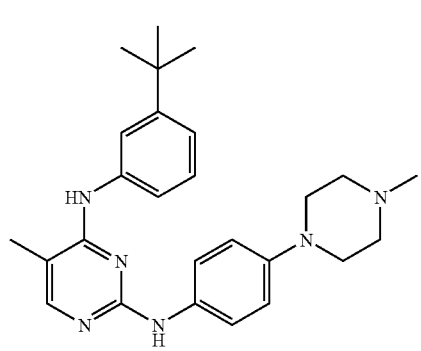
LXXIX
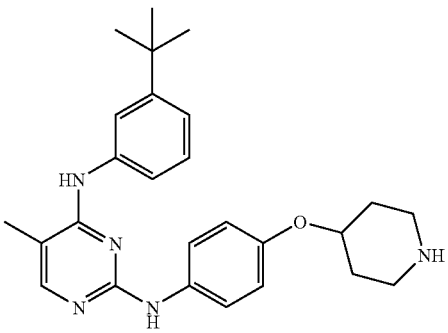
LXXX
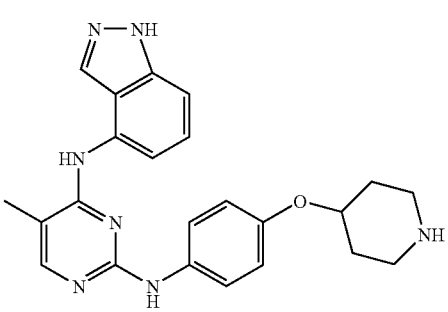
LXXXI
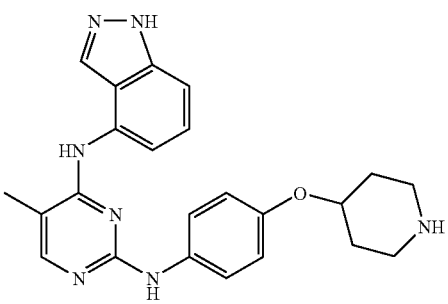
LXXXII
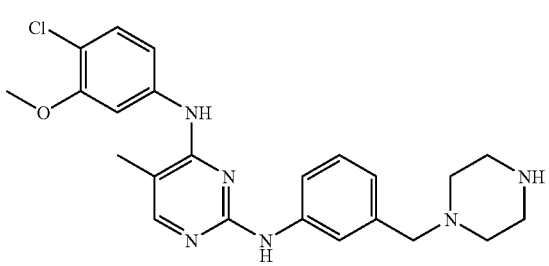
LXXXIII
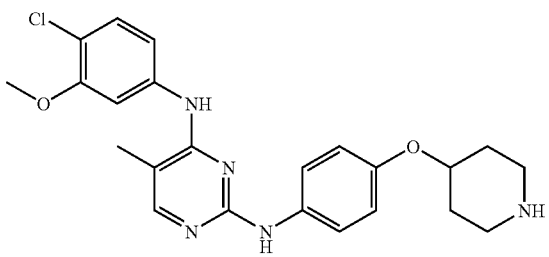

-continued
LXXXIV
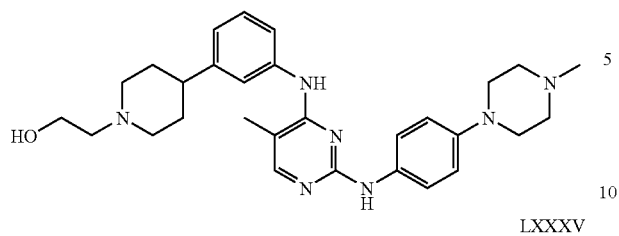
LXXXV
XC
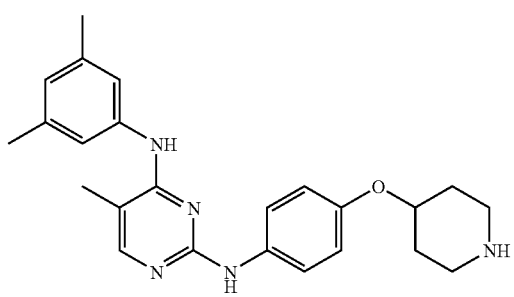
LXXXVI
XCI
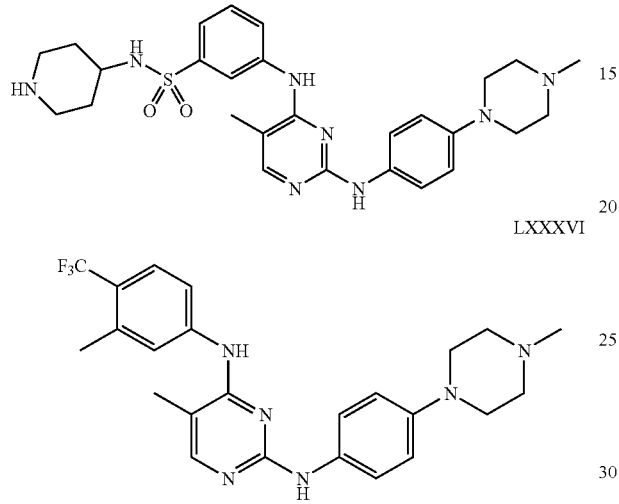
LXXXVII
XCII
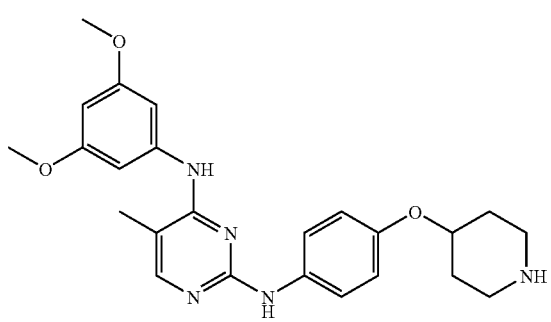
LXXXVIII
XCIII
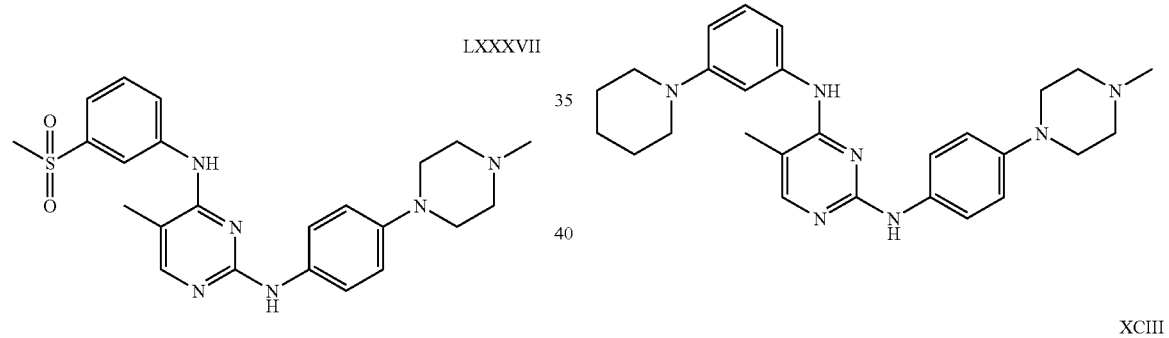
LXXXIX
XCIV
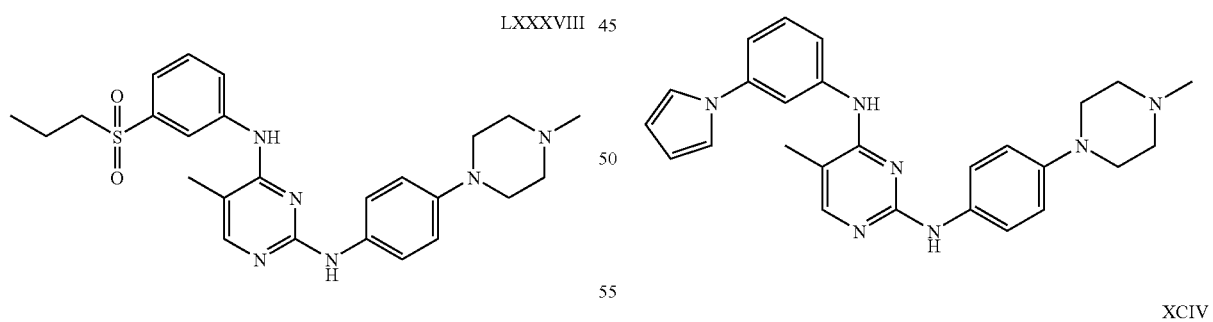
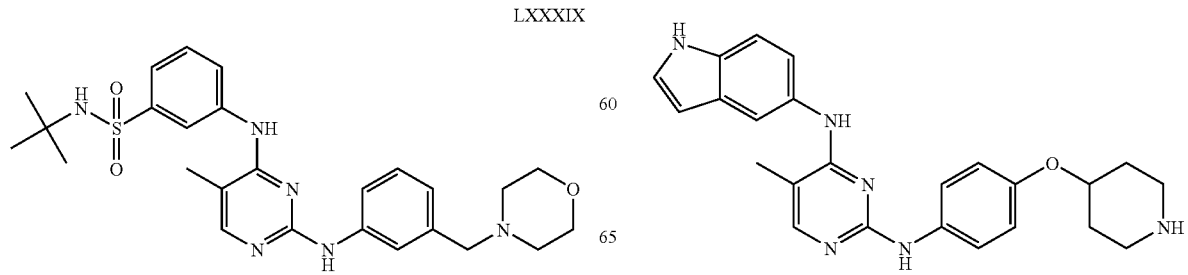

XCV
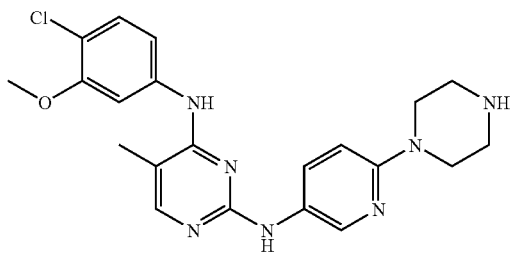
XCVI
XCVII
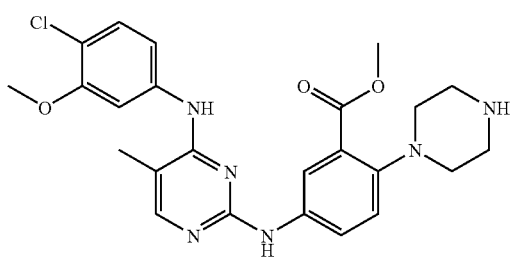
XCVIII
XCIX
C
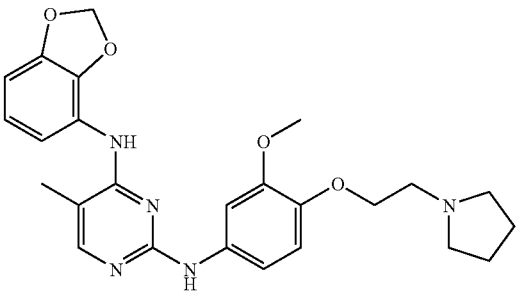
CI
CII
CIII
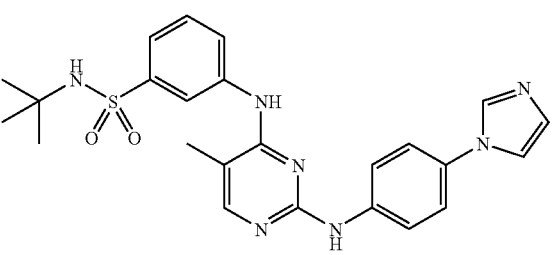
CIV
CV CVI
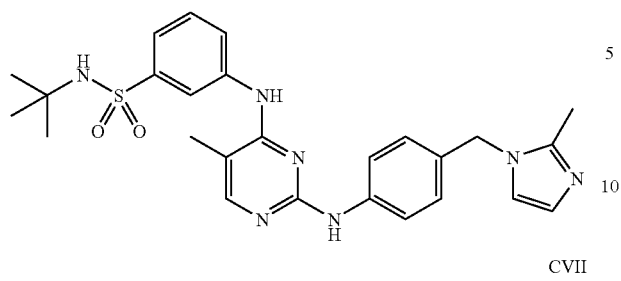
CVII
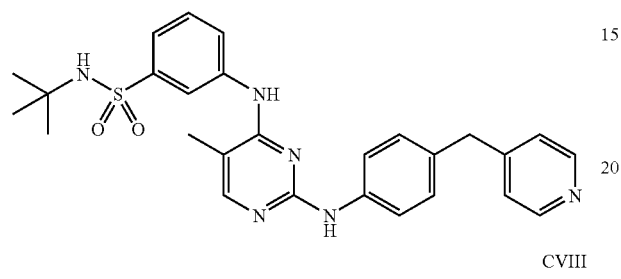
CVIII
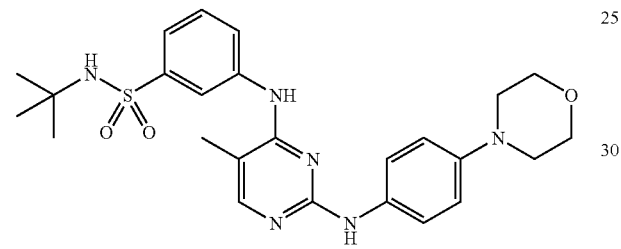
CIX
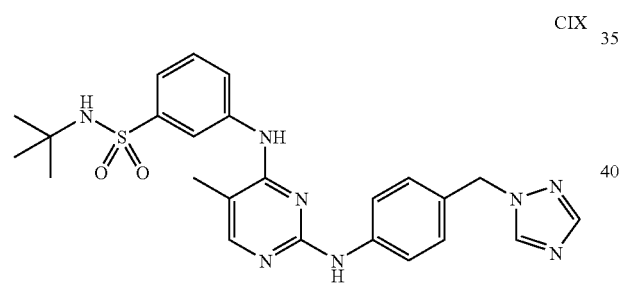
CX
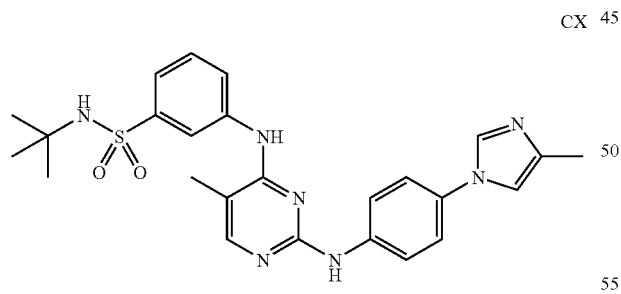
CXI
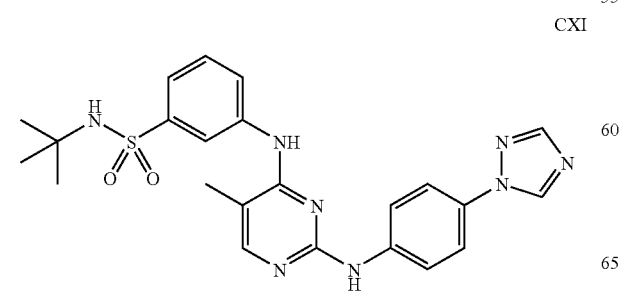
CXII
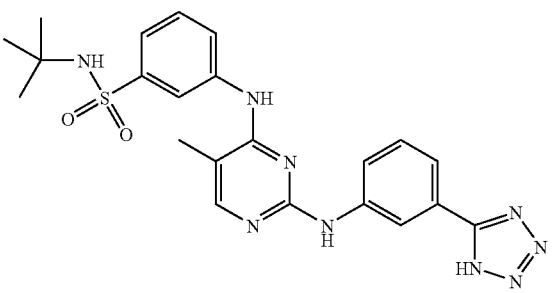
CXIII
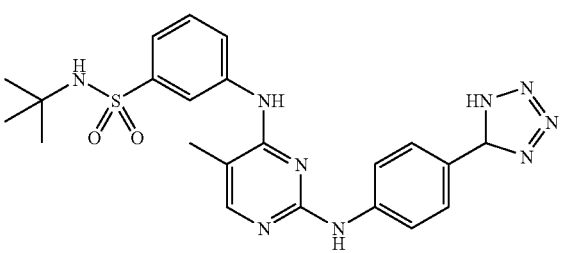
CXIV
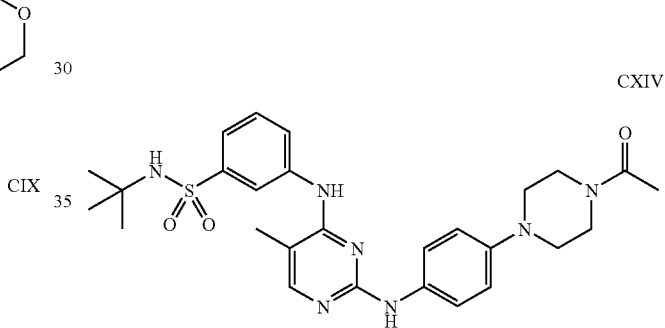
CXV
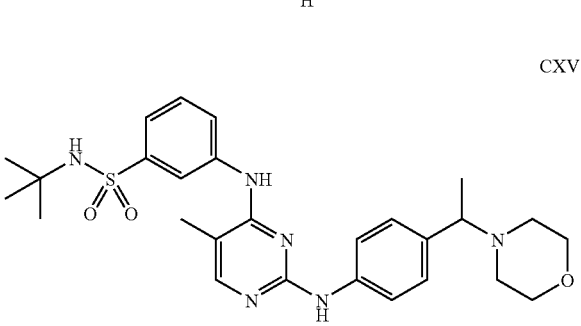
CXVI
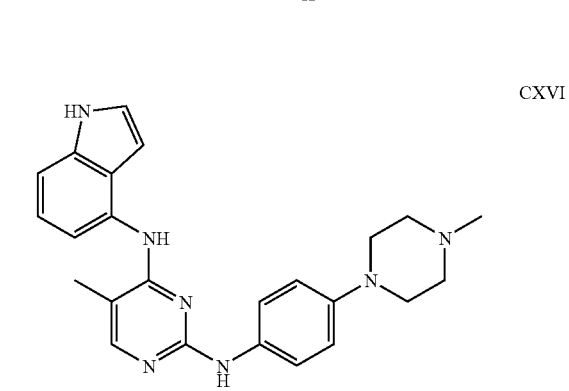

CXVII
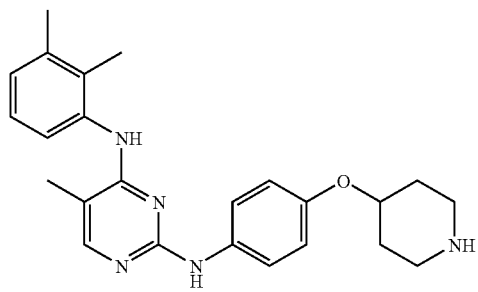
CXVIII
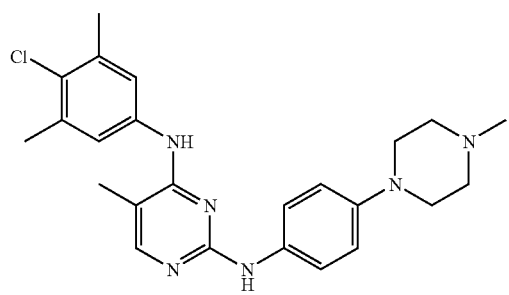
CXIX
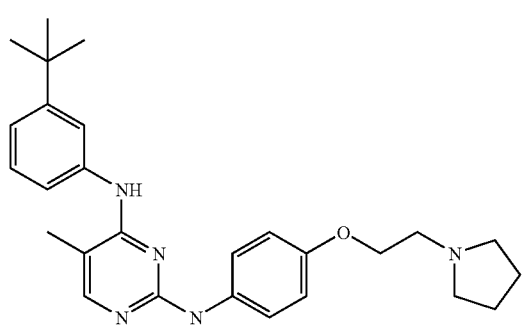
CXX
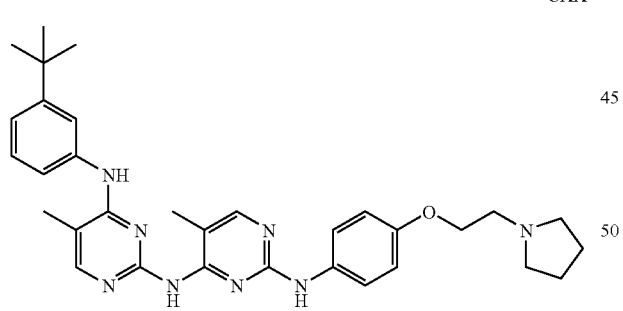
CXXI
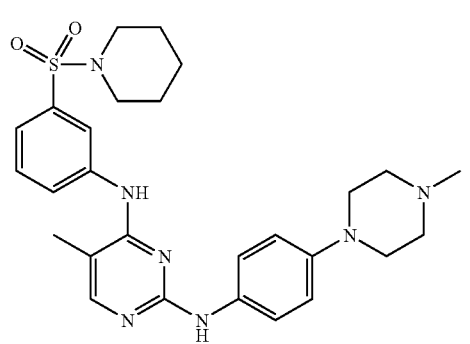
CXXII
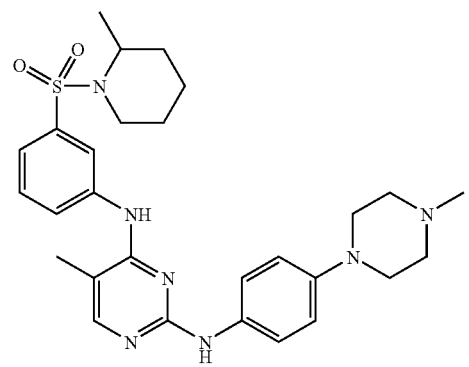
CXXIII
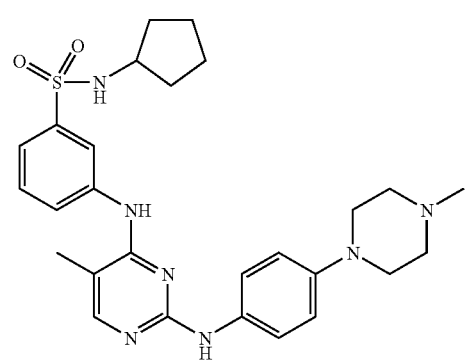
CXXIV
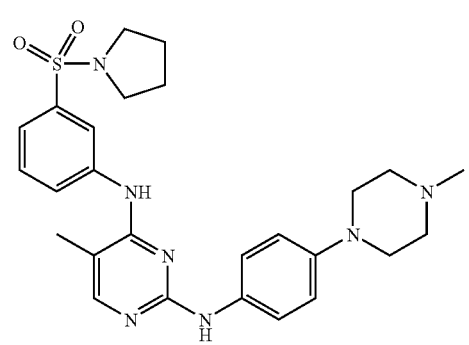
CXXV
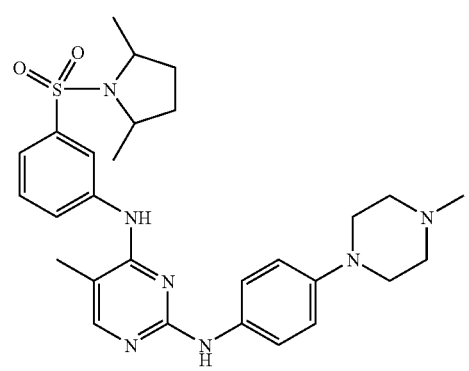

CXXVI
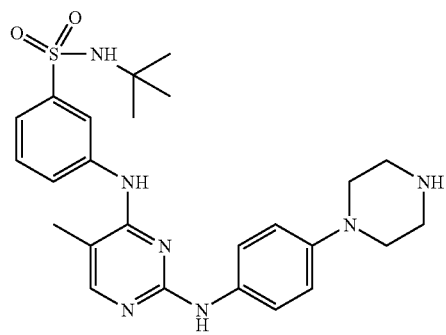
CXXVII
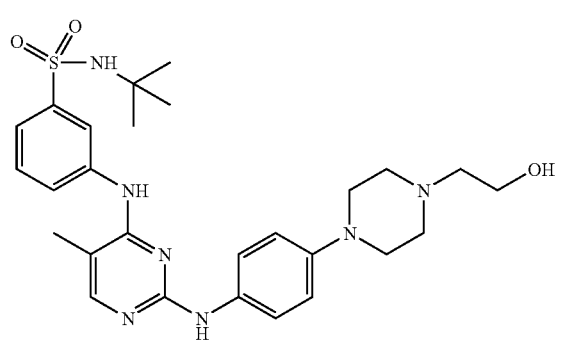
CXXVIII
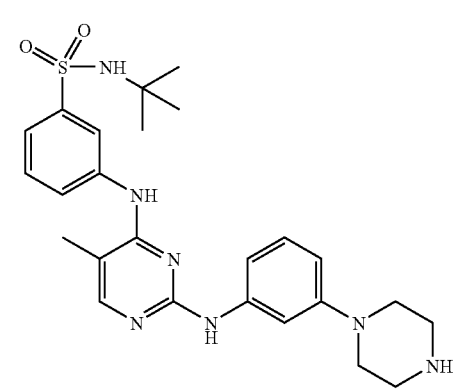
CXXIX
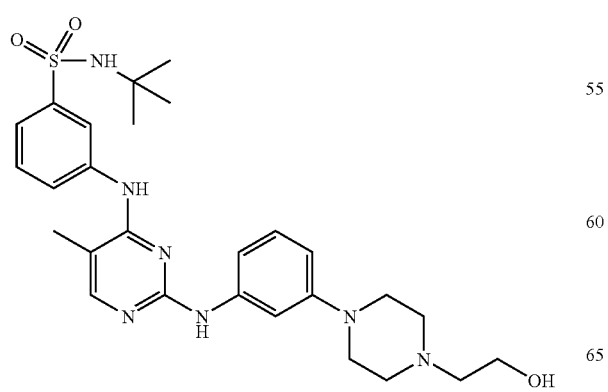
CXXX
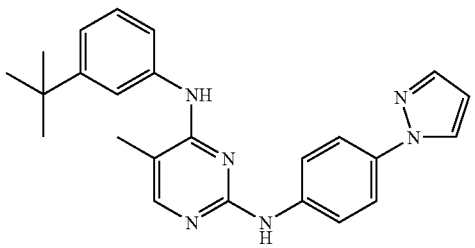
CXXXI
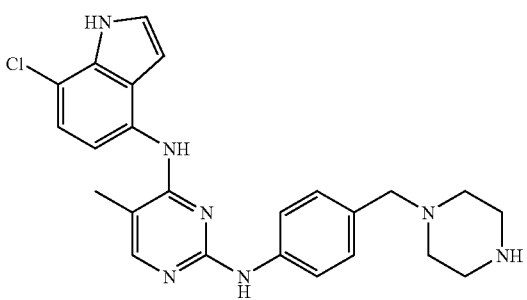
CXXXII
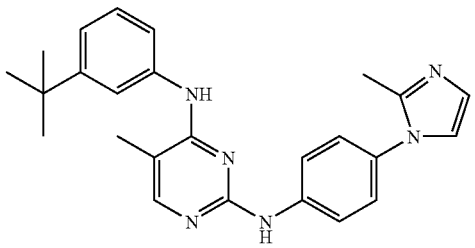
CXXXIII
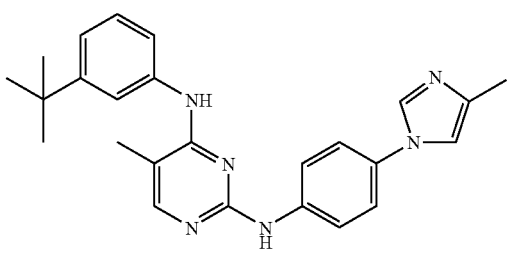
CXXXIV
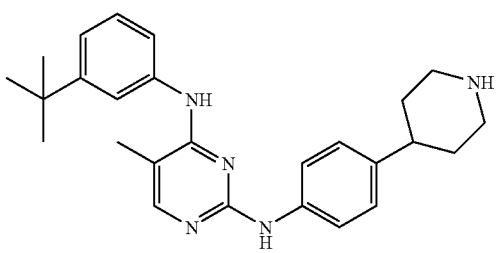

CXXXV
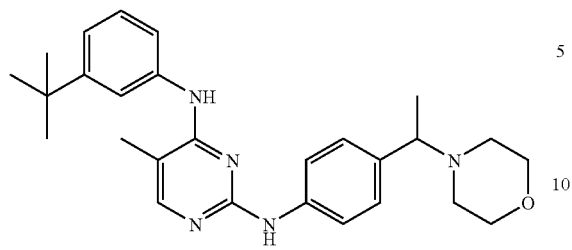
CXLI
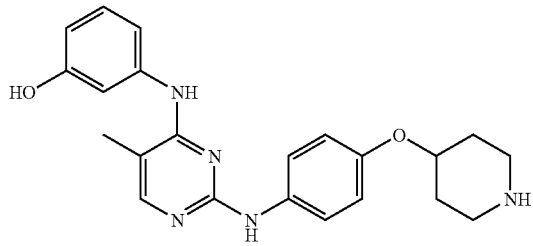
CXXXVI
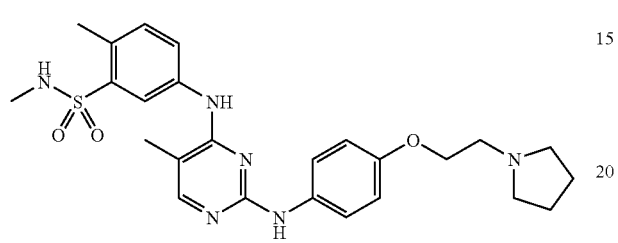
CXLII
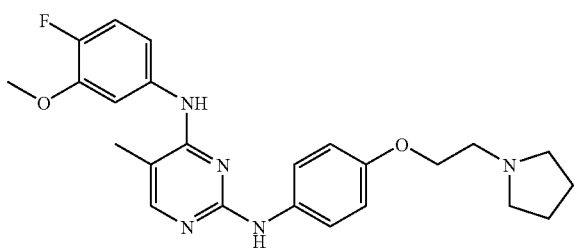
CXXXVII
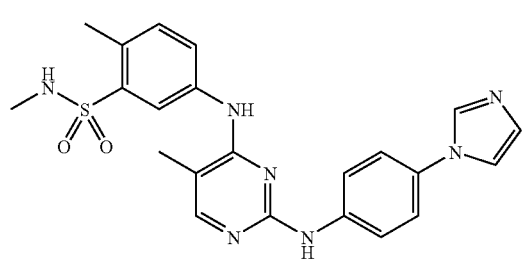
CXLIII
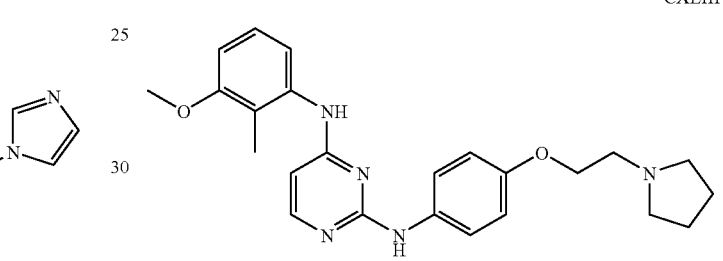
CXXXVIII
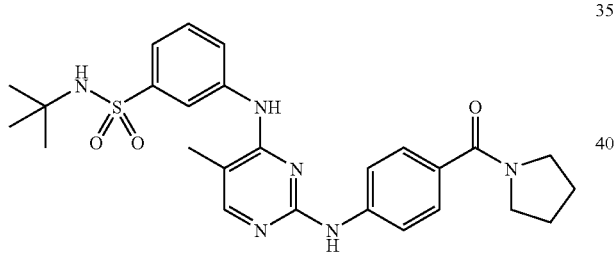
CXLIV
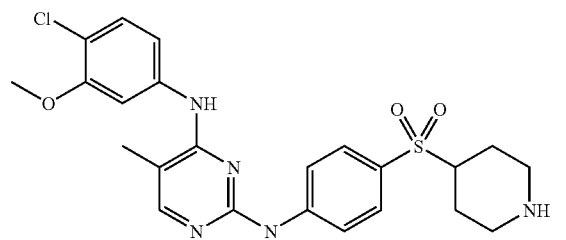
CXXXIX
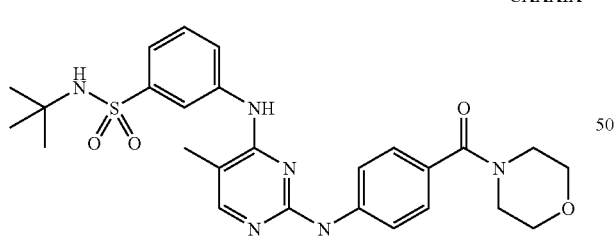
CXLV
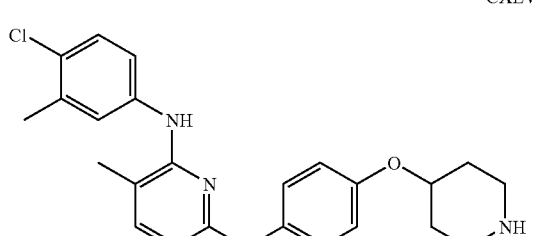
CXL
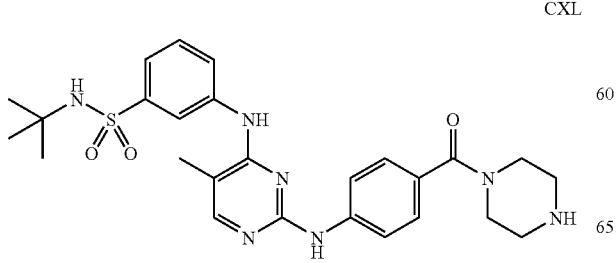
CXLVI
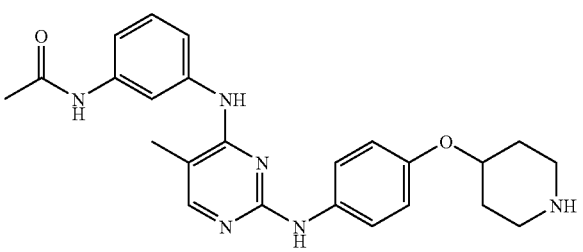

CXLVII
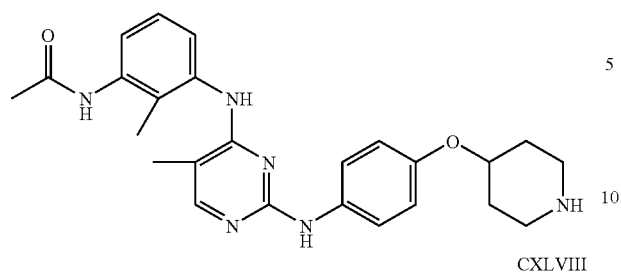
CLIII
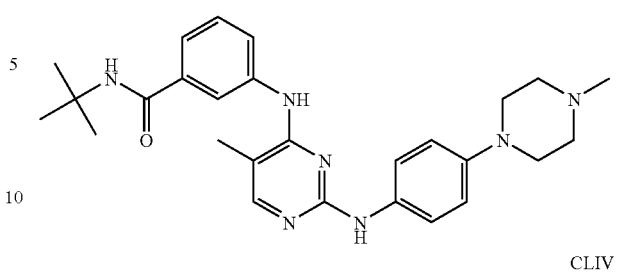
CXLVIII
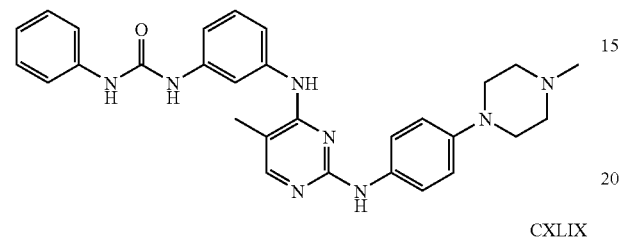
CLIV
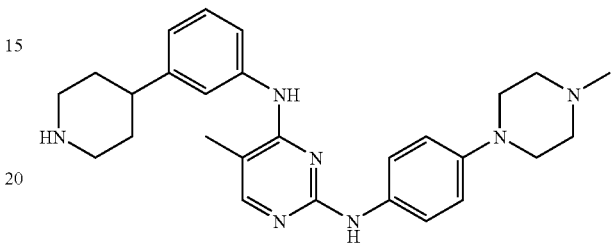
CXLIX
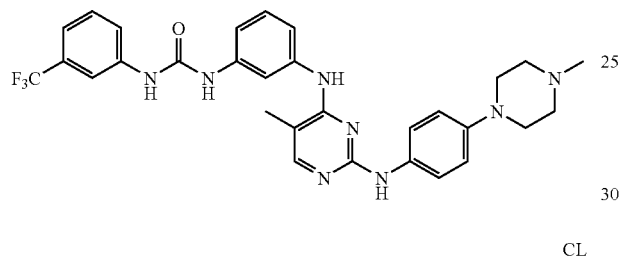
CLV
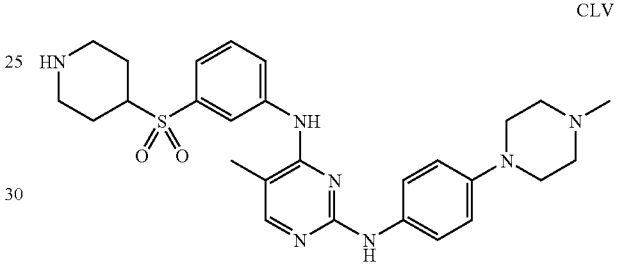
CL
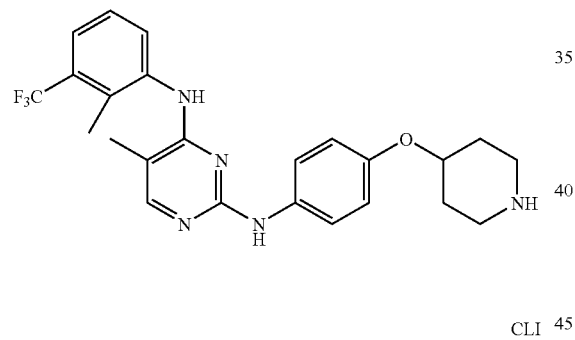
CLVI
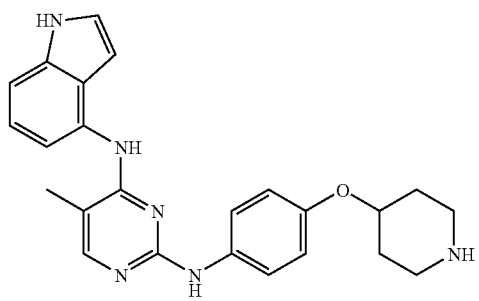
CLI
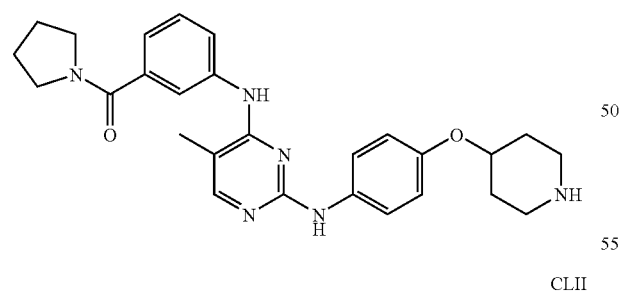
CLVII
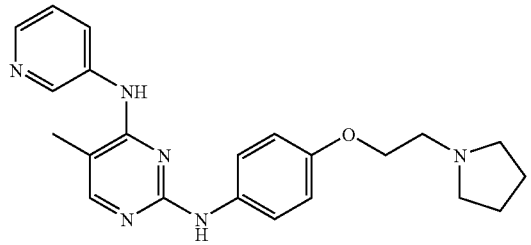
CLII
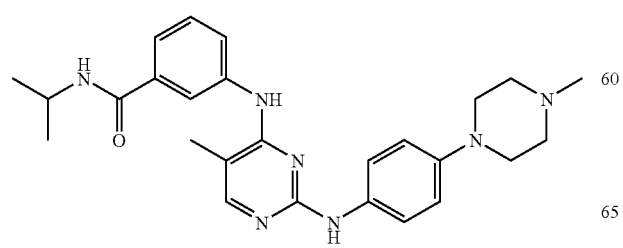
CLVIII
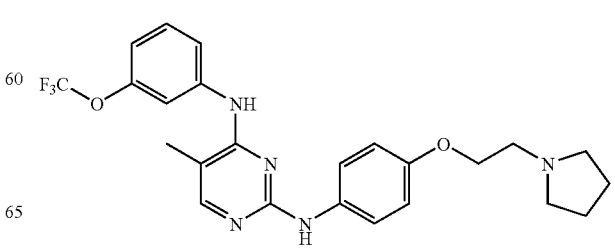

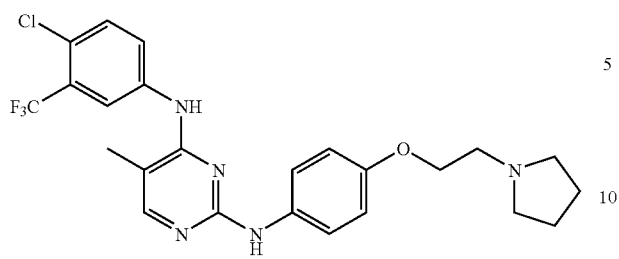
CLIX

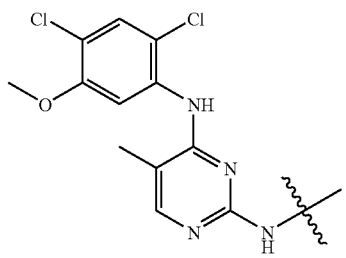

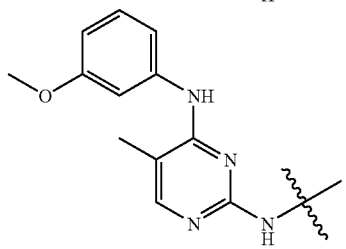

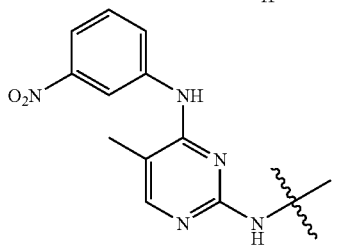

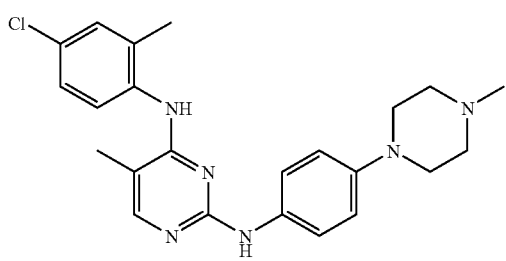
CLX

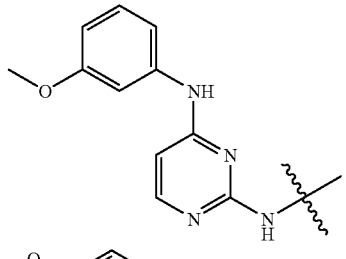

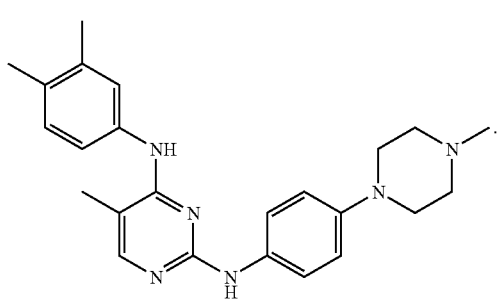
CLXI and

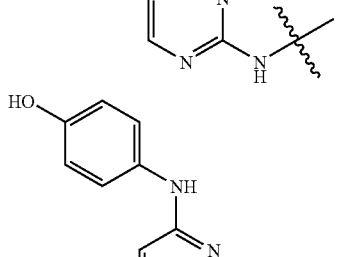

CLXII

According to another embodiment of the invention, compounds having the general structure (Z):

B—C   (Z)

are provided for treatment of various diseases, disorders, and pathologies.

The general structure (Z) includes two chemically connected moieties B and C. The moiety B in the general structure (Z) includes any moiety selected from the following group:

-continued
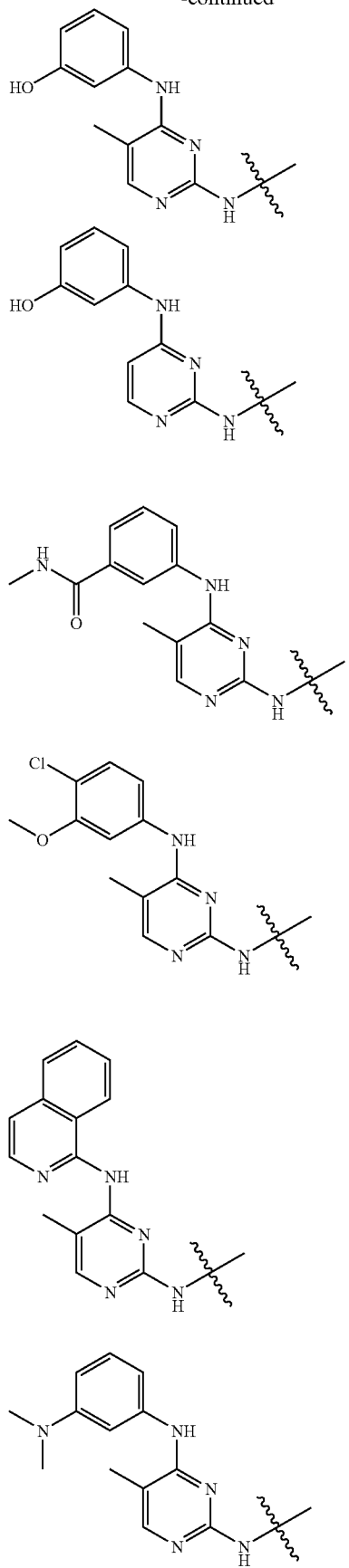
-continued
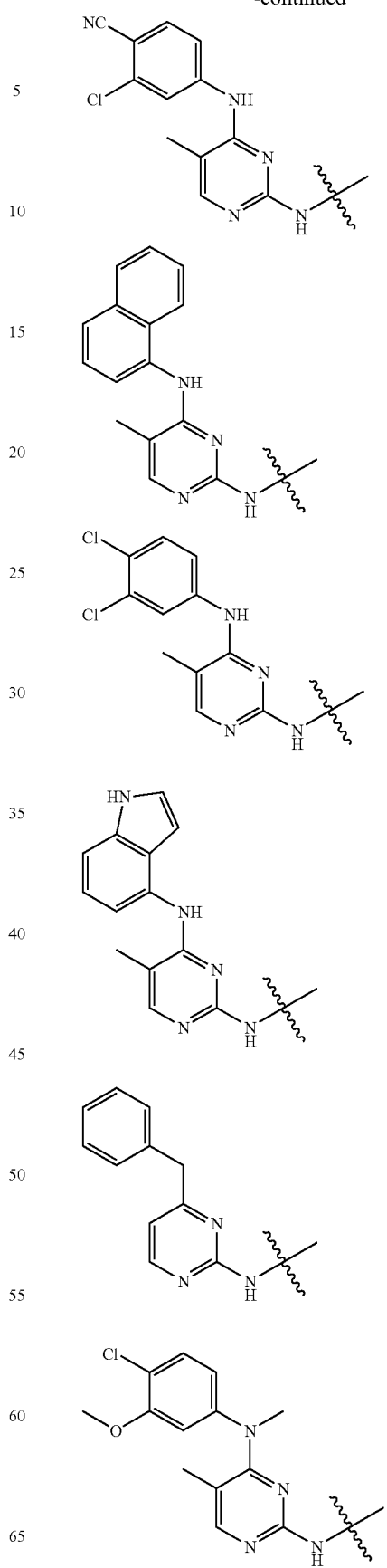

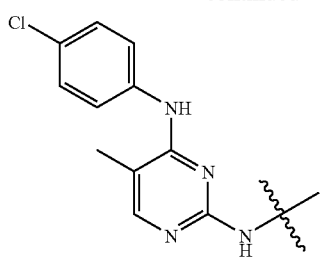
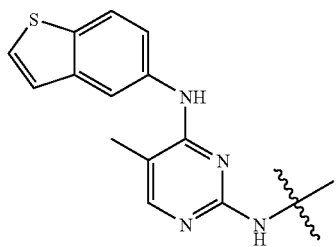
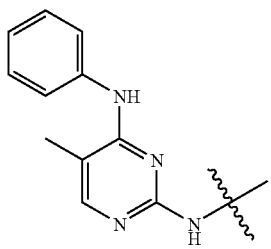
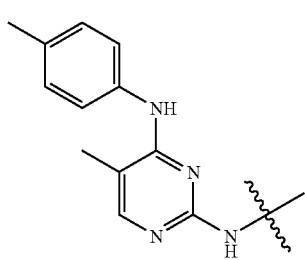
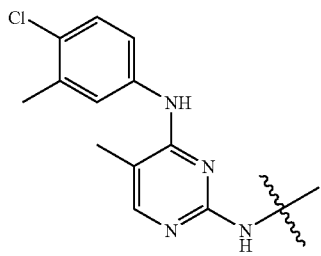
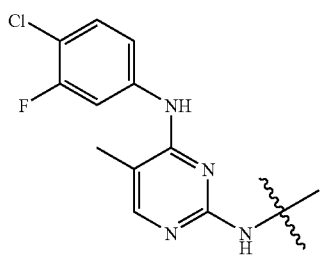
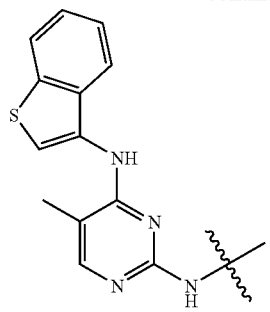
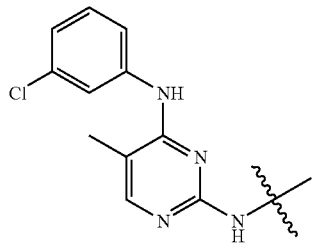
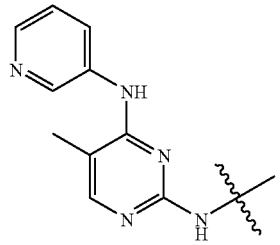
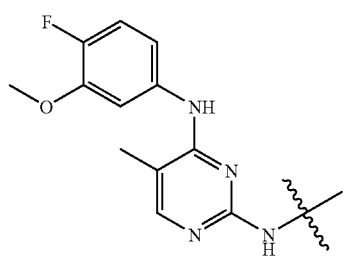
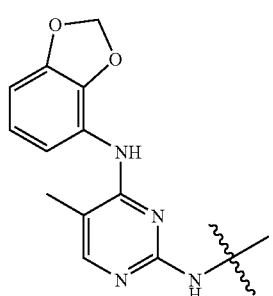
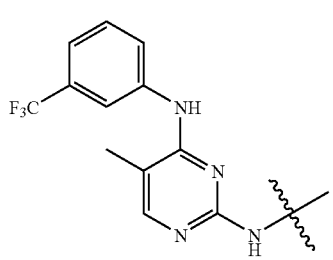

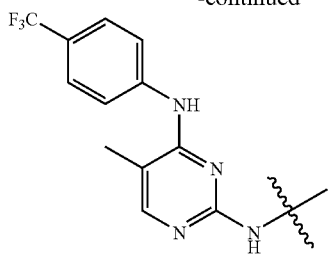
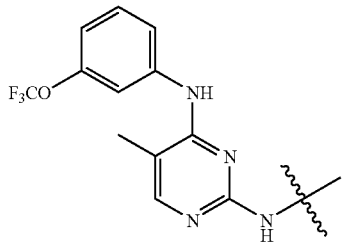
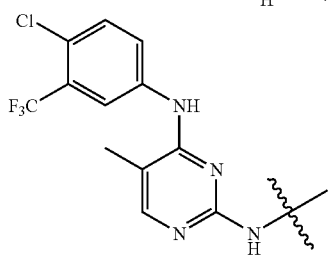
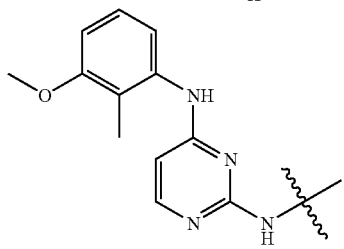
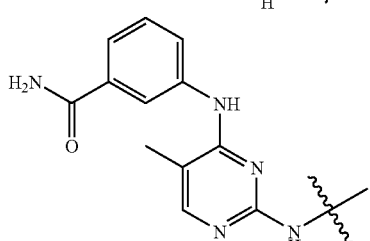
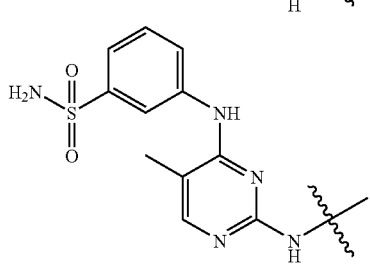
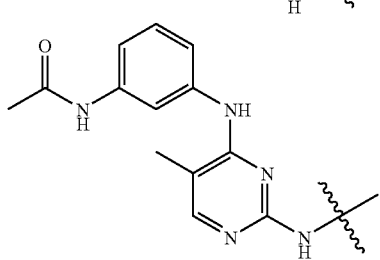
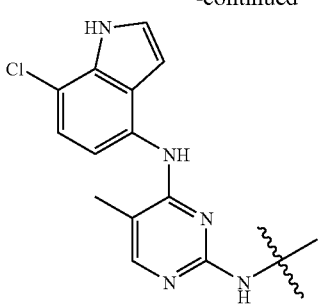
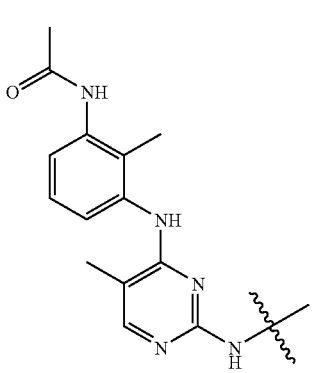
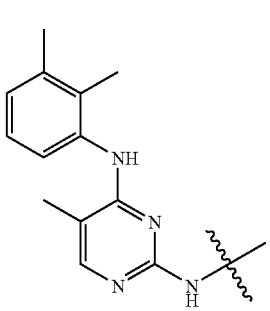
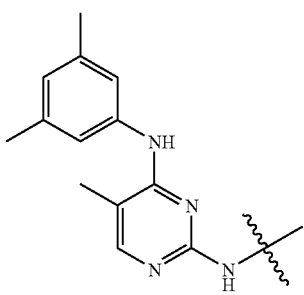
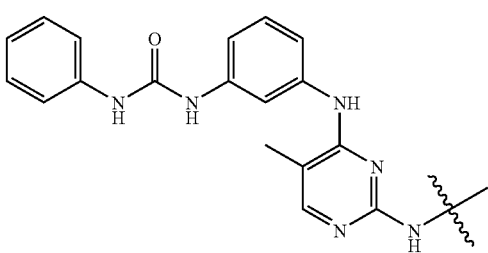

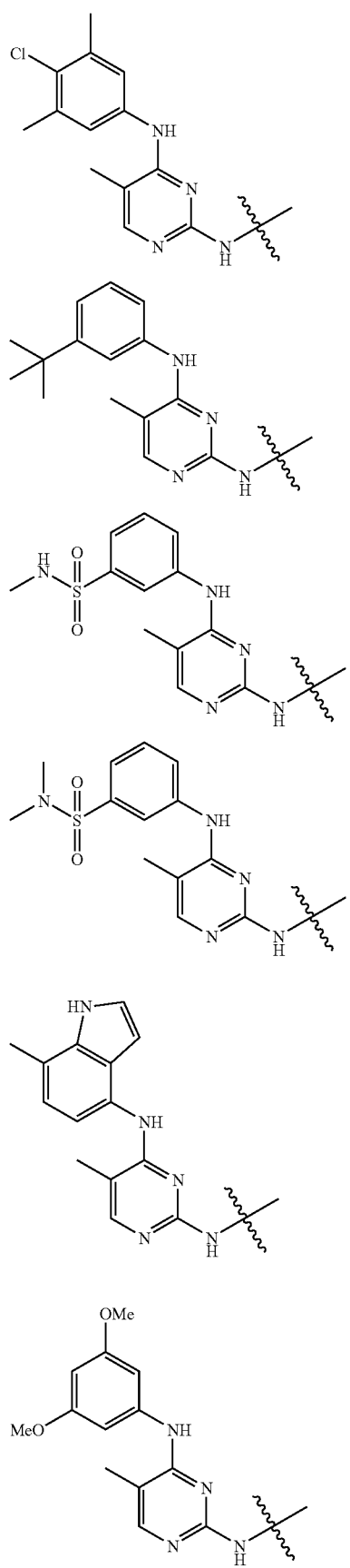
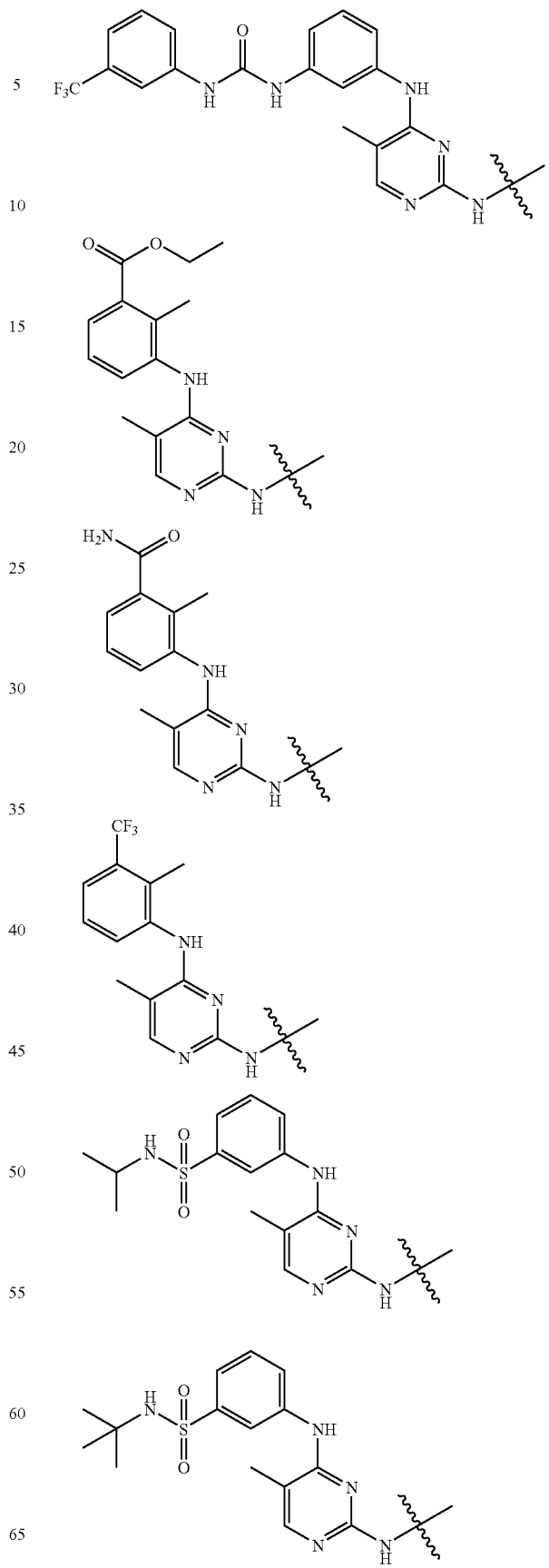

47
-continued
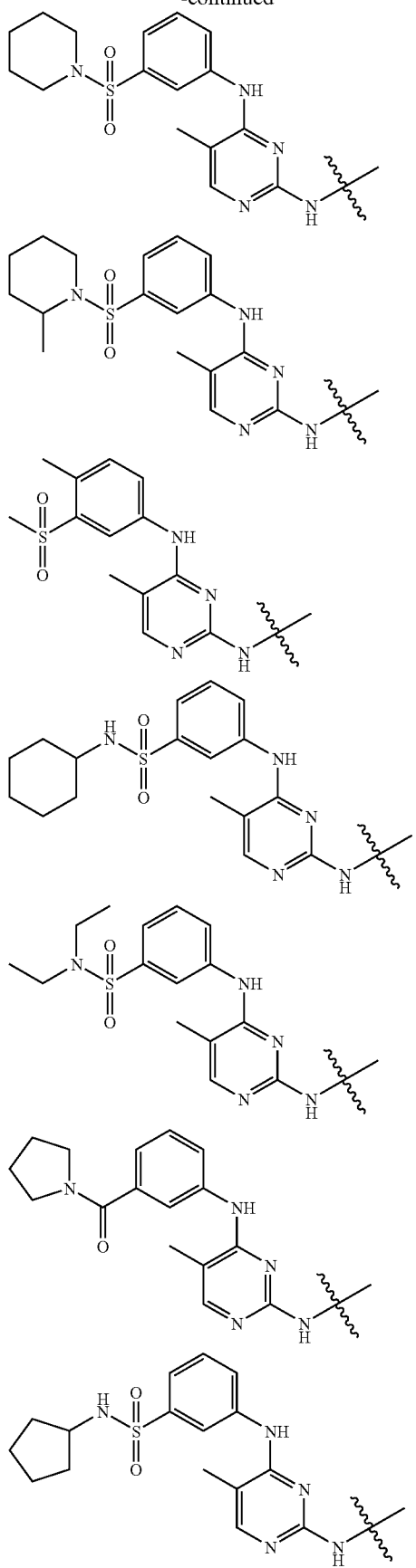
48
-continued
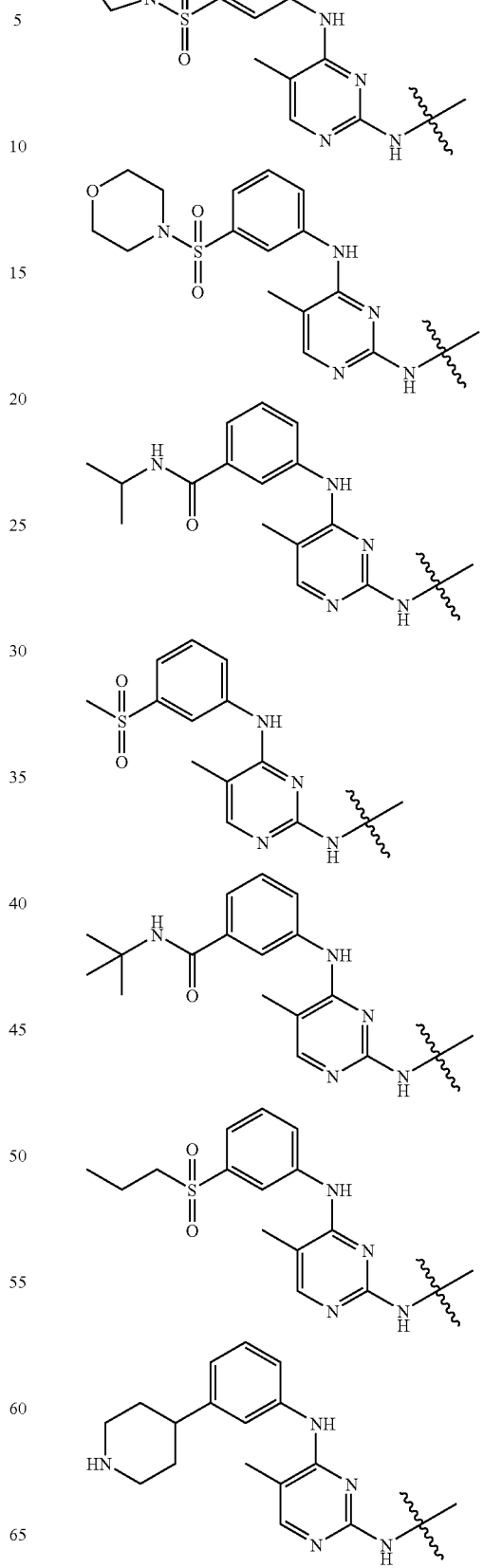

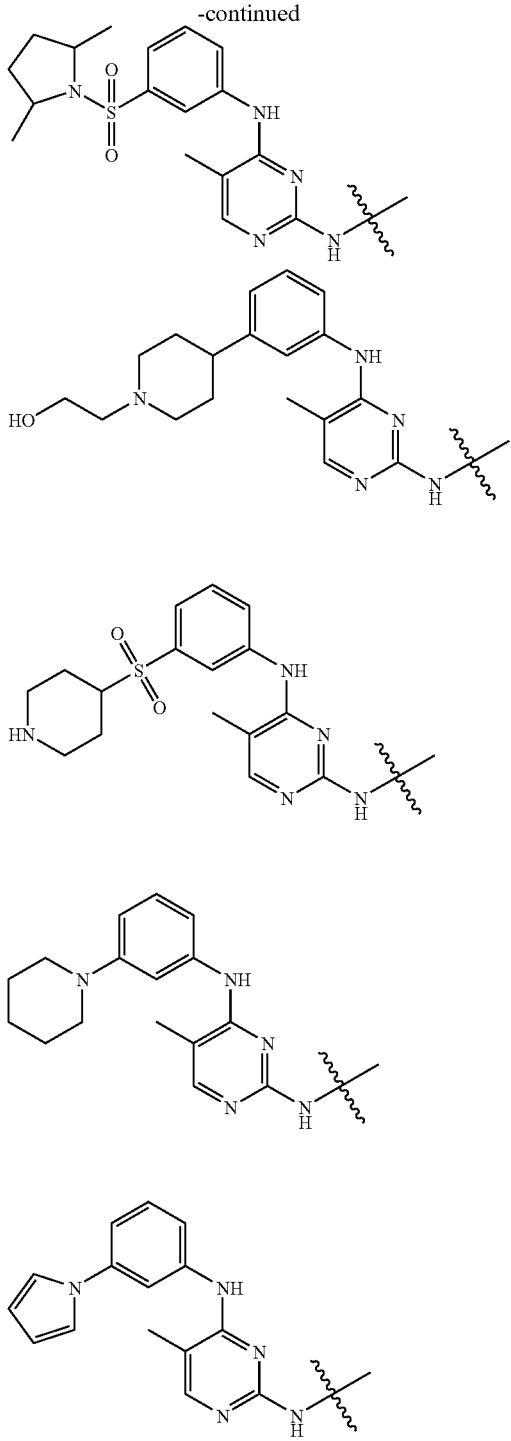
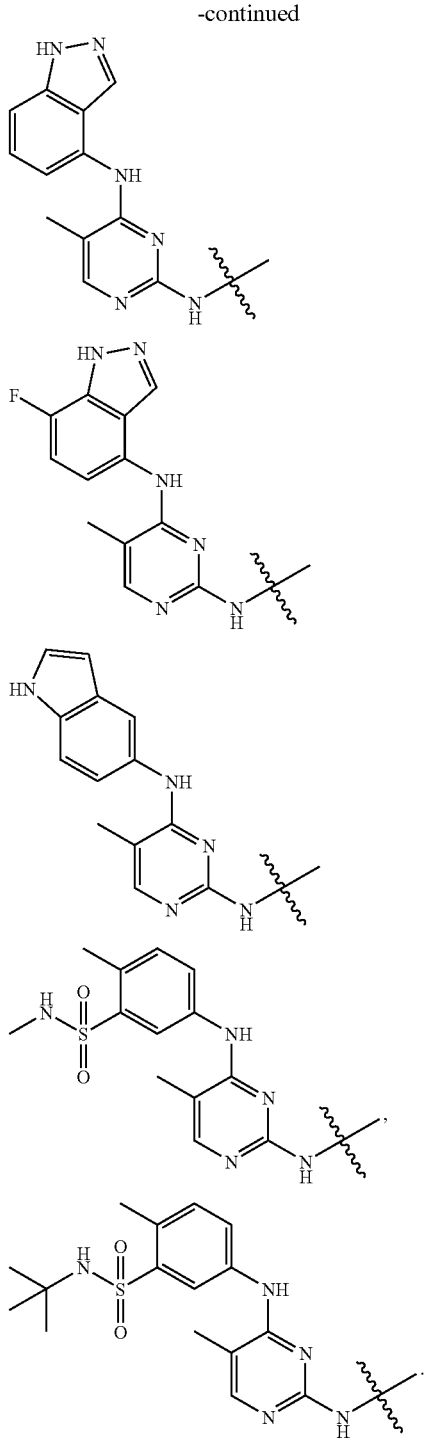
The moiety C in the structure (Z), above, includes any moiety selected from the following group:
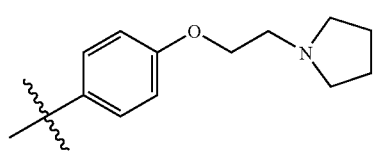

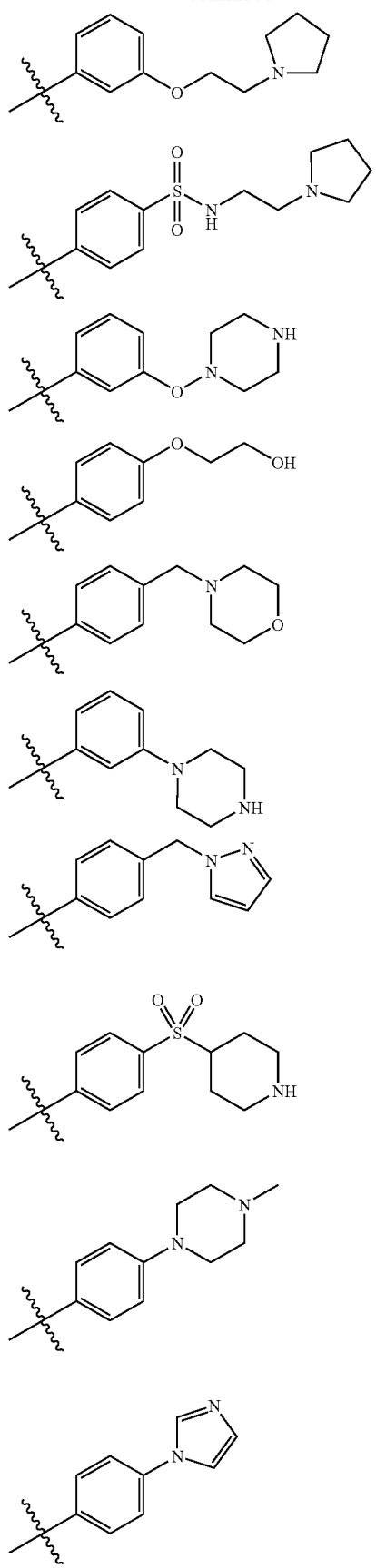
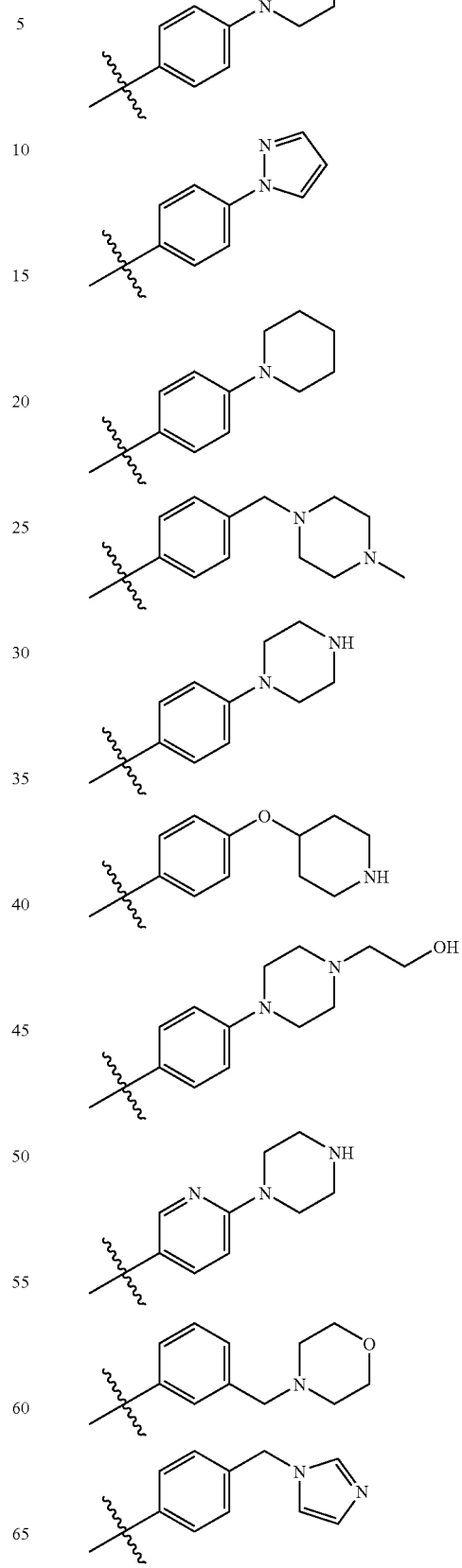

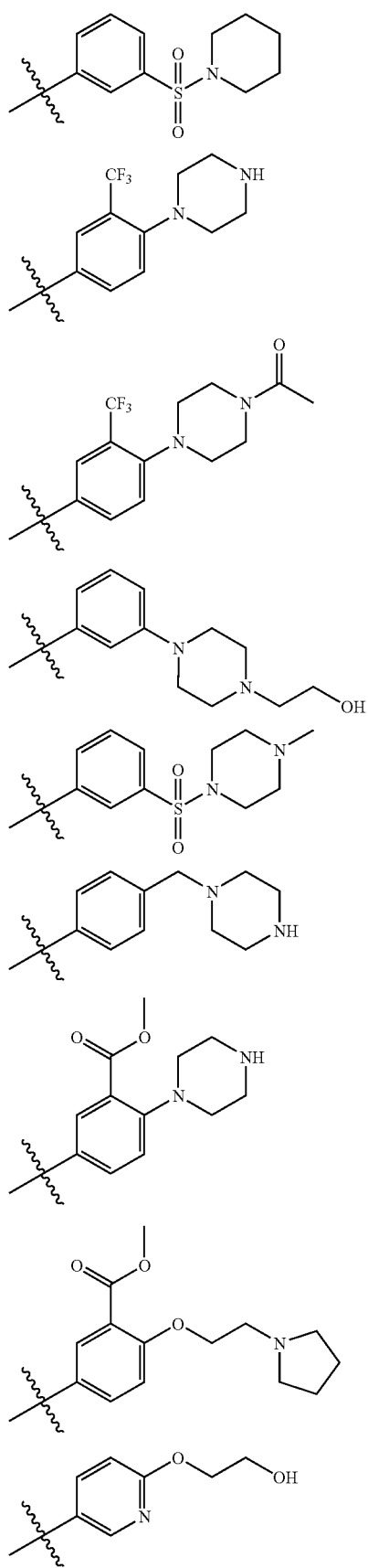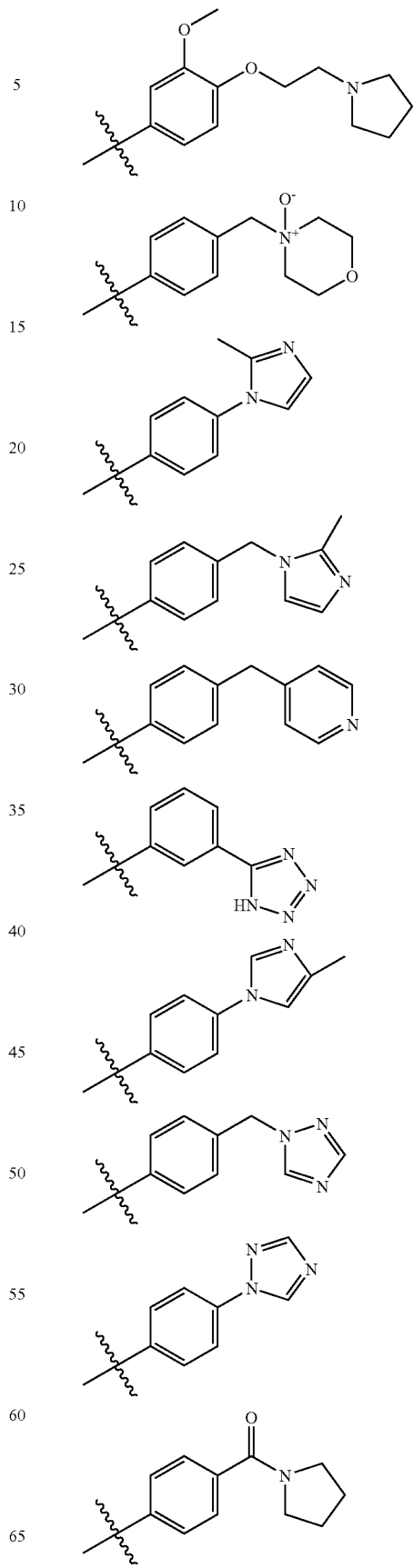

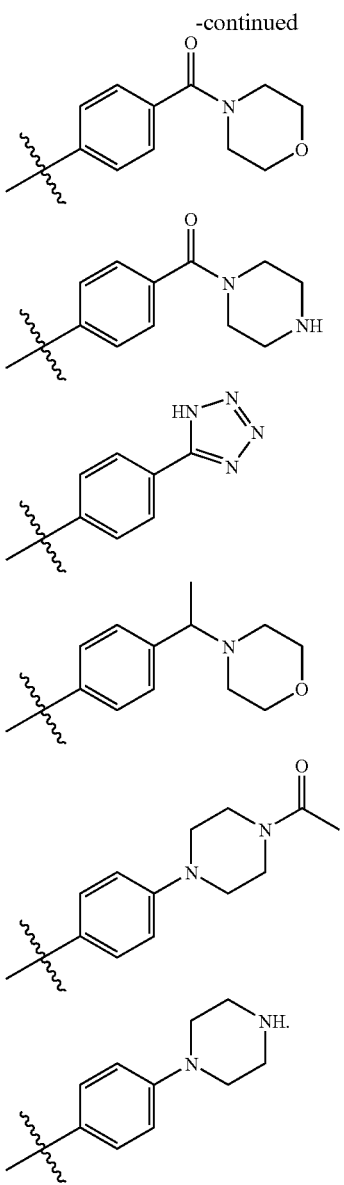

, and

The compounds and methods of the present invention, or pharmaceutically acceptable salts, hydrates, solvates, crystal forms and individual diastereomers thereof, either when administered alone or in combination with other agents (e.g., chemotherapeutic agents or protein therapeutic agents described below) are useful in treating a variety of disorders, including, but not limited to, for example, myeloproliferative disorders, proliferative diabetic retinopathy and other angiogenic-associated disorders including solid tumors and other types of cancer, eye disease, inflammation, psoriasis, and a viral infection. The kinds of cancer that can be treated include, but are not limited to, an alimentary/gastrointestinal tract cancer, colon cancer, liver cancer, skin cancer, breast cancer, ovarian cancer, prostate cancer, lymphoma, leukemia (including acute myelogenous leukemia and chronic myelogenous leukemia), kidney cancer, lung cancer, muscle cancer, bone cancer, bladder cancer or brain cancer.

Some examples of the diseases and disorders that can be treated also include ocular neovascularization, infantile haemangiomas; organ hypoxia, vascular hyperplasia, organ transplant rejection, lupus, multiple sclerosis, rheumatoid arthritis, psoriasis, Type 1 diabetes and complications from diabetes, inflammatory disease, acute pancreatitis, chronic pancreatitis, asthma, allergies, adult respiratory distress syndrome, cardiovascular disease, liver disease, other blood disorders, asthma, rhinitis, atopic, dermatitis, autoimmune thyroid disorders, ulcerative colitis, Crohn's disease, metastatic melanoma, Kaposi's sarcoma, multiple myeloma, conditions associated with cytokines, and other autoimmune diseases including glomerulonephritis, scleroderma, chronic thyroiditis, Graves' disease, autoimmune gastritis, autoimmune hemolytic anemia, autoimmune neutropenia, thrombocytopenia, atopy (e.g., allergic asthma, atopic dermatitis, or allergic rhinitis), chronic active hepatitis, myasthenia gravis, multiple sclerosis, inflammatory bowel disease, graft vs host disease, neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation.

Examples of some additional diseases and disorders that can be treated also include cell mediated hypersensitivity (allergic contact dermatitis, hypersensitivity pneumonitis), rheumatic diseases (e.g., systemic lupus erythematosus (SLE), juvenile arthritis, Sjogren's Syndrome, scleroderma, polymyositis, ankylosing spondylitis, psoriatic arthritis), viral diseases (Epstein Barr Virus, Hepatitis B, Hepatitis C, HIV, HTLV1, Vaicella-Zoster Virus, Human Papilloma Virus), food allergy, cutaneous inflammation, and immune suppression induced by solid tumors.

Embodiments of the present invention also provide articles of manufacture that can include a packaging material and a pharmaceutical composition contained within the packaging material. The packaging material can comprise a label which indicates that the pharmaceutical composition can be used for treatment of one or more disorders identified above.

The pharmaceutical composition can include a compound according to the present invention. In addition to a compound of the present invention, the pharmaceutical may also contain other therapeutic agents, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques known in the art of pharmaceutical formulation.

Thus, in one embodiment, the invention provides a pharmaceutical composition including a therapeutic agent and a compound of the invention. The compound is present in a concentration effective to treat, for example, cancer or to treat another disease or disorder described above.

The compounds of the invention may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like.

Salts of the invention can include amine salts formed by the protonation of an amino group with inorganic acids such as hydrochloric acid, hydrobromic acid, hydroiodic acid, sulfuric acid, phosphoric acid, and the like. Salts of the invention can also include amine salts formed by the protonation of an amino group with suitable organic acids, such as p-toluenesulfonic acid, acetic acid, methanesulfonic acid and the like. Additional excipients which are contemplated for use in the practice of the present invention are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs of the invention compounds are included in the present invention.

Pharmaceutical compositions of the invention may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The pharmaceutical compositions for the administration of the compounds of this embodiment, either alone or in combination with other therapeutic agents, may conveniently be presented in dosage unit form and may be prepared by any of the methods well known in the art of pharmacy. All methods include bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butanediol, polyethylene glycols, polypropylene glycols, ethanol or other alcohols, povidones, various brands of TWEEN surfactant, sodium dodecyl sulfate, sodium deoxycholate, dimethylacetamide, polysorbates, poloxamers, cyclodextrins, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles).

In one embodiment, the invention compounds are administered in combination with an anti-inflammatory agent, antihistamines, chemotherapeutic agent, immunomodulator, therapeutic antibody or a protein kinase inhibitor, e.g., a tyrosine kinase inhibitor, to a subject in need of such treatment. While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecolcine, etoposide, taxane, anthracycline antibiotic, doxorubicin, daunorubicin, caminomycin, epirubicin, idarubicin, mitoxanthrone, 4-dimethoxy-daunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methotrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.);

13) gene therapy techniques; 14) antisense therapy techniques; 15) tumor vaccines; 16) therapies directed against tumor metastases (e.g., Batimistat, etc.); and 17) inhibitors of angiogenesis.

The pharmaceutical composition and method of the present invention may further comprise other therapeutically active compounds as noted herein which are usually applied in the treatment of the above mentioned pathological conditions. Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

Other agents that may be administered in combination with invention compounds include protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay.

The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

When other therapeutic agents are employed in combination with the compounds of the present invention they may be used for example in amounts as noted in the Physician Desk Reference (PDR) or as otherwise determined by one having ordinary skill in the art.

In the treatment or prevention of conditions which involve cellular proliferation, an appropriate dosage level can generally be between about 0.01 and about 1000 mg per 1 kg of patient body weight per day which can be administered in single or multiple doses. For example, the dosage level can be between about 0.01 and about 250 mg/kg per day; more narrowly, between about 0.5 and about 100 mg/kg per day. A suitable dosage level can be between about 0.01 and about 250 mg/kg per day, between about 0.05 and about 100 mg/kg per day, or between about 0.1 and about 50 mg/kg per day, or about 1.0 mg/kg per day. For example, within this range the dosage can be between about 0.05 and about 0.5 mg/kg per day, or between about 0.5 and about 5 mg/kg per day, or between about 5 and about 50 mg/kg per day. For oral administration, the compositions can be provided in the form of tablets containing between about 1.0 and about 1,000 mg of the active ingredient, for example, about 1.0, about 5.0, about 10.0, about 15.0, about 20.0, about 25.0, about 50.0, about 75.0, about 100.0, about 150.0, about 200.0, about 250.0, about 300.0, about 400.0, about 500.0, about 600.0, about 750.0, about 800.0, about 900.0, and about 1,000.0 mg of the active ingredient for the symptomatic adjustment of the dosage to the patient to be treated. The compounds can be administered on a regimen of 1 to 4 times per day, such as once or twice per day. There may be a period of no administration followed by another regimen of administration.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Compounds of the present invention can be used, alone or in combination with an effective amount of a therapeutic antibody (or therapeutic fragment thereof), a chemotherapeutic or an immunotoxic agent, for treatment of tumors. Illustrative examples of chemotherapeutic agents that can be used for this purpose include doxorubicin, docetaxel, or taxol. It should be further understood that the invention includes combination therapy including a compound of the invention, including but not limited to vasculostatic agents, such as tyrosine, serine or threonine kinase inhibitors, and any chemotherapeutic agent or therapeutic antibody.

C. EXAMPLES

The following examples are provided to further illustrate the advantages and features of the present invention, but are not intended to limit the scope of the invention.

Example 1

General Methods

General Methods

All experiments were performed under anhydrous conditions (i.e. dry solvents) in an atmosphere of argon, except where stated, using oven-dried apparatus and employing standard techniques in handling air-sensitive materials. Aqueous solutions of sodium bicarbonate ($NaHCO_3$) and sodium chloride (brine) were saturated. Analytical thin layer chromatography (TLC) was carried out on Merck Kieselgel 60 $F_{254}$ plates with visualization by ultraviolet and/or anisaldehyde, potassium permanganate or phosphomolybdic acid dips. Reverse-phase HPLC chromatography was carried out on Gilson 215 liquid handler equipped with Waters SymmetryShield™ RP18 7 µm (40×100 mm) Prep-Pak cartridge. Mobile phase consisted of standard acetonitrile (ACN) and DI Water, each with 0.1% TFA added. Purification was carried out at a flow rate of 40 mL/min. NMR spectra: $^1$H Nuclear magnetic resonance spectra were recorded at 500 MHz. Data are presented as follows: chemical shift, multiplicity (s=singlet, d=doublet, t=triplet, q=quartet, qn=quintet, dd=doublet of doublets, m=multiplet, br s=broad singlet), coupling constant (J/Hz) and integration. Coupling constants were taken directly from the spectra and are uncorrected. Low resolution mass spectra: Electrospray (ES+) ionization was used. The protonated parent ion (M+H) or fragment of highest mass is quoted. Analytical gradient consisted of 10% ACN in water ramping up to 100% ACN over 5 min unless otherwise stated.

Example 2

N⁴-(4-Methoxy-phenyl)-pyrimidine-2,4-diamine (Intermediate 1)

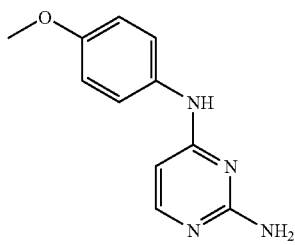

A mixture of 4-chloro-pyrimidin-2-ylamine (0.30 g, 2.3 mmol) and 4-methoxy-phenylamine (0.30 g, 2.4 mmol) were suspended in acetic acid (10 mL) and heated at 100° C. for 2 h. The mixture was allowed to cool to room temperature and acetic acid removed under reduced pressure. The residue was taken in water (20 mL) and neutralized to pH~7 with 7M of NaOH solution. The resulting solution was extracted with EtOAc (30 mL) and the organic layer separated. The organic layer was washed with brine, dried over $MgSO_4$ and filtered. The filtrate was concentrated in vacuo and the crude product purified by flash chromatography on silica gel (hexane to EtOAc) to afford the title intermediate 1 (0.23 g, 45%) as a white solid. ¹H NMR (500 MHz, DMSO-$d_6$): 3.69 (s, 3H), 5.84 (d, J=5.8 Hz, 1H), 6.79 (d, J=9.1 Hz, 2H), 7.63 (d, J=9.1 Hz, 2H), 7.78 (d, J=5.8 Hz, 1H), 8.65 (s, 1H); MS (ESI+): m/z 217 (M+H)⁺.

Example 3

N⁴-(4-Methoxy-phenyl)-N²-[4-(2-pyrrolidin-1-yl-ethoxy)-phenyl]-pyrimidine-2,4-diamine (Compound I)

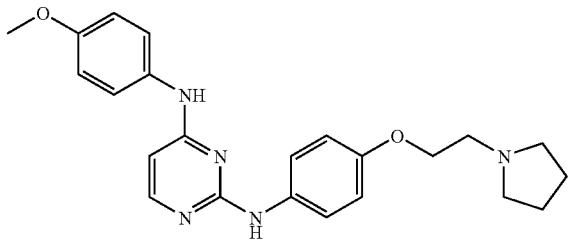

To synthesize compound I, intermediate 1 described above and intermediate 2 were used. Intermediate 2, 1-[2-(4-bromo-phenoxy)-ethyl]-pyrrolidine, shown below is available commercially, and was used as received.

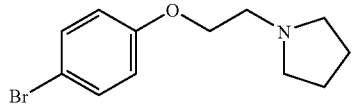

A suspension of intermediate 1 (74 mg, 0.34 mmol), intermediate 2 (0.10 g, 0.37 mmol), Pd(OAc)$_2$ (5 mg, 0.022 mmol), Xantphos (26 mg, 0.05 mmol) and potassium tert-butoxide (80 mg, 0.71 mmol) in dioxane/DMF (3/1; 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC to afford the title compound I (20 mg of TFA salt, 11%) as a brown solid. ¹H NMR (500 MHz, DMSO-$d_6$): 1.80-1.95 (m, 2H), 1.95-2.10 (m, 2H), 3.05-3.20 (m, 2H), 3.55-3.65 (m, 4H), 3.77 (s, 3H), 4.29 (t, J=4.9 Hz, 2H), 6.30 (d, J=6.8 Hz, 1H), 6.96 (d, J=8.3 Hz, 2H), 6.98 (d, J=8.3 Hz, 2H), 7.41 (d, J=8.8 Hz, 2H), 7.55 (d, J=8.8 Hz, 2H), 7.89 (d, J=6.2 Hz, 1H), 9.87 (br s, 1H), 10.22 (br s, 1H), 10.44 (br s, 1H); MS (ESI+): m/z 406 (M+H)⁺.

Example 4

4-[4-(4-Methoxy-phenylamino)-pyrimidin-2-ylamino]-N-(2-pyrrolidin-1-yl-ethyl)-benzene-sulfonamide (Compound II)

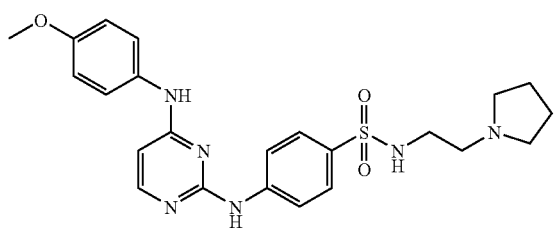

To synthesize compound II, intermediate 1 described above and intermediate 3 were used. Intermediate 3, 4-bromo-N-(2-pyrrolidin-1-yl-ethyl)-benzenesulfonamide, the formula of which is shown below, was synthesized from 4-bromophenylsulfonylchloride and 2-aminoethylpyrrolidine, using commonly known synthetic techniques.

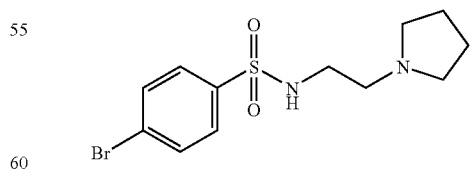

A suspension of intermediate 1 described above (70 mg, 0.32 mmol), intermediate 3 (0.12 g, 0.36 mmol), Pd(OAc)$_2$ (5 mg, 0.022 mmol), Xantphos (26 mg, 0.05 mmol) and potassium tert-butoxide (80 mg, 0.71 mmol) in dioxane/DMF (3/1; 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC to afford the title compound II (0.16 g of TFA salt, 85%) as a white solid. $^1$H NMR (500 MHz, DMSO-d$_6$): 1.80-1.95 (m, 2H), 1.95-2.05 (m, 2H), 2.95-3.05 (m, 4H), 3.23 (q, J=5.8 Hz, 2H), 3.50-3.60 (m, 2H), 3.79 (s, 3H), 6.41 (d, J=6.8 Hz, 1H), 6.99 (d, J=8.9 Hz, 2H), 7.43 (d, J=8.9 Hz, 2H), 7.71 (d, J=8.6 Hz, 2H), 7.85-7.95 (m, 2H), 7.96 (t, J=6.1 Hz, 1H), 8.02 (d, J=6.2 Hz, 1H), 9.64 (br s, 1H), 10.21 (br s, 1H), 10.71 (br s, 1H); MS (ESI+): m/z 469 (M+H)$^+$.

Example 5

4-[4-(4-Hydroxy-phenylamino)-pyrimidin-2-ylamino]-N-(2-pyrrolidin-1-yl-ethyl)-benzenesulfonamide (Compound III)

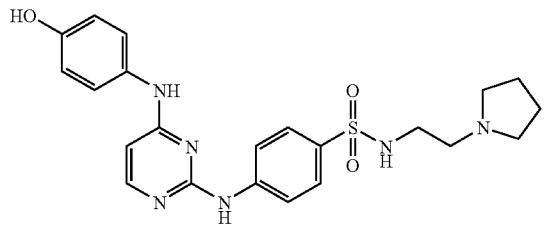

III

To a solution of compound II described above (50 mg, 0.09 mmol) in DCM (6 mL) at room temperature was added BBr$_3$ (0.1 mL) and the mixture stirred at room temperature for 2.5 h. The reaction was quenched with saturated NaHCO$_3$ solution until the pH~7 and the mixture extracted with EtOAc (30 mL). The organic layer was separated and washed with brine, dried over MgSO$_4$ and filtered. The filtrate was concentrated and the resulting solid re-dissolved in minimum of EtOAc. Hexane was added until solid crushed out and the title compound III was filtered as a white solid (25 mg, 64%) without further purification. $^1$H NMR (500 MHz, DMSO-d$_6$): 1.55-1.65 (m, 4H), 2.30-2.40 (m, 4H), 2.43 (t, J=7.0 Hz, 2H), 2.82 (t, J=6.6 Hz, 2H), 6.20 (d, J=5.8 Hz, 1H), 6.70 (d, J=8.8 Hz, 2H), 7.40 (d, J=8.6 Hz, 2H), 7.64 (d, J=8.8 Hz, 2H), 7.92 (d, J=8.4 Hz, 2H), 8.03 (d, J=5.5 Hz, 1H), 8.93 (s, 1H), 9.08 (br s, 1H), 9.70 (s, 1H);
MS (ESI+): m/z 455 (M+H)$^+$.

Example 6

4-(4-Chloro-pyrimidin-2-ylamino)-N-(2-pyrrolidin-1-yl-ethyl)-benzenesulfonamide (Intermediate 4)

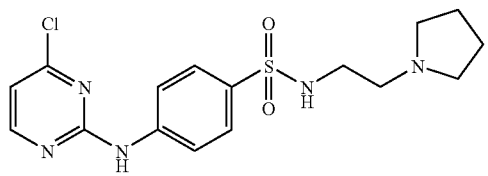

4

A mixture of 4-chloro-pyrimidin-2-ylamine (1.0 g, 7.8 mmol), above-described intermediate 3 (2.6 g, 7.8 mmol), Pd(OAc)$_2$ (90 mg, 0.40 mmol), Xantphos (0.50 g, 0.86 mmol) and potassium tert-butoxide (2.2 g, 20 mmol) were suspended in dioxane (30 mL) and heated at reflux under the argon atmosphere for 16 h. The mixture was poured into water (30 mL) and extracted with EtOAc (60 mL). The organic layer was separated and washed with brine, dried over MgSO$_4$ and filtered. The filtrate was concentrated in vacuo and the crude product purified by flash chromatography on silica gel (DCM to 25% MeOH/DCM) to afford the title intermediate 4 (0.15 g, 5%) as a brown solid. MS (ESI+): m/z 382 (M+H)$^+$.

Example 7

4-[4-(3-Methoxy-phenylamino)-pyrimidin-2-ylamino]-N-(2-pyrrolidin-1-yl-ethyl)-benzenesulfonamide (Compound IV)

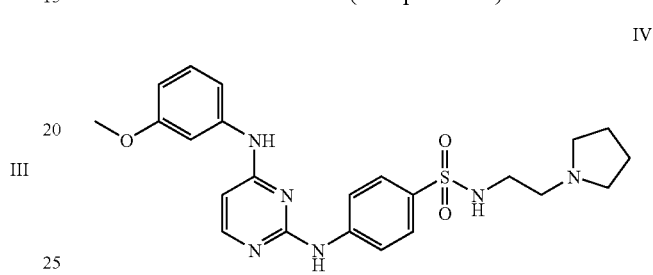

IV

A mixture of the above described intermediate 4 (0.10 g, 0.26 mmol) and 3-methoxy-phenylamine (0.05 mL, 0.45 mmol) were suspended in acetic acid (6 mL) and heated at 100° C. for 1.5 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO$_4$ and filtered. The filtrate was concentrated in vacuo and the crude product purified by HPLC to afford the title compound IV (55 mg of TFA salt, 36%) as a white solid. $^1$H NMR (500 MHz, DMSO-d$_6$): 1.80-1.90 (m, 2H), 1.95-2.05 (m, 2H), 2.95-3.05 (m, 4H), 3.24 (q, J=6.0 Hz, 2H), 3.50-3.60 (m, 2H), 3.73 (s, 3H), 6.40 (d, J=6.3 Hz, 1H), 6.68 (d, J=7.3 Hz, 1H), 7.18 (d, J=8.2 Hz, 1H), 7.26 (t, J=8.0 Hz, 1H), 7.30 (s, 1H), 7.72 (d, J=8.9 Hz, 2H), 7.91 (t, J=6.1 Hz, 1H), 7.95 (d, J=8.7 Hz, 2H), 8.10 (d, J=6.2 Hz, 1H), 9.59 (br s, 1H), 9.87 (br s, 1H), 10.38 (br s, 1H); MS (ESI+): m/z 469 (M+H)$^+$.

Example 8

4-[4-(3-Hydroxy-phenylamino)-pyrimidin-2-ylamino]-N-(2-pyrrolidin-1-yl-ethyl)-benzenesulfonamide (Compound V)

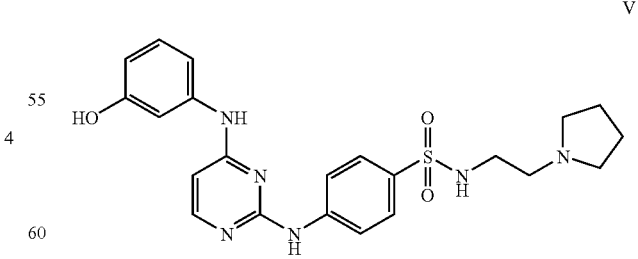

V

To a solution of the above-described compound IV (30 mg, 0.05 mmol) in DCM (6 mL) at room temperature was added BBr$_3$ (0.1 mL) and the mixture stirred at room temperature for 2.5 h. The reaction was quenched with saturated NaHCO$_3$ solution until the pH~7 and the mixture extracted with EtOAc (30 mL). The organic layer was separated and washed with brine, dried over MgSO₄ and filtered. The filtrate was concentrated and the residue purified by HPLC to afford the title compound V (13 mg of TFA salt, 46%) as an off white solid. $^1$H NMR (500 MHz, DMSO-d₆): 1.80-1.90 (m, 2H), 1.95-2.05 (m, 2H), 2.95-3.05 (m, 4H), 3.20-3.30 (m, 2H), 6.39 (d, J=6.3 Hz, 1H), 6.53 (d, J=7.2 Hz, 1H), 7.01 (d, J=9.2 Hz, 1H), 7.09 (s, 1H), 7.14 (t, J=8.1 Hz, 1H), 7.73 (d, J=8.8 Hz, 2H), 7.90 (t, J=6.2 Hz, 1H), 7.97 (d, J=8.8 Hz, 2H), 8.08 (d, J=6.4 Hz, 1H), 9.48 (br s, 1H), 9.57 (br s, 1H), 9.86 (br s, 1H), 10.41 (br s, 1H); MS (ESI+): m/z 455 (M+H)⁺.

Example 9

Benzo[1,3]dioxol-5-yl-(2-chloro-5-methyl-pyrimidin-4-yl)-amine (Intermediate 5)

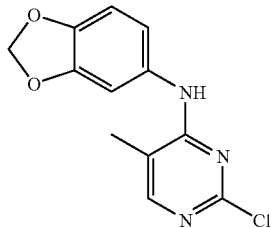

A mixture of 2-chloro-5-methyl-pyrimidin-4-ylamine (0.30 g, 2.1 mmol), 5-bromo-benzo[1,3]dioxole (0.45 g, 2.2 mmol), Pd(OAc)₂ (30 mg, 0.13 mmol), Xantphos (0.15 g, 0.26 mmol) and potassium tert-butoxide (0.45 g, 4.0 mmol) were suspended in dioxane (15 mL) and heated at reflux under the argon atmosphere for 16 h. The reaction mixture was cooled to room temperature and diluted with DCM (20 mL). The mixture was filtered and the filtrate concentrated in vacuo. The residue was purified by flash chromatography on silica gel (hexane to 50% EtOAc/hexane) to afford the title intermediate 5 (0.10 g, 18%) as a white solid. MS (ESI+): m/z 264 (M+H)⁺.

Example 10

N⁴-Benzo[1,3]dioxol-5-yl-5-methyl-N²-[4-(2-pyrrolidin-1-yl-ethoxy)-phenyl]-pyrimidine-2,4-diamine (Compound VI)

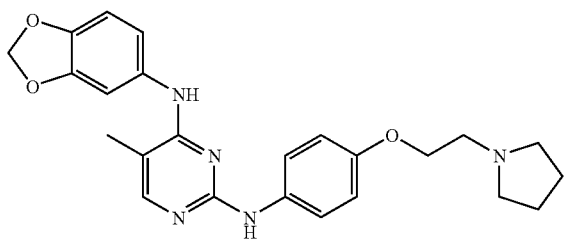

To synthesize compound VI, intermediate 5 described above and intermediate 6 were used. Intermediate 6, 4-(2-pyrrolidin-1-yl-ethoxy)-phenylamine, the formula of which is shown below, was synthesized in two steps, first by alkylation of 4-nitrophenol using 2-chloroethylpyrrolidine, followed by reduction to yield the aniline derivative.

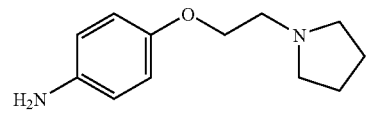

Commonly known synthetic techniques were used to synthesize intermediate 6. A mixture of the above-described intermediate 5 (90 mg, 0.34 mmol), intermediate 6 (95 mg, 0.46 mmol), Pd₂(dba)₃ (20 mg, 0.02 mmol), Xantphos (30 mg, 0.05 mmol) and cesium carbonate (0.30 g, 0.9 mmol) were suspended in dioxane (10 mL) and heated at reflux under the argon atmosphere for 20 h. The reaction mixture was cooled to room temperature and diluted with DCM (20 mL). The mixture was filtered and the filtrate concentrated in vacuo. The residue was purified by HPLC to afford the title compound VI (40 mg of TFA salt, 21%) as a brown solid. $^1$H NMR (500 MHz, DMSO-d₆): 1.85-1.95(m, 2H), 1.95-2.05 (m, 2H), 2.13 (s, 3H), 3.10-3.20 (m, 2H), 4.26 (t, J=5.0 Hz, 2H), 6.07 (s, 2H), 6.90-7.00 (m, 4H), 7.19 (s, 1H), 7.37 (d, J=9.0 Hz, 2H), 7.84 (s, 1H), 9.60 (br s, 1H), 9.89 (br s, 1H), 10.32 (br s, 1H); MS (ESI+): m/z 434 (M+H)⁺.

Example 11

(4-Chloro-3-methoxy-phenyl)-(2-chloro-5-methyl-pyrimidin-4-yl)-amine (Intermediate 7)

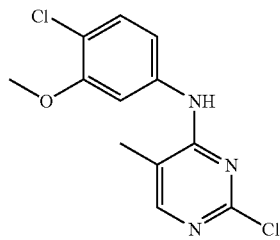

A mixture of 2-chloro-5-methyl-pyrimidin-4-ylamine (0.50 g, 3.5 mmol), 4-bromo-1-chloro-2-methoxy-benzene (0.65 mL, 4.8 mmol), Pd₂(dba)₃ (0.17 g, 0.19 mmol), Xantphos (0.22 g, 0.38 mmol) and cesium carbonate (2.3 g, 7.1 mmol) were suspended in dioxane (20 mL) and heated at reflux under the argon atmosphere for 5 h. The reaction mixture was cooled to room temperature and diluted with DCM (30 mL). The mixture was filtered and the filtrate concentrated in vacuo. The residue was purified by flash chromatography on silica gel (hexane to 40% EtOAc/hexane) to afford the title intermediate 7 (0.55 g, 55%) as a yellow solid. $^1$H NMR (500 MHz, DMSO-d₆): 2.18 (s, 3H), 3.85 (s, 3H), 7.35

(dd, J=8.6 Hz, J=2.3 Hz, 1H), 7.39 (d, J=8.7 Hz, 1H), 7.56 (d, J=2.3 Hz, 1H), 8.09 (d, J=0.9 Hz, 1H), 8.91 (s, 1H); MS (ESI+): m/z 284 (M+H)+.

Example 12

(4-Chloro-3-methoxy-phenyl)-(2-chloro-5-methyl-pyrimidin-4-yl)-methyl-amine (Intermediate 8)

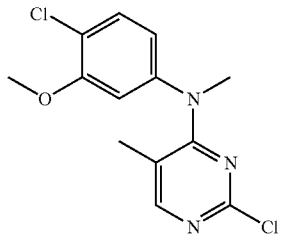

8

A suspension of intermediate 7 (0.50 g, 1.8 mmol) and sodium hydride (60% in mineral oil, 0.15 g, 3.8 mmol) in THF (10 mL) was stirred under the argon atmosphere at 0° C. for 5 min. Methyl iodide (0.15 mL, 2.4 mmol) was syringed at the same temperature to the above mixture. The resulting solution was stirred from 0° C. to room temperature over 15 min and further stirred at room temperature for additional 17 h. The reaction was quenched with water (10 mL) and then extracted with EtOAc (30 mL). The organic layer was separated and washed with brine, dried over MgSO4 and filtered. The filtrate was concentrated and the residue purified by flash chromatography on silica gel (hexane to 20% EtOAc/hexane) to afford the title intermediate 8 (0.20 g, 38%) as a white solid. MS (ESI+): m/z 298 (M+H)+.

Example 13

$N^2$-(4-(2-(pyrrolidin-1-yl)ethoxy)phenyl)-$N^4$-(4-chloro-3-methoxyphenyl)-$N^4$,5-dimethylpyrimidine-2,4-diamine (Compound VII)

VII

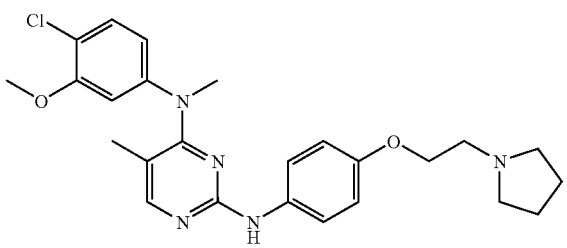

A mixture of intermediate 8 (0.15 g, 0.49 mmol) and intermediate 6 (0.15 g, 0.73 mmol), each of which intermediates is described above, were suspended in acetic acid (8 mL) and heated at 100° C. for 17 h. The mixture was allowed to cool to room temperature and acetic acid removed under reduced pressure. The residue was taken in water (15 mL) and neutralized to pH~7 with 7M of NaOH solution. The resulting solution was extracted with EtOAc (30 mL) and the organic layer separated. The organic layer was washed with brine, dried over MgSO4 and filtered. The filtrate was concentrated in vacuo and the crude product purified by HPLC to afford the title compound VII (0.14 g of TFA salt, 49%) as a white solid. 1H NMR (500 MHz, DMSO-d6): 1.85-1.95 (m, 2H), 2.00-2.10 (m, 2H), 3.08-3.18 (m, 2H), 3.46 (s, 3H), 3.55-3.65 (m, 4H), 3.85 (s, 3H), 4.27 (t, J=5.0 Hz, 2H), 6.86 (d, J=7.4 Hz, 1H), 7.01 (d, J=9.0 Hz, 2H), 7.15 (s, 1H), 7.46 (d, J=8.4 Hz, 1H), 7.58 (d, J=8.9 Hz, 2H), 7.83 (s, 1H), 9.85 (br s, 1H), 10.04 (br s, 1H), 10.32 (br s, 1H); MS (ESI+): m/z 468 (M+H)+.

Example 14

(2-Chloro-5-methyl-pyrimidin-4-yl)-(4-chloro-phenyl)-amine (Intermediate 9)

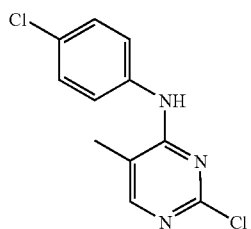

9

A mixture of 2-chloro-5-methyl-pyrimidin-4-ylamine (0.30 g, 2.1 mmol), 1-bromo-4-chloro-benzene (0.60 g, 3.1 mmol), Pd2(dba)3 (95 mg, 0.10 mmol), Xantphos (0.12 g, 0.20 mmol) and cesium carbonate (1.3 g, 4.0 mmol) were suspended in dioxane (20 mL) and heated at reflux under the argon atmosphere for 4 h. The reaction mixture was cooled to room temperature and diluted with DCM (20 mL). The mixture was filtered and the filtrate concentrated in vacuo. The residue was purified by flash chromatography on silica gel (hexane to 30% EtOAc/hexane) to afford the title intermediate 9 (0.15 g, 28%) as a pale yellow solid. MS (ESI+): m/z 254 (M+H)+.

Example 15

$N^4$-(4-Chloro-phenyl)-5-methyl-$N^2$-[4-(2-pyrrolidin-1-yl-ethoxy)-phenyl]-pyrimidine-2,4-diamine (Compound VIII)

VIII

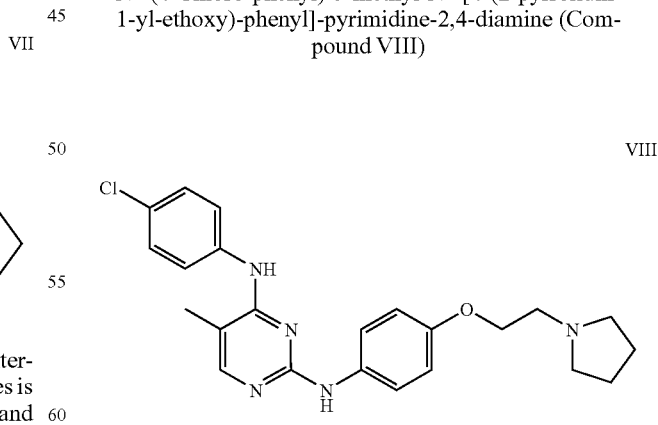

A mixture of the above-described intermediates 9 (0.15 g, 0.60 mmol) and 6 (0.20 g, 0.97 mmol) was suspended in acetic acid (8 mL) and heated at 100° C. for 6 h. The mixture was allowed to cool to room temperature and acetic acid removed under reduced pressure. The residue was taken in water (15 mL) and neutralized to pH~7 with 7M of NaOH solution. The resulting brown solid was filtered and further purified by HPLC to afford the title compound VIII (38 mg of TFA salt, 12%) as a brown oil. $^1$H NMR (500 MHz, DMSO-d$_6$): 1.80-1.95 (m, 2H), 2.00-2.10 (m, 2H), 2.15 (s, 3H), 3.10-3.20(m, 2H), 3.55-3.65 (m, 4H), 3.77 (s, 3H), 4.28 (t, J=5.0 Hz, 2H), 6.95 (d, J=9.0 Hz, 2H), 7.38 (d, J=8.9 Hz, 2H), 7.42 (d, J=8.9 Hz, 2H), 7.62 (d, J=8.8 Hz, 2H), 7.90 (s, 1H), 9.48 (br s, 1H), 9.84 (br s, 1H), 10.10 (br s, 1H); MS (ESI+): m/z 424 (M+H)$^+$.

Example 16

2-(4-Amino-phenoxy)-ethanol (Intermediate 10)

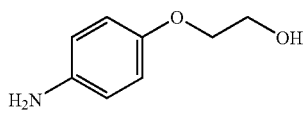

A solution of 2-(4-nitro-phenoxy)-ethanol (2.1 g, 12 mmol) in MeOH (30 mL) was flushed with argon and then charged with Pd/C (10% by wt). The mixture was evacuated under house vacuum and then refilled with hydrogen from hydrogen balloon. The cycle was repeated again and the mixture stirred at room temperature for 2 h. The heterogeneous reaction mixture was filtered through a pad of Celite, washed with MeOH and concentrated in vacuo to furnish the title intermediate 10 (1.8 g, 99%) as a brown solid. MS (ESI+): m/z 154 (M+H)$^+$.

Example 17

2-{4-[4-(4-Chloro-3-methoxy-phenylamino)-5-methyl-pyrimidin-2-ylamino]-phenoxy}-ethanol (Compound IX)

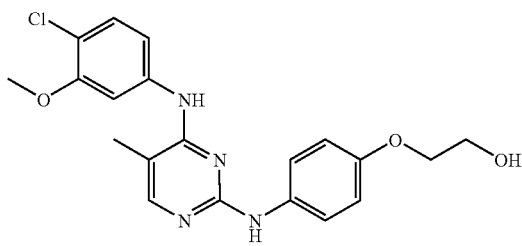

A suspension of the above described intermediates 7 (50 mg, 0.17 mmol), 10 (40 mg, 0.26 mmol), Pd$_2$(dba)$_2$ (8 mg, 0.01 mmol), Xantphos (10 mg, 0.02 mmol) and cesium carbonate (0.13 g, 0.40 mmol) in dioxane (3 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by flash chromatography on silica gel (hexane to EtOAc) to afford the title compound IX (14 mg, 21%) as a light brown solid. $^1$H NMR (500 MHz, DMSO-d$_6$): 2.10 (s, 3H), 3.69 (t, J=5.3 Hz, 2H), 3.75 (s, 3H), 3.92 (t, J=5.1 Hz, 2H), 4.83 (t, J=5.6 Hz, 1H), 6.78 (d, J=9.0 Hz, 2H), 7.29 (d, J=8.5 Hz, 1H), 7.43 (dd, J=8.6 Hz, J=2.2 Hz, 1H), 7.48 (d, J=2.3 Hz, 1H), 7.52 (d, J=9.0 Hz, 2H), 7.88 (s, 1H), 8.31 (s, 1H), 8.80 (s, 1H); MS (ESI+): m/z 401 (M+H)$^+$.

Example 18

5-Methyl-N$^2$-[4-(2-pyrrolidin-1-yl-ethoxy)-phenyl]-pyrimidine-2,4-diamine (Intermediate 11)

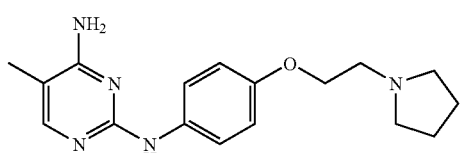

A mixture of 2-chloro-5-methyl-pyrimidin-4-ylamine (0.13 g, 0.87 mmol) and the above described intermediate 6 (0.30 g, 1.5 mmol) were suspended in acetic acid (8 mL) and heated at 100° C. for 2 h. The mixture was allowed to cool to room temperature and acetic acid removed under reduced pressure. The residue was taken in water (15 mL) and neutralized to pH~7 with 7M of NaOH solution. The resulting solid was filtered (30 mg) and washed with ether. The filtrate was extracted with EtOAc (30 mL) and the organic layer separated. The organic layer was washed with brine, dried over MgSO$_4$ and filtered. The filtrate was concentrated to afford the additional solid (0.2 g), which were combined with the first batch and afforded the title intermediate 11 (0.23 g, 85%) as a light brown solid. $^1$H NMR (500 MHz, DMSO-d$_6$): 1.65-1.70 (m, 4H), 1.89 (s, 3H), 2.74 (t, J=6.0 Hz, 2H), 3.98 (t, J=6.1 Hz, 2H), 6.30 (s, 2H), 6.78 (d, J=9.1 Hz, 2H), 7.62 (d, J=9.1 Hz, 2H), 7.64 (s, 1H), 8.50 (s, 1H); MS (ESI+): m/z 314 (M+H)$^+$.

Example 19

5-Methyl-N$^4$-phenyl-N$^2$-[4-(2-pyrrolidin-1-yl-ethoxy)-phenyl]-pyrimidine-2,4-diamine (Compound X)

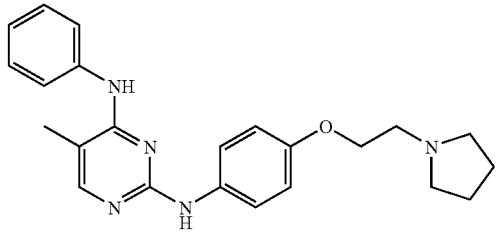

A suspension of the above-described intermediate 11 (25 mg, 0.08 mmol), bromobenzene (0.05 mL, 0.50 mmol), Pd$_2$(dba)$_2$ (5 mg, 0.006 mmol), Xantphos (10 mg, 0.02 mmol) and cesium carbonate (70 mg, 0.21 mmol) in dioxane (3 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by flash chromatography on silica gel (DCM to 30% MeOH/DCM) to afford the title compound X (10 mg, 32%) as a light brown solid. $^1$H NMR (500 MHz, DMSO-$d_6$): 1.65-1.72 (m, 4H), 2.10 (s, 3H), 2.48-2.58 (m, 4H), 2.75-2.82 (m, 2H), 4.00 (t, J=5.9 Hz, 2H), 6.77 (d, J=9.0 Hz, 2H), 7.04 (t, J=7.3 Hz, 1H), 7.32 (t, J=7.9 Hz, 2H), 7.54 (d, J=9.0 Hz, 2H), 7.71 (d, J=7.8 Hz, 2H), 7.84 (s, 1H), 8.20 (s, 1H), 8.76 (s, 1H); MS (ESI+): m/z 390 (M+H)$^+$.

Example 20

(4-Chloro-3-fluoro-phenyl)-(2-chloro-5-methyl-pyrimidin-4-yl)-amine (Intermediate 12)

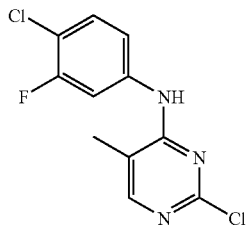

A mixture of 2-chloro-5-methyl-pyrimidin-4-ylamine (0.50 g, 3.5 mmol), 4-Bromo-1-chloro-2-fluoro-benzene (1.0 g, 4.8 mmol), Pd$_2$(dba)$_3$ (0.16 g, 0.17 mmol), Xantphos (0.20 g, 0.34 mmol) and cesium carbonate (2.3 g, 7.0 mmol) were suspended in dioxane (25 mL) and heated at reflux under the argon atmosphere for 15 h. The reaction mixture was cooled to room temperature and diluted with DCM (30 mL). The mixture was filtered and the filtrate concentrated in vacuo. The residue was purified by flash chromatography on silica gel (hexane to 40% EtOAc/hexane) to afford the title intermediate 12 (0.75 g, 80%) as an off white solid. MS (ESI+): m/z 272 (M+H)$^+$.

Example 21

$N^4$-(4-Chloro-3-fluoro-phenyl)-5-methyl-$N^2$-[4-(2-pyrrolidin-1-yl-ethoxy)-phenyl]-pyrimidine-2,4-diamine (Compound XI)

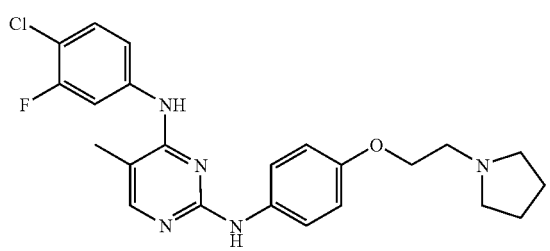

A mixture of the above-described intermediates 12 (0.20 g, 0.74 mmol) and 6 (0.20 g, 0.97 mmol) was suspended in acetic acid (8 mL) and heated at 100° C. for 6 h. The mixture was allowed to cool to room temperature and acetic acid removed under reduced pressure. The residue was taken in water (15 mL) and neutralized to pH~7 with 7M of NaOH solution. The resulting solution was extracted with EtOAc (30 mL) and the organic layer separated. The organic layer was washed with brine, dried over MgSO$_4$ and filtered. The filtrate was concentrated in vacuo and the crude product purified by flash chromatography on silica gel (DCM to 30% MeOH/DCM) to afford the title compound XI (90 mg, 28%) as a white solid. $^1$H NMR (500 MHz, DMSO-$d_6$): 1.65-1.71 (m, 4H), 2.10 (s, 3H), 2.45-2.55 (m, 4H), 2.77 (t, J=6.0 Hz, 2H), 4.01 (t, J=6.0 Hz, 2H), 6.82 (d, J=9.0 Hz, 2H), 7.44 (t, J=8.8 Hz, 1H), 7.50 (d, J=9.0 Hz, 2H), 7.55 (dd, J=8.9 Hz, J=2.0 Hz, 1H), 7.91 (s, 1H), 8.07 (dd, J=12.5 Hz, J=2.0 Hz, 1H), 8.43 (s, 1H), 8.90 (s, 1H); MS (ESI+): m/z 442 (M+H)$^+$.

Example 22

$N^4$-(4-Chloro-3-methoxy-phenyl)-5-methyl-$N^2$-(4-morpholin-4-ylmethyl-phenyl)-pyrimidine-2,4-diamine (Compound XII)

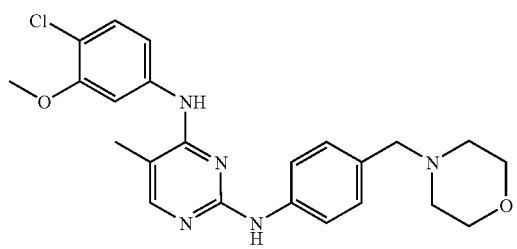

A suspension of the above-described intermediate 7 (50 mg, 0.17 mmol), 4-morpholin-4-ylmethyl-phenylamine (50 mg, 0.26 mmol), Pd$_2$(dba)$_2$ (8 mg, 0.009 mmol), Xantphos (10 mg, 0.02 mmol) and cesium carbonate (0.13 g, 0.40 mmol) in dioxane (3 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC to afford the title compound XII (40 mg of TFA salt, 43%) as a pale yellow solid. $^1$H NMR (500 MHz, DMSO-$d_6$): 2.16 (s, 3H), 3.05-3.15 (m, 2H), 3.10-3.20 (m, 2H), 3.60-3.70 (m, 2H), 3.90-4.00 (m, 2H), 4.28 (s, 2H), 4.01 (t, J=6.0 Hz, 2H), 7.25-7.35 (m, 3H), 7.35-7.41 (m, 2H), 7.65 (d, J=8.3 Hz, 2H), 7.98 (s, 1H), 9.10 (br s, 1H), 9.86 (br s, 1H), 9.95 (br s, 1H); MS (ESI+): m/z 440 (M+H)$^+$.

Example 23

Benzo[b]thiophen-5-yl-(2-chloro-5-methyl-pyrimidin-4-yl)-amine (Intermediate 13)

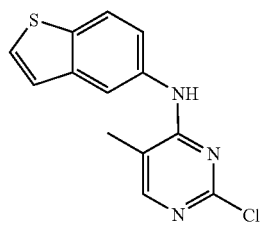

A mixture of 2-chloro-5-methyl-pyrimidin-4-ylamine (0.30 g, 2.1 mmol), 5-bromo-benzo[b]thiophene (0.6 g, 2.8 mmol), Pd$_2$(dba)$_3$ (95 mg, 0.10 mmol), Xantphos (0.12 g, 0.20 mmol) and cesium carbonate (1.3 g, 4.0 mmol) was suspended in dioxane (25 mL) and heated at reflux under the argon atmosphere for 3 h. The reaction mixture was cooled to room temperature and diluted with DCM (30 mL). The mixture was filtered and the filtrate concentrated in vacuo. The residue was purified by flash chromatography on silica gel (hexane to 30% EtOAc/hexane) to afford the title intermediate 13 (0.23 g, 40%) as a white solid. MS (ESI+): m/z 276 (M+H)$^+$.

Example 24

N$^4$-Benzo[b]thiophen-5-yl-5-methyl-N$^2$-[4-(2-pyrrolidin-1-yl-ethoxy)-phenyl]-pyrimidine-2,4-diamine (Compound XIII)

XIII

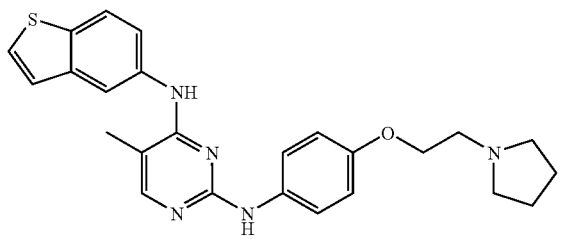

A mixture of the above-described intermediates 13 (0.23 g, 0.83 mmol) and 6 (0.35 g, 1.7 mmol) were suspended in acetic acid (8 mL) and heated at 100° C. for 1 d. The mixture was allowed to cool to room temperature and acetic acid removed under reduced pressure. The residue was taken in water (15 mL) and neutralized to pH~7 with 7M of NaOH solution. The resulting solution was extracted with EtOAc (30 mL) and the organic layer separated. The organic layer was washed with brine, dried over MgSO$_4$ and filtered. The filtrate was concentrated in vacuo and the crude product purified by flash chromatography on silica gel (DCM to 15% MeOH/DCM) to afford the title compound XIII (0.13 g, 35%) as a white solid. $^1$H NMR (500 MHz, DMSO-d$_6$): 1.65-1.75(m, 4H), 2.12 (s, 3H), 2.50-2.62 (m, 4H), 2.75-2.85 (m, 2H), 3.99 (t, J=5.9 Hz, 2H), 6.70 (d, J=9.0 Hz, 2H), 7.36 (d, J=5.4 Hz, 1H), 7.51 (d, J=9.1 Hz, 2H), 7.61 (dd, J=8.7 Hz, J=2.0 Hz, 1H), 7.74 (d, J=5.4 Hz, 1H), 7.85 (d, J=0.8 Hz, 1H), 7.92 (d, J=8.6 Hz, 1H), 8.29 (d, J=1.7 Hz, 1H), 8.34 (s, 1H), 8.76 (s, 1H); MS (ESI+): m/z 446 (M+H)$^+$.

Example 25

Benzo[b]thiophen-3-yl-(2-chloro-5-methyl-pyrimidin-4-yl)-amine (Intermediate 14)

14

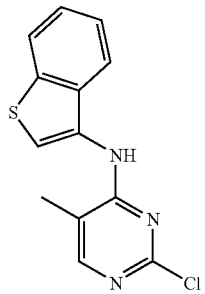

A mixture of 2-chloro-5-methyl-pyrimidin-4-ylamine (0.30 g, 2.1 mmol), 3-bromo-benzo[b]thiophene (0.6 g, 2.8 mmol), Pd$_2$(dba)$_3$ (95 mg, 0.10 mmol), Xantphos (0.12 g, 0.20 mmol) and cesium carbonate (1.3 g, 4.0 mmol) were suspended in dioxane (25 mL) and heated at reflux under the argon atmosphere for 3 h. The reaction mixture was cooled to room temperature and diluted with DCM (30 mL). The mixture was filtered and the filtrate concentrated in vacuo. The residue was purified by flash chromatography on silica gel (hexane to 30% EtOAc/hexane) to afford the title intermediate 14 (65 mg, 11%) as a yellow solid. MS (ESI+): m/z 276 (M+H)$^+$.

Example 26

N$^4$-Benzo[b]thiophen-3-yl-5-methyl-N$^2$-[4-(2-pyrrolidin-1-yl-ethoxy)-phenyl]-pyrimidine-2,4-diamine (Compound XIV)

XIV

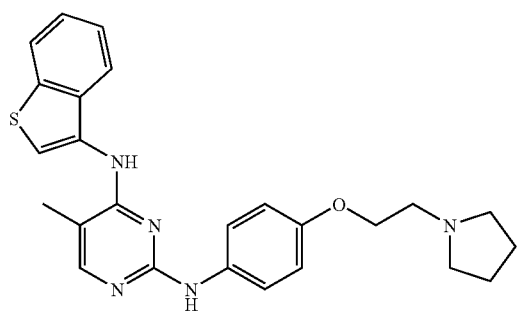

A mixture of the above-described intermediates 14 (50 mg, 0.18 mmol) and 6 (0.10 g, 0.48 mmol) was suspended in acetic acid (8 mL) and heated at 100° C. for 15 h. The mixture was allowed to cool to room temperature and acetic acid removed under reduced pressure. The residue was taken in water (10 mL) and neutralized to pH~7 with 7M of NaOH solution. The resulting solution was extracted with EtOAc (20 mL) and the organic layer separated. The organic layer was washed with brine, dried over MgSO$_4$ and filtered. The filtrate was concentrated in vacuo and the crude product purified by flash chromatography on silica gel (DCM to 15% MeOH/DCM) to afford the title compound XIV (10 mg, 13%) as an off white solid. $^1$H NMR (500 MHz, DMSO-d$_6$): 1.70-1.80 (m, 4H), 2.19 (s, 3H), 2.65-2.80 (m, 4H), 2.85-3.00 (m, 2H), 3.98-4.03 (m, 2H), 6.63 (d, J=8.8 Hz, 2H), 7.37 (d, J=8.6 Hz, 2H), 7.38-7.45 (m, 2H), 7.79-7.83 (m, 1H), 7.87 (s, 1H), 7.90-8.03 (m, 1H), 8.33 (s, 1H), 8.78 (s, 1H); MS (ESI+): m/z 446 (M+H)$^+$.

Example 27

(2-Chloro-5-methyl-pyrimidin-4-yl)-(3-chloro-phenyl)-amine (Intermediate 15)

15

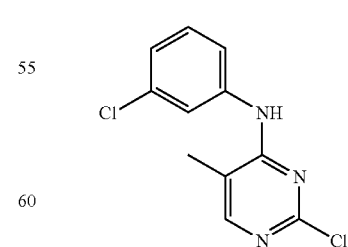

A mixture of 2-chloro-5-methyl-pyrimidin-4-ylamine (0.30 g, 2.1 mmol), 1-bromo-3-chloro-benzene (0.60 g, 3.1 mmol), Pd$_2$(dba)$_3$ (95 mg, 0.10 mmol), Xantphos (0.12 g, 0.20 mmol) and cesium carbonate (1.3 g, 4.0 mmol) was suspended in dioxane (20 mL) and heated at reflux under the argon atmosphere for 4 h. The reaction mixture was cooled to room temperature and diluted with DCM (20 mL). The mixture was filtered and the filtrate concentrated in vacuo. The residue was purified by flash chromatography on silica gel (hexane to 40% EtOAc/hexane) to afford the title intermediate 15 (0.30 g, 56%) as a pale yellow solid. MS (ESI+): m/z 254 (M+H)+.

Example 28

$N^4$-(3-Chloro-phenyl)-5-methyl-$N^2$-[4-(2-pyrrolidin-1-yl-ethoxy)-phenyl]-pyrimidine-2,4-diamine (Compound XV)

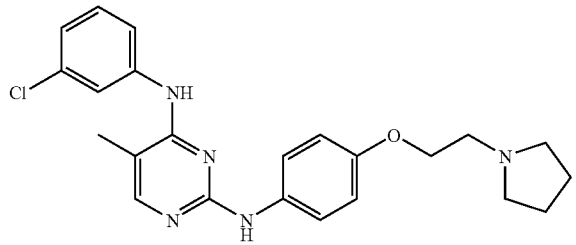

XV

A mixture of the above-described intermediates 15 (0.15 g, 0.59 mmol) and 6 (0.25 g, 1.2 mmol) was suspended in acetic acid (8 mL) and heated at 100° C. for 21 h. The mixture was allowed to cool to room temperature and acetic acid removed under reduced pressure. The residue was taken in water (15 mL) and neutralized to pH~7 with 7M of NaOH solution. The resulting solution was extracted with EtOAc (30 mL) and the organic layer separated. The organic layer was washed with brine, dried over MgSO4 and filtered. The filtrate was concentrated in vacuo and the crude product purified by flash chromatography on silica gel (DCM to 10% MeOH/DCM) to afford the title compound XV (60 mg, 24%) as a white solid. $^1$H NMR (500 MHz, DMSO-$d_6$): 1.65-1.72(m, 4H), 2.10 (s, 3H), 2.50-2.60 (m, 4H), 2.78-2.83 (m, 2H), 4.01 (t, J=5.9 Hz, 2H), 6.81 (d, J=9.1 Hz, 2H), 7.05-7.08 (m, 1H), 7.32 (t, J=8.1 Hz, 1H), 7.52 (d, J=9.0 Hz, 2H), 7.71 (d, J=8.3 Hz, 1H), 7.85 (t, J=2.1 Hz, 1H), 7.89 (d, J=0.7 Hz, 1H), 8.33 (s, 1H), 8.86 (s, 1H); MS (ESI+): m/z 424 (M+H)+.

Example 29

3-Bromo-N-methyl-benzamide (Intermediate 16)

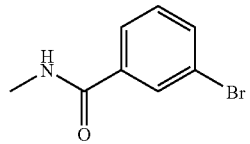

16

A solution of 3-bromo-benzoyl chloride (2.93 g, 13.3 mmol, 1 eq) in 30 mL THF was stirred vigorously and treated with 2.0M methylamine in THF (15 mL, 29.4 mmol, 2.2 eq). A white precipitate was observed and the reaction was allowed to stir for 20 minutes. Reaction was then poured onto ethyl acetate (100 mL) and washed with water (2×150 mL) and brine (1×150 mL). Organic phase cut from aqueous phase and dried over sodium sulfate, filtered and evaporated to afford the title intermediate 16 as a white powder. (2.29 g, 82% yield).

Example 30

3-(2-Chloro-5-methyl-pyrimidin-4-ylamino)-N-methyl-benzamide (Intermediate 17)

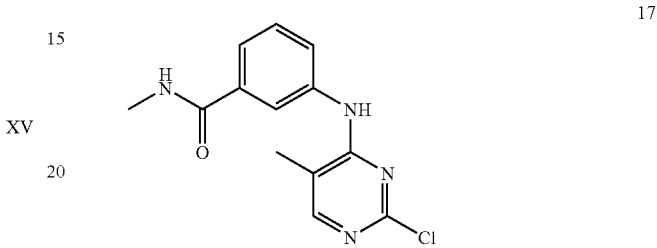

17

In a dry 50 mL round bottom flask, 2-chloro-5-methyl-pyrimidin-4-ylamine (0.3 g, 2.09 mmol, 1 equiv), 3-bromo-N-methyl-benzamide (0.489 g, 2.29 mmol, 1.1 equiv), cesium carbonate (2.04 g, 6.27 mmol, 3 equiv), 4,5-bis(diphenylphosphino)-9,9-dimethyl xanthene (0.242 g, 0.418 mmol, 0.2 equiv) and tris(dibenzylideneacetone) dipalladium (0.191 g, 0.209 mmol, 0.1 equiv) were combined. Reactants were diluted with dioxane (20 mL), flushed with argon and outfitted with reflux condenser. Reaction was heated to reflux for 16 hours. Reaction was then transferred into centrifuge tube, spun down, decanted and evaporated. Resulting yellow solids were diluted with DCM and adsorbed onto silica gel. Chromatography (gradient of 50% ethyl acetate in hexanes up to 100% ethyl acetate) afforded the title intermediate 17 as a pale yellow powder (0.25 g, 43% yield). MS (ESI+): 277.01 (M+H), r.t.=1.92 min.

Example 31

N-Methyl-3-{5-methyl-2-[4-(2-pyrrolidin-1-yl-ethoxy)-phenylamino]-pyrimidin-4-ylamino}-benzamide TFA salt (Compound XVI)

XVI

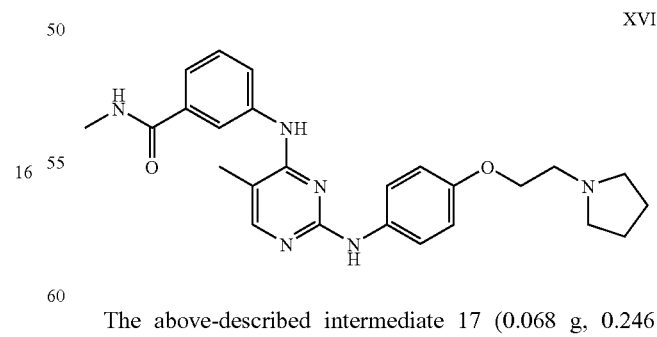

The above-described intermediate 17 (0.068 g, 0.246 mmol, 1 eq), 4-(2-Pyrrolidin-1-yl-ethoxy)-phenylamine (0.061 g, 0.296 mmol, 1.2 eq), cesium carbonate (0.241 g, 0.74 mmol, 3 equiv), 4,5-bis(diphenylphosphino)-9,9-dimethyl xanthene (0.029 g, 0.05 mmol, 0.2 equiv) and tris (dibenzylideneacetone) dipalladium (0.023 g, 0.025 mmol, 0.1 equiv) were combined in 15 ml microwave vessel. Reactants were then diluted with 7 ml dioxane and microwaved for 15 minutes at 160° C. Reaction vessel was then spun down, decanted and evaporated to dryness. HPLC purification afforded the TFA salt of the title product XVI (0.084 g, 76%). MS (ESI+): 447.20 (M+H), r.t.=1.53 min. $^1$H NMR (DMSO-$d_6$): δ 1.87-1.91 (m, 2H), 2.02-2.06 (m, 2H), 2.16 (s, 3H), 2.79 (d, J=4.6 Hz, 3H), 3.11-3.15 (m, 2H), 3.57-3.61 (m, 5H), 4.23 (t, J=5.0 Hz, 3H), 6.84 (d, J=8.8 Hz, 2H), 7.34 (d, J=8.9 Hz, 2H), 7.47 (t, J=7.9 Hz, 1H), 7.68-7.70 (m, 2H), 7.93 (s, 1H), 8.00 (s, 1H), 8.46-8.47 (m, 1H), 9.80 (bs, 1H), 9.93 (bs, 1H) 10.41 (bs, 1H).

Example 32

$N^4$-(4-Chloro-3-methoxy-phenyl)-5-methyl-$N^2$-[4-(2-pyrrolidin-1-yl-ethoxy)-phenyl]-pyrimidine-2,4-diamine TFA salt (Compound XVII)

XVII

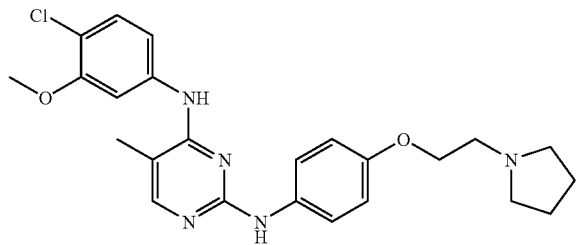

The above-described intermediate 7 (0.083 g, 0.293 mmol, 1 eq), 4-(2-Pyrrolidin-1-yl-ethoxy)-phenylamine (0.073 g, 0.352 mmol, 1.2 eq), cesium carbonate (0.287 g, 0.879 mmol, 3 equiv), 4,5-bis(diphenylphosphino)-9,9-dimethyl xanthene (0.034 g, 0.059 mmol, 0.2 equiv) and tris(dibenzylideneacetone) dipalladium (0.027 g, 0.029 mmol, 0.1 equiv) were combined in 15 ml microwave vessel. Reactants were then diluted with 7 ml dioxane and microwaved for 15 minutes at 160° C. Reaction vessel was then spun down, decanted and evaporated to dryness. HPLC purification afforded the TFA salt of the title product XVII (0.1 g, 75%). MS (ESI+): 454.13 (M+H), r.t.=1.82 min. $^1$H NMR (DMSO-$d_6$): δ 1.87-1.90 (m, 2H), 2.02-2.05 (m, 2H), 2.15 (s, 3H), 3.11-3.14(m, 2H), 3.58-3.61 (m, 5H), 3.70 (s, 3H), 4.26 (t, J=5.0 Hz, 3H), 6.91 (d, J=8.9 Hz, 2H), 7.23 (m, 1H), 7.34-7.4 (m, 4H), 7.93 (s, 1H), 9.63 (bs, 1H), 9.96 (bs, 1H) 10.40 (bs, 1H).

Example 33

N-(2-Chloro-5-methyl-pyrimidin-4-yl)-N',N'-dimethyl-benzene-1,3-diamine (Intermediate 18)

18

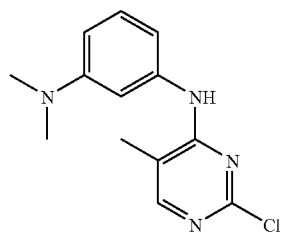

2-Chloro-5-methyl-pyrimidin-4-ylamine (0.343 g, 2.38 mmol, 1 equiv), (3-bromo-phenyl)-dimethyl-amine (0.524 g, 2.62 mmol, 1.1 equiv), cesium carbonate (2.3 g, 7.15 mmol, 3 equiv), 4,5-bis(diphenylphosphino)-9,9-dimethyl xanthene (0.276 g, 0.476 mmol, 0.2 equiv) and tris(dibenzylideneacetone) dipalladium (0.218 g, 0.238 mmol, 0.1 equiv) were combined in 30 ml microwave vessel. Reactants were then diluted with 12 ml dioxane and microwaved for 25 minutes at 160° C. Reaction vessel was then spun down, decanted and evaporated to dryness. Resulting solids were diluted with DCM and adsorbed onto silica gel. Chromatography (gradient of 0% methanol in DCM up to 25% methanol in DCM) afforded the title intermediate 18 as orange solid (0.184 g, 29% yield). MS (ESI+): 263.02 (M+H), r.t.=1.72 min.

Example 34

$N^4$-(3-Dimethylamino-phenyl)-5-methyl-$N^2$-[4-(2-pyrrolidin-1-yl-ethoxy)-phenyl]-pyrimidine-2,4-diamine TFA salt (Compound XVIII)

XVIII

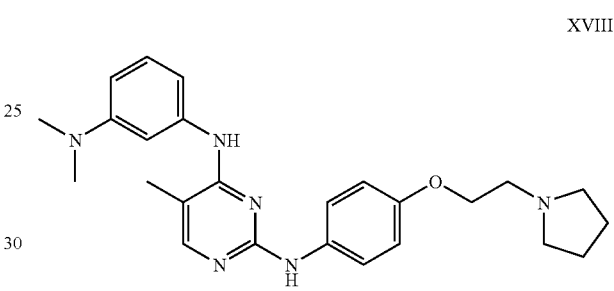

The above-described intermediate 18 (0.092 g, 0.35 mmol, 1 eq), 4-(2-pyrrolidin-1-yl-ethoxy)-phenylamine (0.087 g, 0.42 mmol, 1.2 eq), cesium carbonate (0.343 g, 1.05 mmol, 3 equiv), 4,5-bis(diphenyl phosphino)-9,9-dimethyl xanthene (0.041 g, 0.0702 mmol, 0.2 equiv) and tris(dibenzylideneacetone) dipalladium (0.032 g, 0.035 mmol, 0.1 equiv) were combined in a 15 ml microwave vessel. Reactants were then diluted with 7 ml dioxane and microwaved for 15 minutes at 160° C. Reaction vessel was then spun down, decanted and evaporated to dryness. HPLC purification provided the TFA salt of the title compound XVIII (0.035 g, 23%). MS (ESI+): 433.21 (M+H), r.t.=1.52 min. $^1$H NMR (DMSO-$d_6$): δ 1.87-1.90 (m, 2H), 2.03-2.06 (m, 2H), 2.15 (s, 3H), 2.87 (s, 6H), 3.12-3.15 (m, 2H), 3.57-3.60 (m, 4H), 3.70 (s, 3H), 4.25 (t, J=5.0 Hz, 3H), 6.34 (dd, J=8.4 Hz, J=2.3 Hz, 1H), 6.82-6.90 (m, 4H), 7.20 (t, J=8.0 Hz, 1H), 7.39 (d, J=9.1 Hz, 2H), 7.85 (s, 1H), 9.63 (bs, 1H), 9.90 (bs, 1H) 10.39 (bs, 1H).

Example 35

(2-Chloro-5-methyl-pyrimidin-4-yl)-(3,4-dichlorophenyl)-amine (Intermediate 19)

19

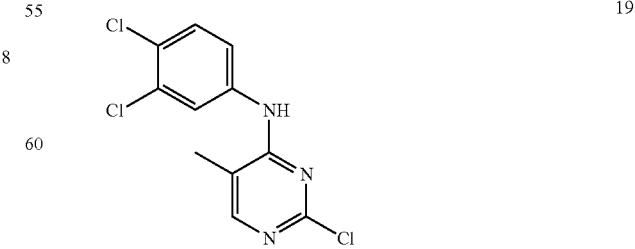

2-chloro-5-methyl-pyrimidin-4-ylamine (0.408 g, 2.83 mmol, 1 equiv), 4-Bromo-1,2-dichloro-benzene (0.704 g, 3.12 mmol, 1.1 equiv), cesium carbonate (2.8 g, 8.49 mmol, 3 equiv), 4,5-bis(diphenylphosphino)-9,9-dimethyl xanthene (0.328 g, 0.57 mmol, 0.2 equiv) and tris(dibenzylideneacetone) dipalladium (0.26 g, 0.283 mmol, 0.1 equiv) were combined in 30 ml microwave vessel. Reactants were then diluted with 12 ml dioxane and microwaved for 25 minutes at 160° C. Reaction vessel was then spun down, decanted and evaporated to dryness. Resulting solids were diluted with DCM and adsorbed onto silica gel. Chromatography (gradient of 15% ethyl acetate in hexanes up to 80% ethyl acetate in hexanes) afforded the title intermediate 19 as a pale yellow powder (0.366 g, 45% yield). MS (ESI+): 287.97 (M+H), r.t.=3.12 min.

Example 36

$N^4$-(3,4-Dichloro-phenyl)-5-methyl-$N^2$-[4-(2-pyrrolidin-1-yl-ethoxy)-phenyl]-pyrimidine-2,4-diamine TFA salt (Compound XIX)

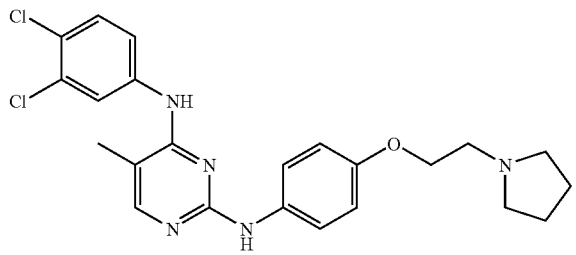

XIX

The above-described intermediate 19 (0.09 g, 0.313 mmol, 1 eq), 4-(2-pyrrolidin-1-yl-ethoxy)-phenylamine (0.078 g, 0.376 mmol, 1.2 eq), cesium carbonate (0.307 g, 0.941 mmol, 3 equiv), 4,5-bis(diphenylphosphino)-9,9-dimethyl xanthene (0.036 g, 0.063 mmol, 0.2 equiv) and tris(dibenzylideneacetone) dipalladium (0.029 g, 0.0314 mmol, 0.1 equiv) were combined in 15 ml microwave vessel. Reactants were then diluted with 7 ml dioxane and microwaved for 15 minutes at 160° C. Reaction vessel was then spun down, decanted and evaporated to dryness. HPLC purification provided the TFA salt of the title compound XIX (0.056 g, 39%). MS (ESI+): 458.1 (M+H), r.t.=1.93 min. $^1$H NMR (DMSO-$d_6$): δ 1.87-1.91 (m, 2H), 2.03-2.06 (m, 2H), 2.14 (s, 3H), 3.12-3.15 (m, 3H), 3.57-3.60 (m, 4H), 4.26 (t, J=5.0 Hz, 2H), 6.97 (d, J=9.0 Hz, 1H), 7.40 (d, J=9 Hz, 2H), 7.60 (s, 2H), 7.97 (d, J=15.35 Hz, 2H), 9.46 (bs, 1H), 9.89 (bs, 1H) 10.17 (bs, 1H).

Example 37

4-{3-[4-(4-Chloro-3-methoxy-phenylamino)-5-methyl-pyrimidin-2-ylamino]-benzyl}-piperazine-1-carboxylic acid tert-butyl ester (Intermediate 20)

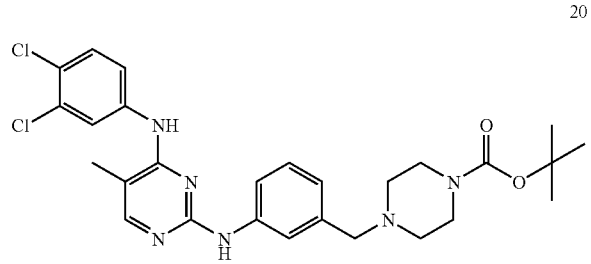

20

(4-Chloro-3-methoxy-phenyl)-(2-chloro-5-methyl-pyrimidin-4-yl)-amine (0.092 g, 0.325 mmol, 1 eq), 4-(3-aminobenzyl)-piperazine-1-carboxylic acid tert-butyl ester (0.114 g, 0.39 mmol, 1.2 eq), cesium carbonate (0.318 g, 0.975 mmol, 3 equiv), 4,5-bis(diphenylphosphino)-9,9-dimethyl xanthene (0.038 g, 0.065 mmol, 0.2 equiv) and tris(dibenzylideneacetone) dipalladium (0.03 g, 0.0325 mmol, 0.1 equiv) were combined in a 15 ml microwave vessel. Reactants were then diluted with 7 ml dioxane and microwaved for 15 minutes at 160° C. Reaction vessel was then spun down, decanted and evaporated to dryness. HPLC purification afforded the TFA salt of the title intermediate 20 (0.075 g, 43%). MS (ESI+): 539.32 (M+H), r.t.=2.09 min.

Example 38

$N^4$-(4-Chloro-3-methoxy-phenyl)-5-methyl-$N^2$-(3-piperazin-1-ylmethyl-phenyl)-pyrimidine-2,4-diamine TFA salt (Compound XX)

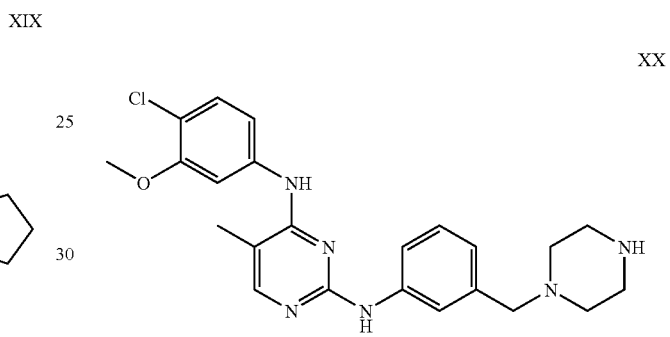

XX

A stirring solution of the above-described intermediate 20 (0.075 g, 0.14 mmol, 1 eq) in DCM (6 ml) was treated with TFA (2 ml). After 2 h, reaction solvents were evaporated and resulting residue triturated with ether to afford the title compound XX as white, hygroscopic solids, TFA salt. (0.05 g, 82%). MS (ESI+): 439.13 (M+H), r.t.=1.67 min. $^1$H NMR (DMSO-$d_6$): δ 2.17 (s, 3H), 2.89 (bs, 4H), 3.2 (bs, 4H), 3.68 (s, 3H), 3.82 (bs, 3H), 7.16-7.20 (m, 2H), 7.28 (t, J=7.7 Hz, 1H), 7.33 (d, J=2.3 Hz, 1H), 7.39 (s, 1H), 7.42 (d, J=8.5 Hz, 1H), 7.49-7.51 (m, 1H), 7.98 (s, 1H), 8.87 (bs, 1H), 9.79 (bs, 1H) 10.57 (bs, 1H).

Example 39

2-(4-(2-(Pyrrolidin-1-yl)ethoxy)phenylamino)-4-aminopyrimidine-5-carbonitrile (Intermediate 21)

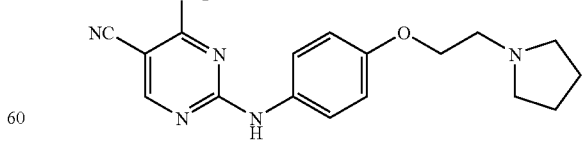

21

To a solution of 2,4-diaminopyrimidine-5-carbonitrile (135 mg, 1.00 mmol) in 1,4-dioxane (20 mL) was added 1-(2-(4-bromophenoxy)ethyl)pyrrolidine (270 mg, 1.0 mmol), $Cs_2CO_3$ (1.3 g, 4.0 mmol), $Pd_2(dba)_3$ (92 mg, 0.1 mmol), and 4,5-bis(diphenylphosphino)-9,9-dimethyxanthene (Xant Phos, 174 mg, 0.3 mmol). The mixture was heated under reflux for 4 h under Ar. The solid was filtered off and the filtrate washed with brine (1×100 mL). The organic solution was separated and dried (Na$_2$SO$_4$). The solvent was removed until 5 mL and hexane (50 mL) was added, the solid was collected by filtration. The crude product was purified by HPLC and afforded the title intermediate 21 (32 mg, 10%).

Example 40

4-(2,4-Dichloro-5-methoxyphenylamino)-2-(4-(2-(pyrrolidin-1-yl)ethoxy)phenyl-amino)pyrimidine-5-carbonitrile (Compound XXI)

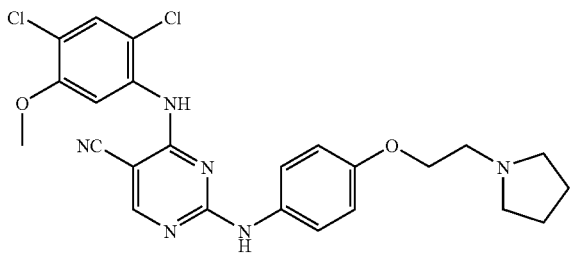

XXI

To a solution of the above-described intermediate 21 (32 mg, 0.1 mmol) in 1,4-dioxane (10 mL) was added 1-bromo-2,4-dichloro-5-methoxybenzene (28 mg, 0.11 mmol), Cs$_2$CO$_3$ (97 mg, 0.3 mmol), Pd$_2$(dba)$_3$ (7 mg, 0.0074 mmol), and 4,5-bis(diphenylphosphino)-9,9-dimethyxanthene (Xant Phos, 13 mg, 0.022 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by chromatograph (SiO$_2$/CH$_2$Cl$_2$, then CH$_2$Cl$_2$:MeOH:NH$_3$.H$_2$O=100:10:1) and afforded the title compound XXI (35 mg, 67%). $^1$H NMR (500 MHz, DMSO-d$^6$): 1.88-1.90(m, 2H); 2.00-2.03 (m, 2H); 3.07-3.11 (m, 2H); 3.54-3.56 (m, 4H); 3.81 (s, 3H); 4.25 (br, 2H); 6.68 (br, 2H); 7.32 (br, 2H); 7.33 (s, 1H); 7.75 (s, 1H); 8.50 (s, 1H); 9.73 (br, 1H); 9.94 (br, 1H); 10.60 (br, 1H). MS (EI): 499.0.

Example 41

2-(3-(2-(Pyrrolidin-1-yl)ethoxy)phenylamino)-4-aminopyrimidine-5-carbonitrile (Intermediate 22)

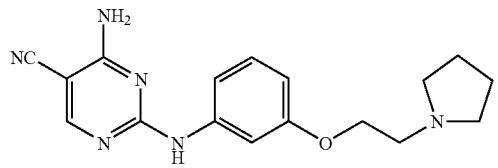

22

To a solution of 2,4-diaminopyrimidine-5-carbonitrile (145 mg, 1.07 mmol) in 1,4-dioxane (20 mL) was added 1-(2-(3-bromophenoxy)ethyl)pyrrolidine (290 mg, 1.07 mmol), Cs$_2$CO$_3$ (1.43 g, 4.4 mmol), Pd$_2$(dba)$_3$ (92 mg, 0.1 mmol), and 4,5-bis(diphenylphosphino)-9,9-dimethyxan-thene (Xant Phos, 174 mg, 0.3 mmol). The mixture was heated under reflux for 4 h under Ar. The solid was filtered off and the filtrate washed with brine (1×100 mL). The organic solution was separated and dried (Na$_2$SO$_4$). The solvent was removed until 5 mL and hexane (50 mL) was added, the solid was collected by filtration. The crude product was purified by HPLC and afforded the title intermediate 22 (55 mg, 16%).

Example 42

4-(2,4-Dichloro-5-methoxyphenylamino)-2-(3-(2-(pyrrolidin-1-yl)ethoxy)phenyl-amino)pyrimidine-5-carbonitrile (Compound XXII)

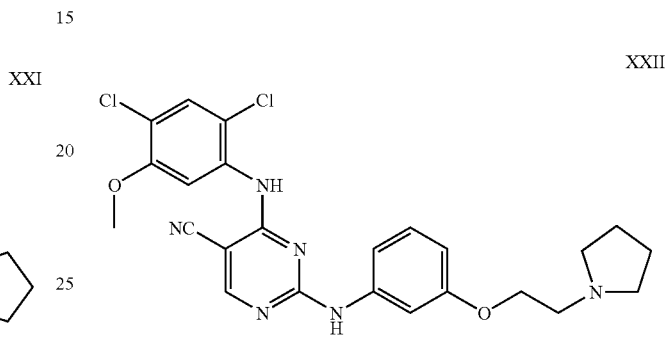

XXII

To a solution of the above-described intermediate 22 (50 mg, 0.15 mmol) in 1,4-dioxane (10 mL) was added 1-bromo-2,4-dichloro-5-methoxybenzene (44 mg, 0.17 mmol), Cs$_2$CO$_3$ (200 mg, 0.62 mmol), Pd$_2$(dba)$_3$ (14 mg, 0.015 mmol), and 4,5-bis(diphenylphosphino)-9,9-dimethyxan-thene (Xant Phos, 27 mg, 0.05 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXII (6 mg, 8%). $^1$H NMR (500 MHz, DMSO-d$^6$): 1.87-1.89 (m, 2H); 1.90-2.03 (m, 2H); 3.04-3.08 (m, 2H); 3.52-3.56 (m, 4H); 3.80 (s, 3H); 4.23 (br, 2H); 6.62 (d, J=6.4 Hz, 2H); 6.97 (br, 1H); 7.14 (br, 2H); 7.34 (s, 1H); 7.74 (s, 1H); 8.54 (s, 1H); 9.70 (br, 1H); 9.95 (br, 1H); 10.83 (br, 1H). MS (EI): 499.0.

Example 43

2-Chloro-N-(2,4-dichloro-5-methoxyphenyl)-5-methylpyrimidin-4-amine (Intermediate 23)

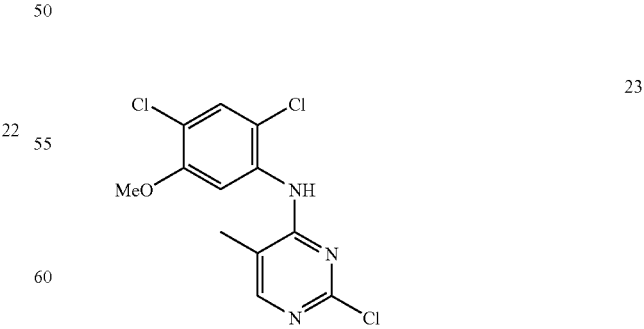

23

To a solution of 2-chloro-5-methylpyrimidin-4-amine (44.8 mg, 0.31 mmol) in 1,4-dioxane (20 mL) was added 1-bromo-2,4-dichloro-5-methoxybenzene (96 mg, 0.37 mmol), Cs$_2$CO$_3$ (408 mg, 1.25 mmol), Pd$_2$(dba)$_3$ (37 mg, 0.04 mmol), and 4,5-bis(diphenylphosphino)-9,9-dimethyxanthene (Xant Phos, 70 mg, 0.12 mmol). The mixture was heated under reflux for 4 h under Ar. The solid was filtered off and the filtrate washed with brine (1×100 mL). The organic solution was separated and dried (Na$_2$SO$_4$). The solvent was removed in vacuo. The crude product was used for next reaction without purification.

Example 44

N$^2$-(3-(2-(pyrrolidin-1-yl)ethoxy)phenyl)-N$^4$-(2,4-dichloro-5-methoxyphenyl)-5-methylpyrimidine-2,4-diamine (Compound XXIII)

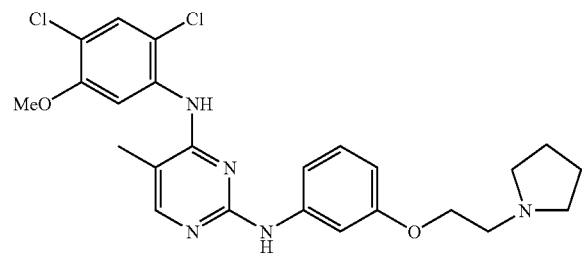

XXIII

To a solution of the above-described intermediate 23 in 1,4-dioxane (10 mL) was added 3-(2-(pyrrolidin-1-yl) ethoxy)benzenamine (77.3 mg, 0.38 mmol), Cs$_2$CO$_3$ (488 mg, 1.25 mmol), Pd$_2$(dba)$_3$ (28 mg, 0.03 mmol), and 4,5-bis(diphenylphosphino)-9,9-dimethyxanthene (Xant Phos, 53 mg, 0.09 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXIII (25 mg, 15%). $^1$H NMR (500 MHz, DMSO-d$^6$): 1.87-1.89 (m, 2H); 1.90-2.03 (m, 2H); 2.18 (s, 3H); 3.04-3.08 (m, 2H); 3.52-3.56 (m, 4H); 3.80 (s, 3H); 4.24 (t, J=5.0 Hz, 2H); 6.71 (d, J=7.65 Hz, 1H); 6.91 (s, 1H); 6.96 (d, J=8.5 Hz, 1H); 7.02 (t, J=8.2 Hz, 1H); 7.37 (s, 1H); 7.83 (s, 1H); 8.02 (s, 1H); 10.09 (br, 1H); 10.66 (br, 1H); 10.82 (br, 1H). MS (EI): 488.2.

Example 45

2-Chloro-N-(3-methoxyphenyl)-5-methylpyrimidin-4-amine (Intermediate 24)

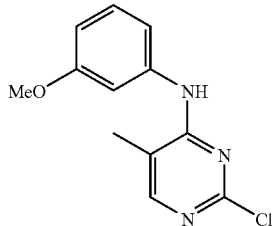

24

To a solution of 2-chloro-5-methylpyrimidin-4-amine (320 mg, 2.23 mmol) in 1,4-dioxane (40 mL) was added 1-bromo-3-methoxybenzene (458.5 mg, 2.45 mmol), Cs$_2$CO$_3$ (2.9 g, 8.9 mmol), Pd$_2$(dba)$_3$ (201 mg, 0.22 mmol), and 4,5-bis(diphenylphosphino)-9,9-dimethyxanthene (Xant Phos, 382 mg, 0.66 mmol). The mixture was heated under reflux for 4 h under Ar. The solid was filtered off and the filtrate washed with brine (1×100 mL). The organic solution was separated and dried (Na$_2$SO$_4$). The solvent was removed until 5 mL and hexane (100 mL) was added, the solid was collected by filtration. The crude product, the title intermediate 24 (500 mg, 90%), was used for next reaction without further purification.

Example 46

N$^2$-(4-(2-(Pyrrolidin-1-yl)ethoxy)phenyl)-N$^4$-(3-methoxyphenyl)-5-methyl-pyrimidine-2,4-diamine (Compound XXIV)

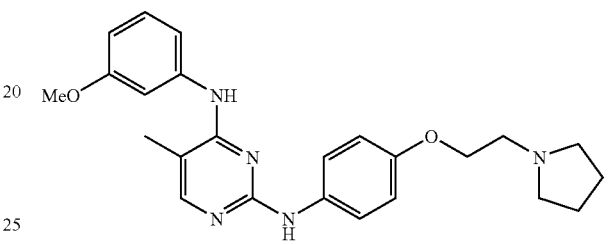

XXIV

To a solution of the above-described intermediate 24 (240 mg, 0.96 mmol) in 1,4-dioxane (20 mL) was added 4-(2-(pyrrolidin-1-yl)ethoxy)benzenamine (200 mg, 0.96 mmol), Cs$_2$CO$_3$ (1.3 mg, 4.0 mmol), Pd$_2$(dba)$_3$ (82 mg, 0.09 mmol), and 4,5-bis(diphenylphosphino)-9,9-dimethyxanthene (Xant Phos, 156 mg, 0.27 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXIV (85 mg, 20%). $^1$H NMR (500 MHz, DMSO-d$^6$): 1.89-1.91 (m, 2H); 1.98-2.05 (m, 2H); 2.16 (s, 3H); 3.07-3.12 (m, 2H); 3.52-3.56 (m, 4H); 3.73 (s, 3H); 4.33 (t, J=4.5 Hz, 2H); 6.83-6.85 (m, 1H); 6.91 (d, J=8.8 Hz, 2H); 7.17 (s, 1H); 7.34 (d, J=8.8 Hz, 2H); 7.41 (t, J=7.7 Hz, 1H); 7.56 (d, J=7.7 Hz, 1H); 7.89 (s, 1H); 9.75 (s, 1H); 10.51 (s, 1H); 10.96 (br, 1H). MS (EI): 420.2.

Example 47

3-(2-(4-(2-(Pyrrolidin-1-yl)ethoxy)phenylamino)-5-methylpyrimidin-4-ylamino)-phenol (Compound XXV)

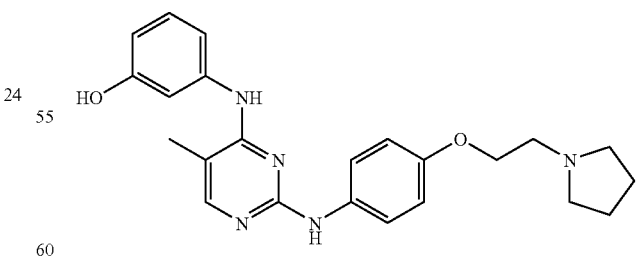

XXV

To a solution of the above-described compound XXIV (50 mg, 0.1 mmol) in anhydrous CH$_2$Cl$_2$ (10 mL) was added 1.0 M BBr$_3$ in CH$_2$Cl$_2$ (0.3 mL, 0.3 mmol). The mixture was stirred for 3 h at room temperature. The saturated NaHCO$_3$ (20 mL) was added and organic layer was separated. The aqueous was extracted with CH$_2$Cl$_2$ (3×10 mL). Combined organic solution was dried (Na$_2$SO$_4$). The product was purified by HPLC and afforded the title compound XXV (17 mg, 35%) as yellow solid. $^1$H NMR (500 MHz, DMSO-d$^6$): 1.89 (br, 2H); 2.00 (br, 2H); 2.14 (s, 3H); 3.09 (br, 2H); 3.42 (br, 4H); 4.33 (br, 2H); 6.72 (d, J=7.1 Hz, 1H); 6.91 (d, J=8.4 Hz, 2H); 6.96 (d, J=7.6 Hz, 1H); 7.00 (s, 1H); 7.18 (t, J=8.0 Hz, 1H); 7.38 (d, J=8.6 Hz, 2H); 7.88 (s, 1H); 9.70 (s, 1H); 9.74 (s, 1H); 10.55 (s, 1H); 11.09 (br, 1H). MS (EI): 406.2.

Example 48

2-Chloro-5-methyl-N-(3-nitrophenyl)pyrimidin-4-amine (Intermediate 25)

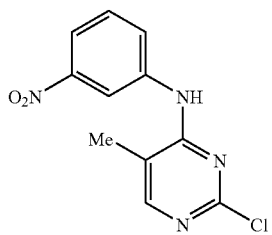

To a solution of 2-chloro-5-methylpyrimidin-4-amine (232 mg, 1.61 mmol) in 1,4-dioxane (40 mL) was added 1-bromo-3-nitrobenzene (359 mg, 1.78 mmol), Cs$_2$CO$_3$ (2.1 g, 6.4 mmol), Pd$_2$(dba)$_3$ (146 mg, 0.16 mmol), and 4,5-bis(diphenylphosphino)-9,9-dimethyxanthene (Xant Phos, 278 mg, 0.48 mmol). The mixture was heated under reflux for 4 h under Ar. The solid was filtered off and the filtrate washed with brine (1×100 mL). The organic solution was separated and dried (Na$_2$SO$_4$). The solvent was removed until 5 mL and hexane (100 mL) was added, the solid was collected by filtration. The crude product, the title intermediate 25, was used for next reaction without further purification.

Example 49

N$^2$-(4-(2-(pyrrolidin-1-yl)ethoxy)phenyl)-5-methyl-N$^4$-(3-nitrophenyl)pyrimidine-2,4-diamine (Compound XXVI)

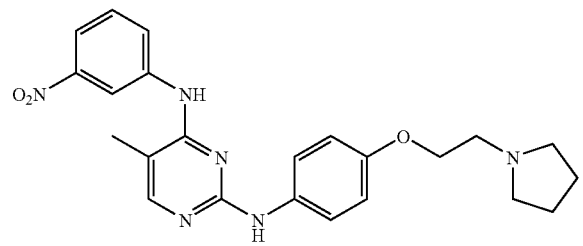

To a solution of the above-described intermediate 25 in 1,4-dioxane (40 mL) was added 4-(2-(pyrrolidin-1-yl)ethoxy)benzenamine (367 mg, 1.78 mmol), Cs$_2$CO$_3$ (2.1 g, 6.4 mmol), Pd$_2$(dba)$_3$ (146 mg, 0.16 mmol), and 4,5-bis(diphenylphosphino)-9,9-dimethyxanthene (Xant Phos, 218 mg, 0.48 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXVI (51 mg, 7%). $^1$H NMR (500 MHz, DMSO-d$^6$): 1.89-1.92 (m, 2H); 1.98-2.05 (m, 2H); 2.21 (s, 3H); 3.10-3.12 (m, 2H); 3.52-3.57 (m, 4H); 4.33 (t, J=4.8 Hz, 2H); 6.90 (d, J=8.9 Hz, 2H); 7.32 (d, J=8.9 Hz, 2H); 7.67 (t, J=8.2 Hz, 1H); 7.99 (s, 1H); 7.56 (dd, J=8.4 Hz, J=1.8 Hz, 1H); 8.09 (d, J=7.4 Hz, 1H); 8.45 (s, 1H); 10.14 (s, 1H); 10.60 (s, 1H); 11.17 (br, 1H). MS (EI): 435.2.

Example 50

4-(2-Chloro-5-methylpyrimidin-4-ylamino)-2-chlorobenzonitrile (Intermediate 26)

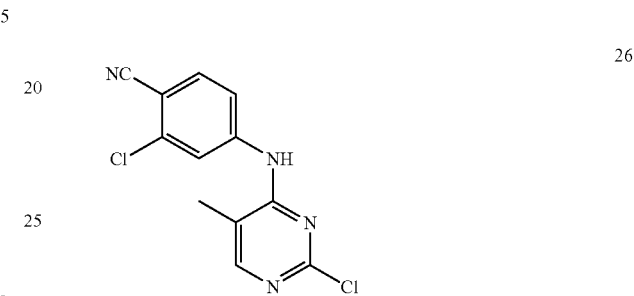

To a solution of 2-chloro-5-methylpyrimidin-4-amine (144 mg, 1.0 mmol) in 1,4-dioxane (20 mL) was added 4-bromo-2-chlorobenzonitrile (217 mg, 1.0 mmol), Cs$_2$CO$_3$ (1.3 g, 4.0 mmol), Pd$_2$(dba)$_3$ (91 mg, 0.1 mmol), and 4,5-bis(diphenylphosphino)-9,9-dimethyxanthene (Xant Phos, 173 mg, 0.3 mmol). The mixture was heated under reflux for 4 h under Ar. The solid was filtered off and the filtrate washed with brine (1×100 mL). The organic solution was separated and dried (Na$_2$SO$_4$). The solvent was removed until 5 mL and hexane (100 mL) was added, the solid was collected by filtration. The crude product, the title intermediate 26, was used for next reaction without further purification.

Example 51

4-(2-(4-(2-(pyrrolidin-1-yl)ethoxy)phenylamino)-5-methylpyrimidin-4-ylamino)-2-chlorobenzonitrile (Compound XXVII)

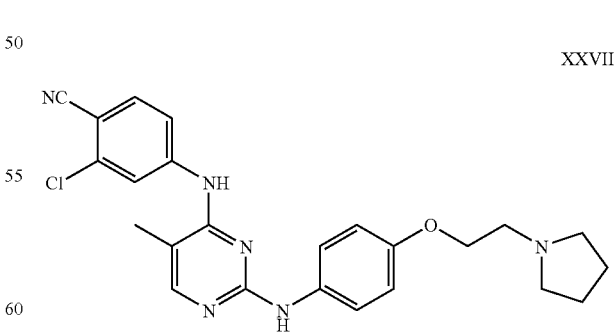

To a solution of the above-described intermediate 26 (140 mg, 0.5 mmol) in 1,4-dioxane (20 mL) was added 4-(2-(pyrrolidin-1-yl)ethoxy)benzenamine (113 mg, 0.55 mmol), Cs$_2$CO$_3$ (660 mg, 2.0 mmol), Pd$_2$(dba)$_3$ (46 mg, 0.05 mmol), and 4,5-bis(diphenylphosphino)-9,9-dimethyxanthene (Xant Phos, 87 mg, 0.15 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXVII (11.5 mg, 5%) as a yellow solid. $^1$H NMR (500 MHz, DMSO-d$^6$): 1.89-1.92 (m, 2H); 1.98-2.05 (m, 2H); 2.20 (s, 3H); 3.08-3.13 (m, 2H); 3.56-3.59 (m, 4H); 4.36 (t, J=4.9 Hz, 2H); 7.03 (d, J=9.0 Hz, 2H); 7.40 (d, J=9.0 Hz, 2H); 7.87 (br, 1H); 7.92 (d, J=8.6 Hz, 1H); 8.03 (s, 1H); 8.16 (s, 1H); 9.82 (br, 1H); 10.37 (br, 1H); 10.90 (br, 1H). MS (EI): 449.1.

Example 52

N$^2$-(4-(2-(pyrrolidin-1-yl)ethoxy)phenyl)-5-methyl-N$^4$-p-tolylpyrimidine-2,4-diamine (Compound XXVIII)

XXVIII

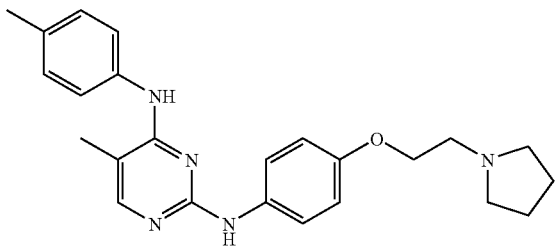

To a solution of the above-described intermediate 11 (50 mg, 0.16 mmol) in 1,4-dioxane (20 mL) was added 1-bromo-4-methylbenzene (28 mg, 0.16 mmol), Cs$_2$CO$_3$ (210 mg, 0.64 mmol), Pd$_2$(dba)$_3$ (10 mg, 0.01 mmol), and 4,5-bis(diphenylphosphino)-9,9-dimethyxanthene (Xant Phos, 18 mg, 0.03 mmol). The mixture was heated under reflux for 4 h under Ar. The solid was filtered off. The solvent was removed in vacuo. The crude product was purified by HPLC and afforded the title compound XXVIII (15.7 mg, 6%) as a yellow solid. $^1$H NMR (500 MHz, DMSO-d$^6$): 1.85-1.89 (m, 2H); 1.96-2.01(m, 2H); 2.12 (s, 3H); 2.31 (s, 3H); 3.04-3.08 (m, 2H); 3.51-3.55 (m, 4H); 4.32 (br, 2H); 6.89 (br, 2H); 7.18 (br, 2H); 7.31 (br, 2H); 7.41 (br, 2H); 7.84 (s, 1H); 9.71 (s, 1H); 10.46 (s, 1H); 11.13 (br, 1H). MS (EI): 404.2.

Example 53

N$^2$-(4-(2-(pyrrolidin-1-yl)ethoxy)phenyl)-N$^4$-(4-chloro-3-methylphenyl)-5-methylpyrimidine-2,4-diamine (Compound XXIX)

XXIX

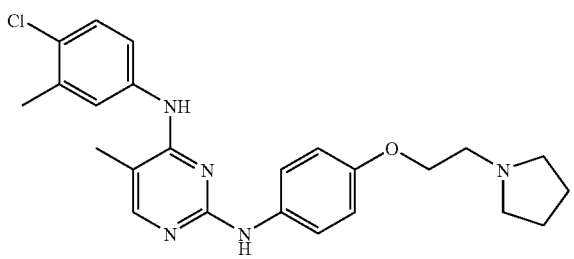

To a solution of the above-described intermediate 11 (80 mg, 0.25 mmol) in 1,4-dioxane (20 mL) was added 4-bromo-1-chloro-2-methylbenzene (63 mg, 0.30 mmol), Cs$_2$CO$_3$ (326 mg, 1.0 mmol), Pd$_2$(dba)$_3$ (18 mg, 0.02 mmol), and 4,5-bis(diphenylphosphino)-9,9-dimethyxanthene (Xant Phos, 36 mg, 0.06 mmol). The mixture was heated under reflux for 4 h under Ar. The solid was filtered off. The solvent was removed in vacuo. The crude product was purified by HPLC and afforded the title compound XXIX (17.5 mg, 15%) as a yellow solid. $^1$H NMR (500 MHz, DMSO-d$^6$): 1.85-1.89 (m, 2H); 1.96-2.01 (m, 2H); 2.12 (s, 3H); 2.25 (s, 3H); 3.04-3.08 (m, 2H); 3.51-3.55 (m, 4H); 4.32 (br, 2H); 6.91 (br, 2H); 7.04 (br, 1H); 7.31 (br, 1H); 7.41 (br, 2H); 7.58 (s, 1H); 7.89 (br, 1H); 9.75 (s, 1H); 10.54 (s, 1H); 11.13 (br, 1H). MS (EI): 438.1.

Example 54

N-(4-(2-(pyrrolidin-1-yl)ethoxy)phenyl)-4-benzyl-5-methylpyrimidin-2-amine (Compound XXX)

XXX

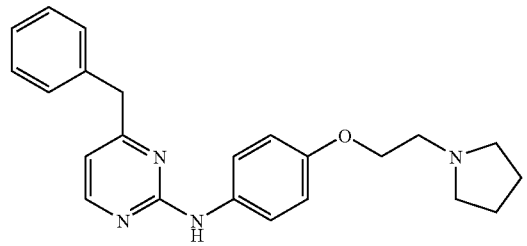

To a solution of 4-benzyl-2-chloropyrimidine (286 mg, 1.4 mmol) in 1,4-dioxane (20 mL) was added 4-(2-(pyrrolidin-1-yl)ethoxy)benzenamine (288 mg, 1.4 mmol), Cs$_2$CO$_3$ (1.82 g, 5.6 mmol), Pd$_2$(dba)$_3$ (92 mg, 0.1 mmol), and 4,5-bis(diphenylphosphino)-9,9-dimethyxanthene (Xant Phos, 173 mg, 0.3 mmol). The mixture was heated under reflux for 4 h under Ar. The solid was filtered off. The solvent was removed in vacuo. The crude product was purified by HPLC and afforded the title compound XXX (42 mg, 10%) as a yellow solid. $^1$H NMR (500 MHz, DMSO-d$^6$): 1.89 (br, 2H); 2.00 (br, 2H); 3.09 (br, 2H); 3.54 (br, 4H); 4.31 (br, 2H); 6.71 (d, J=5.0 Hz, 1H); 6.93 (d, J=8.8 Hz, 2H); 7.24 (m, 1H); 7.32 (m, 4H); 7.62 (d, J=8.8 Hz, 2H); 8.32 (d, J=5.0 Hz, 1H); 9.66 (s, 1H); 10.92 (br, 1H). MS (EI): 375.2.

Example 55

4-((1H-indol-4-yl)methyl)-N-(4-(2-(pyrrolidin-1-yl)ethoxy)phenyl)-5-methylpyrimidin-2-amine (Compound XXXI)

XXXI

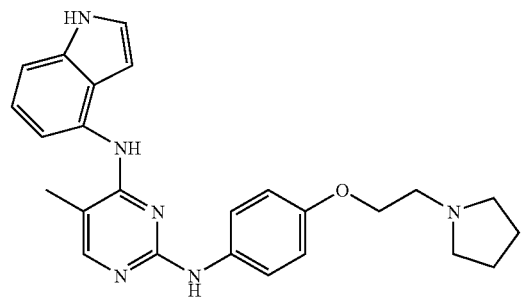

To a solution of the above-described intermediate 11 (460 mg, 1.46 mmol) in 1,4-dioxane (20 mL) was added 4-bromo-1H-indole (288 mg, 1.46 mmol), Cs$_2$CO$_3$ (1.95 g, 6.0 mmol), Pd$_2$(dba)$_3$ (128 mg, 0.14 mmol), and 4,5-bis(diphenylphosphino)-9,9-dimethyxanthene (Xant Phos, 243 mg, 0.42 mmol). The mixture was heated under reflux for overnight under Ar. The solid was filtered off. The solvent was removed in vacuo. The crude product was purified by HPLC and afforded the title compound XXXI (66 mg, 10%) as a yellow solid. ¹H NMR (500 MHz, DMSO-d⁶): 1.87 (br, 2H); 1.98-2.05 (m, 2H); 2.21 (s, 3H); 3.15 (br, 2H); 3.52 (br, 2H); 3.69 (br, 2H); 4.24 (br, 2H); 6.33 (s, 1H); 6.60 (br, 2H); 6.82 (br, 1H); 6.92 (br, 1H); 7.02 (br, 2H); 7.16 (br, 1H); 7.26 (br, 1H); 7.43 (m, 1H); 7.88 (m, 1H); 10.11 (s, 1H); 11.40 (s, 1H). MS (EI): 429.1.

Example 56

2-Chloro-5-methyl-N-(naphthalen-1-yl)pyrimidin-4-amine (Intermediate 27)

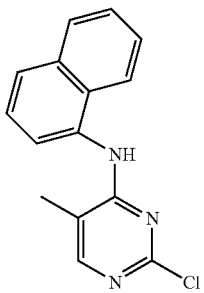

To a solution of 2-chloro-5-methylpyrimidin-4-amine (144 mg, 1.0 mmol) in 1,4-dioxane (40 mL) was added 1-bromonaphthalene (227 mg, 1.1 mmol), Cs₂CO₃ (1.3 g, 4.0 mmol), Pd₂(dba)₃ (91 mg, 0.1 mmol), and 4,5-bis(diphenylphosphino)-9,9-dimethyxanthene (Xant Phos, 183 mg, 0.3 mmol). The mixture was heated under reflux for 4 h under Ar. The solid was filtered off and the filtrate washed with brine (1×100 mL). The organic solution was separated and dried (Na₂SO₄). The solvent was removed until 5 mL and hexane (100 mL) was added, the solid was collected by filtration. The crude product, the title intermediate 27, was used for next reaction without further purification.

Example 57

N-(4-(2-(pyrrolidin-1-yl)ethoxy)phenyl)-5-methyl-4-(naphthalen-1yl) pyrimidin-2-amine (Compound XXXII)

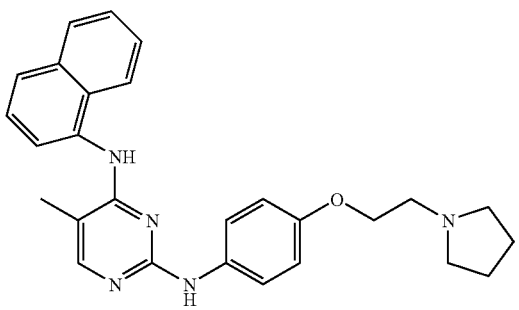

To a solution of the above-described intermediate 27 (235 mg, 0.87 mmol) in 1,4-dioxane (20 mL) was added 4-(2-(pyrrolidin-1-yl)ethoxy)benzenamine (183 mg, 0.87 mmol), Cs₂CO₃ (1.3 g, 4.0 mmol), Pd₂(dba)₃ (46 mg, 0.05 mmol), and 4,5-bis(diphenylphosphino)-9,9-dimethyxanthene (Xant Phos, 87 mg, 0.15 mmol). The mixture was heated under reflux for 4 h under Ar. The solid was filtered off and the filtrate washed with brine (1×50 mL). The organic solution was separated and dried (Na₂SO₄). The solvent was removed in vacuo. The crude product was purified by HPLC and afforded the title compound XXXII (89 mg, 21%) as a yellow solid. ¹H NMR (500 MHz, DMSO-d⁶): 1.88-1.90 (m, 2H); 1.97-2.03 (m, 2H); 2.30 (s, 3H); 3.03-3.08 (m, 2H); 3.50-3.53 (m, 4H); 4.21 (t, J=4.9 Hz, 2H); 6.50 (d, J=7.2 Hz, 2H); 6.82 (d, J=8.6 Hz, 2H); 7.54 (d, J=7.8 Hz, 2H); 7.57-7.61 (m, 1H); 7.63 (t, J=7.4 Hz, 1H); 7.89 (d, J=8.3 Hz, 2H); 7.95 (s, 1H); 8.02 (d, J=8.3 Hz, 1H); 8.08 (d, J=7.7 Hz, 1H); 10.37 (s, 1H); 10.43 (s, 1H); 10.93 (br, 1H). MS (EI): 440.1.

Example 58

1-(2-Chloro-5-methylpyrimidin-4-yl)isoquinoline (Intermediate 28)

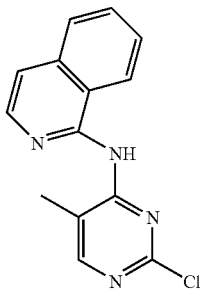

To a solution of 2-chloro-5-methylpyrimidin-4-amine (144 mg, 1.0 mmol) in 1,4-dioxane (40 mL) was added 1-chloroisoquinoline (164 mg, 1.0 mmol), Cs₂CO₃ (1.3 g, 4.0 mmol), Pd₂(dba)₃ (91 mg, 0.1 mmol), and 4,5-bis(diphenylphosphino)-9,9-dimethyxanthene (Xant Phos, 183 mg, 0.3 mmol). The mixture was heated under reflux for 4 h under Ar. The solid was filtered off and the filtrate washed with brine (1×100 mL). The organic solution was separated and dried (Na₂SO₄). The solvent was removed until 5 mL and hexane (100 mL) was added, the solid was collected by filtration. The crude product, the title intermediate 28, was used for next reaction without further purification.

Example 59

N-(4-(2-(pyrrolidin-1-yl)ethoxy)phenyl)-4-(isoquinolin-1-yl)-5-methylpyrimidin-2-amine (Compound XXXIII)

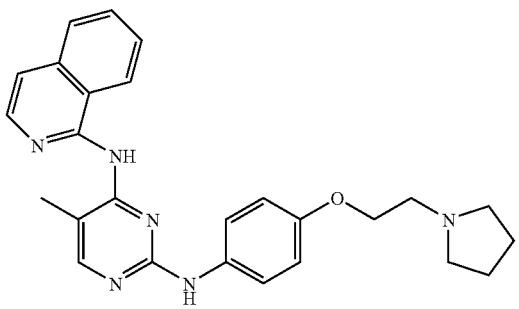

To a solution of the above-described intermediate 28 (90 mg, 0.33 mmol) in 1,4-dioxane (20 mL) was added 4-(2-(pyrrolidin-1-yl)ethoxy)benzenamine (76 mg, 0.37 mmol), Cs$_2$CO$_3$ (391 mg, 1.2 mmol), Pd$_2$(dba)$_3$ (28 mg, 0.03 mmol), and 4,5-bis(diphenylphosphino)-9,9-dimethyxanthene (Xant Phos, 52 mg, 0.09 mmol). The mixture was heated under reflux for 4 h under Ar. The solid was filtered off and the filtrate washed with brine (1×50 mL). The organic solution was separated and dried (Na$_2$SO$_4$). The solvent was removed in vacuo. The crude product was purified by HPLC and afforded the title compound XXXIII (21 mg, 15%) as a yellow solid. $^1$H NMR (500 MHz, DMSO-d$^6$): 1.64-1.70 (m, 6H); 2.23 (s, 3H); 2.78 (t, J=5.9 Hz, 2H); 4.04 (t, J=5.9 Hz, 2H); 6.38 (d, J=7.2 Hz, 1H); 6.93 (d, J=9.0 Hz, 2H); 6.97 (d, J=7.2 Hz, 1H); 7.45 (br, 1H); 7.57 (d, J=8.8 Hz, 1H); 7.58-7.62 (m, 1H); 7.70-7.78 (m, 2H); 8.04 (s, 1H); 8.75 (d, J=8.1 Hz, 1H); 9.06 (s, 1H); 9.19 (s, 1H). MS (EI): 441.2.

Example 60

N$^2$-(4-(2-(pyrrolidin-1-yl)ethoxy)phenyl)-N$^4$-(3-(trifluoromethyl)phenyl)-5-methylpyrimidine-2,4-diamine (Compound XXXIV)

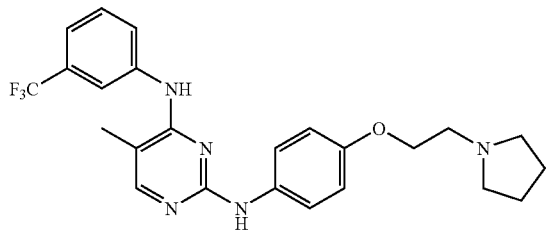

XXXIV

A mixture of 2-chloro-5-methyl-pyrimidin-4-ylamine (143 mg, 1.0 mmol), 1-bromo-3-(trifluoromethyl)benzene (225 mg, 1.0 mmol), Pd$_2$(dba)$_3$ (9.0 mg, 0.01 mmol), Xantphos (12 mg, 0.02 mmol) and cesium carbonate (650 mg, 2.0 mmol) were suspended in dioxane (15 mL) and heated at reflux under the argon atmosphere for 15 h. The reaction mixture was cooled to room temperature and diluted with DCM (30 mL). The mixture was filtered and the filtrate concentrated in vacuo. The residue on purification using HPLC gave N$^4$-(3-(trifluoromethyl)phenyl)-5-methylpyrimidine-2,4-diamine as an off white solid (192 mg, 67%). MS (ESI+): m/z 288 (M+H)$^+$. A mixture of N$^4$-(3-(trifluoromethyl)phenyl)-5-methylpyrimidine-2,4-diamine (28.7 mg, 0.1 mmol) and 4-(2-(pyrrolidin-1-yl)ethoxy)benzenamine (22 mg, 0.12 mmol) were dissolved in acetic acid (5 mL) and heated under microwave at 150° C. for 10 min. The mixture was cooled to room temperature and acetic acid removed under reduced pressure. The residue was purified by HPLC to afford the title compound XXXIV as brown solid (16 mg, 35%). $^1$H NMR (500 MHz, DMSO-d$_6$): 1.65-1.71 (m, 4H), 2.11 (s, 3H), 2.45-2.55 (m, 4H), 2.74 (t, J=6.0 Hz, 2H), 3.98 (t, J=6.0 Hz, 2H), 6.76 (d, J=9.0 Hz, 2H), 7.35 (d, J=5.1 Hz, 1H), 7.45-7.57 (m, 3H), 7.9-7.97 (m, 2H), 8.20 (d, J=7.6 Hz, 1H), 8.41 (s, 1H), 8.85 (s, 1H), m/z 458 (M+H)$^+$.

Example 61

2-chloro-N-(4-(trifluoromethyl)phenyl)-5-methylpyrimidin-4-amine (Intermediate 29)

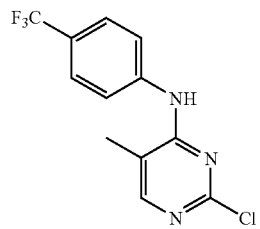

29

A suspension of 2-chloro-5-methylpyrimidin-4-amine (159 µL, 1.2 mmol), 1-bromo-4-(trifluoromethyl)benzene (150 mg, 1.0 mmol), potassium tert-butoxide (224 mg, 2.0 mmol), Xantphos (120 mg, 0.2 mmol), and palladium acetate (26 mg, 0.1 mmol) was sealed in a microwave reaction tube and irradiated at 160° C. for 15 min. The mixture was allowed to cool to room temperature, the solids were filtered using DCM to rinse, and the solution was concentrated under reduced pressure. The residue was purified by flash chromatography on silica gel (hexane to EtOAc) to afford the title intermediate 29 (128.7 mg, 43%) as a white solid. MS (ESI+): m/z 288 (M+H)$^+$.

Example 62

N$^2$-(4-(2-(pyrrolidin-1-yl)ethoxy)phenyl)-N$^4$-(4-(trifluoromethyl)phenyl)-5-methylpyrimidine-2,4-diamine (Compound XXXV)

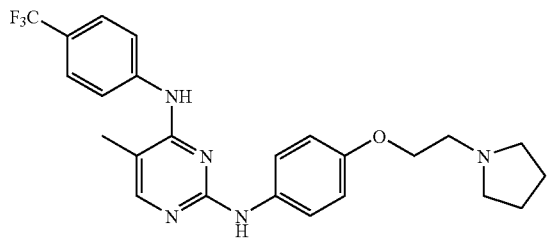

XXXV

A mixture of the above-described intermediates 29 (128 mg, 0.5 mmol) and 6 (212 mg, 1.0 mmol) were suspended in acetic acid (5 mL) and heated at 75° C. for 18 h. The mixture was allowed to cool to room temperature and acetic acid removed under reduced pressure. The residue was basified with sat., aq NaHCO$_3$ (50 mL) and extracted with DCM (2×50 mL). The organic layer was concentrated in vacuo and the crude product purified by reverse phase flash chromatography on C18 (water to CH$_3$CN, 0.1% TFA). The aqueous fractions were neutralized with sat, aq NaHCO$_3$ and extracted with EtOAc. The organics were concentrated in vacuo and the residue taken up in DCM. HCl in dioxane was added along with ether and the resulting solid filtered to afford the hydrochloride salt of the title compound XXXV (166 mg, 70%) as a grey solid. $^1$H NMR (500 MHz, DMSO-d$_6$): 1.80-1.95 (m, 2H), 1.95-2.10 (m, 2H), 2.19 (s, 3H), 3.05-3.20 (m, 2H), 3.55-3.65 (m, 6H), 4.33 (t, J=4.7 Hz, 2H), 6.97 (d, J=8.7 Hz, 2H), 7.34 (d, J=8.8 Hz, 2H), 7.73 (d, J=8.5 Hz, 2H), 7.83 (d, J=8.0 Hz, 2H), 7.94 (s, 1H), 9.92 (br s, 1H), 10.44 (br s, 1H), 10.85 (br s, 1H); MS (ESI+): m/z 458.5 (M+H)$^+$.

Example 63

Benzo[1,3]dioxol-4-yl-(2-chloro-5-methyl-pyrimidin-4-yl)-amine (Intermediate 30)

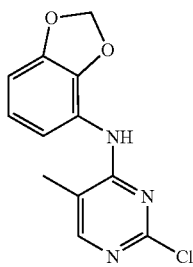

A mixture of 2-chloro-5-methyl-pyrimidin-4-ylamine (1.4 g, 9.7 mmol), 4-bromo-benzo[1,3]dioxole (2.0 g, 10 mmol), Pd$_2$(dba)$_3$ (0.80 g, 0.87 mmol), Xantphos (1.0 g, 1.7 mmol) and cesium carbonate (6.3 g, 19 mmol) was suspended in dioxane (40 mL) and heated at reflux under the argon atmosphere for 5 h. The reaction mixture was cooled to room temperature and diluted with DCM (30 mL). The mixture was filtered and the filtrate concentrated in vacuo. The residue was purified by flash chromatography on silica gel (hexanes to 50% EtOAc/hexanes) to afford the title compound (1.0 g, 39%) as a white solid. $^1$H NMR (500 MHz, DMSO-d$_6$): δ 2.13 (s, 3H), 5.99 (s, 2H), 6.80-6.90 (m, 3H), 8.01 (s, 1H), 8.92 (s, 1H). MS (ES+): m/z 264 (M+H)$^+$.

Example 64

N$^4$-Benzo[1,3]dioxol-4-yl-5-methyl-N$^2$-[4-(2-pyrrolidin-1-yl-ethoxy)-phenyl]-pyrimidine-2,4-diamine (Compound XXXVI)

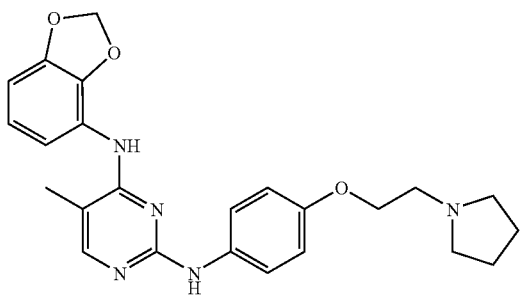

XXXVI

A mixture of intermediate 30 (0.25 g, 0.95 mmol) and 4-(2-pyrrolidin-1-yl-ethoxy)-phenylamine (0.40 g, 1.9 mmol) in acetic acid (15 mL) was heated at 100° C. for 20 h. The mixture was allowed to cool to room temperature and acetic acid removed under reduced pressure. The residue was taken in water (20 mL) and neutralized to pH~7 with 10% NaOH solution. The resulting solution was extracted with EtOAc (2×30 mL) and the organic layer separated. The organic layer was washed with brine, dried over anhydrous Na$_2$SO$_4$ and filtered. The filtrate was concentrated in vacuo and the crude product purified by flash chromatography on silica gel (DCM to 20% MeOH/DCM) to afford the title compound (0.14 g, 34%) as a white solid.

$^1$H NMR (500 MHz, DMSO-d$_6$): δ 1.65-1.75 (m, 4H), 2.06 (s, 3H), 2.55-2.65 (m, 4H), 2.78-2.88 (m, 2H), 3.98 (t, J=5.8 Hz, 2H), 5.89 (s, 2H), 6.65 (d, J=9.0 Hz, 2H), 6.79-6.84 (m, 2H), 6.89 (dd, J=7.7, 1.7 Hz, 1H), 7.45 (d, J=9.1 Hz, 2H), 7.81 (s, 1H), 8.23 (s, 1H), 8.73 (s, 1H). MS (ES+): m/z 434 (M+H)$^+$.

Example 65

N$^4$-Benzo[1,3]dioxol-4-yl-5-methyl-N$^2$-[4-(4-methyl-piperazin-1-yl)-phenyl]-pyrimidine-2,4-diamine (Compound XXXVII)

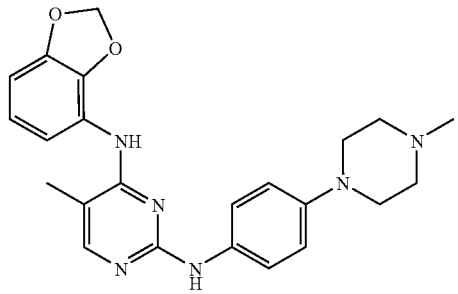

XXXVII

A mixture of intermediate 30 (0.10 g, 0.38 mmol) and 4-(4-methyl-piperazin-1-yl)-phenylamine (0.12 g, 0.51 mmol) in acetic acid (3 mL) was sealed in a microwave reaction tube and irradiated with microwave at 150° C. for 15 min. After cooling to room temperature, the cap was removed and the mixture concentrated. The residue was taken in water (20 mL) and the mixture was neutralized with 10% NaOH solution until solid precipitated. The solid was filtered and then purified by flash chromatography on silica gel (DCM to 15% MeOH/DCM) to afford the title compound (22 mg, 14%) as a light red solid.

$^1$H NMR (500 MHz, DMSO-d$_6$): δ 2.06 (s, 3H), 2.21 (s, 3H), 2.44 (t, J=4.8 Hz, 4H), 2.97 (t, J=4.9 Hz, 4H), 5.89 (s, 2H), 6.67 (d, J=9.1 Hz, 2H), 6.80-6.86 (m, 2H), 6.91 (dd, J=7.6, 1.7 Hz, 1H), 7.41 (d, J=9.0 Hz, 2H), 7.79 (s, 1H), 8.17 (s, 1H), 8.63 (s, 1H). MS (ES+): m/z 419 (M+H)$^+$.

Example 66

(4-Chloro-3-methoxy-phenyl)-(2-chloro-5-methyl-pyrimidin-4-yl)-amine (Intermediate 31)

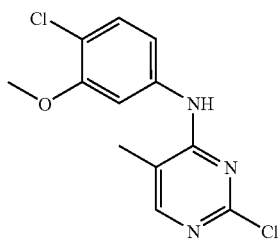

31

A mixture of 2-chloro-5-methyl-pyrimidin-4-ylamine (0.50 g, 3.5 mmol), 4-bromo-1-chloro-2-methoxy-benzene (0.65 mL, 4.8 mmol), Pd₂(dba)₃ (0.17 g, 0.19 mmol), Xantphos (0.22 g, 0.38 mmol) and cesium carbonate (2.3 g, 7.1 mmol) was suspended in dioxane (20 mL) and heated at reflux under the argon atmosphere for 5 h. The reaction mixture was cooled to room temperature and diluted with DCM (30 mL). The mixture was filtered and the filtrate concentrated in vacuo. The residue was purified by flash chromatography on silica gel (hexanes to 40% EtOAc/hexanes) to afford the title compound (0.55 g, 55%) as a yellow solid.

$^1$H NMR (500 MHz, DMSO-d$_6$): δ 2.18 (s, 3H), 3.85 (s, 3H), 7.35 (dd, J=8.6, 2.3 Hz, 1H), 7.39 (d, J=8.7 Hz, 1H), 7.56 (d, J=2.3 Hz, 1H), 8.09 (d, J=0.9 Hz, 1H), 8.91 (s, 1H). MS (ES+): m/z 284 (M+H)$^+$.

Example 67

N$^4$-(4-Chloro-3-methoxy-phenyl)-5-methyl-N$^2$-(4-pyrazol-1-ylmethyl-phenyl)-pyrimidine-2,4-diamine (Compound XXXVIII)

XXXVIII

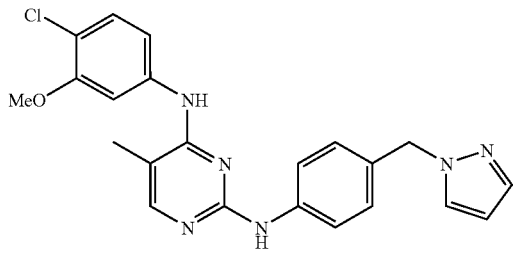

A suspension of intermediate 31 (0.20 g, 0.70 mmol), 4-pyrazol-1-ylmethyl-phenylamine (0.14 g, 0.81 mmol), Pd₂(dba)₃ (40 mg, 0.044 mmol), Xantphos (50 mg, 0.086 mmol) and cesium carbonate (0.50 g, 1.5 mmol) in dioxane/DMF (3/1, 4 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by HPLC. The fractions were combined and poured into saturated NaHCO₃ solution (40 mL). The combined aqueous layers were extracted with EtOAc (2×30 mL) and the combined organic layers washed with brine, dried over anhydrous Na₂SO₄ and filtered. The filtrate was concentrated and the resulting solid was dissolved in minimum amount of EtOAc and hexanes added until solid precipitated. After filtration, the title compound was obtained as an off white solid (0.13 g, 44%).

$^1$H NMR (500 MHz, DMSO-d$_6$): δ 2.11 (s, 3H), 3.74 (s, 3H), 5.22 (s, 2H), 6.25 (t, J=2.1 Hz, 1H), 7.08 (d, J=8.6 Hz, 2H), 7.27 (d, J=9.3 Hz, 1H), 7.40-7.45 (m, 3H), 7.60 (d, J=8.6 Hz, 2H), 7.75 (d, J=1.8 Hz, 1H), 7.91 (s, 1H), 8.36 (s, 1H), 9.04 (s, 1H) MS (ES+): m/z 421 (M+H)$^+$.

Example 68

5-Methyl-N$^2$-[4-(4-methyl-piperazin-1-yl)-phenyl]-pyrimidine-2,4-diamine (Intermediate 32)

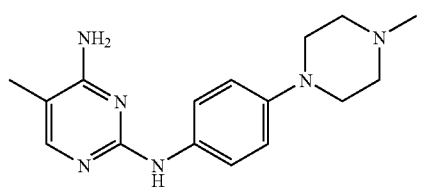

32

A mixture of 2-chloro-5-methyl-pyrimidin-4-ylamine (1.0 g, 6.9 mmol) and 4-(4-methyl-piperazin-1-yl)-phenylamine (1.5 mL, 7.8 mmol) in acetic acid (15 mL) was heated at 100° C. for 2.5 h. The mixture was allowed to cool to room temperature and acetic acid removed under reduced pressure. The residue was taken in water (20 mL) and the mixture was neutralized with 10% NaOH solution until solid precipitated. After filtration and washed with water, the title compound was obtained as a grey solid (1.3 g, 63%).

$^1$H NMR (500 MHz, DMSO-d$_6$): δ 1.88 (s, 3H), 2.21 (s, 3H), 2.21 (s, 3H), 2.44 (t, J=4.8 Hz, 4H), 3.00 (t, J=4.8 Hz, 4H), 6.27 (s, 2H), 6.79 (d, J=9.0 Hz, 2H), 7.57 (d, J=9.0 Hz, 2H), 7.63 (s, 1H), 8.42 (s, 1H). MS (ES+): m/z 299 (M+H)$^+$.

Example 69

N$^4$-(4-Chloro-3-methoxy-phenyl)-5-methyl-N$^2$-[4-(4-methyl-piperazin-1-yl)-phenyl]-pyrimidine-2,4-diamine (Compound XXXIX)

XXXIX

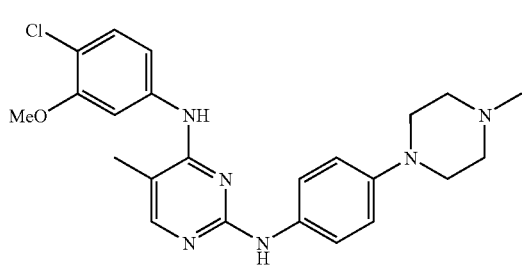

A suspension of intermediate 32 (0.30 g, 1.0 mmol), 4-bromo-1-chloro-2-methoxy-benzene (0.20 mL, 1.5 mmol), Pd₂(dba)₃ (50 mg, 0.055 mmol), Xantphos (65 mg, 0.11 mmol) and cesium carbonate (0.70 g, 2.1 mmol) in dioxane/DMF (3/1, 8 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (40 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/5, 30 mL). After filtration, the title compound was obtained as an off white solid (0.20 g, 46%).

$^1$H NMR (500 MHz, DMSO-d$_6$): δ 2.09 (s, 3H), 2.21 (s, 3H), 2.45 (t, J=4.9 Hz, 4H), 3.02 (t, J=4.9 Hz, 4H), 3.73 (s, 3H), 6.79 (d, J=9.1 Hz, 2H), 7.27 (d, J=8.6 Hz, 1H), 7.42-7.47 (m, 3H), 7.49 (d, J=2.3 Hz, 1H), 7.86 (s, 1H), 8.28 (s, 1H), 8.72 (s, 1H). MS (ES+): m/z 439 (M+H)$^+$.

Example 70

N$^4$-(4-Chloro-3-methoxy-phenyl)-5-methyl-N$^2$-(4-morpholin-4-yl-phenyl)-pyrimidine -2,4-diamine (Compound XL)

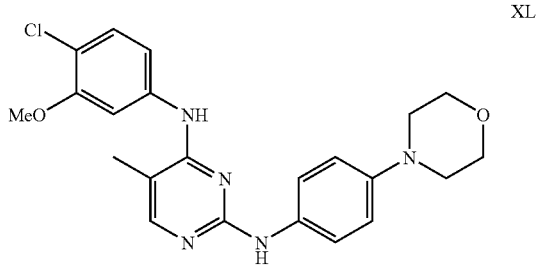

A mixture of intermediate 31 (0.10 g, 0.35 mmol) and 4-morpholin-4-yl-phenylamine (80 mg, 0.45 mmol) in acetic acid (3 mL) was sealed in a microwave reaction tube and irradiated with microwave at 160° C. for 20 min. After cooling to room temperature, the cap was removed and the mixture concentrated. The residue was taken in water (20 mL) and the mixture was neutralized with 10% NaOH solution until solid precipitated. The solid was filtered and then purified by flash chromatography on silica gel (DCM to 10% MeOH/DCM) to afford the title compound (55 mg, 37%) as a light brown solid.

$^1$H NMR (500 MHz, DMSO-d$_6$): δ 2.10 (s, 3H), 3.00 (t, J=4.8 Hz, 4H), 3.71-3.76(m, 7H), 6.80 (d, J=9.0 Hz, 2H), 7.28 (d, J=8.6 Hz, 1H), 7.45 (dd, J=8.7, 2.2 Hz, 1H), 7.47-7.50 (m, 3H), 7.87 (s, 1H), 8.29 (s, 1H), 8.75 (s, 1H). MS (ES+): m/z 426 (M+H)$^+$.

Example 71

N$^4$-(4-Chloro-3-methoxy-phenyl)-5-methyl-N$^2$-(4-pyrazol-1-yl-phenyl)-pyrimidine -2,4-diamine (Compound XLI)

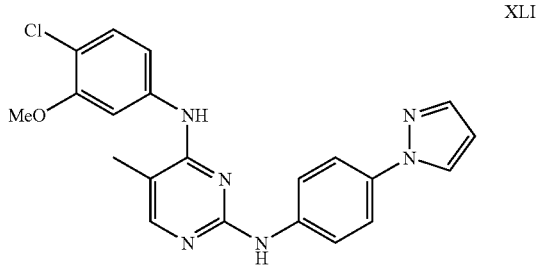

A mixture of intermediate 31 (90 mg, 0.32 mmol) and 4-pyrazol-1-yl-phenylamine (70 mg, 0.44 mmol) in acetic acid (3 mL) was sealed in a microwave reaction tube and irradiated with microwave at 160° C. for 20 min. After cooling to room temperature, the cap was removed and the mixture concentrated. The residue was taken in water (20 mL) and the mixture neutralized with 10% NaOH solution until solid precipitated. The solid was filtered and then purified by HPLC. The corrected fractions were combined and concentrated to afford the title compound (40 mg of TFA salt, 24%) as a white solid.

$^1$H NMR (500 MHz, DMSO-d$_6$): δ 2.17 (s, 3H), 3.75 (s, 3H), 6.54 (t, J=1.9 Hz, 1H), 7.30 (d, J=6.6 Hz, 1H), 7.39 (d, J=2.1 Hz, 1H), 7.40 (d, J=8.6 Hz, 1H), 7.59 (d, J=8.9 Hz, 2H), 7.71 (d, J=8.9 Hz, 2H), 7.73 (d, J=1.6 Hz, 1H), 7.93 (s, 1H), 8.41 (d, J=2.5 Hz, 1H), 9.41 (s, 1H), 10.05 (s, 1H). MS (ES+): m/z 407 (M+H)$^+$.

Example 72

N$^4$-(4-Chloro-3-methoxy-phenyl)-5-methyl-N$^2$-(4-piperidin-1-yl-phenyl)-pyrimidine -2,4-diamine (XLII)

A mixture of intermediate 31 (0.11 g, 0.39 mmol) and 4-piperidin-1-yl-phenylamine (90 mg, 0.51 mmol) in acetic acid (3 mL) was sealed in a microwave reaction tube and irradiated with microwave at 160° C. for 20 min. After cooling to room temperature, the cap was removed and the mixture concentrated. The residue was taken in water (20 mL) and the mixture neutralized with 10% NaOH solution until solid precipitated. The solid was filtered and then purified by flash chromatography on silica gel (hexanes to 70% EtOAc/hexanes) to afford the title compound (10 mg, 6%) as a light brown solid.

$^1$H NMR (500 MHz, DMSO-d$_6$): δ 1.48-1.53 (m, 2H), 1.59-1.65 (m, 4H), 2.09 (s, 3H), 3.00 (t, J=5.4 Hz, 4H), 3.73 (s, 3H), 6.78 (d, J=9.0 Hz, 2H), 7.27 (d, J=8.7 Hz, 1H), 7.40-7.47 (m, 3H), 7.50 (d, J=2.2 Hz, 1H), 7.86 (s, 1H), 8.28 (s, 1H), 8.71 (s, 1H). MS (ES+): m/z 424 (M+H)$^+$.

Example 73

N⁴-(4-Chloro-3-methoxy-phenyl)-5-methyl-N²-[4-(4-methyl-piperazin-1-ylmethyl)-phenyl]-pyrimidine-2,4-diamine (XLIII)

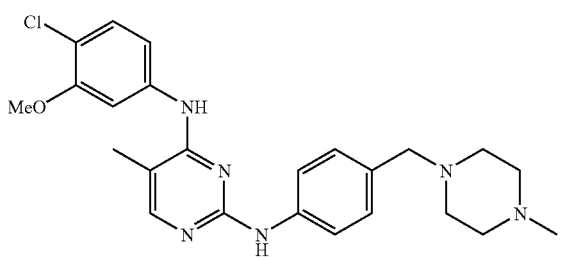

XLIII

A suspension of intermediate 31 (50 mg, 0.18 mmol), 4-(4-methyl-piperazin-1-ylmethyl)-phenylamine (50 mg, 0.24 mmol), Pd$_2$(dba)$_3$ (10 mg, 0.011 mmol), Xantphos (13 mg, 0.022 mmol) and cesium carbonate (0.12 g, 0.37 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by flash chromatography on silica gel (DCM to 10% MeOH/DCM) to afford the title compound (35 mg, 44%) as an off white solid.

$^1$H NMR (500 MHz, DMSO-d$_6$): δ 2.11 (s, 3H), 2.15 (s, 3H), 2.20-2.45 (m, 8H), 3.35 (s, 2H), 3.75 (s, 3H), 7.07 (d, J=8.5 Hz, 2H), 7.28 (d, J=8.5 Hz, 1H), 7.44 (dd, J=8.7, 2.3 Hz, 1H), 7.47 (d, J=2.3 Hz, 1H), 7.57 (d, J=8.5 Hz, 2H), 7.91 (s, 1H), 8.36 (s, 1H), 8.98 (s, 1H). MS (ES+): m/z 453 (M+H)⁺.

Example 74

N⁴-(4-Chloro-3-methoxy-phenyl)-5-methyl-N²-(4-piperazin-1-yl-phenyl)-pyrimidine-2,4-diamine (Compound XLIV)

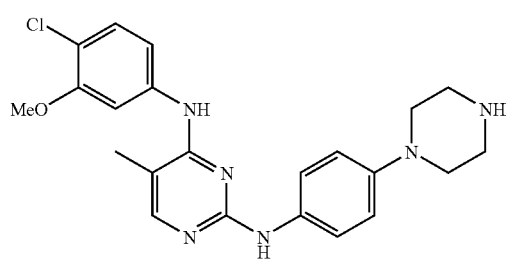

XLIV

A mixture of intermediate 31 (0.20 g, 0.70 mmol) and 4-(4-amino-phenyl)-piperazine-1-carboxylic acid tert-butyl ester (0.22 g, 0.79 mmol) in acetic acid (4 mL) was sealed in a microwave reaction tube and irradiated with microwave at 150° C. for 15 min. After cooling to room temperature, the cap was removed and the mixture concentrated. The residue was purified by HPLC and the corrected fractions combined and poured into saturated NaHCO$_3$ solution (40 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as an off white solid (0.10 g, 33%).

$^1$H NMR (500 MHz, DMSO-d$_6$): δ 2.10 (s, 3H), 3.16 (s, 8H), 3.73 (s, 3H), 6.83 (d, J=9.0 Hz, 2H), 7.29 (d, J=8.8 Hz, 1H), 7.44 (dd, J=8.7, 2.1 Hz, 1H), 7.49-7.52 (m, 3H), 7.88 (s, 1H), 8.32 (s, 1H), 8.81 (s, 1H) MS (ES+): m/z 425 (M+H)⁺.

Example 75

N-tert-Butyl-3-{5-methyl-2-[4-(4-methyl-piperazin-1-yl)-phenylamino]-pyrimidin-4-ylamino}-benzenesulfonamide (Compound XLV)

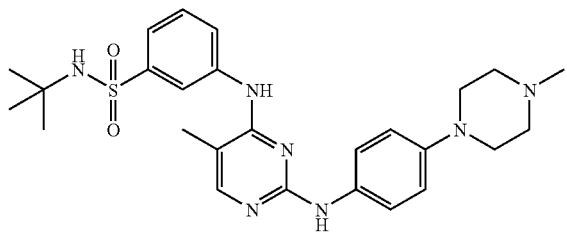

XLV

A suspension of intermediate 32 (0.30 g, 1.0 mmol), 3-bromo-N-tert-butyl-benzenesulfonamide (0.35 g, 1.2 mmol), Pd$_2$(dba)$_3$ (60 mg, 0.066 mmol), Xantphos (70 mg, 0.12 mmol) and cesium carbonate (0.70 g, 2.1 mmol) in dioxane/DMF (3/1, 8 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (40 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/7, 40 mL). After filtration, the title compound was obtained as an off white solid (0.30 g, 59%).

$^1$H NMR (500 MHz, DMSO-d$_6$): δ 1.12 (s, 9H), 2.11 (s, 3H), 2.22 (s, 3H), 2.45 (t, J=4.7 Hz, 4H), 3.02 (t, J=4.8 Hz, 4H), 6.81 (d, J=9.1 Hz, 2H), 7.45-7.52 (m, 4H), 7.56 (s, 1H), 7.89 (s, 1H), 8.10-8.16 (m, 2H), 8.51 (s, 1H), 8.70 (s, 1H) MS (ES+): m/z 510 (M+H)⁺.

Example 76

N-tert-Butyl-3-(2-chloro-5-methyl-pyrimidin-4-ylamino)-benzenesulfonamide (Intermediate 33)

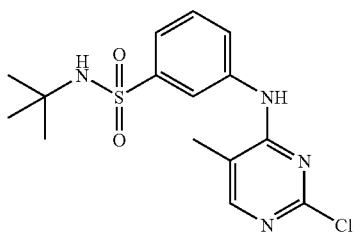

33

A mixture of 2-chloro-5-methyl-pyrimidin-4-ylamine (0.4 g, 2.8 mmol), 3-bromo-N-tert-butyl-benzenesulfonamide (1.0 g, 3.4 mmol), Pd$_2$(dba)$_3$ (0.17 g, 0.19 mmol), Xantphos (0.2 g, 3.5 mmol) and cesium carbonate (2.0 g, 6.1 mmol) was suspended in dioxane (25 mL) and heated at reflux under the argon atmosphere for 3 h. The reaction mixture was cooled to room temperature and diluted with DCM (30 mL). The mixture was filtered and the filtrate concentrated in vacuo. The residue was dissolved in EtOAc and hexanes added until solid precipitated. After filtration, the title compound (1.2 g, 98%) was obtained as a light brown solid. It was used in the next step without purification. MS (ES+): m/z 355 (M+H)$^+$.

Example 77

N-tert-Butyl-3-[5-methyl-2-(4-morpholin-4-ylmethyl-phenylamino)-pyrimidin-4-ylamino]-benzenesulfonamide (Compound XLVI)

XLVI

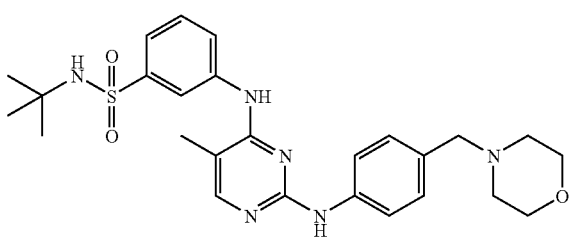

A mixture of intermediate 33 (0.50 g, 1.4 mmol), 4-morpholin-4-ylmethyl-phenylamine (0.35 g, 1.8 mmol), Pd$_2$(dba)$_3$ (0.10 g, 0.11 mmol), Xantphos (0.12 g, 0.21 mmol) and cesium carbonate (1.0 g, 3.1 mmol) was suspended in dioxane (25 mL) and heated at reflux under the argon atmosphere for 3 h. The reaction mixture was cooled to room temperature and diluted with DCM (30 mL). The mixture was filtered and the filtrate concentrated in vacuo. The residue was purified by HPLC and the corrected fractions combined and poured into saturated NaHCO$_3$ solution (50 mL). The combined aqueous layers were extracted with EtOAc (2×50 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as an off white solid (0.23 g, 31%).

$^1$H NMR (500 MHz, DMSO-d$_6$): δ 1.12 (s, 9H), 2.13 (s, 3H), 2.28-2.34 (m, 4H), 3.35 (s, 2H), 3.55 (t, J=4.8 Hz, 4H), 7.10 (d, J=8.5 Hz, 2H), 7.45-7.52 (m, 2H), 7.57 (s, 1H), 7.59 (d, J=8.5 Hz, 2H), 7.94 (s, 1H), 8.10 (s, 1H), 8.13-8.16 (m, 1H), 8.58 (s, 1H), 8.95 (s, 1H). MS (ES+): m/z 511 (M+H)$^+$.

Example 78

N-tert-Butyl-3-{5-methyl-2-[4-(4-oxy-morpholin-4-ylmethyl)-phenylamino]-pyrimidin-4-ylamino}-benzenesulfonamide (Compound XLVII)

XLVII

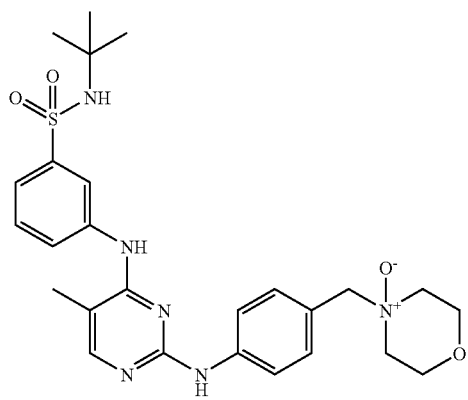

A solution of the above-described compound XLVI (30 mg, 0.06 mmol) and 3-chloroperbenzoic acid (77%, 14 mg, 0.06 mmol) in chloroform (30 mL) was stirred at room temperature for 1 hour. The solvent was removed by rotovap and the resulting mixture was purified by silica gel with 20% CH$_3$OH/CHCl$_3$ as an eluent to afford the title compound as an off-white solid (15 mg, 48%).

$^1$H NMR (500 MHz, DMSO-d$_6$): δ 1.12 (s, 9H), 2.14 (s, 3H), 2.71 (d, J=10.9 Hz, 2H), 3.63 (d, J=9.9 Hz, 2H), 4.08 (t, J=11.6 Hz, 2H), 4.28 (s, 2H), 7.38 (d, J=8.5 Hz, 2H), 7.50 (d, J=5.0 Hz, 2H), 7.61 (s, 1H), 7.66 (d, J=8.5 Hz, 2H), 7.96 (s, 1H), 8.13 (m, 2H), 8.63 (s, 1H), 9.13 (s, 1H). MS (ES+): m/z 527 (M+H)$^+$.

Example 79

N-tert-Butyl-3-[5-methyl-2-(4-pyrazol-1-yl-phenylamino)-pyrimidin-4-ylamino]-benzenesulfonamide (Compound XLVIII)

XLVIII

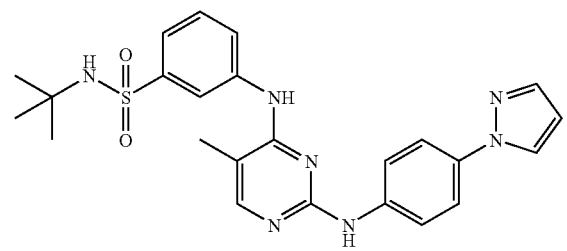

A mixture of intermediate 33 (0.10 g, 0.28 mmol) and 4-pyrazol-1-yl-phenylamine (50 mg, 0.31 mmol) in acetic acid (3 mL) was sealed in a microwave reaction tube and irradiated with microwave at 130° C. for 15 min. After cooling to room temperature, the cap was removed and the mixture concentrated. The residue was taken up in water (20 mL) and neutralized with 10% NaOH solution until solid precipitated. The brown solid was filtered and then purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (15 mg, 11%).

$^1$H NMR (500 MHz, DMSO-d$_6$): δ 1.12 (s, 9H), 2.15 (s, 3H), 6.49 (t, J=2.2 Hz, 1H), 7.50-7.55 (m, 2H), 7.58 (s, 1H), 7.62 (d, J=9.1 Hz, 2H), 7.68 (d, J=1.3 Hz, 1H), 7.77 (d, J=9.1 Hz, 2H), 7.96 (s, 1H), 8.11 (s, 1H), 8.13-8.16 (m, 1H), 8.33 (d, J=2.5 Hz, 1H), 8.64 (s, 1H), 9.17 (s, 1H). MS (ES+): m/z 478 (M+H)$^+$.

Example 80

N-tert-Butyl-3-[5-methyl-2-(6-piperazin-1-yl-pyridin-3-ylamino)-pyrimidin-4-ylamino]-benzenesulfonamide (Compound XLIX)

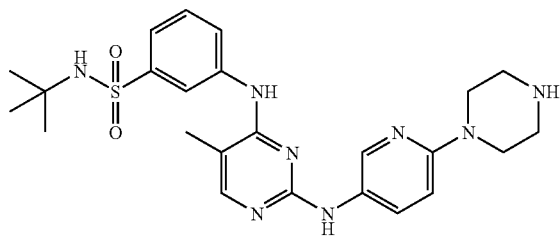

XLIX

A mixture of intermediate 33 (0.10 g, 0.28 mmol) and 4-(5-amino-pyridin-2-yl)-piperazine-1-carboxylic acid tert-butyl ester (90 mg, 0.32 mmol) in acetic acid (3 mL) was sealed in a microwave reaction tube and irradiated with microwave at 130° C. for 15 min. After cooling to room temperature, the cap was removed and the mixture concentrated. The residue was dissolved in DCM (5 mL) and 30% TFA/DCM (6 mL) added. The mixture was stirred at room temperature for 1 h, concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (10 mg, 7%).

$^1$H NMR (500 MHz, DMSO-d$_6$): δ 1.12 (s, 9H), 2.11 (s, 3H), 2.83 (t, J=5.0 Hz, 4H), 3.28-3.33 (m, 4H), 6.73 (d, J=9.1 Hz, 1H), 7.40-7.49 (m, 2H), 7.57 (s, 1H), 7.86 (dd, J=9.1, 2.7 Hz, 1H), 7.88 (s, 1H), 8.10-8.16 (m, 2H), 8.28 (d, J=2.5 Hz, 1H), 8.53 (s, 1H), 8.72 (s, 1H). MS (ES+): m/z 497 (M+H)$^+$.

Example 81

N-tert-Butyl-3-[5-methyl-2-(4-pyrazol-1-ylmethyl-phenylamino)-pyrimidin-4-ylamino]-benzenesulfonamide (Compound L)

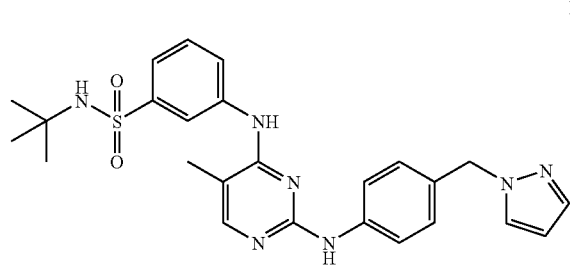

L

A mixture of intermediate 33 (0.10 g, 0.28 mmol) and 4-pyrazol-1-ylmethyl-phenylamine (50 mg, 0.29 mmol) in acetic acid (3 mL) was sealed in a microwave reaction tube and irradiated with microwave at 130° C. for 15 min. After cooling to room temperature, the cap was removed and the mixture concentrated. The residue was purified by HPLC and the corrected fractions combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (12 mg, 9%).

$^1$H NMR (500 MHz, DMSO-d$_6$): δ 1.12 (s, 9H), 2.13 (s, 3H), 5.21 (s, 2H), 6.24 (t, J=1.9 Hz, 1H), 7.08 (d, J=8.5 Hz, 2H), 7.27-7.50 (m, 3H), 7.56 (s, 1H), 7.60 (d, J=8.4 Hz, 2H), 7.75 (d, J=2.1 Hz, 1H), 7.94 (s, 1H), 8.14 (d, J=7.9 Hz, 1H), 8.59 (s, 1H), 9.01 (s, 1H). MS (ES+): m/z 492 (M+H)$^+$.

Example 82

5-Methyl-N$^2$-[3-(piperidine-1-sulfonyl)-phenyl]-pyrimidine-2,4-diamine (Intermediate 34)

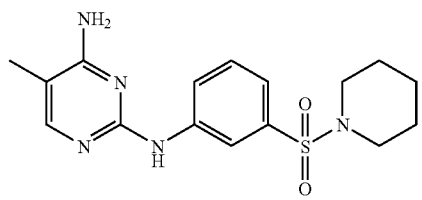

34

A mixture of 2-chloro-5-methyl-pyrimidin-4-ylamine (0.25 g, 1.74 mmol) and 3-(piperidine-1-sulfonyl)-phenylamine (0.50 g, 2.1 mmol) in acetic acid (4 mL) was sealed in a microwave reaction tube and irradiated with microwave at 130° C. for 15 min. After cooling to room temperature, the cap was removed and the mixture concentrated. The residue was taken in water (20 mL) and pH adjusted to ~9 with 10% NaOH solution. The resulting solution was extracted with EtOAc (2×30 mL) and the organic layer separated. The combined organic layers were washed with brine, dried over anhydrous Na$_2$SO$_4$ and filtered. The filtrate was concentrated in vacuo and the crude product (~0.6 g) used in the next step without purification. MS (ES+): m/z 348 (M+H)$^+$.

Example 83

N-tert-Butyl-3-{5-methyl-2-[3-(Piperidine-1-sulfonyl)-phenylamino]-pyrimidin-4-ylamino}-benzenesulfonamide (Compound LI)

LI

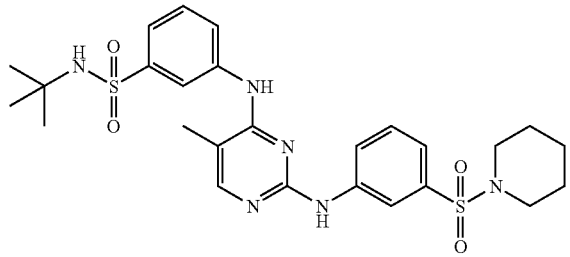

A suspension of intermediate 34 (0.10 g, 0.29 mmol), 3-bromo-N-tert-butyl-benzenesulfonamide (84 mg, 0.29 mmol), Pd$_2$(dba)$_3$ (15 mg, 0.016 mmol), Xantphos (20 mg, 0.035 mmol) and cesium carbonate (0.18 g, 0.55 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue dissolved in minimum amount of EtOAc and hexanes added until solid precipitated. After filtration, the title compound was obtained as a white solid (20 mg, 12%).

$^1$H NMR (500 MHz, DMSO-d$_6$): δ 1.12 (s, 9H), 1.30-1.40 (m, 2H), 1.50-1.56 (m, 4H), 2.16 (s, 3H), 2.88 (t, J=5.3 Hz, 4H), 7.17 (d, J=7.8 Hz, 1H), 7.43 (t, J=8.0 Hz, 1H), 7.59-7.60 (m, 2H), 7.58 (s, 1H), 8.13 (s, 1H), 7.16 (dd, J=7.9, 1.9 Hz, 1H), 8.18-8.22 (m, 1H), 8.67 (s, 1H), 9.37 (s, 1H). MS (ES+): m/z 559 (M+H)$^+$.

Example 84

N-tert-Butyl-3-{5-methyl-2-[4-(4-methyl-piperazin-1-ylmethyl)-phenylamino]-pyrimidin-4-ylamino}-benzenesulfonamide (Compound LII)

LII

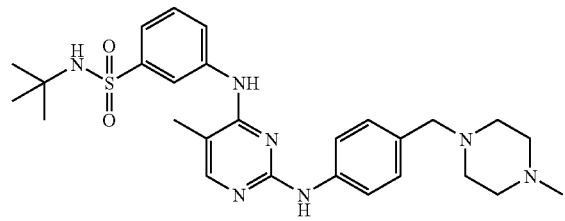

A suspension of intermediate 33 (0.10 g, 0.28 mmol), 4-(4-methyl-piperazin-1-ylmethyl)-phenylamine (65 mg, 0.32 mmol), Pd$_2$(dba)$_3$ (20 mg, 0.022 mmol), Xantphos (25 mg, 0.043 mmol) and cesium carbonate (0.18 g, 0.55 mmol) in dioxane/DMF (3/1, 4 mL) was sealed in a microwave reaction tube and irradiated with microwave at 170° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue dissolved in minimum amount of EtOAc and hexanes added until solid precipitated. After filtration, the title compound was obtained as a white solid (53 mg, 36%).

$^1$H NMR (500 MHz, DMSO-d$_6$): δ 1.12 (s, 9H), 2.13 (s, 3H), 2.15 (s, 3H), 2.20-2.45 (m, 4H), 3.25-3.40 (m, 6H), 7.08 (d, J=8.6 Hz, 2H), 7.45-7.52 (m, 2H), 7.56 (s, 1H), 7.57 (d, J=8.6 Hz, 2H), 7.94 (s, 1H), 8.09 (s, 1H), 8.13-8.16 (m, 1H), 8.58 (s, 1H), 8.94 (s, 1H). MS (ES+): m/z 524 (M+H)$^+$.

Example 85

N-tert-Butyl-3-[5-methyl-2-(4-piperazin-1-yl-3-trifluoromethyl-phenylamino)-pyrimidin-4-ylamino]-benzenesulfonamide (Compound LIII)

LIII

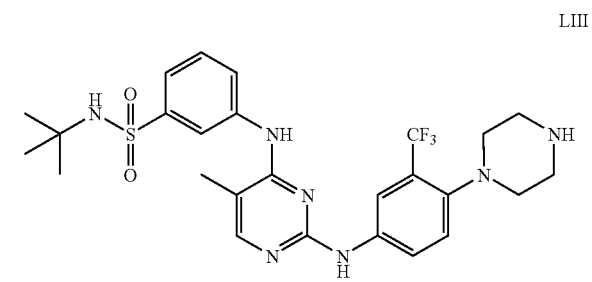

A mixture of intermediate 33 (0.10 g, 0.28 mmol), 4-(4-amino-2-trifluoromethyl-phenyl)-piperazine-1-carboxylic acid tert-butyl ester (0.1 g, 0.29 mmol), Pd$_2$(dba)$_3$ (20 mg, 0.022 mmol), Xantphos (25 mg, 0.043 mmol) and cesium carbonate (0.18 g, 0.55 mmol) in dioxane/DMF (3/1, 4 mL) was sealed in a microwave reaction tube and irradiated with microwave at 170° C. for 15 min. After cooling to room temperature, the cap was removed and the resulting mixture filtered. The filtered solid was washed with DCM and the filtrate concentrated. The residue was dissolved in DCM (5 mL) and 50% TFA/DCM (6 mL) added. The mixture was stirred at room temperature for 2 h, concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (42 mg, 26%).

$^1$H NMR (500 MHz, DMSO-d$_6$): δ 1.12 (s, 9H), 2.14 (s, 3H), 2.70-2.75 (m, 4H), 2.80-2.85 (m, 4H), 7.36 (d, J=8.5 Hz,

2H), 7.45-7.52 (m, 2H), 7.55 (s, 1H), 7.90-8.00(m, 3H), 8.07 (s, 1H), 8.15 (d, J=7.6 Hz, 1H), 8.63 (s, 1H), 9.22 (s, 1H) MS (ES+): m/z 564 (M+H)+.

Example 86

3-{2-[4-(4-Acetyl-piperazin-1-yl)-3-trifluoromethyl-phenylamino]-5-methyl-pyrimidin-4-ylamino}-N-tert-butyl-benzenesulfonamide (Compound LIV)

LIV

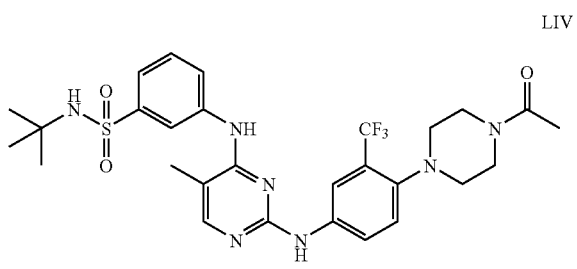

A mixture of intermediate 33 (0.10 g, 0.28 mmol), 1-[4-(4-amino-2-trifluoromethyl-phenyl)-piperazin-1-yl]-ethanone (0.1 g, 0.35 mmol), Pd$_2$(dba)$_3$ (15 mg, 0.016 mmol), Xantphos (20 mg, 0.035 mmol) and cesium carbonate (0.20 g, 0.61 mmol) in dioxane/DMF (3/1, 4 mL) was sealed in a microwave reaction tube and irradiated with microwave at 160° C. for 15 min. After cooling to room temperature, the cap was removed and the resulting mixture filtered. The filtered solid was washed with DCM and the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (64 mg, 38%).

$^1$H NMR (500 MHz, DMSO-d$_6$): δ 1.12 (s, 9H), 2.04 (3, H), 2.14 (s, 3H), 2.73 (t, J=4.9 Hz, 2H), 2.79 (t, J=4.7 Hz, 2H), 3.50-3.60 (m, 4H), 7.40 (d, J=8.7 Hz, 2H), 7.45-7.52 (m, 2H), 7.56 (s, 1H), 7.90-8.00 (m, 3H), 8.07 (s, 1H), 8.14 (d, J=7.2 Hz, 1H), 8.64 (s, 1H), 9.26 (s, 1H). MS (ES+): m/z 606 (M+H)+.

Example 87

5-Methyl-N$^2$-[3-(4-methyl-piperazine-1-sulfonyl)-phenyl]-pyrimidine-2,4-diamine (Intermediate 35)

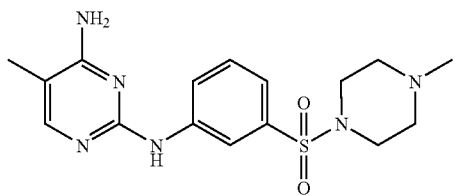

A mixture of 2-chloro-5-methyl-pyrimidin-4-ylamine (0.25 g, 1.74 mmol) and 3-(4-methyl-piperazine-1-sulfonyl)-phenylamine (0.50 g, 2.0 mmol) in acetic acid (4 mL) was sealed in a microwave reaction tube and irradiated with microwave at 130° C. for 15 min. After cooling to room temperature, the cap was removed and the mixture concentrated. The residue was taken in water (20 mL) and pH adjusted to ~9 with 10% NaOH solution. The resulting solution was extracted with EtOAc (2×30 mL) and the organic layer separated. The combined organic layers were washed with brine, dried over anhydrous Na$_2$SO$_4$ and filtered. The filtrate was concentrated in vacuo and the crude product (~0.42 g) used in the next step without purification. MS (ES+): m/z 363 (M+H)+.

Example 88

N-tert-Butyl-3-{5-methyl-2-[3-(4-methyl-piperazine-1-sulfonyl)-phenylamino]-pyrimidin-4-ylamino}-benzenesulfonamide (Compound LV)

LV

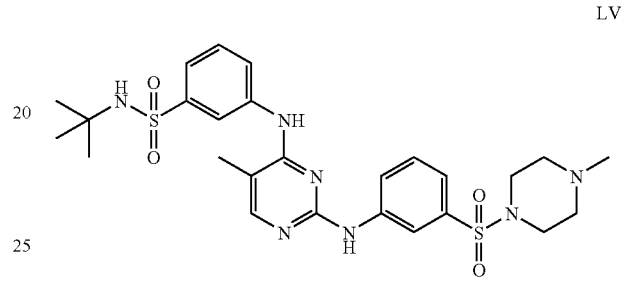

A suspension of intermediate 35 (0.10 g, 0.28 mmol), 3-bromo-N-tert-butyl-benzenesulfonamide (80 mg, 0.27 mmol), Pd$_2$(dba)$_3$ (15 mg, 0.016 mmol), Xantphos (20 mg, 0.035 mmol) and cesium carbonate (0.18 g, 0.55 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue dissolved in minimum amount of EtOAc and hexanes added until solid precipitated. After filtration, the title compound was obtained as a white solid (10 mg, 6%).

$^1$H NMR (500 MHz, DMSO-d$_6$): δ 1.12 (s, 9H), 2.13 (s, 3H), 2.16 (s, 3H), 2.33-2.40 (m, 4H), 2.85-2.94 (m, 4H), 7.18 (d, J=8.1 Hz, 1H), 7.44 (t, J=8.0 Hz, 1H), 7.49-7.54 (m, 2H), 7.58 (s, 1H), 8.00-8.03 (m, 2H), 8.13 (s, 1H), 8.15 (dd, J=8.6, 1.6 Hz, 1H), 8.18-8.23 (m, 1H), 8.66 (s, 1H), 9.38 (s, 1H). MS (ES+): m/z 574 (M+H)+.

Example 89

N-tert-Butyl-3-[5-methyl-2-(4-piperazin-1-ylmethyl-phenylamino)-pyrimidin-4-ylamino]-benzenesulfonamide (Compound LVI)

LVI

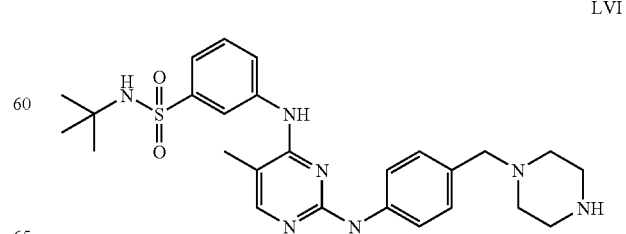

A mixture of intermediate 33 (0.10 g, 0.28 mmol), 4-(4-amino-benzyl)-piperazine-1-carboxylic acid tert-butyl ester (0.1 g, 0.34 mmol), Pd$_2$(dba)$_3$ (15 mg, 0.016 mmol), Xantphos (20 mg, 0.035 mmol) and cesium carbonate (0.20 g, 0.61 mmol) in dioxane/DMF (3/1, 4 mL) was sealed in a microwave reaction tube and irradiated with microwave at 170° C. for 15 min. After cooling to room temperature, the cap was removed and the resulting mixture filtered. The filtered solid was washed with DCM and the filtrate concentrated. The residue was dissolved in DCM (6 mL) and TFA (3 mL) added. The mixture was stirred at room temperature for 1 h, concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid triturated in hexanes/EtOAc (10/1, 55 mL). After filtration, the title compound was obtained as a white solid (32 mg, 22%).

$^1$H NMR (500 MHz, DMSO-d$_6$): δ 1.12 (s, 9H), 2.13 (s, 3H), 2.30-2.40 (m, 4H), 2.85 (t, J=4.7 Hz, 4H), 3.38 (s, 2H), 7.09 (d, J=8.5 Hz, 2H), 7.45-7.52 (m, 2H), 7.56 (s, 1H), 7.59 (d, J=8.5 Hz, 2H), 7.94 (s, 1H), 8.10 (s, 1H), 8.13-8.16 (m, 1H), 8.59 (s, 1H), 8.96 (s, 1H). MS (ES+): m/z 510 (M+H)$^+$.

Example 90

N-tert-Butyl-3-{5-methyl-2-[4-(2-pyrrolidin-1-yl-ethoxy)-phenylamino]-pyrimidin-4-ylamino}-benzenesulfonamide (Compound LVII)

LVII

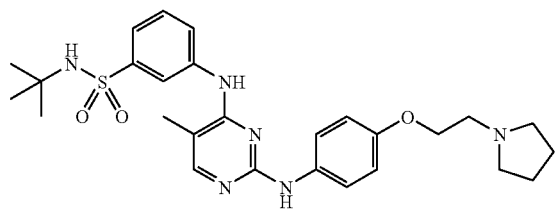

A mixture of intermediate 33 (0.10 g, 0.28 mmol) and 4-(2-pyrrolidin-1-yl-ethoxy)-phenylamine (0.10 g, 0.49 mmol) in acetic acid (3 mL) was sealed in a microwave reaction tube and irradiated with microwave at 150° C. for 20 min. After cooling to room temperature, the cap was removed and the mixture concentrated. The residue was purified by HPLC and the corrected fractions combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid dissolved in minimum amount of EtOAc and hexanes added until solid precipitated. After filtration, the title compound was obtained as a white solid (40 mg, 27%).

$^1$H NMR (500 MHz, DMSO-d$_6$): δ 1.12 (s, 9H), 1.65-1.70 (m, 4H), 2.12 (s, 3H), 2.45-2.55 (m, 4H), 2.76 (t, J=5.8 Hz, 2H), 3.99 (t, J=6.0 Hz, 2H), 6.79 (d, J=9.0 Hz, 2H), 7.46-7.53 (m, 4H), 7.56 (s, 1H), 7.90 (s, 1H), 8.10-8.15 (m, 2H), 8.53 (s, 1H), 8.77 (s, 1H). MS (ES+): m/z 525 (M+H)$^+$.

Example 91

3-{5-Methyl-2-[4-(4-methyl-piperazin-1-yl)-phenylamino]-pyrimidin-4-ylamino}-benzenesulfonamide (Compound LVIII)

LVIII

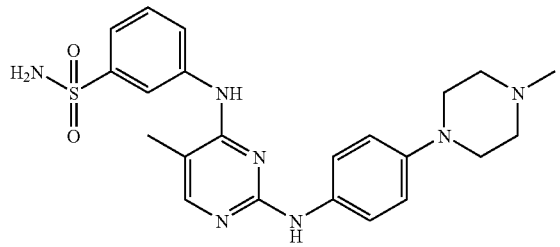

A suspension of intermediate 32 (0.10 g, 0.33 mmol), 3-bromo-benzenesulfonamide (0.10 g, 0.42 mmol), Pd$_2$(dba)$_3$ (20 mg, 0.022 mmol), Xantphos (25 mg, 0.043 mmol) and cesium carbonate (0.25 g, 0.77 mmol) in dioxane (3 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated to afford the title compound as a grey solid (10 mg, 7%).

$^1$H NMR (500 MHz, DMSO-d$_6$): δ 2.10 (s, 3H), 2.22 (s, 3H), 2.44 (t, J=4.9 Hz, 4H), 3.03 (t, J=4.9 Hz, 4H), 6.81 (d, J=9.0 Hz, 2H), 7.34 (s, 2H), 7.45-7.50 (m, 4H), 7.89 (s, 1H), 8.06 (s, 1H), 8.13-8.18 (m, 1H), 8.54 (s, 1H), 8.70 (s, 1H). MS (ES+): m/z 454 (M+H)$^+$.

Example 92

N-Methyl-3-{5-methyl-2-[4-(4-methyl-piperazin-1-yl)-phenylamino]-pyrimidin-4-ylamino}-benzenesulfonamide (Compound LIX)

LIX

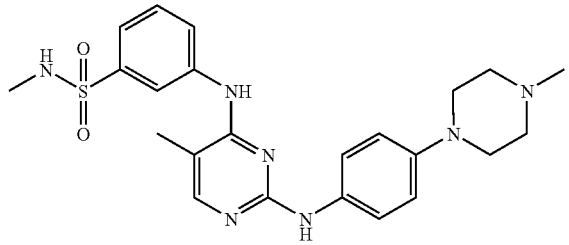

A suspension of intermediate 32 (0.10 g, 0.33 mmol), 3-bromo-N-methyl-benzenesulfonamide (0.11 g, 0.44 mmol), Pd$_2$(dba)$_3$ (20 mg, 0.022 mmol), Xantphos (25 mg, 0.043 mmol) and cesium carbonate (0.25 g, 0.77 mmol) in dioxane/DMF (3/1, 4 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of DCM/Et$_2$O (1/5, 30 mL). After filtration, the title compound was obtained as a light brown solid (65 mg, 42%).

$^1$H NMR (500 MHz, DMSO-d$_6$): δ 2.11 (s, 3H), 2.23 (s, 3H), 2.44 (d, J=5.0 Hz, 3H), 2.45-2.50 (m, 4H), 3.03 (t, J=4.9 Hz, 4H), 6.81 (d, J=9.1 Hz, 2H), 7.40-7.43 (m, 2H), 7.46 (d, J=9.1 Hz, 2H), 7.52 (t, J=8.0 Hz, 1H), 7.89 (s, 1H), 7.94 (t, J=1.8 Hz, 1H), 8.29 (br d, J=8.3 Hz, 1H), 8.56 (s, 1H), 8.72 (s, 1H). MS (ES+): m/z 468 (M+H)$^+$.

Example 93

N,N-Dimethyl-3-{5-methyl-2-[4-(4-methyl-piperazin-1-yl)-phenylamino]-pyrimidin-4-ylamino}-benzenesulfonamide (Compound LX)

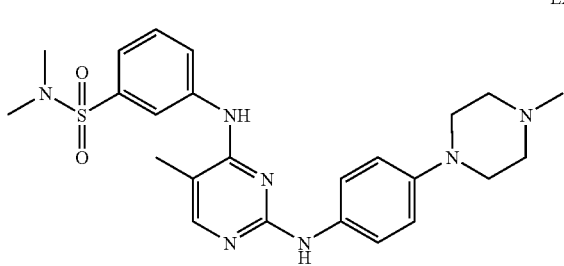

LX

A suspension of intermediate 32 (0.13 g, 0.43 mmol), 3-bromo-N,N-dimethyl-benzenesulfonamide (0.14 g, 0.53 mmol), Pd$_2$(dba)$_3$ (25 mg, 0.027 mmol), Xantphos (30 mg, 0.052 mmol) and cesium carbonate (0.33 g, 1.0 mmol) in dioxane/DMF (3/1, 4 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/5, 30 mL). After filtration, the title compound was obtained as an off white solid (60 mg, 29%).

$^1$H NMR (500 MHz, DMSO-d$_6$): δ 2.17 (s, 3H), 2.23 (s, 3H), 2.44 (d, J=5.0 Hz, 3H), 2.45-2.50 (m, 4H), 2.63 (s, 6H), 3.03 (t, J=4.9 Hz, 4H), 6.81 (d, J=9.1 Hz, 2H), 7.36 (d, J=8.0 Hz, 1H), 7.45 (d, J=9.1 Hz, 2H), 7.54 (t, J=8.0 Hz, 1H), 7.84 (t, J=1.9 Hz, 1H), 7.90 (s, 1H), 8.46 (br d, J=7.8 Hz, 1H), 8.57 (s, 1H), 8.74 (s, 1H). MS (ES+): m/z 482 (M+H)$^+$.

Example 94

N-Isopropyl-3-{5-methyl-2-[4-(4-methyl-piperazin-1-yl)-phenylamino]-pyrimidin-4-ylamino}-benzenesulfonamide (Compound LXI)

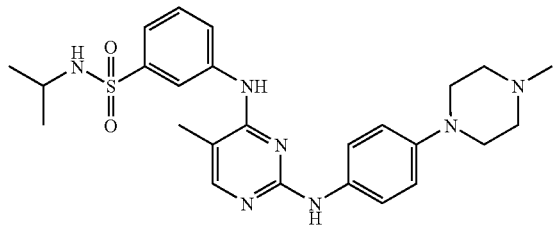

LXI

A suspension of intermediate 32 (0.10 g, 0.33 mmol), 3-bromo-N-isopropyl-benzenesulfonamide (0.11 g, 0.39 mmol), Pd$_2$(dba)$_3$ (20 mg, 0.022 mmol), Xantphos (25 mg, 0.043 mmol) and cesium carbonate (0.25 g, 0.77 mmol) in dioxane/DMF (3/1, 4 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/10, 33 mL). After filtration, the title compound was obtained as an off white solid (47 mg, 29%).

$^1$H NMR (500 MHz, DMSO-d$_6$): δ 0.98 (d, J=6.6 Hz, 6H), 2.11 (s, 3H), 2.24 (s, 3H), 2.45-2.50 (m, 4H), 3.03 (t, J=4.8 Hz, 4H), 3.20-3.27 (m, 1H), 6.80 (d, J=9.0 Hz, 2H), 7.40-7.52 (m, 4H), 7.59 (d, J=7.1 Hz, 1H), 7.89 (s, 1H), 8.21 (br d, J=7.9 Hz, 1H), 8.53 (s, 1H), 8.71 (s, 1H). MS (ES+): m/z 496 (M+H)$^+$.

Example 95

N$^4$-(3-Methanesulfonyl-4-methyl-phenyl)-5-methyl-N$^2$-[4-(4-methyl-piperazin-1-yl)-phenyl]-pyrimidine-2,4-diamine (Compound LXII)

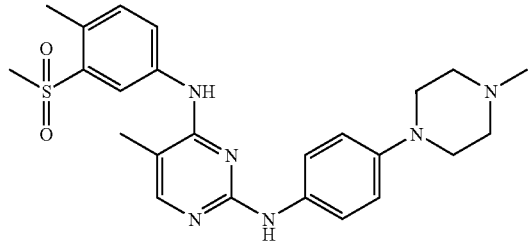

LXII

A suspension of intermediate 32 (0.10 g, 0.33 mmol), 4-bromo-2-methanesulfonyl-1-methyl-benzene (0.10 g, 0.40 mmol), Pd$_2$(dba)$_3$ (20 mg, 0.022 mmol), Xantphos (25 mg, 0.043 mmol) and cesium carbonate (0.25 g, 0.77 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/5, 30 mL). After filtration, the title compound was obtained as a light brown solid (41 mg, 27%).

$^1$H NMR (500 MHz, DMSO-d$_6$): δ 2.09 (s, 3H), 2.22 (s, 3H), 2.45 (t, J=4.7 Hz, 4H), 2.61 (s, 3H), 3.03 (t, J=4.9 Hz, 4H), 3.20 (s, 3H), 6.80 (d, J=9.1 Hz, 2H), 7.35 (d, J=8.5 Hz, 1H), 7.44 (d, J=9.0 Hz, 2H), 7.87 (s, 1H), 8.05 (d, J=2.4 Hz, 1H), 8.21 (br d, J=7.0 Hz, 1H), 8.55 (s, 1H), 8.71 (s, 1H). MS (ES+): m/z 467 (M+H)$^+$.

Example 96

N-Cyclohexyl-3-{5-methyl-2-[4-(4-methyl-piperazin-1-yl)-phenylamino]-pyrimidin-4-ylamino}-benzenesulfonamide (Compound LXIII)

LXIII

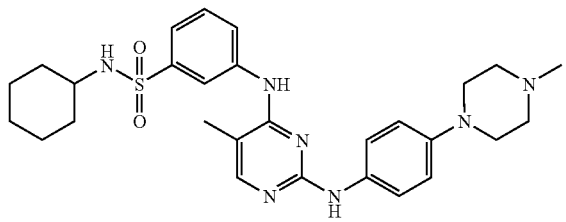

A suspension of intermediate 32 (0.10 g, 0.33 mmol), 3-bromo-N-cyclohexyl-benzenesulfonamide (0.13 g, 0.41 mmol), Pd$_2$(dba)$_3$ (20 mg, 0.022 mmol), Xantphos (25 mg, 0.043 mmol) and cesium carbonate (0.25 g, 0.77 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/10, 33 mL). After filtration, the title compound was obtained as an off white solid (45 mg, 25%).

$^1$H NMR (500 MHz, DMSO-d$_6$): δ 1.07-1.17 (m, 6H), 1.53-1.63 (m, 4H), 2.11 (s, 3H), 2.22 (s, 3H), 2.45 (t, J=4.7 Hz, 4H), 2.90-3.00 (m, 1H), 3.02 (t, J=4.8 Hz, 4H), 6.80 (d, J=9.1 Hz, 2H), 7.43-7.53 (m, 4H), 7.65 (d, J=7.3 Hz, 1H), 7.89 (s, 1H), 8.05 (s, 1H), 8.18 (br d, J=7.7 Hz, 1H), 8.52 (s, 1H), 8.71 (s, 1H). MS (ES+): m/z 536 (M+H)$^+$.

Example 97

N,N-Diethyl-3-{5-methyl-2-[4-(4-methyl-piperazin-1-yl)-phenylamino]-pyrimidin-4-ylamino}-benzenesulfonamide (Compound LXIV)

LXIV

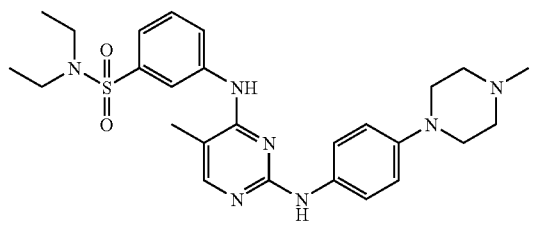

A suspension of intermediate 32 (0.10 g, 0.33 mmol), 3-bromo-N,N-diethyl-benzenesulfonamide (0.12 g, 0.41 mmol), Pd$_2$(dba)$_3$ (20 mg, 0.022 mmol), Xantphos (25 mg, 0.043 mmol) and cesium carbonate (0.25 g, 0.77 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/10, 33 mL). After filtration, the title compound was obtained as an off white solid (45 mg, 27%).

$^1$H NMR (500 MHz, DMSO-d$_6$): δ 1.06 (t, J=7.1 Hz, 6H), 2.11 (s, 3H), 2.22 (s, 3H), 2.44 (t, J=4.7 Hz, 4H), 3.03 (t, J=4.8 Hz, 4H), 3.16 (q, J=7.1 Hz, 4H), 6.80 (d, J=9.1 Hz, 2H), 7.39 (d, J=8.1 Hz, 1H), 7.45 (d, J=9.0 Hz, 2H), 7.50 (t, J=8.1 Hz, 1H), 7.89 (t, J=1.9 Hz, 1H), 7.89 (s, 1H), 8.39 (br d, J=7.9 Hz, 1H), 8.53 (s, 1H), 8.74 (s, 1H). MS (ES+): m/z 510 (M+H)$^+$.

Example 98

5-Methyl-N$^2$-[4-(4-methyl-piperazin-1-yl)-phenyl]-N$^4$-[3-(morpholine-4-sulfonyl)-phenyl]-pyrimidine-2,4-diamine (Compound LXV)

LXV

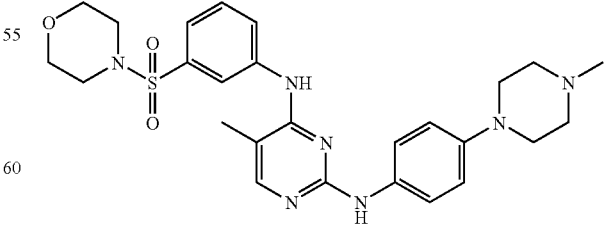

A suspension of intermediate 32 (0.10 g, 0.33 mmol), 4-(3-bromo-benzenesulfonyl)-morpholine (0.12 g, 0.39 mmol), Pd$_2$(dba)$_3$ (20 mg, 0.022 mmol), Xantphos (25 mg, 0.043 mmol) and cesium carbonate (0.25 g, 0.77 mmol) in dioxane/DMF (3/1, 4 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by HPLC. The fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/10, 33 mL). After filtration, the title compound was obtained as a light red solid (90 mg, 52%).

$^1$H NMR (500 MHz, DMSO-d$_6$): δ 2.12 (s, 3H), 2.22 (s, 3H), 2.45 (t, J=4.8 Hz, 4H), 2.89 (t, J=4.6 Hz, 4H), 3.03 (t, J=4.8 Hz, 4H), 3.64 (t, J=4.7 Hz, 4H), 6.81 (d, J=9.1 Hz, 2H), 7.35 (d, J=8.1 Hz, 1H), 7.45 (d, J=9.0 Hz, 2H), 7.56 (t, J=8.1 Hz, 1H), 7.84 (t, J=1.9 Hz, 1H), 7.91 (s, 1H), 8.47 (br d, J=8.4 Hz, 1H), 8.59 (s, 1H), 8.75 (s, 1H). MS (ES+): m/z 524 (M+H)$^+$.

Example 99

3-{5-Methyl-2-[4-(4-methyl-piperazin-1-yl)-phenylamino]-pyrimidin-4-ylamino}-benzoic acid ethyl ester (Intermediate 36)

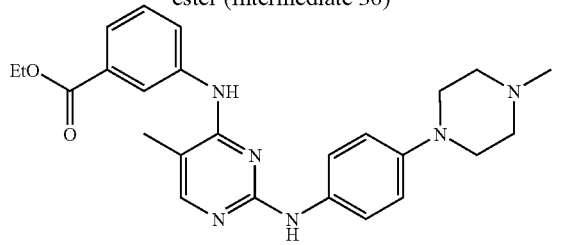

A suspension of intermediate 32 (0.10 g, 0.33 mmol), 3-bromo-benzoic acid ethyl ester (0.07 mL, 0.44 mmol), Pd$_2$(dba)$_3$ (20 mg, 0.022 mmol), Xantphos (25 mg, 0.043 mmol) and cesium carbonate (0.25 g, 0.77 mmol) in dioxane (3 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by flash chromatography on silica gel (DCM to 10% MeOH/DCM) to afford the title compound (0.10 g, 68%). MS (ES+): m/z 447 (M+H)$^+$.

Example 100

3-{5-Methyl-2-[4-(4-methyl-piperazin-1-yl)-phenylamino]-pyrimidin-4-ylamino}-benzamide (Compound LXVI)

LXVI

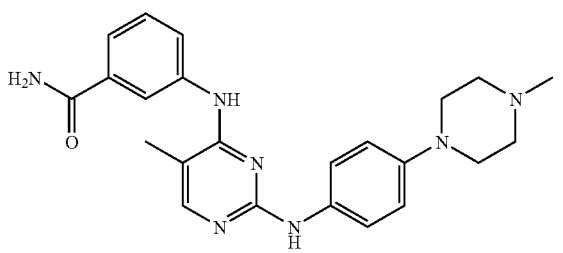

A mixture of intermediate 36 (0.10 g, 0.22 mmol) in concentrated NH$_4$OH was sealed in a reaction tube and heated at 50° C. for 3 d. The mixture was poured into water (15 mL) and extracted with EtOAc (2×30 mL). The combined organic layers were washed with brine, dried over anhydrous Na$_2$SO$_4$ and filtered. The filtrate was concentrated and the residue purified by HPLC. The corrected fractions were combined and poured into saturated NaHCO$_3$ solution (30 mL). The aqueous layer was extracted with EtOAc (2×30 mL) and the combined organic layers washed with brine, dried over anhydrous Na$_2$SO$_4$ and filtered. The filtrate was concentrated and the residue triturated in a mixture of EtOAc/hexanes (1/10, 33 mL). After filtration, the title compound was obtained as a white solid (10 mg, 11%).

$^1$H NMR (500 MHz, DMSO-d$_6$): δ 2.10 (s, 3H), 2.22 (s, 3H), 2.40-2.50 (m, 4H), 2.95-3.05 (m, 4H), 6.75 (d, J=9.1 Hz, 2H), 7.30-7.40 (m, 2H), 7.45 (d, J=9.1 Hz, 2H), 7.53-7.58 (m, 1H), 7.85 (s, 1H), 7.90 (br s, 2H), 8.03 (s, 1H), 8.37 (s, 1H), 8.71 (s, 1H). MS (ES+): m/z 418 (M+H)$^+$.

Example 101

2-Methyl-3-{5-methyl-2-[4-(4-methyl-piperazin-1-yl)-phenylamino]-pyrimidin-4-ylamino}-benzoic acid ethyl ester (Compound LXVII)

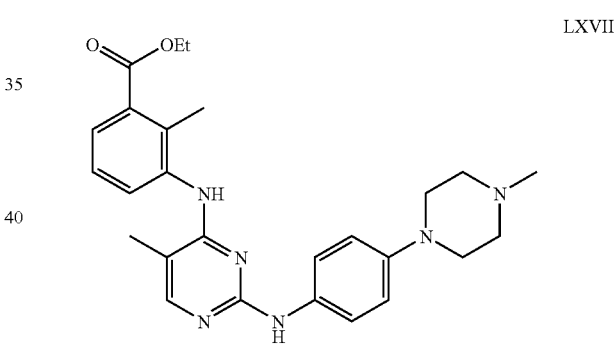

LXVII

A suspension of intermediate 32 (0.10 g, 0.33 mmol), 3-bromo-2-methyl-benzoic acid ethyl ester (0.10 mL, 0.41 mmol), Pd$_2$(dba)$_3$ (20 mg, 0.022 mmol), Xantphos (25 mg, 0.043 mmol) and cesium carbonate (0.25 g, 0.77 mmol) in dioxane (3 mL) was sealed in a microwave reaction tube and irradiated with microwave at 160° C. for 20 min. After cooling to room temperature, the cap was removed and the resulting mixture filtered and the filtered solid washed with DCM. The filtrate was concentrated and the residue purified by flash chromatography on silica gel (DCM to 30% MeOH and 1% TEA in DCM) to afford the title compound (0.14 g, 92%) as a light brown oil.

$^1$H NMR (500 MHz, DMSO-d$_6$): δ 1.32 (t, J=7.1 Hz, 3H), 2.10 (s, 3H), 2.21 (s, 3H), 2.32 (s, 3H), 2.40-2.45 (m, 4H), 2.94 (t, J=4.8 Hz, 4H), 4.30 (q, J=7.1 Hz, 2H), 6.57 (d, J=9.1 Hz, 2H), 7.25 (d, J=8.9 Hz, 2H), 7.35 (t, J=7.8 Hz, 1H), 7.48 (dd, J=7.9, 1.0 Hz, 1H), 7.70 (dd, J=7.8, 1.1 Hz, 1H), 7.78 (s, 1H), 8.23 (s, 1H), 8.58 (s, 1H). MS (ES+): m/z 461 (M+H)$^+$.

Example 102

2-Methyl-3-{5-methyl-2-[4-(4-methyl-piperazin-1-yl)-phenylamino]-pyrimidin-4-ylamino}-benzamide (Compound LXVIII)

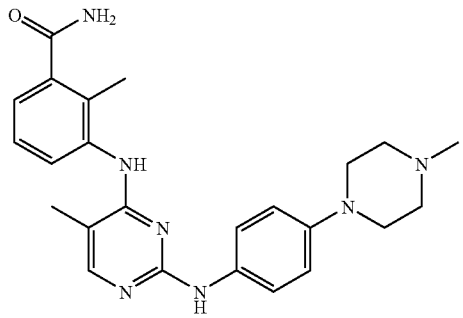

LXVIII

To a mixture of the above-described compound LXVII (0.10 g, 0.22 mmol) and formamide (0.05 mL, 1.3 mmol) in DMF (5 mL) at 100° C. was added NaOMe (0.10 g, 0.46 mmol) under the argon atmosphere. The mixture was stirred at the same temperature for 2 h and then at room temperature for additional 15 h. The mixture was poured into water (15 mL) and extracted with EtOAc (2×15 mL). The combined organic layers were washed with brine, dried over anhydrous $Na_2SO_4$ and filtered. The filtrate was concentrated and the residue purified by HPLC. The corrected fractions were combined and poured into saturated $NaHCO_3$ solution (30 mL). The aqueous layer was extracted with EtOAc (2×30 mL) and the combined organic layers washed with brine, dried over anhydrous $Na_2SO_4$ and filtered. The filtrate was concentrated and the residue triturated in a mixture of EtOAc/hexanes (1/5, 30 mL). After filtration, the title compound was obtained as a white solid (20 mg, 21%).

$^1$H NMR (500 MHz, DMSO-$d_6$): δ 2.09 (s, 3H), 2.21 (s, 3H), 2.23 (s, 3H), 2.40-2.45(m, 4H), 2.97 (t, J=4.8 Hz, 4H), 6.69 (d, J=9.1 Hz, 2H), 7.24-7.28 (m, 2H), 7.35 (d, J=9.0 Hz, 2H), 7.39-7.43 (m, 2H), 7.69 (s, 1H), 7.78 (s, 1H), 8.01 (s, 1H), 8.53 (s, 1H). MS (ES+): m/z 432 (M+H)$^+$.

Example 103

(2-Chloro-5-methyl-pyrimidin-4-yl)-(4-chloro-3-trifluoromethyl-phenyl)-amine (Intermediate 37)

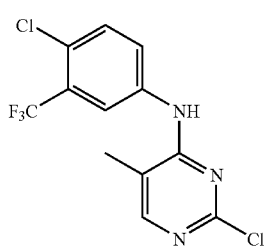

37

A mixture of 2-chloro-5-methyl-pyrimidin-4-ylamine (0.30 g, 2.1 mmol), 4-bromo-1-chloro-2-trifluoromethyl-benzene (0.40 mL, 2.7 mmol), $Pd_2(dba)_3$ (0.10 g, 0.11 mmol), Xantphos (0.13 g, 0.22 mmol) and cesium carbonate (1.5 g, 4.6 mmol) in dioxane/DMF (6/1, 7 mL) was sealed in a microwave reaction tube and irradiated with microwave at 160° C. for 15 min. After cooling to room temperature, the cap was removed and the resulting mixture filtered and the filtered solid washed with DCM. The filtrate was concentrated and the residue purified by flash chromatography on silica gel (hexanes to 50% EtOAc/hexanes) to afford the title compound (0.65 g, 96%) as a white solid. MS (ES+): m/z 322 (M+H)$^+$.

Example 104

$N^4$-(4-Chloro-3-trifluoromethyl-phenyl)-5-methyl-$N^2$-[4-(piperidin-4-yloxy)-phenyl]-pyrimidine-2,4-diamine (Compound LXIX)

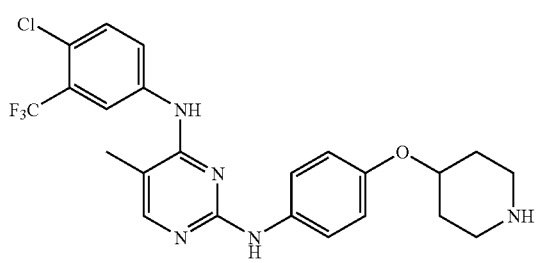

LXIX

A mixture of intermediate 37 (0.10 g, 0.31 mmol) and 4-(4-amino-phenoxy)-piperidine-1-carboxylic acid tert-butyl ester (0.12 g, 0.41 mmol) in acetic acid (3 mL) was sealed in a microwave reaction tube and irradiated with microwave at 150° C. for 15 min. After cooling to room temperature, the cap was removed and the mixture concentrated. The residue was taken in water (20 mL) and neutralized with 10% NaOH solution until solid precipitated. The resulting solid was filtered and purified by HPLC. The corrected fractions were combined and poured into saturated $NaHCO_3$ solution (30 mL). The aqueous layer was extracted with EtOAc (2×30 mL) and the combined organic layers washed with brine, dried over anhydrous $Na_2SO_4$ and filtered. The filtrate was concentrated to afford the title compound as a white solid (30 mg, 20%).

$^1$H NMR (500 MHz, DMSO-$d_6$): δ 1.69-1.77 (m, 2H), 2.00-2.04 (m, 2H), 2.11 (s, 3H), 2.90-3.00 (m, 2H), 3.10-3.20 (m, 2H), 4.40-4.48 (m, 1H), 6.84 (d, J=9.0 Hz, 2H), 7.49 (d, J=9.0 Hz, 2H), 7.58 (d, J=8.8 Hz, 1H), 7.94 (s, 1H), 8.12 (d, J=2.6 Hz, 1H), 8.21 (br d, J=8.2 Hz, 1H), 8.64 (s, 1H), 8.93 (s, 1H). MS (ES+): m/z 478 (M+H)$^+$.

Example 105

5-Methyl-$N^2$-[4-(2-pyrrolidin-1-yl-ethoxy)-phenyl]-pyrimidine-2,4-diamine (Intermediate 38)

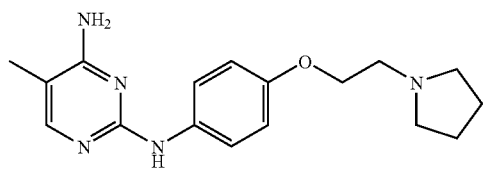

38

A mixture of 2-chloro-5-methyl-pyrimidin-4-ylamine (0.50 g, 3.5 mmol) and 4-(2-pyrrolidin-1-yl-ethoxy)-phenylamine (1.1 g, 5.3 mmol) in acetic acid (8 mL) was sealed in a microwave reaction tube and irradiated with microwave at 150° C. for 15 min. After cooling to room temperature, the cap was removed and the mixture concentrated. The residue was taken in water (30 mL) and neutralized with 10% NaOH solution until pH~10. The resulting aqueous layer was extracted with EtOAc (2×30 mL) and the combined organic layers washed with brine, dried over anhydrous Na$_2$SO$_4$ and filtered. The filtrate was concentrated to afford the title compound as a grey solid (0.80 g, 73%). It was used in the next step without purification. MS (ES+): m/z 314 (M+H)$^+$.

Example 106

3-{5-Methyl-2-[4-(2-pyrrolidin-1-yl-ethoxy)-phenylamino]-pyrimidin-4-ylamino}-benzenesulfonamide (Compound LXX)

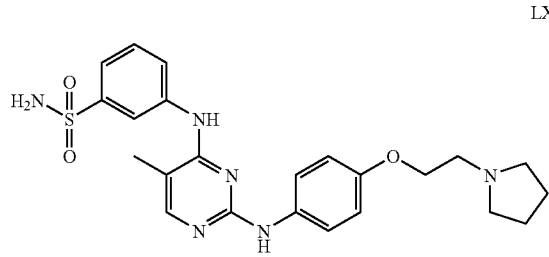

LXX

A mixture of intermediate 38 (0.10 g, 0.32 mmol), 3-bromo-benzenesulfonamide (0.10 g, 0.42 mmol), Pd$_2$(dba)$_3$ (20 mg, 0.022 mmol), Xantphos (25 mg, 0.043 mmol) and cesium carbonate (0.20 g, 0.61 mmol) in dioxane/DMF (3/1, 4 mL) was sealed in a microwave reaction tube and irradiated with microwave at 170° C. for 25 min. After cooling to room temperature, the cap was removed and the resulting mixture filtered and the filtered solid washed with DCM. The filtrate was concentrated and the residue purified by HPLC. The corrected fractions were combined and poured into saturated NaHCO$_3$ solution (30 mL). The aqueous layer was extracted with EtOAc (2×30 mL) and the combined organic layers washed with brine, dried over anhydrous Na$_2$SO$_4$ and filtered. The filtrate was concentrated and solid triturated in a mixture of EtOAc/hexanes (1/10, 33 mL). After filtration, the title compound was obtained as a white solid (11 mg, 7%).
$^1$H NMR (500 MHz, DMSO-d$_6$): δ 1.65-1.72 (m, 4H), 2.11 (s, 3H), 2.49-2.52 (m, 4H), 2.75-2.80 (m, 2H), 4.00 (t, J=5.9 Hz, 2H), 6.80 (d, J=9.0 Hz, 2H), 7.34 (s, 2H), 7.45-7.50 (m, 2H), 7.52 (d, J=9.0 Hz, 2H), 7.90 (s, 1H), 8.05 (s, 1H), 8.10-8.15 (m, 1H), 8.57 (s, 1H), 8.77 (s, 1H). MS (ES+): m/z 469 (M+H)$^+$.

Example 107

5-Methyl-N$^2$-(4-morpholin-4-ylmethyl-phenyl)-pyrimidine-2,4-diamine (Intermediate 39)

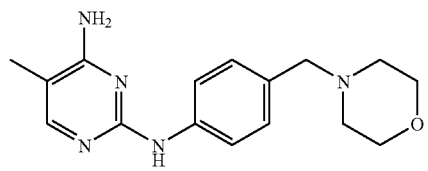

39

A mixture of 2-chloro-5-methyl-pyrimidin-4-ylamine (0.40 g, 2.8 mmol) and 4-morpholin-4-ylmethyl-phenylamine (0.60 g, 3.1 mmol) in acetic acid (15 mL) was heated at 70° C. for 17 h. After cooling to room temperature, the mixture was concentrated. The residue was taken in water (30 mL) and neutralized with 10% NaOH solution until pH~10. The resulting aqueous layer was extracted with EtOAc (2×30 mL) and the combined organic layers washed with brine, dried over anhydrous Na$_2$SO$_4$ and filtered. The filtrate was concentrated to afford the title compound as a brown syrup (0.70 g, 83%). It was used in the next step without purification. MS (ES+): m/z 300 (M+H)$^+$ Example 108

N$^4$-(1H-Indol-4-yl)-5-methyl-N$^2$-(4-morpholin-4-ylmethyl-phenyl)-pyrimidine-2,4-diamine (Compound LXXI)

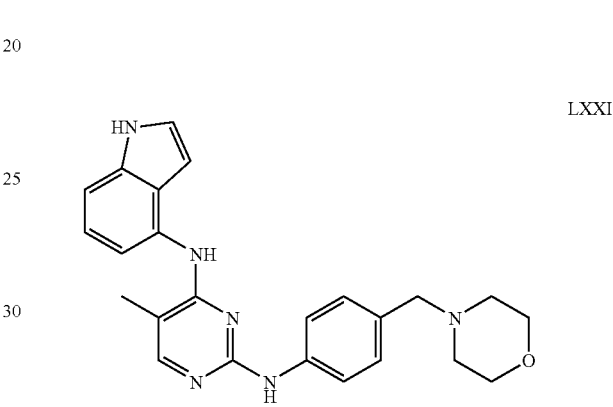

LXXI

A mixture of intermediate 39 (0.40 g, 1.3 mmol), 4-bromo-1-triisopropylsilanyl-1H-indole (0.50 g, 1.4 mmol), Pd$_2$(dba)$_3$ (0.10 g, 0.11 mmol), Xantphos (0.12 g, 0.21 mmol) and cesium carbonate (0.90 g, 2.8 mmol) was suspended in dioxane (20 mL) and heated at reflux under the argon atmosphere for 4 h. The reaction mixture was cooled to room temperature and diluted with DCM (30 mL). The mixture was filtered and the filtrate concentrated in vacuo. The residue was purified by flash chromatography on silica gel (hexanes to EtOAc) to afford the TIPS protected precursor as a yellow oil.

To the above TIPS protected precursor (50 mg, 0.088 mmol) in THF (5 mL) was added TBAF (0.5 mL, 1M in THF). The mixture was stirred at room temperature for 1 h and then poured into water (20 mL). The aqueous layer was extracted with EtOAc (2×20 mL) and the combined organic layers washed with brine, dried over anhydrous Na$_2$SO$_4$ and filtered. The filtrate was concentrated and the residue purified by HPLC.

The corrected fractions were combined and poured into saturated NaHCO$_3$ solution (30 mL). The aqueous layer was extracted with EtOAc (2×30 mL) and the combined organic layers washed with brine, dried over anhydrous Na$_2$SO$_4$ and filtered. The filtrate was concentrated and solid dissolved in minimum amount of EtOAc and then hexanes added until solid precipitated. After filtration, the title compound was obtained as a light brown solid (6 mg, 1% overall yield).
$^1$H NMR (500 MHz, DMSO-d$_6$): δ 2.17 (s, 3H), 2.25-2.30 (m, 4H), 3.29 (s, 2H), 3.54 (t, J=4.5 Hz, 4H), 6.40 (t, J=2.2 Hz, 1H), 6.89 (d, J=8.5 Hz, 2H), 7.09 (t, J=7.8 Hz, 1H), 7.25 (d, J=8.0 Hz, 1H), 7.27 (t, J=2.8 Hz, 1H), 7.30 (d, J=7.5 Hz, 1H), 7.43 (d, J=8.5 Hz, 2H), 7.85 (s, 1H), 8.14 (s, 1H), 8.77 (s, 1H), 11.10 (s, 1H). MS (ES+): m/z 415 (M+H)$^+$.

Example 109

4-[4-(4-Amino-5-methyl-pyrimidin-2-ylamino)-benzyl]-piperazine-1-carboxylic acid tert-butyl ester (Intermediate 40)

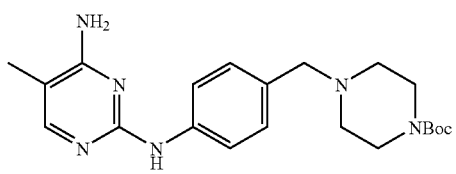

A mixture of 2-chloro-5-methyl-pyrimidin-4-ylamine (0.35 g, 2.4 mmol) and 4-(4-amino-benzyl)-piperazine-1-carboxylic acid tert-butyl ester (0.80 g, 2.8 mmol) in acetic acid (20 mL) was heated at 70° C. for 1 d. After cooling to room temperature, the mixture was concentrated. The residue was taken in water (30 mL) and neutralized with 10% NaOH solution until pH~10. The resulting aqueous layer was extracted with EtOAc (2×30 mL) and the combined organic layers washed with brine, dried over anhydrous $Na_2SO_4$ and filtered. The filtrate was concentrated and the title compound used in the next step without purification. MS (ES+): m/z 399 $(M+H)^+$.

Example 110

$N^4$-(1H-Indol-4-yl)-5-methyl-$N^2$-(4-piperazin-1-ylmethyl-phenyl)-pyrimidine-2,4-diamine (Compound LXXII)

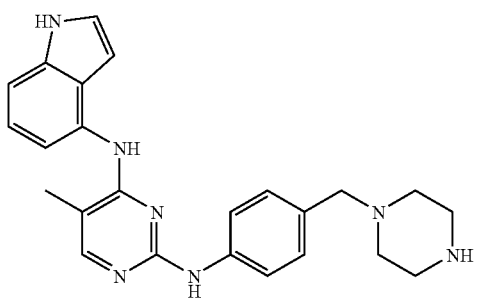

LXXII

A mixture of intermediate 40 (0.78 g, 2.0 mmol), 4-bromo-1-triisopropylsilanyl-1H-indole (0.70 g, 2.0 mmol), $Pd_2(dba)_3$ (0.15 g, 0.16 mmol), Xantphos (0.19 g, 0.32 mmol) and cesium carbonate (1.3 g, 4.0 mmol) was suspended in dioxane (20 mL) and heated at reflux under the argon atmosphere for 4.5 h. The reaction mixture was cooled to room temperature, filtered and the filtered solid was with DCM (30 mL). The filtrate was concentrated and the residue purified by flash chromatography on silica gel (hexanes to 30% EtOAc/hexanes) to afford the TIPS protected precursor.

To the above TIPS protected precursor (0.10 g, 0.15 mmol) in DCM (8 mL) was added TFA (2 mL). The mixture was stirred at room temperature for 2 h and then concentrated. The residue was purified by HPLC and the corrected fractions combined and poured into saturated $NaHCO_3$ solution (30 mL). The aqueous layer was extracted with EtOAc (2×30 mL) and the combined organic layers washed with brine, dried over anhydrous $Na_2SO_4$ and filtered. The filtrate was concentrated and solid triturated in a mixture of EtOAc/hexanes (1/5, 30 mL). After filtration, the title compound was obtained as a white solid (25 mg, 3% overall yield).

$^1$H NMR (500 MHz, DMSO-$d_6$): δ 2.17 (s, 3H), 2.20-2.30 (m, 4H), 2.73 (t, J=4.6 Hz, 4H), 3.28 (s, 2H), 6.41 (t, J=2.2 Hz, 1H), 6.89 (d, J=8.5 Hz, 2H), 7.09 (t, J=7.8 Hz, 1H), 7.24 (d, J=8.3 Hz, 1H), 7.27 (t, J=2.8 Hz, 1H), 7.31 (d, J=7.5 Hz, 1H), 7.44 (d, J=8.5 Hz, 2H), 7.85 (s, 1H), 8.13 (s, 1H), 8.77 (s, 1H), 11.10 (s, 1H) MS (ES+): m/z 414 $(M+H)^+$.

Example 111

5-Methyl-$N^4$-(7-methyl-1H-indol-4-yl)-$N^2$-(4-(4-methylpiperazin-1-yl)phenyl)pyrimidine-2,4-diamine (Compound LXXIII)

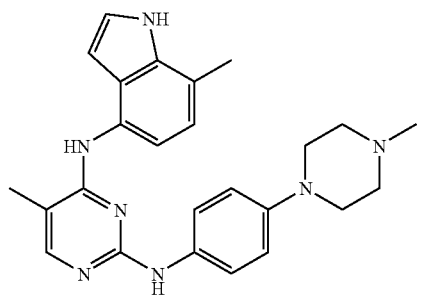

LXXIII

A mixture of intermediate 32 (674 mg, 2.25 mmol), 4-bromo-7-methyl-1H-indole (522 mg, 2.48 mmol), $Pd_2(dba)_3$ (182 mg, 0.2 mmol), Xantphos (360 mg, 0.6 mmol) and cesium carbonate (2.6 g, 8 mmol) was suspended in dioxane (50 mL) and heated at reflux under the argon atmosphere for 20 h. The mixture was filtered and the filtrate concentrated in vacuo. The residue was purified by HPLC to afford the title compound (136 mg of HCl salt, 13%) as a white solid.

$^1$H NMR (500 MHz, DMSO-$d_6$): δ 2.21 (s, 3H), 2.55 (s, 3H), 2.80 (d, J=4.6 Hz, 3H), 3.00-3.05 (m, 2H), 3.10-3.16 (m, 2H), 3.45-3.48 (m, 2H), 3.64-3.66 (m, 2H), 6.33-6.34 (m, 1H), 6.63 (br, 2H), 6.92-6.97 (m, 4H), 7.35 (t, J=2.7 Hz, 1H), 7.83 (s, 1H), 10.04 (s, 1H), 10.24 (s, 1H), 11.08 (br s, 1H), 11.34 (s, 1H), 12.12 (br s, 1H). MS (ES+): m/z 428 $(M+H)^+$.

Example 112

$N^4$-(7-Chloro-1H-indol-4-yl)-5-methyl-$N^2$-(4-(4-methylpiperazin-1-yl)phenyl)pyrimidine-2,4-diamine (Compound LXXIV)

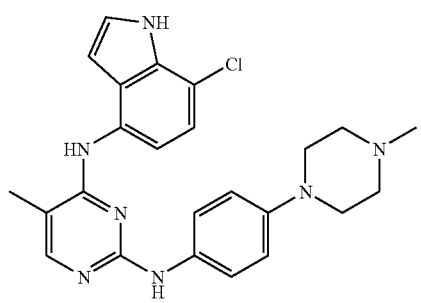

LXXIV

A mixture of intermediate 32 (298 mg, 1.0 mmol), 4-bromo-7-chloro-1H-indole (231 mg, 1.04 mmol), Pd$_2$(dba)$_3$ (92 mg, 0.1 mmol), Xantphos (180 mg, 0.3 mmol) and cesium carbonate (1.3 g, 4 mmol) was suspended in dioxane (50 mL) and heated at reflux under the argon atmosphere for 20 h. The mixture was filtered and the filtrate concentrated in vacuo. The residue was purified by HPLC to afford the title compound (251 mg of HCl salt, 51%) as a white solid.

$^1$H NMR (500 MHz, DMSO-d$_6$): δ 2.21 (s, 3H), 2.80 (d, J=4.6 Hz, 3H), 3.01-3.05(m, 2H), 3.08-3.13 (m, 2H), 3.46-3.48 (m, 2H), 3.65-3.67 (m, 2H), 6.46-6.47 (m, 1H), 6.64 (br s, 1H), 6.93 (d, J=8.9 Hz, 2H), 7.05 (d, J=8.1 Hz, 2H), 7.25 (d, J=8.0 Hz, 2H), 7.43-7.44 (m, 1H), 7.87 (s, 1H), 10.13 (s, 1H), 10.27 (s, 1H), 11.00 (br s, 1H), 11.70 (s, 1H), 12.23 (br s, H). MS (ES+): m/z 448 (M+H)$^+$.

Example 113

N$^2$-(4-(2-(Pyrrolidin-1-yl)ethoxy)phenyl)-5-methyl-N$^4$-(7-methyl-1H-indol-4-yl)pyrimidine-2,4-diamine (Compound LXXV)

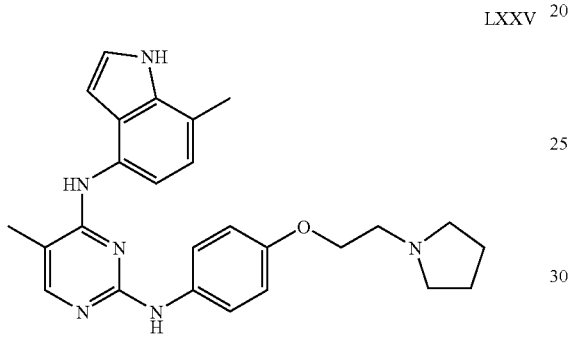

LXXV

A mixture of intermediate 38 (410 mg, 1.3 mmol), 4-bromo-7-methyl-1H-indole (275 mg, 1.3 mmol), Pd$_2$(dba)$_3$ (92 mg, 0.1 mmol), Xantphos (180 mg, 0.3 mmol) and cesium carbonate (1.3 g, 4 mmol) was suspended in dioxane (50 mL) and heated at reflux under the argon atmosphere for 20 h. The mixture was filtered and the filtrate concentrated in vacuo. The residue was purified by HPLC to afford the title compound (92 mg of HCl salt, 15%) as a white solid.

$^1$H NMR (500 MHz, DMSO-d$_6$): δ 1.88-1.90 (m, 2H), 1.93-2.02 (m, 2H), 2.21 (s, 3H), 2.55 (s, 3H), 3.06-3.10 (m, 2H), 3.51-3.54 (m, 4H), 4.26 (t, J=4.9 Hz, 2H), 6.33-6.34 (m, 1H), 6.61 (br d, 2H), 6.93-6.95 (m, 2H), 7.03 (d, J=8.9 Hz, 2H), 7.34 (t, J=2.8 Hz, 1H), 7.85 (s, 1H), 10.07 (s, 1H), 10.33 (s, 1H), 10.91 (br s, 1H), 11.34 (s, 1H), 12.15 (br s, H). MS (ES+): m/z 443 (M+H)$^+$.

Example 114

N$^2$-(4-(2-(Pyrrolidin-1-yl)ethoxy)phenyl)-5-methyl-N$^4$-(7-chloro-1H-indol-4-yl)pyrimidine-2,4-diamine (Compound LXXVI)

LLXVI

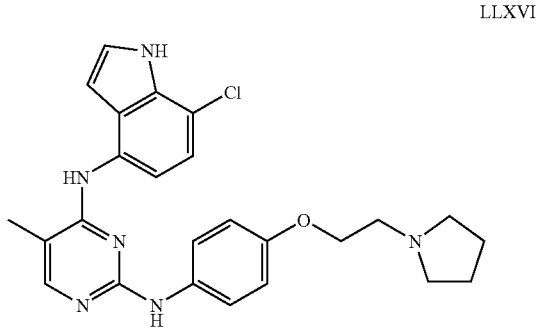

A mixture of intermediate 38 (270 mg, 0.86 mmol), 4-bromo-7-chloro-1H-indole (198 mg, 0.86 mmol), Pd$_2$(dba)$_3$ (72 mg, 0.08 mmol), Xantphos (140 mg, 0.24 mmol) and cesium carbonate (1.3 g, 4 mmol) was suspended in dioxane (50 mL) and heated at reflux under the argon atmosphere for 20 h. The mixture was filtered and the filtrate concentrated in vacuo. The residue was purified by HPLC to afford the title compound (33 mg of HCl salt, 8%) as a white solid.

$^1$H NMR (500 MHz, DMSO-d$_6$): δ 1.88-1.90 (m, 2H), 1.93-2.02 (m, 2H), 2.22 (s, 3H), 3.06-3.10 (m, 2H), 3.51-3.54 (m, 4H), 4.27 (t, J=4.9 Hz, 2H), 6.46-6.47 (m, 1H), 6.63 (br d, 2H), 6.95 (d, J=8.2 Hz, 2H), 7.06 (d, J=8.0 Hz, 1H), 7.25 (d, J=8.0 Hz, 1H), 7.43 (t, J=2.8 Hz, 1H), 7.90 (s, 1H), 10.13 (s, 1H), 10.40 (s, 1H), 10.94 (br s, 1H), 11.70 (s, 1H), 12.33 (br s, H). MS (ES+): m/z 463 (M+H)$^+$.

Example 115

N$^2$-(4-(2-(Pyrrolidin-1-yl)ethoxy)phenyl)-5-methyl-N$^4$-(7-fluoro-1H-indol-4-yl)pyrimidine-2,4-diamine (Compound LXXVII)

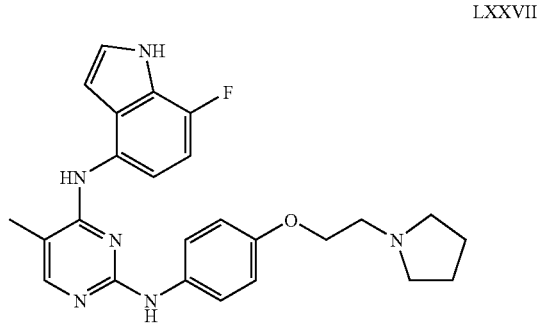

LXXVII

A mixture of intermediate 38 (413 mg, 1.3 mmol), 4-bromo-7-fluoro-1H-indole (310 mg, 1.45 mmol), Pd$_2$(dba)$_3$ (92 mg, 0.1 mmol), Xantphos (180 mg, 0.3 mmol) and cesium carbonate (1.3 g, 4 mmol) was suspended in dioxane (50 mL) and heated at reflux under the argon atmosphere for 20 h. The mixture was filtered and the filtrate concentrated in vacuo. The residue was purified by HPLC to afford the title compound (10 mg of HCl salt, 1.5%) as a brown solid.

$^1$H NMR (500 MHz, DMSO-d$_6$): δ 1.88-1.90 (m, 2H), 1.93-2.02 (m, 2H), 2.21 (s, 3H), 3.06-3.10 (m, 2H), 3.51-3.56 (m, 4H), 4.26 (t, J=4.9 Hz, 2H), 6.42-6.43 (m, 1H), 6.63 (br d, 2H), 6.95-7.04 (m, 3H), 7.35 (d, J=8.9 Hz, 1H), 7.42 (t, J=2.8 Hz, 1H), 7.89 (s, 1H), 10.08 (s, 1H), 10.41 (s, 1H), 10.90 (br s, 1H), 11.85 (s, 1H), 12.33 (br s, H). MS (ES+): m/z 447 (M+H)$^+$.

Example 116

N⁴-(3-tert-Butylphenyl)-5-methyl-N²-(4-(4-methylpiperazin-1-yl)phenyl)pyrimidine-2,4-diamine (Compound LXXVIII)

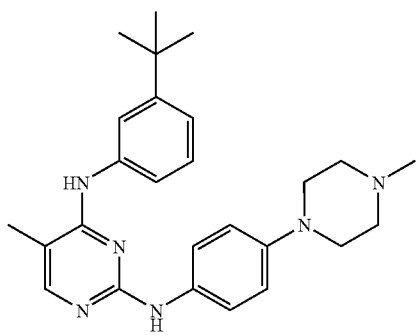

LXXVIII

A mixture of intermediate 32 (298 mg, 1.0 mmol), 1-tert-butyl-3-bromobenzene (256 mg, 1.2 mmol), Pd₂(dba)₃ (92 mg, 0.1 mmol), Xantphos (180 mg, 0.3 mmol) and cesium carbonate (1.3 g, 4 mmol) was suspended in dioxane (50 mL) and heated at reflux under the argon atmosphere for 20 h. The mixture was filtered and the filtrate concentrated in vacuo. The residue was purified by HPLC to afford the title compound (27 mg of HCl salt, 6%) as a white solid.

¹H NMR (500 MHz, DMSO-d₆): δ 1.25 (s, 9H), 2.16 (s, 3H), 2.80 (d, J=4.6 Hz, 3H), 3.04-3.16 (m, 4H), 3.47-3.49 (m, 2H), 3.65-3.67 (m, 2H), 6.90 (d, J=8.9 Hz, 2H), 7.26 (d, J=9.0 Hz, 2H), 7.28-7.35 (m, 2H), 7.45 (t, J=1.8 Hz, 1H), 7.50 (d, J=7.8 Hz, 1H), 7.86 (s, 1H), 9.70 (s, 1H), 10.37 (s, 1H), 11.01 (br s, 1H), 12.34 (br s, H). MS (ES+): m/z 431 (M+H)⁺.

Example 117

N-(3-tert-Butylphenyl)-2-chloro-5-methylpyrimidin-4-amine (Intermediate 41)

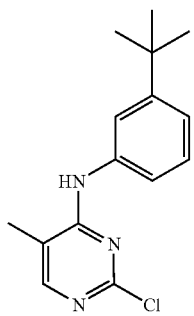

41

A mixture of 2-chloro-5-methylpyrimidin-4-amine (670 mg, 4.7 mmol), 1-tert-butyl -3-bromobenzene (1.5 g, 7 mmol), Pd₂(dba)₃ (366 mg, 0.4 mmol), Xantphos (695 mg, 1.2 mmol) and cesium carbonate (6.2 g, 19 mmol) was suspended in dioxane (150 mL) and heated at reflux under the argon atmosphere for 20 h. The mixture was filtered and the filtrate concentrated in vacuo. The residue was dissolved in EtOAc (10 mL) and added hexanes (100 mL). The solid was collected by filtration and washed with hexanes to afford the crude title compound (1.2 g, 99%) as a yellow solid.

Example 118

N⁴-(3-tert-Butylphenyl)-5-methyl-N²-(4-(piperidin-4-yloxy)phenyl)pyrimidine-2,4-diamine (Compound LXXIX)

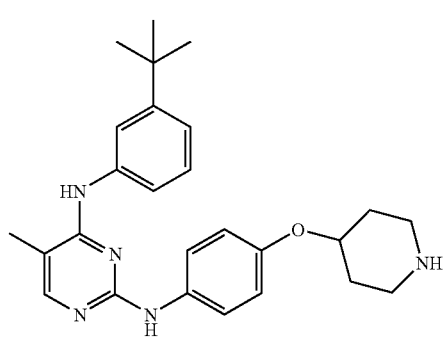

LXXIX

A mixture of intermediate 41 (740 mg, 2.68 mmol) and tert-butyl 4-(4-aminophenoxy)piperidine-1-carboxylate (500 mg, 1.71 mmol) was suspended in acetic acid (10 mL) and heated at 100° C. for 4 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO₄ and filtered. The filtrate was concentrated in vacuo and the crude product purified by HPLC to afford the title compound (276 mg of HCl salt, 35%) as a yellow solid.

¹H NMR (500 MHz, DMSO-d₆): δ 1.22 (s, 9H), 1.77-1.81 (m, 2H), 2.03-2.07 (m, 2H), 2.14 (s, 3H), 3.00-3.04 (m, 2H), 3.18 (br s, 2H), 4.56-4.57 (m, 1H), 6.86 (d, J=8.9 Hz, 2H), 7.26-7.31 (m, 4H), 7.40 (s, 1H), 7.44 (d, J=7.5 Hz, 1H), 7.84 (s, 1H), 8.93 (br s, 1H), 8.99 (br s, 1H), 9.67 (s, 1H), 10.31 (s, 1H). MS (ES+): m/z 432 (M+H)⁺.

Example 119 tert-Butyl 4-(4-(4-amino-5-methylpyrimidin-2-ylamino)phenoxy)piperidine-1-carboxylate (Intermediate 42)

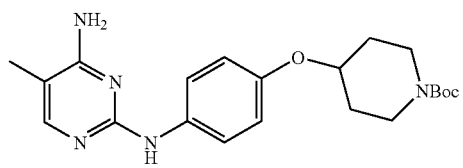

42

A mixture of 2-chloro-5-methylpyrimidin-4-amine (540 mg, 3.7 mmol), tert-butyl 4-(4-aminophenoxy)piperidine-1-carboxylate (1.1 g, 3.7 mmol) was suspended in acetic acid (20 mL) and heated at 70° C. for 1 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO$_4$ and filtered. The filtrate was concentrated in vacuo to afford the title compound (1.4 g, 95%) as a yellow solid.

Example 120

N$^4$-(1H-Indazol-4-yl)-5-methyl-N$^2$-(4-(piperidin-4-yloxy)phenyl)pyrimidine-2,4-diamine (Compound LXXX)

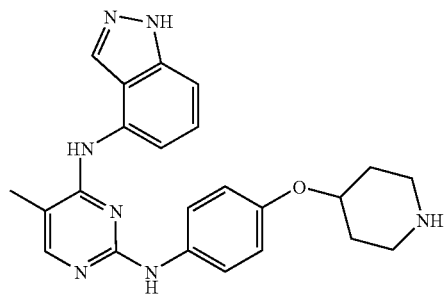

LXXX

A mixture of intermediate 42 (480 mg, 1.2 mmol), 4-bromo-1H-indazole (236 mg, 1.2 mmol), Pd$_2$(dba)$_3$ (92 mg, 0.1 mmol), Xantphos (180 mg, 0.3 mmol) and cesium carbonate (1.3 g, 4 mmol) was suspended in dioxane (50 mL) and heated at reflux under the argon atmosphere for 20 h. The mixture was filtered and the filtrate concentrated in vacuo. The residue was purified by HPLC to afford the title compound (4 mg of HCl salt, 1.2%) as a yellow solid.

$^1$H NMR (500 MHz, DMSO-d$_6$): δ 1.75-1.80 (m, 2H), 2.02-2.07 (m, 2H), 2.24 (s, 3H), 3.05-3.09 (m, 2H), 3.17-3.21 (m, 2H), 4.52 (br s, 1H), 6.63 (d, J=8.6 Hz, 2H), 7.01 (d, J=8.6 Hz, 2H), 7.14 (d, J=7.3 Hz, 2H), 7.38-7.44 (m, 2H), 7.62 (d, J=8.9 Hz, 2H), 7.92 (s, 1H), 8.02 (s, 1H), 9.00 (br s, 1H), 9.04 (br s, 1H), 10.20 (s, 1H), 10.33 (s, 1H). MS (ES+): m/z 416 (M+H)$^+$.

Example 121

4-{3-[4-(4-Chloro-3-methoxy-phenylamino)-5-methyl-pyrimidin-2-ylamino]-benzyl}-piperazine-1-carboxylic acid tert-butyl ester (Intermediate 43)

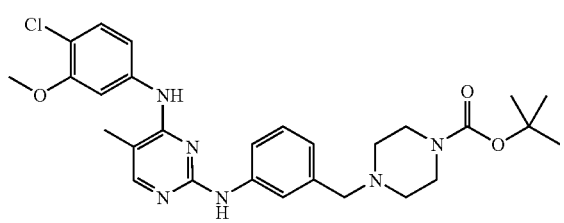

43

A mixture of intermediate 31 (0.092 g, 0.33 mmol), 4-(3-amino-benzyl)-piperazine -1-carboxylic acid tert-butyl ester (0.11 g, 0.39 mmol), Pd$_2$(dba)$_3$ (0.03 g, 0.033 mmol), Xantphos (0.038 g, 0.065 mmol) and cesium carbonate (0.32 g, 0.98 mmol) was suspended in dioxane (5 mL) and microwaved at 160° C. for 15 min. The reaction mixture was cooled to room temperature and centrifuged down. The reaction was decanted and the organic phase concentrated in vacuo. The residue was purified by HPLC to afford the title compound (0.075 g, 43%) as a brown solid.

Example 122

N$^4$-(4-Chloro-3-methoxy-phenyl)-5-methyl-N$^2$-(3-piperazin-1-ylmethyl-phenyl)-pyrimidine-2,4-diamine (Compound LXXXI)

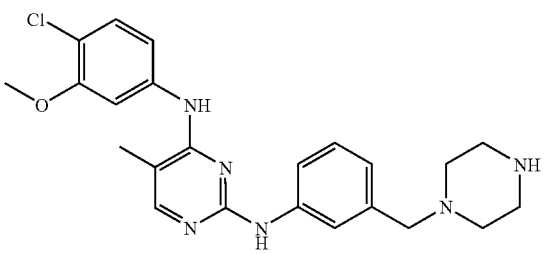

LXXXI

A solution of intermediate 43 (0.075 g, 0.14 mmol) in DCM (8 mL) was treated with TFA (2 mL). After 2 h of stirring, solvents were removed and resulting residue was triturated with diethyl ether resulting in white hygroscopic powder (0.05 g, 82%).

$^1$H NMR (500 MHz, DMSO-d$_6$): δ 2.17 (s, 3H), 2.89 (br s, 4H), 3.2 (br s, 4H), 3.68 (s, 4H), 3.82 (br s, 3H), 7.16-7.19 (m, 2H), 7.28 (t, J=7.9 Hz, 1H), 7.33 (d, J=2.3 Hz, 1H), 7.39 (s, 1H), 7.43 (d, J=8.5 Hz, 1H), 7.49 (d, 8.6 Hz, 1H), 7.98 (s, 1H), 8.8 (br s, 2H), 9.78 (br s, 1H), 10.57 (br s, 1H). MS (ES+): m/z 439 (M+H)$^+$.

Example 123

N$^4$-(4-Chloro-3-methoxy-phenyl)-5-methyl-N$^2$-[4-(piperidin-4-yloxy)-phenyl]-pyrimidine-2,4-diamine (Compound LXXXII)

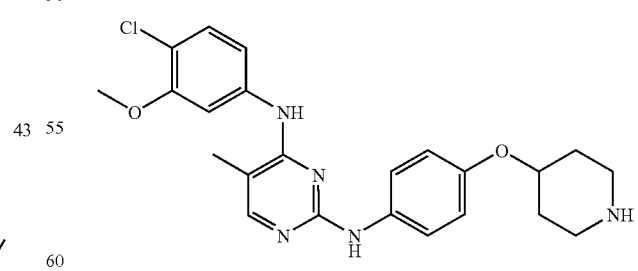

LXXXII

A mixture of intermediate 31 (0.66 g, 2.3 mmol) and 4-(4-amino-phenoxy)-piperidine -1-carboxylic acid tert-butyl ester (0.88 mg, 3.0 mmol) in acetic acid (15 mL) was microwaved at 160° C. for 15 min. The mixture was allowed to cool to room temperature and acetic acid removed under reduced pressure. The residue was taken in water (20 mL) and the mixture was neutralized with 10% NaOH solution until solid precipitated. Filtration followed by column chromatography yielded the title compound as beige solids (0.51 g, 50%).

$^1$H NMR (500 MHz, DMSO-d$_6$): δ 1.37-1.44 (m, 2H), 1.86-1.89 (m, 2H), 2.09 (s, 3H), 2.50-2.56 (m, 2H), 2.91-2.95 (m, 2H), 3.16 (s, 3H), 3.32 (br s, 3H), 3.72 (s, 3H), 4.09 (br s, 1H), 4.21-4.26 (m, 1H), 6.77 (d, J=9 Hz, 2H), 7.27 (d, J=8.5 Hz, 1H), 7.40-7.42(m, 1H), 7.46-7.49 (m, 3H), 7.87 (s, 1H), 8.31 (s, 1H), 8.78 (s, 1H). MS (ES+): m/z 440 (M+H)$^+$.

Example 124

4-{3-[4-(4-Chloro-3-methoxy-phenylamino)-5-methyl-pyrimidin-2-ylamino]-phenyl}-piperazine-1-carboxylic acid tert-butyl ester (Intermediate 44)

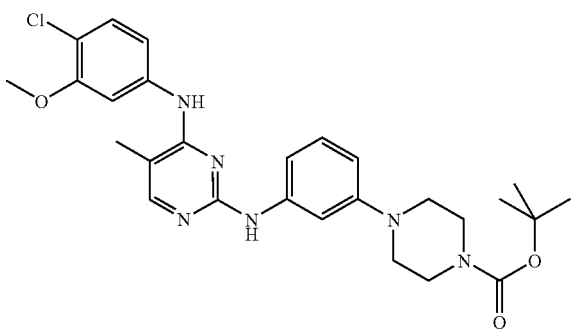

44

A mixture of intermediate 31 (0.13 g, 0.46 mmol) and 4-(3-amino-phenyl)-piperazine-1-carboxylic acid tert-butyl ester (0.19 mg, 0.68 mmol) in acetic acid (8 mL) was heated at 80° C. for 15 h. The mixture was allowed to cool to room temperature and acetic acid removed under reduced pressure. The residue was taken up in water (20 mL) and the mixture was neutralized with 10% NaOH solution. This was then extracted with ethyl acetate, washed with brine and evaporated to oily residue. Column chromatography yielded the title compound as white solids (0.12 g, 48%).

Example 125

N$^4$-(4-Chloro-3-methoxy-phenyl)-5-methyl-N$^2$-(3-piperazin-1-yl-phenyl)-pyrimidine-2,4-diamine (Compound LXXXIII)

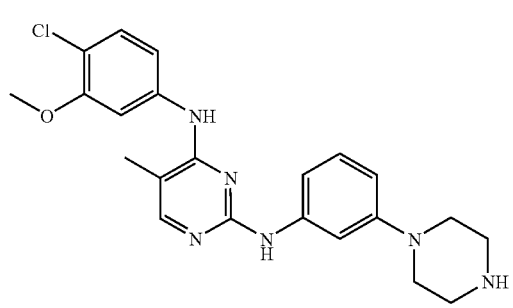

LXXXIII

A solution of intermediate 44 (0.11 g, 0.21 mmol) in DCM (8 mL) was treated with TFA (1 mL). After 3 h of stirring, solvents were removed and resulting residue was taken up in ethyl acetate and washed with 10% sodium bicarbonate solution. Organic phase then dried over sodium sulfate, filtered and evaporated to white powder. This was diluted with DCM (5 mL) and treated with 4M HCl in dioxane (0.5 mL). Solvents were immediately removed affording HCL salt of title compound as white solids (0.06 g, 67%).

$^1$H NMR (500 MHz, DMSO-d$_6$): δ 2.18 (s, 3H), 3.12 (br s, 4H), 3.22 (br s, 4H), 3.65 (s, 3H), 6.80 (d, J=8.1 Hz, 1H), 6.95 (s, 2H), 7.14 (t, J=8.2 Hz, 1H), 7.23 (d, J=7.0 Hz, 1H), 7.37-7.40 (m, 2H), 7.95 (s, 1H), 9.33 (br s, 2H), 9.88 (s, 1H), 10.62 (s, 1H). MS (ES+): m/z 425 (M+H)$^+$.

Example 126

2-[4-(3-Bromo-phenyl)-piperidin-1-yl]-ethanol (Intermediate 45)

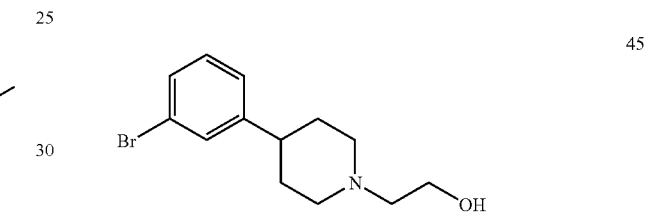

45

4-(3-Bromo-phenyl)-piperidine (1.2 g, 4.8 mmol) and 2-bromoethanol (0.72 mL, 10 mmol) were diluted with DMF (20 mL) and treated with potassium carbonate (2.7 g, 20 mmol). These were stirred at ambient temperature for 18 then poured onto water and extracted with ethyl acetate. Organic phase then washed with brine, dried over sodium sulfate, filtered and evaporated to clear oil (0.6 g, 44%).

Example 127

2-[4-(3-{5-Methyl-2-[4-(4-methyl-piperazin-1-yl)-phenylamino]-pyrimidin-4-ylamino}-phenyl)-piperidin-1-yl]-ethanol (Compound LXXXIV)

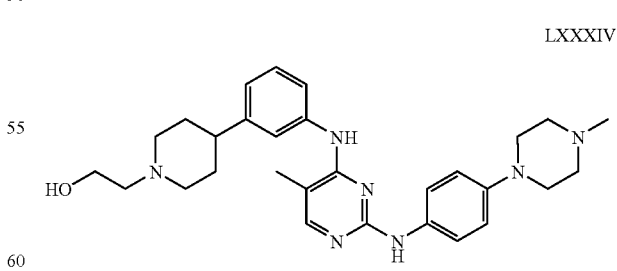

LXXXIV

A mixture of intermediate 32 (0.11 g, 0.38 mmol), intermediate 45 (0.21 g, 0.75 mmol), Pd$_2$(dba)$_3$ (0.034 g, 0.037 mmol), Xantphos (0.043 g, 0.075 mmol) and cesium carbonate (0.37 g, 1.1 mmol) was suspended in dioxane (10 mL) and microwaved at 160° C. for 15 min. The reaction mixture was cooled to room temperature and centrifuged down. The reaction was decanted and the organic phase concentrated in vacuo. The residue was purified by HPLC to afford the title compound (0.075 g, 43%) as a purple solid (0.02 g, 11%).

$^1$H NMR (500 MHz, DMSO-$d_6$): δ 1.60-1.67 (m, 2H), 1.73 (d, J=11.3 Hz, 2H), 2.02-2.07 (m, 2H), 2.08 (s, 3H), 2.21 (s, 3H), 2.39-2.45 (m, 7H), 2.95 (d, J=11.4 Hz, 2H), 3.00 (t, J=4.66 Hz, 4H), 3.50 (t, J=6.44 Hz, 2H), 6.76 (d, J=9 Hz, 2H), 6.92 (d, J=8.5 Hz, 1H), 7.22 (t, J=7.8 Hz, 1H), 7.45-7.49 (m, 3H), 7.66 (d, J=7.7 Hz, 1H), 7.82 (s, 1H), 8.09 (s, 1H), 8.67 (s, 1H). MS (ES+): m/z 502 (M+H)$^+$.

Example 128

4-(3-Bromo-benzenesulfonylamino)-piperidine-1-carboxylic acid tert-butyl ester (Intermediate 46)

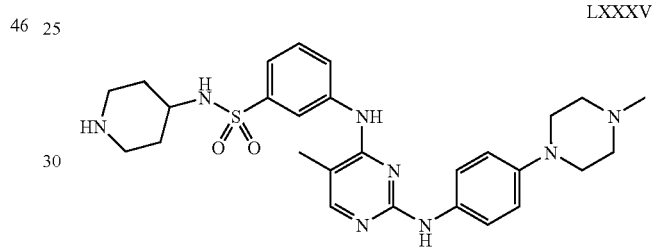

46

3-Bromo-benzenesulfonyl chloride (2.2 g, 8.7 mmol) and 4-amino-piperidine-1-carboxylic acid tert-butyl ester (2 g, 10 mmol) were combined and diluted with DCM (50 mL) and TEA (3.6 mL, 26 mmol). After 16 h, reaction was poured into separatory funnel and washed with water. Organic phase was then washed with brine, dried over sodium sulfate, filtered and evaporated to clear oil which solidified upon standing (3.6 g, 98%).

Example 129

4-(3-{5-Methyl-2-[4-(4-methyl-piperazin-1-yl)-phenylamino]-pyrimidin-4-ylamino}-benzenesulfonylamino)-piperidine-1-carboxylic acid tert-butyl ester (Intermediate 47)

A mixture of intermediate 32 (0.15 g, 0.518 mmol), intermediate 46 (0.28 g, 0.67 mmol), Pd$_2$(dba)$_3$ (0.024 g, 0.026 mmol), Xantphos (0.03 g, 0.052 mmol) and cesium carbonate (0.34 g, 1 mmol) was suspended in dioxane (10 mL) and microwaved at 160° C. for 15 min. The reaction mixture was cooled to room temperature and centrifuged down. The reaction was decanted onto ice. Resulting precipitate dried and carried on directly for deprotection step (0.2 g).

Example 130

3-{5-Methyl-2-[4-(4-methyl-piperazin-1-yl)-phenylamino]-pyrimidin-4-ylamino}-N-piperidin-4-yl-benzenesulfonamide (Compound LXXXV)

LXXXV

Intermediate 47 (0.2 g, 0.32 mmol) was diluted with DCM (10 mL) and treated with TFA (0.3 mL). After 3 h, reaction solvents removed and resulting residue was purified by HPLC (0.01 g, 6%).

$^1$H NMR (500 MHz, DMSO-$d_6$): δ 1.30-1.35 (m, 2H), 1.56-1.58 (m, 2H), 1.98 (s, 2H), 2.11 (s, 3H), 2.21 (s, 3H), 2.43-2.45 (m, 4H), 2.84-2.87 (m, 2H), 3.02 (t, J=4.6 Hz, 2H), 6.80 (d, J=9 Hz, 2H), 7.45-7.51 (m, 4H), 7.78 (br s, 1H), 7.88 (s, 1H), 8.05 (s, 1H), 8.20 (d, J=7.6 Hz, 1H), 8.53 (s, 1H), 8.71 (s, 1H). MS (ES+): m/z 537 (M+H)$^+$.

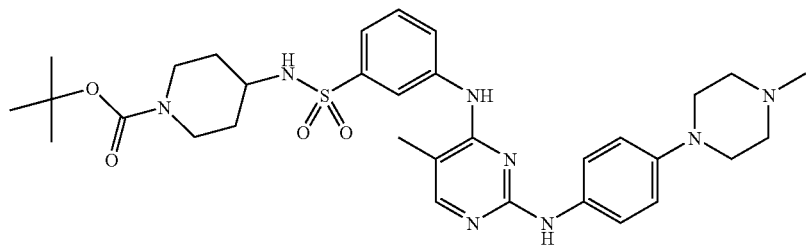

47

Example 131

N[4]-(4-(Trifluoromethyl)-3-methylphenyl)-5-methyl-N[2]-(4-(4-methylpiperazin-1-yl)phenyl)pyrimidine-2,4-diamine hydrochloride (Compound LXXXVI)

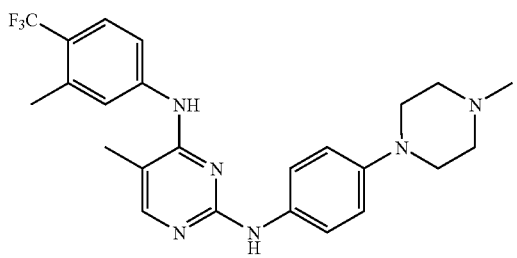

LXXXVI

A suspension of intermediate 32 (0.12 g, 0.40 mmol), 1-bromo-3-(trifluoromethyl)-2-methylbenzene (0.14 g, 0.59 mmol), $Pd_2(dba)_3$ (37 mg, 0.04 mmol), Xantphos (47 mg, 0.08 mmol) and cesium carbonate (0.39 g, 1.20 mmol) in dioxane (20 mL) was degassed with argon for 2 min then refluxed in a sealed tube for overnight. After cooling to room temperature, the solvent was removed by rotovap and the resulting mixture was purified by silica gel with 10% $CH_3OH/CHCl_3$ as an eluent to afford the title compound as a white solid. The white was dissolved in $CHCl_3$ (30 mL) and titrated with 2 M HCl in dioxane to pH 1. The solvent was removed by rotovap and the solid was recrystallized from acetone (25 mg, 13%).

$^1$H NMR (500 MHz, DMSO-$d_6$): δ 2.20 (s, 3H), 2.26 (s, 3H), 2.77 (d, J=4.5 Hz, 3H), 3.00-3.20 (m, 4H), 3.45 (d, J=11.6 Hz, 2H), 3.63 (d, J=12.2 Hz, 2H), 6.71 (d, J=8.1 Hz, 2H), 7.05 (d, J=9.0 Hz, 2H), 7.55 (t, J=7.9 Hz, 1H), 7.63 (d, J=7.8 Hz, 1H), 7.77 (d, J=7.77 Hz, 1H), 7.94 (s, 1H), 10.13 (s, 1H), 10.60 (s, 1H), 11.28 (s, 1H). MS (ES+): m/z 457 (M+H)$^+$.

Example 132

5-Methyl-N[2]-(4-(4-methylpiperazin-1-yl)phenyl)-N[4]-(3-(methylsulfonyl)phenyl)-pyrimidine-2,4-diamine (Compound LXXXVII)

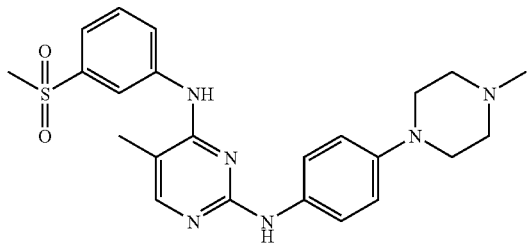

LXXXVII

A suspension of intermediate 32 (0.13 g, 0.44 mmol), 1-bromo-3-(methylsulfonyl)benzene (0.24 g, 1.0 mmol), $Pd_2$(dba)$_3$ (40 mg, 0.04 mmol), Xantphos (50 mg, 0.08 mmol) and cesium carbonate (0.43 g, 1.32 mmol) in dioxane (50 mL) was degassed with argon for 2 min then refluxed for overnight. After cooling to room temperature, the solvent was removed by rotovap and the resulting mixture was purified by silica gel with 30% $CH_3OH/CHCl_3$ as an eluent to afford the title compound as pale yellow solid (35 mg, 15%).

$^1$H NMR (500 MHz, DMSO-$d_6$): δ 2.11 (s, 3H), 2.23 (s, 3H), 2.46 (br s, 4H), 3.03 (t, J=4.4 Hz, 4H), 3.19 (s, 3H), 6.81 (d, J=9.0 Hz, 2H), 7.45 (d, J=8.9 Hz, 2H), 7.5-7.6 (m, 2H), 7.91 (s, 1H), 8.05 (s, 1H), 8.36 (d, J=6.7 Hz, 1H), 8.60 (s, 1H), 8.77 (s, 1H). MS (ES+): m/z 453 (M+H)$^+$.

Example 133

1-Bromo-3-(propylsulfonyl)benzene (Intermediate 48)

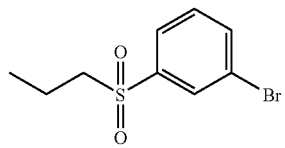

48

To a solution of 3-bromobenzenethiol (0.50 g, 2.6 mmol) in dioxane (50 mL) was added 1-iodopropane (1.1 g, 6.5 mmol) and cesium carbonate (2.2 g, 6.8 mmol) was stirred at reflux until all 3-bromobenzenethiol reacted. The reaction was quenched with saturated $NaHCO_3$ solution (25 mL) and the mixture extracted with $CHCl_3$ (60 mL). The product in the $CHCl_3$ was refluxed with mCPBA (2.9 g, 13 mmol) until all starting reacted. The organic layer was washed with 2M NaOH to remove the excess of mCPBA, dried over $Na_2SO_4$ and filtered. The filtrate was concentrated and the crude product was purified with silica gel column with 1:1 hexanes/$CHCl_3$ as an eluent to yield colorless oil (0.30 g, 43% in 2-steps).

$^1$H NMR (500 MHz, DMSO-$d_6$): 0.92 (t, J=7.4 Hz, 3H), 1.52-1.60 (m, 2H), 3.35-3.38 (m, 2H), 7.63 (t, J=8.0 Hz, 1H), 7.88-7.91 (m, 1H), 7.95-7.98 (m, 1H), 8.04 (t, J=1.8 Hz, 1H).

Example 134

5-Methyl-N[2]-(4-(4-methylpiperazin-1-yl)phenyl)-N[4]-(3-(propylsulfonyl)phenyl)-pyrimidine-2,4-diamine hydrochloride (Compound LXXXVIII)

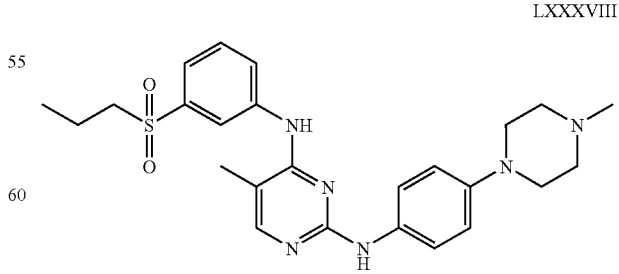

LXXXVIII

A suspension of intermediate 32 (0.25 g, 0.84 mmol), intermediate 48 (0.26 g, 1 mmol), $Pd_2$(dba)$_3$ (8 mg, 0.01 mmol), Xantphos (16 mg, 0.03 mmol) and cesium carbonate (0.82 g, 2.52 mmol) in dioxane (50 mL) was degassed with argon for 2 min then refluxed for overnight. After cooling to room temperature, the solvent was removed by rotovap and the resulting mixture was purified by silica gel with 10% CH₃OH/CHCl₃ as an eluent to afford the title compound as a white solid. The white was dissolved in CHCl₃ (30 mL) and titrated with 2 M HCl in dioxane to pH 1. The solvent was removed by rotovap and the solid was recrystallized from methanol (65 mg, 15%).

$^1$H NMR (500 MHz, DMSO-d$_6$): 0.90 (t, J=7.4 Hz, 3H), 1.50-1.60 (m, 2H), 2.18 (s, 3H), 2.81 (s, 3H), 3.00-3.13 (m, 4H), 3.27 (t, J=7.7 Hz, 2H), 3.48 (d, J=10.9 Hz, 2H), 3.75 (d, J=11.4 Hz, 2H), 6.95 (d, J=8.8 Hz, 2H), 7.27 (d, J=8.9 Hz, 2H), 7.64 (t, J=8.0 Hz, 1H), 7.73 (d, J=7.8 Hz, 1H), 7.93 (s, 1H), 8.00 (s, 1H), 8.07 (s, 1H), 9.92 (s, 1H), 10.36 (s, 1H), 10.99 (s, 1H). MS (ES+): m/z 481 (M+H)$^+$.

Example 135

3-(Morpholinomethyl)benzenamine (Intermediate 49)

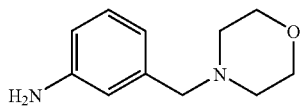

Zinc chloride (0.1 g, 0.73 mmol) was added to the solution of 3-nitrobenzaldehyde (5.9 g, 39.02 mmol), morpholine (3.4 g, 39.02 mmol), sodium cyanoborohydride (2.7 g, 43 mmol) in methanol (50 mL) at room temperature. The solution was heated to reflux for 1 hour. After cooling down, the reaction was quenched by water (2 mL) and the methanol was removed by rotovap. The crude product was dissolved in 2M NaOH (50 mL) and extracted by CHCl₃, dried over Na₂SO₄ and filtered. The filtrate was concentrated under vacuum.

The above crude product in methanol (200 mL) was reduced by Raney Ni and hydrazine at room temperature. The reaction was monitored by TLC in ethyl acetate. After all starting material reacted, the methanol was removed by rotovap. The crude was purified by silica gel with ethyl acetate as an eluent to yield a white solid (1.5 g, 50% in 2-steps).

$^1$H NMR (500 MHz, DMSO-d$_6$): 2.31 (s, 4H), 3.28 (s, 2H), 3.56 (t, J=4.6 Hz, 4H), 4.97 (s, 2H), 6.40-6.45 (m, 2H), 6.53 (t, J=1.8 Hz, 1H), 6.93 (t, J=7.7 Hz, 1H).

Example 136

5-Methyl-N²-(3-(morpholinomethyl)phenyl)pyrimidine-2,4-diamine (Intermediate 50)

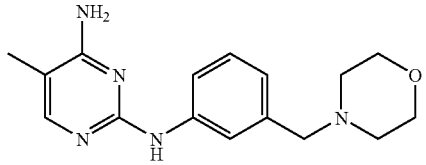

A mixture of 2-chloro-5-methylpyrimidin-4-amine (0.17 g, 1.17 mmol) and intermediate 49 (0.25 g, 1.30 mmol) was suspended in acetic acid (10 mL) and heated at 100° C. for 2 h. The mixture was allowed to cool to room temperature and acetic acid removed under reduced pressure. The residue was taken in water (20 mL) and neutralized to pH~8. The resulting solution was extracted with CHCl₃ (100 mL) and the organic layer separated. The organic layer was washed with brine, dried over Na₂SO₄ and filtered. The filtrate was concentrated in vacuo and the crude product purified by silica gel column with 10% CH₃OH/EtOAc as an eluent to afford the title compound as oil (0.15 g, 43%).

$^1$H NMR (500 MHz, DMSO-d$_6$): 1.91 (s, 3H), 2.35 (s, 4H), 3.17 (s, 2H), 3.57 (t, J=4.4 Hz, 4H), 6.37 (s, 2H), 6.78 (d, J=7.5 Hz, 1H), 7.13 (t, J=7.8 Hz, 1H), 7.59 (s, 1H), 7.69 (s, 1H), 7.74 (d, J=9.3 Hz, 1H), 8.68 (s, 1H).

Example 137

N-tert-Butyl-3-[5-methyl-2-(3-morpholin-4-ylmethyl-phenylamino)-pyrimidin-4-ylamino]-benzenesulfonamide hydrochloride (Compound LXXXIX)

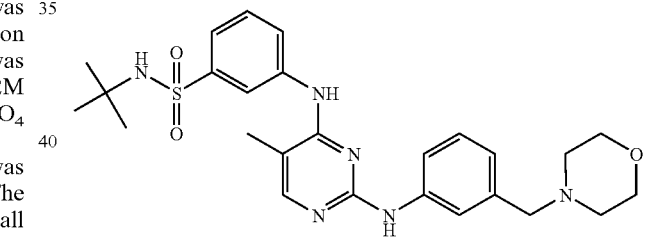

A suspension of intermediate 50 (1.0 g, 3.42 mmol), 3-bromo-N-tert-butyl-benzenesulfonamide (1.28 g, 4.28 mmol), Pd₂(dba)₃ (30 mg, 0.03 mmol), Xantphos (40 mg, 0.07 mmol) and cesium carbonate (3.34 g, 10.24 mmol) in dioxane (50 mL) was degassed with argon for 2 min then refluxed for overnight. After cooling to room temperature, the solvent was removed by rotovap and the resulting mixture was purified by silica gel with 10% CH₃OH/CHCl₃ as an eluent to afford the title compound as a white solid. The white was dissolved in hot dioxane (150 mL) and titrated with 2 M HCl in dioxane to pH 1. The solvent was removed by rotovap and the solid was recrystallized from methanol (0.15 g, 8%).

$^1$H NMR (500 MHz, DMSO-d$_6$): 1.08 (s, 9H), 2.20 (s, 3H), 3.0-3.2 (m, 4H), 3.7-4.0 (m, 4H), 4.23 (s, 2H), 7.33 (t, J=7.9 Hz, 1H), 7.38 (d, J=7.7 Hz, 1H), 7.48 (s, 1H), 7.55-7.65 (m, 3H), 7.71 (d, J=7.9 Hz, 1H), 7.90 (d, J=7.4 Hz, 1H), 8.01 (s, 1H), 9.96 (br s, 1H), 10.61 (br s, 1H), 11.31 (br s, 1H). MS (ES+): m/z 511 (M+H)$^+$.

Example 138

2-Chloro-5-methyl-N-(3,5-dimethylphenyl)pyrimidin-4-amine (Intermediate 51)

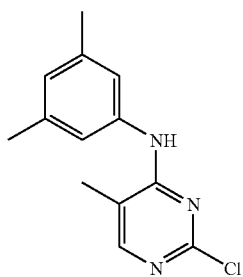

51

A mixture of 1-bromo-3,5-dimethylbenzene (104 μL, 0.77 mmol), 2-chloro-5-methyl-pyrimidin-4-ylamine (104 mg, 0.72 mmol), Pd(OAC)$_2$ (15 mg, 0.07 mmol), Xantphos (83 mg, 0.14 mmol) and potassium tert-butoxide (159 mg, 1.42 mmol) in dioxane (8 mL) was microwaved at 160° C. for 20 min. The reaction mixture was cooled to room temperature and filtered rinsing with DCM and methanol. The filtrate was concentrated and purified using gradient flash chromatography (0-100% ethyl acetate in hexanes) to afford the title compound as a yellow oil (89 mg, 50%). MS (ES+): m/z 248 (M+H)$^+$.

Example 139

5-Methyl-N$^4$-(3,5-dimethylphenyl)-N$^2$-(4-(piperidin-4-yloxy)phenyl)pyrimidine-2,4-diamine (Compound XC)

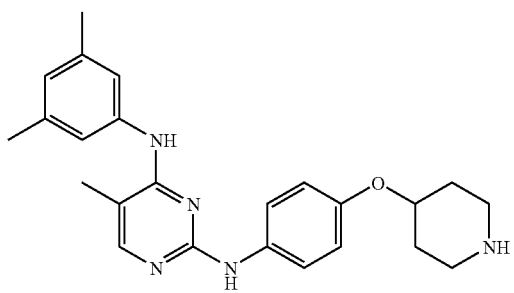

XC

A mixture of intermediate 51 (89 mg, 0.36 mmol), and 4-(4-amino-phenoxy)-piperidine-1-carboxylic acid tert-butyl ester (139 mg, 0.47 mmol) in acetic acid was stirred at room temperature for 16 h, then heated to 95° C. for 2 h. The reaction mixture was concentrated in vacuo, and purified by preparative HPLC. The product was basified with NaHCO$_3$ (aq) (10 mL) and extracted with ethyl acetate (3×30 mL). The combined organic layers were washed with brine (5 mL), dried (Na$_2$SO$_4$), and concentrated. The freebase was taken up in MeOH (5 mL) and conc HCl (5 drops) and after 2 min was concentrated in vacuo in the presence of DCM and hexanes to afford the HCl salt of the title compound as an off-white solid (63 mg, 40%).

$^1$H NMR (500 MHz, DMSO-d$_6$): δ 1.72-1.83 (m, 2H), 2.02-2.08 (m, 2H), 2.14 (d, J=0.6 Hz, 3H), 2.24 (s, 6H), 3.04-3.15 (m, 2H), 3.21-3.31 (m, 2H), 4.57-4.60 (m, 1H), 6.85 (s, 1H), 6.91 (d, J=8.9 Hz, 2H), 7.20 (s, 2H), 7.37 (d, J=8.9 Hz, 2H), 7.85 (s, 1H), 8.50 (br s, 1H), 8.56 (br s, 1H), 9.36 (br s, 1H), 10.10 (br s, 1H). MS (ES+): m/z 404 (M+H)$^+$.

Example 140

2-Chloro-N-(3,5-dimethoxyphenyl)-5-methylpyrimidin-4-amine (Intermediate 52)

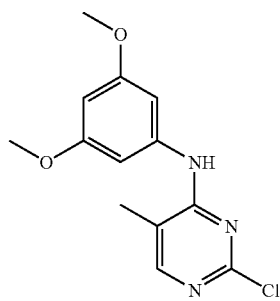

52

A mixture of 1-bromo-3,5-dimethoxybenzene (436 mg, 2.01 mmol), 2-chloro-5-methyl-pyrimidin-4-ylamine (287 mg, 2.00 mmol), Pd(OAc)$_2$ (44 mg, 0.20 mmol), Xantphos (237 mg, 0.41 mmol) and potassium tert-butoxide (448 mg, 3.99 mmol) in dioxane (15 mL) and DMF (5 mL) was microwaved at 160° C. for 20 min. The reaction mixture was cooled to room temperature and filtered rinsing with DCM and methanol. The filtrate was concentrated and purified using gradient flash chromatography (0-100% ethyl acetate in hexanes) to afford the title compound as a yellow solid (182 mg, 33%).

$^1$H NMR (500 MHz, DMSO-d$_6$): δ 2.17 (s, 3H), 3.74 (s, 6H), 6.27 (t, J=2.2 Hz, 1H), 6.99 (d, J=2.2 Hz, 2H), 8.06 (s, 1H), 8.71 (s, 1H). MS (ES+): m/z 280 (M+H)$^+$.

Example 141

N$^4$-(3,5-Dimethoxyphenyl)-5-methyl-N$^2$-(4-(piperidin-4-yloxy)phenyl)pyrimidine-2,4-diamine (Compound XCI)

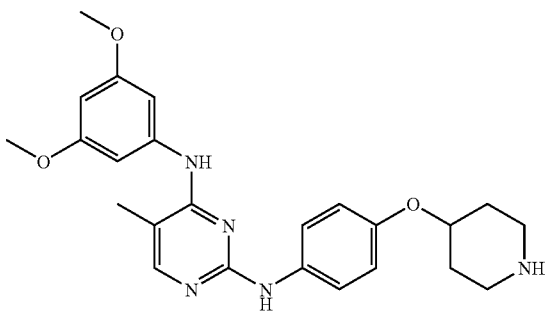

XCI

A mixture of intermediate 52 (100 mg, 0.36 mmol), and 4-(4-amino-phenoxy)-piperidine-1-carboxylic acid tert-butyl ester (106 mg, 0.36 mmol) in acetic acid was heated to 95° C. for 2 h. The reaction mixture was concentrated in vacuo, and purified by preparative HPLC to afford the TFA salt of the title compound as a tan solid (75 mg, 39%).

$^1$H NMR (500 MHz, DMSO-$d_6$): δ 1.74-1.83 (m, 2H), 2.03-2.11 (m, 2H), 2.15 (s, 3H), 3.06-3.15 (m, 2H), 3.21-3.30 (m, 2H), 3.69 (s, 6H), 4.57-4.60 (m, 1H), 6.39 (t, J=2.2 Hz, 1H), 6.80 (d, J=2.2 Hz, 2H), 6.89 (d, J=8.9 Hz, 2H), 7.37 (d, J=9.0 Hz, 2H), 7.86 (s, 1H), 8.53 (br s, 1H), 8.58 (br s, 1H), 9.49 (br s, 1H), 10.24 (br s, 1H). MS (ES+): m/z 436 (M+H)$^+$.

Example 142

5-Methyl-$N^2$-(4-(4-methylpiperazin-1-yl)phenyl)-$N^4$-(3-(piperidin-1-yl)phenyl)pyrimidine-2,4-diamine (Compound XCII)

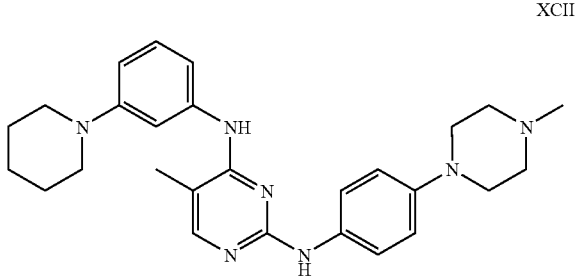

A mixture of 1-(3-bromophenyl)piperidine (91 mg, 0.38 mmol), intermediate 32 (99 mg, 0.33 mmol), Pd$_2$(dba)$_3$ (15 mg, 0.02 mmol), Xantphos (24 mg, 0.04 mmol) and cesium carbonate (219 mg, 0.67 mmol) in dioxane (4 mL) was microwaved at 160° C. for 15 min. The reaction mixture was cooled to room temperature, concentrated in vacuo, taken up in methanol, and filtered rinsing with DCM and methanol. The filtrate was concentrated and purified by preparative HPLC to afford the TFA salt of the title compound as an off-white solid (14 mg, 8%).

$^1$H NMR (500 MHz, DMSO-$d_6$): δ 1.47-1.53 (m, 2H), 1.56-1.61 (m, 4H), 2.07 (s, 3H), 2.21 (s, 3H), 2.44 (t, J=4.9 Hz, 4H), 3.01 (t, J=4.9 Hz, 4H), 3.08 (t, J=5.4 Hz, 4H), 6.63 (dd, J=8.2, 2.3 Hz, 1H), 6.76 (d, J=9.0 Hz, 2H), 7.12 (t, J=8.3 Hz, 1H), 7.14 (s, 1H), 7.27 (d, J=7.6 Hz, 1H), 7.50 (d, J=9.0 Hz, 2H), 7.81 (s, 1H), 8.00 (s, 1H), 8.67 (s, 1H). MS (ES+): m/z 458 (M+H)$^+$.

Example 143

$N^4$-(3-(1H-Pyrrol-1-yl)phenyl)-5-methyl-$N^2$-(4-(4-methylpiperazin-1-yl)phenyl)pyrimidine-2,4-diamine (Compound XCIII)

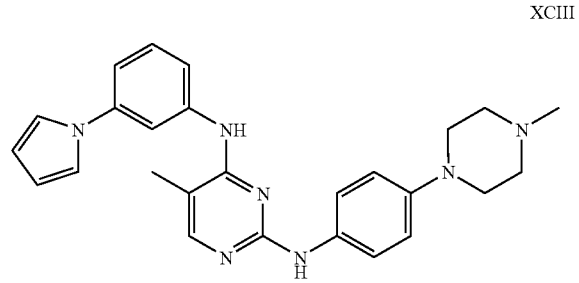

A mixture of 1-(3-bromophenyl)-1H-pyrrole (86 mg, 0.39 mmol), intermediate 32 (99 mg, 0.33 mmol), Pd$_2$(dba)$_3$ (16 mg, 0.02 mmol), Xantphos (26 mg, 0.05 mmol) and cesium carbonate (215 mg, 0.66 mmol) in dioxane (4 mL) was microwaved at 160° C. for 15 min. The reaction mixture was cooled to room temperature, concentrated in vacuo, taken up in methanol, and filtered rinsing with DCM and methanol. The filtrate was concentrated and purified by preparative HPLC to afford the TFA salt of the title compound as an off-white solid (32 mg, 18%).

$^1$H NMR (500 MHz, DMSO-$d_6$): δ 2.11 (s, 3H), 2.21 (s, 3H), 2.42 (t, J=4.9 Hz, 4H), 2.95 (t, J=4.9 Hz, 4H), 6.24 (t, J=2.2 Hz, 2H), 6.58 (d, J=8.9 Hz, 2H), 7.23 (dd, J=7.8, 1.8 Hz, 1H), 7.31 (t, J=2.2 Hz, 2H), 7.37 (t, J=8.1 Hz, 1H), 7.43 (d, J=9.0 Hz, 2H), 7.60 (d, J=8.8 Hz, 1H), 7.86 (t, J=2.2 Hz, 1H), 7.87 (s, 1H), 8.30 (s, 1H), 8.74 (s, 1H). MS (ES+): m/z 440 (M+H)$^+$.

Example 144

5-{2-[4-(1-tert-Butoxycarbonyl-piperidin-4-yloxy)-phenylamino]-5-methyl-pyrimidin-4-ylamino}-indole-1-carboxylic acid tert-butyl ester (Intermediate 53)

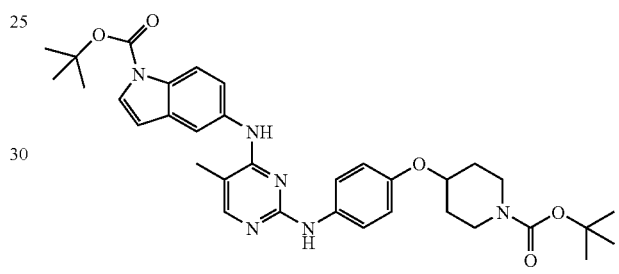

A mixture of tert-butyl 5-bromo-1H-indole-1-carboxylate (161 mg, 0.54 mmol), intermediate 42 (202 mg, 0.50 mmol), Pd$_2$(dba)$_3$ (29 mg, 0.03 mmol), Xantphos (36 mg, 0.07 mmol) and cesium carbonate (321 mg, 0.98 mmol) in dioxane (5 mL) was microwaved at 160° C. for 20 min. The reaction mixture was cooled to room temperature and filtered rinsing with DCM. The filtrate was concentrated and purified by gradient flash chromatography (0-20% MeOH in DCM) to afford the title compound as a light-brown solid (290 mg, 94%). MS (ES+): m/z 615 (M+H)$^+$.

Example 145

$N^4$-(1H-Indol-5-yl)-5-methyl-$N^2$-(4-(piperidin-4-yloxy)phenyl)pyrimidine-2,4-diamine (Compound XCIV)

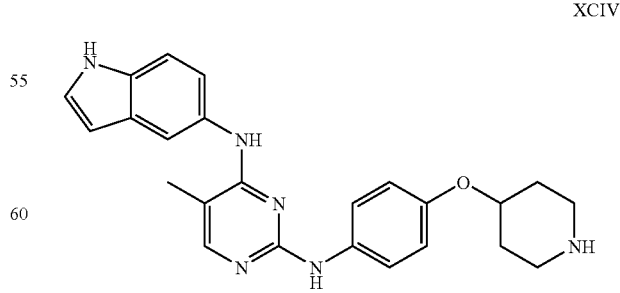

To a solution of acetyl chloride (670 μL, 9.42 mmol) in methanol (22 mL) was added intermediate 53 (290 mg, 0.47 mmol), and the reaction mixture was heated to 60° C. for 4 h.

The mixture was concentrated in vacuo and purified by preparative HPLC to afford the TFA salt of the title compound as a brown solid (6 mg, 2%).

$^1$H NMR (500 MHz, DMSO-d$_6$): δ 1.70-1.78 (m, 2H), 1.98-2.07 (m, 2H), 2.16 (s, 3H), 3.02-3.11 (m, 2H), 3.21-3.30 (m, 2H), 4.44-4.53 (m, 1H), 6.43 (s, 1H), 6.75 (d, J=8.2 Hz, 2H), 7.16 (d, J=8.4 Hz, 1H), 7.31 (d, J=8.7 Hz, 2H), 7.40-7.42 (m, 2H), 7.71 (s, 1H), 7.78 (s, 1H), 8.48 (br s, 1H), 8.54 (br s, 1H), 9.65 (br s, 1H), 9.99 (br s, 1H), 11.18 (s, 1H). MS (ES+): m/z 415 (M+H)$^+$.

Example 146

N4-(4-Chloro-3-methoxy-phenyl)-5-methyl-N2-(6-piperazin-1-yl-pyridin-3-yl)-pyrimidine-2,4-diamine (Compound XCV)

XCV

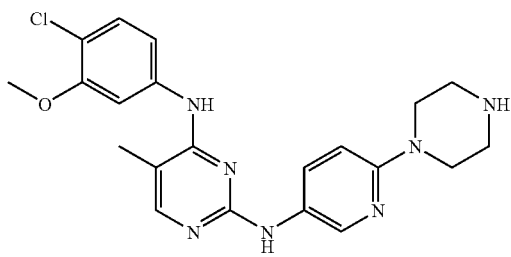

A mixture of intermediate 31 (0.10 g, 0.35 mmol), 4-(5-amino-pyridin-2-yl)-piperazine-1-carboxylic acid tert-butyl ester (0.10 g, 0.36 mmol), Pd$_2$(dba)$_3$ (30 mg, 0.033 mmol), Xantphos (35 mg, 0.06 mmol) and cesium carbonate (0.23 g, 0.71 mmol) in dioxane/DMF (3/1, 4 mL) was sealed in a microwave reaction tube and irradiated with microwave at 170° C. for 30 min. After cooling to room temperature, the cap was removed and the resulting mixture filtered. The filtered solid was washed with DCM and the filtrate concentrated. The residue was purified by flash chromatography on silica gel (hexanes to EtOAc) to afford the Boc-protected precursor. To a solution of the precursor in DCM (5 mL) was added TFA (3 mL). The mixture was stirred at room temperature for 30 min, concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and the resulting solid triturated in a mixture of hexanes/EtOAc (10/1, 55 mL). After filtration, the title compound was obtained as a white solid (20 mg, 13%).

$^1$H NMR (500 MHz, DMSO-d$_6$): δ 2.09 (s, 3H), 2.81 (t, J=5.0 Hz, 4H), 3.29-3.31(m, 4H), 3.73 (s, 3H), 6.70 (d, J=9.1 Hz, 1H), 7.26 (d, J=8.6 Hz, 1H), 7.42 (d, J=9.1 Hz, 1H), 7.49 (d, J=2.2 Hz, 1H), 7.76 (dd, J=9.1, 2.6 Hz, 1H), 7.86 (s, 1H), 8.29 (s, 1H), 8.31 (d, J=2.6 Hz, 1H), 8.71 (s, 1H). MS (ES+): m/z 426 (M+H)$^+$.

Example 147

4-(4-Amino-2-methoxycarbonyl-phenyl)-piperazine-1-carboxylic acid tert-butyl ester (Intermediate 54)

54

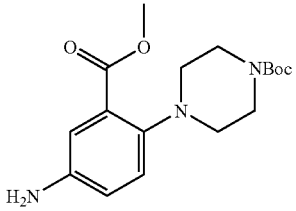

To a solution of 4-(2-methoxycarbonyl-4-nitro-phenyl)-piperazine-1-carboxylic acid tert-butyl ester (1.0 g, 2.7 mmol) in MeOH (30 mL) was added 10 wt % Pd/C (0.1 equiv by wt) under argon atmosphere. The mixture was evacuated and then refilled with hydrogen (3 cycles) and stirred at room temperature for 2 h. The heterogeneous reaction mixture was filtered through a pad of Celite, washed with MeOH and concentrated in vacuo. The crude amino-compound was used in the next step without purification. MS (ES+): m/z 336 (M+H)$^+$.

Example 148

5-[4-(4-Chloro-3-methoxy-phenylamino)-5-methyl-pyrimidin-2-ylamino]-2-piperazin-1-yl-benzoic acid methyl ester (Compound XCVI)

XCVI

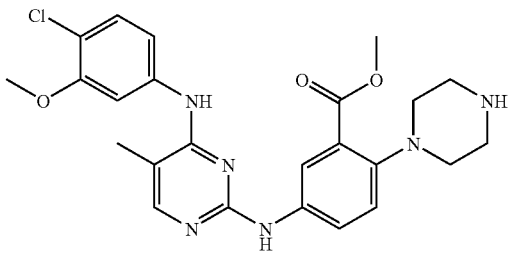

A mixture of intermediate 31 (0.10 g, 0.35 mmol), intermediate 54 (0.14 g, 0.42 mmol), Pd$_2$(dba)$_3$ (30 mg, 0.033 mmol), Xantphos (35 mg, 0.06 mmol) and cesium carbonate (0.23 g, 0.71 mmol) was suspended in dioxane (15 mL) and heated at reflux under the argon atmosphere for 2.5 h. The reaction mixture was cooled to room temperature and diluted with DCM (30 mL). The mixture was filtered and the filtrate concentrated. The residue was purified by flash chromatography on silica gel (hexanes to 60% EtOAc/hexanes) to afford the Boc-protected precursor. To a solution of the precursor in DCM (5 mL) was added TFA (2 mL). The mixture was stirred at room temperature for 1 h, concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na₂SO₄ and filtered. The filtrate was concentrated and then taken up in minimum amount of EtOAc. Hexanes were added until solid precipitated. After filtration, the title compound was obtained as a white solid (40 mg, 24%).

¹H NMR (500 MHz, DMSO-d₆): δ 2.11 (s, 3H), 2.80-2.90 (m, 8H), 3.73 (s, 3H), 3.74 (s, 3H), 6.98 (d, J=8.9 Hz, 1H), 7.25 (d, J=8.5 Hz, 1H), 7.40-7.48 (m, 2H), 7.69 (dd, J=8.9, 2.6 Hz, 1H), 7.90 (d, J=2.6 Hz, 1H), 7.91 (s, 1H), 8.36 (s, 1H), 9.04 (s, 1H). MS (ES+): m/z 483 (M+H)⁺.

Example 149

5-Amino-2-(2-pyrrolidin-1-yl-ethoxy)-benzoic acid methyl ester (Intermediate 55)

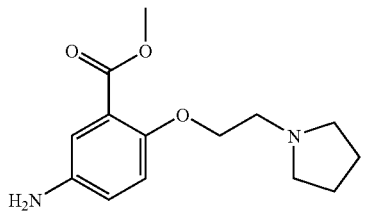

55

A suspension of 5-amino-2-hydroxy-benzoic acid methyl ester (1.0 g, 6.0 mmol), 1-(2-chloro-ethyl)-pyrrolidine hydrochloride (1.2 g, 7.1 mmol) and cesium carbonate (5.0 g, 15 mmol) in DMF (40 mL) was heated at 60° C. for 17 h. The mixture was allowed to cool to room temperature, poured into water (60 mL) and extracted with EtOAc (2×50 mL). The combined extracts were washed with brine, dried over anhydrous Na₂SO₄ and filtered. The filtrate was concentrated and the residue purified by flash chromatography on silica gel (DCM to 30% MeOH/DCM) to afford the title compound (0.2 g, 13%) as a light brown solid. MS (ES+): m/z 265 (M+H)⁺.

Example 150

5-[4-(Benzo[1,3]dioxol-4-ylamino)-5-methyl-pyrimidin-2-ylamino]-2-(2-pyrrolidin-1-yl-ethoxy)-benzoic acid methyl ester (Compound XCVII)

XCVII

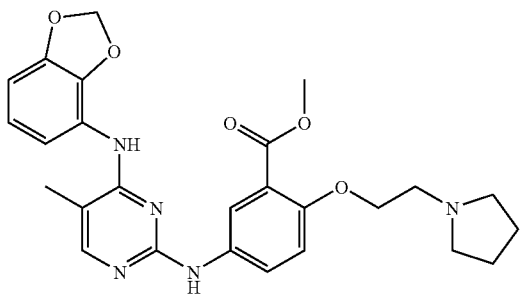

A mixture of intermediate 30 (0.15 g, 0.57 mmol), intermediate 55 (0.20 g, 0.75 mmol), Pd₂(dba)₃ (50 mg, 0.055 mmol), Xantphos (60 mg, 0.10 mmol) and cesium carbonate (0.30 g, 0.92 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO₃ solution (30 mL). The combined aqueous layers were extracted with EtOAc (2×30 mL) and the combined organic layers washed with brine, dried over anhydrous Na₂SO₄ and filtered. The filtrate was concentrated and then taken up in minimum amount of EtOAc. Hexanes were added until solid precipitated. After filtration, the title compound was obtained as an off white solid (30 mg, 11%).

¹H NMR (500 MHz, DMSO-d₆): δ 1.65-1.72 (m, 4H), 2.07 (s, 3H), 2.50-2.62 (m, 4H), 2.75-2.85 (m, 2H), 3.73 (s, 3H), 4.02 (t, J=5.8 Hz, 2H), 5.88 (s, 2H), 6.78-6.88 (m, 3H), 6.92 (dd, J=8.0, 2.1 Hz, 1H), 7.75-7.80 (m, 2H), 7.83 (s, 1H), 8.22 (s, 1H), 8.89 (s, 1H). MS (ES+): m/z 492 (M+H)⁺.

Example 151

N-tert-Butyl-3-{5-methyl-2-[4-(Piperidin-4-yloxy)-phenylamino]-pyrimidin-4-ylamino}-benzenesulfonamide (Compound XCVIII)

XCVIII

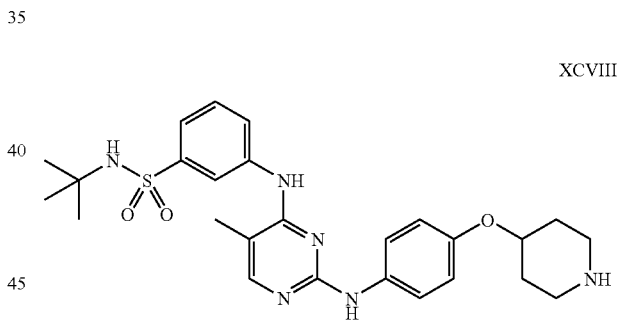

A mixture of intermediate 33 (0.15 g, 0.42 mmol) and 4-(4-amino-phenoxy)-piperidine-1-carboxylic acid tert-butyl ester (0.15 g, 0.51 mmol) in acetic acid (3 mL) was sealed in a microwave reaction tube and irradiated with microwave at 150° C. for 20 min. After cooling to room temperature, the cap was removed and the mixture concentrated. The residue was taken in water (20 mL) and the pH adjusted with 10% NaOH solution until solid precipitated. The solid was filtered and then purified by HPLC. The corrected fractions were combined, poured into saturated NaHCO₃ solution (30 mL) and extracted with EtOAc (2×30 mL). The combined extracts were washed with brine, dried over anhydrous Na₂SO₄ and filtered. The filtrate was concentrated and then taken up in minimum amount of EtOAc. Hexanes were added until solid precipitated. After filtration, the title compound was obtained as a white solid (20 mg, 9%).

¹H NMR (500 MHz, DMSO-d₆): δ 1.12 (s, 9H), 1.65-1.73 (m, 2H), 1.95-2.05 (m, 2H), 2.12 (s, 3H), 2.89-2.95 (m, 2H), 3.10-3.20 (m, 2H), 4.40-4.45 (m, 1H), 6.84 (d, J=9.1 Hz, 2H), 7.45-7.60 (m, 6H), 7.90 (s, 1H), 8.10-8.15 (m, 2H), 8.55 (s, 1H), 8.81 (s, 1H). MS (ES+): m/z 511 (M+H)+.

Example 152

2-(5-Amino-pyridin-2-yloxy)-ethanol (Intermediate 56)

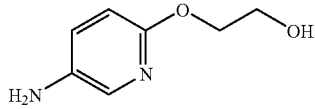

To a solution of 2-(5-nitro-pyridin-2-yloxy)-ethanol (1.0 g, 5.4 mmol) in MeOH (30 mL) was added 10 wt % Pd/C (0.1 equiv by wt) under argon atmosphere. The mixture was evacuated and then refilled with hydrogen (3 cycles) and stirred at room temperature for 1 h. The heterogeneous reaction mixture was filtered through a pad of Celite, washed with MeOH and concentrated in vacuo. The crude amino-compound was used in the next step without purification. MS (ES+): m/z 155 (M+H)+.

Example 153

2-{5-[4-(Benzo[1,3]dioxol-4-ylamino)-5-methyl-pyrimidin-2-ylamino]-pyridin-2-yloxy}-ethanol (Compound XCIX)

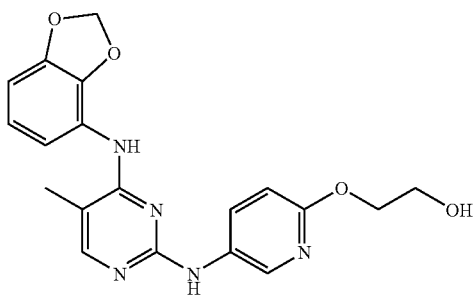

A mixture of intermediate 30 (0.10 g, 0.38 mmol), intermediate 56 (0.10 g, 0.65 mmol), Pd$_2$(dba)$_3$ (30 mg, 0.033 mmol), Xantphos (35 mg, 0.06 mmol) and cesium carbonate (0.26 g, 0.80 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as an off white solid (50 mg, 35%).

$^1$H NMR (500 MHz, DMSO-d$_6$): δ 2.06 (s, 3H), 3.66 (q, J=5.4 Hz, 2H), 4.15 (t, J=5.2 Hz, 2H), 4.77 (t, J=5.5 Hz, 2H), 5.91 (s, 2H), 6.52 (d, J=9.0 Hz, 1H), 6.78-6.90(m, 3H), 7.82 (s, 1H), 7.96 (dd, J=8.9, 2.7 Hz, 1H), 8.22 (d, J=2.6 Hz, 1H), 8.27 (s, 1H), 8.84 (s, 1H). MS (ES+): m/z 382 (M+H)+.

Example 154

1-[2-(2-Methoxy-4-nitro-phenoxy)-ethyl]-pyrrolidine (Intermediate 57)

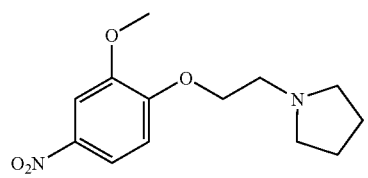

A suspension of potassium 2-methoxy-4-nitro-phenolate (2.0 g, 9.7 mmol), 1-(2-chloro-ethyl)-pyrrolidine hydrochloride (2.0 g, 12 mmol) and cesium carbonate (7.0, 22 mmol) in DMF (35 mL) was heated at 80° C. for 16 h. The mixture was allowed to cool to room temperature, poured into water (60 mL) and extracted with EtOAc (2×50 mL). The combined extracts were washed with brine, dried over anhydrous Na$_2$SO$_4$ and filtered. The filtrate was concentrated and used in the next step without purification. MS (ES+): m/z 267 (M+H)+.

Example 155

3-Methoxy-4-(2-pyrrolidin-1-yl-ethoxy)-phenylamine (Intermediate 58)

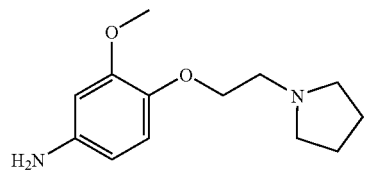

To a solution of intermediate 57 (1.7 g, 6.4 mmol) in MeOH (30 mL) was added 10 wt % Pd/C (0.1 equiv by wt) under argon atmosphere. The mixture was evacuated and then refilled with hydrogen (3 cycles) and stirred at room temperature for 1 h. The heterogeneous reaction mixture was filtered through a pad of Celite, washed with MeOH and concentrated in vacuo. The crude amino-compound was used in the next step without purification. MS (ES+): m/z 237 (M+H)+.

Example 156

N⁴-Benzo[1,3]dioxol-4-yl-N²-[3-methoxy-4-(2-pyr-rolidin-1-yl-ethoxy)-phenyl]-5-methyl-pyrimidine-2,4-diamine (Compound C)

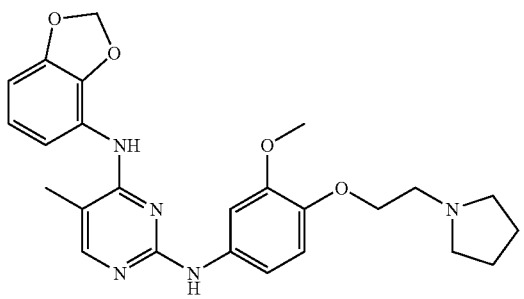

C

A mixture of intermediate 30 (0.10 g, 0.38 mmol), intermediate 58 (0.11 g, 0.46 mmol), Pd$_2$(dba)$_3$ (30 mg, 0.033 mmol), Xantphos (35 mg, 0.06 mmol) and cesium carbonate (0.25 g, 0.77 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (50 mg, 28%).

$^1$H NMR (500 MHz, DMSO-d$_6$): δ 1.65-1.72 (m, 4H), 2.06 (s, 3H), 2.50-2.62 (m, 4H), 2.75-2.85 (m, 2H), 3.50 (s, 3H), 3.94 (t, J=6.1 Hz, 2H), 5.84 (s, 2H), 6.67 (d, J=8.8 Hz, 1H), 6.78 (dd, J=7.8, 1.1 Hz, 1H), 6.83 (t, J=7.9 Hz, 1H), 6.92 (dd, J=8.1, 1.1 Hz, 1H), 7.14 (dd, J=8.7, 2.4 Hz, 1H), 7.23 (d, J=2.4 Hz, 1H), 7.83 (s, 1H), 8.21 (s, 1H), 8.69 (s, 1H). MS (ES+): m/z 464 (M+H)⁺.

Example 157

N-tert-Butyl-3-[2-(4-imidazol-1-yl-phenylamino)-5-methyl-pyrimidin-4-ylamino]-benzenesulfonamide (Compound CI)

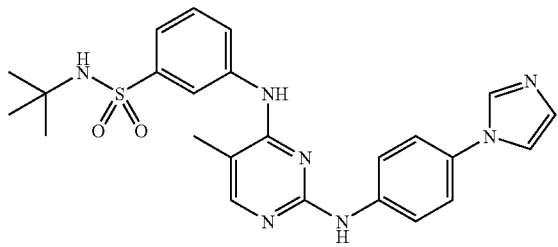

CI

A mixture of intermediate 33 (0.40 g, 1.1 mmol), 4-imidazol-1-yl-phenylamine (0.20 g, 1.3 mmol), Pd$_2$(dba)$_3$ (0.10 g, 0.11 mmol), Xantphos (0.12 g, 0.21 mmol) and cesium carbonate (0.80 g, 2.5 mmol) in dioxane/DMF (3/1, 8 mL) was sealed in a microwave reaction tube and irradiated with microwave at 160° C. for 30 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (40 mL). The combined aqueous layers were extracted with EtOAc (2×40 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as an off white solid (0.15 g, 28%).

$^1$H NMR (500 MHz, DMSO-d$_6$): δ 1.12 (s, 9H), 2.15 (s, 3H), 7.07 (s, 1H), 7.43 (d, J=9.0 Hz, 2H), 7.50-7.60 (m, 3H), 7.61 (s, 1H), 7.79 (d, J=9.0 Hz, 2H), 7.98 (s, 1H), 8.08-8.13 (m, 3H), 8.64 (s, 1H), 9.19 (s, 1H). MS (ES+): m/z 478 (M+H)⁺.

Example 158

N-tert-Butyl-3-[2-(4-imidazol-1-ylmethyl-phenylamino)-5-methyl-pyrimidin-4-ylamino]-benzenesulfonamide (Compound CII)

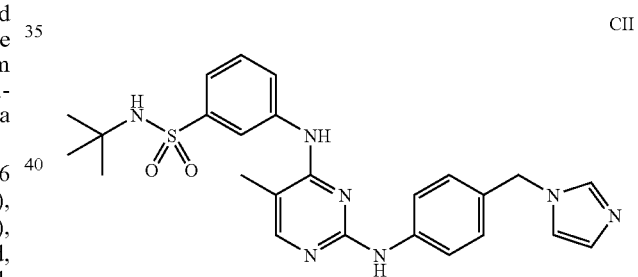

CII

A mixture of intermediate 33 (0.10 g, 0.28 mmol), 4-imidazol-1-ylmethyl-phenylamine (60 mg, 0.35 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (40 mg, 29%).

$^1$H NMR (500 MHz, DMSO-d$_6$): δ 1.12 (s, 9H), 2.13 (s, 3H), 5.07 (s, 2H), 6.89 (s, 1H), 7.12 (d, J=8.6 Hz, 2H), 7.15 (s, 1H), 7.46 (t, J=7.9 Hz, 1H), 7.49-7.52 (m, 1H), 7.56 (s, 1H), 7.63 (d, J=8.6 Hz, 2H), 7.72 (s, 1H), 7.94 (s, 1H), 8.09 (s, 1H), 8.14 (d, J=8.1 Hz, 1H), 8.60 (s, 1H), 9.02 (s, 1H). MS (ES+): m/z 492 (M+H)+.

Example 159

2-(4-Amino-phenoxy)-ethanol (Intermediate 59)

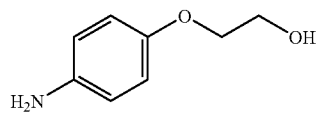

A solution of 2-(4-nitro-phenoxy)-ethanol (2.1 g, 12 mmol) in MeOH (30 mL) was flushed with argon and then charged with 10 wt % Pd/C (0.1 equiv by wt). The mixture was evacuated under house vacuum and then refilled with hydrogen from hydrogen balloon. The cycle was repeated again and the mixture stirred at room temperature for 2 h. The heterogeneous reaction mixture was filtered through a pad of Celite, washed with MeOH and concentrated in vacuo to furnish the title compound (1.8 g, 99%) as a brown solid. MS (ES+): m/z 154 (M+H)+.

Example 160

N-tert-Butyl-3-{2-[4-(2-hydroxy-ethoxy)-phenylamino]-5-methyl-pyrimidin-4-ylamino}-benzenesulfonamide (Compound CIII)

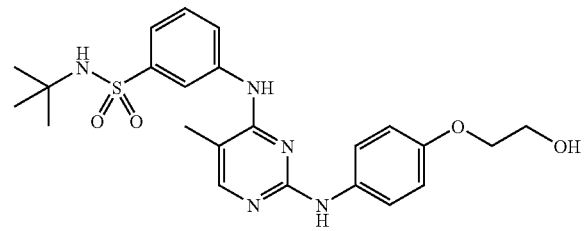

A mixture of intermediate 33 (0.10 g, 0.28 mmol), intermediate 59 (55 mg, 0.36 mmol), Pd2(dba)3 (25 mg, 0.027 mmol), Xantphos (30 mg, 0.052 mmol) and cesium carbonate (0.20 g, 0.61 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO3 solution (30 mL). The combined aqueous layers were extracted with EtOAc (2×30 mL) and the combined organic layers washed with brine, dried over anhydrous Na2SO4 and filtered. The filtrate was concentrated and then taken up in minimum amount of EtOAc. Hexanes were added until solid precipitated. After filtration, the title compound was obtained as a white solid (15 mg, 11%).

$^1$H NMR (500 MHz, DMSO-d$_6$): δ 1.12 (s, 9H), 2.12 (s, 3H), 3.69 (q, J=5.2 Hz, 2H), 3.91 (t, J=5.1 Hz, 2H), 4.82 (t, J=5.5 Hz, 2H), 6.80 (d, J=9.1 Hz, 2H), 7.45-7.50(m, 2H), 7.52 (d, J=9.0 Hz, 2H), 7.55 (s, 1H), 7.90 (s, 1H), 8.08-8.15 (m, 2H), 8.53 (s, 1H), 8.77 (s, 1H). MS (ES+): m/z 472 (M+H)+.

Example 160

N$^4$-(4-Chloro-3-methoxy-phenyl)-5-methyl-N$^2$-(4-piperazin-1-ylmethyl-phenyl)-pyrimidine-2,4-diamine (Compound CIV)

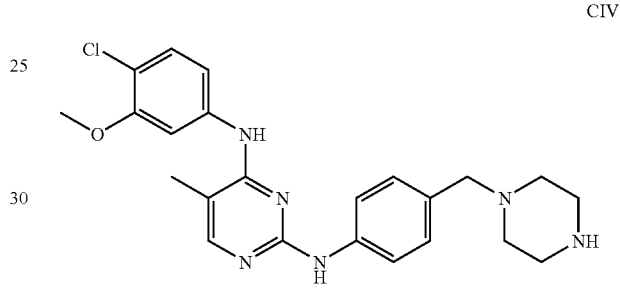

A mixture of intermediate 31 (0.10 g, 0.35 mmol), 4-(4-amino-benzyl)-piperazine -1-carboxylic acid tert-butyl ester (0.12 g, 0.41 mmol), Pd2(dba)3 (30 mg, 0.033 mmol), Xantphos (35 mg, 0.06 mmol) and cesium carbonate (0.23 g, 0.71 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM and the filtrate concentrated. The residue was purified by flash chromatography on silica gel (hexanes to 60% EtOAc/hexanes) to afford the Boc-protected precursor. To a solution of the precursor in DCM (5 mL) was added TFA (3 mL). The mixture was stirred at room temperature for 1 h, concentrated and the residue purified by HPLC. The corrected fractions were combined and poured into saturated NaHCO3 solution (30 mL). The combined aqueous layers were extracted with EtOAc (2×30 mL) and the combined organic layers washed with brine, dried over anhydrous Na2SO4 and filtered. The filtrate was concentrated and then taken up in minimum amount of EtOAc. Hexanes were added until solid precipitated. After filtration, the title compound was obtained as a white solid (13 mg, 9%).

$^1$H NMR (500 MHz, DMSO-d$_6$): δ 2.11 (s, 3H), 2.30-2.40 (m, 4H), 2.83 (t, J=4.8 Hz, 4H), 3.37 (s, 2H), 3.75 (s, 3H), 7.08 (d, J=8.6 Hz, 2H), 7.29 (d, J=8.6 Hz, 1H), 7.43 (dd, J=8.6, 2.2 Hz, 1H), 7.47 (d, J=2.2 Hz, 1H), 7.59 (d, J=8.6 Hz, 2H), 7.91 (s, 1H), 8.37 (s, 1H), 8.99 (s, 1H). MS (ES+): m/z 439 (M+H)+.

Example 161

N-tert-Butyl-3-{5-methyl-2-[4-(2-methyl-imidazol-1-yl)-phenylamino]-pyrimidin-4-ylamino}-benzene-sulfonamide (Compound CV)

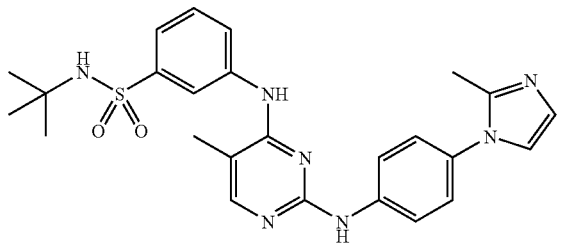

CV

A mixture of intermediate 33 (0.10 g, 0.28 mmol), 4-(2-methyl-imidazol-1-yl)-phenylamine (60 mg, 0.35 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (30 mg, 22%).

$^1$H NMR (500 MHz, DMSO-d$_6$): δ 1.11 (s, 9H), 2.15 (s, 3H), 2.24 (s, 3H), 6.87 (d, J=1.2 Hz, 1H), 7.18 (d, J=1.3 Hz, 1H), 7.22 (d, J=8.9 Hz, 2H), 7.50-7.55 (m, 2H), 7.56 (s, 1H), 7.79 (d, J=8.9 Hz, 2H), 7.98 (s, 1H), 8.07-8.10 (m, 2H), 8.65 (s, 1H), 9.26 (s, 1H). MS (ES+): m/z 492 (M+H)$^+$.

Example 162

N-tert-Butyl-3-{5-methyl-2-[4-(2-methyl-imidazol-1-ylmethyl)-phenylamino]-pyrimidin-4-ylamino}-benzenesulfonamide (Compound CVI)

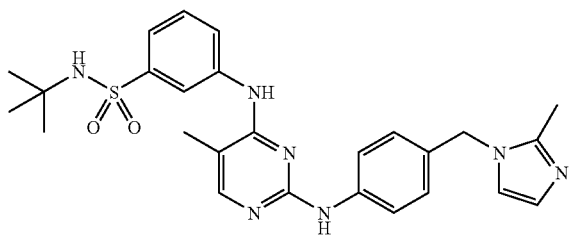

CVI

A mixture of intermediate 33 (0.10 g, 0.28 mmol), 4-(2-methyl-imidazol-1-ylmethyl)-phenylamine (65 mg, 0.35 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (30 mg, 21%).

$^1$H NMR (500 MHz, DMSO-d$_6$): δ 1.12 (s, 9H), 2.13 (s, 3H), 2.24 (s, 3H), 5.01 (s, 2H), 6.73 (d, J=1.2 Hz, 1H), 7.01 (d, J=8.6 Hz, 2H), 7.07 (d, J=1.1 Hz, 1H), 7.44 (t, J=7.9 Hz, 1H), 7.48-7.51 (m, 1H), 7.56 (s, 1H), 7.62 (d, J=8.6 Hz, 2H), 7.94 (s, 1H), 8.08 (s, 1H), 8.12 (d, J=8.1 Hz, 1H), 8.60 (s, 1H), 9.02 (s, 1H). MS (ES+): m/z 506 (M+H)$^+$.

Example 163

N-tert-Butyl-3-[5-methyl-2-(4-pyridin-4-ylmethyl-phenylamino)-pyrimidin -4-ylamino]-benzene-sulfonamide (Compound CVII)

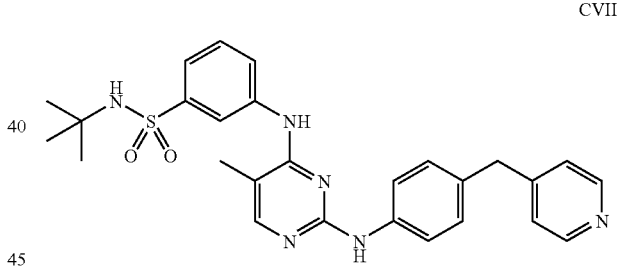

CVII

A mixture of intermediate 33 (0.10 g, 0.28 mmol), 4-Pyridin-4-ylmethyl-phenylamine (65 mg, 0.35 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (45 mg, 32%).

$^1$H NMR (500 MHz, DMSO-d$_6$): δ 1.11 (s, 9H), 2.13 (s, 3H), 3.87 (s, 2H), 7.07 (d, J=8.6 Hz, 2H), 7.22 (d, J=6.0 Hz, 2H), 7.43 (t, J=7.9 Hz, 1H), 7.47-7.50 (m, 1H), 7.56 (d, J=6.3

Hz, 2H), 7.58 (s, 1H), 7.93 (s, 1H), 8.09 (s, 1H), 8.13 (d, J=8.0 Hz, 1H), 8.44 (d, J=5.8 Hz, 2H), 8.58 (s, 1H), 8.94 (s, 1H). MS (ES+): m/z 503 (M+H)+.

Example 164

N-tert-Butyl-3-[5-methyl-2-(4-morpholin-4-yl-phenylamino)-pyrimidin-4-ylamino]-benzenesulfonamide (Compound CVIII)

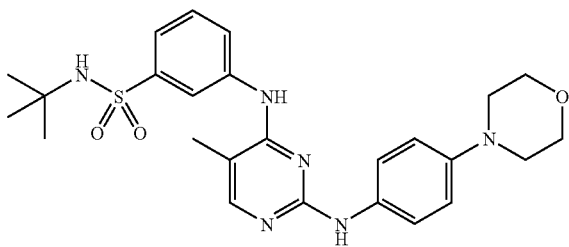

CVIII

A mixture of intermediate 33 (0.10 g, 0.28 mmol), 4-morpholin-4-yl-phenylamine (60 mg, 0.34 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1, 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a grey solid (45 mg, 32%).

$^1$H NMR (500 MHz, DMSO-d$_6$): δ 1.12 (s, 9H), 2.12 (s, 3H), 3.00 (t, J=4.8 Hz, 4H), 3.73 (t, J=4.8 Hz, 4H), 6.82 (d, J=9.1 Hz, 2H), 7.45-7.52 (m, 4H), 7.56 (s, 1H), 7.89 (s, 1H), 8.10-8.17 (m, 2H), 8.52 (s, 1H), 8.73 (s, 1H). MS (ES+): m/z 497 (M+H)+.

Example 165

N-tert-Butyl-3-[5-methyl-2-(4-[1,2,4]triazol-1-ylmethyl-phenylamino)-pyrimidin-4-ylamino]-benzenesulfonamide (Compound CIX)

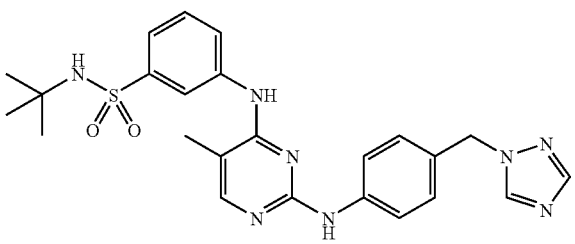

CIX

A mixture of intermediate 33 (0.10 g, 0.28 mmol), 4-[1,2,4]triazol-1-ylmethyl-phenylamine (60 mg, 0.34 mmol), Pd$_2$(dba)$_3$ (25 mg, 0.027 mmol), Xantphos (30 mg, 0.052 mmol) and cesium carbonate (0.20 g, 0.61 mmol) in dioxane (4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (37 mg, 27%).

$^1$H NMR (500 MHz, DMSO-d$_6$): δ 1.17 (s, 9H), 2.13 (s, 3H), 5.29 (s, 2H), 7.14 (d, J=8.6 Hz, 2H), 7.46 (t, J=7.8 Hz, 1H), 7.48-7.51 (m, 1H), 7.56 (s, 1H), 7.63 (d, J=8.6 Hz, 2H), 7.94 (s, 1H), 7.95 (s, 1H), 8.08 (s, 1H), 8.13 (d, J=8.0 Hz, 1H), 8.59 (s, 1H), 8.60 (s, 1H), 9.04 (s, 1H). MS (ES+): m/z 493 (M+H)+.

Example 166

N-tert-Butyl-3-{5-methyl-2-[4-(4-methyl-imidazol-1-yl)-phenylamino]-pyrimidin-4-ylamino}-benzenesulfonamide (Compound CX)

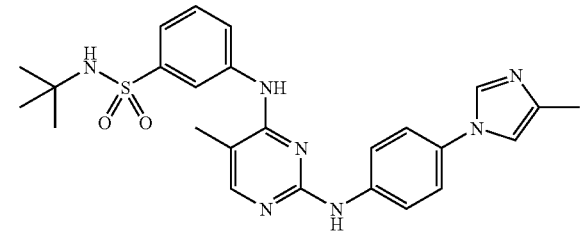

CX

A mixture of intermediate 33 (0.10 g, 0.28 mmol), 4-(4-methyl-imidazol-1-yl)-phenylamine (60 mg, 0.35 mmol), Pd$_2$(dba)$_3$ (25 mg, 0.027 mmol), Xantphos (30 mg, 0.052 mmol) and cesium carbonate (0.20 g, 0.61 mmol) in dioxane (3 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as an off white solid (20 mg, 15%).

$^1$H NMR (500 MHz, DMSO-d$_6$): δ 1.12 (s, 9H), 2.15 (s, 3H), 2.16 (s, 3H), 7.30 (s, 1H), 7.38 (d, J=9.0 Hz, 2H), 7.50-7.56 (m, 2H), 7.57 (s, 1H), 7.76 (d, J=9.0 Hz, 2H), 7.96

(s, 1H), 7.97 (s, 1H), 8.09-8.13 (m, 2H), 8.63 (s, 1H), 9.16 (s, 1H). MS (ES+): m/z 492 (M+H)+.

Example 167

N-tert-Butyl-3-[5-methyl-2-(4-[1,2,4]triazol-1-yl-phenylamino)-pyrimidin-4-ylamino]-benzene-sulfonamide (Compound CXI)

CXI

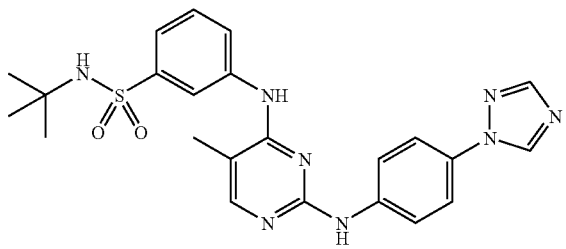

A mixture of intermediate 33 (0.10 g, 0.28 mmol), 4-[1,2,4]triazol-1-yl-phenylamine (55 mg, 0.34 mmol), Pd$_2$(dba)$_3$ (25 mg, 0.027 mmol), Xantphos (30 mg, 0.052 mmol) and cesium carbonate (0.20 g, 0.61 mmol) in dioxane (3 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (40 mg, 29%).
$^1$H NMR (500 MHz, DMSO-d$_6$): δ 1.12 (s, 9H), 2.15 (s, 3H), 7.50-7.58 (m, 3H), 7.63 (d, J=9.1 Hz, 2H), 7.83 (d, J=9.0 Hz, 2H), 7.99 (s, 1H), 8.09 (s, 1H), 8.10-8.15 (m, 1H), 8.17 (s, 1H), 8.66 (s, 1H), 9.12 (s, 1H), 9.27 (s, 1H). MS (ES+): m/z 479 (M+H)+.

Example 168

N-tert-Butyl-3-{5-methyl-2-[3-(1H-tetrazol-5-yl)-phenylamino]-pyrimidin-4-ylamino}-benzene-sulfonamide (Compound CXII)

CXII

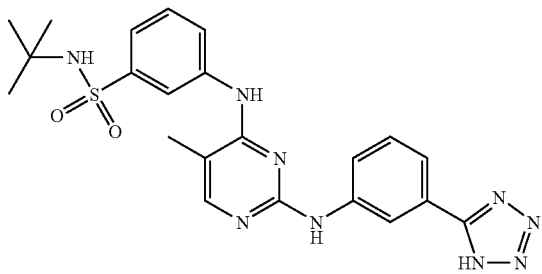

A mixture of intermediate 33 (0.10 g, 0.28 mmol), 3-(1H-tetrazol-5-yl)-phenylamine (55 mg, 0.34 mmol), Pd$_2$(dba)$_3$ (25 mg, 0.027 mmol), Xantphos (30 mg, 0.052 mmol) and cesium carbonate (0.20 g, 0.61 mmol) in dioxane (3 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (15 mg, 11%).
$^1$H NMR (500 MHz, DMSO-d$_6$): δ 1.13 (s, 9H), 2.15 (s, 3H), 7.26 (t, J=7.9 Hz, 1H), 7.38 (t, J=8.0 Hz, 1H), 7.44 (dd, J=7.9, 1.1 Hz, 1H), 7.50 (d, J=7.6 Hz, 1H), 7.58 (s, 1H), 7.79 (dd, J=8.1, 1.4 Hz, 1H), 7.98 (s, 1H), 8.16 (s, 1H), 8.22 (s, 1H), 8.27 (d, J=7.8 Hz, 1H), 8.57 (s, 1H), 9.08 (s, 1H). MS (ES+): m/z 480 (M+H)+.

Example 169

4-(1H-Tetrazol-5-yl)-phenylamine (Intermediate 60)

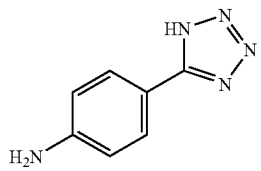

60

To a solution of 5-(4-nitro-phenyl)-1H-tetrazole (1.0 g, 5.2 mmol) in MeOH (30 mL) was added 10 wt % Pd/C (0.1 equiv by wt) under argon atmosphere. The mixture was evacuated, refilled with hydrogen (3 cycles) and stirred at room temperature for 1.5 h. The heterogeneous reaction mixture was filtered through a pad of Celite, washed with MeOH and concentrated in vacuo. The crude amino-compound was used in the next step without purification. MS (ES+): m/z 162 (M+H)+.

Example 170

N-tert-Butyl-3-{5-methyl-2-[4-(1H-tetrazol-5-yl)-phenylamino]-pyrimidin-4-ylamino}-benzene-sulfonamide (Compound CXIII)

CXIII

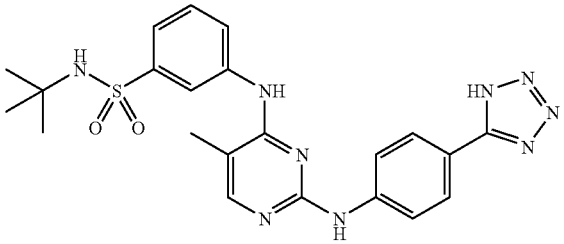

A mixture of intermediate 33 (0.10 g, 0.28 mmol), intermediate 60 (60 mg, 0.37 mmol), Pd$_2$(dba)$_3$ (25 mg, 0.027 mmol), Xantphos (30 mg, 0.052 mmol) and cesium carbonate (0.20 g, 0.61 mmol) in dioxane/DMF (3/1; 4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (15 mg, 11%).

$^1$H NMR (500 MHz, DMSO-d$_6$): δ 1.13 (s, 9H), 2.16 (s, 3H), 7.52-7.56 (m, 2H), 7.57 (s, 1H), 7.83 (s, 4H), 8.01 (s, 1H), 8.08 (s, 1H), 8.13-8.19 (m, 1H), 8.69 (s, 1H), 9.34 (s, 1H). MS (ES+): m/z 480 (M+H)$^+$.

Example 171

3-{2-[4-(4-Acetyl-piperazin-1-yl)-phenylamino]-5-methyl-pyrimidin -4-ylamino}-N-tert-butyl-benzenesulfonamide (Compound CXIV)

CXIV

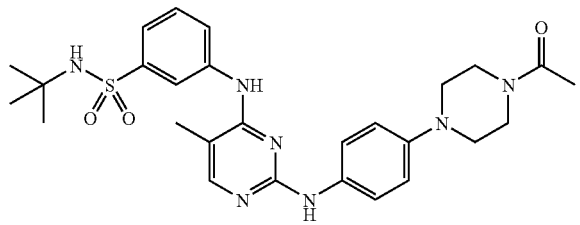

A mixture of intermediate 33 (0.10 g, 0.28 mmol), 1-[4-(4-amino-phenyl)-piperazin -1-yl]-ethanone (80 mg, 0.36 mmol), Pd$_2$(dba)$_3$ (25 mg, 0.027 mmol), Xantphos (30 mg, 0.052 mmol) and cesium carbonate (0.20 g, 0.61 mmol) in dioxane (3 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as an off white solid (55 mg, 37%).

$^1$H NMR (500 MHz, DMSO-d$_6$): δ 1.12 (s, 9H), 2.04 (s, 3H), 2.12 (s, 3H), 2.97 (t, J=5.2 Hz, 2H), 3.03 (t, J=5.1 Hz, 2H), 3.57 (q, J=5.4 Hz, 4H), 6.85 (d, J=9.0 Hz, 2H), 7.46-7.52 (m, 4H), 7.56 (s, 1H), 7.90 (s, 1H), 8.10-8.17 (m, 2H), 8.52 (s, 1H), 8.75 (s, 1H). MS (ES+): m/z 538 (M+H)$^+$.

Example 172

N-tert-Butyl-3-{5-methyl-2-[4-(1-morpholin-4-yl-ethyl)-phenylamino]-pyrimidin-4-ylamino}-benzenesulfonamide (Compound CXV)

CXV

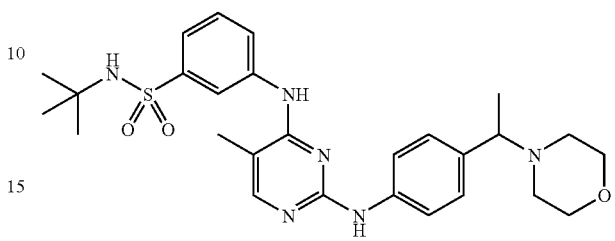

A mixture of intermediate 33 (0.10 g, 0.28 mmol), 4-(1-morpholin-4-yl-ethyl)-phenylamine (80 mg, 0.39 mmol), Pd$_2$(dba)$_3$ (30 mg, 0.033 mmol), Xantphos (35 mg, 0.061 mmol) and cesium carbonate (0.26 g, 0.80 mmol) in dioxane (4 mL) was sealed in a microwave reaction tube and irradiated with microwave at 160° C. for 20 min. After cooling to room temperature, the cap was removed and the resulting mixture filtered. The filtered solid was washed with DCM, the filtrate concentrated and the residue purified by HPLC. The corrected fractions were combined and poured into saturated NaHCO$_3$ solution (30 mL). The combined aqueous layers were extracted with EtOAc (2×30 mL) and the combined organic layers washed with brine, dried over anhydrous Na$_2$SO$_4$ and filtered. The filtrate was concentrated and then taken up in minimum amount of EtOAc. Hexanes were added until solid precipitated. After filtration, the title compound was obtained as a white solid (40 mg, 27%).

$^1$H NMR (500 MHz, DMSO-d$_6$): δ 1.12 (s, 9H), 1.25 (d, J=6.6 Hz, 3H), 2.13 (s, 3H), 2.20-2.30 (m, 2H), 2.30-2.40 (m, 2H), 3.24 (q, J=6.6 Hz, 1H), 3.54 (t, J=4.4 Hz, 4H), 7.10 (d, J=8.5 Hz, 2H), 7.45-7.52 (m, 2H), 7.55 (s, 1H), 7.57 (d, J=8.5 Hz, 2H), 7.93 (s, 1H), 8.09 (s, 1H), 8.15 (d, J=7.7 Hz, 1H), 8.57 (s, 1H), 8.92 (s, 1H). MS (ES+): m/z 525 (M+H)$^+$.

Example 173

N$^4$-(1H-Indol-4-yl)-5-methyl-N$^2$-(4-(4-methylpiperazin-1-yl)phenyl)pyrimidine-2,4-diamine (Compound CXVI)

CXVI

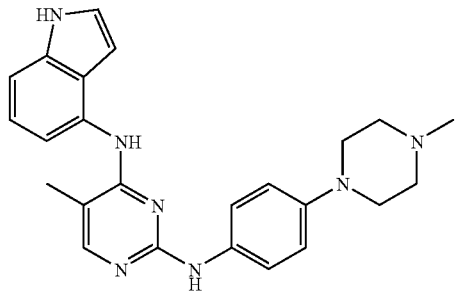

A mixture of intermediate 32 (270 mg, 0.9 mmol), 4-bromo-1H-indole (196 mg, 0.9 mmol), Pd$_2$(dba)$_3$ (91 mg, 0.09 mmol), Xantphos (157 mg, 0.27 mmol) and cesium carbonate (1.2 g, 3.6 mmol) were suspended in dioxane (100 mL) and heated at reflux under the argon atmosphere for 20 h.

The mixture was filtered and the filtrate concentrated in vacuo. The residue was purified by HPLC to afford the title compound (55 mg of HCl salt, 14%) as a white solid.

$^1$H NMR (500 MHz, DMSO-d$_6$): δ 2.22 (s, 3H), 2.79 (d, J=4.3 Hz, 3H), 2.98-3.03(m, 2H), 3.08-3.14 (m, 2H), 3.46-3.48 (m, 2H), 3.64-3.66 (m, 2H), 6.35-6.36 (m, 1H), 6.63 (br d, J=8.0 Hz, 1H), 6.98 (d, J=9.1 Hz, 2H), 7.05 (d, J=7.4 Hz, 1H), 7.16 (t, J=7.6 Hz, 1H), 7.36 (t, J=2.8 Hz, 2H), 7.43 (d, J=8.0 Hz, 1H), 7.86 (s, 1H), 10.07 (s, 1H), 10.27 (s, 1H), 11.00 (br s, 1H), 11.38 (s, 1H), 12.16 (br s, H). MS (ES+): m/z 414 (M+H)$^+$.

Example 174

2-Chloro-5-methyl-N-(2,3-dimethylphenyl)pyrimidin-4-amine (Intermediate 61)

61

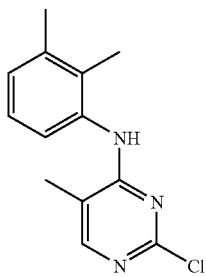

A mixture of 2-chloro-5-methylpyrimidin-4-amine (143.6 mg, 1 mmol), 1-bromo-2,3-dimethylbenzene (222 mg, 1.2 mmol), Pd$_2$(dba)$_3$ (92 mg, 0.1 mmol), Xantphos (174 mg, 0.3 mmol) and cesium carbonate (1.3 g, 4 mmol) were suspended in dioxane (150 mL) and heated at reflux under the argon atmosphere for 20 h. The mixture was filtered and the filtrate concentrated in vacuo. The residue was dissolved in EtOAc (10 mL) and added hexanes (100 mL). The solid was collected by filtration and washed with hexanes to afford the crude title compound as a yellow solid.

Example 175

5-Methyl-N$^4$-(2,3-dimethylphenyl)-N$^2$-(4-(piperidin-4-yloxy)phenyl)pyrimidine-2,4-diamine (Compound CXVII)

CXVII

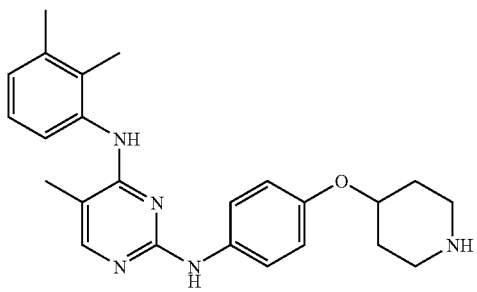

A mixture of intermediate 61 (1.0 mmol) and tert-butyl 4-(4-aminophenoxy)piperidine-1-carboxylate (292.4 mg, 1.0 mmol) were suspended in acetic acid (10 mL) and heated at 100° C. for 4 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO$_4$ and filtered. The filtrate was concentrated in vacuo and the crude product purified by HPLC to afford the title compound (105 mg of HCl salt, 24%) as a yellow solid.

$^1$H NMR (500 MHz, DMSO-d$_6$): δ 1.76-1.83 (m, 2H), 2.03 (s, 3H), 2.05-2.09 (m, 2H), 2.17 (s, 3H), 2.30 (s, 3H), 3.02-3.05 (m, 2H), 3.18 (br s, 2H), 4.53-4.56 (m, 1H), 6.72 (d, J=8.5 Hz, 2H), 7.11-7.14 (m, 3H), 7.19-7.24 (m, 2H), 7.87 (s, 1H), 9.06 (br s, 1H), 9.13 (br s, 1H), 9.92 (s, 1H), 10.43 (s, 1H). MS (ES+): m/z 404 (M+H)$^+$.

Example 176

N$^4$-(4-Chloro-3,5-dimethylphenyl)-5-methyl-N$^2$-(4-(4-methylpiperazin-1-yl)phenyl)pyrimidine-2,4-diamine (Compound CXVIII)

CXVIII

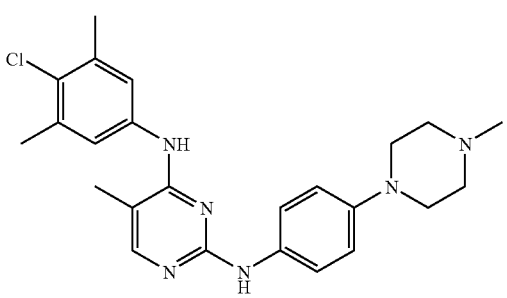

A mixture of intermediate 32 (240 mg, 0.8 mmol), 5-bromo-2-chloro-1,3-dimethylbenzene (212 mg, 0.96 mmol), Pd$_2$(dba)$_3$ (92 mg, 0.1 mmol), Xantphos (170 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was purified by HPLC to afford the title compound (63 mg of HCl salt, 17%) as a white solid.

$^1$H NMR (500 MHz, DMSO-d$_6$): δ 2.15 (s, 3H), 2.17 (s, 3H), 2.80 (d, J=4.5 Hz, 3H), 3.06-3.14 (m, 4H), 3.48-3.52 (m, 2H), 3.75-3.77 (m, 2H), 6.93 (d, J=8.9 Hz, 2H), 7.29 (d, J=8.9 Hz, 2H), 7.46 (s, 2H), 7.90 (s, 1H), 9.65 (s, 1H), 10.49 (s, 1H), 11.13 (br s, 2H). MS (ES+): m/z 437 (M+H)$^+$.

Example 177

N²-(4-(2-(Pyrrolidin-1-yl)ethoxy)phenyl)-N⁴-(3-tert-butylphenyl)-5-methyl-pyrimidine-2,4-diamine (Compound CXIX)

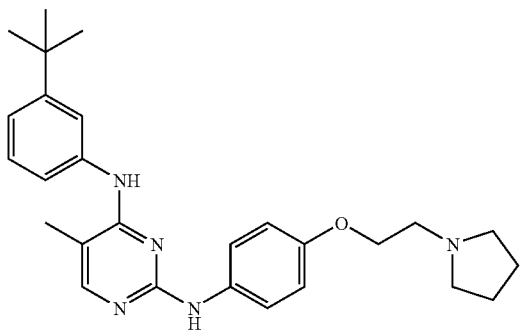

A mixture of intermediate 41 (365 mg, 1.32 mmol) and 4-(2-(pyrrolidin-1-yl)ethoxy)benzenamine (410 mg, 1.98 mmol) were suspended in acetic acid (20 mL) and heated at 100° C. for 4 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO₄ and filtered. The filtrate was concentrated in vacuo and the crude product purified by HPLC to afford the title compound (127 mg of HCl salt, 20%) as a white solid.

¹H NMR (500 MHz, DMSO-d₆): δ 1.89-1.91 (m, 2H), 1.98-2.02 (m, 2H), 2.17 (s, 3H), 3.07-3.12 (m, 2H), 3.52-3.57 (m, 4H), 4.32 (t, J=4.8 Hz, 2H), 6.90 (d, J=8.9 Hz, 2H), 7.29-7.38 (m, 4H), 7.43-7.44 (m, 1H), 7.48 (d, J=7.9 Hz, 1H), 7.89 (s, 1H), 9.75 (s, 1H), 10.51 (s, 1H), 11.07 (br, 1H). MS (ESI+): m/z 446 (M+H)⁺.

Example 178

N²-(4-(2-(Pyrrolidin-1-yl)ethoxy)phenyl)-N⁴-(4-(3-tert-butylphenylamino)-5-methylpyrimidin-2-yl)-5-methylpyrimidine-2,4-diamine (Compound CXX)

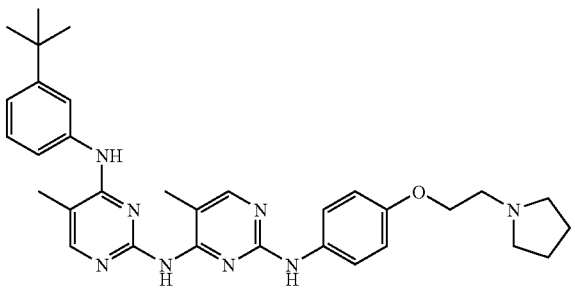

A mixture of intermediate 41 (210 mg, 0.67 mmol), intermediate 38 (185 mg, 0.67 mmol), Pd₂(dba)₃ (55 mg, 0.06 mmol), Xantphos (104 mg, 0.18 mmol) and cesium carbonate (782 g, 2.4 mmol) were suspended in dioxane (50 mL) and heated at reflux under the argon atmosphere for 20 h. The mixture was filtered and the filtrate concentrated in vacuo. The residue was purified by HPLC to afford the title compound (94 mg of HCl salt, 24%) as a yellow solid.

¹H NMR (500 MHz, DMSO-d₆): δ 1.29 (s, 9H), 1.84-1.88 (m, 2H), 1.94-2.01 (m, 2H), 2.14 (s, 3H), 2.27 (s, 3H), 3.06-3.10 (m, 2H), 3.51-3.56 (m, 4H), 4.29 (t, J=4.9 Hz, 2H), 6.97 (d, J=9.1 Hz, 2H), 7.27 (d, J=8.6 Hz, 2H), 7.34 (t, J=7.9 Hz, 2H), 7.57 (t, J=1.9 Hz, 2H), 7.65 (d, J=9.1 Hz, 1H), 7.72 (d, J=8.6 Hz, 2H), 8.15 (s, 1H), 8.39 (s, 1H), 9.82 (s, 1H), 10.21 (br s, 1H), 10.68 (br s, 1H), 10.93 (br s, 1H). MS (ES+): m/z 553 (M+H)⁺.

Example 179

5-Methyl-N²-[4-(4-methyl-piperazin-1-yl)-phenyl]-N⁴-[3-(piperidine-1-sulfonyl)-phenyl]-pyrimidine-2,4-diamine (Compound CXXI)

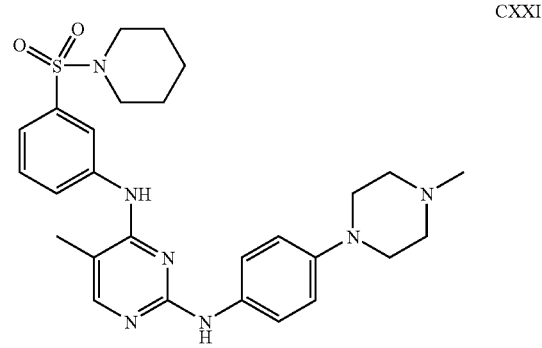

A mixture of intermediate 32 (150 mg, 0.5 mmol), 1-(3-bromo-benzenesulfonyl)-piperidine (152 mg, 0.5 mmol), Pd₂(dba)₃ (46 mg, 0.05 mmol), Xantphos (87 mg, 0.15 mmol) and cesium carbonate (652 mg, 2 mmol) were suspended in dioxane (20 mL) and heated at reflux under the argon atmosphere for 20 h. The mixture was filtered and the filtrate concentrated in vacuo. The residue was purified by HPLC to afford the title compound (84 mg of HCl salt, 37%) as a white solid.

¹H NMR (500 MHz, DMSO-d₆): δ 1.30-1.34 (m, 2H), 1.50-1.55 (m, 4H), 2.17 (s, 3H), 2.81 (d, J=4.5 Hz, 3H), 2.88 (t, J=5.3 Hz, 4H), 3.04-3.16 (m, 4H), 3.47-3.51 (m, 2H), 3.75-3.77 (m, 2H), 6.33-6.34 (m, 1H), 6.95 (d, J=9.0 Hz, 2H), 7.25 (d, J=9.0 Hz, 2H), 7.56-7.63 (m, 2H), 7.83 (t, J=1.7 Hz, 1H), 7.92 (s, 1H), 8.05 (d, J=9.3 Hz, 1H), 9.94 (s, 1H), 10.38 (s, 1H), 10.88 (br s, 1H). MS (ES+): m/z 522 (M+H)⁺.

Example 180

5-Methyl-$N^2$-[4-(4-methyl-piperazin-1-yl)-phenyl]-$N^4$-[3-(2-methyl-piperidine-1-sulfonyl)-phenyl]-pyrimidine-2,4-diamine (Compound CXXII)

CXXII

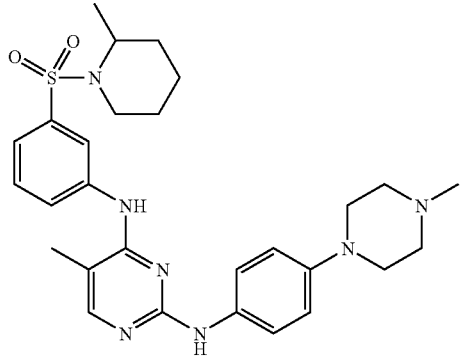

A mixture of intermediate 32 (161 mg, 0.54 mmol), 1-(3-bromo-benzenesulfonyl)-2-methyl-piperidine (172 mg, 0.54 mmol), $Pd_2(dba)_3$ (46 mg, 0.05 mmol), Xantphos (87 mg, 0.15 mmol) and cesium carbonate (652 mg, 2 mmol) were suspended in dioxane (20 mL) and heated at reflux under the argon atmosphere for 20 h. The mixture was filtered and the filtrate concentrated in vacuo. The residue was purified by HPLC to afford the title compound (10 mg of HCl salt, 3%) as a white solid.

$^1$H NMR (500 MHz, DMSO-$d_6$): δ 0.98 (d, J=6.9 Hz, 3H), 1.15-1.21 (m, 1H), 1.36-1.40 (m, 3H), 1.47-1.53 (m, 2H), 2.18 (s, 3H), 2.80 (d, J=4.5 Hz, 3H), 2.94-2.99 (m, 1H), 3.05-3.16 (m, 4H), 3.47-3.49 (m, 2H), 3.59-3.61 (m, 2H), 3.73-3.76 (m, 2H), 4.08-4.10 (m, 1H), 6.93 (d, J=8.9 Hz, 2H), 7.25 (d, J=8.9 Hz, 2H), 7.58 (t, J=8.0 Hz, 1H), 7.65 (d, J=8.0 Hz, 1H), 7.92 (d, J=7.1 Hz, 2H), 7.96 (br, 1H), 9.95 (s, 1H), 10.45 (s, 1H), 11.00 (br s, 1H). MS (ES+): m/z 536 (M+H)$^+$.

Example 181

N-Cyclopentyl-3-{5-methyl-2-[4-(4-methyl-piperazin-1-yl)-phenylamino]-pyrimidine-4-ylamino}-benzenesulfonamide (Compound CXXIII)

CXXIII

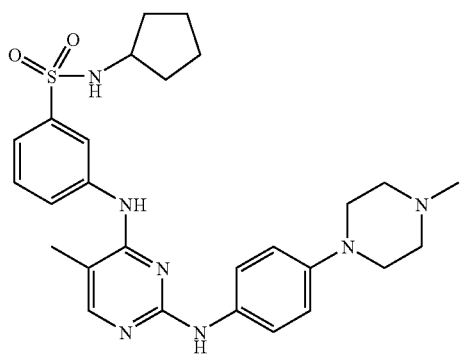

A mixture of intermediate 32 (229 mg, 0.78 mmol), 3-bromo-N-cyclopentyl-benzenesulfonamide (280 mg, 0.92 mmol), $Pd_2(dba)_3$ (92 mg, 0.1 mmol), Xantphos (180 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was purified by HPLC to afford the title compound (130 mg of HCl salt, 25%) as a white solid.

$^1$H NMR (500 MHz, DMSO-$d_6$): δ 1.27-1.36 (m, 4H), 1.36-1.58 (m, 4H), 2.18 (s, 3H), 2.80 (d, J=4.6 Hz, 3H), 3.05-3.15 (m, 4H), 3.36-3.42 (m, 1H), 3.47-3.49 (m, 2H), 3.74-3.76 (m, 2H), 6.94 (d, J=8.7 Hz, 2H), 7.26 (d, J=8.9 Hz, 2H), 7.59 (t, J=8.0 Hz, 1H), 7.68 (d, J=8.0 Hz, 1H), 7.75 (d, J=7.1 Hz, 2H), 7.92 (br, 2H), 7.93 (br, 1H), 9.96 (s, 1H), 10.45 (s, 1H), 11.98 (br s, 1H). MS (ES+): m/z 522 (M+H)$^+$.

Example 182

5-Methyl-$N^2$-[4-(4-methyl-piperazin-1-yl)-phenyl]-$N^4$-[3-(pyrrolidine-1-sulfonyl) phenyl]-pyrimidine-2,4-diamine (Compound CXXIV)

CXXIV

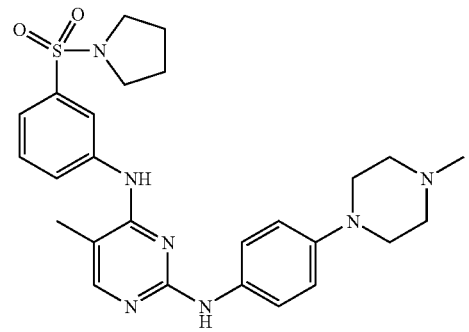

A mixture of intermediate 32 (298 mg, 1.0 mmol), 1-(3-bromo-benzenesulfonyl)-pyrrolidine (360 mg, 1.24 mmol), $Pd_2(dba)_3$ (92 mg, 0.1 mmol), Xantphos (180 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was purified by HPLC to afford the title compound (200 mg of HCl salt, 37%) as a white solid.

$^1$H NMR (500 MHz, DMSO-$d_6$): δ 1.61-1.65 (m, 4H), 2.19 (s, 3H), 2.80 (br, 3H), 3.06-3.16 (m, 10H), 3.74-3.77 (br, 2H), 6.94 (d, J=9.0 Hz, 2H), 7.26 (d, J=9.0 Hz, 2H), 7.60 (t, J=8.0 Hz, 1H), 7.65 (d, J=8.0 Hz, 1H), 7.91 (t, J=1.7 Hz, 1H), 7.93 (s, 1H), 8.05 (d, J=7.5 Hz, 1H), 9.95 (s, 1H), 10.43 (s, 1H), 11.07 (br s, 1H). MS (ES+): m/z 508 (M+H)$^+$.

Example 183

$N^4$-[3-(2,5-Dimethyl-pyrrolidine-1-sulfonyl)-phenyl]-5-methyl-$N^2$-[4-(4-methyl-piperazin-1-yl)-phenyl]-pyrimidine-2,4-diamine (Compound CXXV)

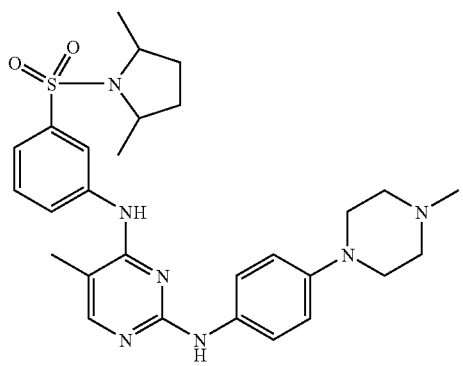

CXXV

A mixture of intermediate 32 (298 mg, 1.0 mmol), 1-(3-bromo-benzenesulfonyl)-2,5-dimethyl-pyrrolidine (318 mg, 1.0 mmol), Pd$_2$(dba)$_3$ (92 mg, 0.1 mmol), Xantphos (180 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was purified by HPLC to afford the title compound (100 mg of HCl salt, 17%) as a white solid.

$^1$H NMR (500 MHz, DMSO-d$_6$): δ 1.26 (s, 3H), 1.27 (s, 3H), 1.45-1.48 (m, 4H), 2.19 (s, 3H), 2.80 (d, J=4.6 Hz, 3H), 3.06-3.15 (m, 4H), 3.47-3.50 (m, 2H), 3.60-3.64 (m, 2H), 3.74-3.76 (m, 2H), 6.94 (d, J=9.0 Hz, 2H), 7.25 (d, J=9.0 Hz, 2H), 7.59 (t, J=8.0 Hz, 1H), 7.68 (d, J=7.6 Hz, 1H), 7.93 (br, 2H), 8.02 (br, 1H), 9.97 (s, 1H), 10.47 (s, 1H), 11.07 (br s, 1H). MS (ES+): m/z 536 (M+H)$^+$.

Example 184

N-tert-Butyl-3-[5-methyl-2-(4-piperazin-1-yl-phenylamino)-pyrimidin-4-ylamino]-benzenesulfonamide (Compound CXXVI)

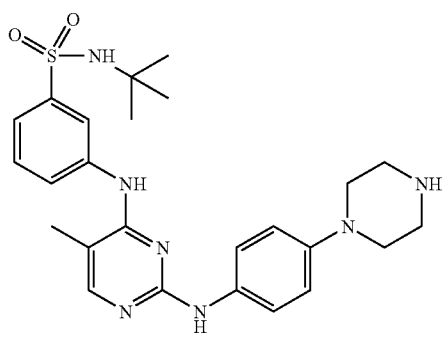

CXXVI

A mixture of intermediate 33 (355 mg, 1.0 mmol), tert-butyl 4-(4-aminophenyl)piperazine-1-carboxylate (278 mg, 1.0 mmol), Pd$_2$(dba)$_3$ (92 mg, 0.1 mmol), Xantphos (180 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was dissolved in CH$_2$Cl$_2$ (10 mL) and trifluoroacetic acid (2 mL) was added. The mixture was stirred for 4 h at room temperature before 10% NaOH was added. The organic layer was separated and aqueous was extracted with CH$_2$Cl$_2$ (10 mL×2). The combined organic layers were dried (Na$_2$SO$_4$). The solvent was removed in vacuo. The residue was purified by HPLC to afford the title compound (62 mg, 12%) as a white solid.

$^1$H NMR (500 MHz, DMSO-d$_6$): δ 1.10 (s, 9H), 2.18 (s, 3H), 3.20 (br, 4H), 3.33 (br, 4H), 6.94 (d, J=9.0 Hz, 2H), 7.25 (d, J=9.0 Hz, 2H), 7.57 (t, J=8.0 Hz, 1H), 7.63 (s, 1H), 7.71 (d, J=8.1 Hz, 1H), 7.87 (br, 1H), 7.92 (br, 1H), 7.96 (br, 1H), 9.30 (br, 1H), 9.96 (s, 1H), 10.46 (s, 1H). MS (ES+): m/z 496 (M+H)$^+$.

Example 185

N-tert-Butyl-3-(2-{4-[4-(2-hydroxy-ethyl)-piperazin-1-yl]-phenylamino}-[5-methyl-pyrimidin-4-ylamino]-benzenesulfonamide (Compound CXXVII)

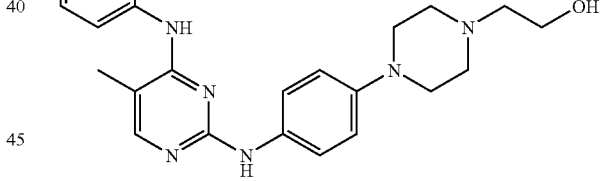

CXXVII

The above-described compound CXXVI (31 mg, 0.06 mmol) was dissolved in DMF (10 mL) followed by adding 2-bromoethanol (16 mg, 0.13 mmol) and diisopropylethylamine (33 mg, 0.25 mmol). The mixture was stirred for 48 h at room temperature. Solvent was removed in vacuo and residue was dissolved in EtOAc (20 mL). The solution was washed with saturated NaHCO$_3$ and brine. The combined organic layers were dried and concentrated until 2 mL solution followed by adding Et$_2$O (20 mL). The solid was collected by centrifugation and transferred to its HCl salt (10.7 mg, 30%).

$^1$H NMR (500 MHz, DMSO-d$_6$): δ 1.09 (s, 9H), 2.17 (s, 3H), 3.12-3.23 (m, 4H), 3.56-3.60 (m, 2H), 3.69-3.74 (m, 2H), 3.83 (br, 2H), 4.13 (br, 2H), 6.94 (d, J=9.0 Hz, 2H), 7.25 (d, J=9.0 Hz, 2H), 7.57 (t, J=8.0 Hz, 1H), 7.63 (s, 1H), 7.71 (d, J=8.1 Hz, 1H), 7.87 (br, 1H), 7.93 (br, 1H), 7.95 (br, 1H), 9.98 (s, 1H), 10.53 (s, 1H), 10.75 (br, 1H). MS (ES+): m/z 540 (M+H)$^+$.

Example 186

N-tert-Butyl-3-[5-methyl-2-(3-piperazin-1-yl-phenylamino)-pyrimidin-4-ylamino]-benzenesulfonamide (Compound CXXVIII)

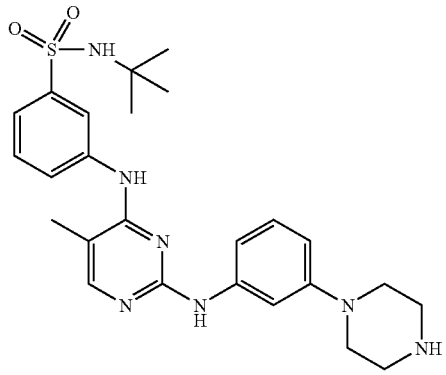

CXXVIII

A mixture of intermediate 33 (240 mg, 0.67 mmol), tert-butyl 4-(3-aminophenyl)piperazine-1-carboxylate (166 mg, 0.6 mmol), Pd$_2$(dba)$_3$ (55 mg, 0.06 mmol), Xantphos (104 mg, 0.18 mmol) and cesium carbonate (782 mg, 2.4 mmol) were suspended in dioxane (100 mL) and heated at reflux under the argon atmosphere for 20 h. The mixture was filtered and the filtrate concentrated in vacuo. The residue was dissolved in CH$_2$Cl$_2$ (10 mL) and trifluoroacetic acid (2 mL) was added. The mixture was stirred for 4 h at room temperature before 10% NaOH was added. The organic layer was separated and aqueous was extracted with CH$_2$Cl$_2$ (10 mL×2). The combined organic layers were dried (Na$_2$SO$_4$). The solvent was removed in vacuo. The residue was purified by HPLC to afford the title compound (18 mg, 6%) as a white solid.

$^1$H NMR (500 MHz, DMSO-d$_6$): δ 1.10 (s, 9H), 2.19 (s, 3H), 3.17 (br, 4H), 3.27-3.29 (m, 4H), 6.80 (d, J=8.1 Hz, 1H), 6.87 (br, 1H), 6.96 (d, J=8.1 Hz, 1H), 7.16 (t, J=8.1 Hz, 1H), 7.53 (t, J=8.3 Hz, 1H), 7.61 (s, 1H), 7.70 (d, J=7.8 Hz, 1H), 7.94 (br, 3H), 9.19 (br, 2H), 9.93 (s, 1H), 10.48 (s, 1H). MS (ES+): m/z 496 (M+H)$^+$.

Example 187

N-tert-Butyl-3-(2-{3-[4-(2-hydroxy-ethyl)-piperazin-1-yl]-phenylamino}-[5-methyl-pyrimidin-4-ylamino]-benzenesulfonamide (Compound CXXIX)

CXXIX

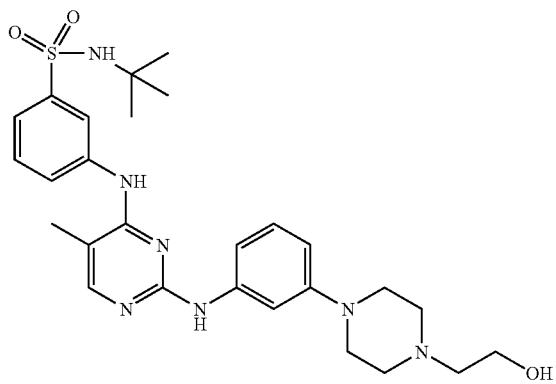

The above-described compound CXXVI (12 mg, 0.024 mmol) was dissolved in DMF (10 mL) followed by adding 2-bromoethanol (6.1 mg, 0.048 mmol) and diisopropylethylamine (12 mg, 0.092 mmol). The mixture was stirred for 48 h at room temperature. Solvent was removed in vacuo and residue was dissolved in EtOAc (20 mL). The solution was washed with saturated NaHCO$_3$ and brine. The combined organic layers were dried and concentrated until 2 mL solution followed by adding Et$_2$O (20 mL). The solid was collected by centrifugation and transferred to its HCl salt (7 mg, 51%).

$^1$H NMR (500 MHz, DMSO-d$_6$): δ 1.09 (s, 9H), 2.19 (s, 3H), 3.12-3.22 (m, 4H), 3.56-3.60 (m, 2H), 3.69-3.74 (m, 2H), 3.81 (br, 2H), 4.12 (br, 2H), 6.80 (br, 1H), 6.88 (br, 1H), 6.96 (br, 1H), 7.16 (br, 1H), 7.57 (br, 1H), 7.60 (s, 1H), 7.69 (d, J=7.8 Hz, 1H), 7.94 (br, 3H), 9.94 (s, 1H), 10.49 (s, 1H). MS (ES+): m/z 540 (M+H)$^+$.

Example 188

N$^2$-(4-(1H-Pyrazol-1-yl)phenyl)-N$^4$-(3-tert-butylphenyl)-5-methylpyrimidine-2,4-diamine (Compound CXXX)

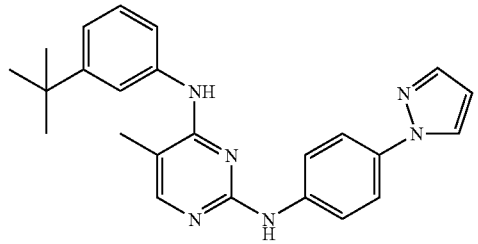

CXXX

A mixture of intermediate 41 (580 mg, 2.1 mmol) and 4-(1H-pyrazol-1-yl)benzenamine (335 mg, 2.1 mmol) were suspended in acetic acid (10 mL) and heated at 100° C. for 4 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO$_4$ and filtered. The filtrate was concentrated in vacuo and the crude product purified by HPLC to afford the title compound (31 mg, 4%) as a yellow solid.

$^1$H NMR (500 MHz, DMSO-d$_6$): δ 1.24 (s, 9H), 2.18 (s, 3H), 6.53 (t, J=2.0 Hz, 1H), 7.33 (d, J=8.0 Hz, 1H), 7.38 (t, J=7.9 Hz, 1H), 7.44 (s, 1H), 7.47 (d, J=8.2 Hz, 1H), 7.50 (d, J=8.9 Hz, 2H), 7.67 (d, J=8.9 Hz, 2H), 7.73 (s, 1H), 7.95 (s, 1H), 8.43 (d, J=2.4 Hz, 1H), 9.81 (br s, 1H), 10.67 (s, 1H). MS (ES+): m/z 399 (M+H)$^+$.

Example 189

N⁴-(7-Chloro-1H-indol-4-yl)-5-methyl-N²-(4-((piperazin-1-yl)methyl)phenyl)-pyrimidine-2,4-diamine (Compound CXXXI)

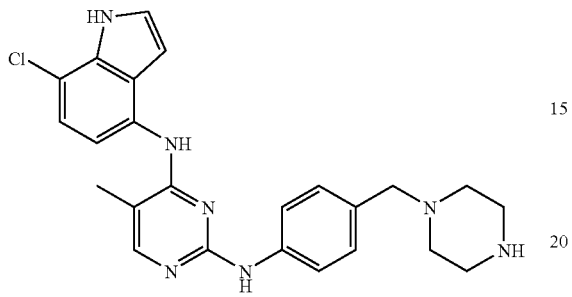

CXXXI

A mixture of intermediate 40 (150 mg, 0.37 mmol), 4-bromo-7-chloro-1H-indole (87 mg, 0.37 mmol), Pd₂(dba)₃ (38 mg, 0.04 mmol), Xantphos (76 mg, 0.12 mmol) and cesium carbonate (521 mg, 1.6 mmol) were suspended in dioxane (50 mL) and heated at reflux under the argon atmosphere for 20 h. The mixture was filtered and the filtrate concentrated in vacuo. The residue was dissolved in CH₂Cl₂ (10 mL) and trifluoroacetic acid (2 mL) was added. The mixture was stirred for 4 h at room temperature before 10% NaOH was added. The organic layer was separated and aqueous was extracted with CH₂Cl₂ (10 mL×2). The combined organic layers were dried (Na₂SO₄). The solvent was removed in vacuo. The residue was purified by HPLC to afford the title compound (26 mg, 15%) as a white solid.

¹H NMR (500 MHz, DMSO-d₆): δ 2.21 (s, 3H), 3.30 (br, 4H), 3.50 (br, 4H), 4.42 (br, 2H), 6.91 (s, 1H), 7.11 (d, J=8.3 Hz, 1H), 7.40 (d, J=7.5 Hz, 1H), 7.42 (t, J=2.7 Hz, 1H), 7.70 (br, 4H), 8.03 (s, 1H), 9.87 (br, 1H), 9.95 (s, 1H), 10.64 (s, 1H), 11.64 (s, 1H). MS (ES+): m/z 448 (M+H)⁺.

Example 190

N⁴-(3-tert-Butylphenyl)-5-methyl-N²-(4-(2-methyl-1H-imidazol-1-yl)phenyl)-pyrimidine-2,4-diamine (Compound CXXXII)

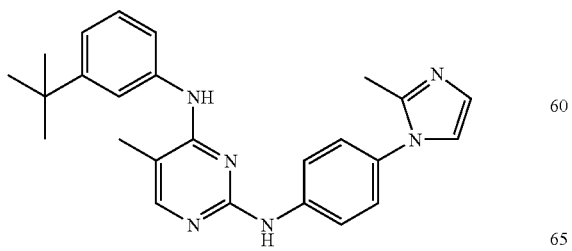

CXXXII

A mixture of intermediate 41 (180 mg, 0.65 mmol) and 4-(2-methyl-1H-imidazol-1-yl)benzenamine (113 mg, 0.65 mmol), Pd₂(dba)₃ (55 mg, 0.06 mmol), Xantphos (104 mg, 0.18 mmol) and cesium carbonate (782 mg, 2.4 mmol) were suspended in dioxane (100 mL) and heated at reflux under the argon atmosphere for 20 h. The mixture was filtered and the filtrate concentrated in vacuo. The residue was purified by HPLC to afford the title compound (78 mg of HCl salt, 27%) as a white solid.

¹H NMR (500 MHz, DMSO-d₆): δ 1.26 (s, 9H), 2.21 (s, 3H), 2.50 (s, 3H), 7.31-7.36 (m, 1H), 7.40 (t, J=7.8 Hz, 1H), 7.44 (d, J=8.9 Hz, 2H), 7.47 (d, J=8.0 Hz, 2H), 7.65 (d, J=8.9 Hz, 2H), 7.75 (d, J=2.1 Hz, 1H), 7.79 (d, J=2.1 Hz, 2H), 8.03 (s, 1H), 10.02 (s, 1H), 11.26 (s, 1H). MS (ES+): m/z 413 (M+H)⁺.

Example 191

4-(4-Methyl-1H-imidazol-1-yl)benzenamine (Intermediate 62)

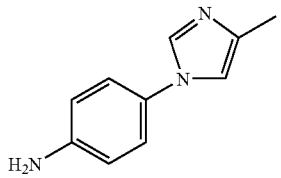

62

To a solution of 1-fluoro-4-nitrobenzene (1.7 g, 12 mmol) in DMF (100 mL) was added 4-methyl-1H-imidazole (0.82 g, 10 mmol) and K₂CO₃ (11 g, 80 mmol). The mixture was heated at reflux under the argon atmosphere for 20 h. The mixture was filtered and the filtrate concentrated in vacuo. The residue was dissolved in EtOAc (100 mL) and washed with brine (100 mL×2). The organic layer was dried and concentrated. The solid was dissolved in MeOH and bubbled with Ar for 2 min. before adding 10% Pd—C. The hydrogenation was finished in 4 h. The catalyst was removed by filtration and solvent was removed in vacuo to afford title compound (1.5 g, 87%) as brown solid.

Example 192

N⁴-(3-tert-Butylphenyl)-5-methyl-N²-(4-(4-methyl-1H-imidazol-1-yl)phenyl)pyrimidine-2,4-diamine (Compound CXXXIII)

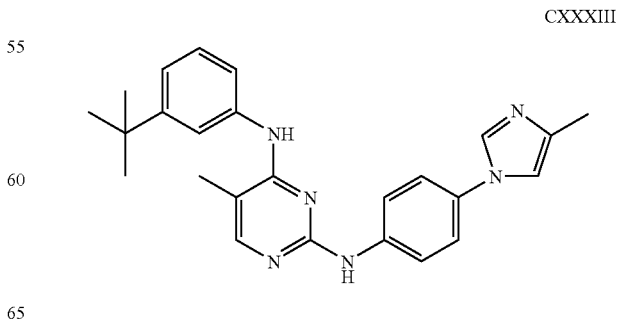

CXXXIII

A mixture of intermediate 41 (318 mg, 1.15 mmol) and intermediate 62 (200 mg, 1.15 mmol), Pd₂(dba)₃ (92 mg, 0.1 mmol), Xantphos (180 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was purified by HPLC to afford the title compound (66 mg of HCl salt, 20%) as a white solid.

$^1$H NMR (500 MHz, DMSO-d$_6$): δ 1.26 (s, 9H), 2.19 (s, 3H), 2.36 (s, 3H), 7.30 (d, J=7.9 Hz, 1H), 7.41 (d, J=7.9 Hz, 1H), 7.44 (t, J=1.8 Hz, 1H), 7.54 (d, J=7.9 Hz, 1H), 7.59 (d, J=9.0 Hz, 2H), 7.68 (d, J=9.0 Hz, 2H), 7.94 (s, 1H), 7.99 (s, 1H), 9.53 (d, J=1.3 Hz, 1H), 9.72 (br s, 1H), 10.81 (br s, 1H). MS (ES+): m/z 413 (M+H)$^+$.

Example 193 tert-Butyl 4-(4-aminophenyl)piperidine-1-carboxylate (Intermediate 63)

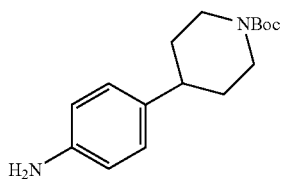

To a solution of 4-(4-nitrophenyl)piperidine (412 mg, 2 mmol) in CH2Cl2 (100 mL) was added di-tert-butyl carbonate (480 mg, 2.2 mmol) and N,N-dimethylpyridin-4-amine (50 mg, 0.4 mmol). The mixture was stirred for 20 h at room temperature. The mixture was added saturated NaHCO3 (100 mL). The organic layer was separated and aqueous was extracted with CH2Cl2 (50 mL×2). The combined organic solution was dried and concentrated in vacuo. The residue was dissolved in MeOH and bubbled with Ar for 2 min. before adding 10% Pd—C. The hydrogenation was finished in 4 h. The catalyst was removed by filtration and solvent was removed in vacuo to afford title compound (460 mg, 83%) as white solid.

Example 194

N$^4$-(3-tert-Butylphenyl)-5-methyl-N$^2$-(4-(piperidin-4-yl)phenyl)pyrimidine-2,4-diamine (Compound CXXXIV)

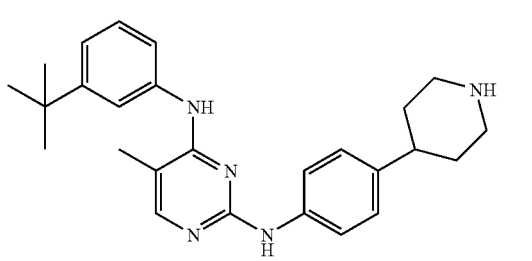

A mixture of intermediate 41 (170 mg, 0.6 mmol) and intermediate 63 (170 mg, 0.6 mmol) were suspended in acetic acid (10 mL) and heated at 100° C. for 4 h. The mixture was allowed to cool to room temperature and acetic acid removed under reduced pressure. The residue was taken in water (20 mL) and neutralized to pH~7. The resulting solution was extracted with EtOAc (30 mL) and the organic layer separated. The organic layer was washed with brine, dried over MgSO$_4$ and filtered. The filtrate was concentrated in vacuo and the crude product purified by HPLC to afford the title compound (8 mg, 3%) as a white solid.

$^1$H NMR (500 MHz, DMSO-d$_6$): δ 1.26 (s, 9H), 1.76-1.88 (m, 4H), 2.17 (s, 3H), 2.76-2.81 (m, 1H), 2.93-3.00 (m, 2H), 3.36-3.40 (m, 2H), 7.07 (d, J=8.5 Hz, 1H), 7.30-7.36 (m, 4H), 7.44 (s, 1H), 7.46 (d, J=8.7 Hz, 1H), 7.91 (s, 1H), 8.84 (br s, 1H), 8.92 (br s, 1H), 9.73 (s, 1H), 10.45 (s, 1H). MS (ES+): m/z 416 (M+H)$^+$.

Example 195

N$^4$-(3-tert-Butylphenyl)-5-methyl-N$^2$-(4-(1-morpholinoethyl)phenyl)pyrimidine-2,4-diamine (Compound CXXXV)

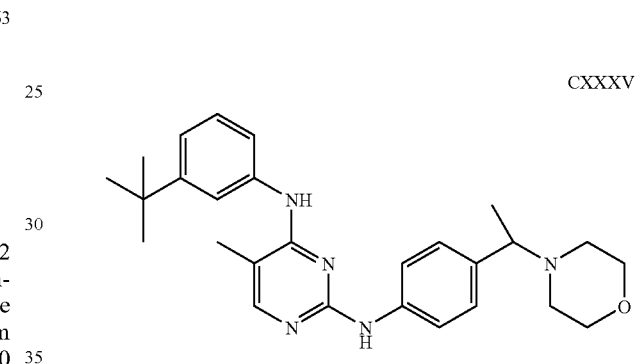

A mixture of intermediate 41 (276 mg, 1.0 mmol) and 4-(1-morpholinoethyl)benzenamine (210 mg, 1.0 mmol), Pd$_2$(dba)$_3$ (92 mg, 0.1 mmol), Xantphos (180 mg, 0.3 mmol) and cesium carbonate (1.3 g, 4 mmol) were suspended in dioxane (100 mL) and heated at reflux under the argon atmosphere for 20 h. The mixture was filtered and the filtrate concentrated in vacuo. The residue was purified by HPLC to afford the title compound (17 mg of HCl salt, 4%) as a yellow solid.

$^1$H NMR (500 MHz, DMSO-d$_6$): δ 1.26 (s, 9H), 1.66 (d, J=6.8 Hz, 3H), 2.19 (s, 3H), 2.79 (br, 2H), 2.92 (br, 1H), 3.61-3.64 (m, 2H), 3.77-3.82 (m, 2H), 3.94-3.99 (m, 2H), 7.32 (d, J=7.8 Hz, 1H), 7.42 (t, J=1.9 Hz, 1H), 7.43 (d, J=7.8 Hz, 1H), 7.46-7.52 (m, 5H), 7.97 (s, 1H), 9.86 (s, 1H), 10.78 (s, 1H), 11.72 (br s, 1H). MS (ES+): m/z 446 (M+H)$^+$.

Example 196

5-Bromo-2-methyl-benzenesulfonyl chloride (Intermediate 64)

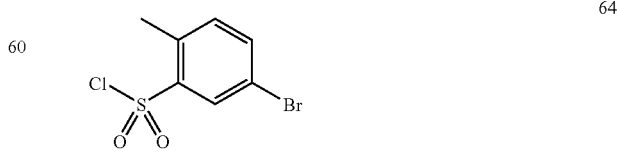

Bromide (1.99 g, 11.61 mmol) was stirred vigorously and treated with chlorosulfonic acid (1.55 mL, 23.22 mmol).

Once addition was complete, resulting red syrup was heated to 60° C. Reaction TLC after 10 min showed no starting material and reaction was quenched by pouring onto ice. Product was extracted by washing with EtOAc (2×150 mL). Organic phase dried over Na$_2$SO$_4$, filtered and evaporated to yellow oil (2.2 g, 70%).

Example 197

5-Bromo-2,N-dimethyl-benzenesulfonamide (Intermediate 65)

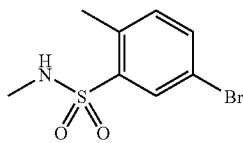

65

A stirring suspension of intermediate 64 (0.43 g, 1.58 mmol) in DCM (5 mL) was treated with 2.0M methylamine solution in THF (2.4 mL, 4.8 mmol). After 16 h reaction solvents were removed and resulting residue diluted with EtOAc (150 mL) and washed with water. Organic phase dried over Na$_2$SO$_4$, filtered and evaporated to white solids (0.37 g, 89%).

Example 198

2,N-Dimethyl-5-{5-methyl-2-[4-(2-pyrrolidin-1-yl-ethoxy)-phenylamino]-pyrimidin-4-ylamino}-benzenesulfonamide (Compound CXXXVI)

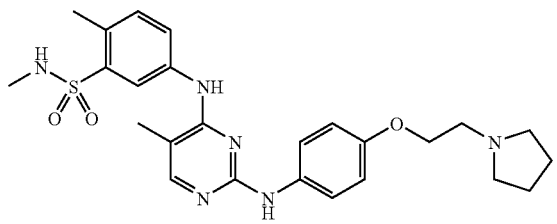

CXXXVI

A mixture of intermediate 65 (0.14 g, 0.52 mmol), intermediate 38 (0.14 g, 0.43 mmol), Pd$_2$(dba)$_3$ (0.040 g, 0.043 mmol), Xantphos (0.050 g, 0.087 mmol) and cesium carbonate (0.43 g, 1.3 mmol) were suspended in dioxane (10 mL), sealed in a microwave reaction tube and irradiated with microwaves at 160° C. for 15 min. The reaction mixture was cooled to room temperature and centrifuged down. The reaction was decanted and the organic phase concentrated in vacuo. The residue was purified by HPLC to afford the title compound as a white solid (0.052 g, 24%).

$^1$H NMR (500 MHz, DMSO-d$_6$): δ 1.66-1.70 (m, 4H), 2.08 (s, 3H), 2.43 (d, J=4.9 Hz, 3H), 2.5 (br s, 4H), 2.78, (t, J=5.7 Hz), 4.00 (t, J=5.9 Hz), 6.79 (d, J=9.0 Hz, 2H), 7.31 (d, J=9.7 Hz, 1H), 7.42 (q, J=9.8 Hz, 1H), 7.49 (d, J=9.0 Hz, 1H), 7.87 (s, 1H), 7.97 (d, J=2.3 Hz, 1H), 8.07-8.09 (m, 1H), 8.49 (s, 1H), 8.75 (s, 1H). MS (ES+): m/z 497 (M+H)$^+$.

Example 199

5-Bromo-N-tert-butyl-2-methyl-benzenesulfonamide (Intermediate 66)

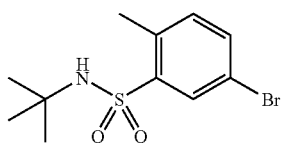

66

A stirring suspension of intermediate 64 (1.22 g, 4.5 mmol) in DCM (25 mL) was treated with tert-butylamine (1.4 mL, 13.6 mmol). After 16 h, reaction solvents were removed and resulting solids triturated with water. Solids were dried under vacuum overnight (1.3 g, 94%).

Example 200

N-tert-Butyl-5-(2-chloro-5-methyl-pyrimidin-4-ylamino)-2-methyl-benzenesulfonamide (Intermediate 67)

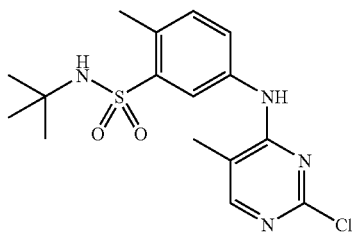

67

A mixture of intermediate 66 (0.90 g, 2.96 mmol), 2-chloro-5-methyl-pyrimidin-4-ylamine (0.33 g, 2.28 mmol), Pd$_2$(dba)$_3$ (0.21 g, 0.23 mmol), Xantphos (0.264 g, 0.46 mmol) and cesium carbonate (2.2 g, 6.8 mmol) were suspended in dioxane (15 mL), sealed in a microwave reaction tube and irradiated with microwaves at 160° C. for 15 min. The reaction mixture was cooled to room temperature and centrifuged down. The reaction was decanted and the organic phase concentrated in vacuo. The residue was purified on silica gel column to afford the title compound as a white solid (0.12 g, 14%).

Example 201

N-tert-Butyl-5-[2-(4-imidazol-1-yl-phenylamino)-5-methyl-pyrimidin-4-ylamino]-2-methyl-benzenesulfonamide (Compound CXXXVII)

CXXXVII

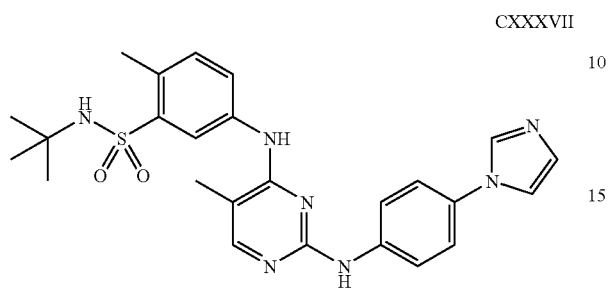

A mixture of intermediate 67 (0.113 g, 0.31 mmol), 4-imidazol-1-yl-phenylamine (0.059 g, 0.37 mmol), Pd$_2$(dba)$_3$ (0.028 g, 0.03 mmol), Xantphos (0.036 g, 0.06 mmol) and cesium carbonate (0.3 g, 0.92 mmol) were suspended in dioxane (6 mL), sealed in a microwave reaction tube and irradiated with microwaves at 160° C. for 15 min. The reaction was decanted and the organic phase concentrated in vacuo. The residue was purified by HPLC to afford the title compound as a white solid (0.052 g, 24%).

$^1$H NMR (500 MHz, DMSO-d$_6$): δ 1.11 (s, 9H), 2.13 (s, 3H), 2.58 (s, 3H), 7.07 (s, 1H), 7.34 (d, J=8.5 Hz, 1H), 7.42 (d, J=8.9 Hz, 2H), 7.48 (s, 1H), 7.60 (s, 1H), 7.78 (d, J=8.9 Hz, 2H), 7.94 (s, 1H), 7.98-8.00 (m, 1H), 8.09 (s, 1H), 8.12 (d, J=2.3 Hz, 1H), 8.56 (s, 1H), 9.16 (s, 1H). MS (ES+): m/z 492 (M+H)$^+$.

Example 202

N-tert-Butyl-3-{5-methyl-2-[4-(Pyrrolidine-1-carbonyl)-phenylamino]-pyrimidin-4-ylamino}-benzenesulfonamide (Compound CXXXVIII)

CXXXVIII

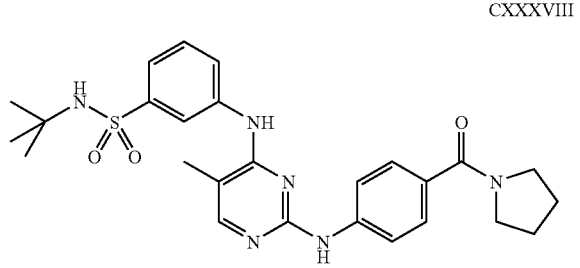

A mixture of intermediate 33 (0.11 g, 0.32 mmol), (4-amino-phenyl)-pyrrolidin-1-yl-methanone (0.072 g, 0.38 mmol), Pd$_2$(dba)$_3$ (0.029 g, 0.032 mmol), Xantphos (0.037 g, 0.063 mmol) and cesium carbonate (0.3 g, 0.95 mmol) were suspended in dioxane (6 mL), sealed in a microwave reaction tube and irradiated with microwaves at 160° C. for 15 min. The reaction was decanted and the organic phase concentrated in vacuo. The residue was purified by HPLC to afford the title compound as a white solid (0.040 g, 25%).

$^1$H NMR (500 MHz, DMSO-d$_6$): δ 1.11 (s, 9H), 1.8 (br s, 4H), 2.14 (s, 3H), 3.44 (t, J=6.6 Hz, 4H), 7.38 (d, J=9.0 Hz, 2H), 7.52-7.54 (m, 2H), 7.56 (s, 1H), 7.70 (d, J=9.8 Hz, 2H), 7.98 (s, 1H), 8.08-8.10 (m, 2H), 8.60 (br s, 1H), 9.24 (s, 1H). MS (ES+): m/z 509 (M+H)$^+$.

Example 203

N-tert-Butyl-3-{5-methyl-2-[4-(morpholine-4-carbonyl)-phenylamino]-pyrimidin-4-ylamino}-benzenesulfonamide (Compound CXXXIX)

CXXXIX

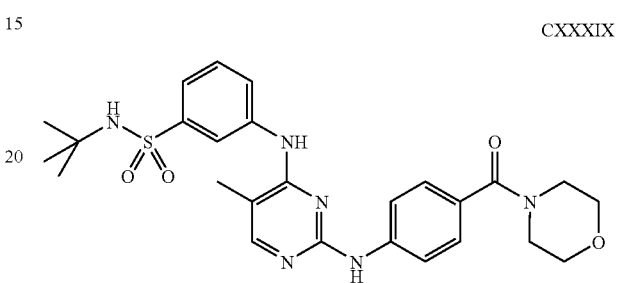

A mixture of intermediate 33 (0.13 g, 0.37 mmol), (4-amino-phenyl)-morpholin-4-yl-methanone (0.092 g, 0.45 mmol), Pd$_2$(dba)$_3$ (0.034 g, 0.037 mmol), Xantphos (0.043 g, 0.075 mmol) and cesium carbonate (0.37 g, 1.1 mmol) were suspended in dioxane (6 mL), sealed in a microwave reaction tube and irradiated with microwaves at 160° C. for 15 min. The reaction was decanted and the organic phase concentrated in vacuo. The residue was purified by HPLC to afford the title compound as a white solid (0.065 g, 33%).

$^1$H NMR (500 MHz, DMSO-d$_6$): δ 1.11 (s, 9H), 2.14 (s, 3H), 3.49 (br s, 4H), 3.59 (br s, 4H), 5.75 (s, 1H), 7.25 (d, J=9.0 Hz, 2H), 7.52-7.54 (m, 2H), 7.56 (s, 1H), 7.71 (d, J=9.0 Hz, 2H), 7.98 (s, 1H), 8.06-8.08 (m, 2H), 8.65 (br s, 1H), 9.26 (s, 1H). MS (ES+): m/z 525 (M+H)$^+$.

Example 204

N-tert-Butyl-3-{5-methyl-2-[4-(piperazine-1-carbonyl)-phenylamino]-pyrimidin-4-ylamino}-benzenesulfonamide (Compound CXL)

CXL

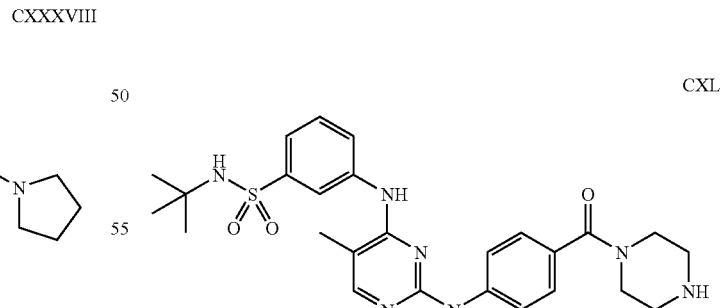

A mixture of intermediate 33 (0.12 g, 0.33 mmol), 4-(4-amino-benzoyl)-piperazine-1-carboxylic acid tert-butyl ester (0.12 g, 0.45 mmol), Pd$_2$(dba)$_3$ (0.030 g, 0.037 mmol), Xantphos (0.038 g, 0.075 mmol) and cesium carbonate (0.33 g, 1.1 mmol) were suspended in dioxane (6 mL), sealed in a microwave reaction tube and irradiated with microwaves at 160° C. for 15 min. The reaction was decanted and the organic phase concentrated in vacuo. The residue was purified by silica gel chromatography (25%-100% EtOAc in Hexanes). Product was then treated with 20 mL of 20% TFA solution in DCM. Solvents then removed by rotary evaporation. Resulting material purified by HPLC to afford the title compound as a white solid (0.045 g, 26%).

$^1$H NMR (500 MHz, DMSO-$d_6$): δ 1.11 (s, 9H), 2.14 (s, 3H), 2.82 (br s, 4H), 3.48 (br s, 4H), 7.24 (d, J=9.0 Hz, 2H), 7.51-7.53 (m, 2H), 7.55 (s, 1H), 7.71 (d, J=9.0 Hz, 2H), 7.94 (s, 1H), 8.06-8.08 (m, 2H), 8.65 (br s, 1H), 9.25 (s, 1H). MS (ES+): m/z 524 (M+H)$^+$.

Example 205 tert-Butyl 4-(4-(4-(3-methoxyphenylamino)-5-methylpyrimidin-2-ylamino)phenoxy)piperidine-1-carboxylate (Intermediate 68)

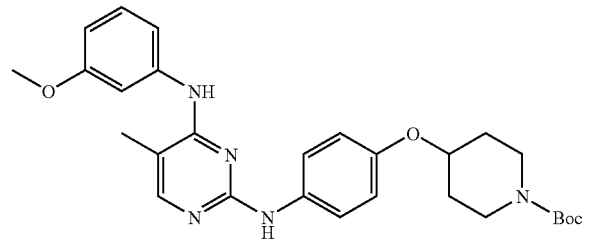

A mixture of 1-bromo-3-methoxybenzene (69.5 μL, 0.56 mmol), intermediate 42 (205 mg, 0.51 mmol), Pd$_2$(dba)$_3$ (23 mg, 0.03 mmol), Xantphos (33 mg, 0.06 mmol) and cesium carbonate (359 mg, 1.10 mmol) in dioxane (3 mL) was irradiated in the microwave at 160° C. for 20 min. The reaction mixture was cooled to room temperature, filtered and the filtrate rinsed with DCM and MeOH. The combined liquids were concentrated in vacuo, and purified using gradient flash chromatography (0-100% ethyl acetate in hexanes) to afford the title compound as a beige solid (215 mg, 83%).

Example 206

3-(2-(4-(Piperidin-4-yloxy)phenylamino)-5-methylpyrimidin-4-ylamino)phenol (Compound CXLI)

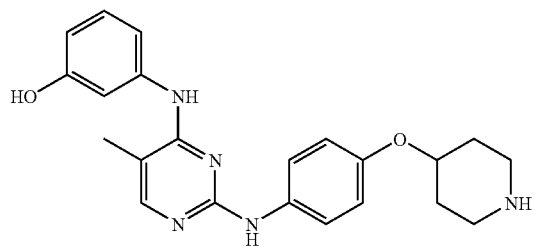

To a mixture of intermediate 68 (215 mg, 0.42 mmol) in DCM (4 mL) was added BBr$_3$ (120 μL, 1.27 mmol) and stirred at room temperature for 64 h. The reaction was quenched with MeOH and concentrated in vacuo. The residue was purified by preparative HPLC and the fractions concentrated in vacuo to afford the TFA salt of the title compound (116 mg, 56%). The TFA salt was taken up in MeOH and passed through SPE PL-HCO$_3$ MP-Resin cartridges, concentrated in vacuo, triturated with ether, and filtered to provide the title compound as a white solid (31 mg, 69% recovery).

$^1$H NMR (500 MHz, DMSO-$d_6$): δ 1.51-1.60 (m, 2H), 1.90-1.98 (m, 2H), 2.07 (s, 3H), 2.70-2.78 (m, 2H), 3.02-3.09 (m, 2H), 4.28-4.36 (m, 1H), 6.48 (dd, J=8.1, 2.2 Hz, 1H), 6.79 (d, J=9.1 Hz, 2H), 7.06-7.11 (m, 2H), 7.16 (d, J=8.5 Hz, 1H), 7.57 (d, J=9.1 Hz, 2H), 7.82 (s, 1H), 8.08 (s, 1H), 8.73 (s, 1H), 9.27 (br s, 1H). MS (ES+): m/z 392 (M+H)$^+$.

Example 207

(2-Chloro-5-methyl-pyrimidin-4-yl)-(4-fluoro-3-methoxy-phenyl)-amine (Intermediate 69)

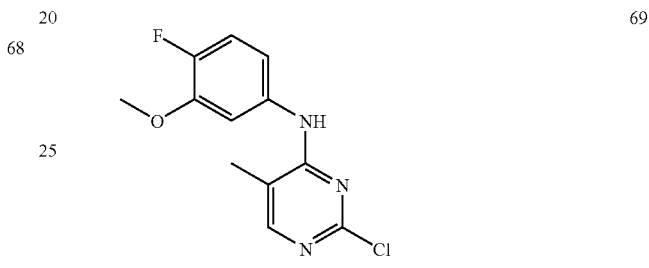

A mixture of 2-chloro-5-methyl-pyrimidin-4-ylamine (1.2 g, 8.1 mmol), 4-bromo-1-fluoro-2-methoxy-benzene (1.8 g, 8.9 mmol), Pd$_2$(dba)$_3$ (0.74 g, 0.81 mmol), Xantphos (0.93 g, 1.6 mmol) and cesium carbonate (7.88 g, 24.2 mmol) were suspended in dioxane (60 mL) and heated at reflux under the argon atmosphere for 5 h. The reaction mixture was cooled to room temperature and diluted with DCM (30 mL). The mixture was filtered and the filtrate concentrated in vacuo. The residue was purified by flash chromatography on silica gel to afford the title compound (0.3 g, 14%) as a beige solid.

Example 208

N$^4$-(4-Fluoro-3-methoxy-phenyl)-5-methyl-N$^2$-[4-(2-pyrrolidin-1-yl-ethoxy)-phenyl]-pyrimidine-2,4-diamine (Compound CXLII)

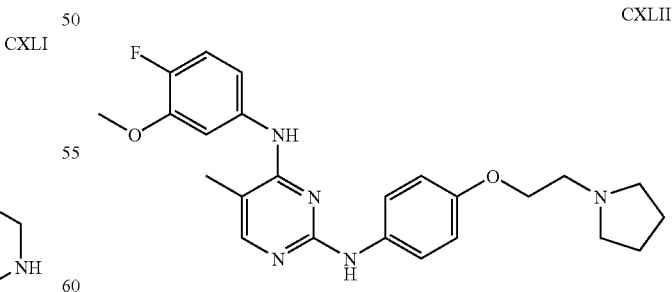

A mixture of intermediate 69 (0.1 g, 0.37 mmol) and 4-(2-pyrrolidin-1-yl-ethoxy)-phenylamine (0.16 g, 0.75 mmol) were suspended in acetic acid (10 mL) and heated to 110° C. for 16 h. The reaction mixture was cooled to room temperature and concentrated in vacuo. The residue was purified by HPLC to afford the title compound (0.03 g, 17%) as green solids. ¹H NMR (500 MHz, DMSO-d₆): δ 1.88 (br s, 2H), 2.0 (br s, 2H), 2.15 (s, 3H), 3.08 (br s, 2H), 3.55 (br s, 4H), 3.7 (s, 3H), 4.32 (br s, 2H), 6.9 (d, J=7.9 Hz, 2H), 7.13 (br s, 1H), 7.21-7.25 (m, 1H), 7.32-7.34 (m, 3H), 7.89 (s, 1H), 9.78 (br s, 1H), 10.48 (br s, 1H), 10.92 (br s, 1H). MS (ES+): m/z 438 (M+H)⁺.

Example 209

(2-Chloro-pyrimidin-4-yl)-(3-methoxy-2-methyl-phenyl)-amine (Intermediate 70)

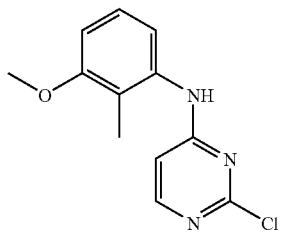

70

A mixture of 3-methoxy-2-methyl-phenylamine (0.68 g, 5 mmol) and 2,4-dichloro-pyrimidine (0.74 g, 5 mmol) were suspended in ethyl alcohol (10 mL) and stirred at room temperature for 20 h. The reaction mixture was diluted with DCM (50 mL), filtered and concentrated in vacuo. The residue was purified by silica gel column chromatography to afford the title compound (0.085 g, 7%) as yellow solids.

Example 210

N⁴-(3-Methoxy-2-methyl-phenyl)-N²-[4-(2-pyrrolidin-1-yl-ethoxy)-phenyl]-pyrimidine-2,4-diamine (Compound CXLIII)

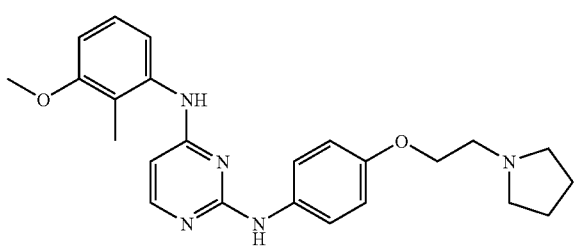

CXLIII

A mixture of intermediate 70 (0.08 g, 0.32 mmol) and 4-(2-pyrrolidin-1-yl-ethoxy)-phenylamine (0.13 g, 0.64 mmol) were suspended in acetic acid (10 mL) and heated to 80° C. for 16 h. The reaction mixture was cooled to room temperature and concentrated in vacuo. The residue was purified by HPLC to afford the title compound (0.03 g, 17%) as grey solids.

¹H NMR (500 MHz, DMSO-d₆): δ 1.89 (br s, 2H), 2.0 (br s, 4H), 3.08 (br s, 2H), 3.4 (br s, 4H), 3.54 (br s, 4H), 3.83 (s, 3H), 4.31 (br s, 2H), 6.86 (br s, 2H), 6.97 (d, J=8.1 Hz, 2H), 7.26 (t, J=8.1 Hz 1H), 7.34 (br s, 2H), 7.89 (s, 1H), 9.73 (br s, 1H), 10.62 (br s, 2H), 11.01 (br s, 1H). MS (ES+): m/z 420 (M+H)⁺.

Example 211

4-(4-Acetylamino-benzenesulfonyl)-piperidine-1-carboxylic acid tert-butyl ester (Intermediate 71)

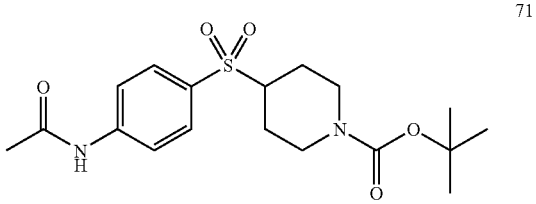

71

A mixture of 4-(4-bromo-benzenesulfonyl)-piperidine-1-carboxylic acid tert-butyl ester (4 g, 9.92 mmol), acetamide (0.88 g, 14.9 mmol), Pd₂(dba)₃ (0.46 g, 0.49 mmol), Xantphos (0.56 g, 0.99 mmol) and cesium carbonate (9.7 g, 29.8 mmol) were suspended in dioxane (60 mL) and heated at reflux under the argon atmosphere for 4 h. The reaction mixture was cooled to room temperature and poured onto ice. Resulting yellow solids collected by filtration and dried. Crude product was purified by flash chromatography on silica gel to afford the title compound as a beige solid (3.12 g, 82%).

Example 212

4-(4-Amino-benzenesulfonyl)-piperidine-1-carboxylic acid tert-butyl ester (Intermediate 72)

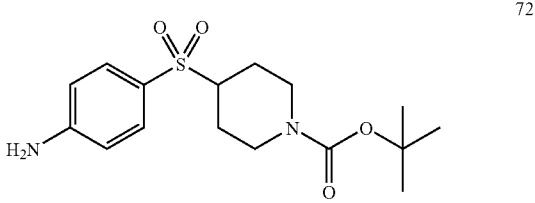

72

A suspension of intermediate 71 (2.6 g, 6.7 mmol) was diluted with 60 mL of Claisen's alkali (88 g KOH dissolved in 63 mL H₂O diluted up to 250 mL with MeOH) and heated to 90° C. After 2 h, reaction was removed from heating, cooled to room temperature and diluted with water (50 mL). Grey solids collected by suction filtration, washed with water and dried overnight (2.2 g, 97%).

Example 213

N[4]-(4-Chloro-3-methoxy-phenyl)-5-methyl-N[2]-[4-(Piperidine-4-sulfonyl)-phenyl]-pyrimidine-2,4-diamine (Compound CXLIV)

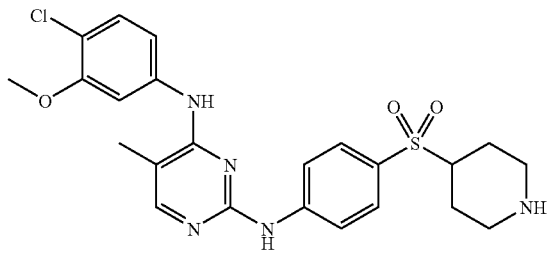

CXLIV

A mixture of intermediate 31 (0.14 g, 0.51 mmol), intermediate 72 (0.19 g, 0.56 mmol), Pd$_2$(dba)$_3$ (0.046 g, 0.051 mmol), Xantphos (0.59 g, 0.1 mmol) and cesium carbonate (0.5 g, 1.52 mmol) were suspended in dioxane (8 mL) and microwaved at 160° C. for 15 min. The reaction mixture was cooled to room temperature and centrifuged down. Solvents were then decanted and evaporated. Resulting residue was purified by flash chromatography on silica gel to afford the N-protected precursor of title compound. These solids were treated with 20% TFA in DCM solution and immediately evaporated. Residue was dissolved in minimum amount to EtOAc and added dropwise to large excess of diethyl ether. Resulting light yellow powder was collected by filtration and dried (0.16 g, 55%).

$^1$H NMR (500 MHz, DMSO-d$_6$): δ 1.61-1.69 (m, 2H), 1.98-2.01 (m, 2H), 2.16 (s, 3H), 2.86 (q, J=12 Hz, 2H), 3.35 (d, J=12.6 Hz, 2H), 3.64 (tt, J=11.7 Hz, J=3.8 Hz, 1H), 3.79 (s, 3H), 7.34 (dd, J=8.7 Hz, J=2.0 Hz, 1H), 7.39-7.41 (m, 2H), 7.6 (d, J=8.9 Hz, 2H), 7.91 (d, J=8.9 Hz, 2H), 8.02 (s, 1H), 8.19-8.21 (m, 1H), 8.6-8.63 (m, 1H), 8.89 (br s, 1H). MS (ES+): m/z 488 (M+H)$^+$.

Example 214

(4-Chloro-3-methyl-phenyl)-(2-chloro-5-methyl-pyrimidin-4-yl)-amine (Intermediate 73)

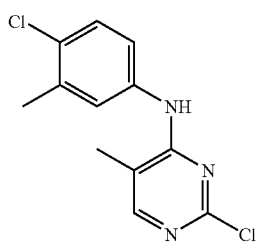

73

A mixture of 2-chloro-5-methyl-pyrimidin-4-ylamine (0.34 g, 2.34 mmol), 4-bromo-1-chloro-2-methyl-benzene (0.58 g, 2.8 mmol), Pd$_2$(dba)$_3$ (0.21 g, 0.23 mmol), Xantphos (0.47 g, 0.47 mmol) and cesium carbonate (2.3 g, 7 mmol) were suspended in dioxane (9 mL) microwaved at 160° C. for 20 min. The reaction mixture was cooled to room temperature and centrifuged down. Solvents were then decanted and evaporated. Resulting residue was purified by flash chromatography on silica gel to afford title compound as yellow solids (0.24 g, 38%).

Example 215

N[4]-(4-Chloro-3-methyl-phenyl)-5-methyl-N[2]-[4-(piperidin-4-yloxy)-phenyl]-pyrimidine-2,4-diamine (Compound CXLV)

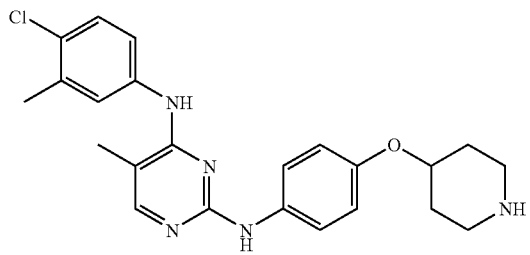

CXLV

A mixture of intermediate 73 (0.071 g, 0.27 mmol) and 4-(4-amino-phenoxy)-piperidine-1-carboxylic acid tert-butyl ester (0.1 g, 0.35 mmol) were diluted with HOAc (5 mL) and microwaved at 150° C. for 15 min. Solvents then removed and resulting residue purified on HPLC. Title compound isolated as white solids (0.025 g, 22%).

$^1$H NMR (500 MHz, DMSO-d$_6$): δ 1.76-1.83 (m, 2H), 2.05-2.09 (m, 2H), 2.13 (s, 3H), 2.27 (s, 3H), 3.10 (br s, 2H), 3.16 (br s, 2H), 4.58-4.61 (m, 1H), 6.93 (d, J=9 Hz, 2H), 7.34-7.39 (m, 3H), 7.43-7.45 (m, 1H), 7.59 (s, 1H), 7.87 (s, 1H), 8.51 (br s, 1H), 8.55 (br s, 1H), 9.38 (br s, 1H), 10.0 (br s, 1H). MS (ES+): m/z 424 (M+H)$^+$.

Example 216

N-(3-Bromo-phenyl)-acetamide (Intermediate 74)

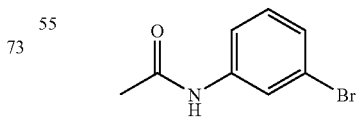

74

A solution of 3-bromo-phenylamine (1.04 g, 6 mmol) was treated with DIEA (2.3 mL, 13.3 mmol) and chilled to zero degrees. Acetyl chloride (0.47 mL, 6.7 mmol) was added dropwise via syringe. Reaction was allowed to return to room temperature and stir for 1 hour. Reaction was then poured onto water and washed once. Organic phase was evaporated to beige solids (1.25 g, 98%).

Example 217

N-[3-(2-Chloro-5-methyl-pyrimidin-4-ylamino)-phenyl]-acetamide (Intermediate 75)

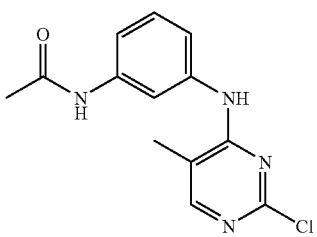

75

A mixture of 2-chloro-5-methyl-pyrimidin-4-ylamine (0.71 g, 4.9 mmol), intermediate 74 (1.25 g, 5.9 mmol), Pd$_2$(dba)$_3$ (0.45 g, 0.49 mmol), Xantphos (0.57 g, 0.98 mmol) and cesium carbonate (4.8 g, 14.7 mmol) were suspended in dioxane (40 mL) refluxed for 18 h. The reaction mixture was then cooled to room temperature, filtered and solvents evaporated. Resulting residue was purified by flash chromatography on silica gel to afford title compound as white solids (0.44, 32%).

Example 218

N-(3-{5-Methyl-2-[4-(piperidin-4-yloxy)-phenylamino]-pyrimidin-4-ylamino}-phenyl)-acetamide (Compound CXLVI)

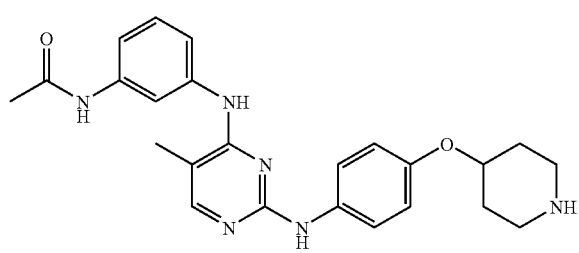

CXLVI

A mixture of intermediate 75 (0.074 g, 0.27 mmol) and 4-(4-amino-phenoxy)-piperidine-1-carboxylic acid tert-butyl ester (0.1 g, 0.35 mmol) were diluted with HOAc (5 mL) and microwaved at 150° C. for 15 min. Solvents then removed and resulting residue purified on HPLC. Title compound isolated as white solids (0.072 g, 62%).

$^1$H NMR (500 MHz, DMSO-d$_6$): δ 1.74-1.81 (m, 2H), 2.03-2.07 (m, 5H), 2.15 (s, 3H), 3.09 (br s, 2H), 3.24 (br s, 2H), 4.54-4.57 (m, 1H), 6.85 (d, J=8.8 Hz, 2H), 7.22 (d, J=7.7 Hz, 2H), 7.29-7.39 (m, 4H), 7.77 (s, 1H), 7.87 (s, 1H), 8.55 (br s, 1H), 8.60 (br s, 1H), 9.67 (s, 1H), 10.0 (br s, 1H), 10.2 (br s, 1H). MS (ES+): m/z 433 (M+H)$^+$.

Example 219

N-(3-Bromo-2-methyl-phenyl)-acetamide (Intermediate 76)

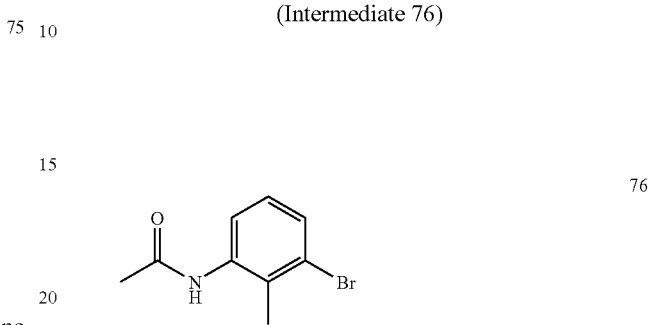

76

A solution of 3-bromo-2-methyl-phenylamine (4.1 g, 21.9 mmol) was treated with DIEA (8.4 mL, 48 mmol) and chilled to zero degrees. Acetyl chloride (1.7 mL, 24.1 mmol) was added dropwise via syringe. Reaction was allowed to return to room temperature and stir for 1 hour. Reaction was then poured onto water and washed once. Organic phase was evaporated to off-white solids. Trituration with hexanes afforded title compound as white solids (4.4 g, 89%).

Example 220

N-[3-(2-Chloro-5-methyl-pyrimidin-4-ylamino)-2-methyl-phenyl]-acetamide (Intermediate 77)

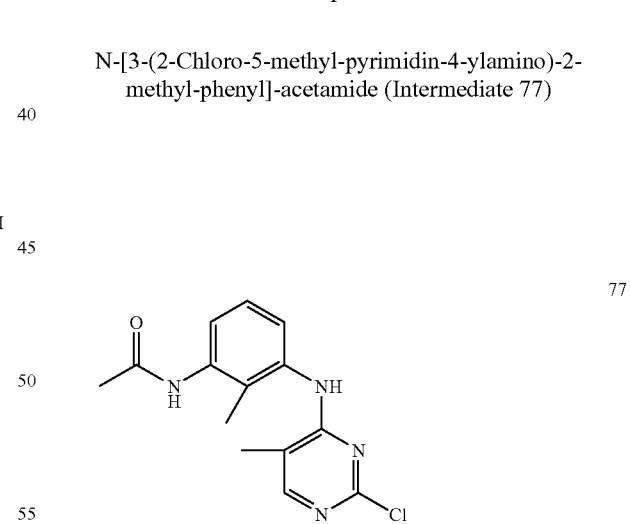

77

A mixture of 2-chloro-5-methyl-pyrimidin-4-ylamine (0.86 g, 5.9 mmol), intermediate 76 (1.6 g, 7.1 mmol), Pd$_2$(dba)$_3$ (0.55 g, 0.59 mmol), Xantphos (0.69 g, 1.2 mmol) and cesium carbonate (5.8 g, 17.8 mmol) were suspended in dioxane (40 mL) refluxed for 16 h. The reaction mixture was then cooled to room temperature, filtered and solvents evaporated. Resulting residue was purified by flash chromatography on silica gel to afford title compound as white solids (0.56 g, 32%).

Example 221

N-(2-Methyl-3-{5-methyl-2-[4-(Piperidin-4-yloxy)-phenylamino]-pyrimidin-4-ylamino}-phenyl)-acetamide (Compound CXLVII)

CXLVII

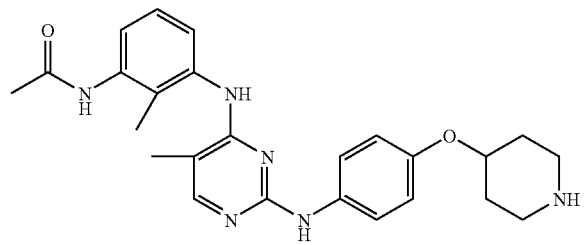

A mixture of intermediate 77 (0.15 g, 0.5 mmol) and 4-(4-Amino-phenoxy)-piperidine-1-carboxylic acid tert-butyl ester (0.19 g, 0.65 mmol) were diluted with HOAc (5 mL) and microwaved at 150° C. for 15 min. Solvents then removed and resulting residue purified on HPLC. Title compound isolated as white solids (0.091 g, 41%).

$^1$H NMR (500 MHz, DMSO-d$_6$): δ 1.71-1.78 (m, 2H), 2.02-2.08 (m, 8H), 2.16 (s, 3H), 3.09 (br s, 2H), 3.24 (br s, 2H), 4.50-4.52 (m, 1H), 6.77 (d, J=8.4 Hz, 2H), 7.09-7.15 (m, 3H), 7.27 (t, J=7.9 Hz, 1H), 7.49 (d, J=8.1 Hz, 1H), 7.86 (s, 1H), 8.54 (br s, 1H), 8.59 (br s, 1H), 9.45 (s, 1H), 9.84 (br s, 1H), 10.34 (br s, 1H). MS (ES+): m/z 447 (M+H)$^+$.

Example 222

5-Methyl-N$^2$-[4-(4-methyl-piperazin-1-yl)-phenyl]-N$^4$-(3-nitro-phenyl)-pyrimidine-2,4-diamine (Intermediate 78)

78

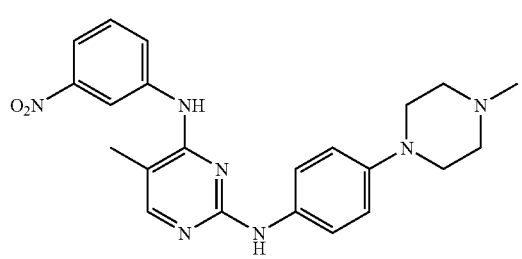

A mixture of 1-bromo-3-nitro-benzene (0.77 g, 3.8 mmol), intermediate 32 (0.95 g, 3.2 mmol), Pd$_2$(dba)$_3$ (0.29 g, 0.32 mmol), Xantphos (0.37 g, 0.64 mmol) and cesium carbonate (3.1 g, 9.6 mmol) were suspended in dioxane (40 mL) refluxed for 16 h. The reaction mixture was then cooled to room temperature, filtered and solvents evaporated. Resulting residue was purified by flash chromatography on silica gel to afford title compound as white solids (0.53 g, 40%).

Example 223

N$^4$-(3-Amino-phenyl)-5-methyl-N$^2$-[4-(4-methyl-piperazin-1-yl)-phenyl]-pyrimidine-2,4-diamine (Intermediate 79)

79

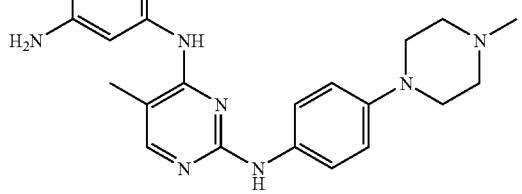

Slurry of intermediate 78 (0.23 g, 0.54 mmol) in MeOH (25 mL) was purged with argon and treated with Pd/C 10% wt. (0.18 g). Reaction atmosphere was replaced with hydrogen and stirred for 4 h. Hydrogen balloon was then removed and argon was flushed through reaction before filtration through Celite. Solvents were then evaporated to pale brown solids (0.17 g, 83%).

Example 224

1-(3-{5-Methyl-2-[4-(4-methyl-piperazin-1-yl)-phenylamino]-pyrimidin-4-ylamino}-phenyl)-3-phenyl-urea (Compound CXLVIII)

CXLVIII

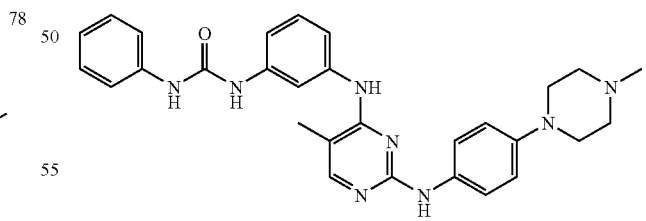

A suspension of intermediate 79 (0.17 g, 0.45 mmol) in DCM (10 mL) was treated with phenyl isocyanate (0.058 mL, 0.54 mmol) and stirred for 1 hour. Reaction solvents then removed and resulting residue purified by HPLC to provide title compound as white solids (0.075 g, 33%).

$^1$H NMR (500 MHz, DMSO-d$_6$): δ 2.09 (s, 3H), 2.15 (s, 3H), 2.30-2.32 (m, 4H), 2.92-2.94 (m, 4H), 6.74 (d, J=8.4 Hz, 2H), 6.94-6.97 (m, 1H), 7.19-7.28 (m, 5H), 7.45 (d, J=8.8 Hz,

2H), 7.53 (d, J=9.0 Hz, 2H), 7.73 (br s, 1H), 7.83 (s, 1H), 8.23 (s, 1H), 8.68 (s, 1H), 8.74 (s, 1H), 8.78 (s, 1H). MS (ES+): m/z 509 (M+H)⁺.

Example 225

1-(3-{5-Methyl-2-[4-(4-methyl-piperazin-1-yl)-phenylamino]-pyrimidin-4-ylamino}-phenyl)-3-(3-trifluoromethyl-phenyl)-urea (Compound CXLIX)

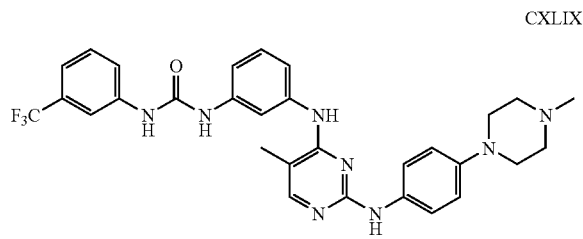

CXLIX

A suspension of intermediate 79 (0.1 g, 0.26 mmol) in DCM (8 mL) was treated with 1-isocyanato-3-trifluoromethyl-benzene (0.043 mL, 0.31 mmol) and stirred for 1 hour. Reaction solvents then removed and resulting residue purified by HPLC to provide title compound as white solids (0.039 g, 26%).

¹H NMR (500 MHz, DMSO-d₆): δ 2.16 (s, 3H), 2.82 (s, 3H), 2.86 (br s, 2H), 3.08 (br s, 2H), 3.42 (br s, 2H), 3.69 (br s, 2H), 6.88 (d, J=8.4 Hz, 2H), 7.20 (br s, 1H), 7.29-7.33 (m, 5H), 7.52 (t, J=7.9 Hz, 1H), 7.57 (d, J=8.5 Hz, 1H), 7.77 (s, 1H), 7.84 (s, 1H), 8.09 (s, 1H), 9.42 (s, 1H), 9.66 (s, 1H), 9.71 (br s, 1H), 10.1 (br s, 1H). MS (ES+): m/z 577 (M+H)⁺.

Example 226

(2-Chloro-5-methyl-pyrimidin-4-yl)-(2-methyl-3-trifluoromethyl-phenyl)-amine (Intermediate 80)

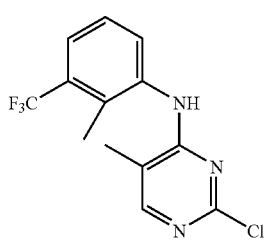

80

A mixture of 2-chloro-5-methyl-pyrimidin-4-ylamine (0.18 g, 5.9 mmol), 1-bromo-2-methyl-3-trifluoromethyl-benzene (0.33 g, 1.4 mmol), Pd₂(dba)₃ (0.12 g, 0.13 mmol), Xantphos (0.15 g, 0.25 mmol) and cesium carbonate (1.23 g, 3.8 mmol) were suspended in dioxane (8 mL) microwaved at 160° C. for 18 min. Reaction vessel was then centrifuged down and decanted. Solvents then evaporated and resulting residue was purified by flash chromatography on silica gel to afford title compound as white solids (0.095 g, 25%).

Example 227

5-Methyl-N⁴-(2-methyl-3-trifluoromethyl-phenyl)-N²-[4-(piperidin-4-yloxy)-phenyl]-pyrimidine-2,4-diamine (Compound CL)

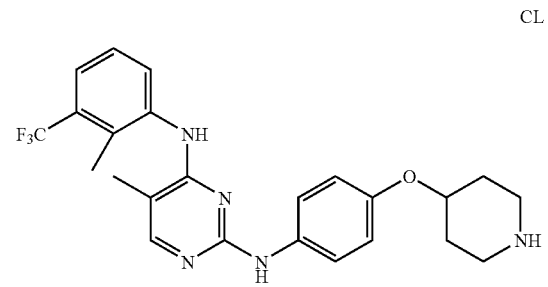

CL

A mixture of intermediate 80 (0.058 g, 0.2 mmol) and 4-(4-amino-phenoxy)-piperidine-1-carboxylic acid tert-butyl ester (0.073 g, 0.25 mmol) were diluted with HOAc (5 mL) and microwaved at 150° C. for 15 min. Solvents then removed and resulting residue purified on HPLC. Title compound isolated as white solids (0.025 g, 30%).

¹H NMR (500 MHz, DMSO-d₆): δ 1.71-1.78 (m, 2H), 2.00-2.04 (m, 2H), 2.18 (s, 3H), 2.25 (s, 3H), 3.08 (br s, 2H), 3.22 (br s, 2H), 4.50-4.52 (m, 1H), 6.70 (d, J=8.3 Hz, 2H), 7.10 (d, J=8.9 Hz, 2H), 7.54 (t, J=7.8, 1H), 7.62 (d, J=7.7 Hz, 1H), 7.75 (d, J=7.8 Hz, 1H), 7.91 (s, 1H), 8.54 (br s, 1H), 8.61 (br s, 1H), 9.88 (s, 1H), 10.34 (br s, 1H). MS (ES+): m/z 458 (M+H)⁺.

Example 228

(3-Bromo-phenyl)-pyrrolidin-1-yl-methanone (Intermediate 81)

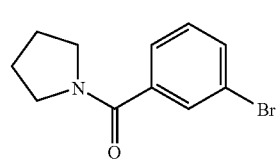

81

A solution of 3-bromo-benzoyl chloride (2.7 g, 12 mmol) in DCM (40 mL) was chilled to zero degrees and treated with pyrrolidine (3 mL, 36.8 mmol). Reaction was allowed to come to room temperature and stir for 4 h. Mixture was then poured onto water and washed once. Organic phase then washed with brine, dried over sodium sulfate, filtered and evaporated to amber oil (3.1 g, 100%).

Example 229

[3-(2-Chloro-5-methyl-pyrimidin-4-ylamino)-phenyl]-pyrrolidin-1-yl-methanone (Intermediate 82)

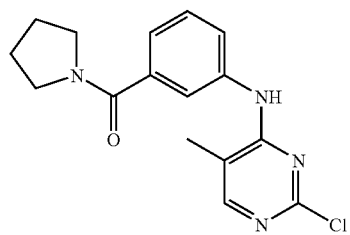

A mixture of 2-chloro-5-methyl-pyrimidin-4-ylamine (0.22 g, 1.5 mmol), intermediate 81 (0.46 g, 1.8 mmol), Pd$_2$(dba)$_3$ (0.14 g, 0.15 mmol), Xantphos (0.17 g, 0.3 mmol) and cesium carbonate (1.5 g, 4.5 mmol) were suspended in dioxane (8 mL) microwaved at 160° C. for 18 min. Reaction vessel was then centrifuged down and decanted. Solvents then evaporated and resulting residue was purified by flash chromatography on silica gel to afford title compound as white solids (0.25 g, 53%).

Example 230

(3-{5-Methyl-2-[4-(piperidin-4-yloxy)-phenylamino]-pyrimidin-4-ylamino}-phenyl)-pyrrolidin-1-yl-methanone (Compound CLI)

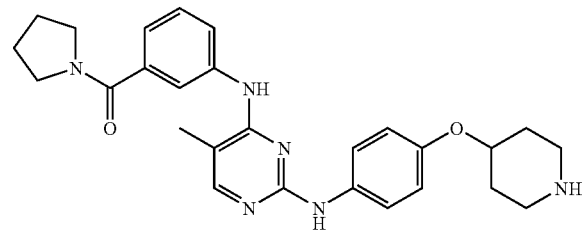

A mixture of intermediate 82 (0.1 g, 0.32 mmol) and 4-(4-amino-phenoxy)-piperidine-1-carboxylic acid tert-butyl ester (0.12 g, 0.41 mmol) were diluted with HOAc (6 mL) and microwaved at 150° C. for 15 min. Solvents then removed and resulting residue purified on HPLC. Title compound isolated as white solids (0.005 g, 3%).

$^1$H NMR (500 MHz, DMSO-d$_6$): δ 1.74-1.81 (m, 4H), 1.83-1.88 (m, 2H), 2.05-2.09(m, 2H), 2.16 (s, 3H), 2.25 (s, 3H), 3.25 (br s, 2H), 3.34 (t, J=6.5 Hz, 2H), 3.46 (t, J=6.9 Hz, 2H), 4.45-4.59 (m, 1H), 6.91 (d, J=8.8 Hz, 2H), 7.32 (d, J=8.9 Hz, 2H), 7.36 (d, J=7.7 Hz, 1H), 7.43 (t, J=7.8, 1H), 7.67 (d, J=7.9 Hz, 1H), 7.70 (s, 1H), 7.89 (s, 1H), 8.50 (br s, 1H), 8.56 (br s, 1H), 9.64 (br s, 1H), 10.21 (br s, 1H). MS (ES+): m/z 473 (M+H)$^+$.

Example 231

3-Bromo-N-isopropyl-benzamide (Intermediate 83)

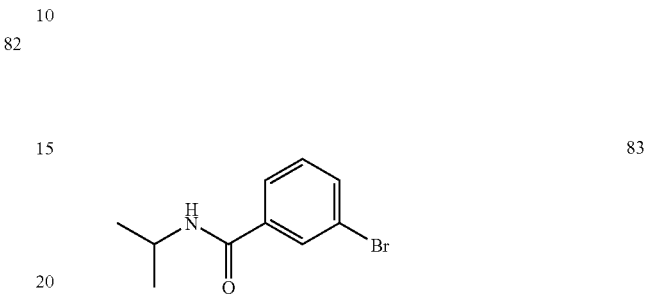

A solution of 3-bromo-benzoyl chloride (0.83 g, 3.8 mmol) in DCM (40 mL) was chilled to zero degrees and treated with isopropylamine (0.96 mL, 11.32 mmol). Reaction was allowed to come to room temperature and stir for 24 h. Mixture was then poured onto water and washed once. Organic phase then washed with brine, dried over sodium sulfate, filtered and evaporated to white solids (0.6 g, 66%).

Example 232

N-Isopropyl-3-{5-methyl-2-[4-(4-methyl-piperazin-1-yl)-phenylamino]-pyrimidin-4-ylamino}-benzamide (Compound CLII)

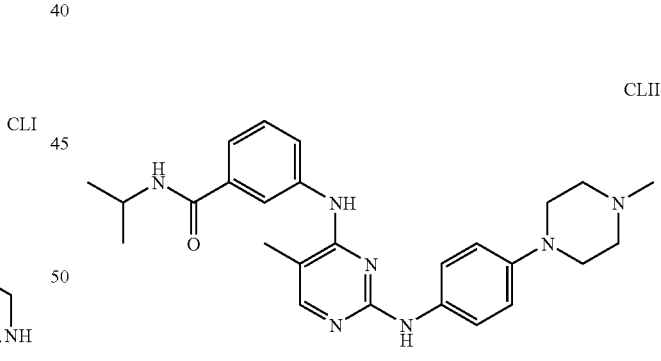

A mixture of intermediate 32 (0.1 g, 0.34 mmol), intermediate 83 (0.13 g, 0.54 mmol), Pd$_2$(dba)$_3$ (0.031 g, 0.034 mmol), Xantphos (0.039 g, 0.067 mmol) and cesium carbonate (0.33 g, 1 mmol) were suspended in dioxane (8 mL) microwaved at 160° C. for 15 min. Reaction vessel was then centrifuged down and decanted. Solvents then evaporated and resulting residue was purified by HPLC to afford title compound as white solids (0.011 g, 7%).

$^1$H NMR (500 MHz, DMSO-d$_6$): δ 1.14 (d, J=6.7 Hz, 6H), 2.16 (s, 4H), 2.87 (s, 4H), 3.10 (br s, 2H), 3.51 (s, 2H), 4.22 (m, 1H), 6.85 (d, J=8.8 Hz, 2H), 7.30-7.32 (m, 2H), 7.45 (t, J=7.8 Hz, 1H), 7.69-7.70 (m, 2H), 7.90 (s, 1H), 7.99 (s, 1H), 8.24 (d, J=7.7 Hz, 1H), 9.70 (br s, 1H), 9.94 (br s, 1H), 10.2 (br s, 1H). MS (ES+): m/z 460 (M+H)+.

Example 233

3-Bromo-N-tert-butyl-benzamide (Intermediate 84)

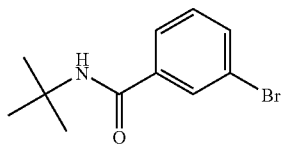

A solution of 3-bromo-benzoyl chloride (0.83 g, 3.8 mmol) in DCM (10 mL) was chilled to zero degrees and treated with tert-butylamine (1.2 mL, 11.3 mmol). Reaction was allowed to come to room temperature and stir for 4 h. Mixture was then poured onto water and washed once. Organic phase then washed with brine, dried over sodium sulfate, filtered and evaporated to amber oil (0.9 g, 94%).

Example 234

N-tert-Butyl-3-{5-methyl-2-[4-(4-methyl-piperazin-1-yl)-phenylamino]-pyrimidin-4-ylamino}-benzamide (Compound CLIII)

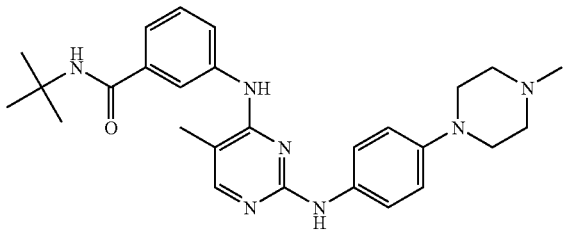

A mixture of intermediate 32 (0.1 g, 0.34 mmol), intermediate 84 (0.1 g, 0.4 mmol), Pd$_2$(dba)$_3$ (0.031 g, 0.034 mmol), Xantphos (0.039 g, 0.067 mmol) and cesium carbonate (0.33 g, 1 mmol) were suspended in dioxane (8 mL) microwaved at 160° C. for 15 min. Reaction vessel was then centrifuged down and decanted. Solvents then evaporated and resulting residue was purified by HPLC to afford title compound as white solids (0.055 g, 35%).

$^1$H NMR (500 MHz, DMSO-d$_6$): δ 1.36 (s, 9H), 2.09 (s, 3H), 2.21 (s, 3H), 2.43 (t, J=2.8 Hz, 4H), 3.00 (t, J=2.8 Hz, 4H), 6.74 (d, J=9.1 Hz, 2H), 7.35 (t, J=7.9 Hz, 1H), 7.44-7.48 (m, 3H), 7.67 (s, 1H), 7.85 (s, 1H), 7.88-7.92 (m, 2H), 8.36 (s, 1H), 8.74 (s, 1H). MS (ES+): m/z 474 (M+H)+.

Example 235

5-Methyl-N$^2$-[4-(4-methyl-piperazin-1-yl)-phenyl]-N$^4$-(3-piperidin-4-yl-phenyl)-pyrimidine-2,4-diamine (Compound CLIV)

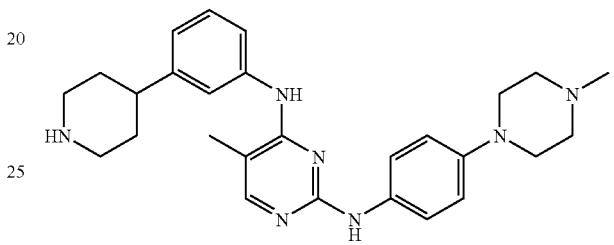

A mixture of intermediate 32 (0.08 g, 0.27 mmol), 4-(3-bromo-phenyl)-piperidine (0.084 g, 0.35 mmol), Pd$_2$(dba)$_3$ (0.025 g, 0.027 mmol), Xantphos (0.031 g, 0.054 mmol) and cesium carbonate (0.26 g, 0.81 mmol) were suspended in dioxane (8 mL) microwaved at 160° C. for 15 min. Reaction vessel was then centrifuged down and decanted. Solvents then evaporated and resulting residue was purified by HPLC to afford title compound as white solids (0.007 g, 6%).

$^1$H NMR (500 MHz, DMSO-d$_6$): δ 1.74-1.79 (m, 3H), 2.09 (s, 3H), 2.21 (s, 3H), 2.43 (t, J=2.8 Hz, 4H), 3.00 (t, J=2.8 Hz, 4H), 6.76 (d, J=9.1 Hz, 2H), 6.90 (d, J=7.7 Hz, 1H), 7.24 (t, J=7.9 Hz, 1H), 7.47-7.53 (m, 3H), 7.68 (d, J=8.2 Hz, 1H), 7.82 (s, 1H), 8.18 (s, 1H), 8.67 (s, 1H). MS (ES+): m/z 458 (M+H)+.

Example 236

4-(3-{5-Methyl-2-[4-(4-methyl-piperazin-1-yl)-phenylamino]-pyrimidin-4-ylamino}-benzenesulfonyl)-piperidine-1-carboxylic acid benzyl ester (Intermediate 85)

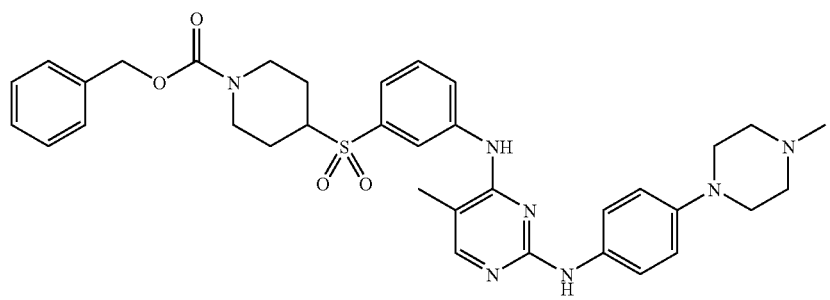

A mixture of intermediate 32 (0.17 g, 0.58 mmol), 4-(3-bromo-benzenesulfonyl)-piperidine-1-carboxylic acid benzyl ester (0.28 g, 0.64 mmol), Pd$_2$(dba)$_3$ (0.053 g, 0.058 mmol), Xantphos (0.067 g, 0.12 mmol) and cesium carbonate (0.57 g, 1.74 mmol) were suspended in dioxane (8 mL) microwaved at 160° C. for 15 min. Reaction vessel was then centrifuged down and decanted onto ice. Yellow solids collected, dried and used without further purification (0.4 g, 100%).

Example 237

5-Methyl-N$^2$-[4-(4-methyl-piperazin-1-yl)-phenyl]-N$^4$-[3-(piperidine-4-sulfonyl)-phenyl]-pyrimidine-2,4-diamine (Compound CLV)

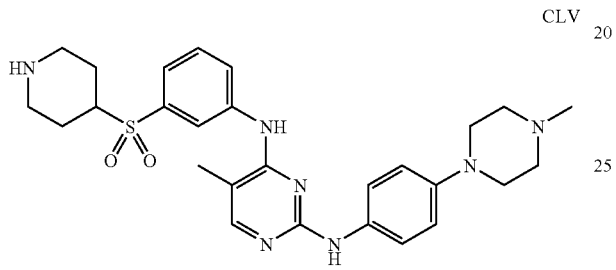

CLV

A stirring solution of intermediate 85 (0.17 g, 0.26 mmol) in DCM (15 mL) was treated with 1M BBr$_3$ in DCM (2 mL, 2 mmol). After 4 h, reaction was quenched by slow addition of MeOH (4 mL) followed by removal of solvents. Residue purified by HPLC to provide title compound as purple powder (0.008 g, 6%).

$^1$H NMR (500 MHz, DMSO-d$_6$): δ 1.31-1.40 (m, 2H), 1.75 (d, J=10.8 Hz, 2H), 2.12 (s, 3H), 2.21 (s, 3H), 2.36-2.41 (m, 2H), 2.44 (t, J=4.9 Hz, 4H), 2.95 (d, J=12.5 Hz, 2H), 3.02 (t, J=4.9 Hz, 4H), 3.24 (tt, J=11.7 Hz, J=3.8 Hz, 1H), 6.81 (d, J=9.0 Hz, 2H), 7.44 (m, 3H), 7.56 (t, J=8.0 Hz, 1H), 7.90-7.91 (m, 2H), 8.49 (d, J=7.6 Hz, 1H), 8.60 (s, 1H), 8.74 (s, 1H). MS (ES+): m/z 522 (M+H)$^+$.

Example 238 tert-Butyl 4-(4-(4-(1H-indol-4-ylamino)-5-methylpyrimidin-2-ylamino)phenoxy)piperidine-1-carboxylate (Intermediate 86)

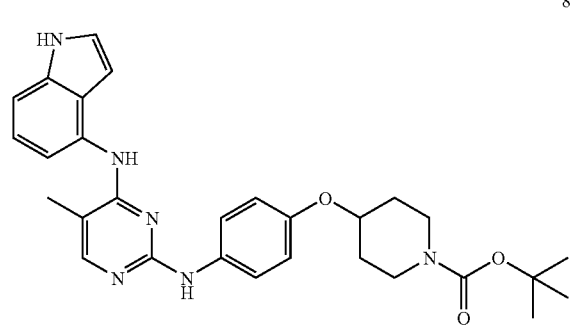

86

A mixture of 4-bromo-1H-indole (41 μL, 0.33 mmol), intermediate 42 (131 mg, 0.33 mmol), Pd$_2$(dba)$_3$ (30 mg, 0.03 mmol), Xantphos (60 mg, 0.10 mmol) and cesium carbonate (428 mg, 1.31 mmol) in dioxane (3 mL) was irradiated in the microwaved at 160° C. for 20 min. The reaction mixture was cooled to room temperature and filtered rinsing with DCM. The filtrate was concentrated and purified by gradient flash chromatography (0-15% MeOH in DCM) to afford the title compound as a white solid (30 mg, 17%).

Example 239

N$^4$-(1H-Indol-4-yl)-5-methyl-N$^2$-(4-(piperidin-4-yloxy)phenyl)pyrimidine-2,4-diamine (Compound CLVI)

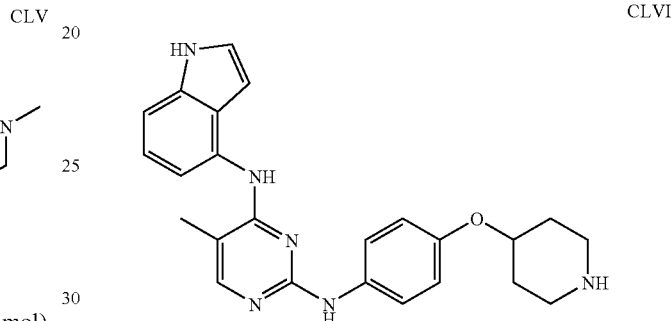

CLVI

A mixture of intermediate 86 (27 mg, 0.05 mmol) in 30% TFA/DCM (1 mL) was stirred for 3 h. The reaction mixture was concentrated in vacuo and purified by preparative HPLC. The resulting fractions were concentrated in vacuo to obtain the TFA salt of the title compound as a tan solid (11 mg, 43%).

$^1$H NMR (500 MHz, DMSO-d$_6$): δ 1.71-1.77 (m, 2H), 1.98-2.06 (m, 2H), 2.22 (s, 3H), 3.03-3.12 (m, 2H), 3.19-3.27 (m, 2H), 4.44-4.53 (m, 1H), 6.34-6.37 (m, 1H), 6.64 (br d, J=8.3 Hz, 2H), 7.08 (t, J=7.2 Hz, 3H), 7.14 (t, J=7.8 Hz, 1H), 7.36 (t, J=2.7 Hz, 1H), 7.39 (d, J=8.1 Hz, 1H), 7.84 (s, 1H), 8.48 (br s, 1H), 8.55 (br s, 1H), 9.85 (br s, 1H), 9.98 (br s, 1H), 11.27 (s, 1H).

Example 240

2-Chloro-N-{2-[4-(2-pyrrolidin-1-yl-ethoxy)-phenylamino]-pyrimidin-5-yl}-5-(3-trifluoromethyl-benzoylamino)-benzamide (Compound CLVII)

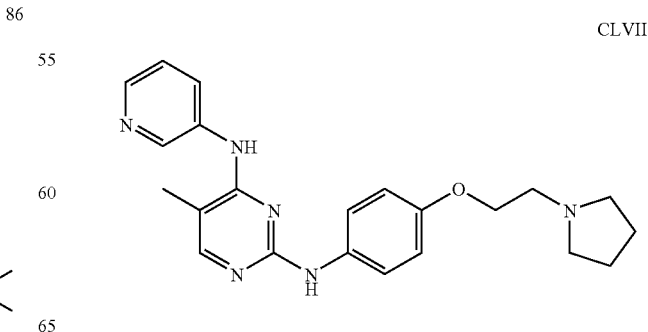

CLVII

A mixture of 3-bromopyridine (379 mg, 2.4 mmol), 4-amino-2-chloro-5-methylpyrimidine (287 mg, 2.0 mmol), Pd$_2$(dba)$_3$ (18 mg, 0.02 mmol), xantphos (23 mg, 0.04 mmol) and cesium carbonate (975 mg, 3.0 mmol) in dioxane (15 mL) was heated under refluxed for 1 h under argon. The solvent was removed and the residue on purification by HPLC gave an intermediate, 2-chloro-5-methyl-N-(pyridin-3-yl)pyrimidin-4-amine as yellow solid (252 mg, 57%). For second Buckwald, a mixture of 2-chloro-5-methyl-N-(pyridin-3-yl)pyrimidin-4-amine (80 mg, 0.36 mmol), 4-(2-(pyrrolidin-1-yl)ethoxy)benzenamine (74 mg, 0.34 mmol), Pd$_2$(dba)$_3$ (3.2 mg, 0.003 mmol), xantphos (4.2 mg, 0.007 mmol) and cesium carbonate (234 mg, 0.72 mmol) in dioxane (5 mL) was heated under refluxed for 1 h under argon. The crude reaction mixture on purification using HPLC gave the title compound as light brown solid (28 mg, 20%).

$^1$H NMR (500 MHz, DMSO-d$_6$): δ 1.85-1.95 (m, 2H), 2.0-2.09 (m, 2H), 2.18 (s, 3H), 3.09-3.18 (m, 2H), 3.55-3.65 (m, 4H), 4.27 (dd, J=5.2, 4.7 Hz, 2H), 6.94 (d, J=8.9 Hz, 2H), 7.35 (d, J=8.9 Hz, 2H), 7.50 (dd, J=8.2, 4.8 Hz, 1H), 7.92-7.96 (m, 1H), 8.08-8.15 (m, 1H), 8.45 (dd, J=4.8, 1.4, 1H), 8.84, 9.75, 9.85, 10.24 (4 br s, 1H each). MS (ES+): m/z 329 (M+H)$^+$.

Example 241

N$^2$-(4-(2-(pyrrolidin-1-yl)ethoxy)phenyl)-5-methyl-N$^4$-(3-(trifluoromethoxy)phenyl)pyrimidine-2,4-diamine (Compound CLVIII)

CLVIII

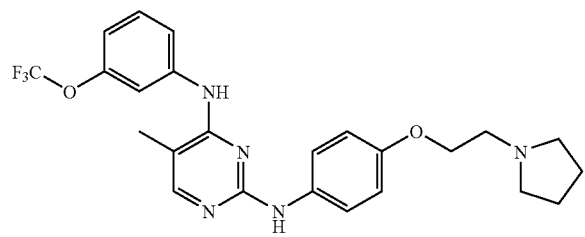

A mixture of 1-bromo-3-(trifluoromethoxy)benzene (241 mg, 1.0 mmol), 4-amino-2-chloro-5-methylpyrimidine (143 mg, 1.0 mmol), Pd$_2$(dba)$_3$ (9 mg, 0.01 mmol), xantphos (14 mg, 0.02 mmol) and cesium carbonate (650 mg, 2.0 mmol) in dioxane (15 mL) was heated under refluxed for 10 h under argon. The solvent was removed and the residue on purification by HPLC gave an intermediate, 2-chloro-5-methyl-N-(pyridin-3-yl)pyrimidin-4-amine as brown solid (260 mg, 85%). A mixture of this intermediate (100 mg, 0.33 mmol) and 4-(2-(pyrrolidin-1-yl)ethoxy)benzenamine (67 mg, 0.33 mmol) in glacial acetic acid (5 mL) was heated under refluxed for 3 h under argon. The crude reaction mixture on purification using HPLC gave the title compound as white solid (11 mg, 7%).

$^1$H NMR (500 MHz, DMSO-d$_6$): δ 1.65-1.72 (m, 4H), 2.11 (s, 3H), 2.51-2.55 (m, 2H, superimposed with solvent peak), 2.75 (t, J=5.9 Hz, 2H), 3.25-3.34 (m, 2H, superimposed with water peak), 3.99 (t, J=5.9 Hz, 2H), 6.79 (d, J=8.9 Hz, 2H), 6.98 (d, J=8.0 Hz, 1H), 7.40 (dd, J=7.6, 7.4 Hz, 1H), 7.50 (d, J=8.9 Hz, 2H), 7.76 (br s, 1H), 7.87 (d, J=8.4 1H), 7.90, 8.31, 8.41, 8.84 (4 s, 1H each). MS (ES+): m/z 474 (M+H)$^+$.

Example 242

N$^2$-(4-(2-(pyrrolidin-1-yl)ethoxy)phenyl)-N$^4$-(4-chloro-3-(trifluoromethyl)phenyl)-5-methylpyrimidine-2,4-diamine (Compound CLIX)

CLIX

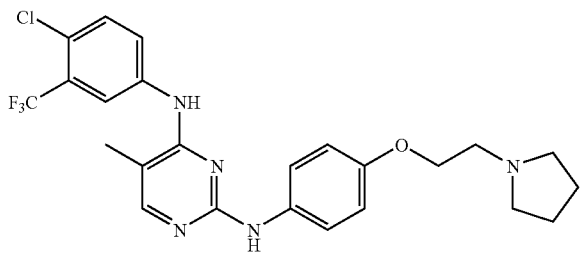

A mixture of 4-bromo-1-chloro-2-(trifluoromethyl)benzene (259 mg, 1.0 mmol), 4-amino-2-chloro-5-methylpyrimidine (143 mg, 1.0 mmol), Pd$_2$(dba)$_3$ (9 mg, 0.01 mmol), xantphos (14 mg, 0.02 mmol) and cesium carbonate (650 mg, 2.0 mmol) in dioxane (15 mL) was heated under refluxed for 10 h under argon. The solvent was removed and the residue was purified by HPLC to give an intermediate 2-chloro-N-(4-chloro-3-(trifluoromethyl)phenyl)-5-methylpyrimidin-4-amine as brown solid (200 mg, 62%). A mixture of this intermediate (161 mg, 0.5 mmol) and 4-(2-(pyrrolidin-1-yl)ethoxy)benzenamine (103 mg, 0.5 mmol) in glacial acetic acid (5 mL) was heated under refluxed for 3 h under argon. The crude reaction mixture on purification using HPLC gave the title compound as brown solid (75 mg, 31%).

$^1$H NMR (500 MHz, DMSO-d$_6$): δ 1.65-1.72 (m, 4H), 2.10 (s, 3H), 2.51-2.55 (m, 4H, superimposed with solvent peak), 2.75 (t, J=6.0 Hz, 2H), 4.0 (t, J=5.9 Hz, 2H), 6.79 (d, J=8.5 Hz, 2H), 7.47 (d, J=9.0 Hz, 2H), 7.58 (d, J=9.0 Hz, 2H), 7.93 (s, 1H), 8.01 (d, J=2.5 Hz, 1H), 8.22 (d, J=8.5 Hz, 2H), 8.60, 8.88 (2 s, 1H each). MS (ES+): m/z 492 (M+H)$^+$.

Example 243

IC$_{50}$ Value Determinations for Jak2 Kinase

The IC$_{50}$ values for compounds were determined using a luminescence-based kinase assay with recombinant JAK2 obtained from Upstate Cell Signaling Solutions. In white, flat-bottom, 96-well plates (Nunc) parallel assays were run at room temperature at a final volume of 50 µL. Each well contained 40 µL of buffer consisting of 40 mM Tris buffer, pH 7.4, containing 50 mM MgCl$_2$, 800 µM EGTA, 350 µM Triton X-100, 2 mM β-mercaptoethanol, 100 µM peptide substrate (PDKtide; Upstate Cell Signaling Solutions) and an appropriate amount of JAK2 (75-25 ng/well) such that the assay was linear over 60 min. The final concentrations of TargeGen compounds for IC$_{50}$ value determinations ranged from 1000 to 0.01 µM by adding the appropriate amount of compound in 2.5 µL of DMSO; the DMSO present in each assay was constant at 5%. The reaction was initiated by the addition of 10 µL of ATP to a final assay concentration of 3 µM. After the reaction had proceeded for 60 min, 50 µL of Kinase-Glo reagent (Promega) was added to terminate the reaction. This solution was then allowed to proceed for an additional 10 min to maximize the luminescence reaction.

Values were then measured using an Ultra 384 instrument (Tecan) set for luminosity measurements. Two control reactions were also ran: one reaction containing no compound and the second containing neither inhibitor nor peptide substrate. $IC_{50}$ values were derived from experimental data using the non-linear curve fitting capabilities of Prism (Version 4; GraphPad Software). The results are shown in Table 1.

TABLE 1

Compounds of the Invention And Their IC Values for Jak2 Kinase

| Structure | Name | JAK2 IC50 |
|---|---|---|
| 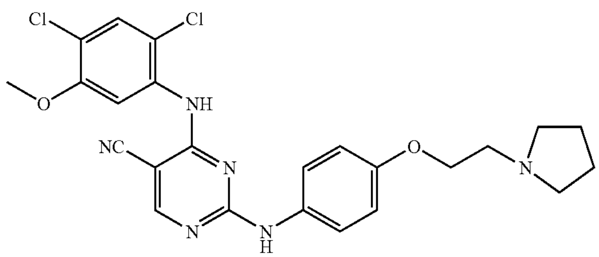 | 4-(2,4-Dichloro-5-methoxy-phenylamino)-2-[4-(2-pyrrolidin-1-yl-ethoxy)-phenylamino]-pyrimidine-5-carbonitrile | 6240 |
| 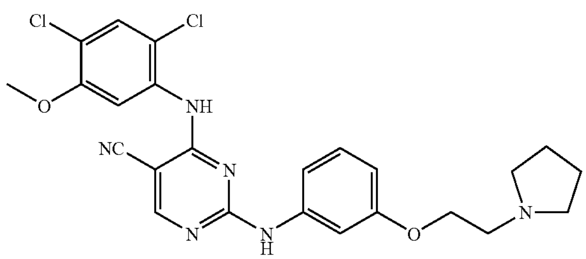 | 4-(2,4-Dichloro-5-methoxy-phenylamino)-2-[3-(2-pyrrolidin-1-yl-ethoxy)-phenylamino]-pyrimidine-5-carbonitrile | 10500 |
| 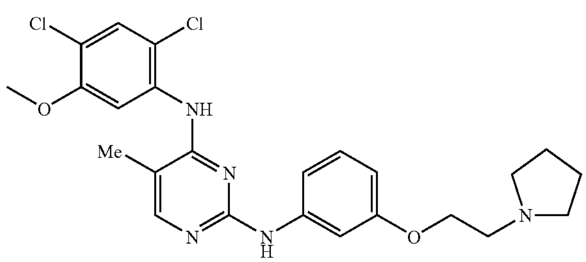 | N4-(2,4-Dichloro-5-methoxy-phenyl)-5-methyl-N2-[3-(2-pyrrolidin-1-yl-ethoxy)-phenyl]-pyrimidine-2,4-diamine | 2040 |
| 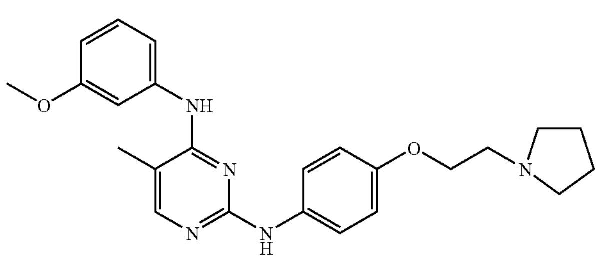 | N2-(4-(2-(pyrrolidin-1-yl)ethoxy)phenyl)-N4-(3-methoxyphenyl)-5-methylpyrimidine-2,4-diamine Hydrochloride | 52.8 |
| 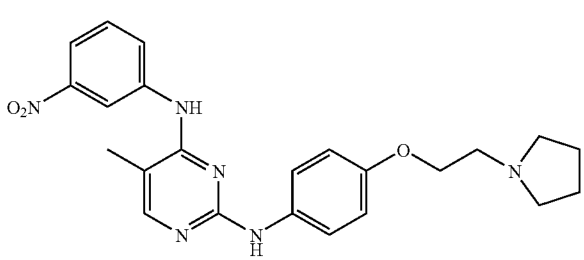 | N2-(4-(2-(pyrrolidin-1-yl)ethoxy)phenyl)-5-methyl-N4-(3-nitrophenyl)pyrimidine-2,4-diamine Hydrochloride | 61.1 |

TABLE 1-continued

Compounds of the Invention And Their IC Values for Jak2 Kinase

| Structure | Name | JAK2 IC50 |
|---|---|---|
| 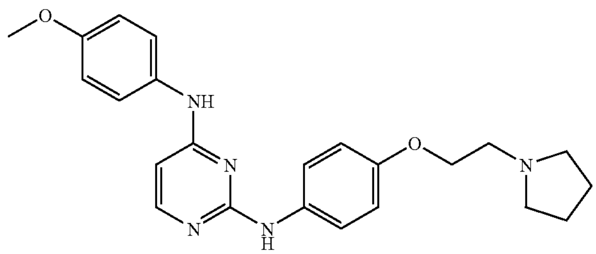 | N4-(4-Methoxy-phenyl)-N2-[4-(2-pyrrolidin-1-yl-ethoxy)-phenyl]-pyrimidine-2,4-diamine trifluoroacetate | 4330 |
| 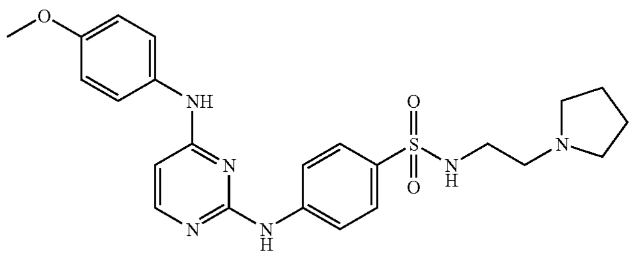 | 4-[4-(4-Methoxy-phenylamino)-pyrimidin-2-ylamino]-N-(2-pyrrolidin-1-yl-ethyl)-benzenesulfonamide trifluoroacetate | 10700 |
| 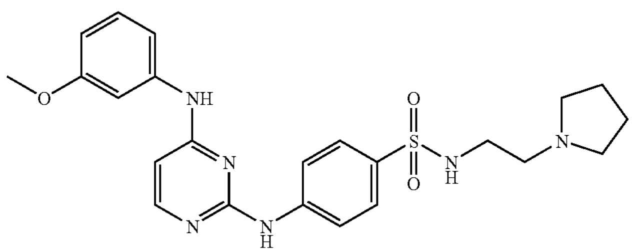 | 4-[4-(3-Methoxy-phenylamino)-pyrimidin-2-ylamino]-N-(2-pyrrolidin-1-yl-ethyl)-benzenesulfonamide trifluoroacetate | 638 |
| 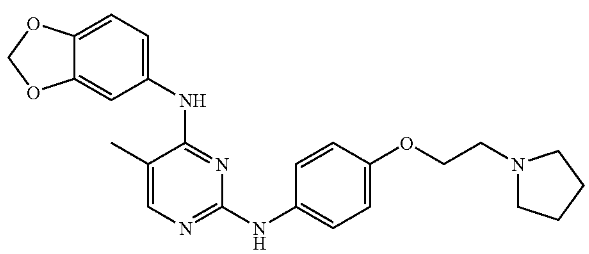 | N4-Benzo[1,3]dioxol-5-yl-5-methyl-N2-[4-(2-pyrrolidin-1-yl-ethoxy)-phenyl]-pyrimidine-2,4-diamine trifluoroacetate | 87.2 |
| 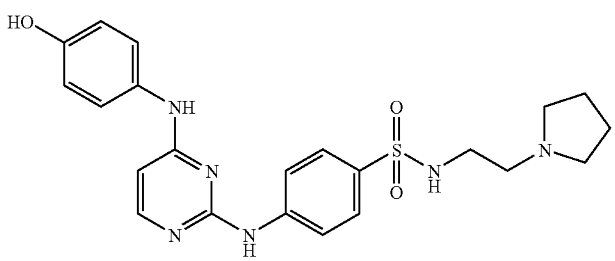 | 4-[4-(4-Hydroxy-phenylamino)-pyrimidin-2-ylamino]-N-(2-pyrrolidin-1-yl-ethyl)-benzenesulfonamide | 9740 |
| 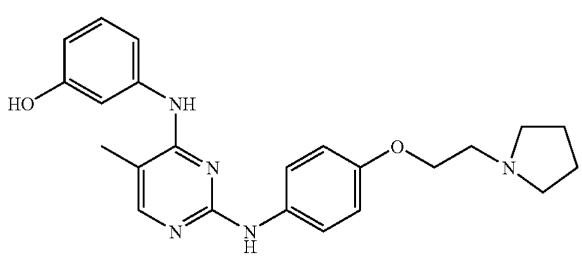 | 3-(2-(4-(2-pyrrolidin-1-yl)ethoxy)phenylamino)-5-methylpyrimidin-4-ylamino)phenol Hydrochloride | 203 |

TABLE 1-continued

Compounds of the Invention And Their IC Values for Jak2 Kinase

| Structure | Name | JAK2 IC50 |
|---|---|---|
| 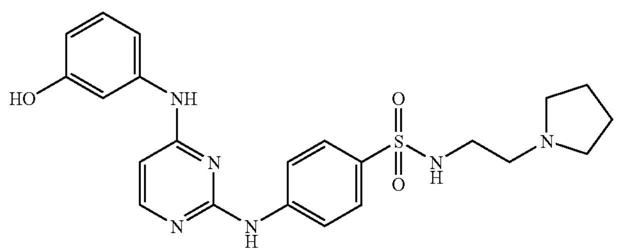 | 4-[4-(3-Hydroxy-phenylamino)-pyrimidin-2-ylamino]-N-(2-pyrrolidin-1-yl-ethyl)-benzenesulfonamide trifluoroacetate | 3620 |
| 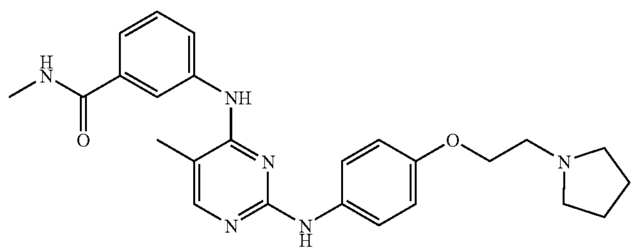 | N-Methyl-3-{5-methyl-2-[4-(2-pyrrolidin-1-yl-ethoxy)-phenylamino]-pyrimidin-4-ylamino}-benzamide | 257 |
| 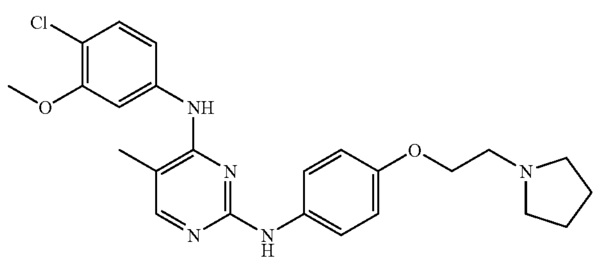 | N4-(4-Chloro-3-methoxy-phenyl)-5-methyl-N2-[4-(2-pyrrolidin-1-yl-ethoxy)-phenyl]-pyrimidine-2,4-diamine | 7.96 |
| 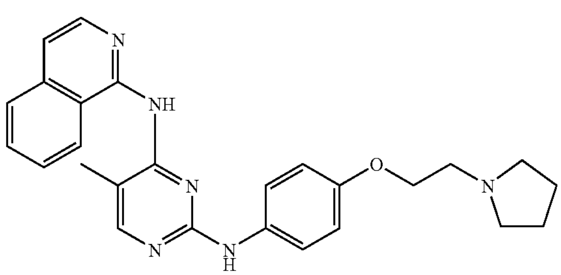 | N2-(4-(2-(pyrrolidin-1-yl)ethoxy)phenyl)-N4-(isoquinolin-1-yl)-5-methylpyrimidine-2,4-diamine | 1050 |
| 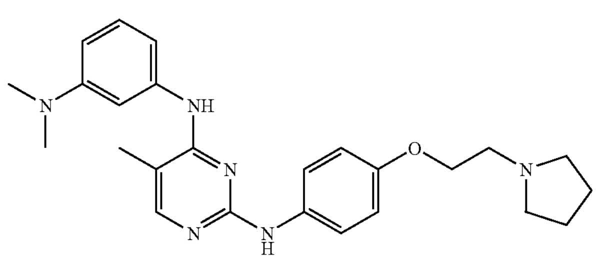 | N4-(3-Dimethylamino-phenyl)-5-methyl-N2-[4-(2-pyrrolidin-1-yl-ethoxy)-phenyl]-pyrimidine-2,4-diamine | 19.7 |

TABLE 1-continued

Compounds of the Invention And Their IC Values for Jak2 Kinase

| Structure | Name | JAK2 IC50 |
|---|---|---|
| 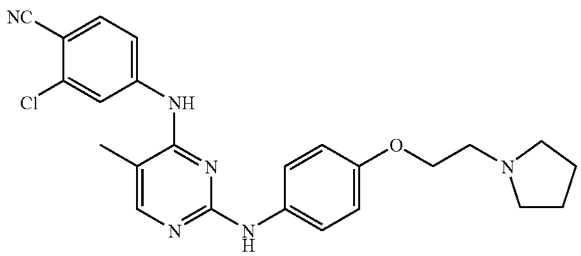 | 4-(2-(4-(2-(pyrrolidin-1-yl)ethoxy)phenylamino)-5-methylpyrimidin-4-ylamino)-2-chlorobenzonitrile Hydrochloride | 67.5 |
| 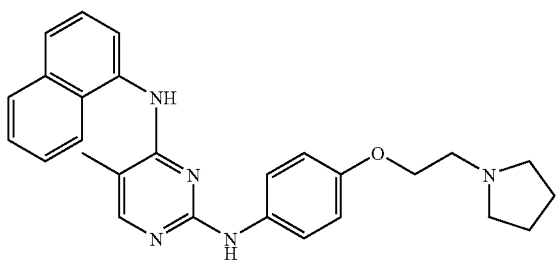 | N2-(4-(2-(pyrrolidin-1-yl)ethoxy)phenyl)-5-methyl-N4-(naphthalen-1-yl)pyrimidine-2,4-diamine Hydrochloride | 20 |
| 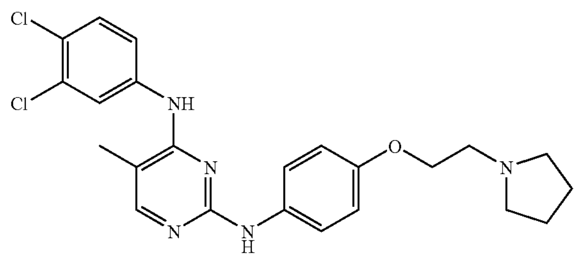 | N4-(3,4-Dichloro-phenyl)-5-methyl-N2-[4-(2-pyrrolidin-1-yl-ethoxy)-phenyl]-pyrimidine-2,4-diamine | 25.7 |
| 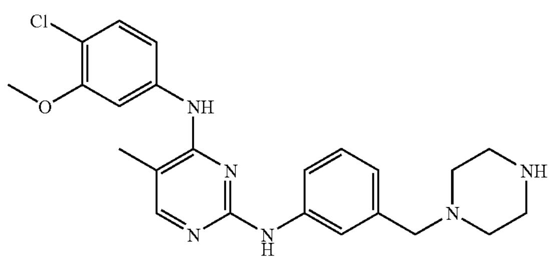 | N4-(4-Chloro-3-methoxy-phenyl)-5-methyl-N2-(3-piperazin-1-ylmethyl-phenyl)-pyrimidine-2,4-diamine | 15.8 |
| 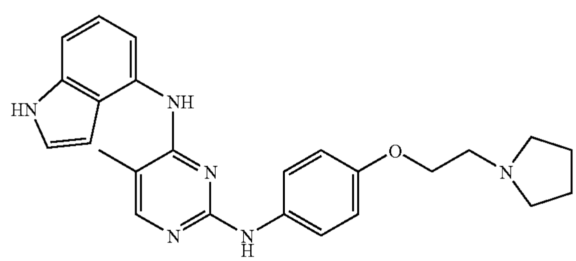 | N2-(4-(2-(pyrrolidin-1-yl)ethoxy)phenyl)-N4-(1H-indol-4-yl)-5-methylpyrimidine-2,4-diamine Hydrochloride | 19.2 |
| 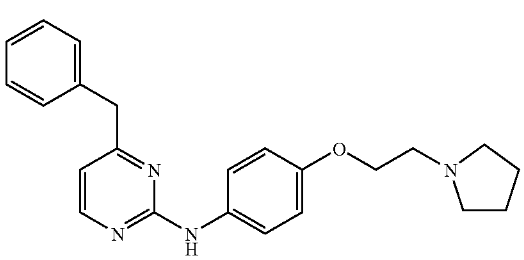 | N-(4-(2-(pyrrolidin-1-yl)ethoxy)phenyl)-4-benzylpyrimidin-2-amine | 702.000000 |

TABLE 1-continued

Compounds of the Invention And Their IC Values for Jak2 Kinase

| Structure | Name | JAK2 IC50 |
|---|---|---|
| 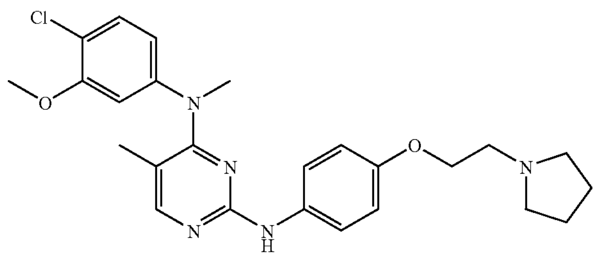 | N2-(4-(2-(pyrrolidin-1-yl)ethoxy)phenyl)-N4-(4-chloro-3-methoxyphenyl)-N4,5-dimethylpyrimidine-2,4-diamine trifluoroacetate | 4900 |
| 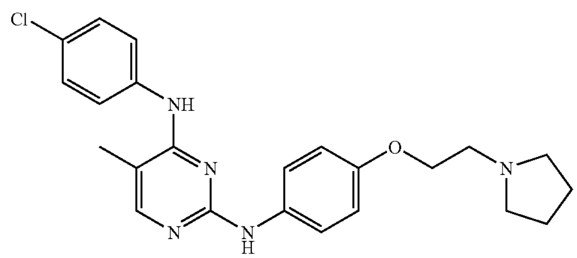 | N4-(4-Chloro-phenyl)-5-methyl-N2-[4-(2-pyrrolidin-1-yl-ethoxy)-phenyl]-pyrimidine-2,4-diamine trifluoroacetate | 18.2 |
| 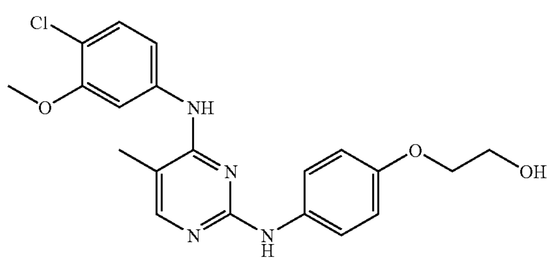 | 2-{4-[4-(4-Chloro-3-methoxy-phenylamino)-5-methyl-pyrimidin-2-ylamino]-phenoxy}-ethanol | 9.14 |
| 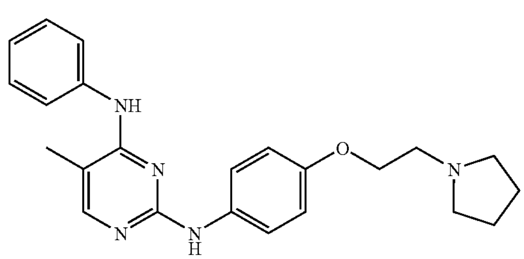 | 5-Methyl-N4-phenyl-N2-[4-(2-pyrrolidin-1-yl-ethoxy)-phenyl]-pyrimidine-2,4-diamine | 16.7 |
| 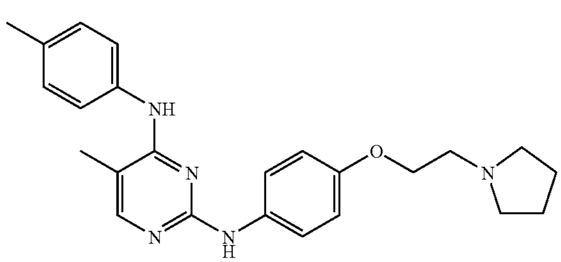 | N2-(4-(2-(pyrrolidin-1-yl)ethoxy)phenyl)-5-methyl-N4-p-tolylpyrimidine-2,4-diamine Hydrochloride | 35.7 |

TABLE 1-continued

Compounds of the Invention And Their IC Values for Jak2 Kinase

| Structure | Name | JAK2 IC50 |
|---|---|---|
| 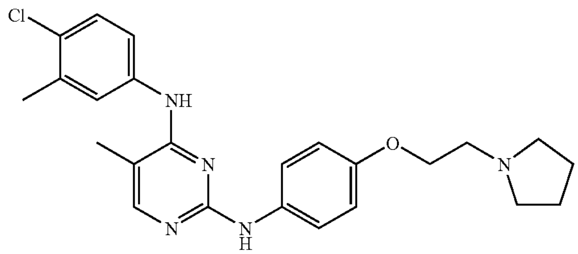 | N2-(4-(2-(pyrrolidin-1-yl)ethoxy)phenyl)-N4-(4-chloro-3-methylphenyl)-5-methylpyrimidine-2,4-diamine Hydrochloride | 12.4 |
| 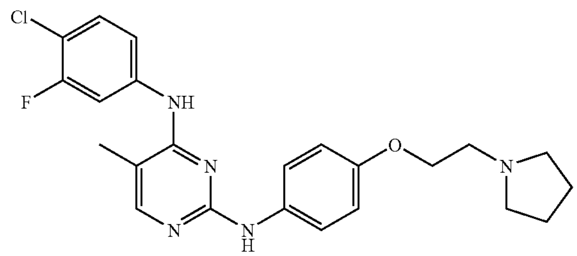 | N4-(4-Chloro-3-fluoro-phenyl)-5-methyl-N2-[4-(2-pyrrolidin-1-yl-ethoxy)-phenyl]-pyrimidine-2,4-diamine | 40.1 |
| 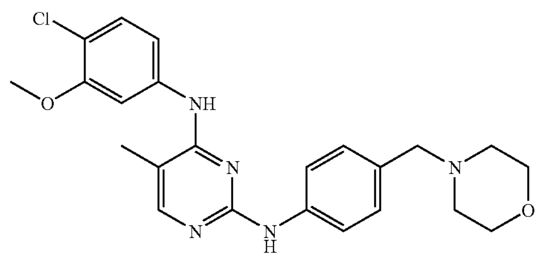 | N4-(4-Chloro-3-methoxy-phenyl)-5-methyl-N2-(4-morpholin-4-ylmethyl-phenyl)-pyrimidine-2,4-diamine trifluoroacetate | 13.3 |
| 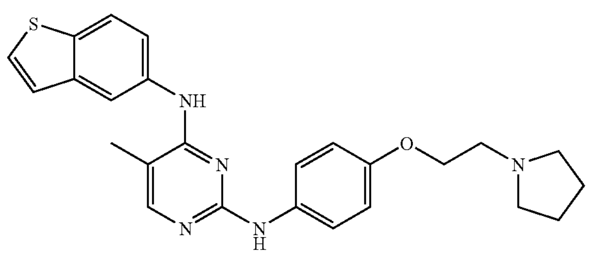 | N4-Benzo[b]thiophen-5-yl-5-methyl-N2-[4-(2-pyrrolidin-1-yl-ethoxy)-phenyl]-pyrimidine-2,4-diamine | 28.5 |
| 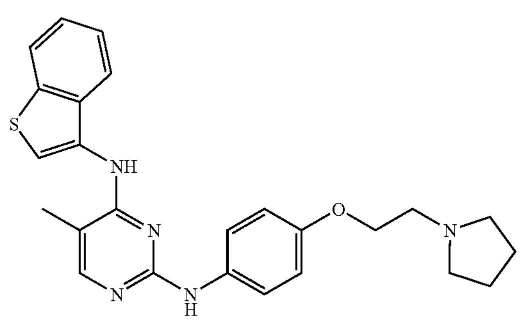 | N4-Benzo[b]thiophen-3-yl-5-methyl-N2-[4-(2-pyrrolidin-1-yl-ethoxy)-phenyl]-pyrimidine-2,4-diamine | 12.4 |

TABLE 1-continued

Compounds of the Invention And Their IC Values for Jak2 Kinase

| Structure | Name | JAK2 IC50 |
|---|---|---|
| 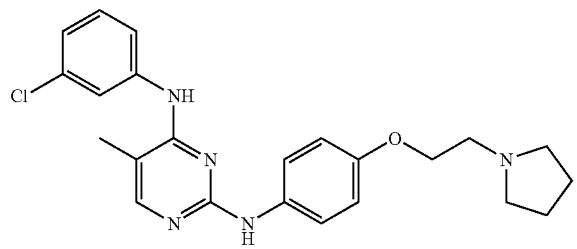 | N4-(3-Chloro-phenyl)-5-methyl-N2-[4-(2-pyrrolidin-1-yl-ethoxy)-phenyl]-pyrimidine-2,4-diamine | 20.8 |
| 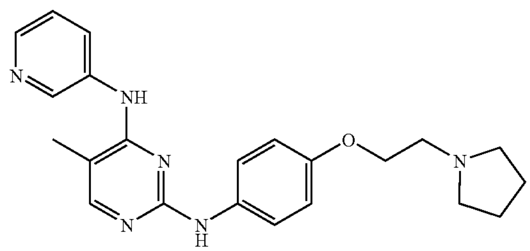 | 2-Chloro-N-{2-[4-(2-pyrrolidin-1-yl-ethoxy)-phenylamino]-pyrimidin-5-yl}-5-(3-trifluoromethyl-benzoylamino)-benzamide | 304 |
| 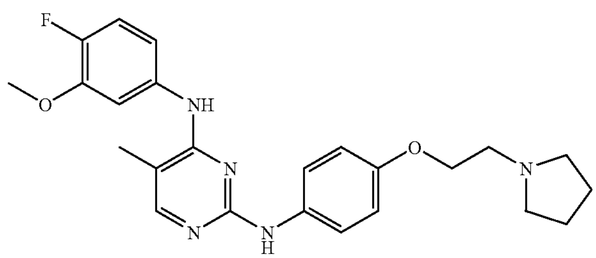 | N4-(4-Fluoro-3-methoxy-phenyl)-5-methyl-N2-[4-(2-pyrrolidin-1-yl-ethoxy)-phenyl]-pyrimidine-2,4-diamine | 14.8 |
| 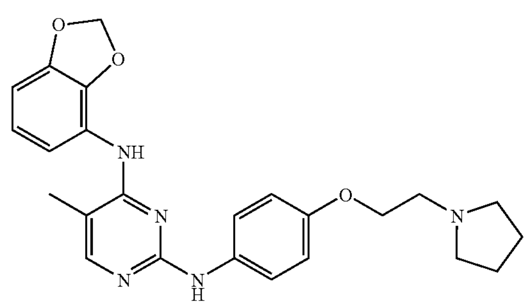 | N4-Benzo[1,3]dioxol-4-yl-5-methyl-N2-[4-(2-pyrrolidin-1-yl-ethoxy)-phenyl]-pyrimidine-2,4-diamine | 16.9 |
| 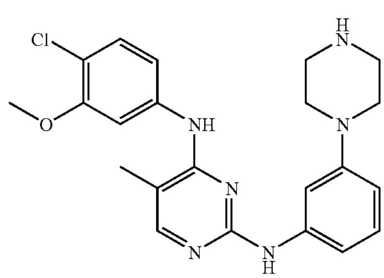 | N4-(4-Chloro-3-methoxy-phenyl)-5-methyl-N2-(3-piperazin-1-yl-phenyl)-pyrimidine-2,4-diamine | 9.52 |

TABLE 1-continued

Compounds of the Invention And Their IC Values for Jak2 Kinase

| Structure | Name | JAK2 IC50 |
|---|---|---|
| 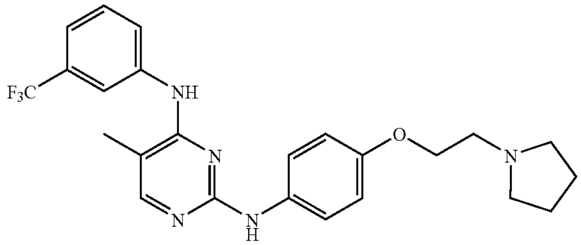 | N2-(4-(2-(pyrrolidin-1-yl)ethoxy)phenyl)-N4-(3-(trifluoromethyl)phenyl)-5-methylpyrimidine-2,4-diamine | 17.6 |
| 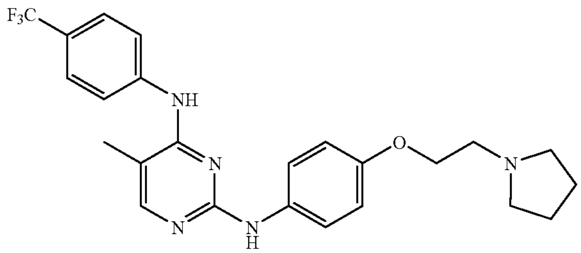 | N2-(4-(2-(pyrrolidin-1-yl)ethoxy)phenyl)-N4-(4-(trifluoromethyl)phenyl)-5-methylpyrimidine-2,4-diamine hydrochloride | 39.8 |
| 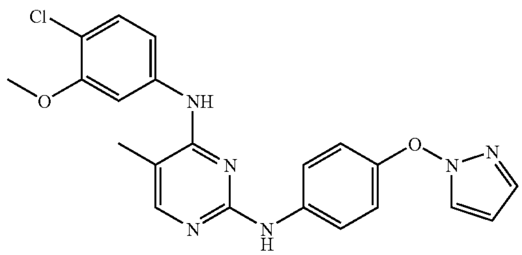 | N4-(4-Chloro-3-methoxy-phenyl)-5-methyl-N2-(4-pyrazol-1-ylmethyl-phenyl)-pyrimidine-2,4-diamine | 18.9 |
| 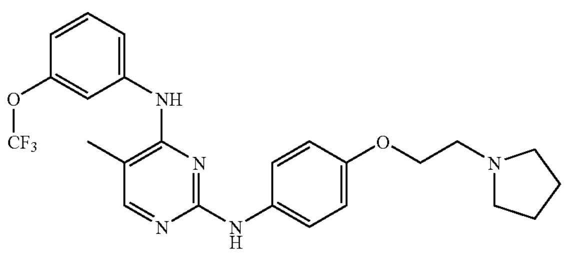 | N2-(4-(2-(pyrrolidin-1-yl)ethoxy)phenyl)-5-methyl-N4-(3-(trifluoromethoxy)phenyl)pyrimidine-2,4-diamine | 20.7 |
| 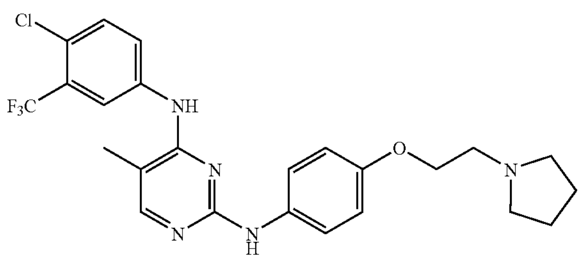 | N2-(4-(2-(pyrrolidin-1-yl)ethoxy)phenyl)-N4-(4-chloro-3-(trifluoromethyl)phenyl)-5-methylpyrimidine-2,4-diamine | 23.4 |
| 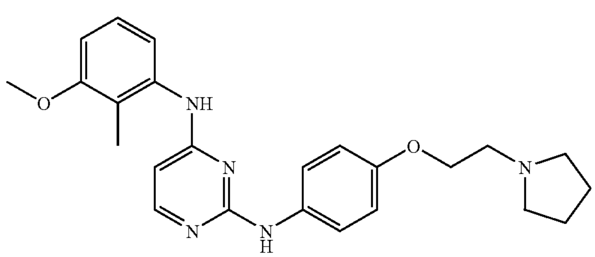 | N4-(3-Methoxy-2-methyl-phenyl)-N2-[4-(2-pyrrolidin-1-yl-ethoxy)-phenyl]-pyrimidine-2,4-diamine | 371 |

TABLE 1-continued

Compounds of the Invention And Their IC Values for Jak2 Kinase

| Structure | Name | JAK2 IC50 |
|---|---|---|
| 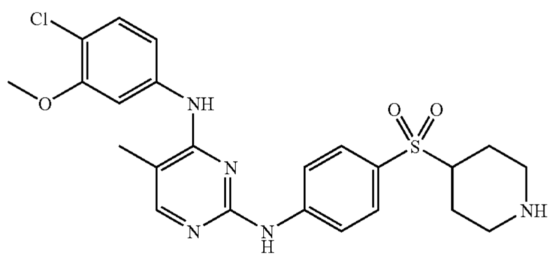 | N4-(4-Chloro-3-methoxy-phenyl)-5-methyl-N2-[4-(piperidine-4-sulfonyl)-phenyl]-pyrimidine-2,4-diamine | 13 |
| 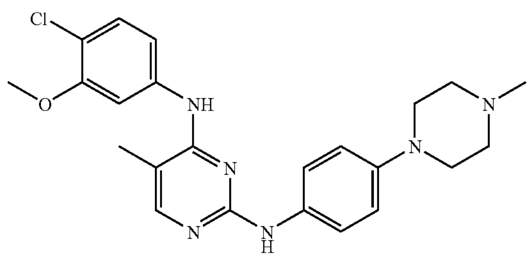 | N4-(4-Chloro-3-methoxy-phenyl)-5-methyl-N2-[4-(4-methyl-piperazin-1-yl)-phenyl]-pyrimidine-2,4-diamine | 5.5 |
| 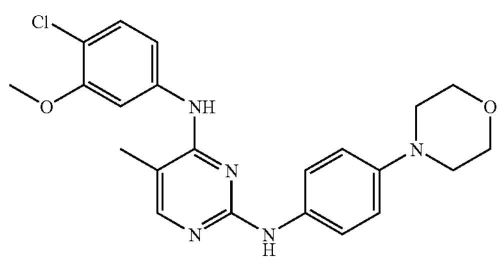 | N4-(4-Chloro-3-methoxy-phenyl)-5-methyl-N2-(4-morpholin-4-yl-phenyl)-pyrimidine-2,4-diamine | 130 |
| 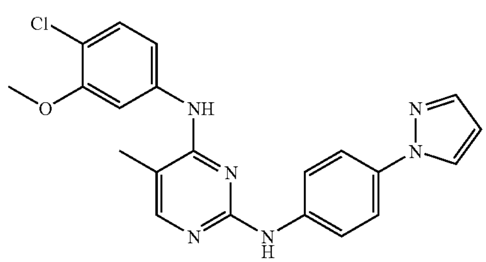 | N4-(4-Chloro-3-methoxy-phenyl)-5-methyl-N2-(4-pyrazol-1-yl-phenyl)-pyrimidine-2,4-diamine trifluoroacetate | 35.3 |
| 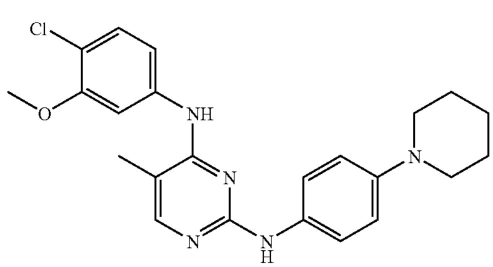 | N4-(4-Chloro-3-methoxy-phenyl)-5-methyl-N2-(4-piperidin-1-yl-phenyl)-pyrimidine-2,4-diamine | 35.3 |

TABLE 1-continued

Compounds of the Invention And Their IC Values for Jak2 Kinase

| Structure | Name | JAK2 IC50 |
|---|---|---|
| 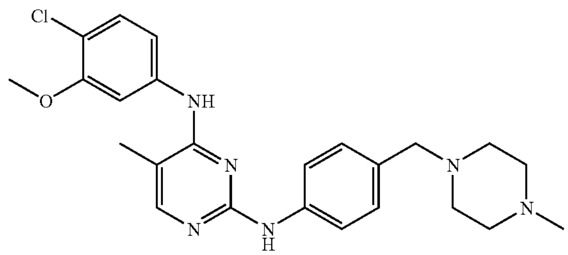 | N4-(4-Chloro-3-methoxy-phenyl)-5-methyl-N2-[4-(4-methyl-piperazin-1-ylmethyl)-phenyl]-pyrimidine-2,4-diamine | 12 |
| 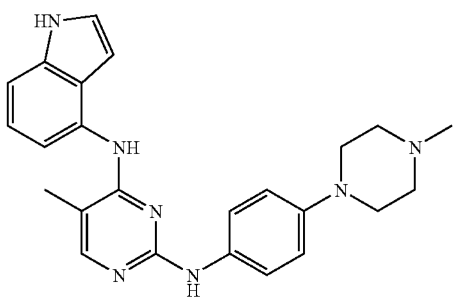 | N4-(1H-indol-4-yl)-5-methyl-N2-(4-(4-methylpiperazin-1-yl)phenyl)pyrimidine-2,4-diamine Hydrochloride | 9.53 |
| 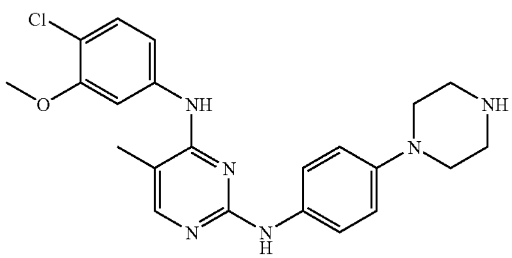 | N4-(4-Chloro-3-methoxy-phenyl)-5-methyl-N2-(4-piperazin-1-yl-phenyl)-pyrimidine-2,4-diamine | 6.15 |
| 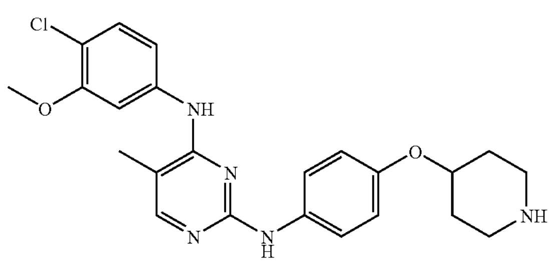 | N4-(4-Chloro-3-methoxy-phenyl)-5-methyl-N2-[4-(piperidin-4-yloxy)-phenyl]-pyrimidine-2,4-diamine | 4.14 |
| 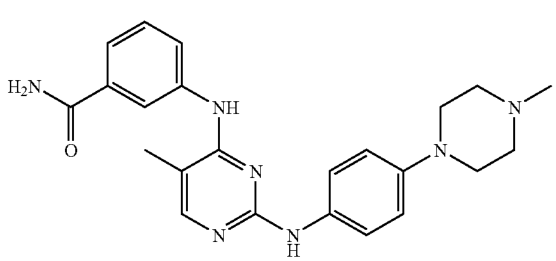 | 3-{5-Methyl-2-[4-(4-methyl-piperazin-1-yl)-phenylamino]-pyrimidin-4-ylamino}-benzamide | 23 |

TABLE 1-continued

Compounds of the Invention And Their IC Values for Jak2 Kinase

| Structure | Name | JAK2 IC50 |
|---|---|---|
| 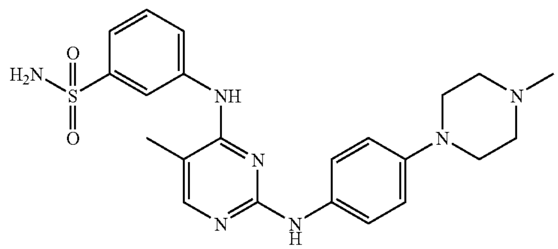 | 3-{5-Methyl-2-[4-(4-methyl-piperazin-1-yl)-phenylamino]-pyrimidin-4-ylamino}-benzenesulfonamide | 13.6 |
| 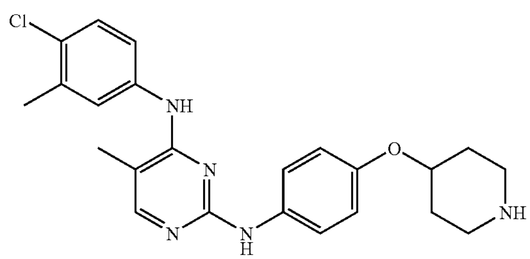 | N4-(4-Chloro-3-methyl-phenyl)-5-methyl-N2-[4-(piperidin-4-yloxy)-phenyl]-pyrimidine-2,4-diamine | 8.41 |
| 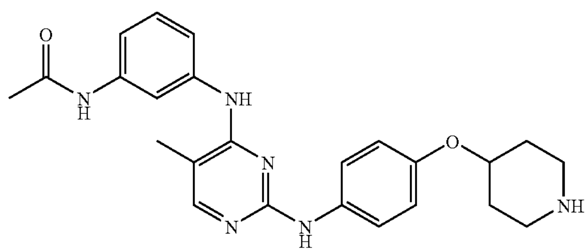 | N-(3-{5-Methyl-2-[4-(piperidin-4-yloxy)-phenylamino]-pyrimidin-4-ylamino}-phenyl)-acetamide | 137 |
| 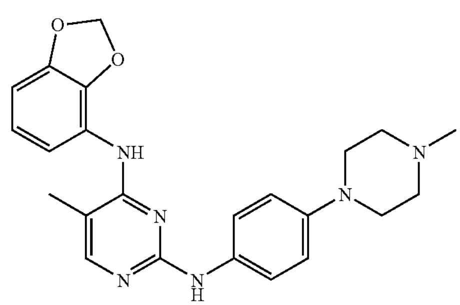 | N4-Benzo[1,3]dioxol-4-yl-5-methyl-N2-[4-(4-methyl-piperazin-1-yl)-phenyl]-pyrimidine-2,4-diamine | 14.2 |
| 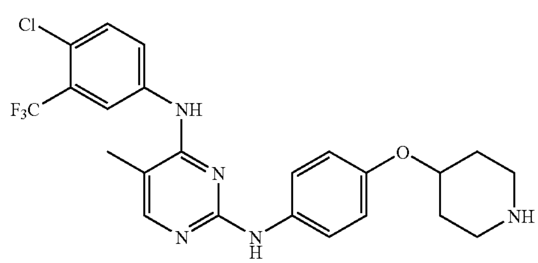 | N4-(4-Chloro-3-trifluoromethyl-phenyl)-5-methyl-N2-[4-(piperidin-4-yloxy)-phenyl]-pyrimidine-2,4-diamine | 11.4 |

TABLE 1-continued

Compounds of the Invention And Their IC Values for Jak2 Kinase

| Structure | Name | JAK2 IC50 |
|---|---|---|
| 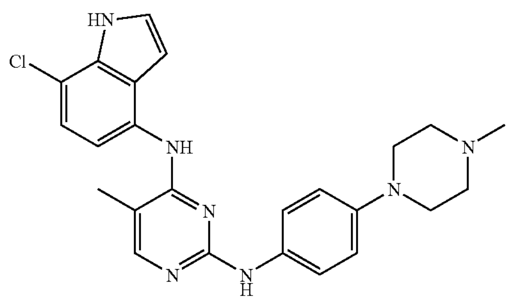 | N4-(7-chloro-1H-indol-4-yl)-5-methyl-N2-(4-(4-methylpiperazin-1-yl)phenyl)pyrimidine-2,4-diamine | 5.36 |
| 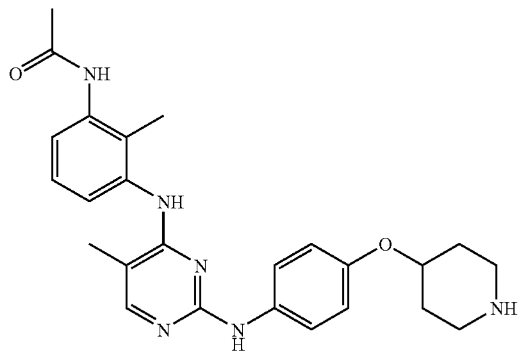 | N-(2-Methyl-3-{5-methyl-2-[4-(piperidin-4-yloxy)-phenylamino]-pyrimidin-4-ylamino}-phenyl)-acetamide | 146 |
| 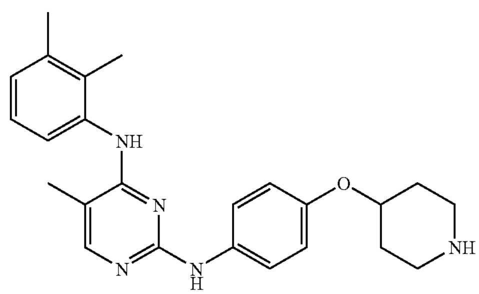 | 5-methyl-N4-(2,3-dimethylphenyl)-N2-(4-(piperidin-4-yloxy)phenyl)pyrimidine-2,4-diamine Hydrochloride | 4.38 |
| 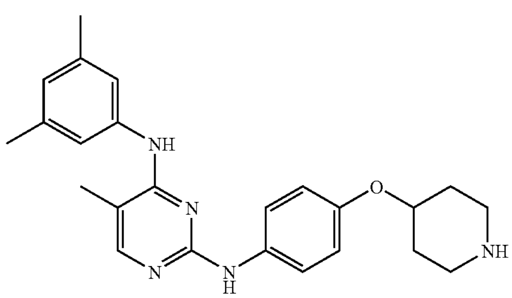 | 5-methyl-N4-(3,5-dimethylphenyl)-N2-(4-(piperidin-4-yloxy)phenyl)pyrimidine-2,4-diamine hydrochloride | 37.2 |
| 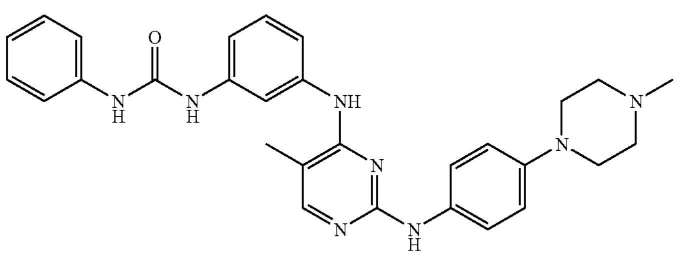 | 1-(3-{5-Methyl-2-[4-(4-methyl-piperazin-1-yl)-phenylamino]-pyrimidin-4-ylamino}-phenyl)-3-phenyl-urea | 63.6 |

TABLE 1-continued

Compounds of the Invention And Their IC Values for Jak2 Kinase

| Structure | Name | JAK2 IC50 |
|---|---|---|
| 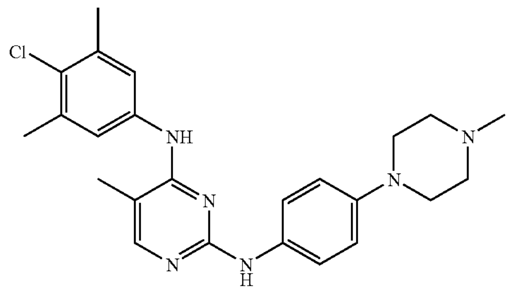 | N4-(4-chloro-3,5-dimethylphenyl)-5-methyl-N2-(4-(4-methylpiperazin-1-yl)phenyl)pyrimidine-2,4-diamine Hydrochloride | 38 |
| 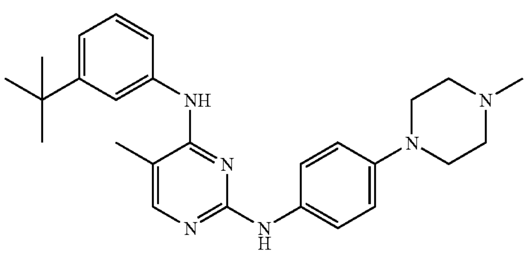 | N4-(3-tert-butylphenyl)-5-methyl-N2-(4-(4-methylpiperazin-1-yl)phenyl)pyrimidine-2,4-diamine Hydrochloride | 4.7 |
| 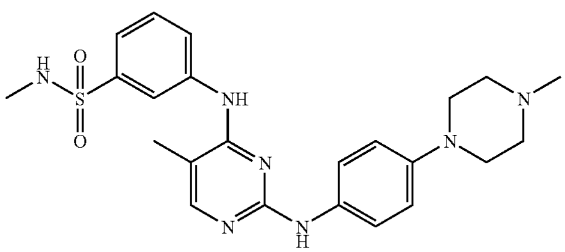 | N-Methyl-3-{5-methyl-2-[4-(4-methyl-piperazin-1-yl)-phenylamino]-pyrimidin-4-ylamino}-benzenesulfonamide | 16.1 |
| 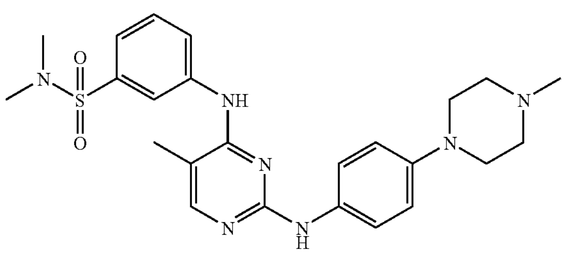 | N,N-Dimethyl-3-{5-methyl-2-[4-(4-methyl-piperazin-1-yl)-phenylamino]-pyrimidin-4-ylamino}-benzenesulfonamide | 9.5 |
| 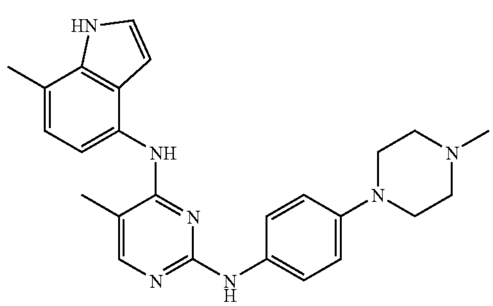 | 5-methyl-N4-(7-methyl-1H-indol-4-yl)-N2-(4-(4-methylpiperazin-1-yl)phenyl)pyrimidine-2,4-diamine Hydrochloride | 3.84 |

TABLE 1-continued

Compounds of the Invention And Their IC Values for Jak2 Kinase

| Structure | Name | JAK2 IC50 |
|---|---|---|
| 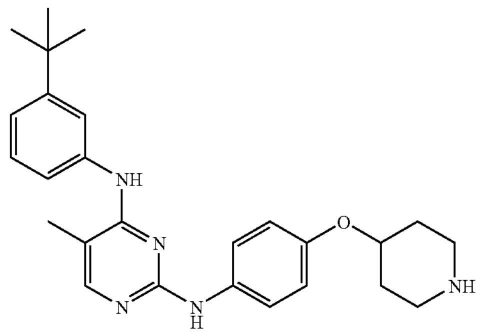 | N4-(3-tert-butylphenyl)-5-methyl-N2-(4-(piperidin-4-yloxy)phenyl)pyrimidine-2,4-diamine Hydrochloride | 2.73 |
| 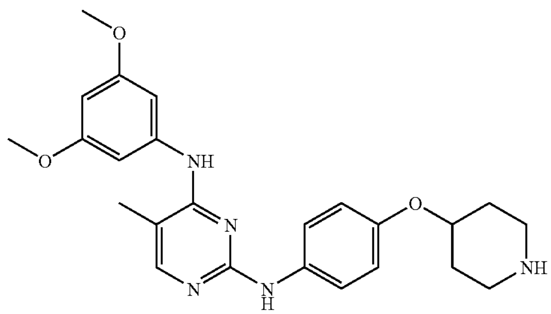 | N4-(3,5-dimethoxyphenyl)-5-methyl-N2-(4-(piperidin-4-yloxy)phenyl)pyrimidine-2,4-diamine trifluoroacetate | 137 |
| 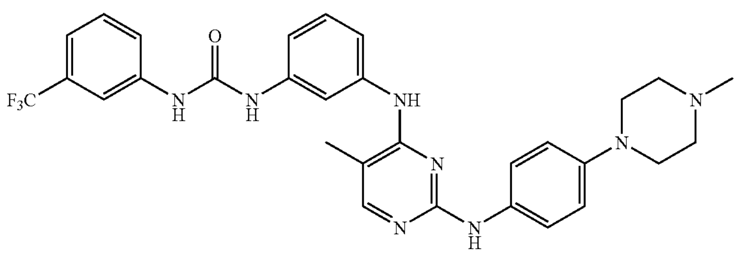 | 1-(3-{5-Methyl-2-[4-(4-methyl-piperazin-1-yl)-phenylamino]-pyrimidin-4-ylamino}-phenyl)-3-(3-trifluoromethyl-phenyl)-urea | 126 |
| 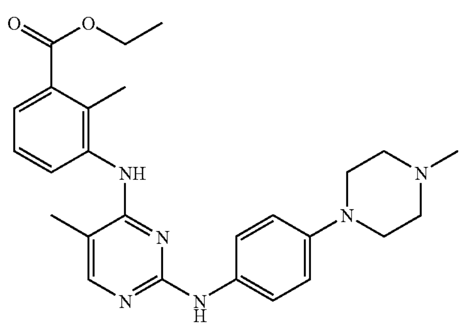 | 2-Methyl-3-{5-methyl-2-[4-(4-methyl-piperazin-1-yl)-phenylamino]-pyrimidin-4-ylamino}-benzoic acid ethyl ester | 27.8 |
| 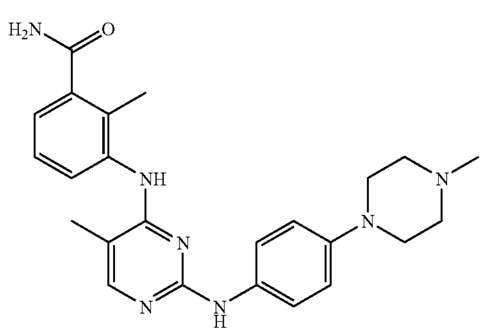 | 2-Methyl-3-{5-methyl-2-[4-(4-methyl-piperazin-1-yl)-phenylamino]-pyrimidin-4-ylamino}-benzamide | 26.2 |

TABLE 1-continued

Compounds of the Invention And Their IC Values for Jak2 Kinase

| Structure | Name | JAK2 IC50 |
|---|---|---|
| 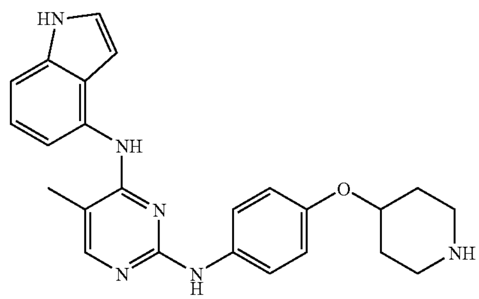 | N4-(1H-indol-4-yl)-5-methyl-N2-(4-(piperidin-4-yloxy)phenyl)pyrimidine-2,4-diamine trifluoroacetic acid salt | 4.27 |
| 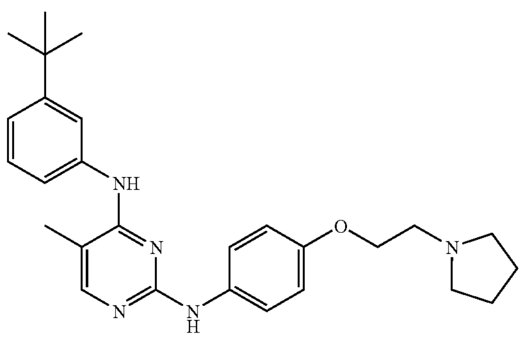 | N2-(4-(2-(pyrrolidin-1-yl)ethoxy)phenyl)-N4-(3-tert-butylphenyl)-5-methylpyrimidine-2,4-diamine Hydrochloride | 6.71 |
| 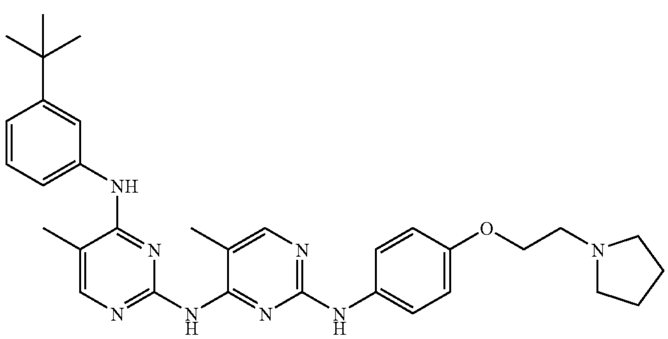 | N2-(4-(2-(pyrrolidin-1-yl)ethoxy)phenyl)-N4-(4-(3-tert-butylphenylamino)-5-methylpyrimidine-2,4-diamine Hydrochloride | 153 |
| 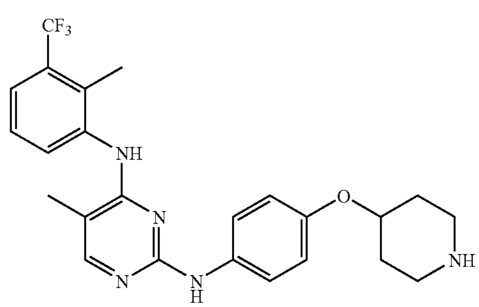 | 5-Methyl-N4-(2-methyl-3-trifluoromethyl-phenyl)-N2-[4-(piperidin-4-yloxy)-phenyl]-pyrimidine-2,4-diamine | 52.9 |
| 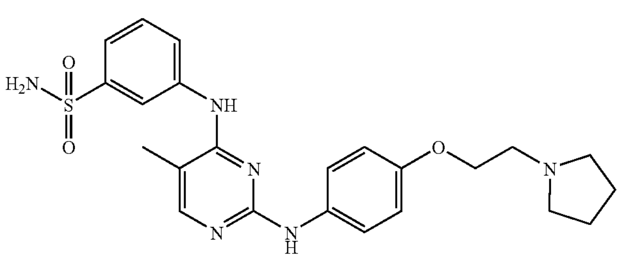 | 3-{5-Methyl-2-[4-(2-pyrrolidin-1-yl-ethoxy)-phenylamino]-pyrimidin-4-ylamino}-benzenesulfonamide | 72.2 |

TABLE 1-continued

Compounds of the Invention And Their IC Values for Jak2 Kinase

| Structure | Name | JAK2 IC50 |
|---|---|---|
| 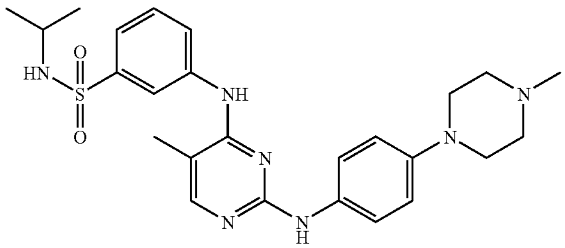 | N-Isopropyl-3-{5-methyl-2-[4-(4-methyl-piperazin-1-yl)-phenylamino]-pyrimidin-4-ylamino}-benzenesulfonamide | 11.8 |
| 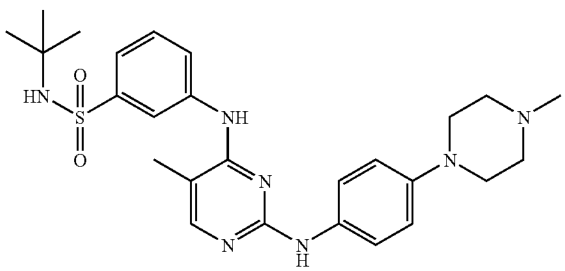 | N-tert-Butyl-3-{5-methyl-2-[4-(4-methyl-piperazin-1-yl)-phenylamino]-pyrimidin-4-ylamino}-benzenesulfonamide | 6.06 |
| 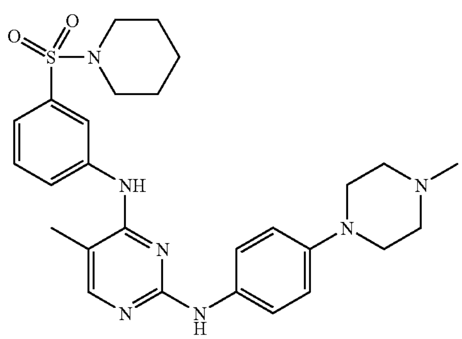 | 5-Methyl-N2-[4-(4-methyl-piperazin-1-yl)-phenyl]-N4-[3-(piperidine-1-sulfonyl)-phenyl]-pyrimidine-2,4-diamine Hydrochloride | 24.8 |
| 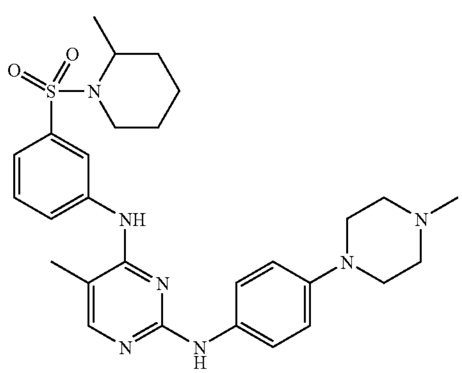 | 5-Methyl-N2-[4-(4-methyl-piperazin-1-yl)-phenyl]-N4-[3-(2-methyl-piperidine-1-sulfony)-phenyl]-pyrimidine-2,4-diamine Hydrochloride | 33.5 |
| 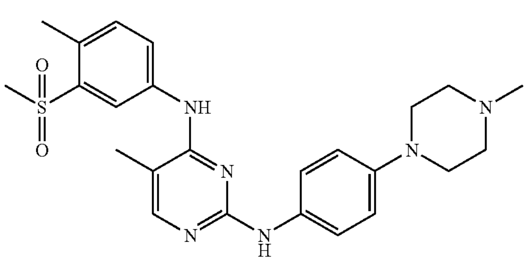 | N4-(3-Methanesulfonyl-4-methyl-phenyl)-5-methyl-N2-[4-(4-methyl-piperazin-1-yl)-phenyl]-pyrimidine-2,4-diamine | 160 |

TABLE 1-continued

Compounds of the Invention And Their IC Values for Jak2 Kinase

| Structure | Name | JAK2 IC50 |
|---|---|---|
| 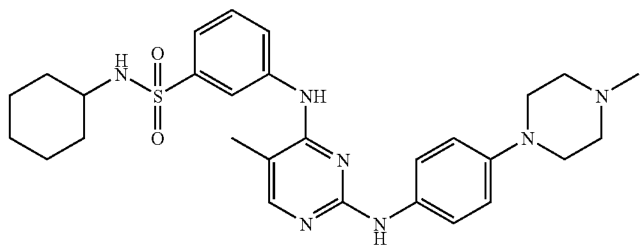 | N-Cyclohexyl-3-{5-methyl-2-[4-(4-methyl-piperazin-1-yl)-phenylamino]-pyrimidin-4-ylamino}-benzenesulfonamide | 39.4 |
| 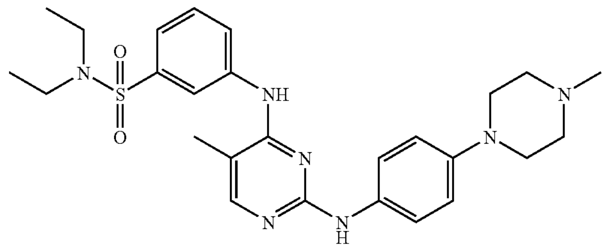 | N,N-Diethyl-3-{5-methyl-2-[4-(4-methyl-piperazin-1-yl)-phenylamino]-pyrimidin-4-ylamino}-benzenesulfonamide | 60.3 |
| 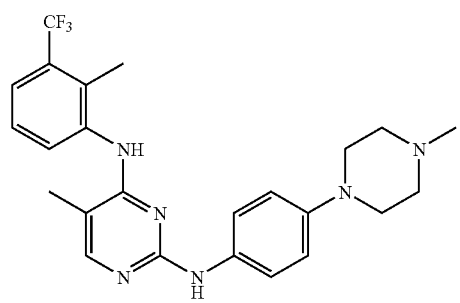 | N4-(3-(trifluoromethyl)-2-methylphenyl)-5-methyl-N2-(4-(4-methylpiperazin-1-yl)phenyl)pyrimidine-2,4-diamine hydrochloride | 87.1 |
| 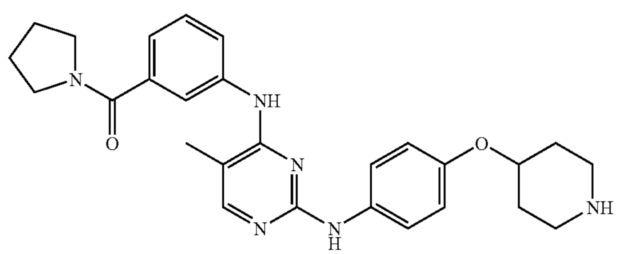 | (3-{5-Methyl-2-[4-(piperidin-4-yloxy)-phenylamino]-pyrimidin-4-ylamino}-phenyl)-pyrrolidin-1-yl-methanone | 113 |
| 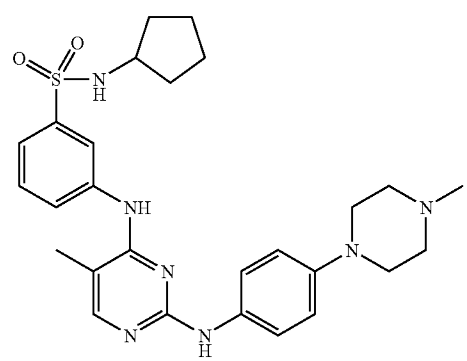 | N-Cyclopentyl3-{5-Methyl-2-[4-(4-methyl-piperazin-1-yl)-phenylamino]-pyrimidine-4-ylamino}-benzenesulfonamide Hydrochloride | 19.8 |

TABLE 1-continued

Compounds of the Invention And Their IC Values for Jak2 Kinase

| Structure | Name | JAK2 IC50 |
|---|---|---|
| 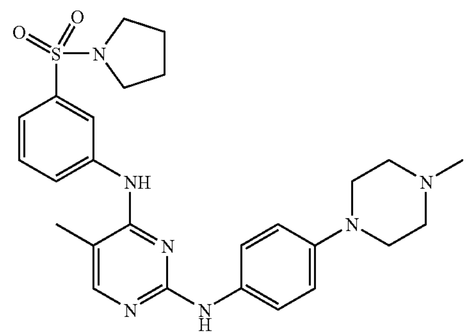 | 5-Methyl-N2-[4-(4-methyl-piperazin-1-yl)-phenyl]-N4-[3-(pyrrolidine-1-sulfonyl)-phenyl]-pyrimidine-2,4-diamine Hydrochloride | 17.1 |
| 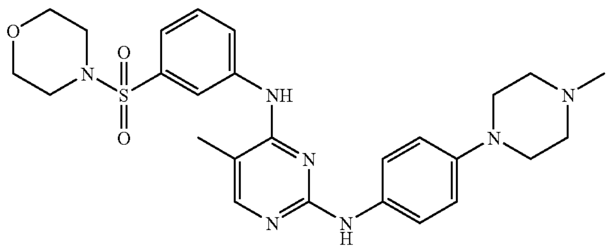 | 5-Methyl-N2-[4-(4-methyl-piperazin-1-yl)-phenyl]-N4-[3-(morpholine-4-sulfonyl)-phenyl]-pyrimidine-2,4-diamine | 20.7 |
| 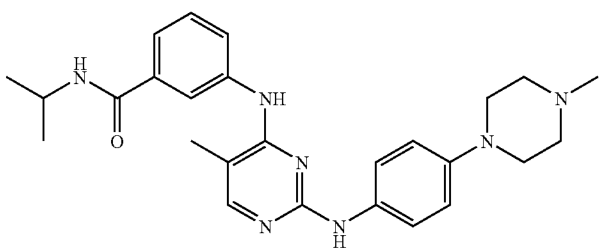 | N-Isopropyl-3-{5-methyl-2-[4-(4-methyl-piperazin-1-yl)-phenylamino]-pyrimidin-4-ylamino}-benzamide | 541 |
| 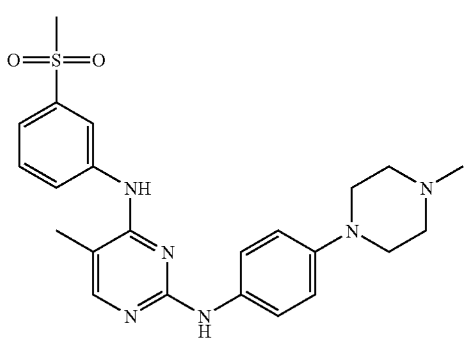 | 5-methyl-N2-(4-(4-methylpiperazin-1-yl)phenyl)-N4-(3-(methylsulfonyl)phenyl)pyrimidine-2,4-diamine | 215 |
| 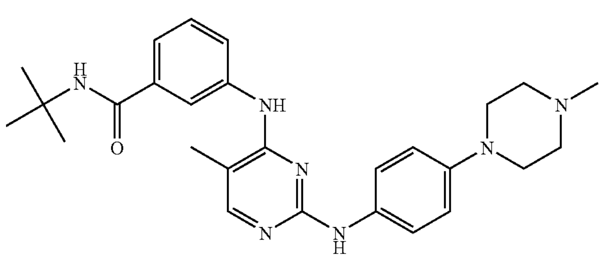 | N-tert-Butyl-3-{5-methyl-2-[4-(4-methyl-piperazin-1-yl)-phenylamino]-pyrimidin-4-ylamino}-benzamide | 890 |

TABLE 1-continued

Compounds of the Invention And Their IC Values for Jak2 Kinase

| Structure | Name | JAK2 IC50 |
|---|---|---|
| 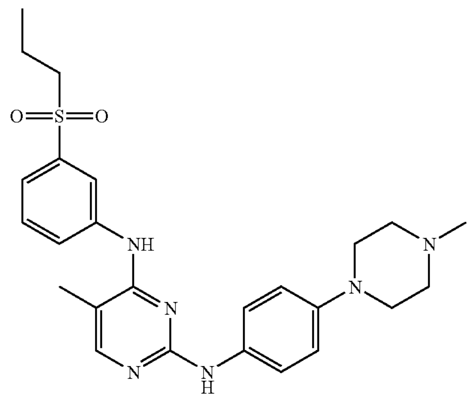 | 5-methyl-N2-(4-(4-methylpiperazin-1-yl)phenyl)-N4-(3-(propylsulfonyl)phenyl)pyrimidine-2,4-diamine | 8 |
| 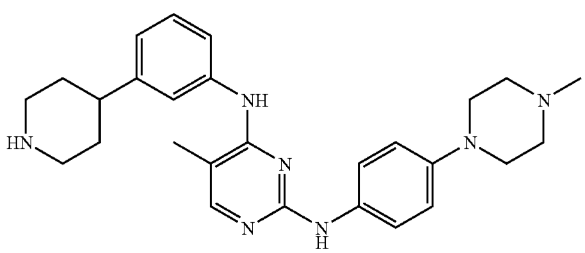 | 5-Methyl-N2-[4-(4-methyl-piperazin-1-yl)-phenyl]-N4-(3-piperidin-4-yl-phenyl)-pyrimidine-2,4-diamine | 42.5 |
| 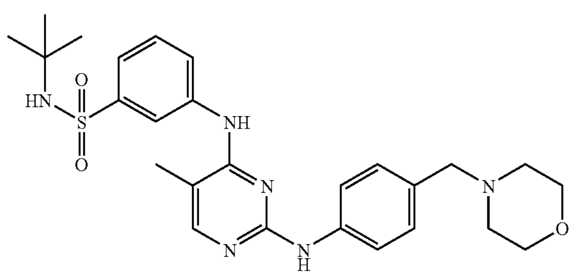 | N-tert-Butyl-3-[5-methyl-2-(4-morpholin-4-ylmethyl-phenylamino)-pyrimidin-4-ylamino]-benzenesulfonamide | 12.5 |
| 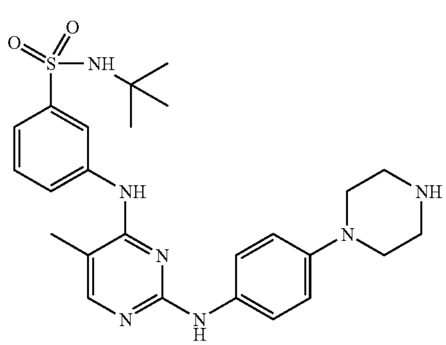 | N-tert-Butyl-3-[5-methyl-2-(4-piperazin-1-yl-phenylamino)-pyrimidin-4-ylamino]-benzenesulfonamide Hydrochloride | 7.59 |

TABLE 1-continued

Compounds of the Invention And Their IC Values for Jak2 Kinase

| Structure | Name | JAK2 IC50 |
|---|---|---|
| 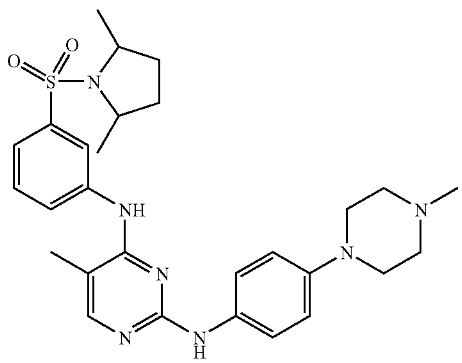 | N4-[3-(2,5-Dimethyl-pyrrolidine-1-sulfonyl)-phenyl]-5-methyl-N2-[4-(4-methyl-piperazin-1-yl)-phenyl]-pyrimidin-2,4-diamine Hydrochloride | 18.8 |
| 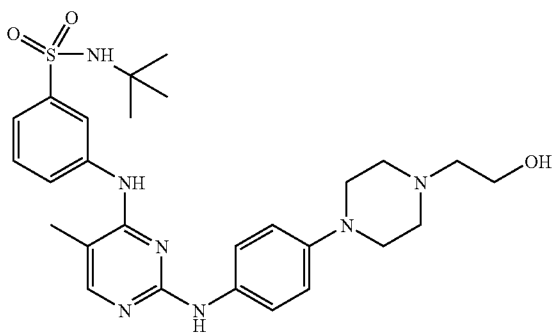 | N-tert-Butyl-3-(2-{4-[4-(2-hydroxy-ethyl)-piperazin-1-yl]-phenylamino}-[5-methyl-pyrimidin-4-ylamino]-benzenesulfonamide Hydrochloride | 7.09 |
| 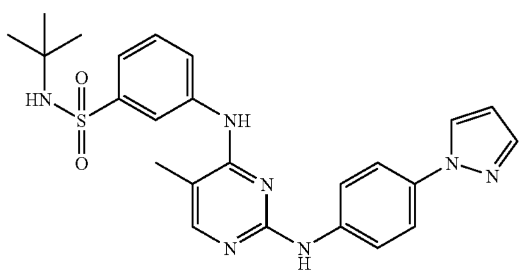 | N-tert-Butyl-3-[5-methyl-2-(4-pyrazol-1-yl-phenylamino)-pyrimidin-4-ylamino]-benzenesulfonamide | 19 |
| 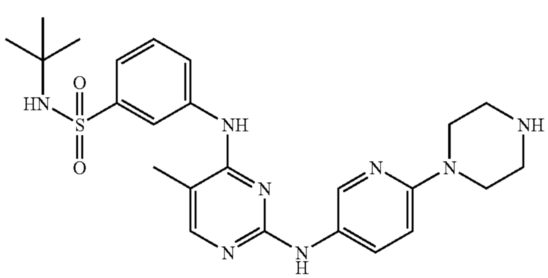 | N-tert-Butyl-3-[5-methyl-2-(6-piperazin-1-yl-pyridin-3-ylamino)-pyrimidin-4-ylamino]-benzenesulfonamide | 10 |
| 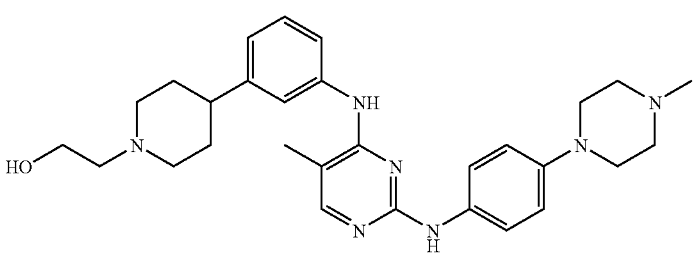 | 2-[4-(3-{5-Methyl-2-[4-(4-methyl-piperazin-1-yl)-phenylamino]-pyrimidin-4-ylamino}-phenyl)-piperidin-1-yl]-ethanol | 8.46 |

TABLE 1-continued

Compounds of the Invention And Their IC Values for Jak2 Kinase

| Structure | Name | JAK2 IC50 |
|---|---|---|
| 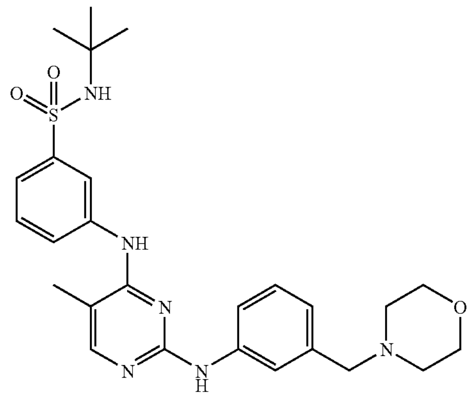 | N-tert-Butyl-3-[5-methyl-2-(3-morpholin-4-ylmethyl-phenylamino)-pyrimidin-4-ylamino]-benzenesulfonamide | 7.06 |
|  | N-tert-Butyl-3-{5-methyl-2-(4-pyrazol-1-ylmethyl-phenylamino)-pyrimidin-4-ylamino}-benzenesulfonamide | 18.6 |
| 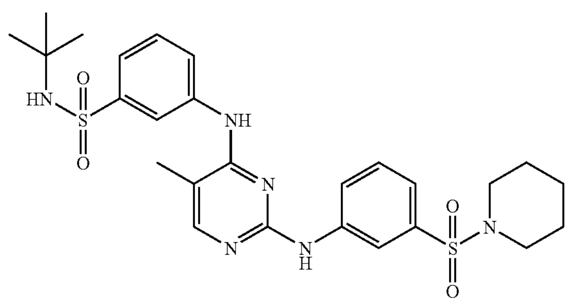 | N-tert-Butyl-3-{5-methyl-2-[3-(piperidine-1-sulfonyl)-phenylamino]-pyrimidin-4-ylamino}-benzenesulfonamide | 316 |
| 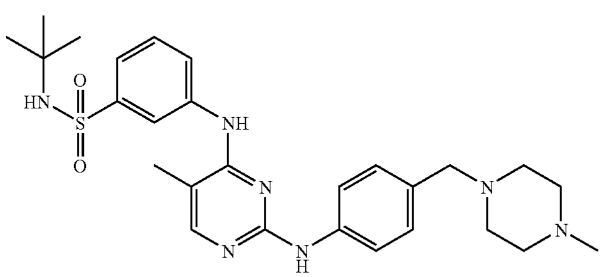 | N-tert-butyl-3-{[5-methyl-2-({4-[(4-methylpiperazin-1-yl)methyl]phenyl}amino)pyrimidin-4-yl]amino}benzenesulfonamide | 29.8 |
| 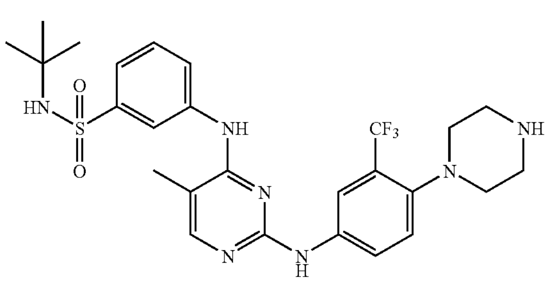 | N-tert-butyl-3-[(5-methyl-2-{[4-piperazin-1-yl-3-(trifluoromethyl)phenyl]amino}pyrimidin-4-yl)amino]benzenesulfonamide | 22.5 |

TABLE 1-continued

Compounds of the Invention And Their IC Values for Jak2 Kinase

| Structure | Name | JAK2 IC50 |
|---|---|---|
| 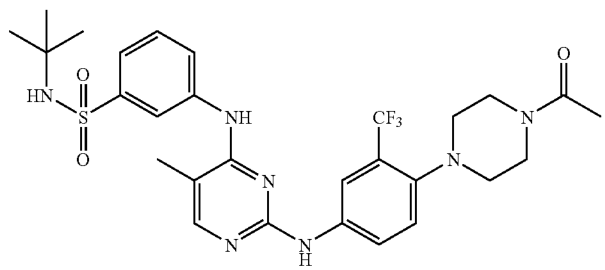 | 3-[(2-{[4-(4-acetylpiperazin-1-yl)-3-(trifluoromethyl)phenyl]amino}-5-methylpyrimidin-4-yl)amino]-N-tert-butylbenzenesulfonamide | 35.7 |
| 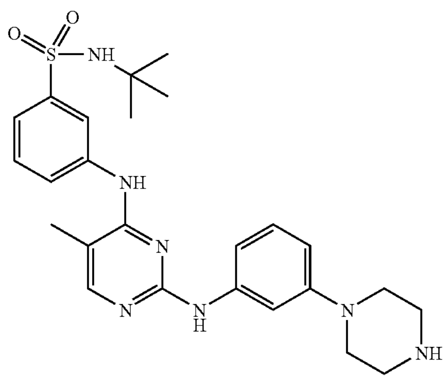 | N-tert-Butyl-3-[5-methyl-2-(3-piperazin-1-yl-phenylamino)-pyrimidin-4-ylamino]-benzenesulfonamide Hydrochloride | 18 |
| 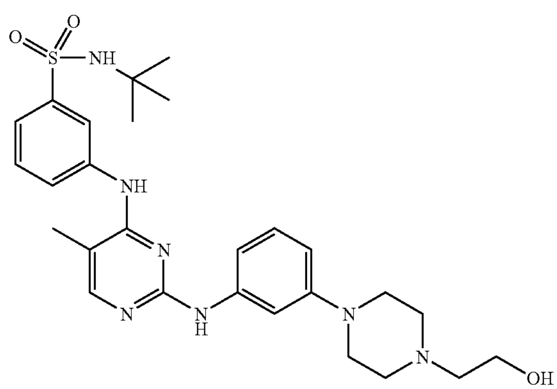 | N-tert-Butyl-3-(2-{3-[4-(2-hydroxy-ethyl)-piperazin-1-yl]-phenylamino}-[5-methyl-pyrimidin-4-ylamino]-benzenesulfonamide Hydrochloride | 40.5 |
| 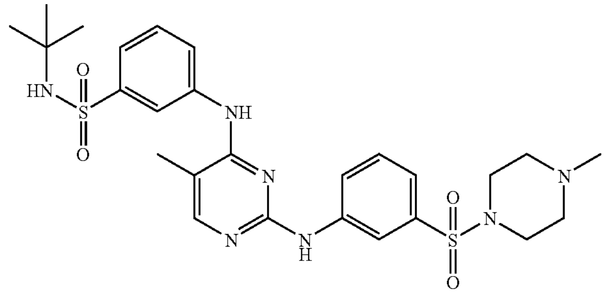 | N-tert-butyl-3-{[5-methyl-2-({3-[(4-methylpiperazin-1-yl)sulfonyl]phenyl}amino)pyrimidin-4-yl]amino}benzenesulfonamide | 650 |

TABLE 1-continued

Compounds of the Invention And Their IC Values for Jak2 Kinase

| Structure | Name | JAK2 IC50 |
|---|---|---|
| 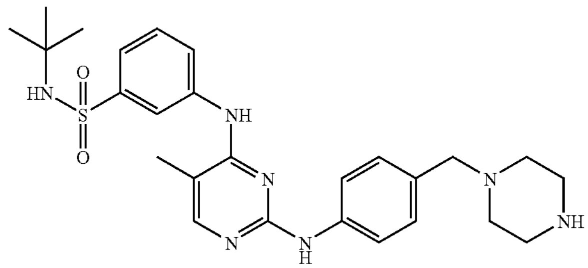 | N-tert-butyl-3-[(5-methyl-2-{[4-(piperazin-1-ylmethyl)phenyl]amino}pyrimidin-4-yl)amino]benzenesulfonamide | 4.6 |
| 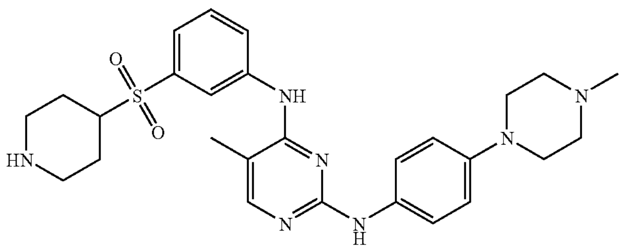 | 5-Methyl-N2-[4-(4-methyl-piperazin-1-yl)-phenyl]-N4-[3-(piperidine-4-sulfonyl)-phenyl]-pyrimidine-2,4-diamine | 198 |
| 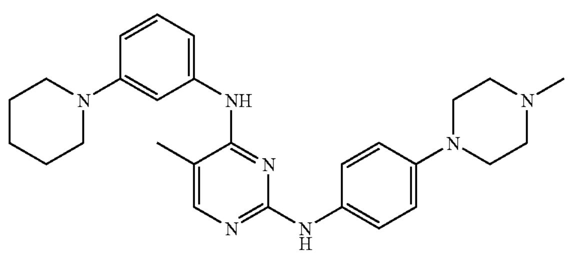 | 5-methyl-N2-(4-(4-methylpiperazin-1-yl)phenyl)-N4-(3-(piperidin-1-yl)phenyl)pyrimidine-2,4-diamine | 46.3 |
| 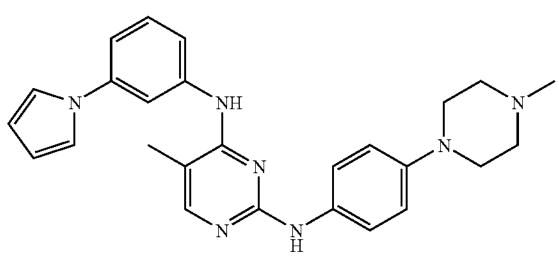 | N4-(3-(1H-pyrrol-1-yl)phenyl)-5-methyl-N2-(4-(4-methylpiperazin-1-yl)phenyl)pyrimidine-2,4-diamine | 33.8 |
| 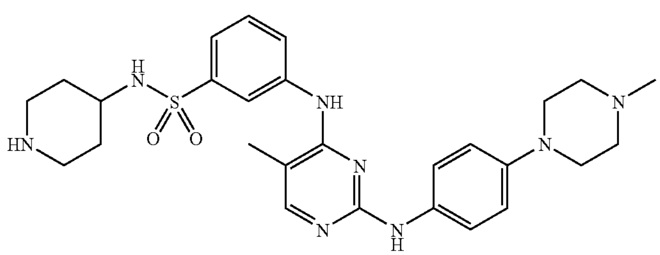 | 3-{5-Methyl-2-[4-(4-methyl-piperazin-1-yl)-phenylamino]-pyrimidin-4-ylamino}-N-piperidin-4-yl-benzenesulfonamide | 543 |

TABLE 1-continued

Compounds of the Invention And Their IC Values for Jak2 Kinase

| Structure | Name | JAK2 IC50 |
|---|---|---|
| 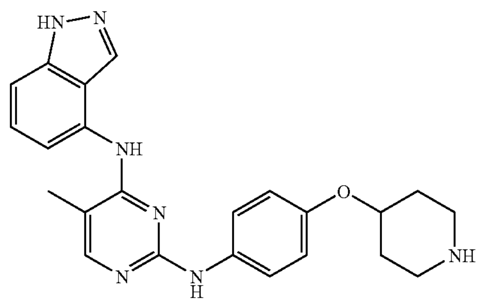 | N4-(1H-indazol-4-yl)-5-methyl-N2-(4-(piperidin-4-yloxy)phenyl)pyrimidine-2,4-diamine Hydrochloride | |
| 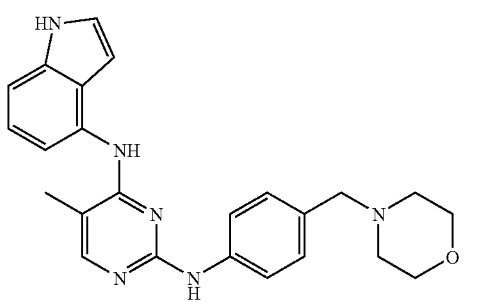 | N4-(1H-Indol-4-yl)-5-methyl-N2-(4-morpholin-4-ylmethyl-phenyl)-pyrimidine-2,4-diamine | 7.42 |
| 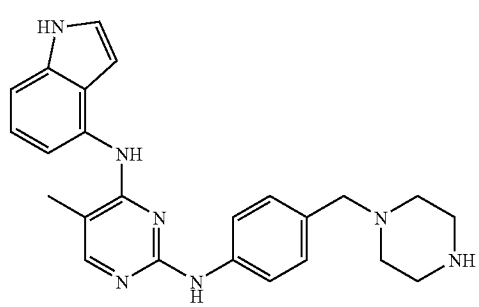 | N4-(1H-Indol-4-yl)-5-methyl-N2-(4-piperazin-1-ylmethyl-phenyl)-pyrimidine-2,4-diamine | 10.1 |
| 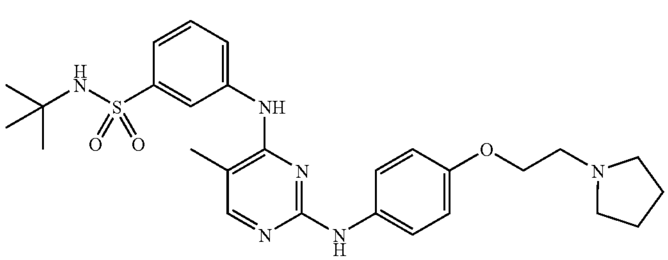 | N-tert-Butyl-3-{5-methyl-2-[4-(2-pyrrolidin-1-yl-ethoxy)-phenylamino]-pyrimidin-4-ylamino}-benzenesulfonamide | 12.5 |
| 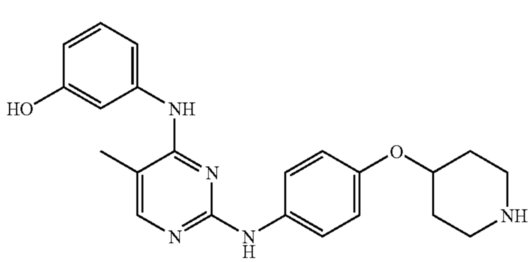 | 3-(2-(4-(piperidin-4-yloxy)phenylamino)-5-methylpyrimidin-4-ylamino)phenol | 51.9 |

TABLE 1-continued

Compounds of the Invention And Their IC Values for Jak2 Kinase

| Structure | Name | JAK2 IC50 |
|---|---|---|
| 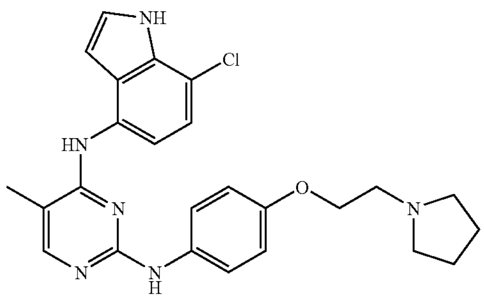 | N2-(4-(2-(pyrrolidin-1-yl)ethoxy)phenyl)-N4-(7-chloro-1H-indol-4-yl)-5-methylpyrimidine-2,4-diamine Hydrochloride | 1.16 |
| 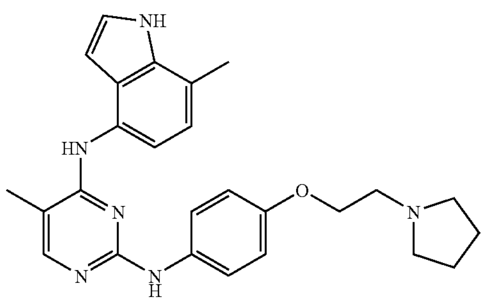 | N2-(4-(2-(pyrrolidin-1-yl)ethoxy)phenyl)-5-methyl-N4-(7-methyl-1H-indol-4-yl)pyrimidine-2,4-diamine Hydrochloride | 6.98 |
| 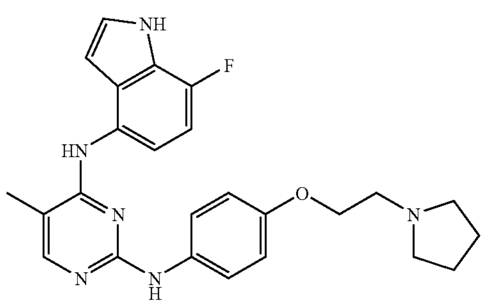 | N2-(4-(2-(pyrrolidin-1-yl)ethoxy)phenyl)-N4-(7-fluoro-1H-indol-4-yl)-5-methylpyrimidine-2,4-diamine Hydrochloride | 9.28 |
| 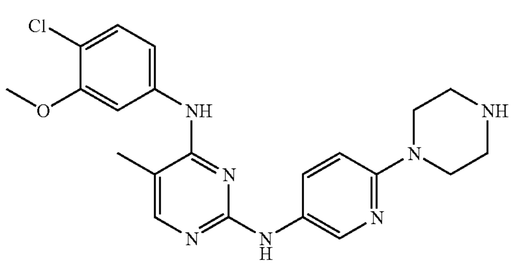 | N4-(4-Chloro-3-methoxy-phenyl)-5-methyl-N2-(6-piperazin-1-yl-pyridin-3-yl)-pyrimidine-2,4-diamine | 12.1 |
| 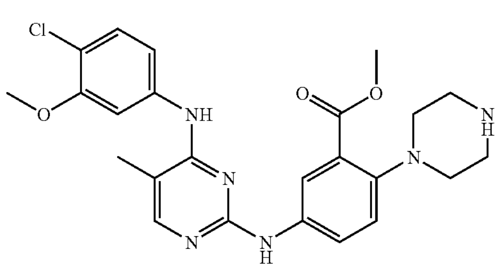 | 5-[4-(4-Chloro-3-methoxy-phenylamino)-5-methyl-pyrimidin-2-ylamino]-2-piperazin-1-yl-benzoic acid methyl ester | 5.12 |

TABLE 1-continued

Compounds of the Invention And Their IC Values for Jak2 Kinase

| Structure | Name | JAK2 IC50 |
|---|---|---|
| 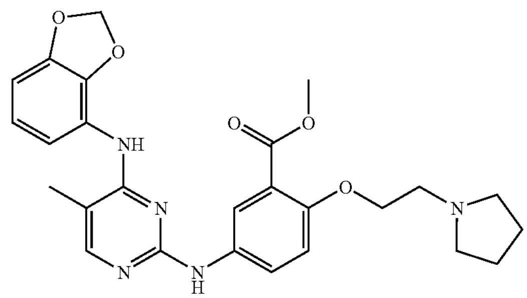 | 5-[4-(Benzo[1,3]dioxol-4-ylamino)-5-methyl-pyrimidin-2-ylamino]-2-(2-pyrrolidin-1-yl-ethoxy)-benzoic acid methyl ester | 16.4 |
| 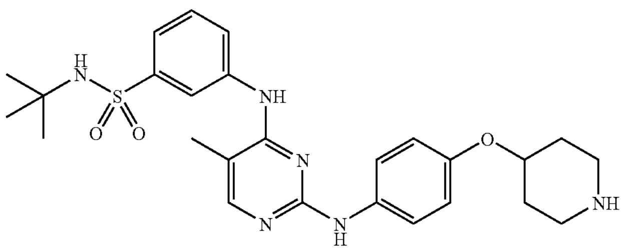 | N-tert-Butyl-3-{5-methyl-2-[4-(piperidin-4-yloxy)-phenylamino]-pyrimidin-4-ylamino}-benzenesulfonamide | 7.3 |
| 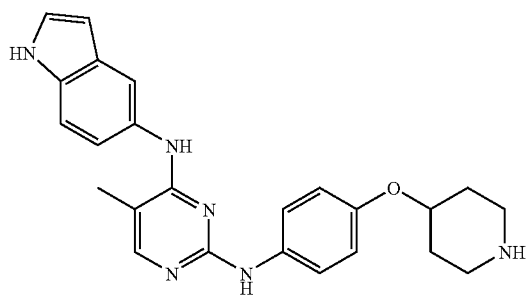 | N4-(1H-Indol-5-yl)-5-methyl-N2-[4-(piperidin-4-yloxy)-phenyl]-pyrimidine-2,4-diamine | |
| 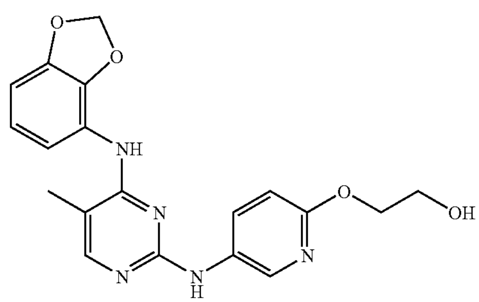 | 2-{5-[4-(Benzo[1,3]dioxol-4-ylamino)-5-methyl-pyrimidin-2-ylamino]-pyridin-2-yloxy}-ethanol | 116 |
| 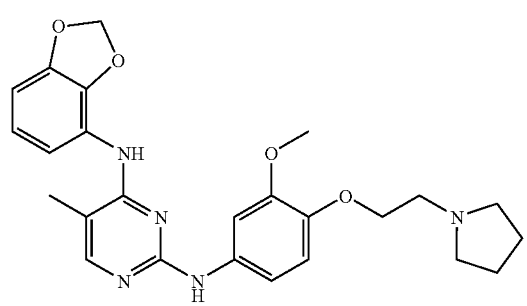 | N4-Benzo[1,3]dioxol-4-yl-N2-[3-methoxy-4-(2-pyrrolidin-1-yl-ethoxy)-phenyl]-5-methyl-pyrimidine-2,4-diamine | 9.34 |

TABLE 1-continued

Compounds of the Invention And Their IC Values for Jak2 Kinase

| Structure | Name | JAK2 IC50 |
|---|---|---|
| 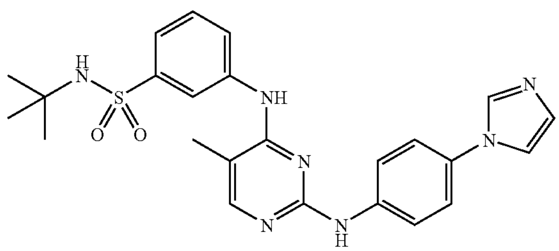 | N-tert-Butyl-3-[2-(4-imidazol-1-yl-phenylamino)-5-methyl-pyrimidin-4-ylamino]-benzenesulfonamide | 12.3 |
| 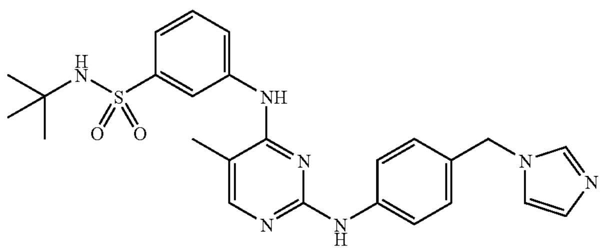 | N-tert-Butyl-3-[2-(4-imidazol-1-ylmethyl-phenylamino)-5-methyl-pyrimidin-4-ylamino]-benzenesulfonamide | 8.42 |
| 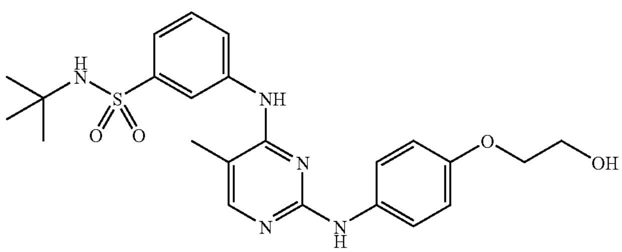 | N-tert-Butyl-3-{2-[4-(2-hydroxy-ethoxy)-phenylamino]-5-methyl-pyrimidin-4-ylamino}-benzenesulfonamide | 20.3 |
| 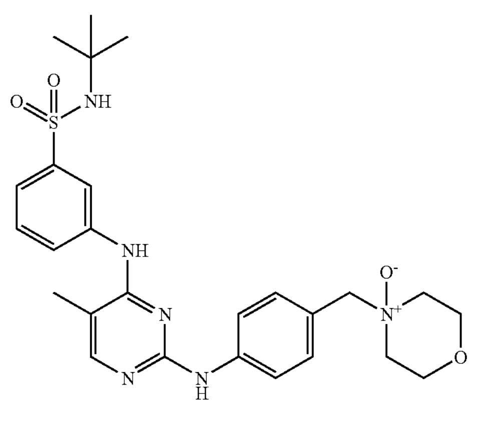 | N-tert-Butyl-3-{5-methyl-2-[4-(4-oxy-morpholin-4-ylmethyl)-phenylamino]-pyrimidin-4-ylamino}-benzenesulfonamide | 48.6 |
| 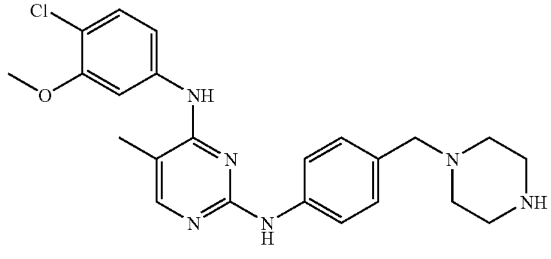 | N4-(4-Chloro-3-methoxy-phenyl)-5-methyl-N2-(4-piperazin-1-ylmethyl-phenyl)-pyrimidine-2,4-diamine | 15.2 |

TABLE 1-continued

Compounds of the Invention And Their IC Values for Jak2 Kinase

| Structure | Name | JAK2 IC50 |
|---|---|---|
| 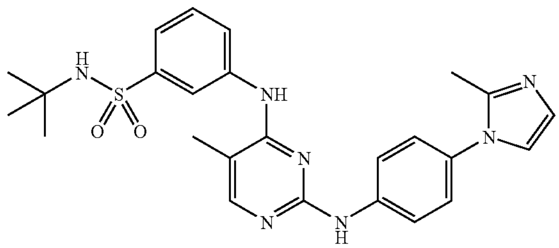 | N-tert-Butyl-3-{5-methyl-2-[4-(2-methyl-imidazol-1-yl)-phenylamino]-pyrimidin-4-ylamino}-benzenesulfonamide | 34.3 |
| 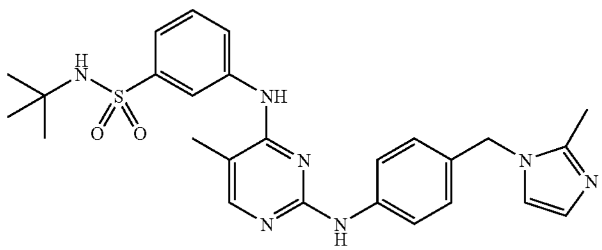 | N-tert-Butyl-3-{5-methyl-2-[4-(2-methyl-imidazol-1-ylmethyl)-phenylamino]-pyrimidin-4-ylamino}-benzenesulfonamide | 21.9 |
| 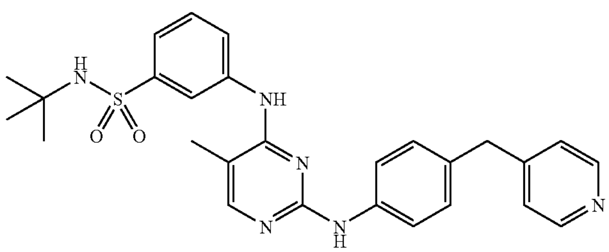 | N-tert-Butyl-3-{5-methyl-2-(4-pyridin-4-ylmethyl-phenylamino)-pyrimidin-4-ylamino]-benzenesulfonamide | 80.7 |
| 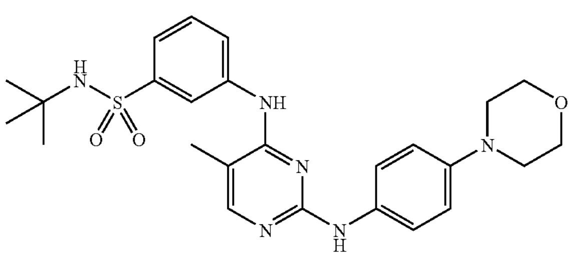 | N-tert-Butyl-3-[5-methyl-2-(4-morpholin-4-yl-phenylamino)-pyrimidin-4-ylamino]-benzenesulfonamide | 12.1 |
| 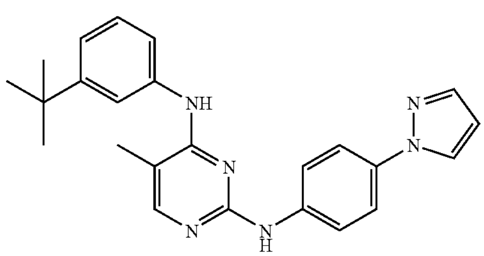 | N2-(4-(1H-pyrazol-1-yl)phenyl)-N4-(3-tert-butylphenyl)-5-methylpyrimidin-2,4-diamine | 151 |

TABLE 1-continued

Compounds of the Invention And Their IC Values for Jak2 Kinase

| Structure | Name | JAK2 IC50 |
|---|---|---|
| 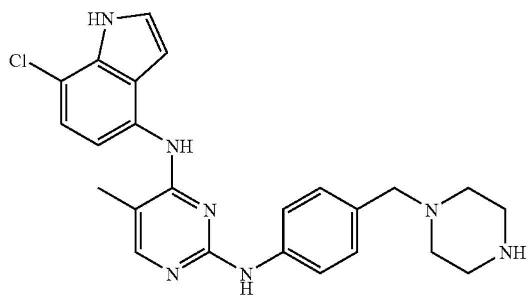 | N4-(7-chloro-1H-indol-4-yl)-5-methyl-N2-(4-((piperazin-1-yl)methyl)phenyl)pyrimidine-2,4-diamine Hydrochloride | 694 |
|  | N4-(3-tert-butylphenyl)-5-methyl-N2-(4-(2-methyl-1H-imidazol-1-yl)phenyl)pyrimidine-2,4-diamine Hydrochloride | 38.4 |
|  | N4-(3-tert-butylphenyl)-5-methyl-N2-(4-(2-methyl-1H-imidazol-1-yl)phenyl)pyrimidine-2,4-diamine Hydrochloride | 94.1 |
| 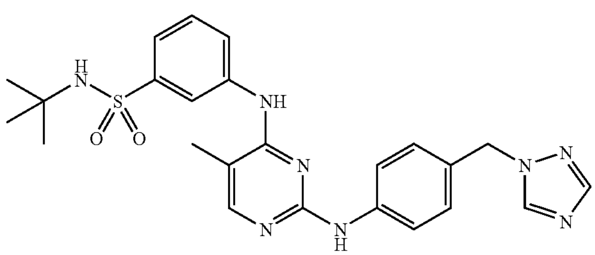 | N-tert-Butyl-3-[5-methyl-2-(4-[1,2,4]triazol-1-ylmethyl-phenylamino)-pyrimidin-4-ylamino]-benzenesulfonamide | 35.4 |
| 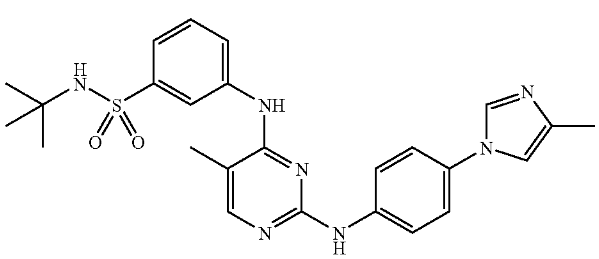 | N-tert-Butyl-3-{5-methyl-2-[4-(4-methyl-imidazol-1-yl)-phenylamino]-pyrimidin-4-ylamino}-benzenesulfonamide | 41.7 |

TABLE 1-continued

Compounds of the Invention And Their IC Values for Jak2 Kinase

| Structure | Name | JAK2 IC50 |
|---|---|---|
| 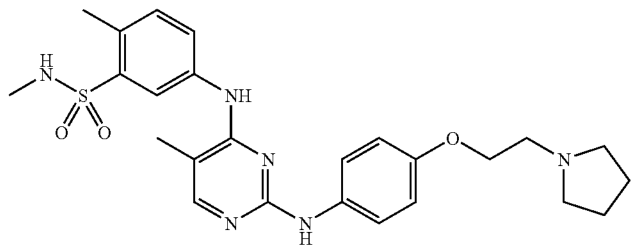 | 2,N-Dimethyl-5-{5-methyl-2-[4-(2-pyrrolidin-1-yl-ethoxy)-phenylamino]-pyrimidin-4-ylamino}-benzenesulfonamide | 127 |
| 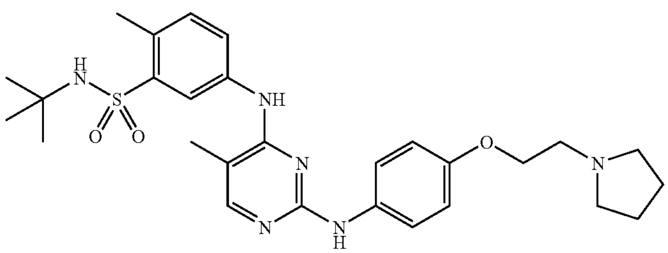 | N-tert-Butyl-2-methyl-5-{5-methyl-2-[4-(2-pyrrolidin-1-yl-ethoxy)-phenylamino]-pyrimidin-4-ylamino}-benzenesulfonamide | 44.4 |
| 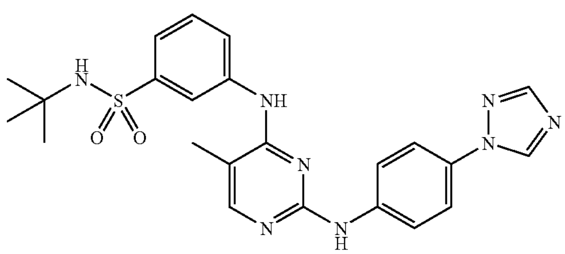 | N-tert-Butyl-3-[5-methyl-2-(4-[1,2,4]triazol-1-yl-phenylamino)-pyrimidin-4-ylamino]-benzenesulfonamide | 41.4 |
| 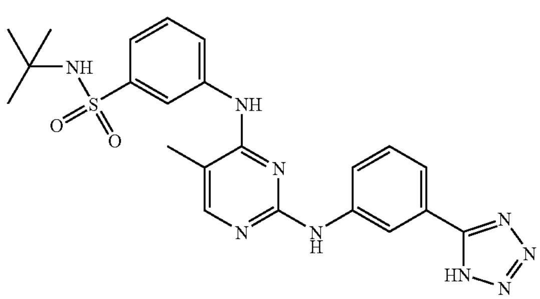 | N-tert-Butyl-3-{5-methyl-2-[3-(1H-tetrazol-5-yl)-phenylamino]-pyrimidin-4-ylamino}-benzenesulfonamide | 55.9 |
| 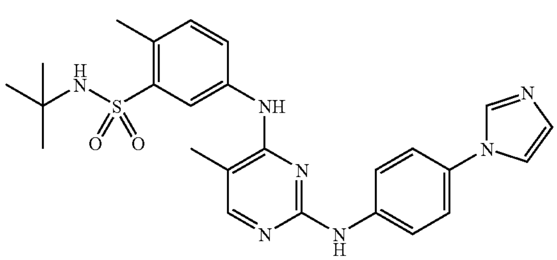 | N-tert-Butyl-5-[2-(4-imidazol-1-yl-phenylamino)-5-methyl-pyrimidin-4-ylamino]-2-methyl-benzenesulfonamide | 88.2 |

TABLE 1-continued

Compounds of the Invention And Their IC Values for Jak2 Kinase

| Structure | Name | JAK2 IC50 |
|---|---|---|
| 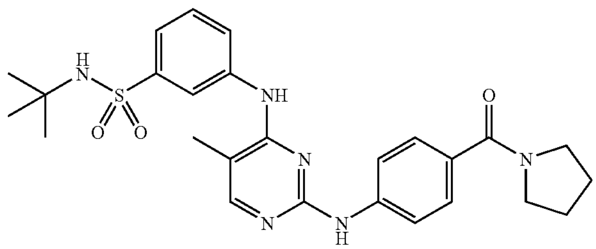 | N-tert-Butyl-3-{5-methyl-2-[4-(pyrrolidine-1-carbonyl)-phenylamino]-pyrimidin-4-ylamino}-benzenesulfonamide | 33.5 |
| 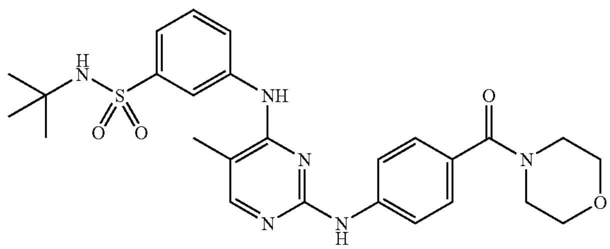 | N-tert-Butyl-3-{5-methyl-2-[4-(morpholine-4-carbonyl)-phenylamino]-pyrimidin-4-ylamino}-benzenesulfonamide | 32.9 |
| 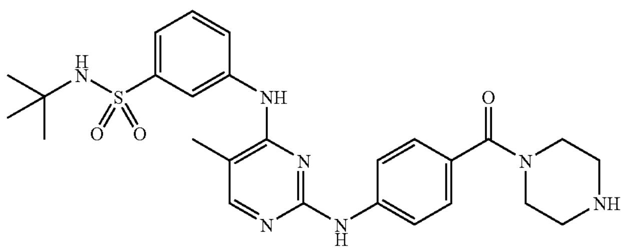 | N-tert-Butyl-3-{5-methyl-2-[4-(piperazine-1-carbonyl)-phenylamino]-pyrimidin-4-ylamino}-benzenesulfonamide | 69 |
| 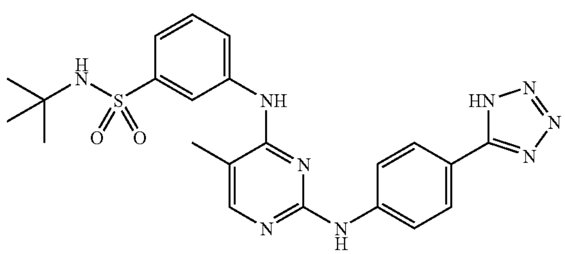 | N-tert-Butyl-3-{5-methyl-2-[4-(1H-tetrazol-5-yl)-phenylamino]-pyrimidin-4-ylamino}-benzenesulfonamide | 96.7 |
| 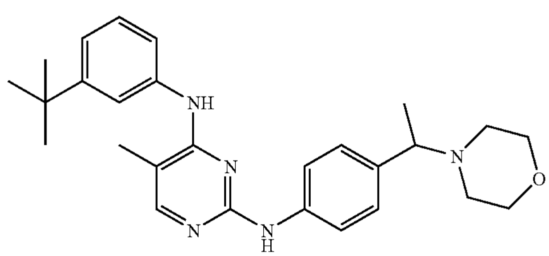 | N4-(3-tert-butylphenyl)-5-methyl-N2-(4-(1-morpholinoethyl)-phenyl)pyrimidine-2,4-diamine Hydrochloride | 19.9 |
| 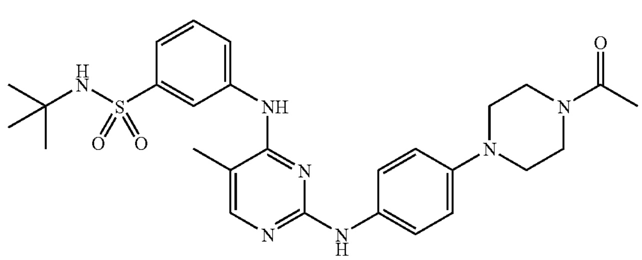 | 3-{2-[4-(4-Acetyl-piperazin-1-yl)-phenylamino]-5-methyl-pyrimidin-4-ylamino}-N-tert-butyl-benzenesulfonamide | 18.6 |

TABLE 1-continued

Compounds of the Invention And Their IC Values for Jak2 Kinase

| Structure | Name | JAK2 IC50 |
|---|---|---|
| 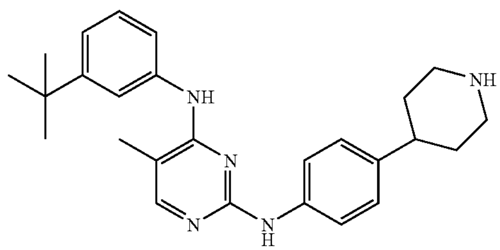 | N4-(3-tert-butylphenyl)-5-methyl-N2-(4-(piperidin-4-yl)phenyl)pyrimidine-2,4-diamine Hydrochloride | 20.9 |
| 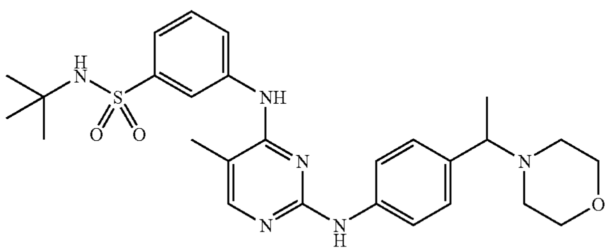 | N-tert-Butyl-3-{5-methyl-2-[4-(1-morpholin-4-yl-ethyl)-phenylamino]-pyrimidin-4-ylamino}-benzenesulfonamide | 29.7 |
| 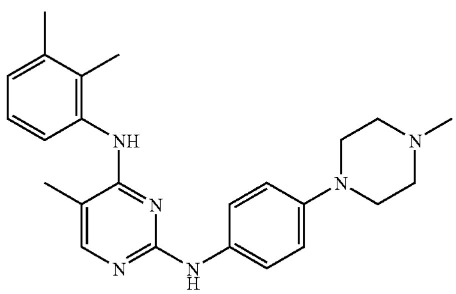 | 5-methyl-N4-(2,3-dimethylphenyl)-N2-(4-(4-methylpiperazin-1-yl)phenyl)pyrimidine-2,4-diamine Hydrochloride | 16 |
| 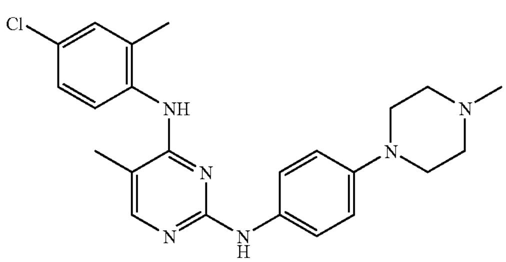 | N4-(4-chloro-2-methylphenyl)-5-methyl-N2-(4-(4-methylpiperazin-1-yl)phenyl)pyrimidine-2,4-diamine Hydrochloride | 15.9 |
| 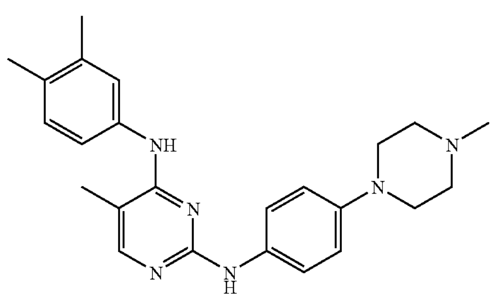 | 5-methyl-N4-(3,4-dimethylphenyl)-N2-(4-(4-methylpiperazin-1-yl)phenyl)pyrimidine-2,4-diamine Hydrochloride | 16.6 |

Example 244

Determination of Efficacy of Selected Compounds

HEL, CTLL-2 & normal human dermal fibroblasts (NHDF) were from the American Tissue Culture Collection (Rockville, Md.). BaF/3 cells were obtained from DKFZ Cancer Research Center (Heidelberg, Germany).

BaF/3, HEL & NHDF cells were grown in RPMI 1640 medium (Gibco BRL, Gaithersburg, Md.) supplemented with penicillin, streptomycin, L-glutamine, and 10% fetal bovine serum (FBS). CTLL-2 cells were grown in the same media further supplemented with 20 U/mL recombinant IL-2 (Hoffmann-LaRoche, Nutley, N.J.). Plasmid containing the human JAK2 coding sequence was purchased from Invitrogen (Madison, Wis.). JAK2$^{V617F}$ cDNA was generated by using site-directed mutagenesis to introduce the V617F mutation into the human JAK2 coding sequence followed by verification using two-directional sequencing. This cDNA was subsequently subcloned into a retroviral vector and transduced into BaF/3 cells. Permanently transduced BaF/3 cells expressing JAK2$^{V617F}$ were selected and maintained with 1 mg/ml G418. GFP was introduced into this cells by lentiviral transduction using pLenti6-GFP (Invitrogen) followed by selection with blasticidin and confirmation of GFP expression using FACs analysis.

Cell proliferation assay was performed using the XTT cell proliferation kit according to the manufacturer's instructions (Roche, Alameda, Calif.). In brief, approximately 2.5×103 cells were plated in triplicate into microtiter-plate wells in 100 µL RPMI growth media plus various doses of XLV. After 72 hour incubation twenty microliters of XTT was added to the wells and allowed to incubate for 4-6 hours. The colored formazan product that is formed was measured spectrophotometrically using the Vmax spectrophotometer (Molecular Devices, Sunnyvale, Calif.) at 450 nm with correction at 650 nm. IC50 values were determined using the GraphPad Prism 4.0 software (San Diego, Calif.), wherefore OD values were plotted on y-axis (linear scale) and concentration (mM) on the x-axis (log scale). Data was subjected to a non-linear regression fit analysis and IC$_{50}$ values were determined as the concentration which inhibited proliferation 50%.

Proliferation EC50:
HEL—270 nM
Baf3:JAK2V617F—297 nM
Control data: IL-2-induced JAK3-dependent proliferation—3395 nM
Control data: Normal human dermal fibroblast control—6487 nM Apoptosis Assays BaF/3-JAK$^{V617F}$ cells cultured in growth medium (RPMI, 10% FBS, 1 mg/ml G418 and 10 µg/ml blasticidin) were treated with XLV at 1, 3 and 10 µM for 24 h. Following harvesting cells by centrifugation at 890 RCF (relative centrifugation force) for 5 min, genomic DNA was isolated from cell pellets using a DNA isolation kit (Puregen, Chino, Calif.). 5 µg genomic DNA of each sample was subjected to 1.2% agarose gel electrophoresis to detect genomic DNA fragmentation (DNA laddering assay). As a control, adherent normal human dermal fibroblasts (NHDF) cultured in growth medium (Cambrex, Walkersville, Md.) at 60% confluence were treated with XLV as described above. Following 2 washes with ice cold PBS, genomic DNA was isolated from the NHDF cells for agarose gel electrophoresis.

Immunoblotting

BaF/3-JAK$^{V617F}$ cells treated with XLV or vehicle control were centrifuged, washed 2× with ice-cold PBS and lysed using RIPA buffer. Protein concentration was determined using the BCA method (Pierce, Rockford, Ill.) and 100 µg of total cellular protein of each sample in 1× Laemmli buffer were subjected to Western blot analysis. The protein blot was probed with an anti-phospho-STAT5 (Tyr694/699) (Upstate Biotechnology, Charlottesville, Va.), subsequently stripped and re-probed with an anti-STAT5antibody (Cell Signaling Technology, Danvers, Mass.). The phospho-STAT5 or STAT5 protein was visualized by the enhanced chemoluminescence method (Pierce). In vivo signaling studies were done in a similar fashion. Briefly, on day 11 after cell injection, animals were orally dosed with either vehicle or 100 mg/kg of XLV. Spleens were harvested 7 h after dosing and quickly homogenized in a FastPrep machine (Qbiogen, Irvine, Calif.). 100 µg of each spleen homogenate were subjected to Western blot analysis. The protein blot was probed with an anti-phospho-STAT5 (Tyr694/699) and subsequently with an anti-STAT5 antibody and visualized by the enhanced chemoluminescence method.

FACs Analysis of Circulating Tumor Burden

On day 11 after injection of BaF/3-JAK2$^{V617F}$ cell suspension, 1 mL blood was collected by a terminal cardiac bleeding method from one mouse that received vehicle, moreover, 0.1 mL blood was collected by a non-lethal retro-orbital collection method from 10 mice of each of the three groups dosed with 10, 30 or 100 mg/kg of XLV and pooled together within the dose groups. Blood mono-nucleated cells were isolated by a Ficoll (Sigma-Aldrich, St. Louis, Mo.) cushion centrifugation method (600 RCF and 30 min). The isolated cells were subjected to FACS analysis to determine the percentage of GFP positive BaF/3:JAK2$^{V617F}$ cells. The results are shown in FIG. 1

Circulating Tumor Model

Figure 2:
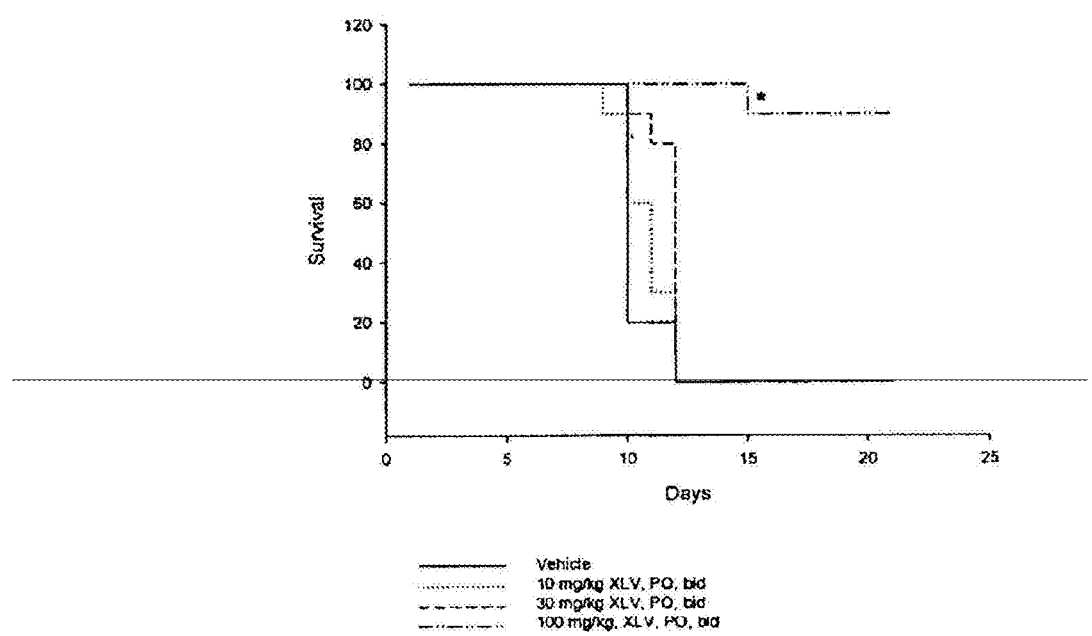
FIG. 2 depicts an in vivo study of compound XLV using a circulating tumor model as described in Example 244.

SCID mice were intravenously injected with BaF/3 cells expressing JAK2 V617F and GFP. XLV was dosed orally at the indicated doses beginning 3 days after infusion and ending 20 days after infusion. On day 11 blood was taken from animals in each group and subjected to FACs analysis to determine the percentage of circulating cells which were GFP positive. In a parallel study animals were treated as described above with the exception that they were given a single 100 mg/kg dose of drug on day 11 followed 4 hours later by sacrifice and analysis of STAT5 phosphorylation in the tumor-bearing enlarged spleen. The results are shown in FIG. 2

Ocular Exposure and Efficacy Data

Exposure Data of Compounds at 0.1% Via Eye Drop Administration:

On topical dosing of compounds formulated as 0.1% doses in 0.2% tyloxapol/1% HPMC/4% Mannitol, exposure levels in found in back of the eye tissues of the mouse are shown at two different time points, namely at 2 h and at 7 h. The efficacy data for selected compounds are shown in Table 2.

TABLE 2

Concentration (nM) in mouse ocular tissues following bilateral topical instillation of 0.1% formulation QDX1

| Formulation concentration for selected compounds | Time (hr) | Concentration (nM) | | |
|---|---|---|---|---|
| | | retina | Sclera/choroid | Cornea |
| 0.1% XVII | 2 | 495 | 6040 | 8840 |
| | 6 | 351 | 2970 | 3780 |
| 0.1% XXXVI | 2 | 816 | 7250 | 7870 |
| | 7 | 11200 | 34800 | 18600 |
| 0.1% XLIV | 2 | 406 | 4840 | 103000 |
| | 7 | 321 | 3180 | 26600 |
| 0.1% LXXXII | 2 | 267 | 2340 | 69900 |
| | 7 | 592 | 2250 | 45400 |
| 0.1% LXXIV | 2 | 2120 | 6090 | 45000 |
| | 7 | 2150 | 7350 | 21000 |

Compound XVII in an Ocular Efficacy Study in an Oxygen-Induced Retinopathy (OIR) Model Compound XVII was tested using the mouse oxygen-induced retinopathy (OIR) model, in which retinal neovascularization is triggered by cycling mouse pups from normoxia to hyperoxia and then back to normoxia. Litters of C57BL/6 mice were transferred to a hyperoxic environment (70% $O_2$) starting on postnatal day 7 (P7). After 5 days, litters were returned to a normoxic environment (21% $O_2$), where they were then maintained for an additional 5 days, during which time they received topical applications of either compound XVII or an appropriate vehicle. At the end of this period, retinal whole-mounts were prepared and stained with a fluorescently-labeled lectin (BSL I) that recognizes murine endothelium. Finally, digital images were obtained by fluorescence microscopy and analyzed with an image analysis software program in order to quantify vascular area. In one study, animals dosed with a 0.1% formulation of compound XVII twice daily (bid) showed a 29% reduction in vascular area as compared to vehicle-treated animals (P<0.05, n=11-15); in a second study, a 22% reduction was observed (P<0.02, n=6). The results are summarized in Table 3.

TABLE 3

| Study # | Treatment Group | Vascular Area ($mm^2$, mean ± SD) | % Change vs. Vehicle Control |
|---|---|---|---|
| OIR-004 | Vehicle | 4.9 ± 1.6 | — |
|  | 0.1% XVII | 3.5 ± 0.6 | −29% |
| OIR-007 | Vehicle | 8.3 ± 0.8 | — |
|  | 0.1% XVII | 6.4 ± 1.6 | −22% |

Although the invention has been described with reference to the above examples, it will be understood that modifications and variations are encompassed within the spirit and scope of the invention. Accordingly, the invention is limited only by the following claims.

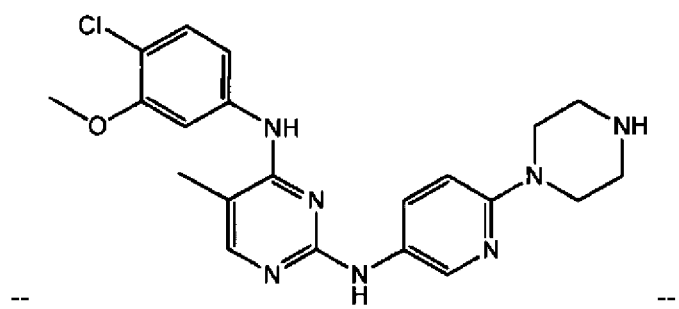

What is claimed is:

1. A method of inhibiting JAK2 kinase activity in a subject wherein the subject has a myeloproliferative disorder, comprising administering to the subject with a myeloproliferative disorder an effective amount of a compound having the structure (A):

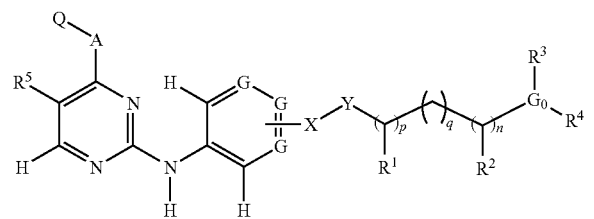

(A)

wherein:
X is selected from a group consisting of a bond, O and $CH_2$;
Y is selected from a group consisting of a bond or $NR^9$;
or X and Y taken together is a bond;
each of $R^1$ and $R^2$ is independently selected from a group consisting of H, $C_1$-$C_6$ alkyl, cycloalkyl, or $R^1$ and $R^2$ taken together is a bond; or $R^1$ and $R^2$ taken together form a moiety selected from a group consisting of $(CH_2)_m$, $(CH_2)_r$—S—$(CH_2)_m$, $(CH_2)_r$—SO—$(CH_2)_m$, $(CH_2)_r$—$SO_2$—$(CH_2)_m$, $(CH_2)_r$—$NR^9$—$(CH_2)_m$, and $(CH_2)_r$—O—$(CH_2)_m$;
each of p, q, r, n, m is independently an integer having the value between 0 and 6,
each $R^9$ is independently selected from a group consisting of H, $C_1$-$C_6$ alkyl, $C_3$-$C_6$ cycloalkyl, $C_3$-$C_6$ branched alkyl, $C_1$-$C_6$ aminoalkyl, and $C_1$-$C_6$ hydroxyalkyl;

$G_0$ is selected from a group consisting of N and CH,
each G is independently $CR^6$ or C when bonded to X;
$R^5$ is methyl;

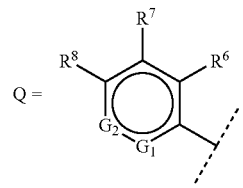

each of $R^6$, $R^7$ and $R^8$ is independently selected from a group consisting of H, $C_2$-$C_6$ alkenyl, $C_2$-$C_6$ alkynyl, $C_1$-$C_6$ hydroxyalkyl or aminoalkyl, $C_3$-$C_6$ cycloalkyl, a halogen, $CF_3$, $OCF_3$, $SO_2H$, $SO_2(C_1$-$C_6$ alkyl), $SO_2$-heterocycle, $SO_2$-cycloalkyl, $SO_2N(C_1$-$C_6$ alkyl)H, $SO_2N(C_1$-$C_6$ alkyl)($C_1$-$C_6$ alkyl), $SO_2NH(C_3$-$C_6$ cycloalkyl), $SO_2NH$-heterocycle, ($SO_2N(C_3$-$C_6$ branched alkyl)H, $NO_2$, CN, $CONH_2$, CO—($C_1$-$C_6$ alkyl), COOH, COO—($C_1$-$C_6$ alkyl), and NHCO—($C_1$-$C_6$ alkyl), or $R^6$ and $R^7$ taken together, or $R^7$ and $R^8$, taken together, form a moiety independently selected from the group consisting of —CH=CH—CH=CH—, and —O—$(CH_2)_n$—O—;
A is selected from a group consisting of NH, and N—($C_1$-$C_6$ alkyl);
$G_1$ is CH;
$G_2$ is $CR^7$, with each group $R^7$ being independent of every other group $R^7$; and
$R^3$ and $R^4$ are taken together with $G_0$ to form a heterocyclic ring system;
wherein alkyl, alkenyl, alkynyl, cycloalkyl, or heterocycle, for each occurrence if any, are optionally substituted by one or more substituents selected from the group consisting of hydroxy, alkoxy, mercapto, halogen, cyano, nitro, amino, amido, aldehyde, acyl, oxyacyl, carboxyl, sulfonyl, sulfonamide, or sulfuryl;
or a pharmaceutically acceptable salt thereof.

2. The method of claim 1, wherein the compound is selected from the group consisting of compounds having the formulae:

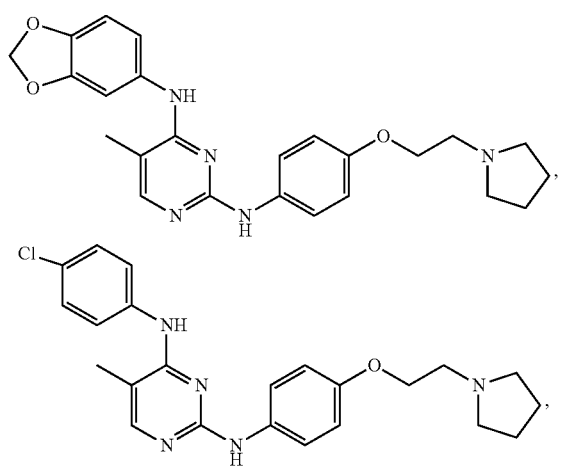

267
-continued
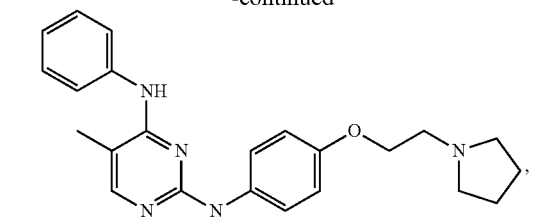
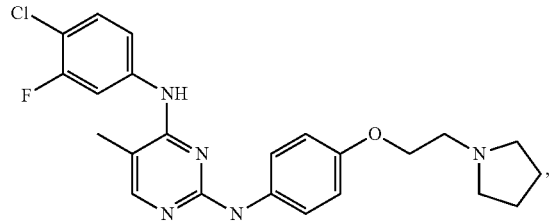
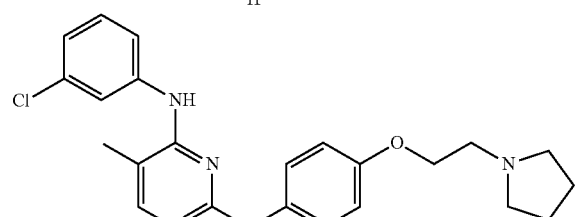
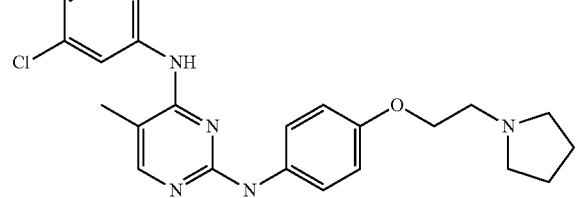
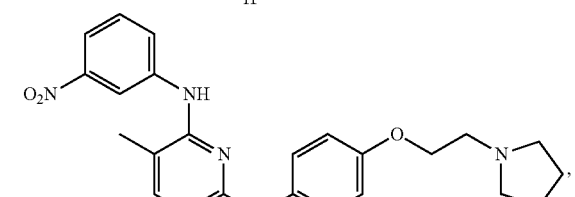
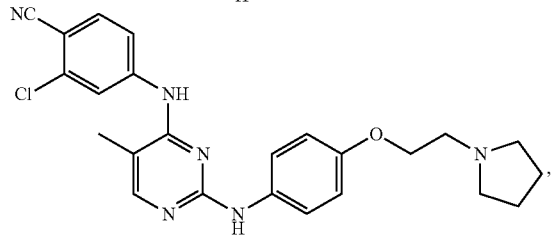
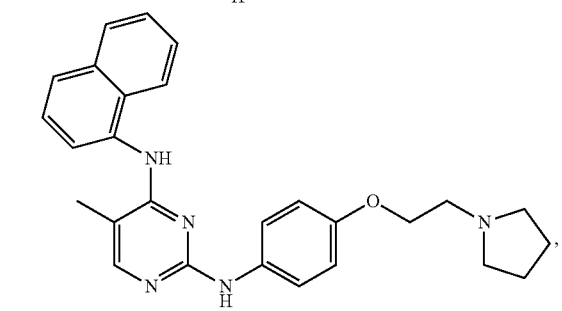
268
-continued
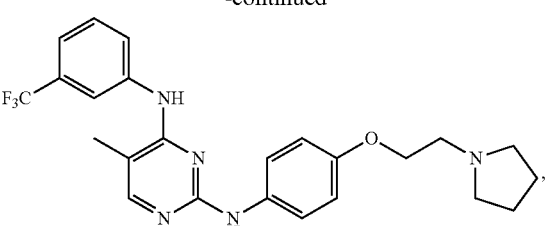
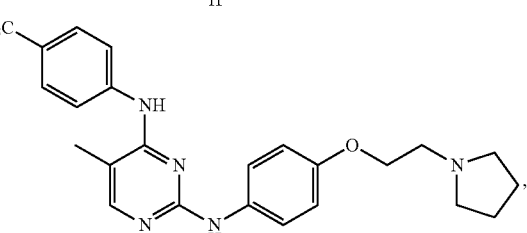
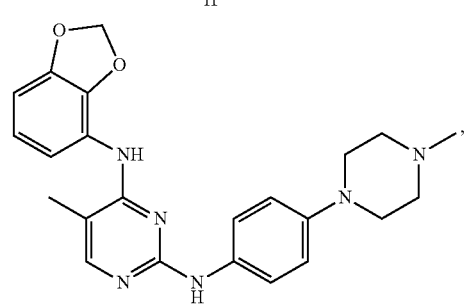
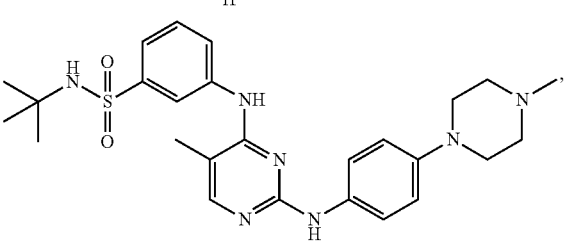
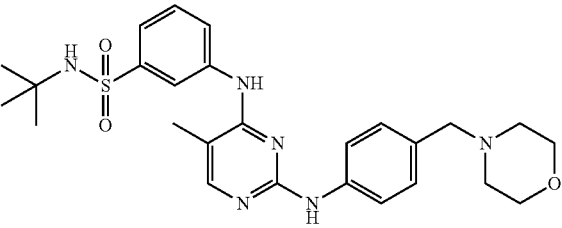
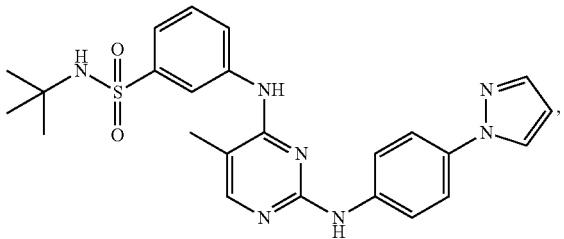
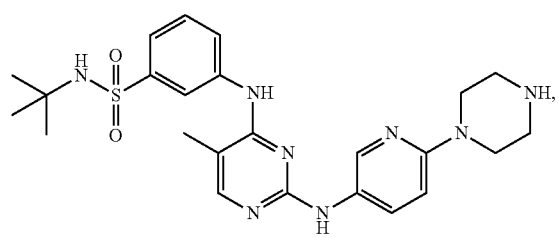

269
-continued
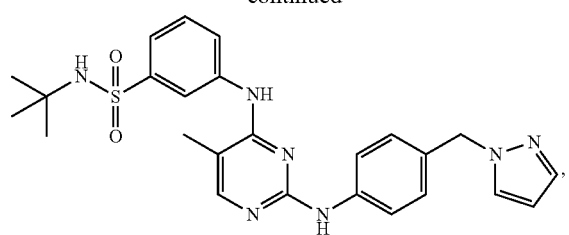
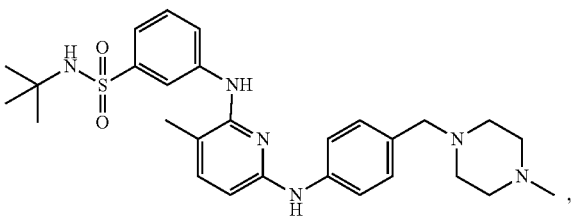
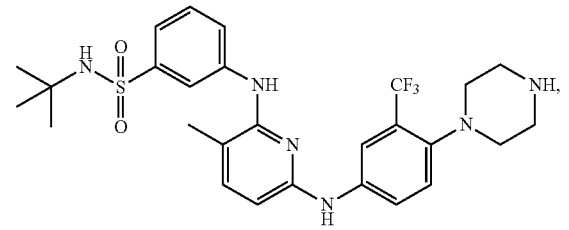
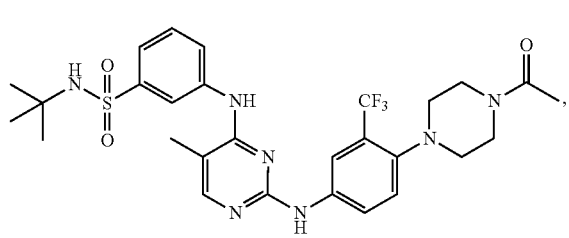
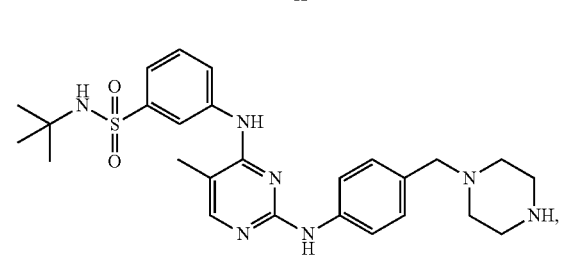
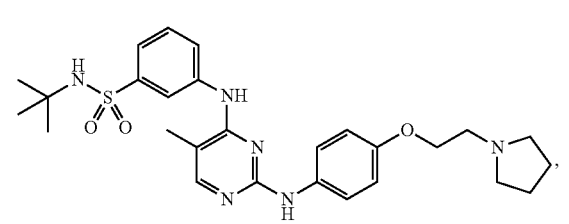
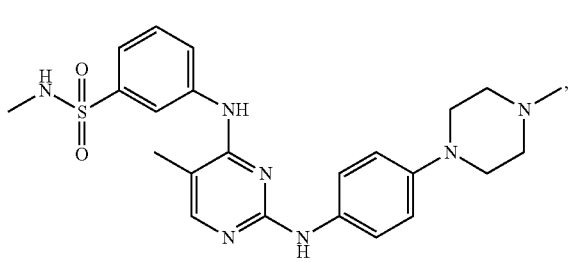
270
-continued
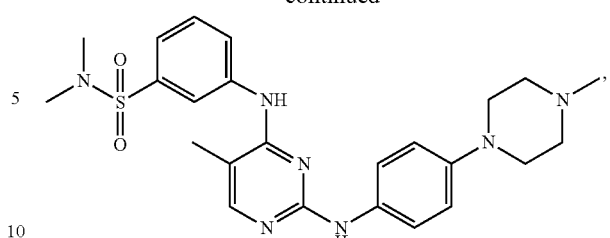
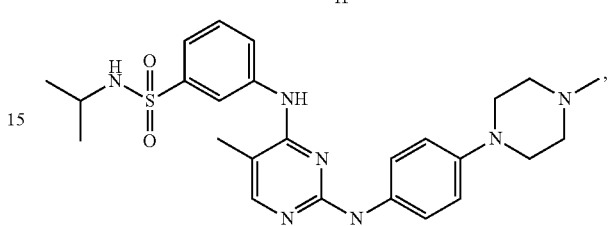
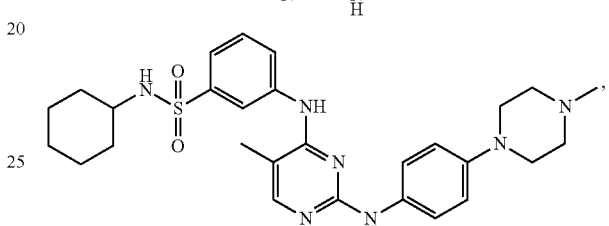
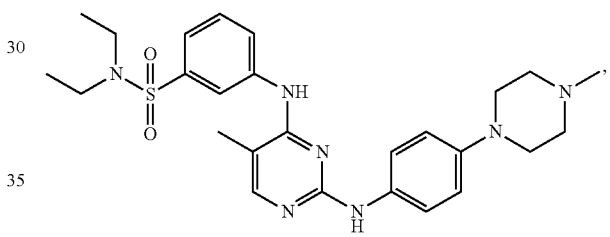
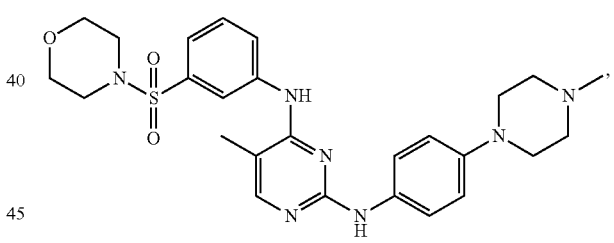
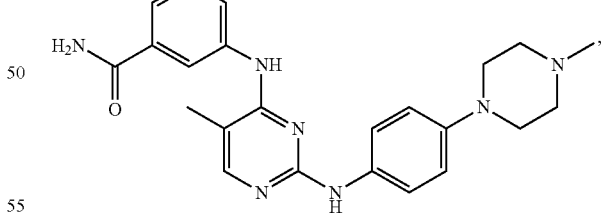
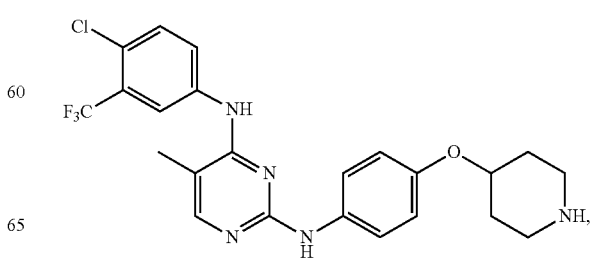

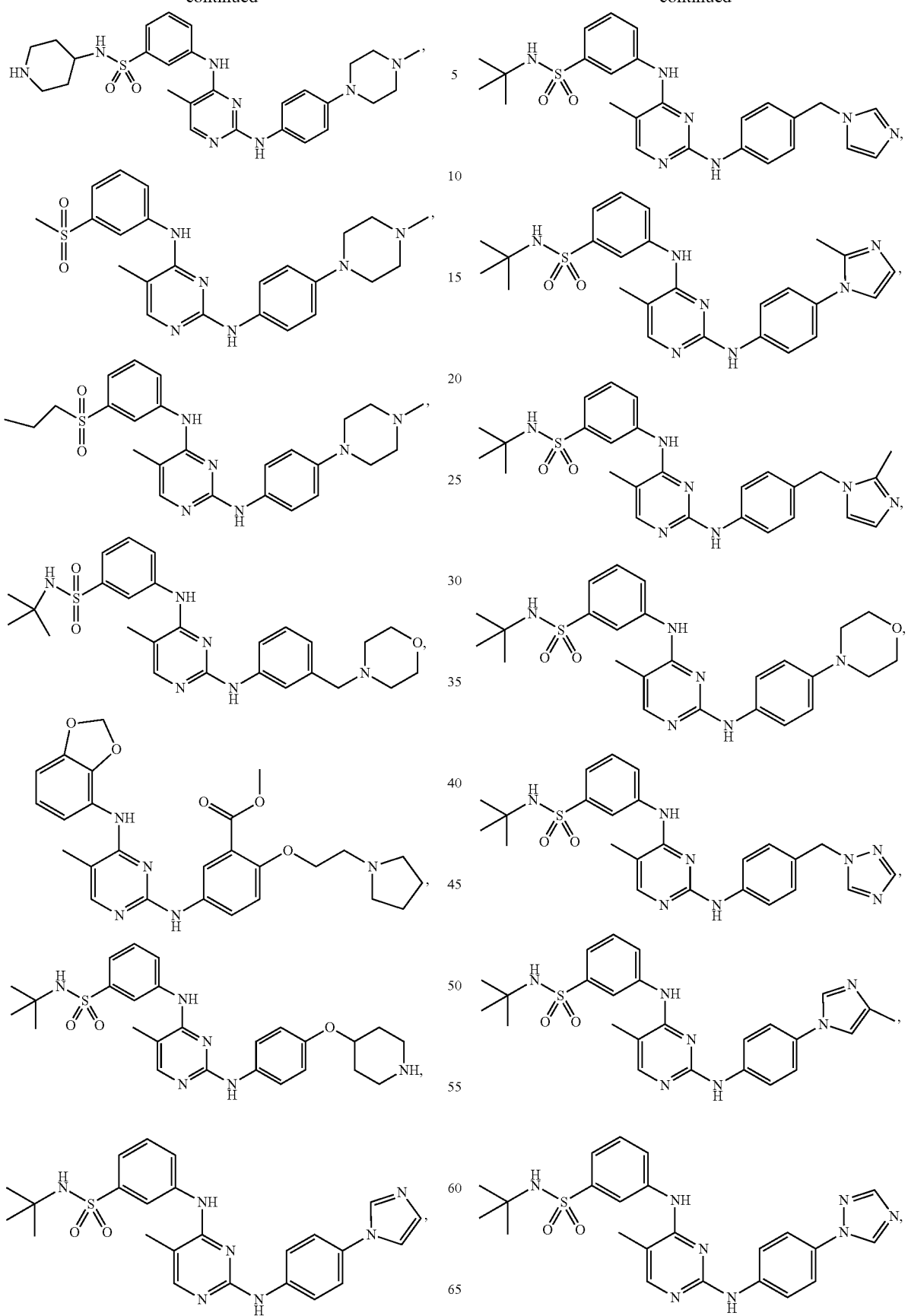

273
-continued
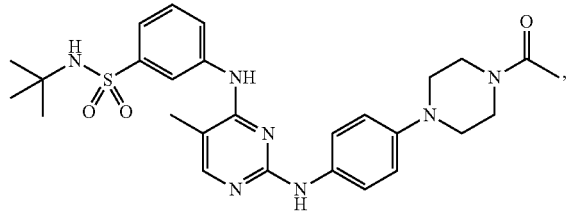
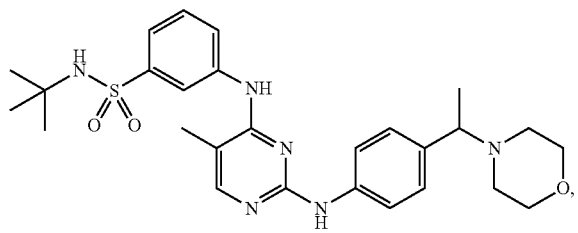
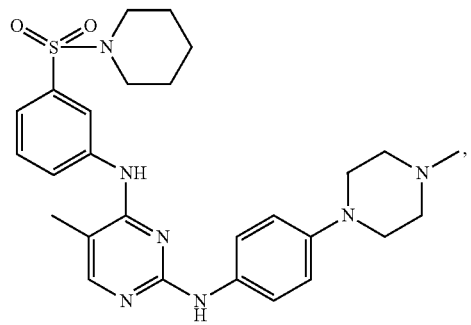
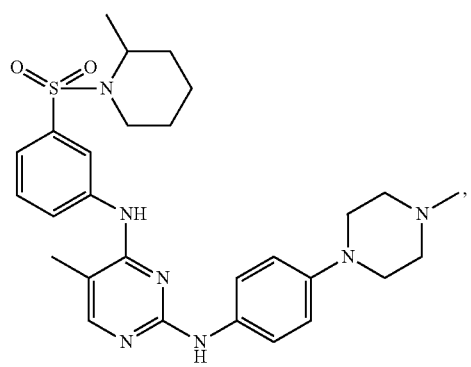
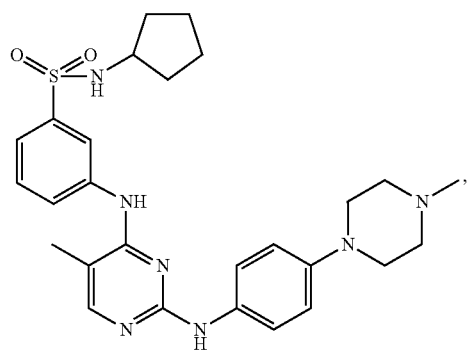
274
-continued
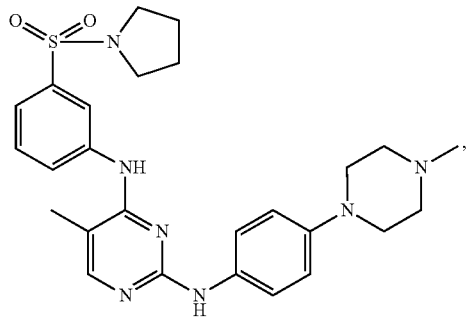
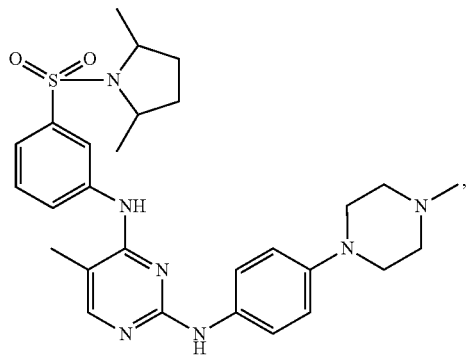
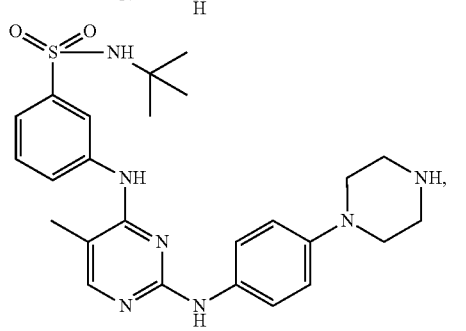
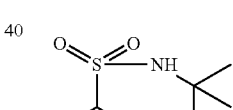
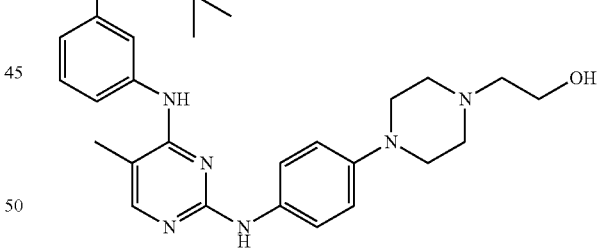
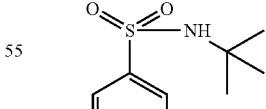
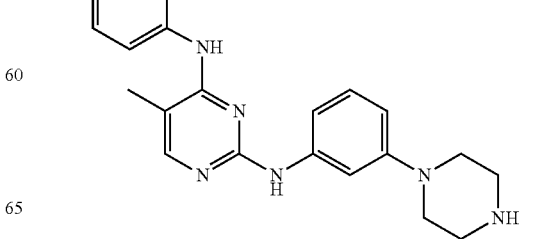

-continued

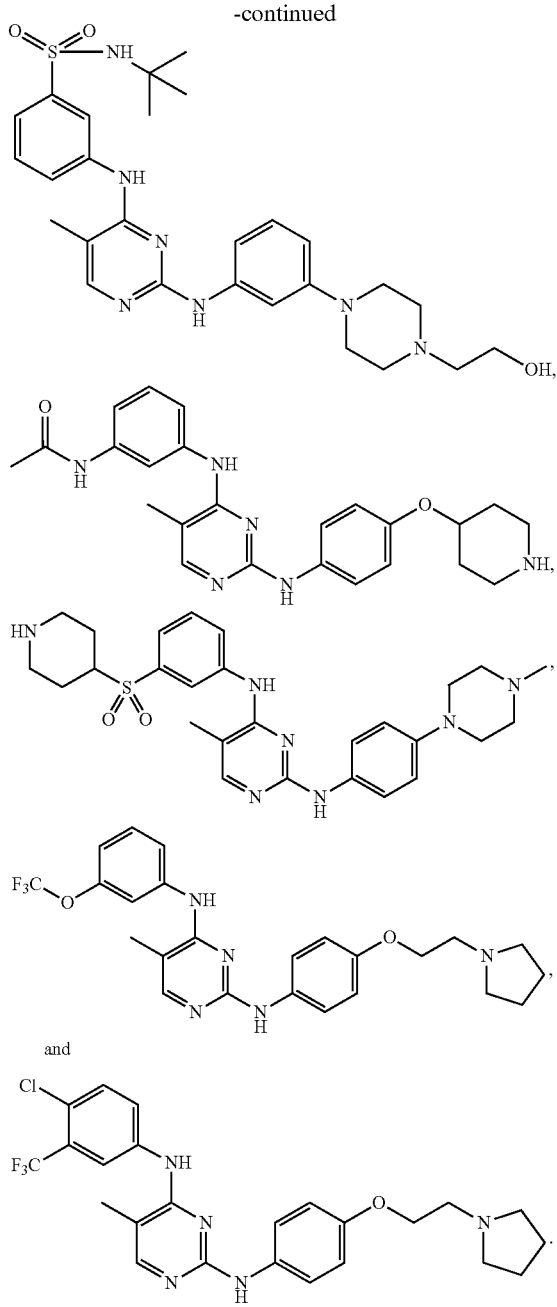

and or a pharmaceutically acceptable salt thereof.

3. The method of claim 1, wherein the myeloproliferative disorder is polycythemia vera, essential thrombocythemia, or myeloid fibrosis with myeloid metaplasia.

4. The method of claim 1, wherein the myeloproliferative disorder arises due to mutations in a kinase.

5. The method of claim 4, wherein the kinase is a JAK2 kinase.

6. The method of claim 5, wherein the myeloproliferative disorder arises due to gain-of-function of a JAK2 kinase pathway.

7. The method of claim 5, wherein the myeloproliferative disorder arises as a result of gene or protein fusions due to gain-of-function of a JAK2 kinase pathway.

8. The method of claim 1, wherein X is O.

9. The method of claim 1, wherein $G_0$ is N.

10. The method of claim 8, wherein $G_0$ is N.

11. The method of claim 10, wherein Y is a bond, and $R^1$ and $R^2$ are each H.

12. The method of claim 11, wherein $R^7$ is $SO_2NH$—($C_3$-$C_6$ branched alkyl).

13. The method of claim 12, wherein $G_2$ is CH, $R^8$ is H and $R^6$ is H.

14. A method of inhibiting JAK2 kinase activity in a subject wherein the subject has a myeloproliferative disorder, comprising administering to the subject with a myeloproliferative disorder an effective amount of the compound:

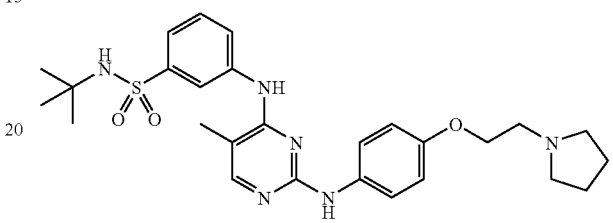

or a pharmaceutically acceptable salt thereof.

15. The method of claim 14, wherein the myeloproliferative disorder is polycythemia vera.

16. The method of claim 14, wherein the myeloproliferative disorder is essential thrombocythemia.

17. The method of claim 14, wherein the myeloproliferative disorder is myeloid fibrosis with myeloid metaplasia.

18. The method of claim 14, wherein the disorder is a myeloproliferative myeloid-linked disorder.

19. The method of claim 1, wherein the compound is:

XLV

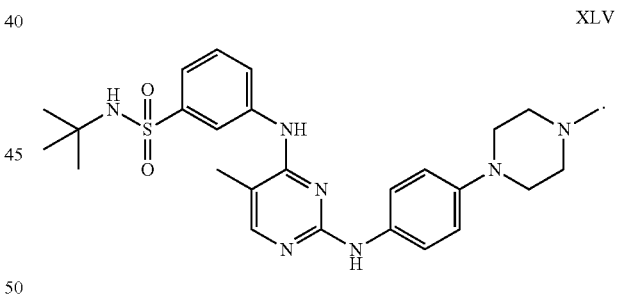

or a pharmaceutically acceptable salt thereof.

20. The method of claim 1, wherein the compound is selected from the group consisting of:

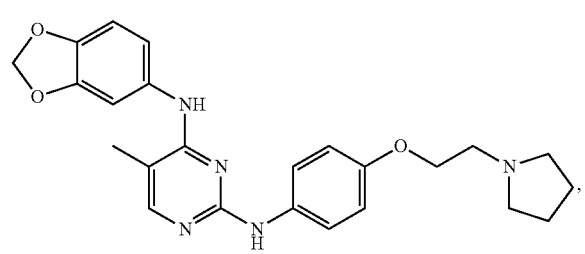

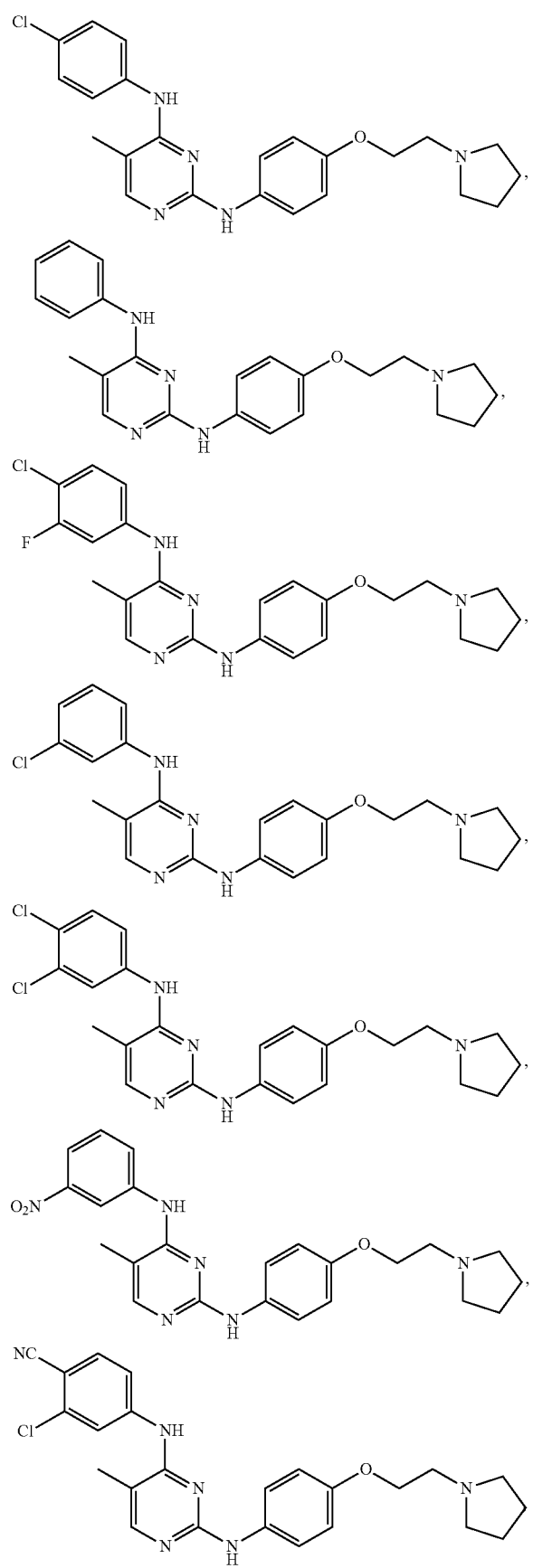
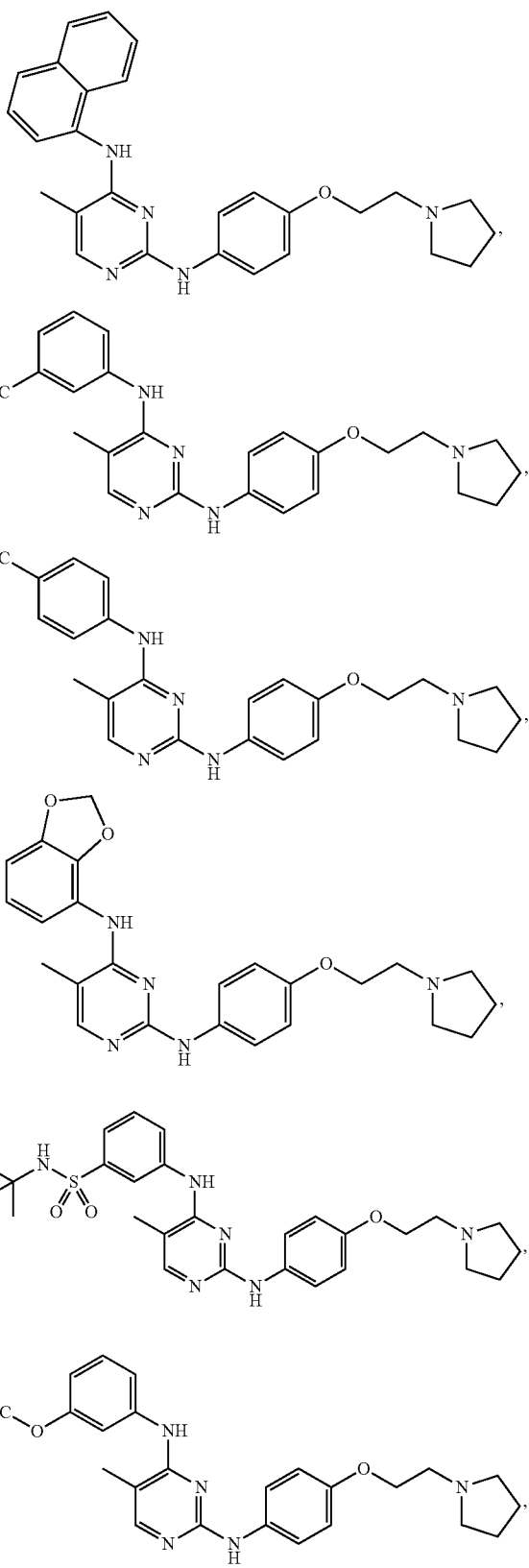
-continued
and

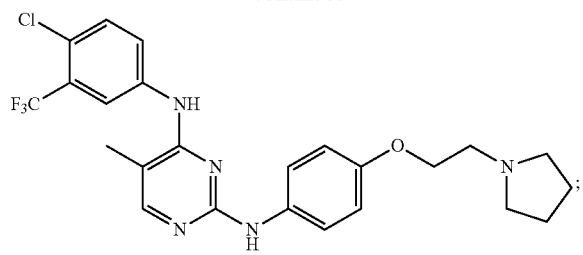

or a pharmaceutically acceptable salt thereof.

21. The method of claim 1, wherein the compound is selected from the group consisting of:

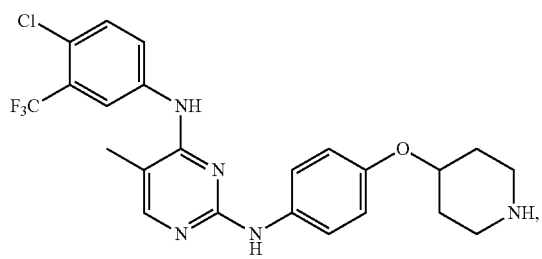

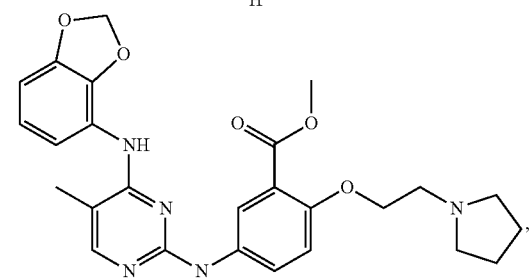

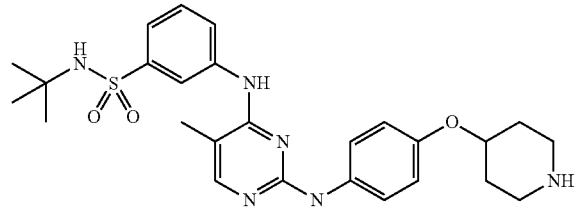

and

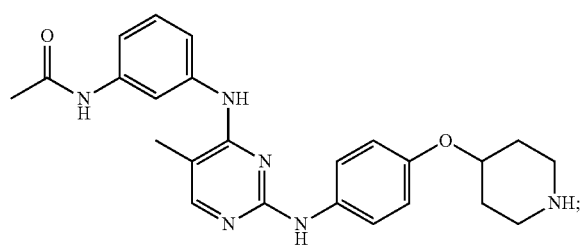

or a pharmaceutically acceptable salt thereof.

22. The method of claim 1, wherein the compound is selected from the group consisting of:

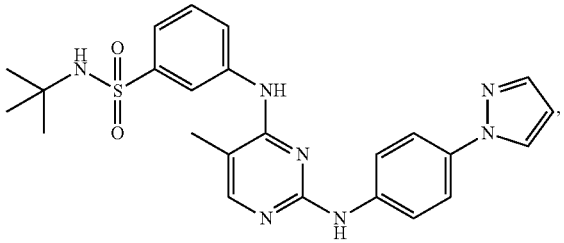

and or a pharmaceutically acceptable salt thereof.

23. The method of claim 1, wherein the compound is selected from the group consisting of:

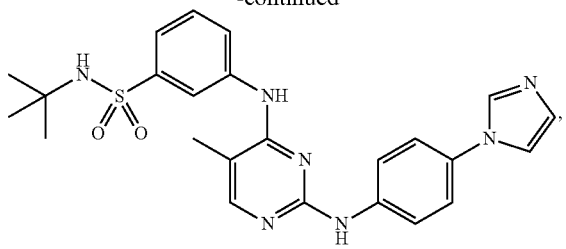
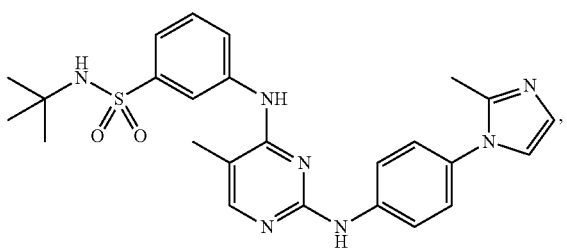
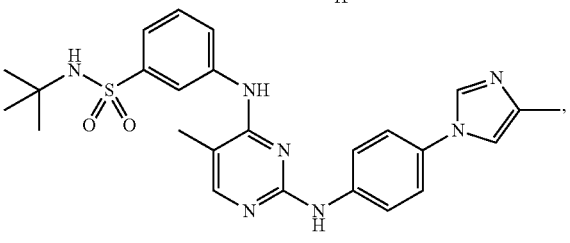
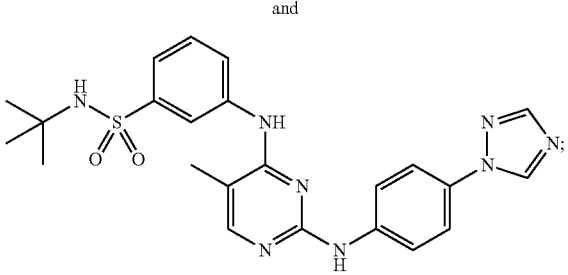
or a pharmaceutically acceptable salt thereof.
24. The method of claim 1, wherein the compound is selected from the group consisting of:
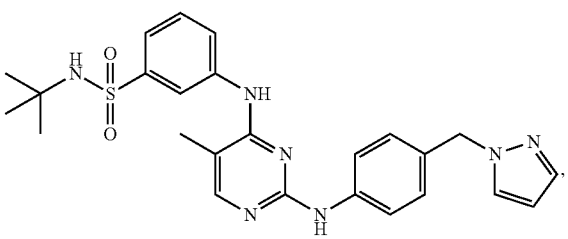
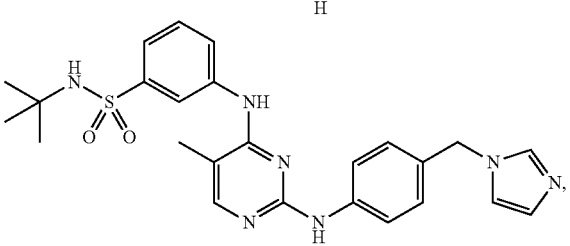
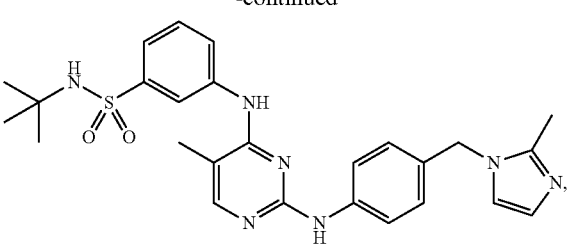
and
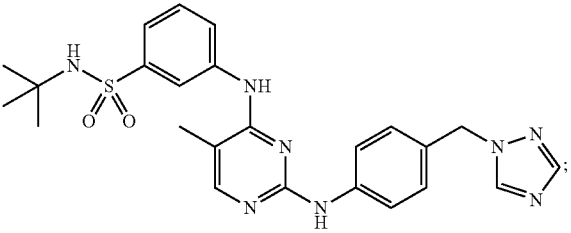
or a pharmaceutically acceptable salt thereof.
25. The method of claim 1, wherein the compound is selected from the group consisting of:
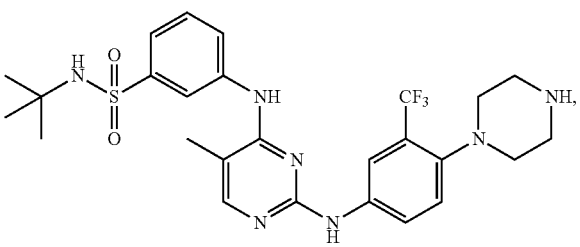
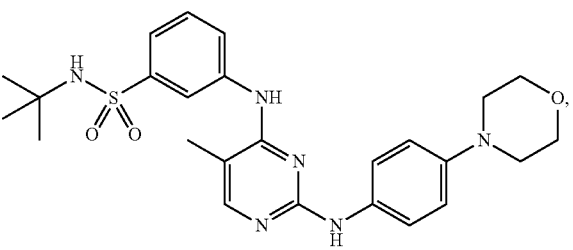
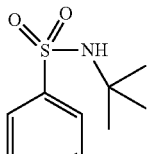
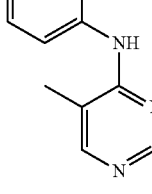

283
-continued
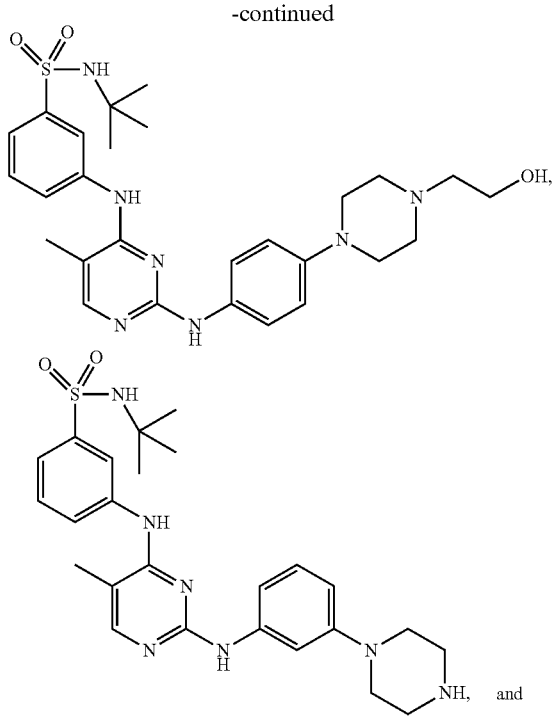
or a pharmaceutically acceptable salt thereof.
26. The method of claim 1, wherein the compound is selected from the group consisting of:
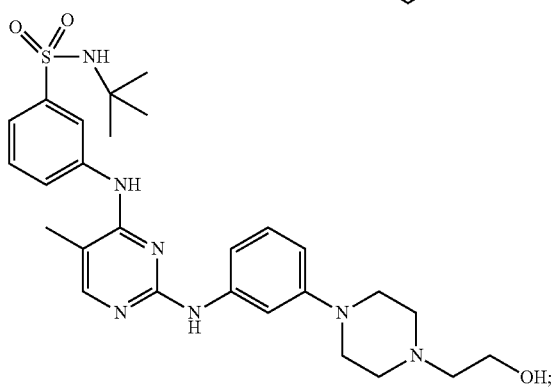
284
-continued
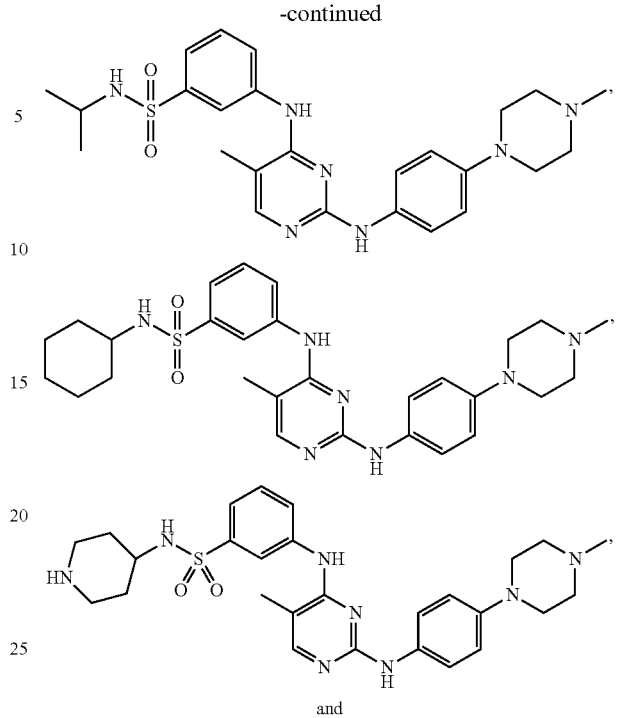
or a pharmaceutically acceptable salt thereof.
27. The method of claim 1, wherein the compound is selected from the group consisting of:
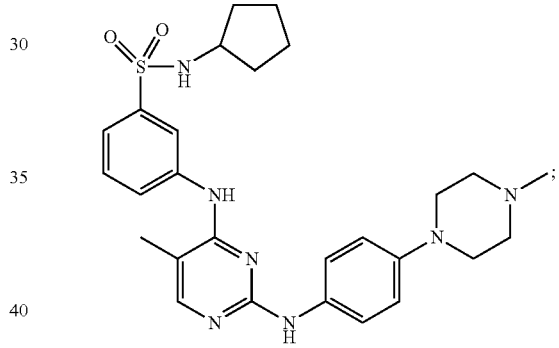
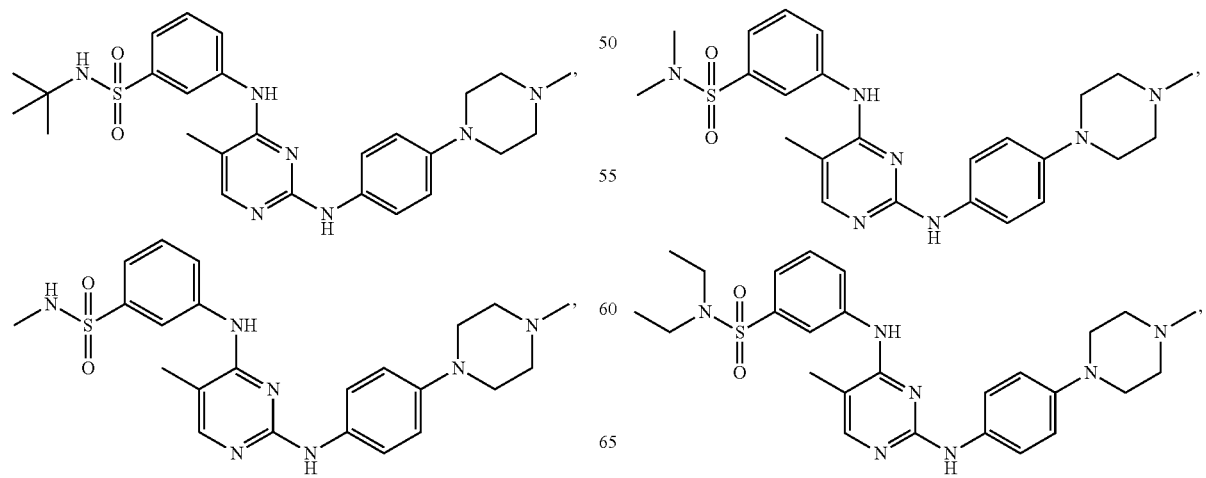

285

-continued

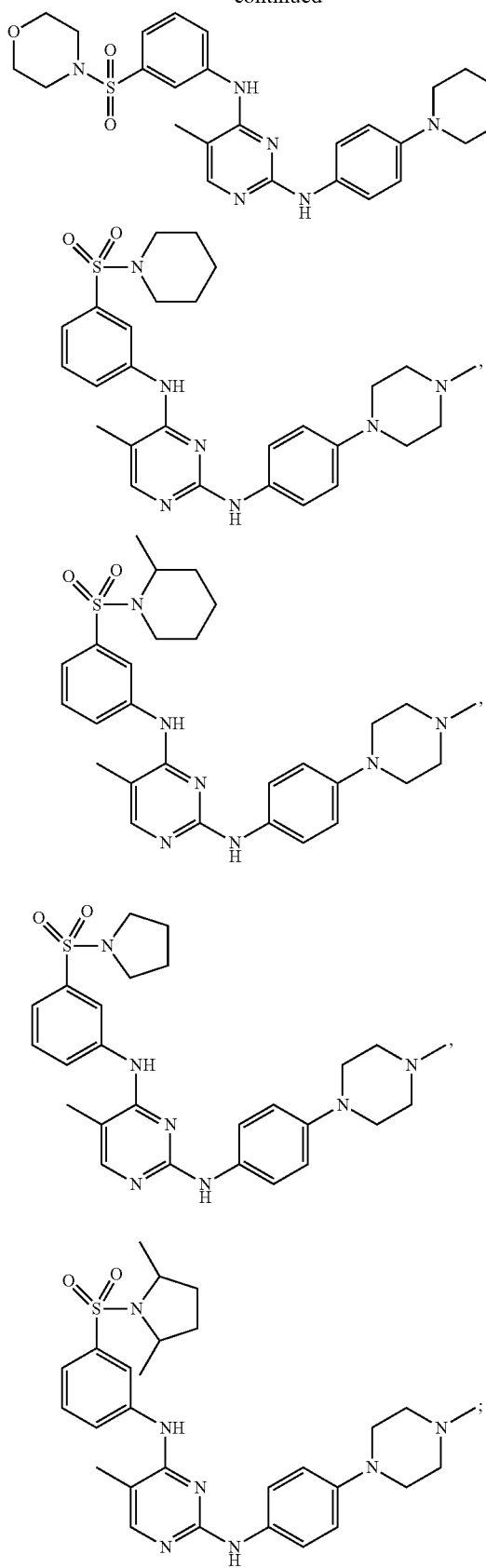

or a pharmaceutically acceptable salt thereof.

286

28. The method of claim 1, wherein the compound is selected from the group consisting of:

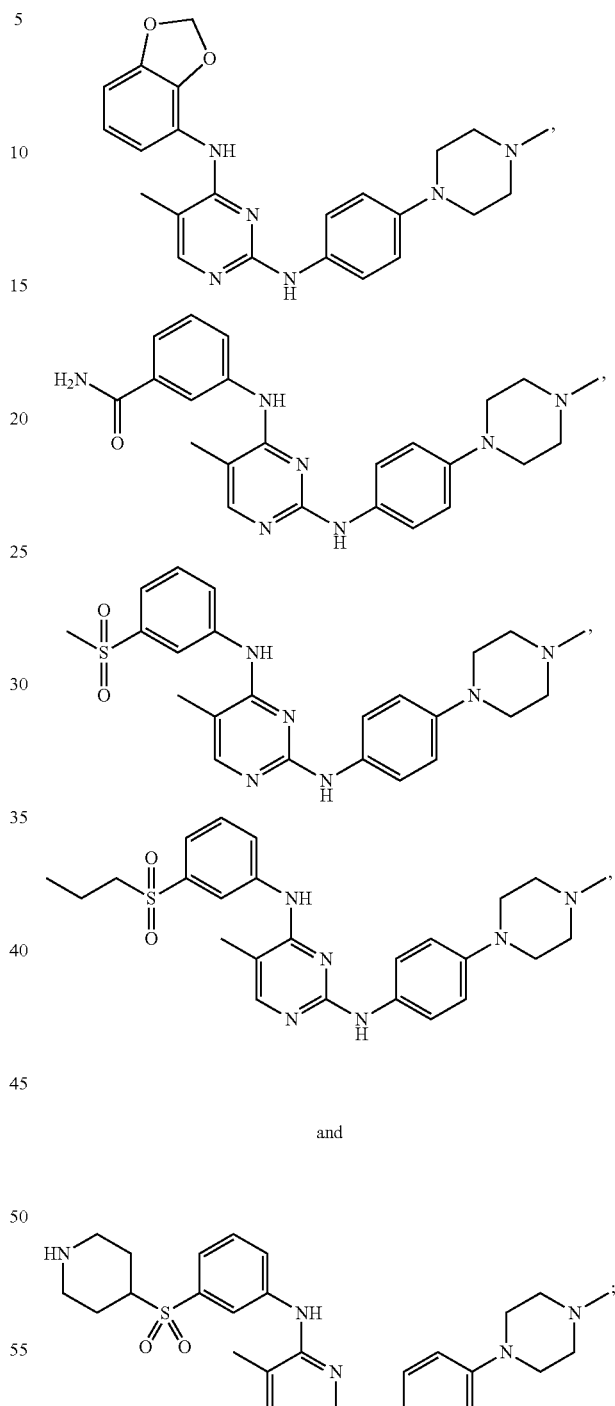

or a pharmaceutically acceptable salt thereof.

29. A method of inhibiting JAK2 kinase activity in a subject wherein the subject has a myeloproliferative disorder, comprising administering to the subject with a myeloproliferative disorder a compound selected from the group consisting of compounds having the formulae:

287
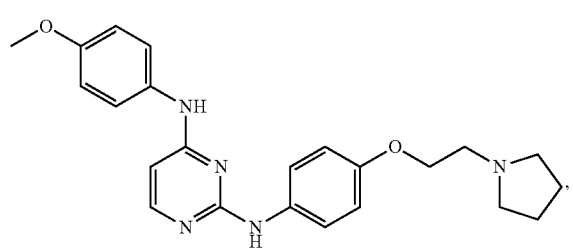
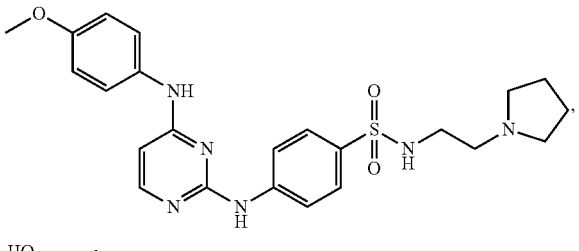
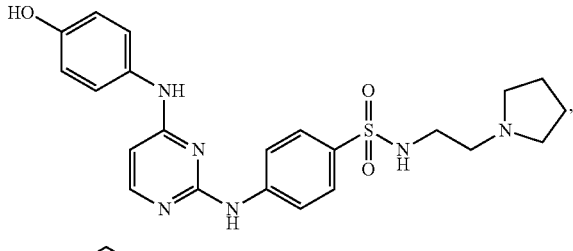
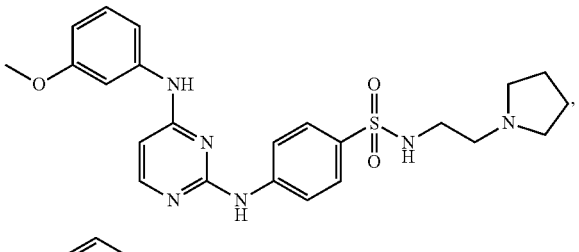
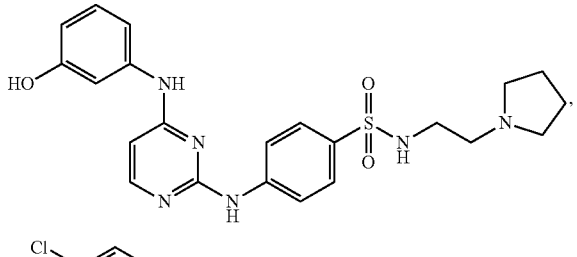
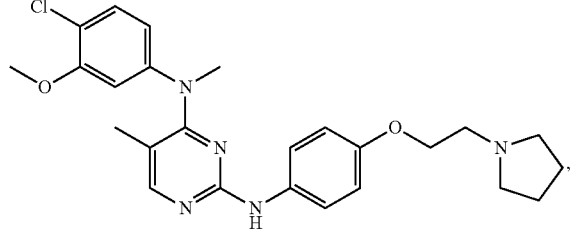
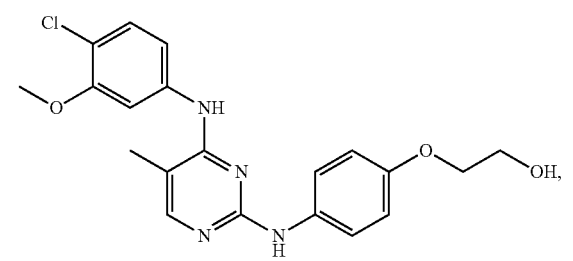
288
-continued
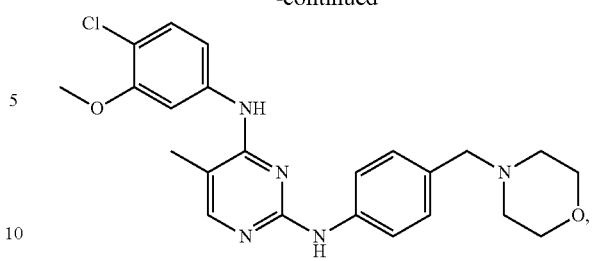
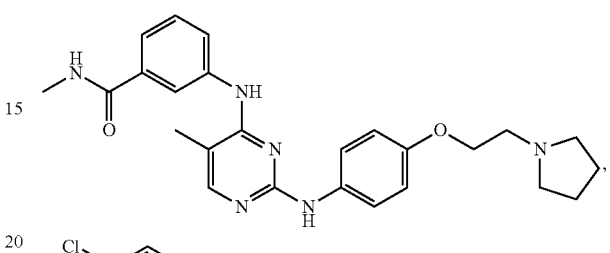
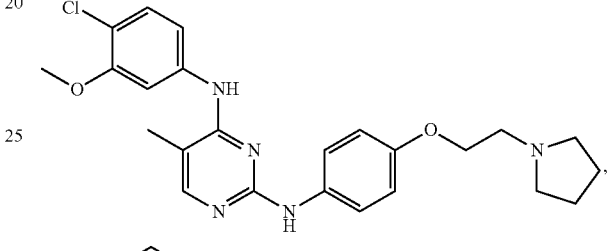
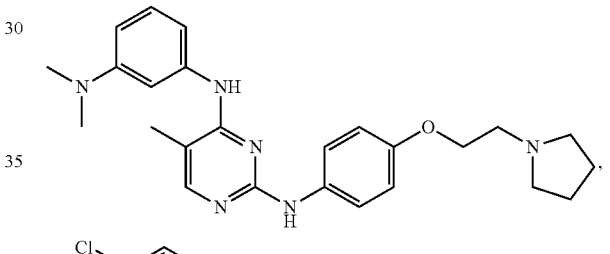
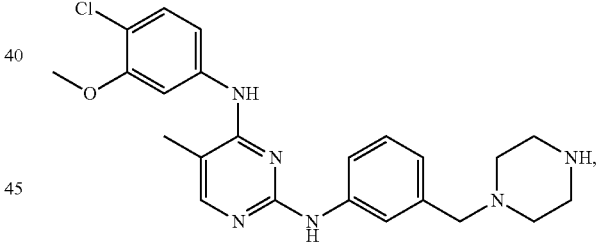
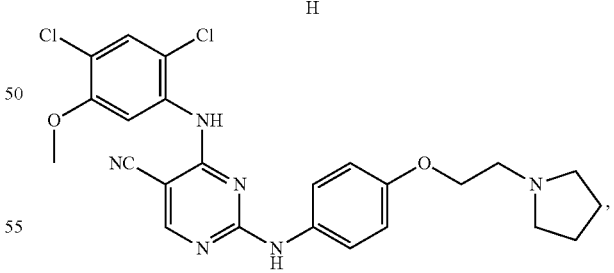
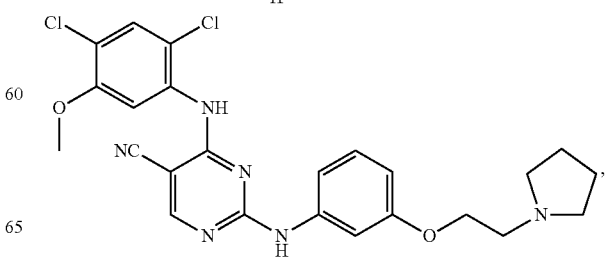

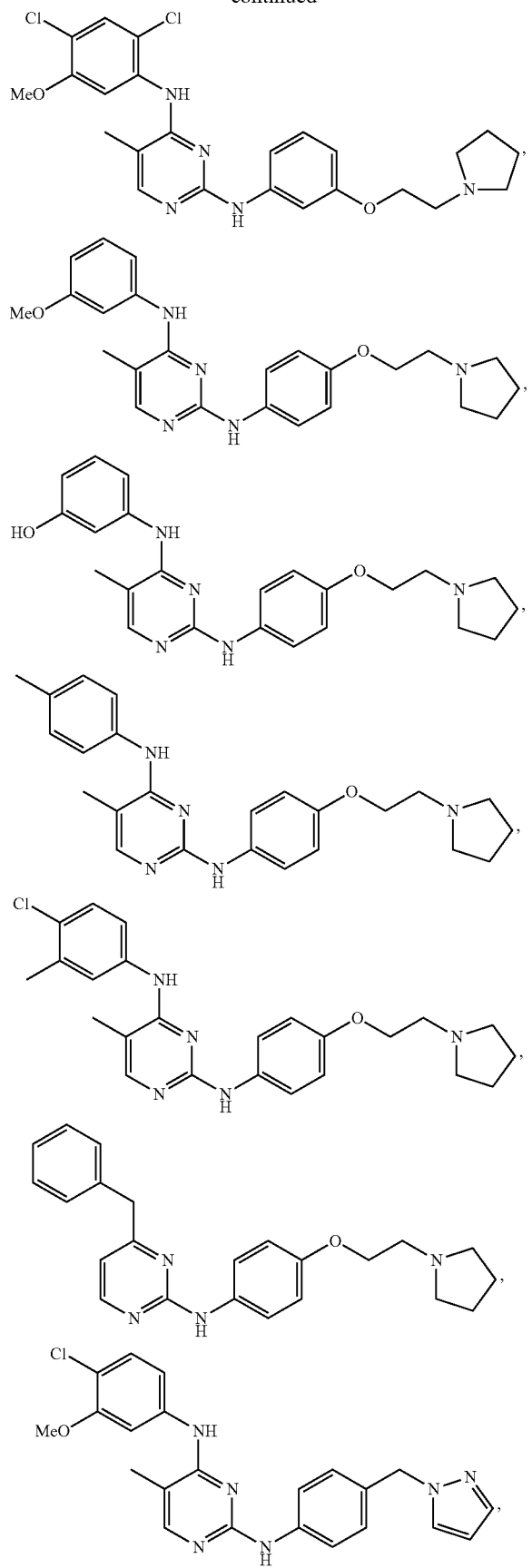
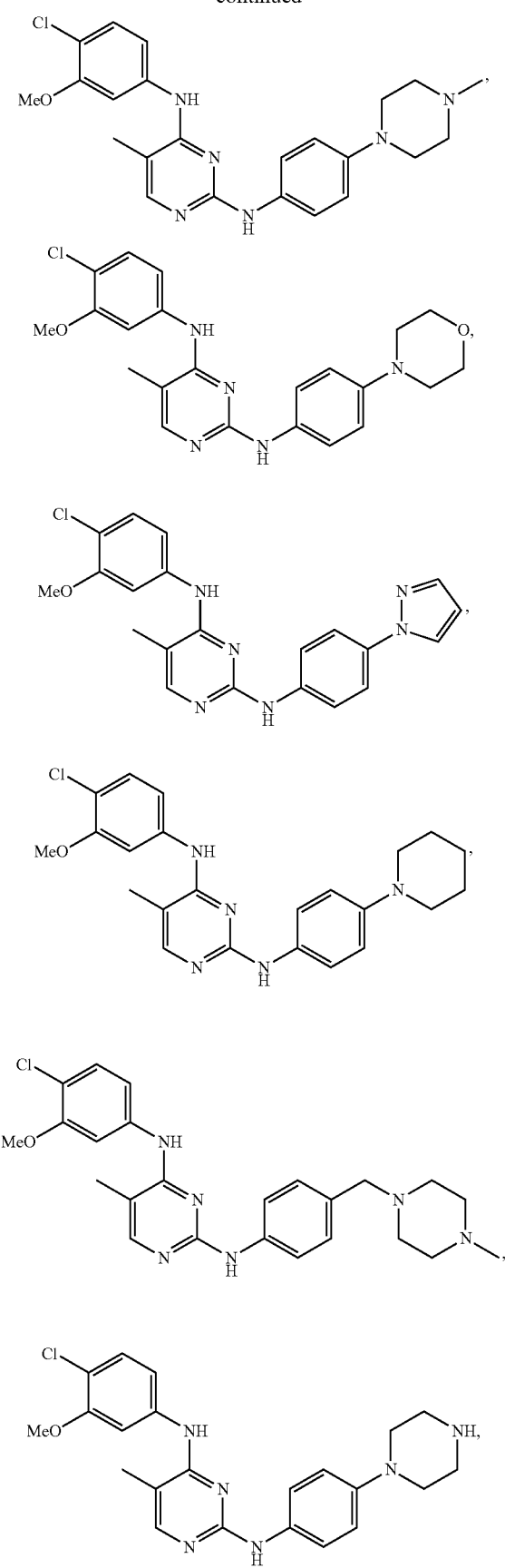

291
-continued
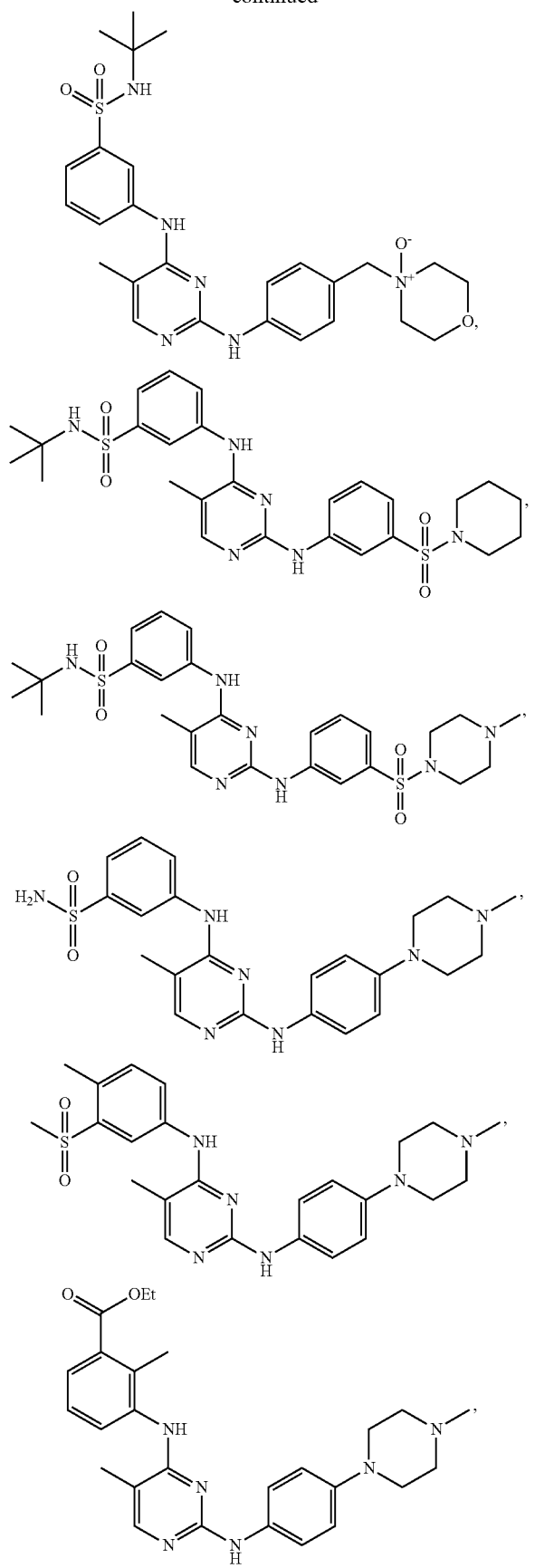
292
-continued
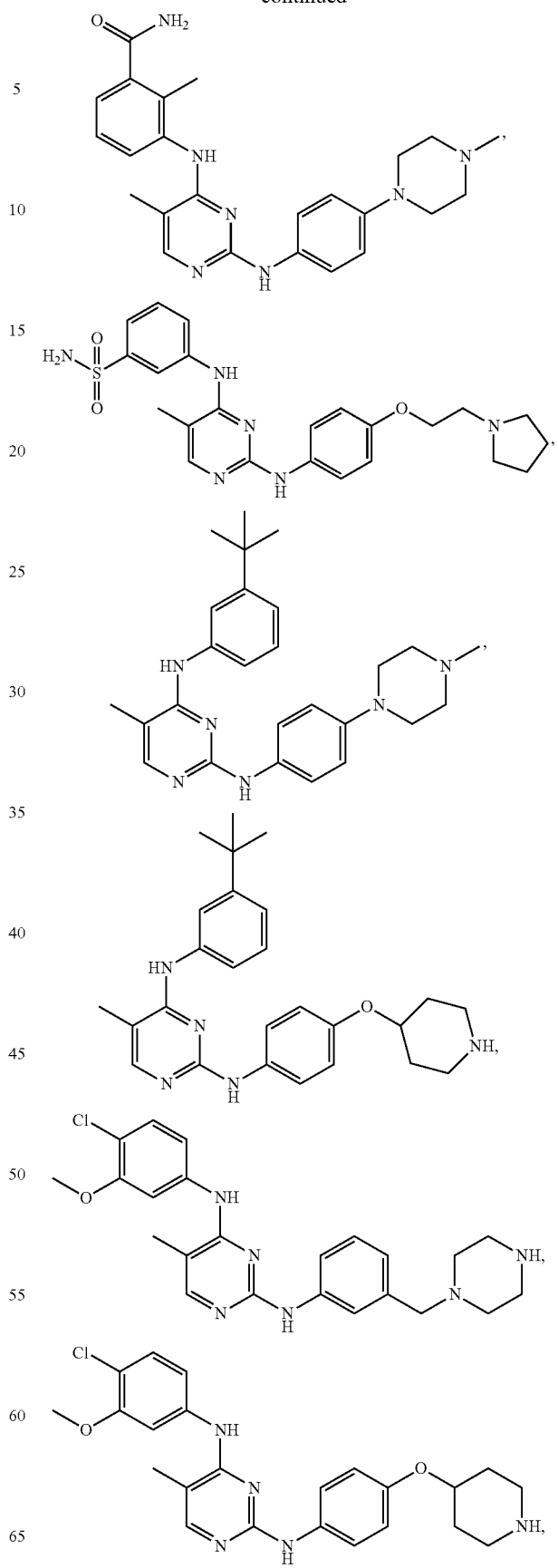

293
-continued
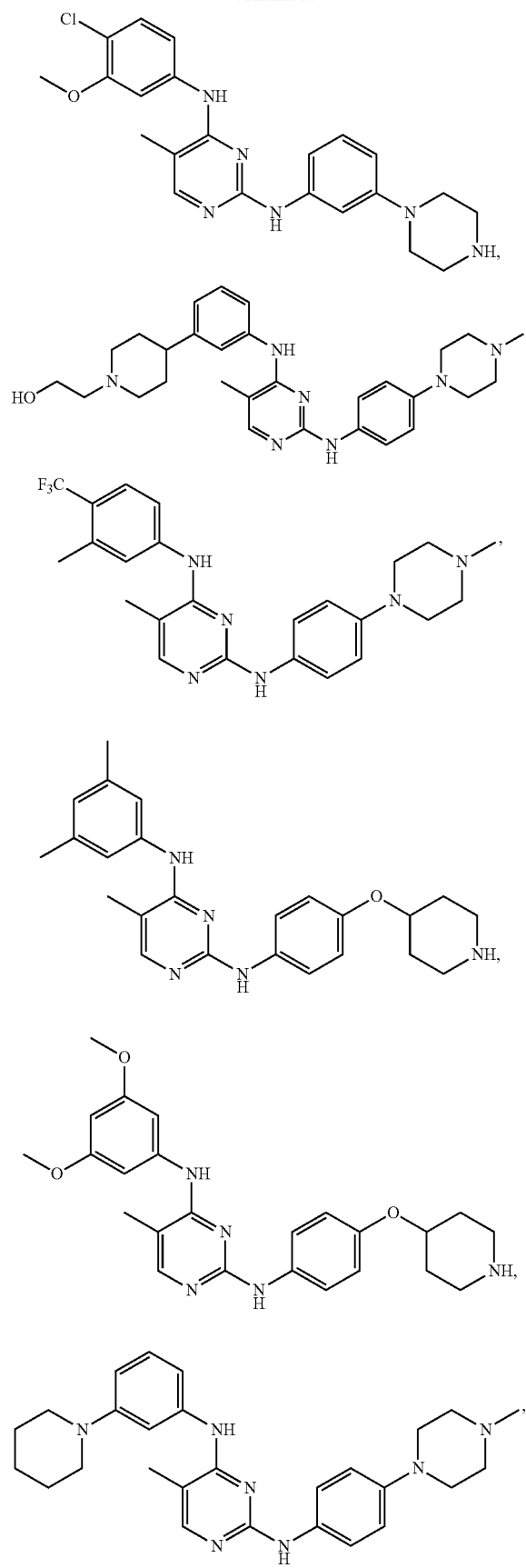
294
-continued
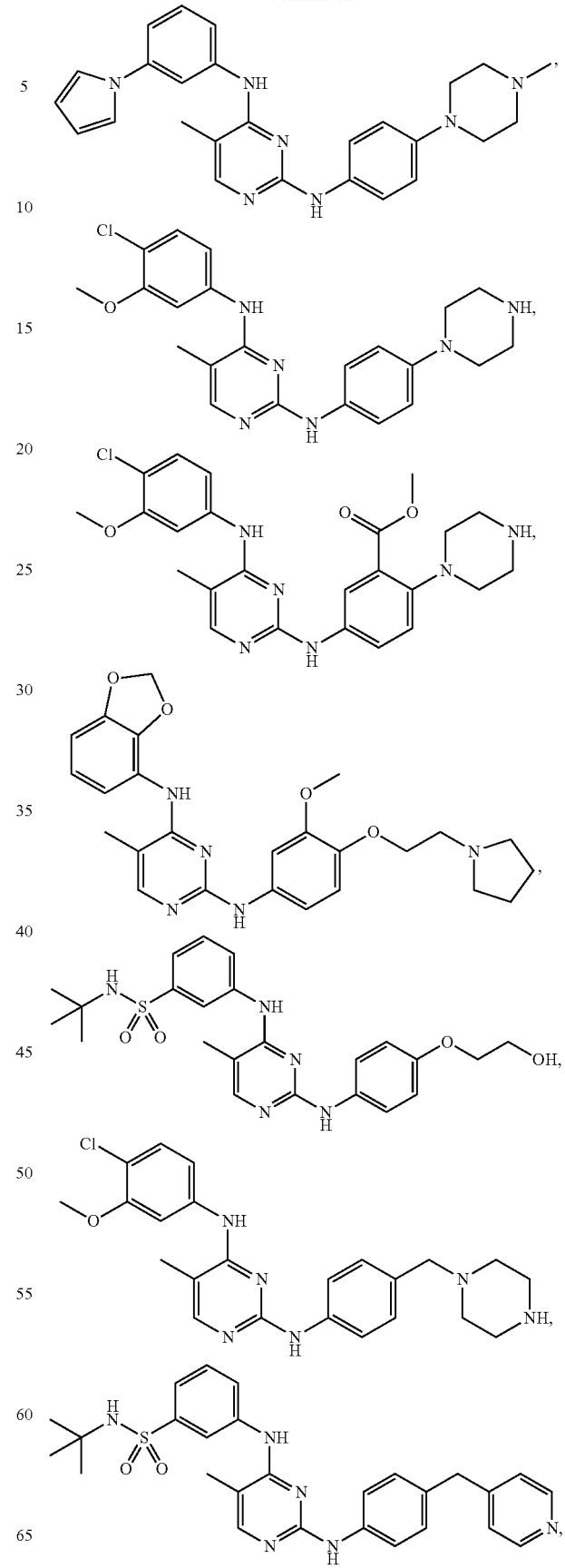

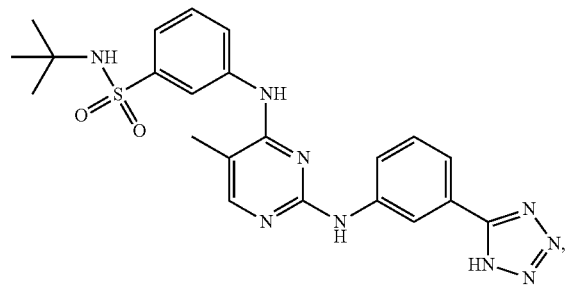
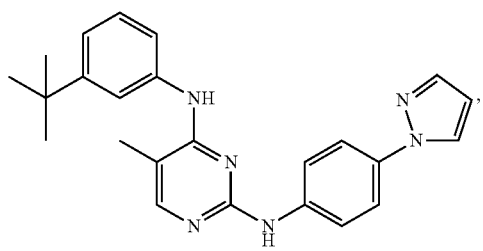
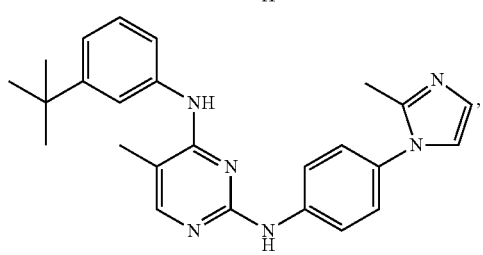
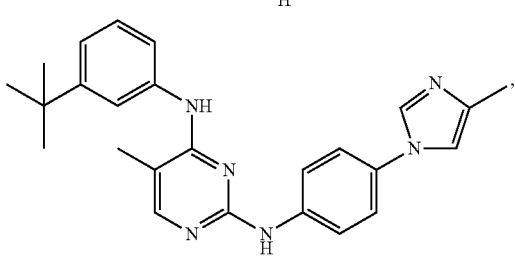
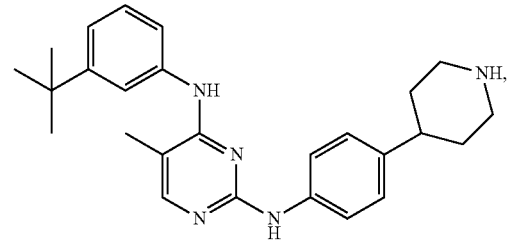
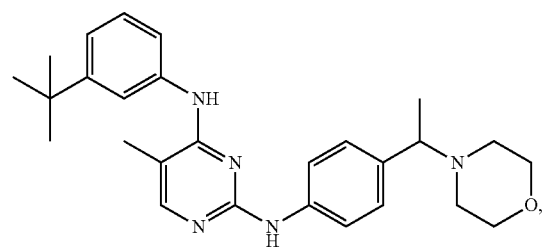
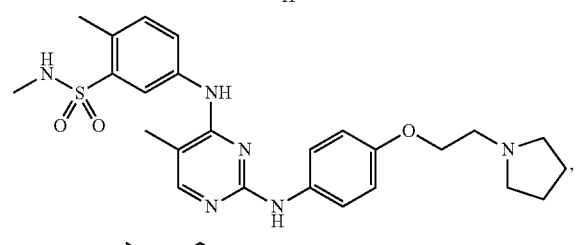
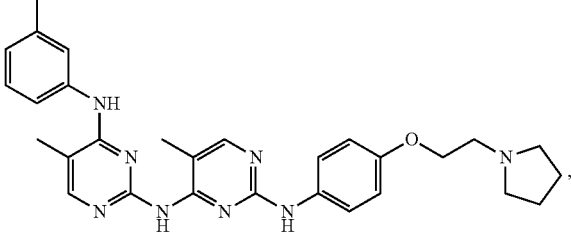

297
-continued
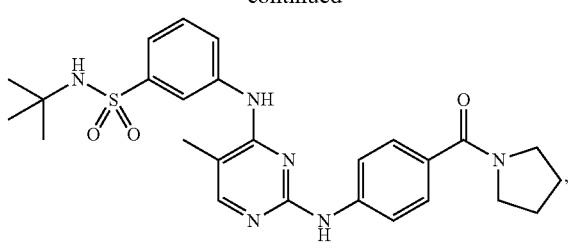
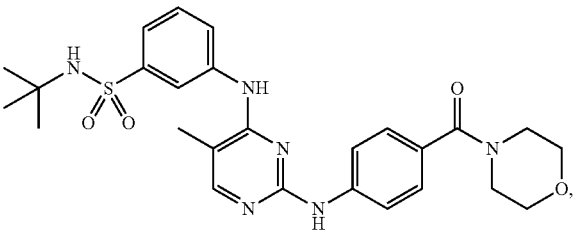
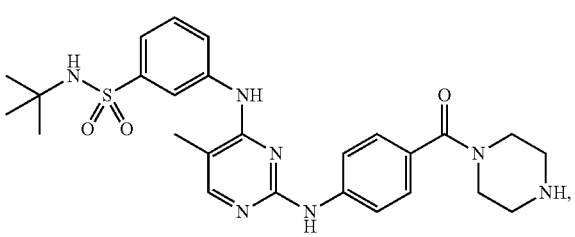
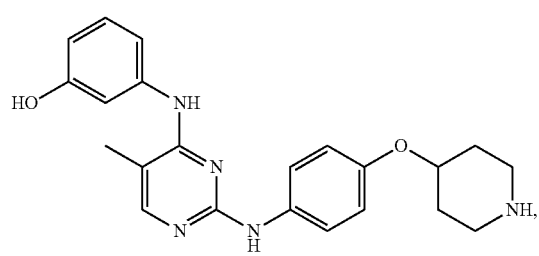
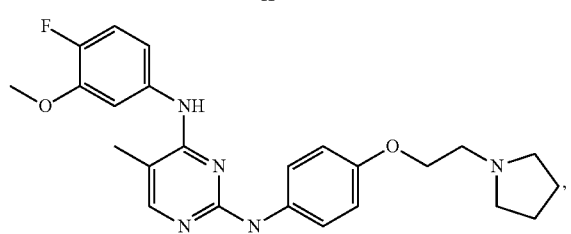
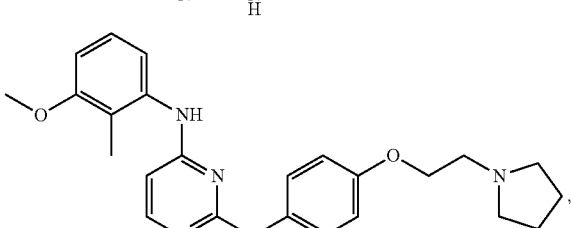
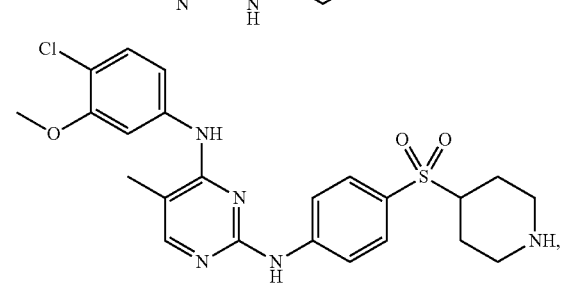
298
-continued
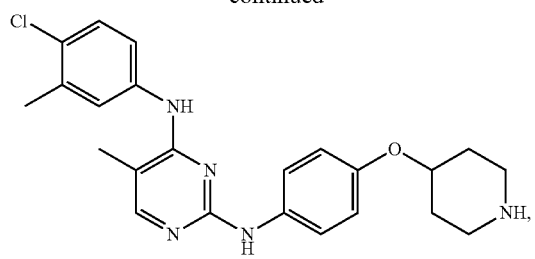
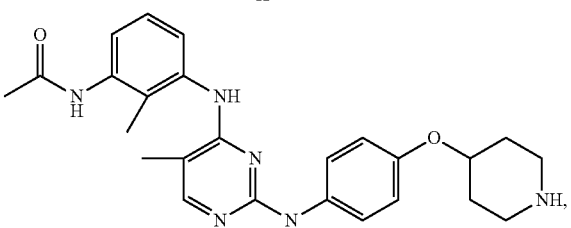
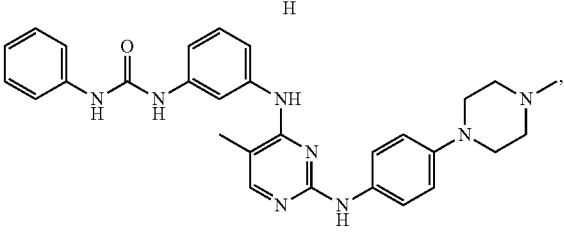
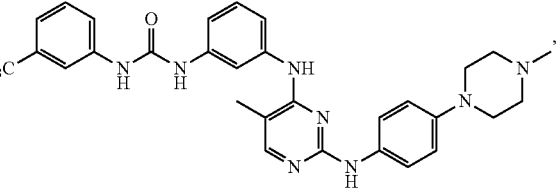
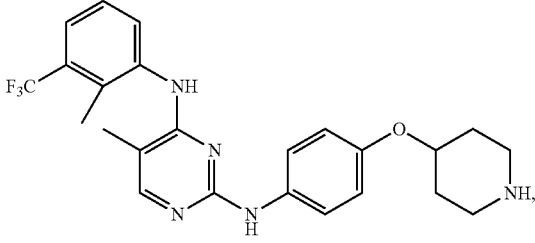
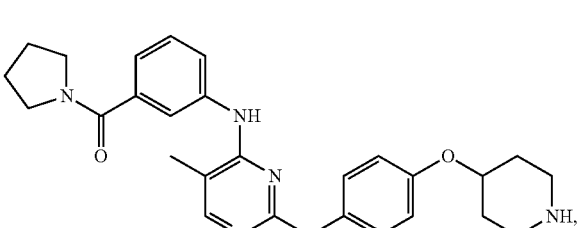
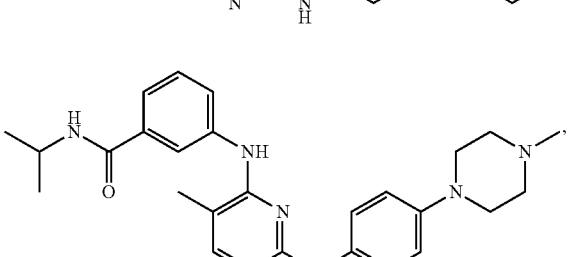

-continued

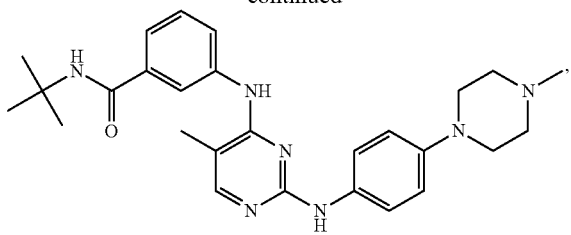

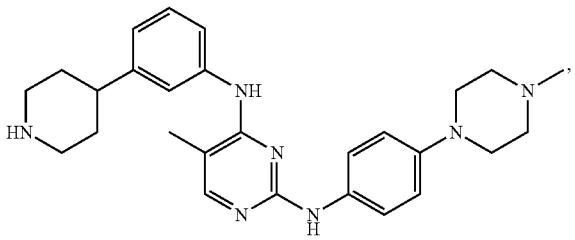

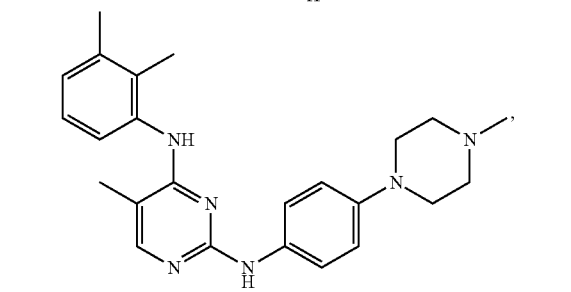

-continued

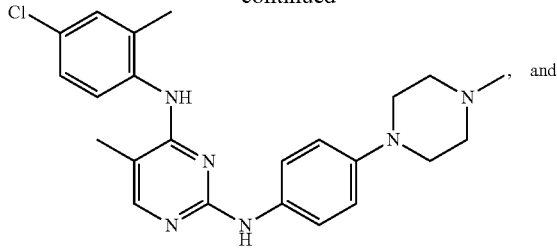

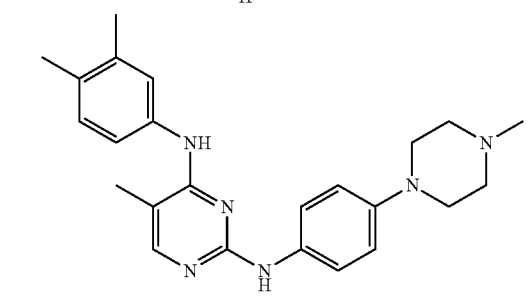

or a pharmaceutically acceptable salt thereof.

30. The method of claim 1, wherein the compound, or a pharmaceutically acceptable salt thereof, is in the form of a pharmaceutical composition which comprises the compound and a pharmaceutically acceptable carrier.

31. The method of claim 30, wherein the pharmaceutical composition is administered orally.

* * * * *

UNITED STATES PATENT AND TRADEMARK OFFICE
CERTIFICATE OF CORRECTION

| | | |
|---|---|---|
| PATENT NO. | : 8,138,199 B2 | |
| APPLICATION NO. | : 12/253374 | |
| DATED | : March 20, 2012 | |
| INVENTOR(S) | : Noronha et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 613 days.

In column 28, lines 18-27, please replace the second chemical structure for the top

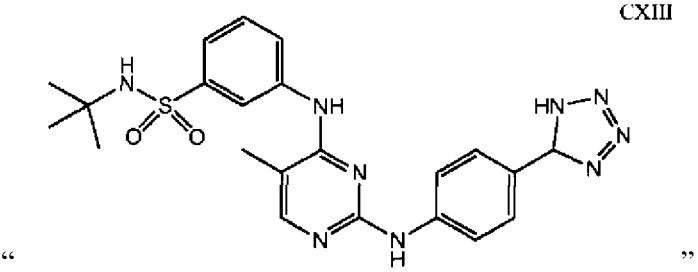

"                                                                                    "

with

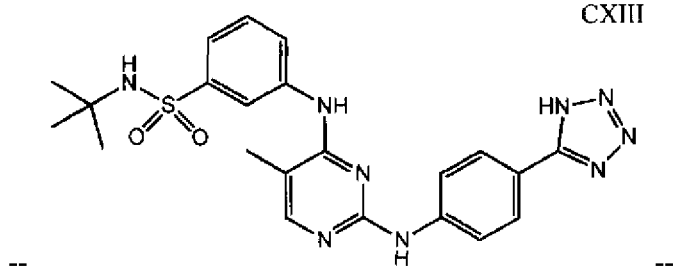

--                                                                                    --

Signed and Sealed this
Twenty-fourth Day of July, 2012

David J. Kappos
*Director of the United States Patent and Trademark Office*

In column 50, lines 13-23, please replace the second chemical structure from the top
"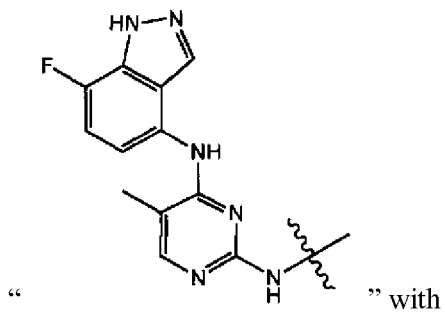" with
"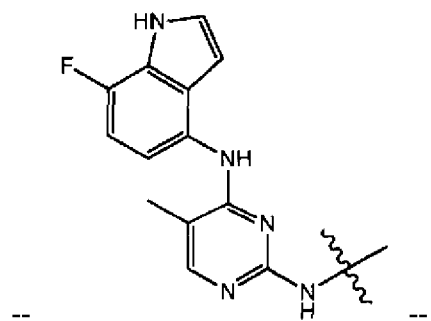"
In column 51, lines 14-19, please replace the third chemical structure from the top
"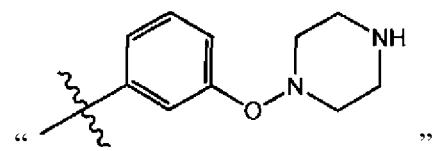"
with
"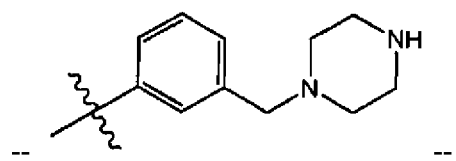"

CERTIFICATE OF CORRECTION (continued)
U.S. Pat. No. 8,138,199 B2

In column 55, lines 37-44, please replace the last chemical structure

" 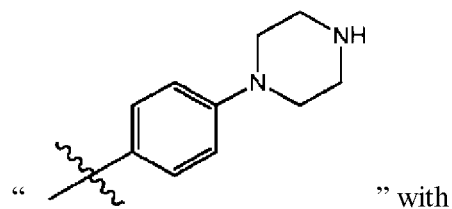 " with

-- 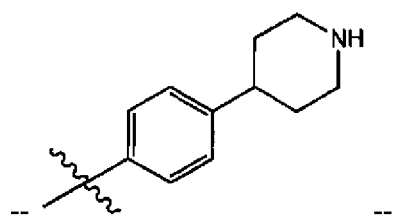 --

In column 213, please replace the third chemical structure for the top

" 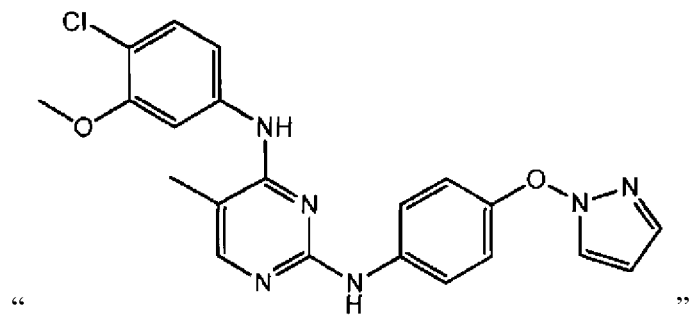 "

with

-- 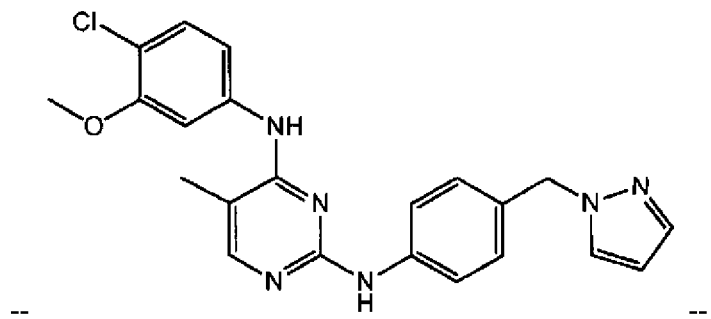 --

CERTIFICATE OF CORRECTION (continued)
U.S. Pat. No. 8,138,199 B2

Page 4 of 4

In column 268, between lines 10-19 (second chemical structure from the top) and lines 20-29 (third chemical structure from the top), insert the following chemical structure

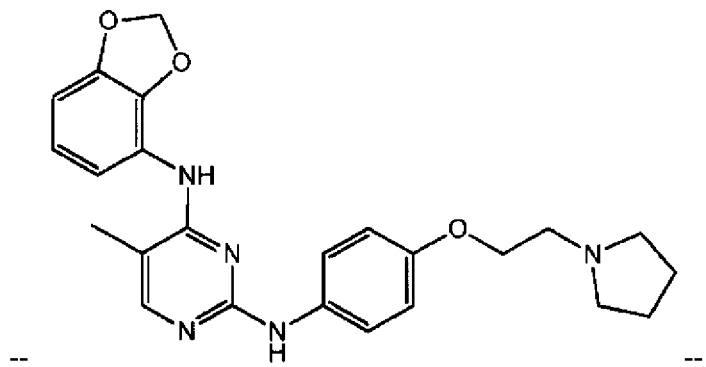

In column 294, lines 10-19, please replace the second chemical structure from the top

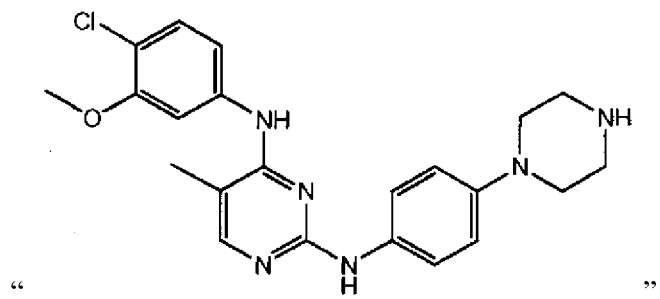

with